(12) United States Patent
Marx et al.

(10) Patent No.: US 11,702,418 B2
(45) Date of Patent: Jul. 18, 2023

(54) SOS1 INHIBITORS

(71) Applicant: Mirati Therapeutics, Inc., San Diego, CA (US)

(72) Inventors: Matthew Arnold Marx, San Diego, CA (US); John Michael Ketcham, Carlsbad, CA (US); Christopher Ronald Smith, San Diego, CA (US); John David Lawson, San Diego, CA (US); Aaron Craig Burns, San Diego, CA (US); Xiaolun Wang, San Diego, CA (US); Svitlana Kulyk, Redwood City, CA (US); Anthony Ivetac, San Diego, CA (US)

(73) Assignee: MIRATI THERAPEUTICS, INC., San Diego, CA (US)

( * ) Notice: Subject to any disclaimer, the term of this patent is extended or adjusted under 35 U.S.C. 154(b) by 102 days.

(21) Appl. No.: 17/127,582

(22) Filed: Dec. 18, 2020

(65) Prior Publication Data

US 2021/0188857 A1 Jun. 24, 2021

Related U.S. Application Data

(60) Provisional application No. 62/951,812, filed on Dec. 20, 2019, provisional application No. 62/975,645, filed on Feb. 12, 2020, provisional application No. 63/044,802, filed on Jun. 26, 2020.

(51) Int. Cl.
| | | |
|---|---|---|
| *C07D 487/04* | (2006.01) | |
| *C07D 237/34* | (2006.01) | |
| *C07D 403/04* | (2006.01) | |
| *C07D 409/12* | (2006.01) | |
| *C07D 409/14* | (2006.01) | |
| *C07D 413/04* | (2006.01) | |
| *C07D 471/04* | (2006.01) | |
| *C07D 471/08* | (2006.01) | |
| *C07D 487/08* | (2006.01) | |
| *C07D 487/10* | (2006.01) | |
| *C07D 498/10* | (2006.01) | |
| *C07D 471/10* | (2006.01) | |

(52) U.S. Cl.
CPC ......... *C07D 487/04* (2013.01); *C07D 237/34* (2013.01); *C07D 403/04* (2013.01); *C07D 409/12* (2013.01); *C07D 409/14* (2013.01); *C07D 413/04* (2013.01); *C07D 471/04* (2013.01); *C07D 471/08* (2013.01); *C07D 471/10* (2013.01); *C07D 487/08* (2013.01); *C07D 487/10* (2013.01); *C07D 498/10* (2013.01)

(58) Field of Classification Search
CPC .. C07D 487/04; C07D 237/34; C07D 403/04; C07D 409/12; C07D 409/14; C07D 413/04; C07D 471/04; C07D 471/08; C07D 471/10; C07D 487/08; C07D 487/10; C07D 498/10

See application file for complete search history.

(56) References Cited

U.S. PATENT DOCUMENTS

| | | |
|---|---|---|
| 8,163,763 B2 | 4/2012 | Bergeron et al. |
| 8,426,401 B2 | 4/2013 | Bian et al. |
| 9,562,019 B2 | 2/2017 | Djaballah et al. |
| 9,840,516 B2 | 12/2017 | Li et al. |
| 10,125,134 B2 | 11/2018 | Blake et al. |
| 2003/0191143 A1 | 10/2003 | Pitts et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2018/0015087 A1 | 1/2018 | Liu et al. |
| 2018/0118757 A1 | 5/2018 | Li et al. |
| 2018/0118761 A1 | 5/2018 | Sebti et al. |

(Continued)

FOREIGN PATENT DOCUMENTS

| | | |
|---|---|---|
| WO | 02/053558 A1 | 7/2002 |
| WO | 02/087513 A2 | 11/2002 |

(Continued)

OTHER PUBLICATIONS

Chemical Abstracts Registry No. 1014470-43-9, indexed in the Registry file on ACS on STN, Apr. 14, 2008.*

(Continued)

*Primary Examiner* — Rebecca L Anderson

(74) *Attorney, Agent, or Firm* — Wood, Phillips, Katz, Clark & Mortimer

(57) ABSTRACT

The present invention relates to compounds that inhibit Son of sevenless homolog 1 (SOS1) activity. In particular, the present invention relates to compounds, pharmaceutical compositions and methods of use, such as methods of treating cancer using the compounds and pharmaceutical compositions of the present invention.

72 Claims, No Drawings

(56) References Cited

U.S. PATENT DOCUMENTS

| | | |
|---|---|---|
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2020/0262837 A1 | 8/2020 | Marx et al. |
| 2020/0399297 A1 | 12/2020 | Campbell et al. |

FOREIGN PATENT DOCUMENTS

| | | |
|---|---|---|
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |

(56) References Cited

FOREIGN PATENT DOCUMENTS

| WO | 2021145521 A1 | 7/2021 |
|---|---|---|
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |

OTHER PUBLICATIONS

Chemical Abstracts Registry No. 1960573-90-3, indexed in the Registry file on ACS on STN, Jul. 27, 2016.*

International Search Report and Written Opinion for PCT Application No. PCT/US2020/066003 dated Apr. 20, 2021.

Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col., Para 2.

Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.

Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.

Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.

Burgess, M. et al., "KRAS Allelic Imbalance Enhances Fitness and Modulates MAP Kinase Dependence in Cancer", Cell 168, 817-829, Feb. 23, 2017, Elsevier Inc.

Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.

Costa-Cabral, S. et al., "CDK1 Is a Synthetic Lethal Target for KRAS Mutant Tumours", PLOS ONE | DOI:10.1371/journal.pone. 0149099 Feb. 16, 2016.

Cully, "Closing the door on KRAS-mutant lung cancer", Nature Reviews Drug Discovery | Published online Nov. 3, 2016; doi:10. 1038/nrd.2016.216, MacMillan Publishers.

Dharmaiah, S. et al., "Structural basis of recognition of farnesylated and methylated KRAS4b by PDEδ", E6766-E6775, PNAS, Published online Oct. 17, 2016.

Fiala, O. et al., "The dominant role of G12C over other KRAS mutation types in the negative prediction of efficacy of epidermal growth factor receptor tyrosine kinase inhibitors in nonsmall cell lung cancer", Cancer Genetics 206 (2013) 26-31.

Ford, B. et al., "Structure of the G60A Mutant of Ras Implications for the Dominant Negative Effect", J. Biol. Chem., vol. 280, No. 27, Issue of Jul. 8, pp. 25697-25705, 2005.

Hall, B. et al., "The structural basis for the transition from Ras-GTP to Ras-GDP", PNAS, vol. 99, No. 19, pp. 12138-12142, Sep. 17, 2002.

Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.

Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.

Jarvis, L., "Have drug hunters finally cracked KRas?", c&en, vol. 94, Issue 23, pp. 28-33, Jun. 6, 2016.

Kamerkar, S. et al., "Exosomes facilitate therapeutic targeting of oncogenic KRAS in pancreatic cancer", Nature 546, 498-503 (Jun. 22, 2017) doi:10.1038/nature22341.

Kaufman, J. et al., "Treatment of KRAS-Mutant Non-Small Cell Lung Cancer the End of the Beginning for Targeted Therapies", JAMA May 9, 2017 vol. 317, No. 18.

Kerr, E. et al., "Mutant Kras copy number defines metabolic reprogramming and therapeutic susceptibilities", Nature 531, 110-113, (Mar. 3, 2016) doi:10.1038/nature16967.

Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.

Kim, J. et al., "XPO1-dependent nuclear export is a druggable vulnerability in KRAS-mutant lung cancer", Nature 538, 114-117 (Oct. 6, 2016) doi:10.1038/nature19771.

Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.

Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.

Lim, S. et all., "Therapeutic Targeting of Oncogenic K-Ras by a Covalent Catalytic Site Inhibitor", Angew. Chem. Int. Ed. 2014, 53, 199-204.

Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.

Manchado, E. et al., "A combinatorial strategy for treating KRAS-mutant lung cancer", Nature 534, 647-651 (Jun. 30, 2016) doi:10. 1038/nature18600.

Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.

(56) References Cited

OTHER PUBLICATIONS

Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Rudoni, S. et al., "Role of guanine nucleotides in the regulation of the Ras/cAMP pathway in *Saccharomyces cerevisiae*". Biochimica et Biophysica Acta 1538 (2001) 181189.
Samatar, A. et al., "Targeting RAS-ERK signalling in cancer: promises and challenges", Nature Reviews Drug Discovery, vol. 13, pp. 928-942, Dec. 2014.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.

Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
O'Bryan, J., "Pharmacological Targeting of RAS: Recent Success with Direct Inhibitors", Pharmacological Research (2018), https://doi.org/10.1016/j.phrs.2018.10.021.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancerres.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer a Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Calles, et al., "Immunohistochemical Loss of LKB1 Is a Biomarker for MOre Aggressive Biology in KRAS-Mutant Lung Adenocarcinoma", Clin Cancer Res. 2015. 21(12).
Torralvo et al., "The Activity of Immune Checkpoint Inhibition in KRAS Mutated Non-small Cell Lung Cancer: A Single Centre Experience", Cancer Genomics & Proteomics, 2019. 16: 577-582.
Sung, Y. et al., "Mutagenesis of the H-ras p21 at Glycine-60 Residue Disrupts GTP-Induced Conformational Change", Biochemistry 1995, 34, 3470-3477, American Chemical Society.
Tape, C. et al., "Oncogenic KRAS Regulates Tumor Cell Signaling via Stromal Reciprocation", Cell 165, 1-11 May 5, 2016.
Thierry, A. et al., "Clinical validation of the detection of KRAS and BRAF mutations from circulating tumor DNA", Nature Medicine, vol. 20, No. 4, pp. 430-436, Apr. 2014.
Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.
Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.
Wang, Y. et al., "Ezh2 Acts as a Tumor Suppressor in Kras-driven Lung Adenocarcinoma", International Journal of Biological Sciences 2017; 13(5): 652-659 doi: 10.7150/ijbs.19108.

(56) References Cited

OTHER PUBLICATIONS

Welsch, M. et al., "Multivalent Small-Molecule Pan—RAS Inhibitors", Welsch et al., 2017, Cell 168, 878-889 Feb. 23, 2017; 2017 Elsevier Inc. http://dx.doi.org/10.1016/j.cell.2017.02.006.
Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.
Wood, K. et al., "Reply" Comments & Response, Letters JAMA Oncology Published online Jul. 21, 2016, American Medical Association.
Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.
Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.
Janes et al., "Targeting KRAS Mutant Cancers with a Covalent G12C-Specific Inhibitor", Cell 172, 578-589, Jan. 25, 2018.
Singh et al., A Gene Expression Signature Associated with "K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.

Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop start control of cancer growth", Oncogene (2010) 29, 6064-6070, 2010 Macmillan Publishers Limited.
Grant et al., "Novel Allosteric Sites on Ras for Lead Generation", PLOS ONE, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 dated Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.

\* cited by examiner

SOS1 INHIBITORS

FIELD OF THE INVENTION

The present invention relates to compounds that inhibit Son of sevenless homolog 1 (SOS1) GTP-mediated nucleotide exchange. In particular, the present invention relates to compounds, pharmaceutical compositions comprising the compounds and methods for use therefor.

BACKGROUND OF THE INVENTION

The Ras family comprises v-Ki-ras2 Kirsten rat sarcoma viral oncogene homolog (KRAS), neuroblastoma RAS viral oncogene homolog (NRAS), and Harvey murine sarcoma virus oncogene (HRAS) and critically regulates cellular division, growth and function in normal and altered states including cancer (see e.g., Simanshu et al. Cell, 2017. 170(1): p. 17-33; Matikas et al., Crit Rev Oncol Hematol, 2017. 110: p. 1-12). RAS proteins are activated by upstream signals, including receptor tyrosine kinases (RTKs), and transduce signals to several downstream signaling pathways such as the mitogen-activated protein kinase (MAPK)/extracellular signal-regulated kinases (ERK) pathway. Hyperactivation of RAS signaling is frequently observed in cancer as a result of mutations or alterations in RAS genes or other genes in the RAS pathway. The identification of strategies to inhibit RAS and RAS signaling are predicted to be useful for the treatment of cancer and RAS-regulated disease states.

RAS proteins are guanosine triphosphatases (GTPases) that cycle between an inactive, guanosine diphosphate (GDP)-bound state and an active guanosine triphosphate (GTP)-bound state. Son of sevenless homolog 1 (SOS1) is a guanine nucleotide exchange factor (GEF) that mediates the exchange of GDP for GTP, thereby activating RAS proteins. RAS proteins hydrolyze GTP to GDP through their intrinsic GTPase activity which is greatly enhanced by GTPase-activating proteins (GAPs). This regulation through GAPs and GEFs is the mechanism whereby activation and deactivation are tightly regulated under normal conditions. Mutations at several residues in all three RAS proteins are frequently observed in cancer and result in RAS remaining predominantly in the activated state (Sanchez-Vega et al., Cell, 2018. 173: p. 321-337 Li et al., Nature Reviews Cancer, 2018. 18: p. 767-777). Mutations at codon 12 and 13 are the most frequently mutated RAS residues and prevent GAP-stimulated GTP hydrolysis by blocking the interaction of GAP proteins and RAS. Recent biochemical analyses however, demonstrated these mutated proteins still require nucleotide cycling for activation based on their intrinsic GTPase activity and/or partial sensitivity to extrinsic GTPases. As such, mutant RAS proteins are sensitive to inhibition of upstream factors such as SOS1 or SHP2, another upstream signaling molecule required for RAS activation (Hillig, 2019; Patricelli, 2016; Lito, 2016; Nichols, 2018).

The three main RAS-GEF families that have been identified in mammalian cells are SOS, RAS-GRF and RAS-GRP (Rojas, 2011). RAS-GRF and RAS-GRP are expressed in the cells of the central nervous system and hematopoietic cells, respectively, while the SOS family is ubiquitously expressed and is responsible for transducing RTK signaling. The SOS family comprises SOS1 and SOS2 and these proteins share approximately 70% sequence identity. SOS1 appears to be much more active than SOS2 due to the rapid degradation of SOS2. The mouse SOS2 knockout is viable whereas the SOS1 knockout is embryonic lethal. A tamoxifen-inducible SOS1 knockout mouse model was used to interrogate the role of SOS1 and SOS2 in adult mice and demonstrated the SOS1 knockout was viable but the SOS1/2 double knockout was not viable (Baltanas, 2013) suggesting functional redundancy and that selective inhibition of SOS1 may have a sufficient therapeutic index for the treatment of SOS1-RAS activated diseases.

SOS proteins are recruited to phosphorylated RTKs through an interaction with growth factor receptor bound protein 2 (GRB2). Recruitment to the plasma membrane places SOS in close proximity to RAS and enables SOS-mediated RAS activation. SOS proteins bind to RAS through a binding site that promotes nucleotide exchange as well as through an allosteric site that binds GTP-bound RAS-family proteins and increases the function of SOS (Freedman et al., Proc. Natl. Acad. Sci, USA 2006. 103(45): p. 16692-97). Binding to the allosteric site relieves steric occlusion of the RAS substrate binding site and is therefore required for nucleotide exchange. Retention of the active conformation at the catalytic site following interaction with the allosteric site is maintained in isolation due to strengthened interactions of key domains in the activated state. SOS1 mutations are found in Noonan syndrome and several cancers including lung adenocarcinoma, embryonal rhabdomyosarcoma, Sertoli cell testis tumor and granular cell tumors of the skin (see e.g., Denayer, E., et al, Genes Chromosomes Cancer, 2010. 49(3): p. 242-52).

GTPase-activating proteins (GAPs) are proteins that stimulate the low intrinsic GTPase activity of RAS family members and therefore converts active GTP-bound RAS proteins into inactive, GDP-bound RAS proteins (e.g., see Simanshu, D. K., Cell, 2017, Ras Proteins and their Regulators in Human Disease). While activating alterations in the GEF SOS1 occur in cancers, inactivating mutations and loss-of-function alterations in the GAPs neurofibromin 1 (NF-1) or neurofibromin 2 (NF-2) also occur creating a state where SOS1 activity is unopposed and activity downstream of the pathway through RAS proteins is elevated.

Thus, the compounds of the present invention that block the interaction between SOS1 and Ras-family members prevent the recycling of KRas into the active GTP-bound form and, therefore, may provide therapeutic benefit for a wide range of cancers, particularly Ras family member-associated cancers. The compounds of the present invention offer potential therapeutic benefit as inhibitors of SOS1-KRas interaction that may be useful for negatively modulating the activity of KRas through blocking SOS1-KRas interaction in a cell for treating various forms of cancer, including Ras-associated cancer, SOS1-associated cancer andNFl/NF2-associated cancer.

SUMMARY OF THE INVENTION

There is a need to develop new SOS1 inhibitors that are capable of blocking the interaction between SOS1 and Ras-family members, prevent the recycling of KRas into the active GTP-bound form and, therefore, may provide therapeutic benefit for a wide range of cancers, particularly including Ras-associated cancers, SOS1-associated cancers andNFl/NF2-associated cancers.

In one aspect of the invention, compounds are provided represented by Formula (I):

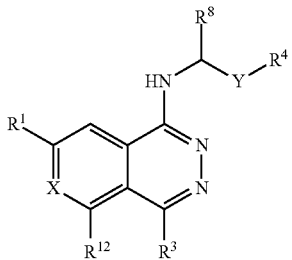

Formula (I)

or a pharmaceutically acceptable salt thereof, wherein:

$R^1$ is hydrogen, hydroxyl, C1-C6 alkyl, alkoxy, —$N(R^6)_2$, —$NR^6C(O)R^6$, —$C(O)N(R^6)_2$, —$SO_2$alkyl, —$SO_2NR^6$alkyl, cycloalkyl, -Q-heterocyclyl, aryl, or heteroaryl, wherein the cycloalkyl, the heterocyclyl, the aryl, and the heteroaryl are each optionally substituted with one or more $R^2$ or L-R2;

each Q is independently a bond, O or $NR^6$;

X is N or $CR^7$;

each $R^2$ is independently C1-C3 alkyl, oxo (i.e., C=O), hydroxy, halogen, cyano, hydroxyalkyl, haloalkyl, alkoxy, —$C(O)N(R^6)_2$, —$N(R^6)_2$, —$SO_2$alkyl, —$NR^6C(O)$C1-C3 alkyl, —C(O)cycloalkyl, —C(O)C1-C3 alkyl, —C(O)heterocyclyl, aryl, heteroaryl or heterocyclyl, wherein the cycloalkyl, the heterocyclyl, the aryl, the heteroaryl or the heterocyclyl are each optionally substituted with one or more $R^{11}$;

$R^3$ is hydrogen, C1-C6 alkyl, alkoxy, —$N(R^{10})_2$, -L-N$(R^{10})_2$, cycloalkyl, haloalkyl or heterocyclyl, wherein the C1-C6 alkyl, the cycloalkyl and the heterocyclyl are each optionally substituted with one or more $R^9$;

Y is a bond or heteroarylene;

$R^4$ is aryl or heteroaryl, each optionally substituted with one or more $R^5$;

each $R^5$ is independently hydroxy, halogen, cyano, hydroxyalkyl, alkoxy, C1-C3 alkyl, haloalkyl, haloalkyl-OH, —$N(R^6)_2$, -L-$N(R^6)_2$ or —$SO_2$alkyl;

L is C1-C3 alkylene;

each $R^6$ is independently hydrogen, C1-C3 alkyl, haloalkyl, or cycloalkyl;

$R^7$ is hydrogen, cyano, or alkoxy;

$R^8$ is C1-C2 alkyl or haloC1-C2 alkyl;

each $R^9$ is independently hydroxy, halogen, amino, cyano, alkoxy, or C1-C3 alkyl;

each $R^{10}$ is independently hydrogen, C1-C3 alkyl or cycloalkyl;

each $R^{11}$ is independently C1-C3 alkyl, halogen or haloalkyl; and $R^{12}$ is hydrogen, halogen or C1-C3 alkyl.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect, the invention provides methods for inhibiting the activity of a Ras-family member by inhibiting the associaton between the Ras-family member and SOS1 in a cell, comprising contacting the cell with a compound of Formula (I). In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided herein are methods for treating cancer in a subject in need thereof, the method comprising (a) determining that cancer is associated with a Ras-family member mutation (e.g., a KRas G12C-associated cancer) (e.g., as determined using a regulatory agency-approved, e.g., FDA-approved, assay or kit); and (b) administering to the patient a therapeutically effective amount of compound of Formula (I), or pharmaceutically acceptable salts or pharmaceutical compositions thereof.

Also provided herein are methods for treating cancer in a subject in need thereof, the method comprising (a) determining that cancer is associated with a SOS1 mutation (e.g., a SOS1-associated cancer) (e.g., as determined using a regulatory agency-approved, e.g., FDA-approved, assay or kit); and (b) administering to the patient a therapeutically effective amount of compound of Formula (I), or pharmaceutically acceptable salts or pharmaceutical compositions thereof.

Also provided herein are methods for treating cancer in a subject in need thereof, the method comprising (a) determining that cancer is associated with a NF-1 or NF-2 loss-of-function mutation (e.g., a NF1/NF2-associated cancer) (e.g., as determined using a regulatory agency-approved, e.g., FDA-approved, assay or kit); and (b) administering to the patient a therapeutically effective amount of compound of Formula (I), or pharmaceutically acceptable salts or pharmaceutical compositions thereof.

Also provided herein is a use of a compound of Formula (I), or a pharmaceutically acceptable salt or solvate thereof, as defined herein in the manufacture of a medicament for the inhibition of activity of SOS1.

Also provided herein is the use of a compound of Formula (I), or a pharmaceutically acceptable salt or solvate thereof, as defined herein, in the manufacture of a medicament for the treatment of a SOS1-associated disease or disorder.

DETAILED DESCRIPTION OF THE INVENTION

The present invention relates to SOS1 inhibitors. In particular, the present invention relates to compounds that inhibit SOS1 activity, pharmaceutical compositions comprising a therapeutically effective amount of the compounds, and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variant p.Gly12Asp.

As used herein, "KRas G12S" refers to a mutant form of a mammalian KRas protein that contains an amino acid substitution of a serine for a glycine at amino acid position 12. The assignment of amino acid codon and residue positions for human KRas is based on the amino acid sequence identified by UniProtKB/Swiss-Prot P01116: Variant p.Gly12Ser.

As used herein, "KRas G12A" refers to a mutant form of a mammalian KRas protein that contains an amino acid substitution of an alanine for a glycine at amino acid position 12. The assignment of amino acid codon and residue positions for human KRas is based on the amino acid sequence identified by UniProtKB/Swiss-Prot P01116: Variant p.Gly12Ala.

As used herein, "KRas G13D" refers to a mutant form of a mammalian KRas protein that contains an amino acid substitution of an aspartic acid for a glycine at amino acid position 13. The assignment of amino acid codon and residue positions for human KRas is based on the amino acid sequence identified by UniProtKB/Swiss-Prot P01116: Variant p.Gly13Asp.

As used herein, "KRas G13C" refers to a mutant form of a mammalian KRas protein that contains an amino acid substitution of a cysteine for a glycine at amino acid position 13. The assignment of amino acid codon and residue positions for human KRas is based on the amino acid sequence identified by UniProtKB/Swiss-Prot P01116: Variant p.Gly13Cys.

As used herein, "KRas Q61L" refers to a mutant form of a mammalian KRas protein that contains an amino acid substitution of a leucine for a glutamine at amino acid position 41. The assignment of amino acid codon and residue positions for human KRas is based on the amino acid sequence identified by UniProtKB/Swiss-Prot P01116: Variant p.Gln61Leu.

As used herein, "KRas A146T" refers to a mutant form of a mammalian KRas protein that contains an amino acid substitution of a threonine for an alanine at amino acid position 146. The assignment of amino acid codon and residue positions for human KRas is based on the amino acid sequence identified by UniProtKB/Swiss-Prot P01116: Variant p.Ala146Thr.

As used herein, "KRas A146V" refers to a mutant form of a mammalian KRas protein that contains an amino acid substitution of a valine for an alanine at amino acid position 146. The assignment of amino acid codon and residue positions for human KRas is based on the amino acid sequence identified by UniProtKB/Swiss-Prot P01116: Variant p.Ala146Val.

As used herein, "KRas A146P" refers to a mutant form of a mammalian KRas protein that contains an amino acid substitution of a proline for an alanine at amino acid position 146. The assignment of amino acid codon and residue positions for human KRas is based on the amino acid sequence identified by UniProtKB/Swiss-Prot P01116: Variant p.Ala146Pro.

As used herein, "HRas G12C" refers to a mutant form of a mammalian HRas protein that contains an amino acid substitution of a cysteine for a glycine at amino acid position 12. The assignment of amino acid codon and residue positions for human HRas is based on the amino acid sequence identified by UniProtKB/Swiss-Prot P01112: Variant p.Gly12Cys.

As used herein, "HRas G12D" refers to a mutant form of a mammalian HRas protein that contains an amino acid substitution of an aspartic acid for a glycine at amino acid position 12. The assignment of amino acid codon and residue positions for human HRas is based on the amino acid sequence identified by UniProtKB/Swiss-Prot P01112: Variant p.Gly12Asp.

As used herein, "HRas G12S" refers to a mutant form of a mammalian HRas protein that contains an amino acid substitution of a serine for a glycine at amino acid position 12. The assignment of amino acid codon and residue positions for human HRas is based on the amino acid sequence identified by UniProtKB/Swiss-Prot P01112: Variant p.Gly12Ser.

As used herein, "HRas G12A" refers to a mutant form of a mammalian HRas protein that contains an amino acid substitution of an alanine for a glycine at amino acid position 12. The assignment of amino acid codon and residue positions for human KRas is based on the amino acid sequence identified by UniProtKB/Swiss-Prot P01112: Variant p.Gly12Ala.

As used herein, "HRas G13D" refers to a mutant form of a mammalian HRas protein that contains an amino acid substitution of an aspartic acid for a glycine at amino acid position 13. The assignment of amino acid codon and residue positions for human HRas is based on the amino acid sequence identified by UniProtKB/Swiss-Prot P01112: Variant p.Gly13Asp.

As used herein, "HRas G13C" refers to a mutant form of a mammalian HRas protein that contains an amino acid substitution of a cysteine for a glycine at amino acid position 13. The assignment of amino acid codon and residue positions for human HRas is based on the amino acid sequence identified by UniProtKB/Swiss-Prot P01112: Variant p.Gly13Cys.

As used herein, "HRas Q61L" refers to a mutant form of a mammalian HRas protein that contains an amino acid substitution of a leucine for a glutamine at amino acid position 41. The assignment of amino acid codon and residue positions for human HRas is based on the amino acid sequence identified by UniProtKB/Swiss-Prot P01112: Variant p.Gln61Leu.

As used herein, "HRas A146T" refers to a mutant form of a mammalian HRas protein that contains an amino acid substitution of a threonine for an alanine at amino acid position 146. The assignment of amino acid codon and residue positions for human NRas is based on the amino acid sequence identified by UniProtKB/Swiss-Prot P01112: Variant p.Ala146Thr.

As used herein, "HRas A146V" refers to a mutant form of a mammalian HRas protein that contains an amino acid substitution of a valine for an alanine at amino acid position 146. The assignment of amino acid codon and residue positions for human NRas is based on the amino acid sequence identified by UniProtKB/Swiss-Prot P01112: Variant p.Ala146Val.

As used herein, "HRas A146P" refers to a mutant form of a mammalian HRas protein that contains an amino acid substitution of a proline for an alanine at amino acid position 146. The assignment of amino acid codon and residue positions for human NRas is based on the amino acid sequence identified by UniProtKB/Swiss-Prot P01112: Variant p.Ala146Pro.

As used herein, "NRas G12C" refers to a mutant form of a mammalian NRas protein that contains an amino acid substitution of a cysteine for a glycine at amino acid position 12. The assignment of amino acid codon and residue positions for human NRas is based on the amino acid sequence identified by UniProtKB/Swiss-Prot P01111: Variant p.Gly12Cys.

As used herein, "NRas G12D" refers to a mutant form of a mammalian NRas protein that contains an amino acid substitution of an aspartic acid for a glycine at amino acid position 12. The assignment of amino acid codon and residue positions for human NRas is based on the amino acid sequence identified by UniProtKB/Swiss-Prot P01111: Variant p.Gly12Asp.

As used herein, "NRas G12S" refers to a mutant form of a mammalian NRas protein that contains an amino acid substitution of a serine for a glycine at amino acid position 12. The assignment of amino acid codon and residue positions for human NRas is based on the amino acid sequence identified by UniProtKB/Swiss-Prot P01111: Variant p.Gly12Ser.

As used herein, "NRas G12A" refers to a mutant form of a mammalian NRas protein that contains an amino acid substitution of an alanine for a glycine at amino acid position 12. The assignment of amino acid codon and residue positions for human KRas is based on the amino acid sequence identified by UniProtKB/Swiss-Prot P01111: Variant p.Gly12Ala.

As used herein, "NRas G13D" refers to a mutant form of a mammalian NRas protein that contains an amino acid substitution of an aspartic acid for a glycine at amino acid position 13. The assignment of amino acid codon and residue positions for human NRas is based on the amino acid sequence identified by UniProtKB/Swiss-Prot P01111: Variant p.Gly13 Asp.

As used herein, "HNRas G13C" refers to a mutant form of a mammalian NRas protein that contains an amino acid substitution of a cysteine for a glycine at amino acid position 13. The assignment of amino acid codon and residue positions for human NRas is based on the amino acid sequence identified by UniProtKB/Swiss-Prot P01111: Variant p.Gly13Cys.

As used herein, "HRas Q61L" refers to a mutant form of a mammalian HRas protein that contains an amino acid substitution of a leucine for a glutamine at amino acid position 41. The assignment of amino acid codon and residue positions for human HRas is based on the amino acid sequence identified by UniProtKB/Swiss-Prot P01112: Variant p.Gln61Leu.

As used herein, "NRas A146T" refers to a mutant form of a mammalian NRas protein that contains an amino acid substitution of a threonine for an alanine at amino acid position 146. The assignment of amino acid codon and residue positions for human NRas is based on the amino acid sequence identified by UniProtKB/Swiss-Prot P01111: Variant p.Ala146Thr.

As used herein, "NRas A146V" refers to a mutant form of a mammalian NRas protein that contains an amino acid substitution of a valine for an alanine at amino acid position 146. The assignment of amino acid codon and residue positions for human NRas is based on the amino acid sequence identified by UniProtKB/Swiss-Prot P01111: Variant p.Ala146Val.

As used herein, "NRas A146P" refers to a mutant form of a mammalian NRas protein that contains an amino acid substitution of a proline for an alanine at amino acid position 146. The assignment of amino acid codon and residue positions for human NRas is based on the amino acid sequence identified by UniProtKB/Swiss-Prot P01111: Variant p.Ala146Pro.

As used herein, "a Ras family member" or "Ras family" refers to KRas, HRas, NRas, and activating mutants thereof, including at positions G12, G13, Q61 and A146.

A "Ras family-associated disease or disorder" as used herein refers to diseases or disorders associated with or mediated by or having an activating Ras mutation, such as one at position G12, G13, Q61 or A146. Non-limiting examples of Ras family-associated disease or disorder are a KRas, HRas or NRas G12C-associated cancer, a KRas, HRas or NRas G12D-associated cancer, a KRas, HRas or NRas G12S-associated cancer, a KRas, HRas or NRas G12A-associated cancer, a KRas, HRas or NRas G13D-associated cancer, a KRas, HRas or NRas G13C-associated cancer, a KRas, HRas or NRas Q61X-associated cancer, a KRas, HRas or NRas A146T-associated cancer, a KRas, HRas or NRas A146V-associated cancer or a KRas, HRas or NRas A146P-associated cancer.

As used herein, "SOS1" refers to a mammalian Son of sevenless homolog 1 (SOS1) enzyme.

A "SOS1-associated disease or disorder" as used herein refers to diseases or disorders associated with or mediated by or having an activating SOS1 mutation. Examples of activating SOS1 mutations include SOS1 N233S and SOS1 N233Y mutations.

As used herein, "SOS1 N233S" refers to a mutant form of a mammalian SOS1 protein that contains an amino acid substitution of a serine for a glutamine at amino acid position 233. The assignment of amino acid codon and residue positions for human SOS1 is based on the amino acid sequence identified by UniProtKB/Swiss-Prot Q07889: Variant p.Gln233Ser.

As used herein, "SOS1 N233Y" refers to a mutant form of a mammalian SOS1 protein that contains an amino acid substitution of a tyrosine for a glutamine at amino acid position 233. The assignment of amino acid codon and residue positions for human SOS1 is based on the amino acid sequence identified by UniProtKB/Swiss-Prot Q07889: Variant p.Gln233Tyr.

As used herein, an "SOS1 inhibitor" refers to compounds of the present invention that are represented by Formula (I) as described herein. These compounds are capable of negatively inhibiting all or a portion of the interaction of SOS1 with Ras family mutant or SOS1 activating mutation thereby reducing and/or modulating the nucleotide exchange activity of Ras family member—SOS1 complex.

As used herein, a "NF-1/NF-2-associated disease or disorder" refers to diseases or disorders associated with or mediated by or having a loss-of-function mutation in the neurofibromin (NF-1) gene or neurofibromin 2 (NF-2) gene.

As used herein, a "loss-of-function mutation" refers to any point mutation(s), splice site mutation(s), fusions, nonsense mutations (an amino acid is mutated to a stop codon), in-frame or frame-shifting mutations, including insertions and deletions, and a homozygous deletion of the genes encoding the protein in a target cell or cancer cell that results in a partial or complete loss of the presence, activity and/or function of the encoded protein.

The term "amino" refers to —$NH_2$.

The term "acetyl" refers to "—$C(O)CH_3$.

As herein employed, the term "acyl" refers to an alkylcarbonyl or arylcarbonyl substituent wherein the alkyl and aryl portions are as defined herein.

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —$OC1$-$C6$ alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or $NR^x$, wherein $R^x$ is hydrogen or C1-C3 alkyl. Examples of heteroalkyl groups include methoxymethyl, m ethoxy ethyl and methoxypropyl.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl. An "aryl" group also includes fused multicyclic (e.g, bicyclic) ring systems in which one or more of the fused rings is non-aromatic, provided that at least one ring is aromatic, such as indenyl.

An "aralkyl" or "arylalkyl" group comprises an aryl group covalently linked to an alkyl group wherein the moiety is linked to another group via the alkyl moiety. An exemplary aralkyl group is —(C1-C6)alkyl(C6-C10)aryl, including, without limitation, benzyl, phenethyl, and naphthylmethyl.

A "heterocyclyl" or "heterocyclic" group is a mono- or bicyclic (fused, spiro or bridged) ring structure having from 3 to 12 atoms (3, 4, 5, 6, 7, 8, 9, 10, 11 or 12 atoms), or having from 3 to 12 atoms (3, 4, 5, 6, 7, 8, 9, 10, 11, 12 or 13 atoms), for example 4 to 8 atoms, wherein one or more ring atoms are independently —C(O)—, N, $NR^4$, O, S or $S(O)_2$, and the remainder of the ring atoms are quaternary or carbonyl carbons. Examples of heterocyclic groups include, without limitation, epoxy, oxiranyl, oxetanyl, azetidinyl, aziridinyl, tetrahydrofuranyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl.

As used herein, "heterocyclyl" refers to a heterocyclyl group covalently linked to another group via a bond.

As used herein, the term "heteroaryl" refers to a group having 5 to 14 ring atoms, preferably 5, 6, 10, 13 or 14 ring atoms; having 6, 10, or 14 n electrons shared in a cyclic array, which may include 1, 2 or 3 rings, and having, in addition to carbon atoms, from one to three heteroatoms that are each independently N, O, or S. "Heteroaryl" also includes fused multi cyclic (e.g., bicyclic, tricyclic) ring systems in which one or more of the fused rings is non-aromatic (regardless of which ring is attached), provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroaralkyl" or "heteroarylalkyl" group comprises a heteroaryl group covalently linked to another group via a bond. Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is an bivalent aryl, heteroaryl, or heterocyclyl group, respectively, as defined hereinabove, that is positioned between and serves to connect two other chemical groups.

As employed herein, when a moiety (e.g., cycloalkyl, aryl, heteroaryl, heterocyclyl, urea, etc.) is described as "optionally substituted" without expressly stating the substituents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, chloromethyl, and fluoromethyl.

The term "hydroxyalkyl" refers to -alkylene-OH.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12 or G13 mutation (e.g., as determined using a regulatory agency-approved, e.g., FDA-approved, assay or kit). In some embodiments, the subject has a tumor that is positive for a KRas G12C mutation, a KRas G12D mutation, a KRas G12S mutation, a KRas G12A mutaation, a KRas G13D mutation or a KRas G13C mutation (e.g., as determined using a regulatory agency-approved assay or kit). The subject can be a subject with a tumor(s) that is positive for a a KRas G12C mutation, a KRas G12D mutation, a KRas G12S mutation, a KRas G12A mutaation, a KRas G13D mutation or a KRas G13C mutation (e.g., identified as positive using a regulatory agency-approved, e.g., FDA-approved, assay or kit). The subject can be a subject whose tumors have a KRas G12C mutation, a KRas G12D mutation, a KRas G12S mutation, a KRas G12A mutaation, a KRas G13D mutation or a KRas G13C mutation (e.g., where the tumor is identified as such using a regulatory agency-approved, e.g., FDA-approved, kit or assay). In some embodiments, the subject is suspected of having a KRas G12 or G13 gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994.

As used herein, "an effective amount" of a compound is an amount that is sufficient to negatively modulate or inhibit the activity of SOS1 enzyme.

As used herein, a "therapeutically effective amount" of a compound is an amount that is sufficient to ameliorate or in some manner reduce a symptom or stop or reverse progression of a condition, or negatively modulate or inhibit the activity of SOS1. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, "amelioration of the symptoms of a particular disorder by administration of a particular compound or pharmaceutical composition" refers to any lessening, whether permanent or temporary, lasting or transient, that can be attributed to or associated with administration of the composition.

Compounds

In one aspect of the invention, compounds are provided represented by Formula (I):

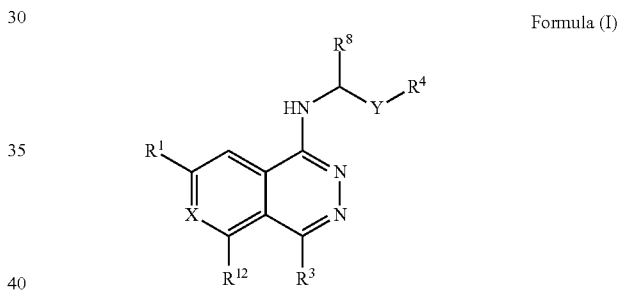

Formula (I)

or a pharmaceutically acceptable salt thereof, wherein:

$R^1$ is hydrogen, hydroxyl, C1-C6 alkyl, alkoxy, —N($R^6$)$_2$, —$NR^6C(O)R^6$, —C(O)N($R^6$)$_2$, —SO$_2$alkyl, —SO$_2NR^6$alkyl, cycloalkyl, -Q-heterocyclyl, aryl, or heteroaryl, wherein the cycloalkyl, the heterocyclyl, the aryl, and the heteroaryl are each optionally substituted with one or more $R^2$ or L-$R^2$;

each Q is independently a bond, O or $NR^6$;

X is N or $CR^7$;

each $R^2$ is independently C1-C3 alkyl, oxo (i.e., (C=O), hydroxy, halogen, cyano, hydroxyalkyl, haloalkyl, alkoxy, —C(O)N($R^6$)$_2$, —N($R^6$)$_2$, —SO$_2$alkyl, —$NR^6C(O)$C1-C3 alkyl, —C(O)cycloalkyl, —C(O)C1-C3 alkyl, —C(O)heterocyclyl, aryl, heteroaryl or heterocyclyl, wherein the cycloalkyl, the heterocyclyl, the aryl, the heteroaryl or the heterocyclyl are each optionally substituted with one or more $R^{11}$;

$R^3$ is hydrogen, C1-C6 alkyl, alkoxy, —N($R^{10}$)$_2$, -L-N($R^{10}$)$_2$, cycloalkyl, haloalkyl or heterocyclyl, wherein the C1-C6 alkyl, the cycloalkyl and the heterocyclyl are each optionally substituted with one or more $R^9$;

Y is a bond or heteroarylene;

$R^4$ is aryl or heteroaryl, each optionally substituted with one or more $R^5$;

each $R^5$ is independently hydroxy, halogen, cyano, hydroxyalkyl, alkoxy, C1-C3 alkyl, haloalkyl, haloalkyl-OH, —N($R^6$)$_2$, -L-N($R^6$)$_2$ or —SO$_2$alkyl;

L is C1-C3 alkylene;

each $R^6$ is independently hydrogen, C1-C3 alkyl, haloalkyl, or cycloalkyl;

$R^7$ is hydrogen, cyano, or alkoxy;

$R^8$ is C1-C2 alkyl or haloC1-C2 alkyl;

each $R^9$ is independently hydroxy, halogen, amino, cyano, alkoxy, or C1-C3 alkyl;

each $R^{10}$ is independently hydrogen, C1-C3 alkyl or cycloalkyl;

each $R^{11}$ is independently C1-C3 alkyl, halogen or haloalkyl; and $R^{12}$ is hydrogen, halogen or C1-C3 alkyl.

In one embodiment for compounds of Formula (I), X is N. In certain embodiments wherein X is N, $R^1$ is alkoxy. In one embodiment, the alkoxy is methoxy.

In one embodiment for compounds of Formula (I), X is N. In certain embodiments wherein X is N, $R^1$ is -Q-heterocyclyl optionally substituted with one or more $R^2$. In certain embodiments, $R^1$ is -Q-heterocyclyl, and wherein Q is a bond and the heterocyclyl is morpholinyl, piperazinyl, or piperazinone optionally substituted with one or more $R^2$. In certain embodiments, the heterocyclyl is morpholinyl or piperazinyl, Y is a bond, and $R^4$ is aryl optionally substituted with one or more $R^5$. In one embodiment, the heterocyclyl is morpholinyl, piperazinyl, or piperazinone, Y is heteroarylene, and $R^4$ is aryl optionally substituted with one or more $R^5$.

In certain embodiments of the invention, $R^1$ is -Q-heterocyclyl, and wherein the heterocyclyl is bridged morpholinyl, bridged piperazinyl, or bridged piperazinone.

In certain embodiments of the invention, $R^1$ is -Q-heterocyclyl, and wherein the heterocyclyl is spirocyclic ring system containing two or more rings. In certain of these embodiments, the spirocyclic ring system comprises two rings each containing a heteroatom. In certain other of these embodiments, the spirocyclic ring system contains a ring with no heteroatom (i.e., one ring rith a heteroatom, and one ring without a heteroatom).

In certain embodiments of the invention, $R^1$ is heteroaryl, wherein the heterocyclyl is optionally substituted with one or more $R^2$ or L-$R^2$. In certain of these embodiments, the heteroaryl is a bicyclic or tricyclic ring system comprising, in additional to one or more aromatic ring, a non-aromatic ring, for example a bicyclic or tricyclic ring system such as 5,6,7,8-tetrahydro-[1,2,4]triazolopyrazinyl, 5,6,7,8-tetrahydroimidazopyrazinyl, 2,4,5,6-tetrahydropyrrolopyrazolyl, 1,2,3,4-tetrahydrobenzo[4,5]imidazopyrazinyl or 4,5,6,7-tetrahy dropyrazolopyrazinyl.

In one embodiment for compounds of Formula (I), X is C$R^7$. In one embodiment when X is C$R^7$, $R^7$ is cyano.

In one embodiment for compounds of Formula (I), X is C$R^7$. In one embodiment when X is C$R^7$, $R^7$ is hydrogen.

In one embodiment for compounds of Formula (I), X is C$R^7$, $R^7$ is hydrogen, $R^1$ is hydrogen. In another embodiment, $R^1$ is hydroxyl. In certain embodiments, $R^1$ is —N($R^6$)$_2$. In one embodiment, wherein $R^1$ is —N($R^6$)$_2$ and each $R^6$ is C1-C3 alkyl. In one embodiment, each C1-C3 alkyl group is methyl. In other embodiments $R^1$ is —N$R^6$C(O)$R^6$. In one embodiment, each C1-C3 alkyl is methyl. In one embodiment, the $R^6$ of the N$R^6$ is hydrogen and $R^6$ of the C(O)$R^6$ is C1-C3 alkyl.

In another embodiment when X is C$R^7$ and $R^7$ is hydrogen, $R^1$ is —C(O)N($R^6$)$_2$. In one embodiment, each C1-C3 alkyl is methyl. In one embodiment, each C1-C3 alkyl is hydrogen. In certain embodiments, $R^1$ is —SO$_2$alkyl or —SO$_2$N$R^6$alkyl. In one embodiment, R1 is —SO$_2$N$R^6$alkyl and $R^6$ is hydrogen. In other embodiments, $R^1$ is cycloalkyl optionally substituted with one or more $R^2$. In one embodiment, the cycloalkyl is cyclobutyl, cyclopentyl or cyclohexyl, each optionally substituted with one or more $R^2$. In one embodiment, the cyclobutyl, cyclopentyl or the cyclohexyl are substituted with one $R^2$, wherein $R^2$ is C1-C3 alkyl, alkoxy, hydroxyl or —N($R^6$)$_2$. In one embodiment, $R^2$ is —N($R^6$)$_2$ and each $R^6$ is C1-C3 alkyl. In one embodiment, each C1-C3 alkyl is methyl.

In another embodiment when X is C$R^7$ and $R^7$ is hydrogen, $R^1$ is -Q-heterocyclyl optionally substituted with one or more $R^2$. In one embodiment, Q is a bond and the heterocyclyl is morpholinyl, piperdinyl, piperazinyl, N-methyl piperazinyl, piperazinone, 1-methyl-piperazin-2-one, diazepanyl, 6,6-difluoro-1,4-diazepan-1-yl or 4-methylthiomorpholine 1,1-dioxide. In another embodiment, Q is a bond and the heterocyclyl is pyrrolidinyl or tetrahydropyranyl, each optionally substituted with one or more $R^2$. In one embodiment, the pyrrolidinyl or the tetrahydropyranyl are substituted with one $R^2$, wherein $R^2$ is C1-C3 alkyl, alkoxy, hydroxyl or —N($R^6$)$_2$.

In another embodiment when X is C$R^7$ and $R^7$ is hydrogen, $R^1$ is -Q-heterocyclyl, Q is a bond and the heterocyclyl is piperazinyl substituted with one $R^2$, wherein $R^2$ is heteroaryl optionally substituted with one or more $R^{11}$. In one embodiment, the heteroaryl is pyrazolyl substituted with two $R^{11}$, wherein each $R^{11}$ is C1-C3 alkyl.

In another embodiment when X is C$R^7$ and $R^7$ is hydrogen, $R^1$ is -Q-heterocyclyl, Q is a bond and the heterocyclyl is piperazinyl substituted with one $R^2$, wherein $R^2$ is —C(O)cycloalkyl or —C(O)heterocyclyl, wherein the cycloalkyl or heterocyclyl portion of the —C(O)cycloalkyl or —C(O)heterocyclyl are each optionally substituted with one or more $R^{11}$. In one embodiment, $R^2$ is —C(O)cycloalkyl and the cycloalkyl is cyclopropyl substituted with one $R^{11}$, wherein $R^{11}$ is C1-C3 alkyl or haloalkyl. In one embodiment, $R^2$ is —C(O)heterocyclyl, wherein the heterocyclyl is oxetanyl, tetrahydrofuranyl or tetrahydropyranyl.

In one embodiment, Q is a bond and the heterocyclyl is a bicyclic heterocyclyl. In certain embodiments, the bicyclic heterocyclyl is diazabicyclo[3.2.0]heptan-2-yl, (1R,5R)-2,6-diazabicyclo[3.2.0]heptan-2-yl, diazabicyclo[3.2.0]heptan-6-yl, (1R,5R)-2,6-diazabicyclo[3.2.0]heptan-6-yl, 6,7-dihydropyrazolo[1,5-a]pyrazin-5(4H)-yl, 5,6-dihydroimidazo[1,5-a]pyrazin-7(8H)-yl, 1,3-dimethyl-5,6-dihydroimidazo[1,5-a]pyrazin-7(8H)-yl or (R)-2-methylhexahydropyrrolo[1,2-a]pyrazin-6(2H)-one.

In yet another embodiment, Q is O and the heterocyclyl is azetidinyl, tetrahydrofuranyl, pyrrolidinyl, or piperdinyl.

In another embodiment when X is C$R^7$ and $R^7$ is hydrogen, $R^1$ is aryl optionally substituted with one or more $R^2$. In one embodiment, the aryl is phenyl optionally substituted with one or more $R^2$. In certain embodiments, the phenyl is substituted with one $R^2$, wherein $R^2$ is C1-C3 alkyl, alkoxy, hydroxyl or —N($R^6$)$_2$. In one embodiment, $R^2$ is —N($R^6$)$_2$ and each $R^6$ is C1-C3 alkyl. In one embodiment, each C1-C3 alkyl is methyl. In other embodiments, $R^1$ is heteroaryl optionally substituted with one or more $R^2$. In one embodiment, the heteroaryl is pyrazolyl optionally substituted with one or more $R^2$. In one embodiment, the pyrazolyl is substituted with one $R^2$, wherein $R^2$ is C1-C3 alkyl, alkoxy, hydroxyl or —N($R^6$)$_2$. In one embodiment, $R^2$ is —N($R^6$)$_2$ and each $R^6$ is C1-C3 alkyl. In one embodiment, each C1-C3 alkyl is methyl.

In one embodiment for compounds of Formula (I), X is CR⁷ and R⁷ is alkoxy. In one embodiment, the alkoxy is methoxy. In certain embodiments wherein X is CR⁷ and R⁷ is alkoxy, R¹ is alkoxy. In one embodiment, the R⁷ alkoxy is methoxy and the R¹ alkoxy is methoxy.

In certain embodiments for compounds of Formula (I) wherein X is N or CR⁷, Y is heteroarylene. In one embodiment, the heteroarylene is thiophenylene.

In certain embodiments for compounds of Formula (I) wherein X is N or CR⁷, Y is a bond.

In certain embodiments for compounds of Formula (I), R⁴ is aryl or heteroaryl, each optionally substituted with one or more R⁵. In one embodiment, R⁴ is aryl optionally substituted with one or more R⁵. In one embodiment, the aryl is phenyl optionally substituted with one or more R⁵. In certain embodiments, the phenyl is substituted with one R⁵, wherein R⁵ is C1-C4 alkyl, haloalkyl or -L-N(R⁶)₂.

In one embodiment, R⁵ is -L-N(R⁶)₂, wherein L is methylene and one R⁶ is hydrogen and the second R⁶ is C1-C3 alkyl. In one embodiment, the C1-C3 alkyl is methyl. In another embodiment, R⁵ is -L-N(R⁶)₂, wherein L is methylene and each R⁶ is C1-C3 alkyl. In one embodiment, each of the C1-C3 alkyl is methyl.

In certain embodiments wherein R⁴ is aryl, R⁴ is phenyl substituted with two R⁵, wherein one R⁵ is C1-C4 alkyl and the second R⁵ is haloalkyl. In one embodiment, the C1-C4 alkyl is methyl and the haloalkyl is trifluoromethyl. In certain embodiments, R⁴ is phenyl substituted with two R⁵, wherein one R⁵ is C1-C4 alkyl and the second R⁵ is -L-N(R⁶)₂. In one embodiment, L is methylene and each R⁶ is C1-C3 alkyl.

In one embodiment for compounds of Formula (I), R³ is hydrogen.

In certain embodiments for compounds of Formula (I), R³ is C1-C6 alkyl optionally substituted with one or more R⁹. In one embodiment, the C1-C6 alkyl is methyl, ethyl or isopropyl.

In certain embodiments for compounds of Formula (I), R³ is alkoxy. In one embodiment, the alkoxy is methoxy.

In certain embodiments for compounds of Formula (I), R³ is haloalkyl. In one embodiment, the haloalkyl is trifluoromethyl.

In certain embodiments for compounds of Formula (I), R³ is cycloalkyl optionally substituted with one or more R⁹. In one embodiment, the cycloalkyl is cyclopropyl. In one embodiment, the cycloalkyl is substituted with one R⁹, wherein the one R⁹ is halogen amino, hydroxyl or alkoxy.

In certain embodiments for compounds of Formula (I), R³ is —N(R¹⁰)₂. In one embodiment, each R¹⁰ is C1-C3 alkyl. In certain embodiments, each C1-C3 alkyl is methyl.

In certain embodiments for compounds of Formula (I), R³ is -L-N(R¹⁰)₂. In one embodiment, each R¹⁰ is C1-C3 alkyl. In certain embodiments, each C1-C3 alkyl is methyl.

In certain embodiments for compounds of Formula (I), R³ is heterocyclyl, aryl, or heteroaryl, wherein the heterocyclyl, the aryl, and the heteroaryl are each optionally substituted with one or more R⁹.

In certain embodiments for compounds of Formula (I), R⁸ is C1-C2 alkyl. In one embodiment, the C1-C2 alkyl is methyl.

In certain embodiments for compounds of Formula (I), R⁸ is haloC1-C2 alkyl. In one embodiment, the haloC1-C2 alkyl is fluoromethyl, difluoromethyl or trifluoromethyl.

In one embodiment, the compound of Formula (I) is:

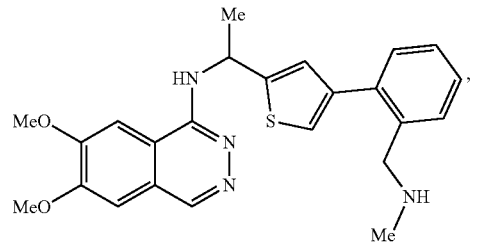

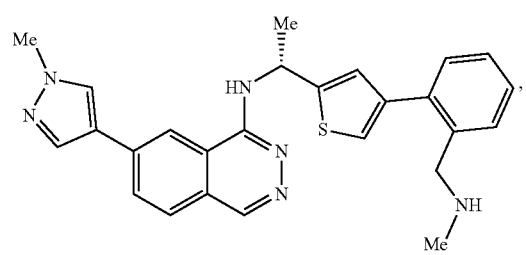

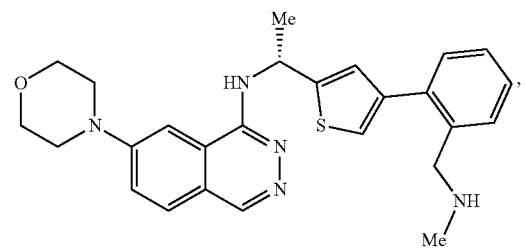

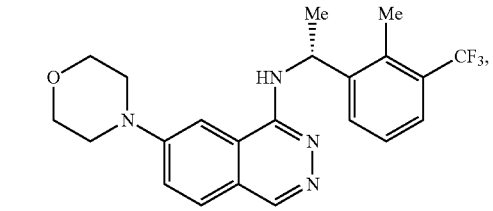

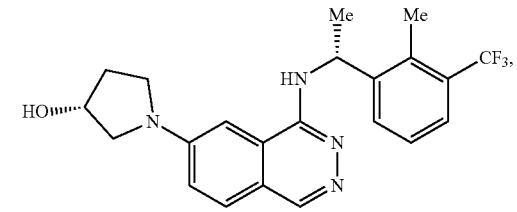

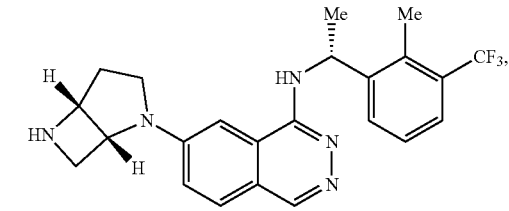

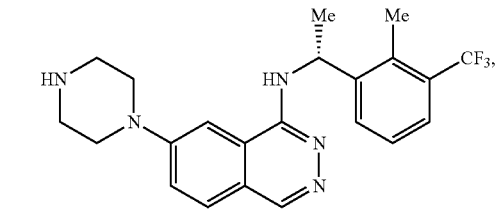

-continued
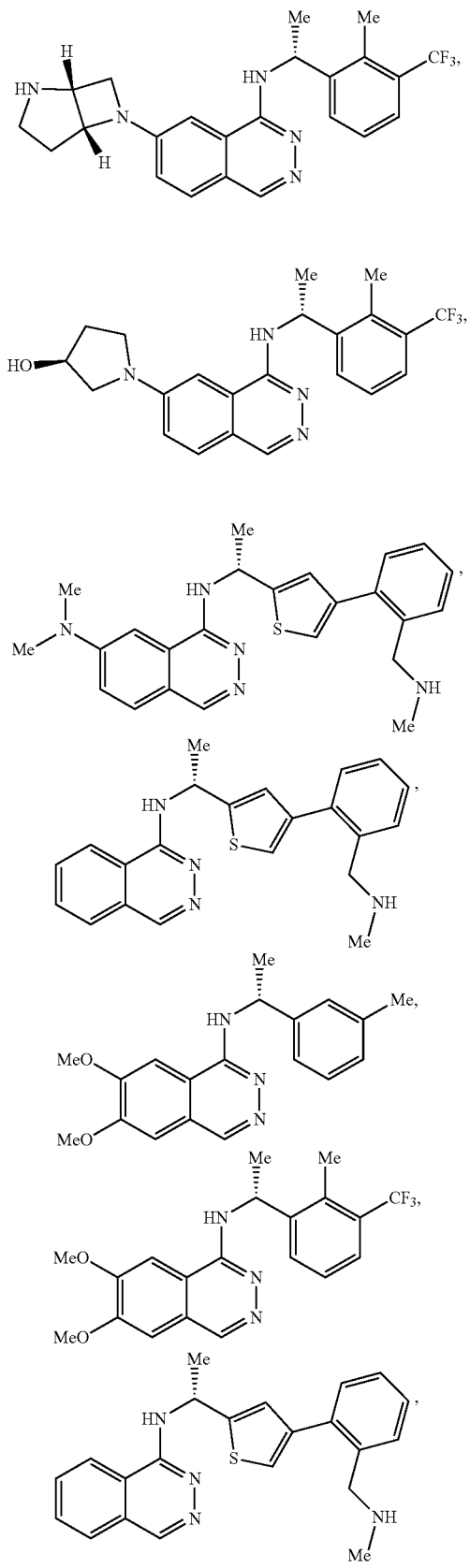
-continued
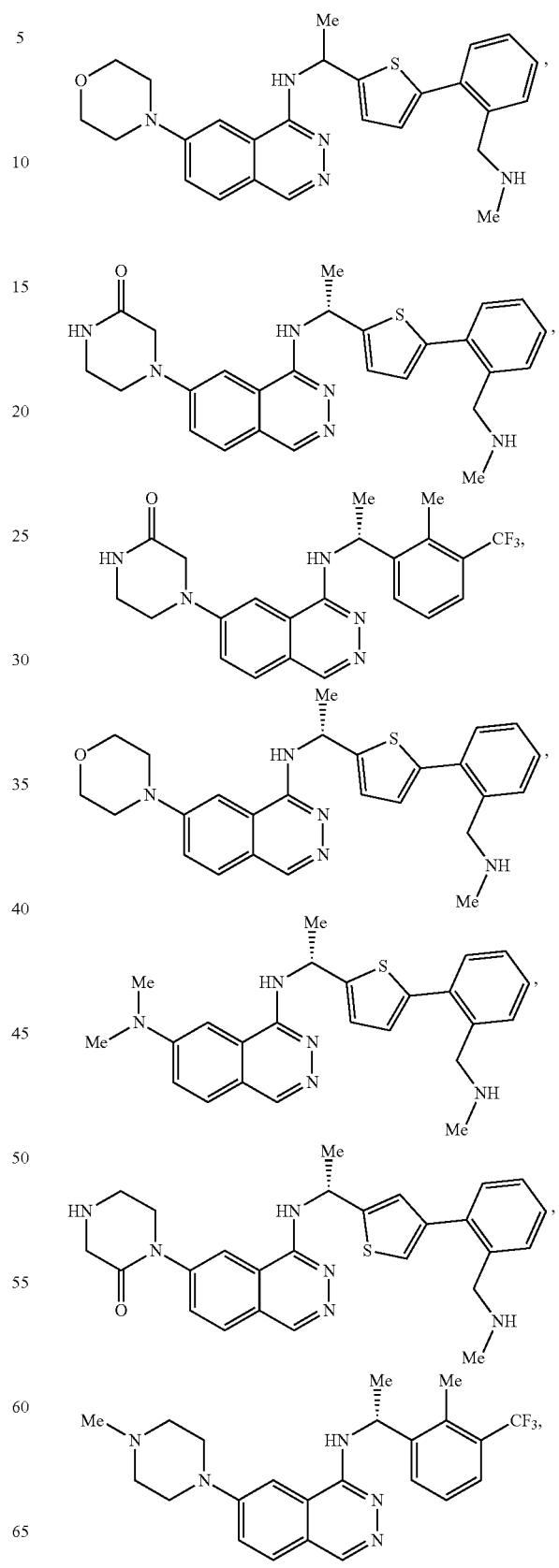

-continued
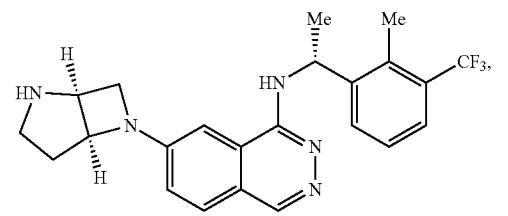
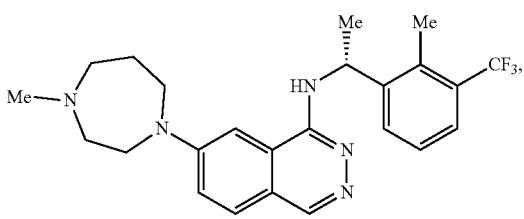
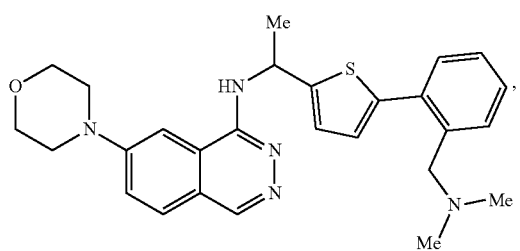
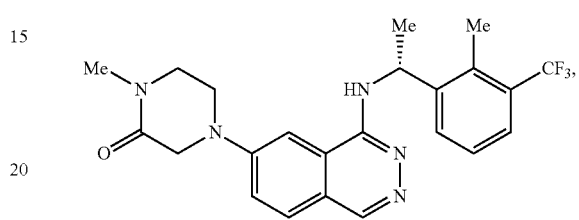
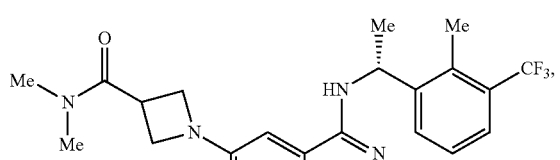
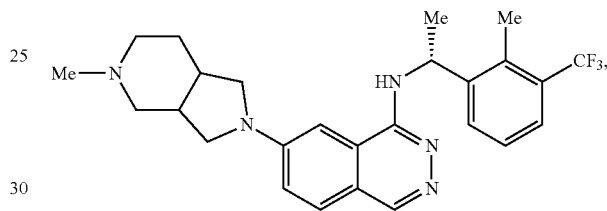
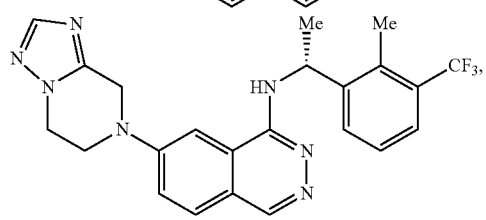
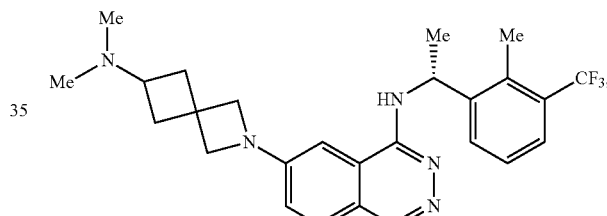
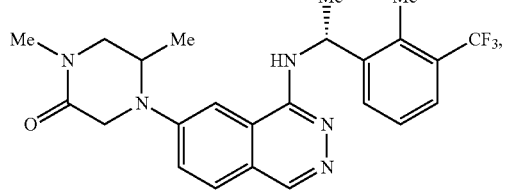
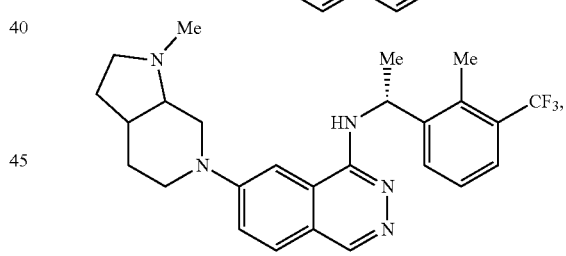
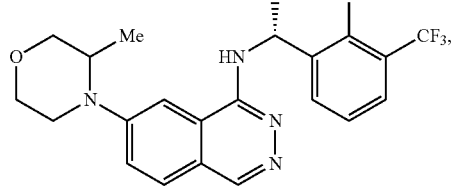
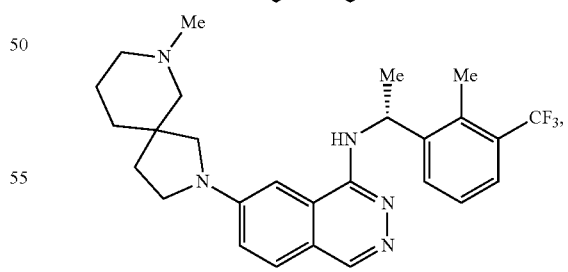
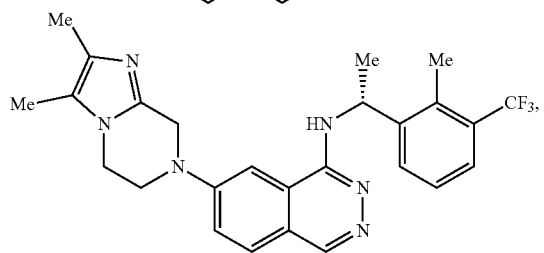
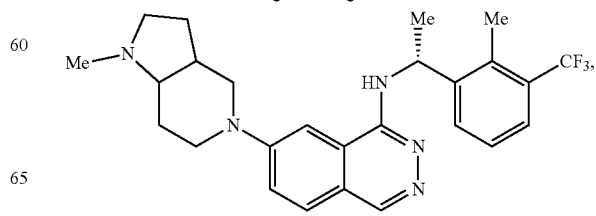

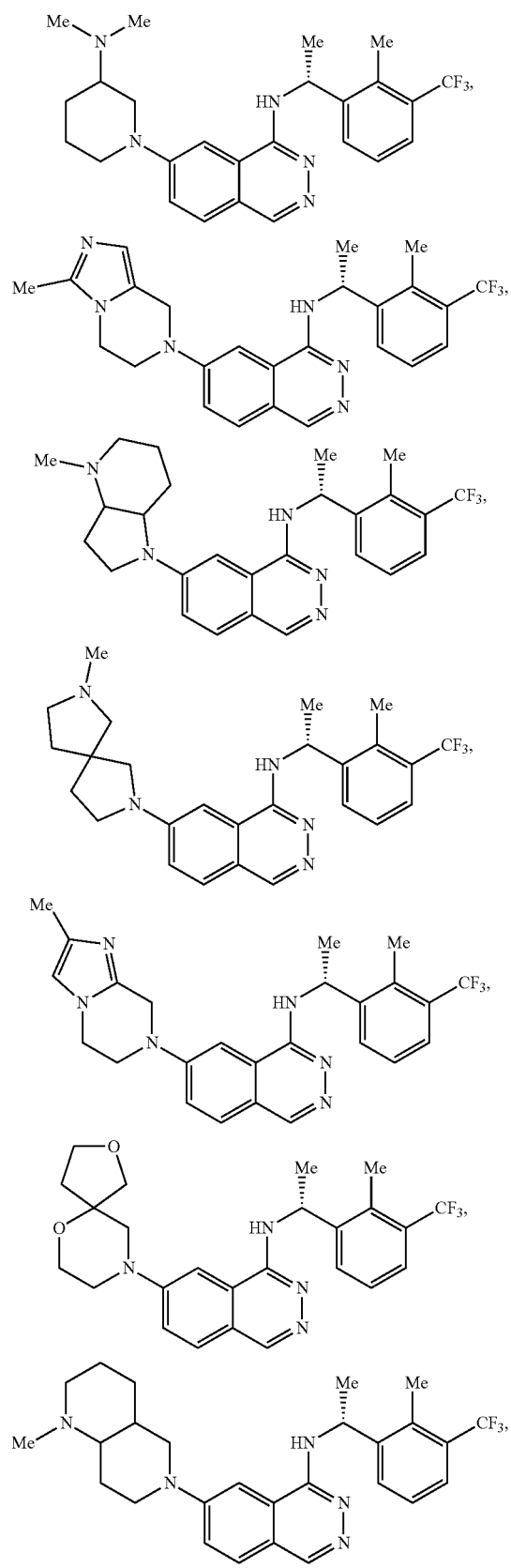
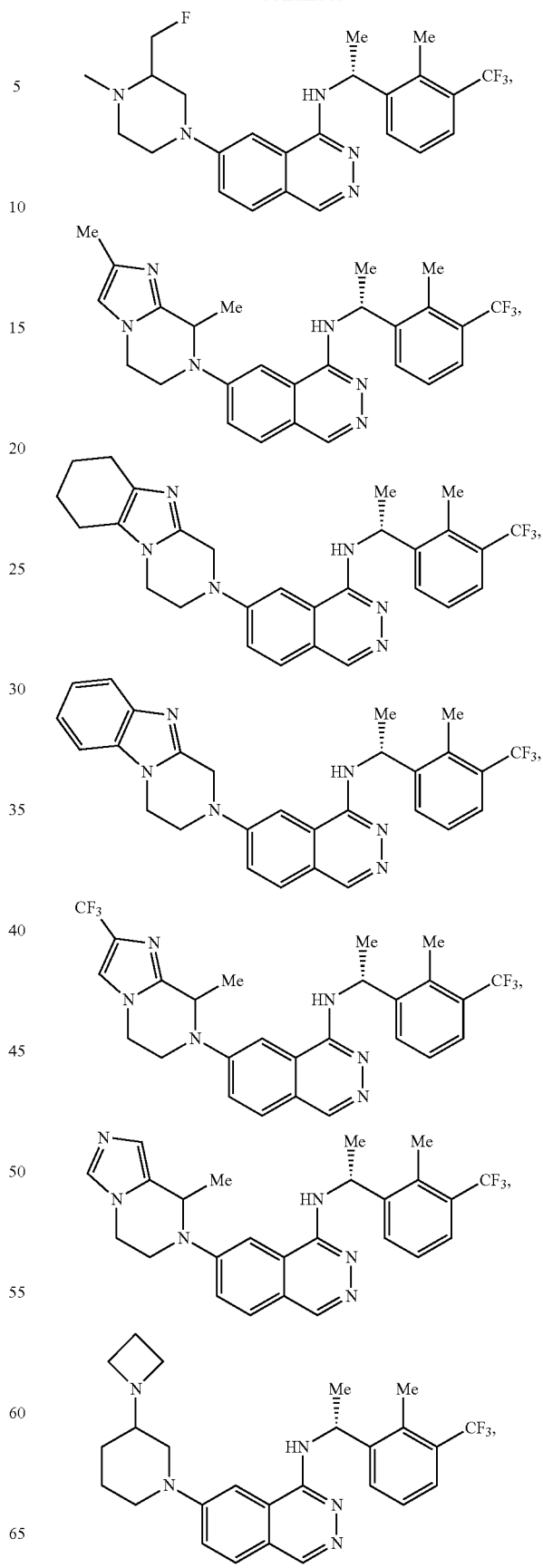

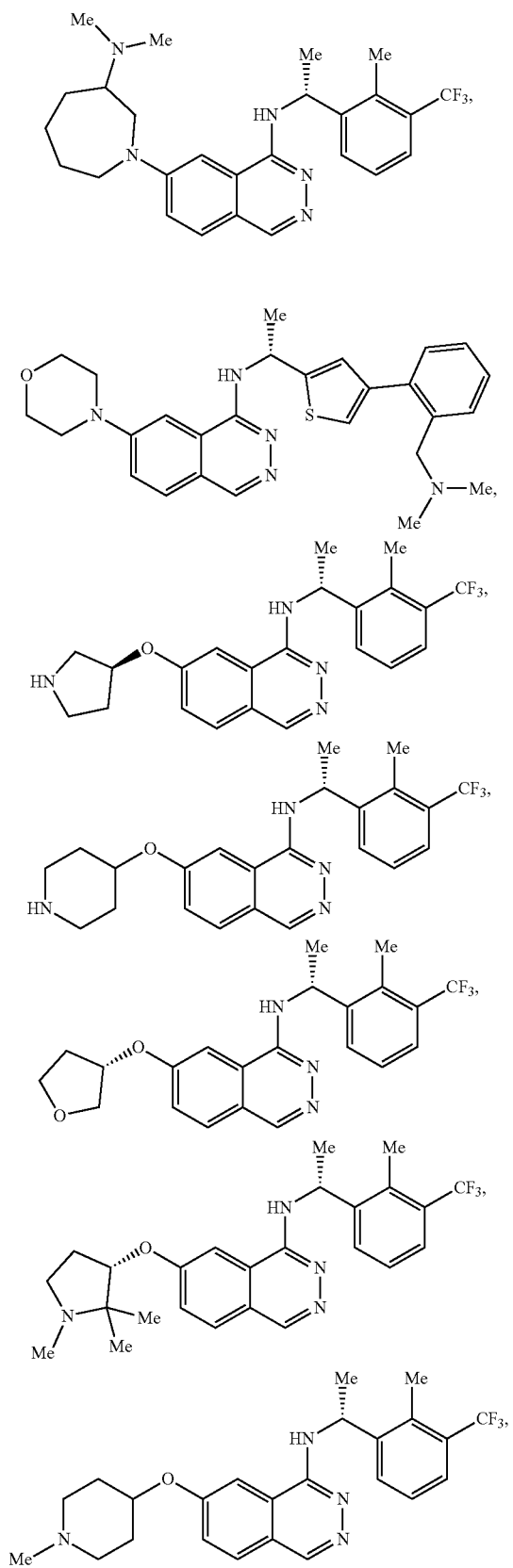
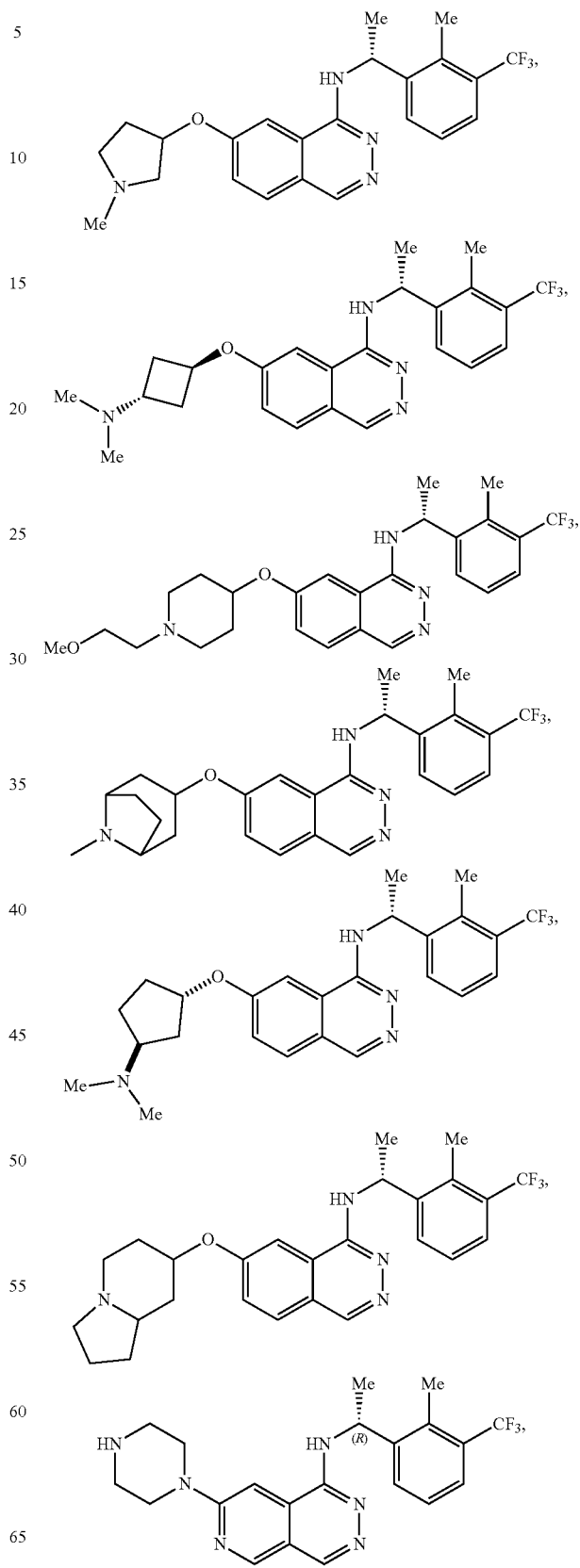

-continued
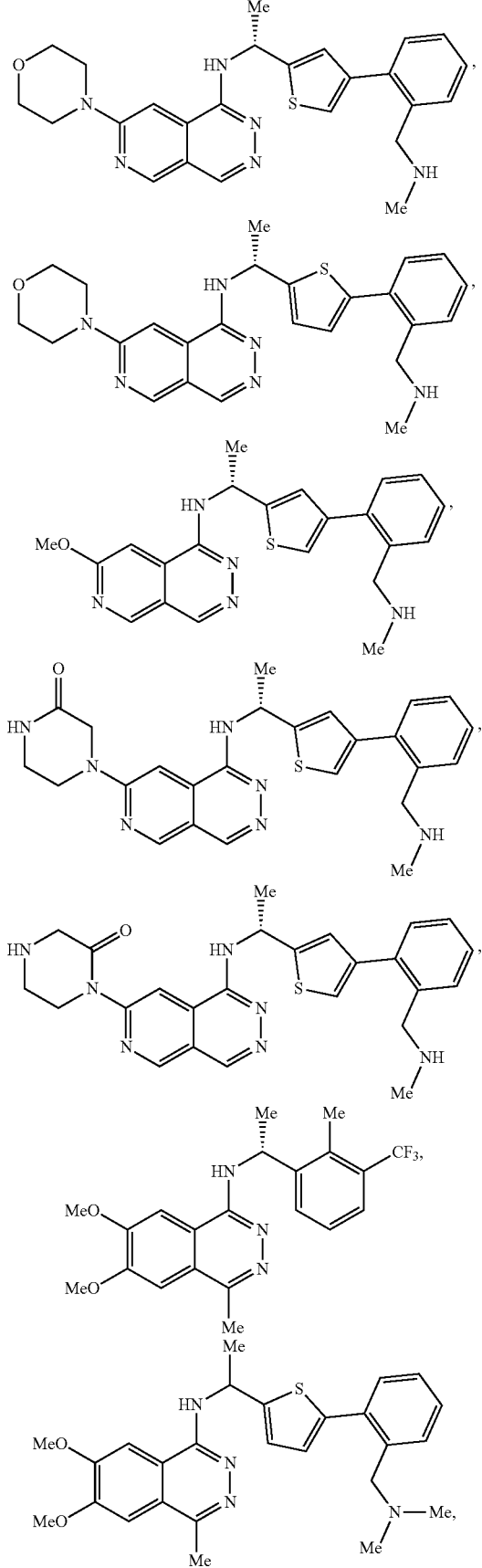
-continued
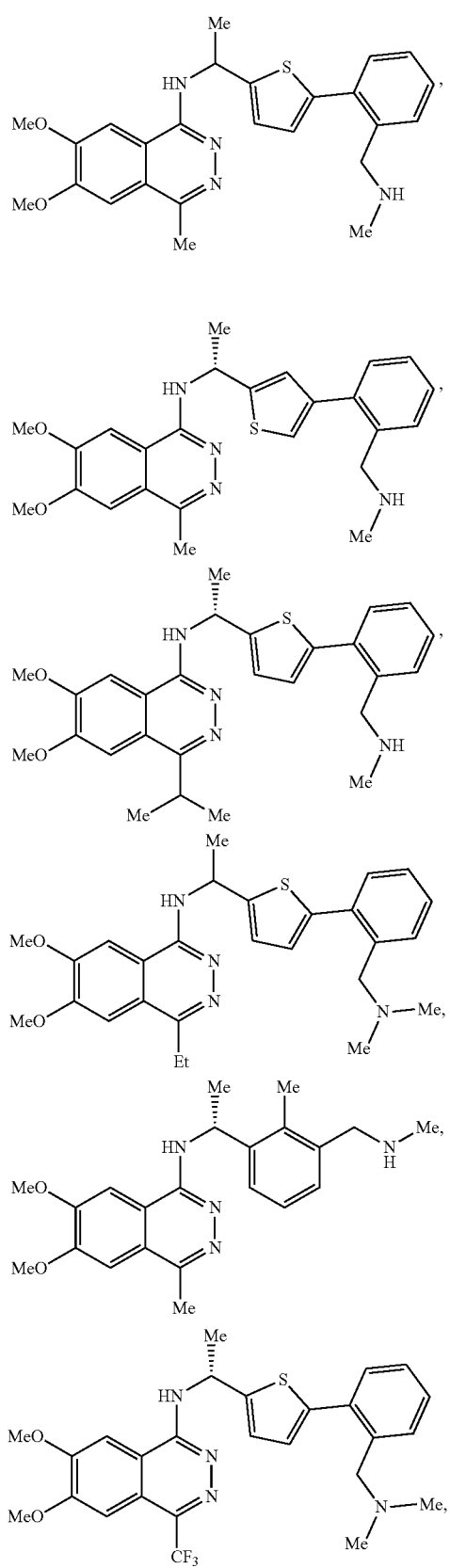

-continued
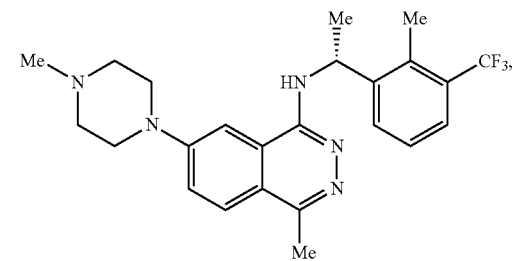
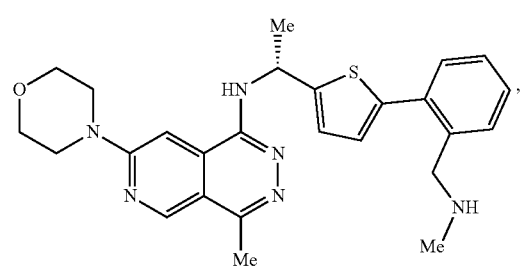
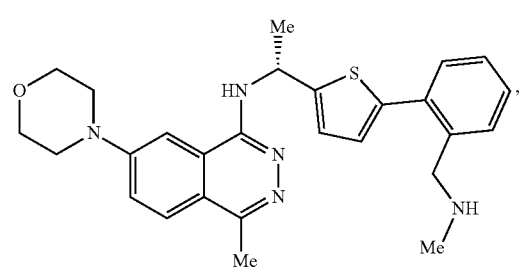
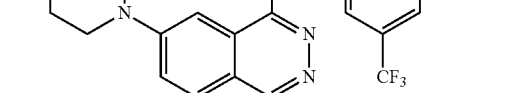
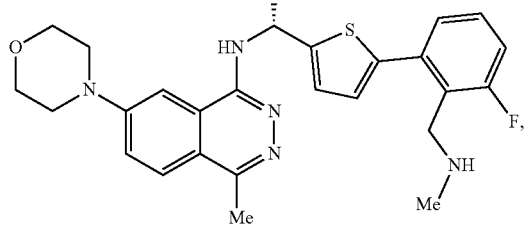
-continued
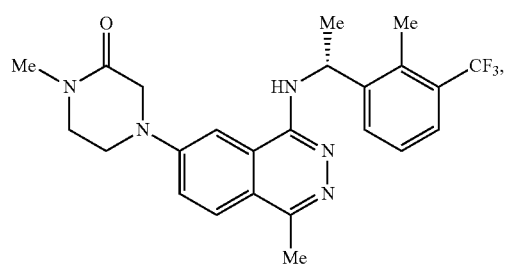
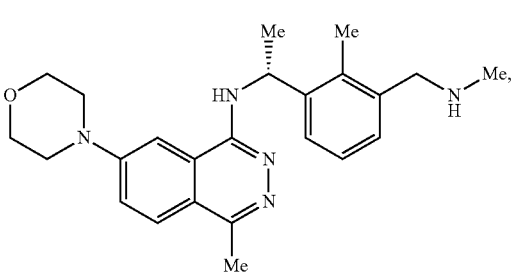
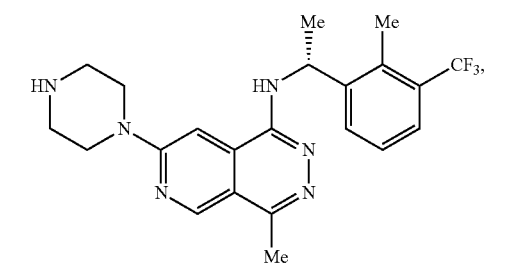
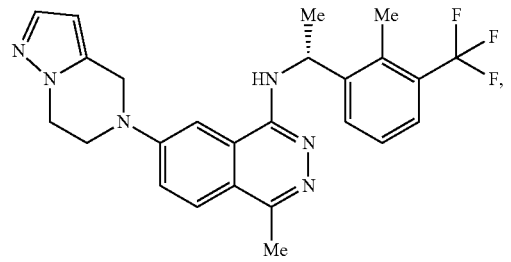
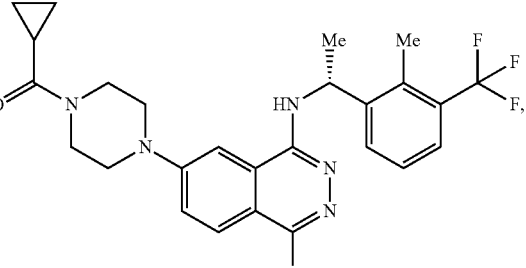
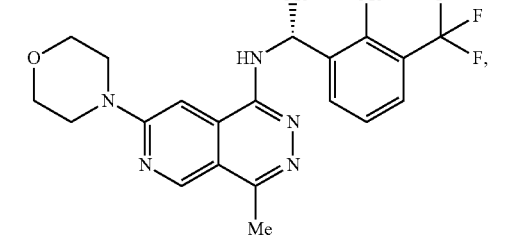

-continued
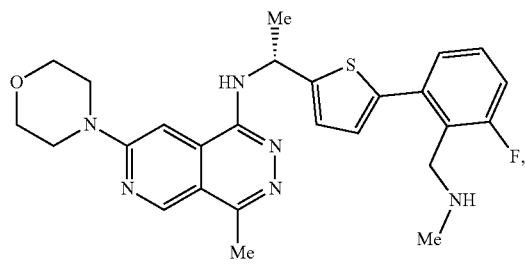
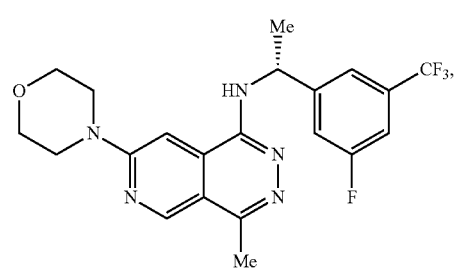
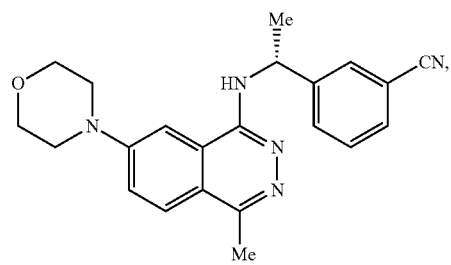
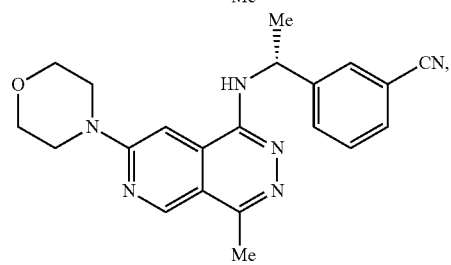
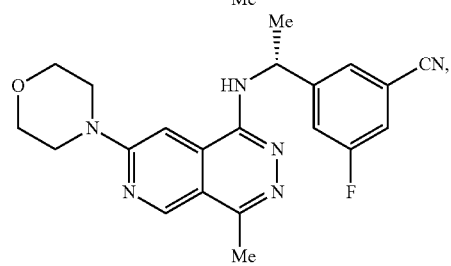
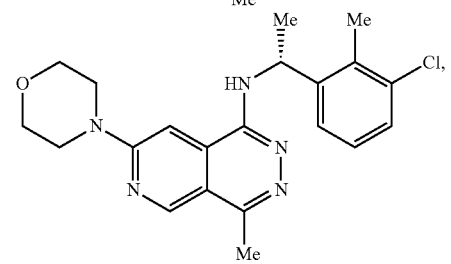
-continued
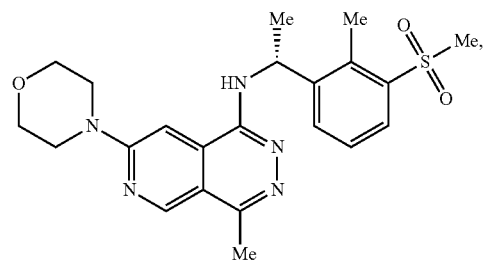
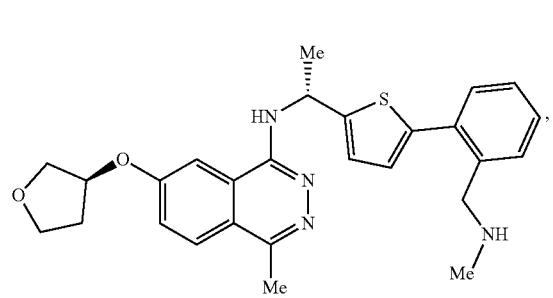
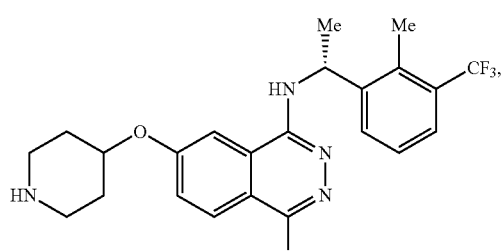
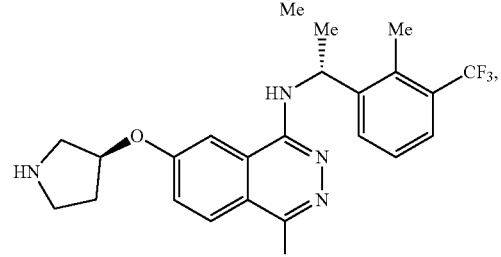
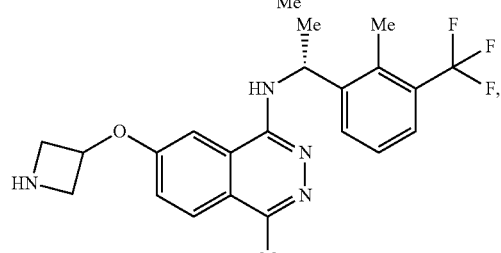
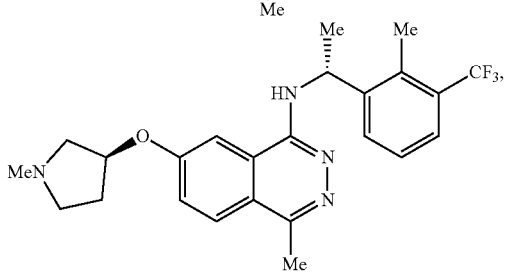

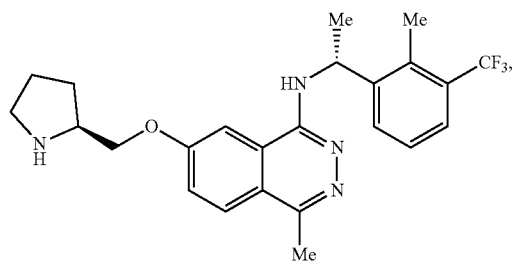
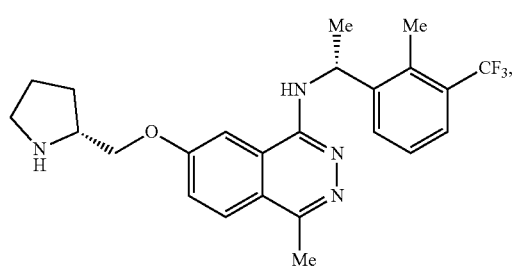
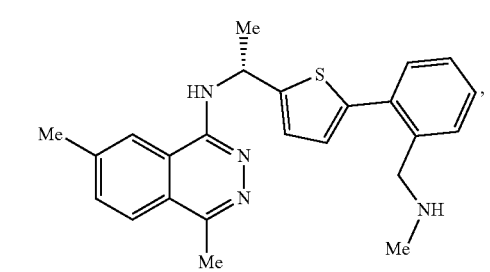
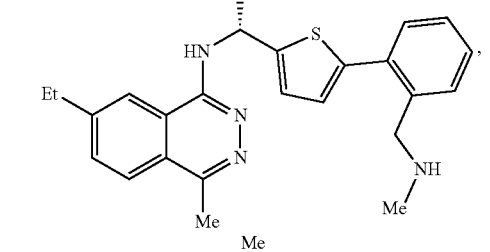
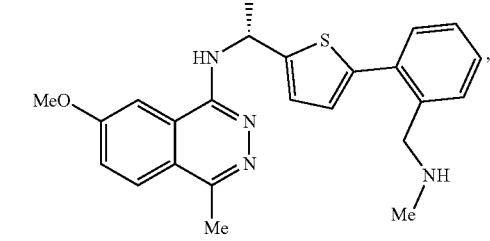
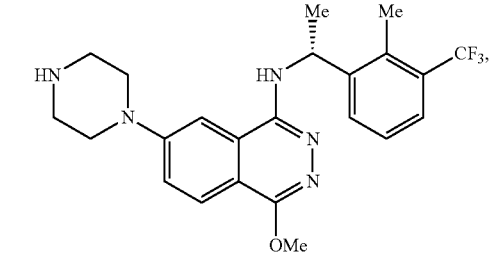
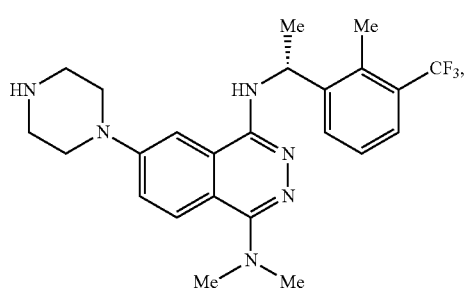
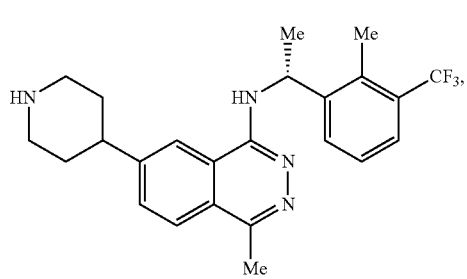
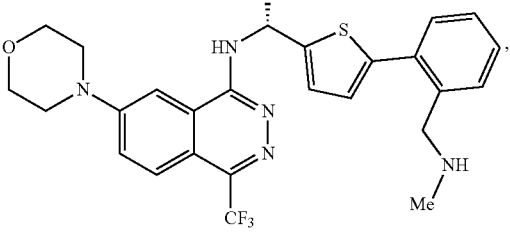
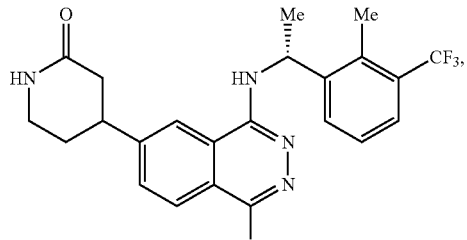
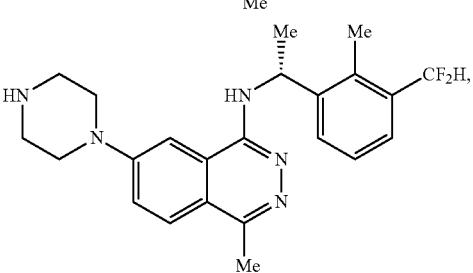
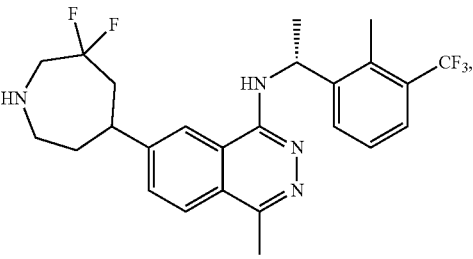

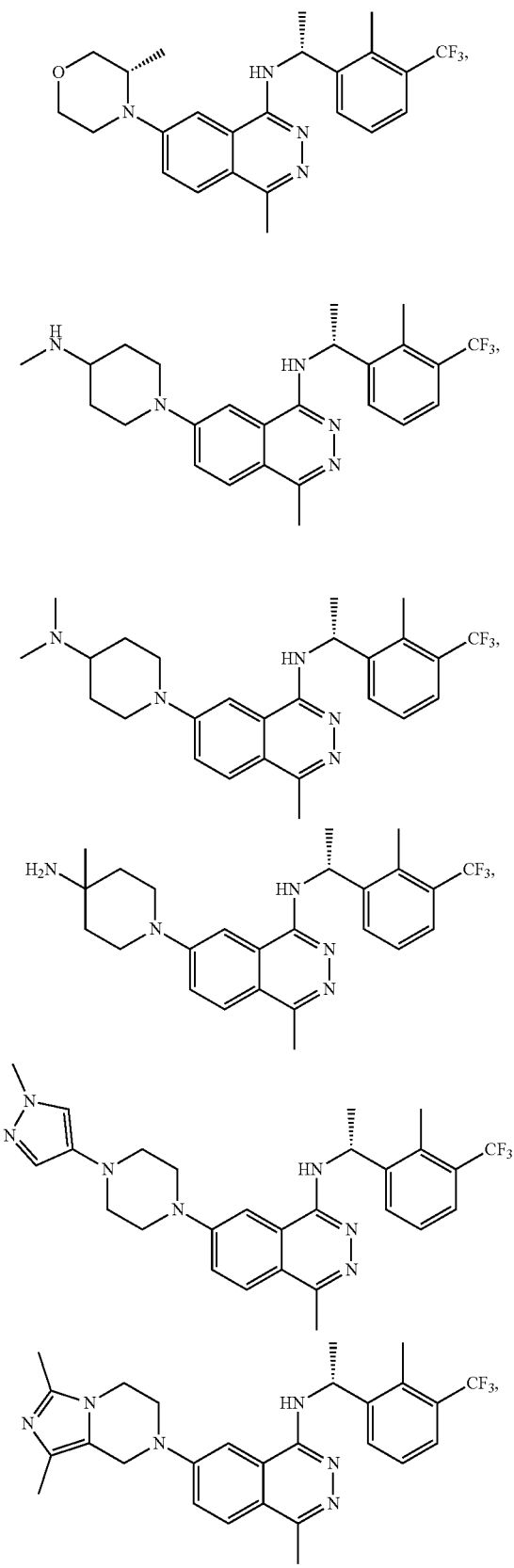
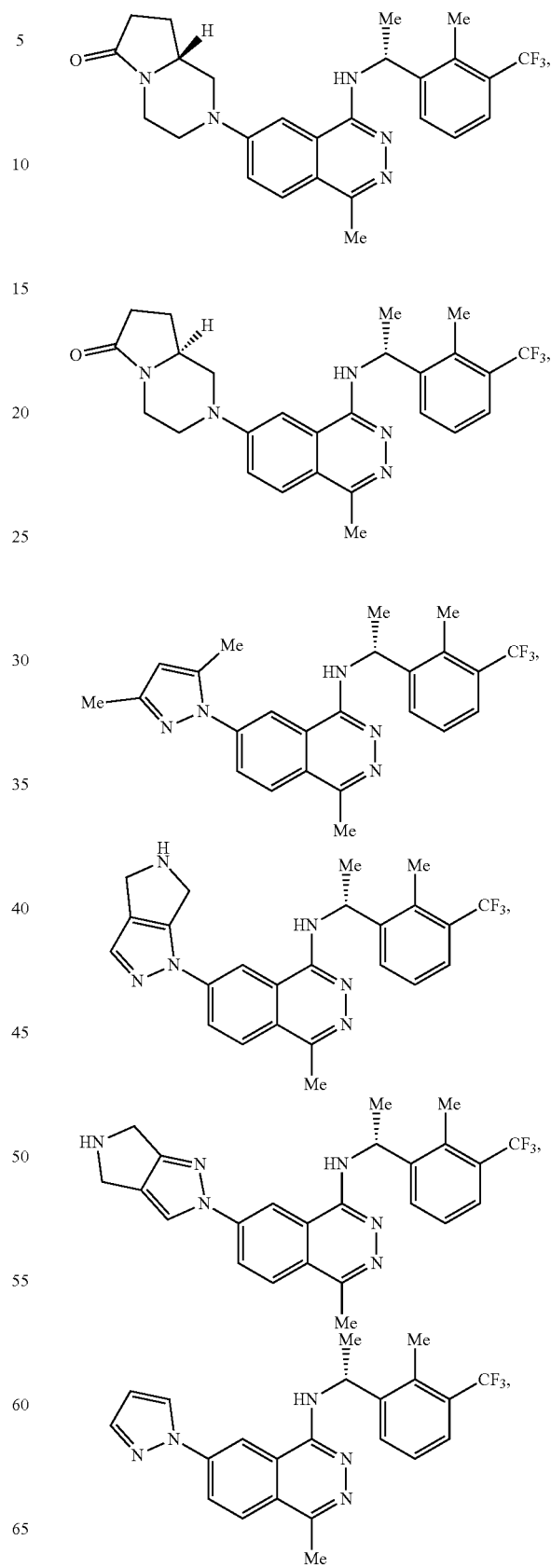

35
-continued
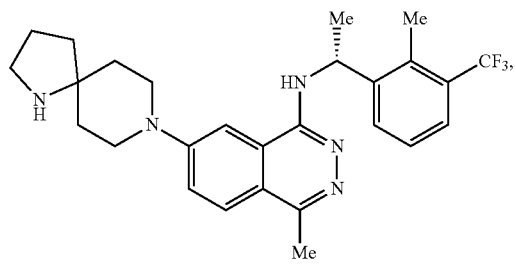
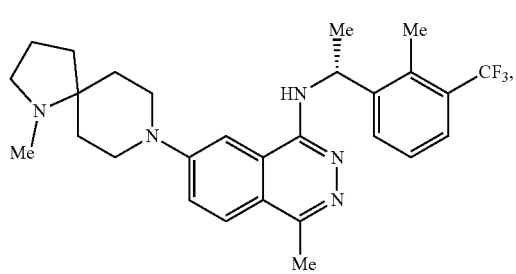
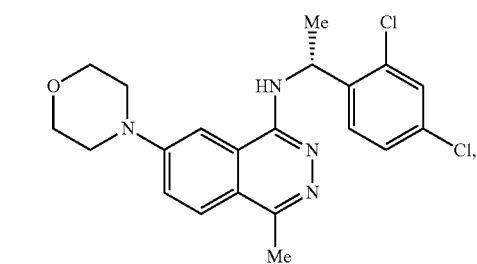
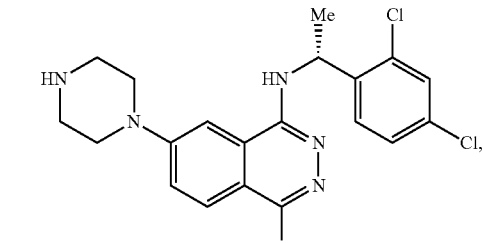
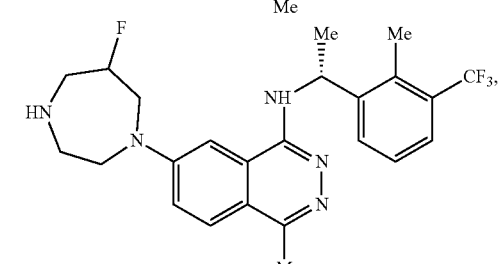
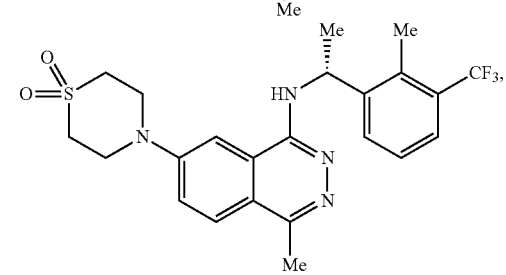
36
-continued
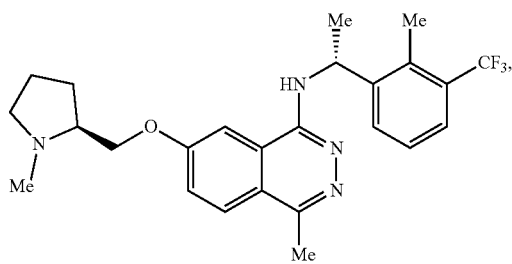
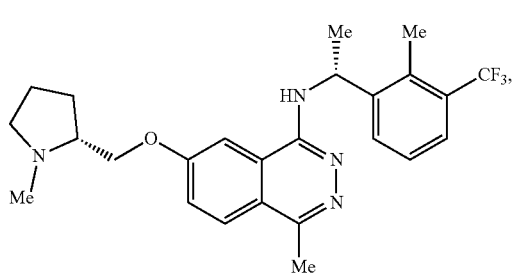
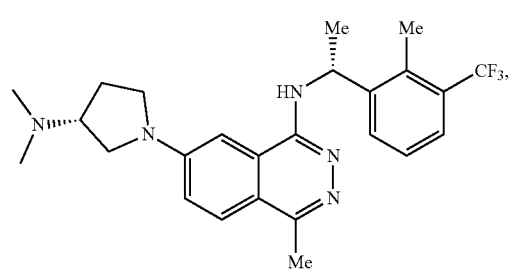
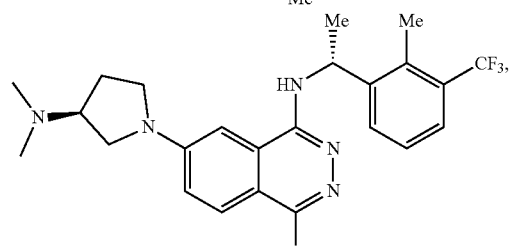
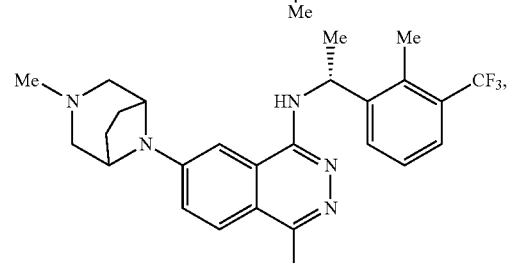
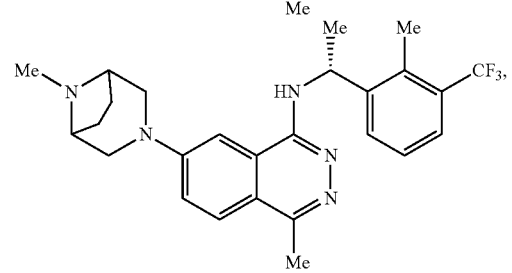

-continued
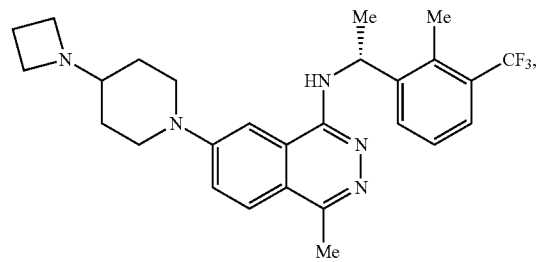
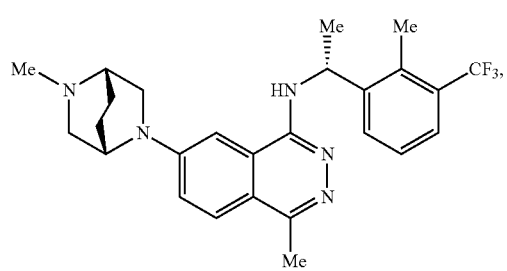
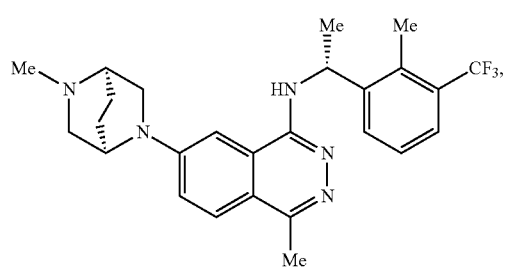
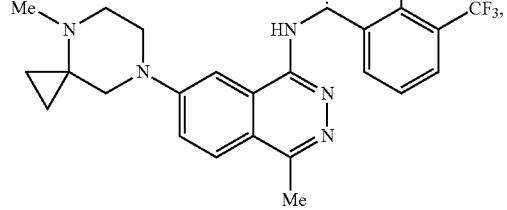
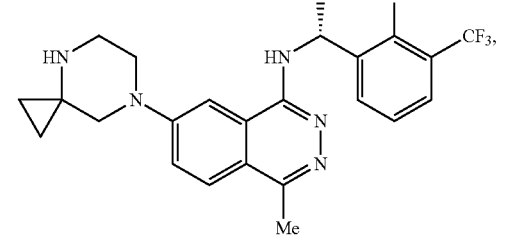
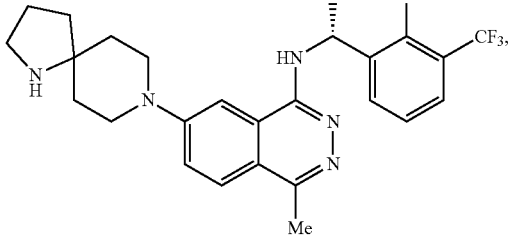
-continued
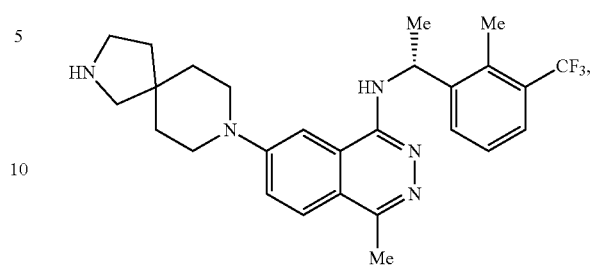
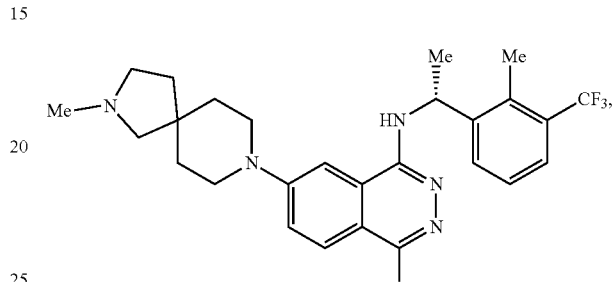
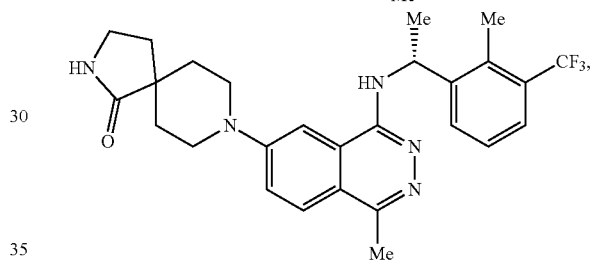
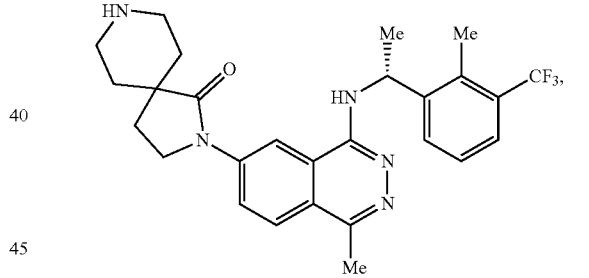
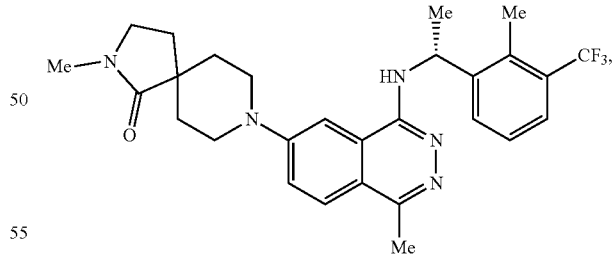
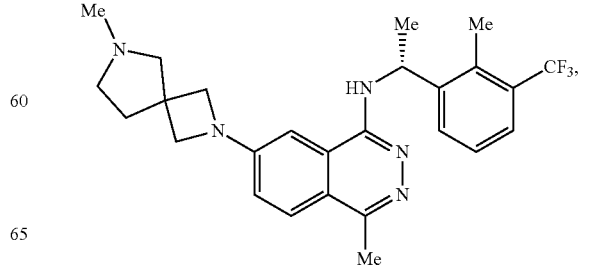

-continued
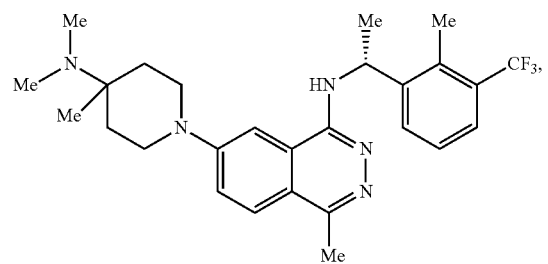
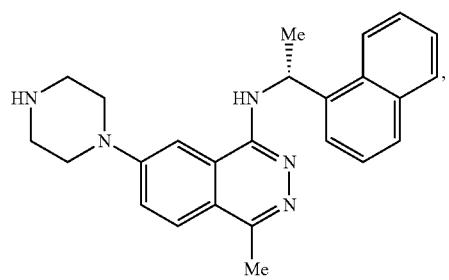
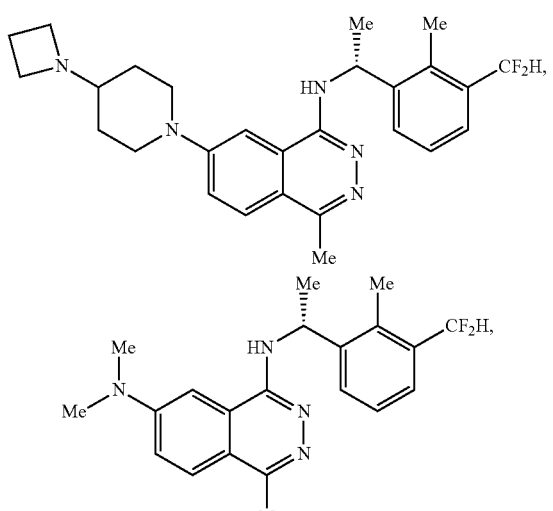
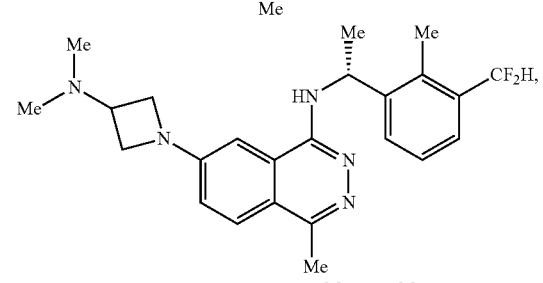
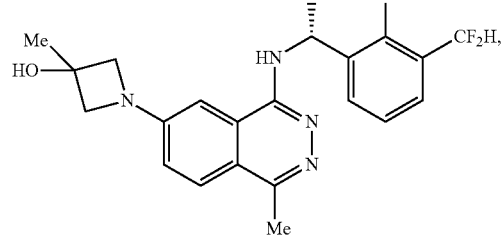
-continued
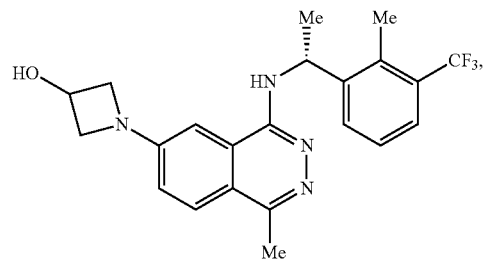
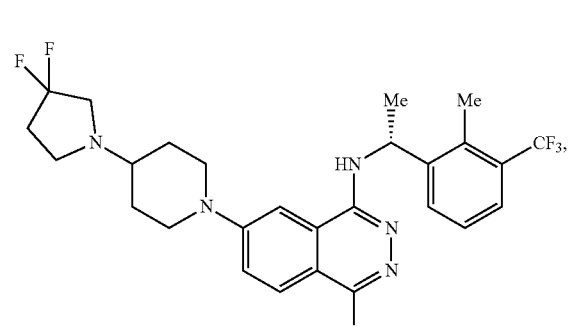
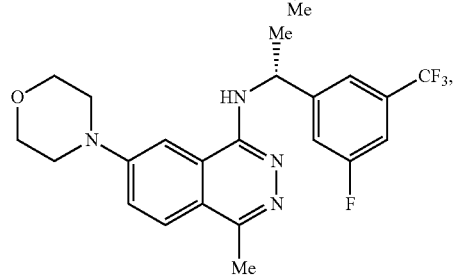
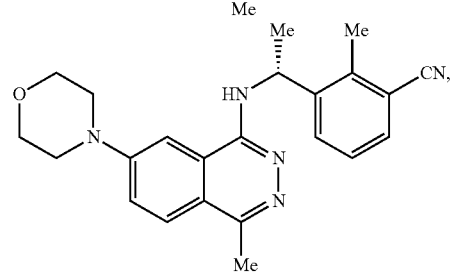
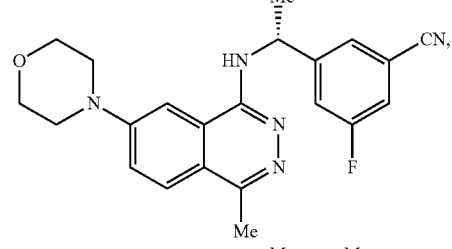
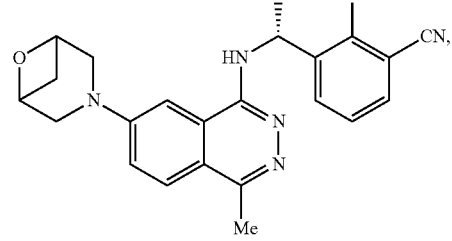

41
-continued
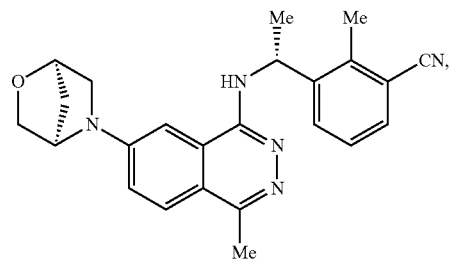
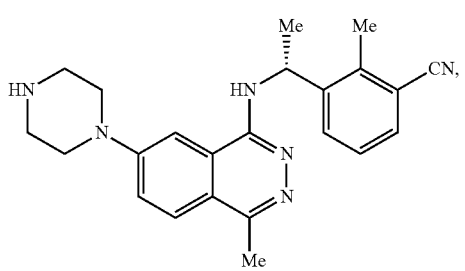
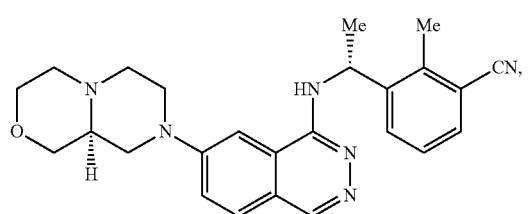
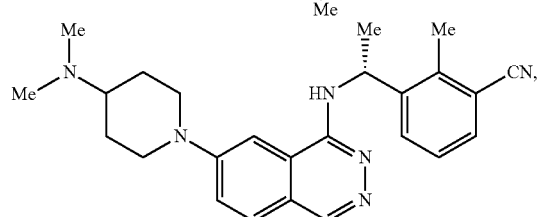
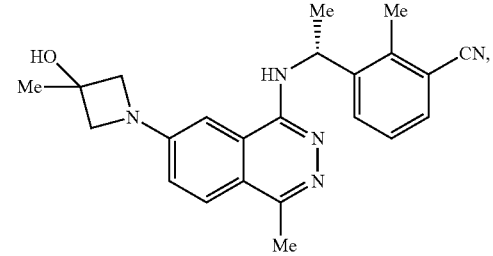
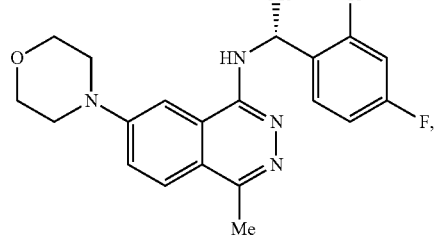
42
-continued
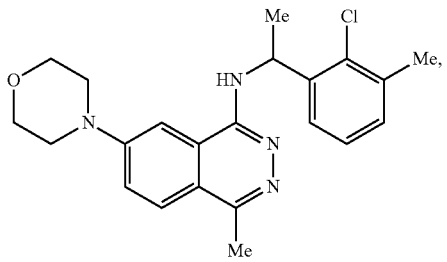
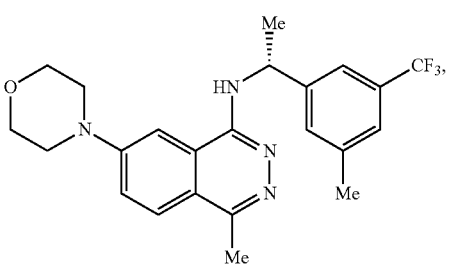
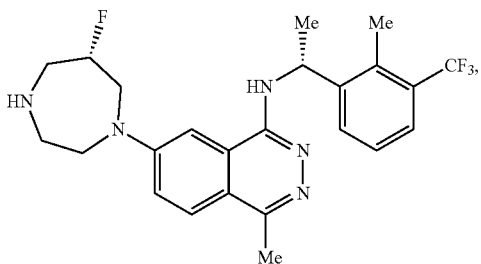
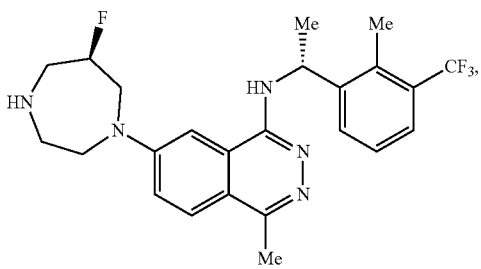
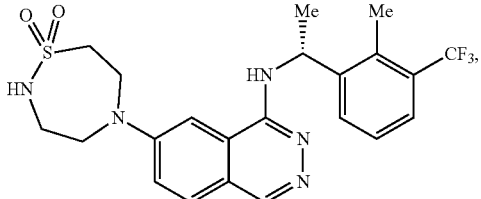
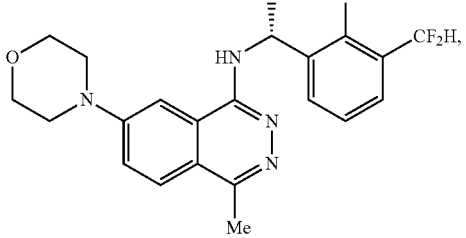

-continued
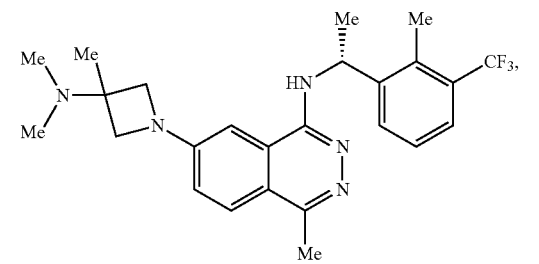
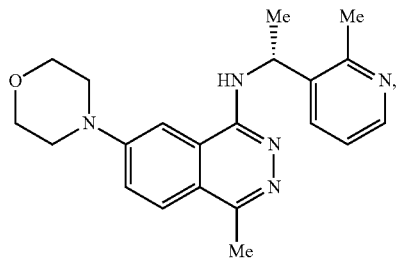

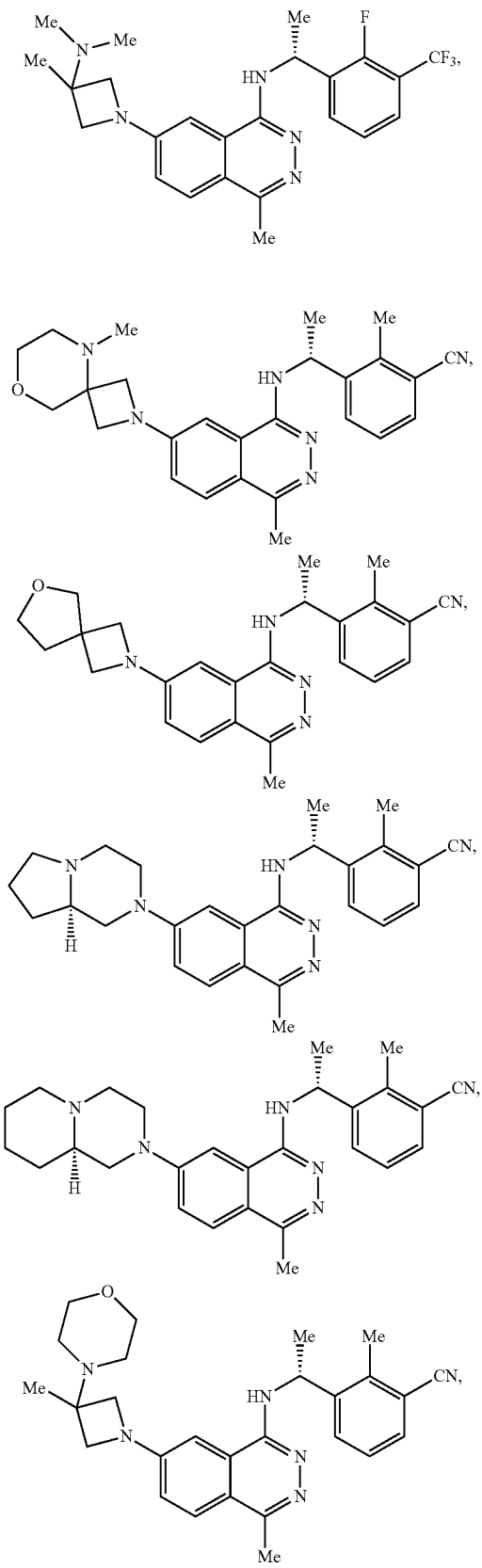
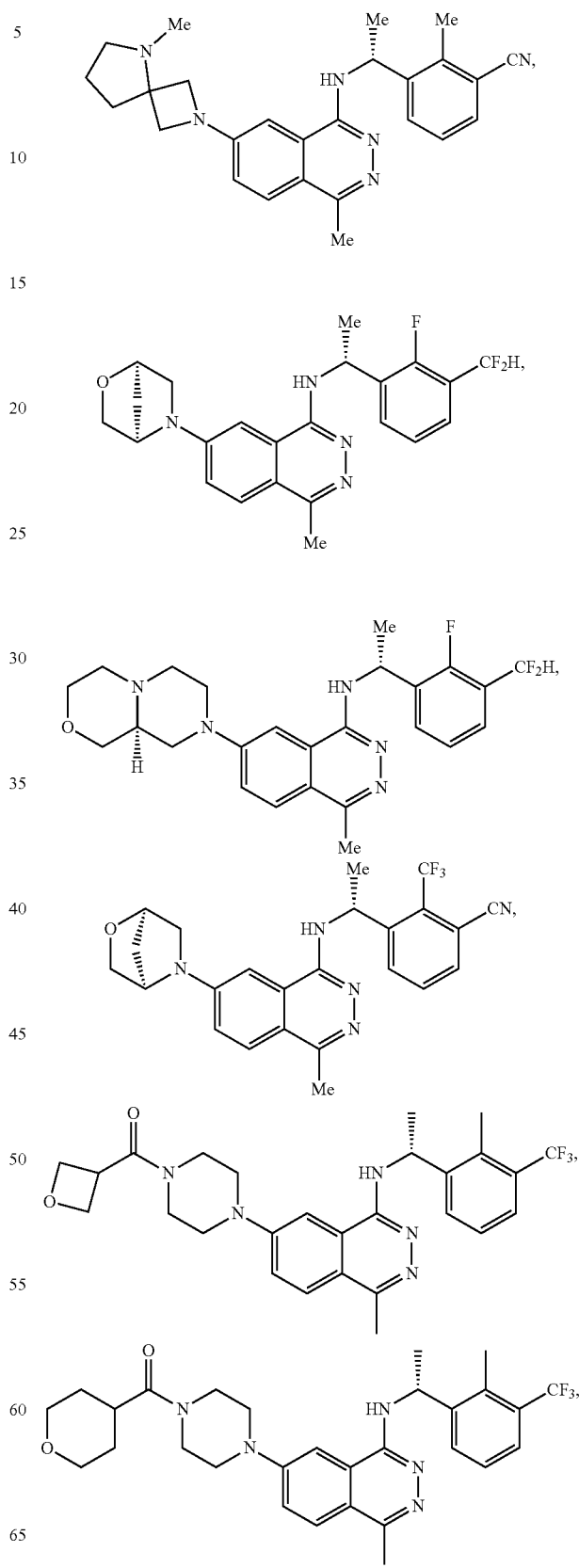

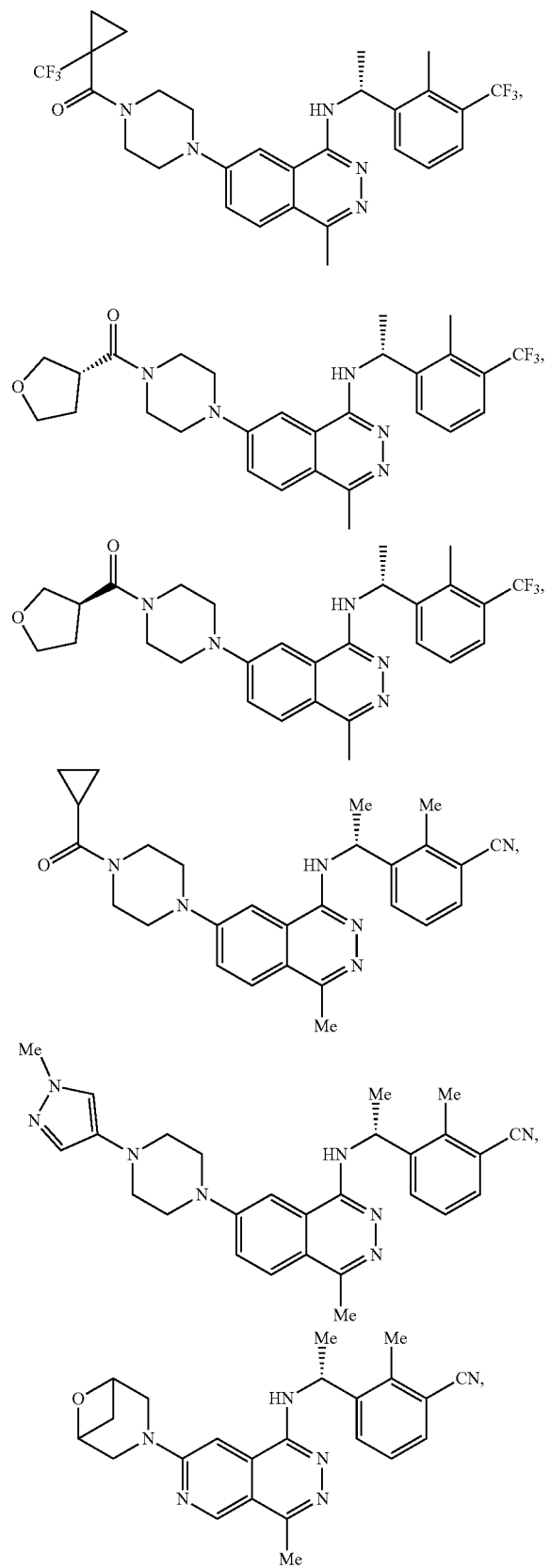
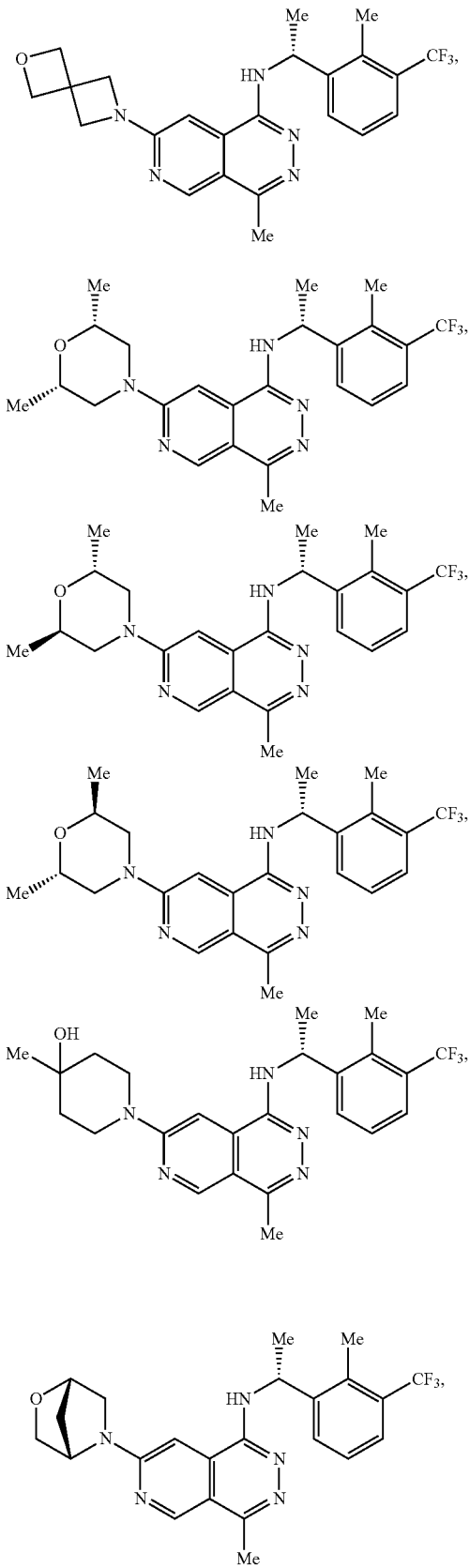

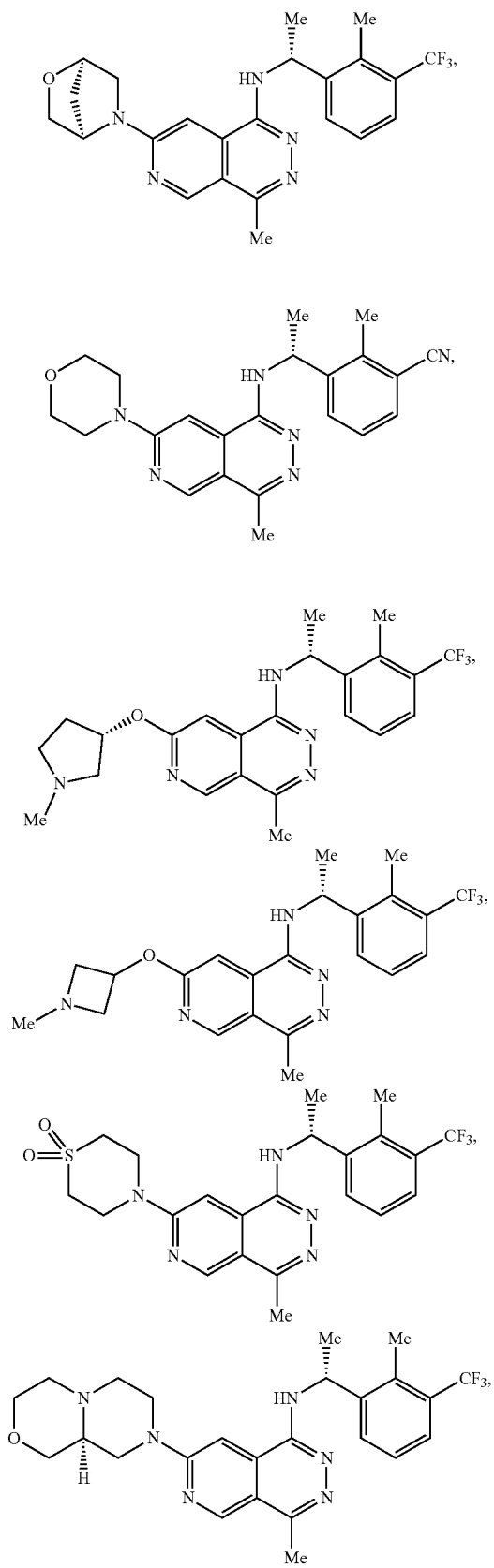
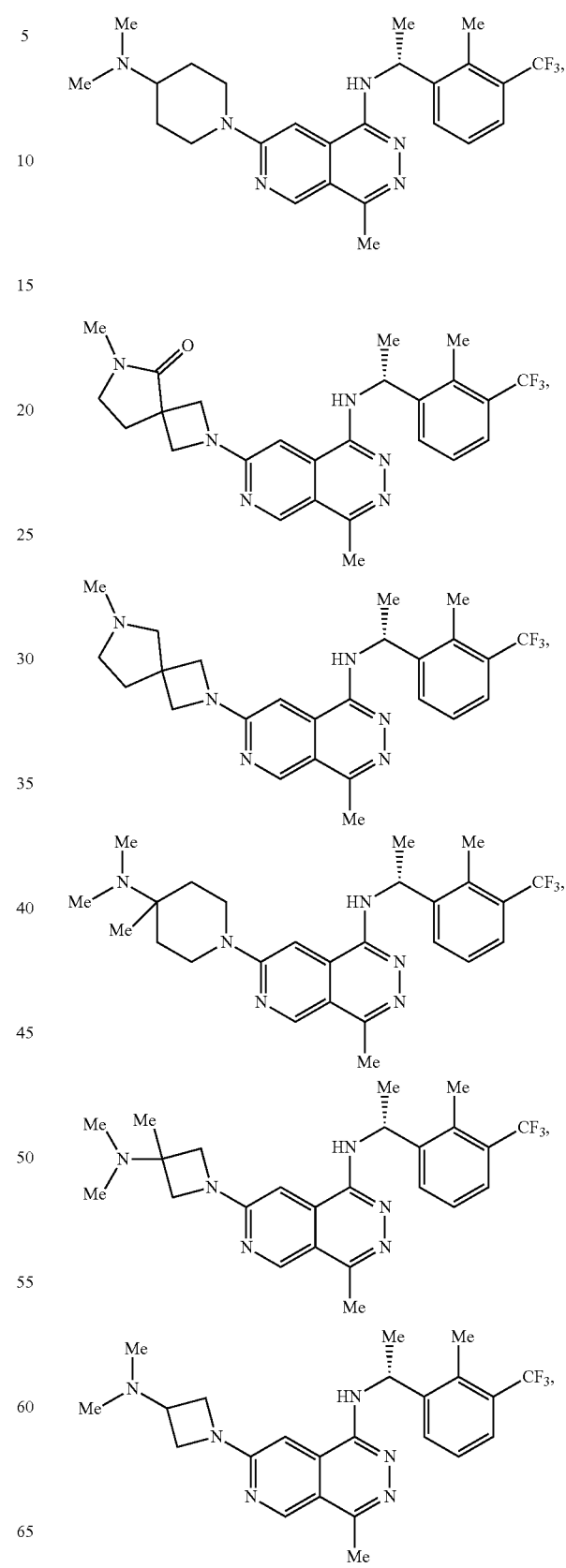

51
-continued
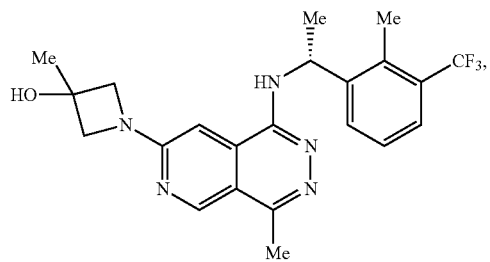
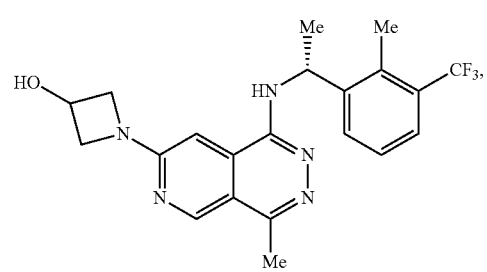
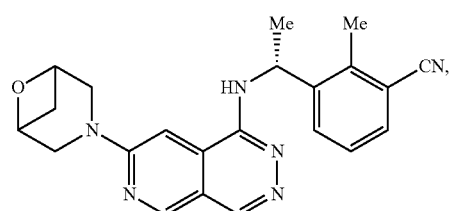
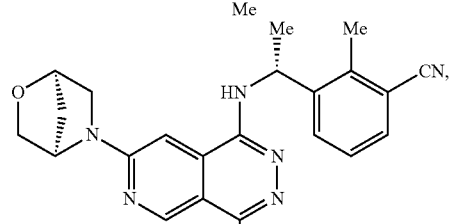
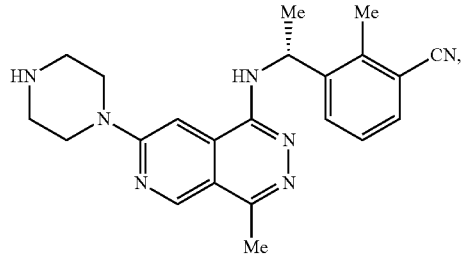
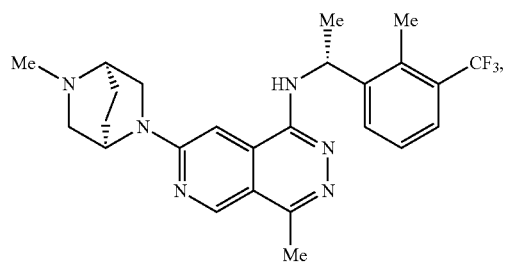
52
-continued
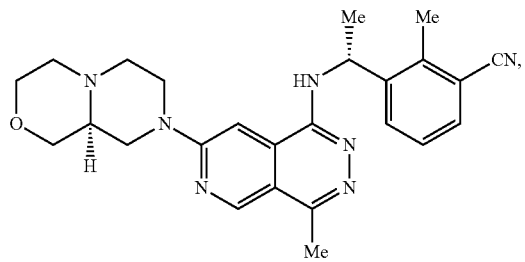
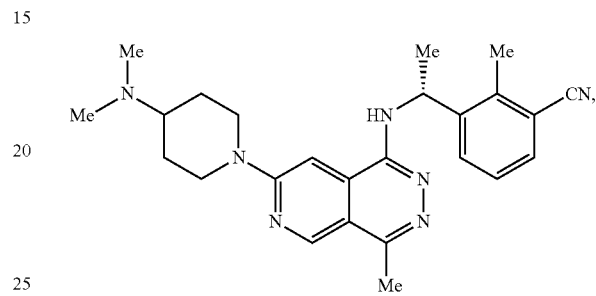
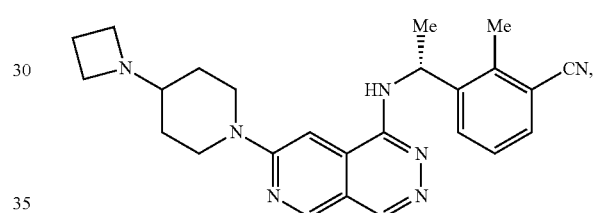
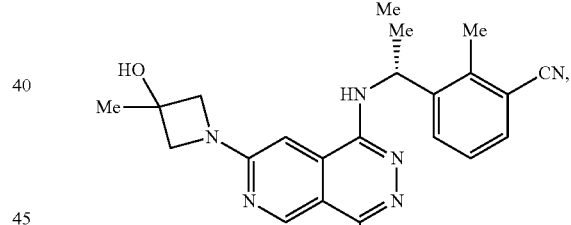
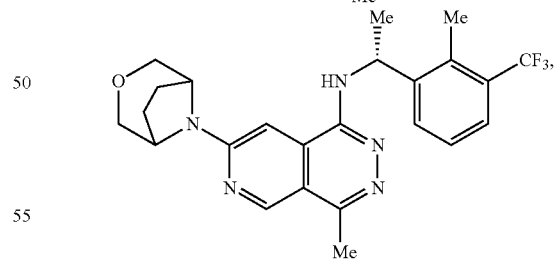
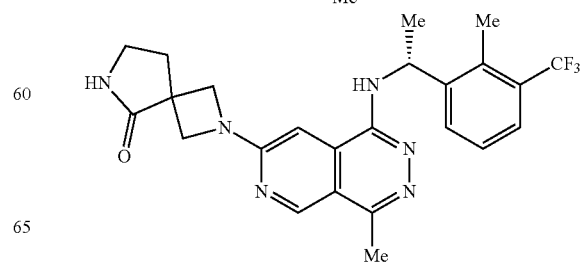

53
-continued

54
-continued

55
-continued
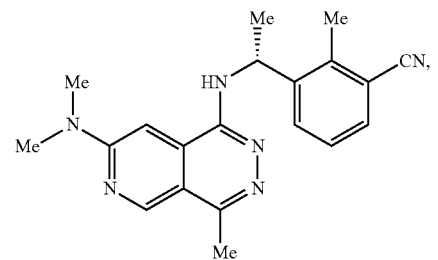
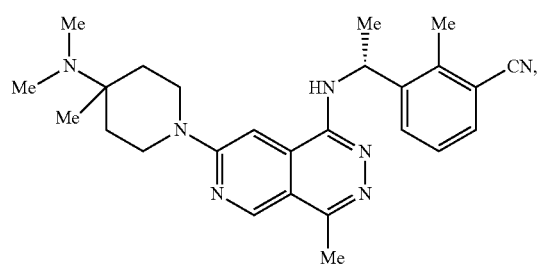
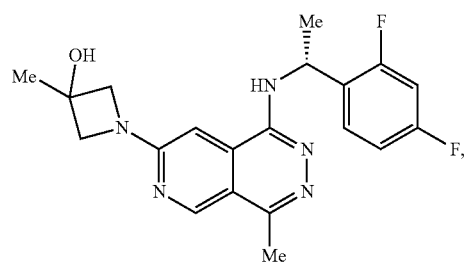
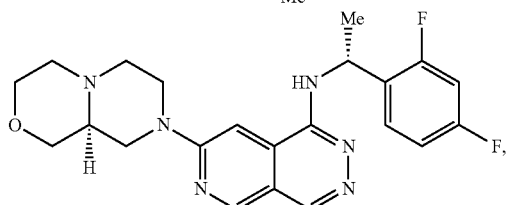
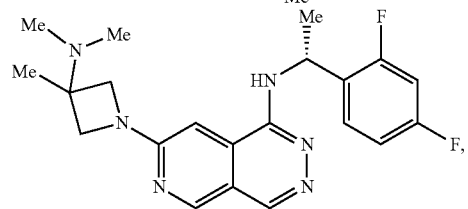
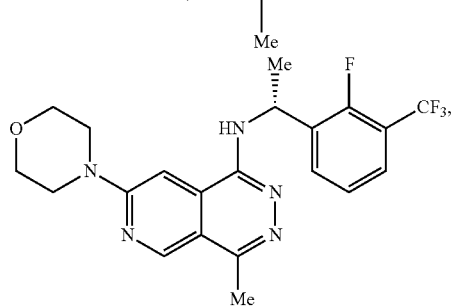
56
-continued
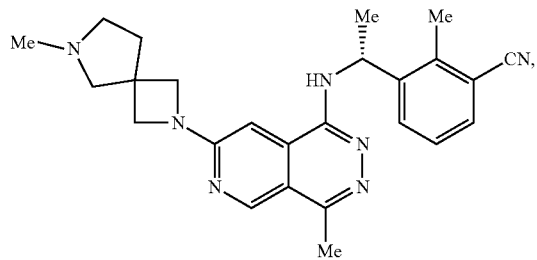
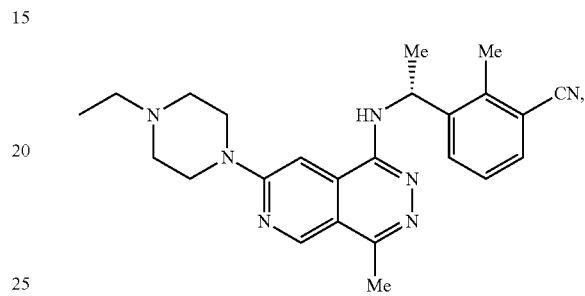
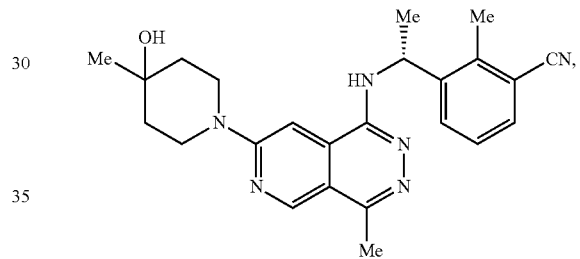
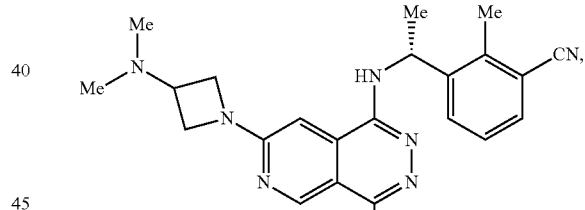
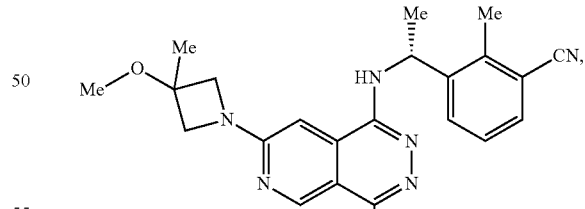
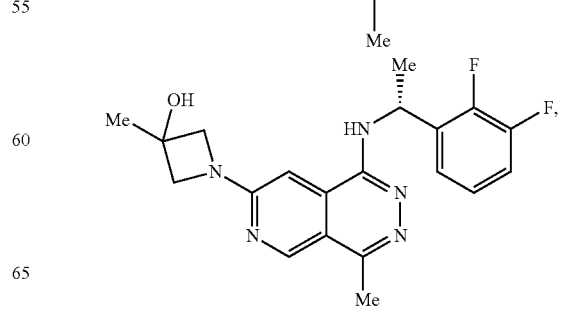

57
-continued
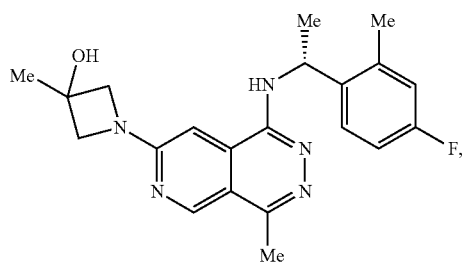
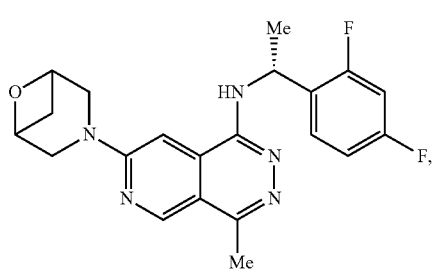
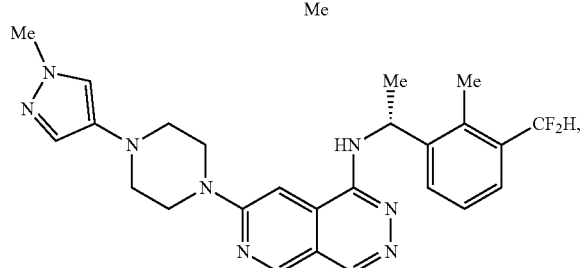
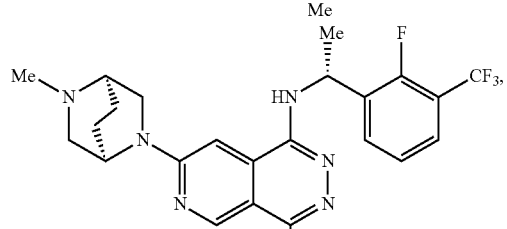
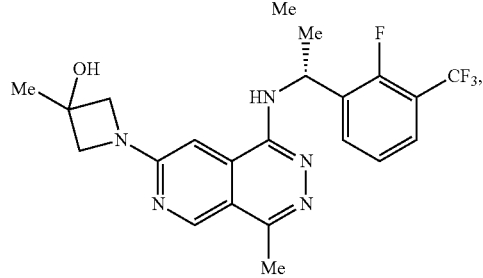
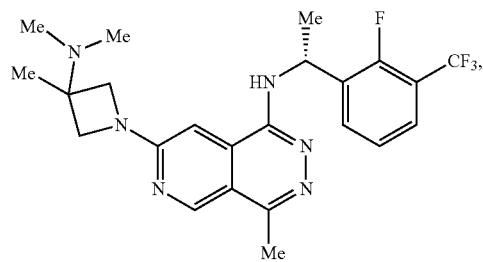
58
-continued
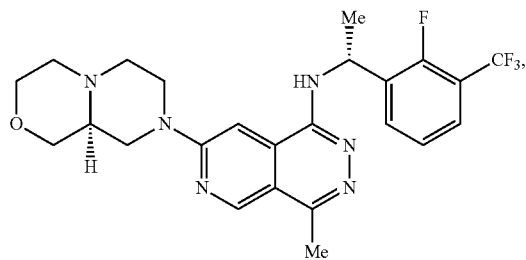
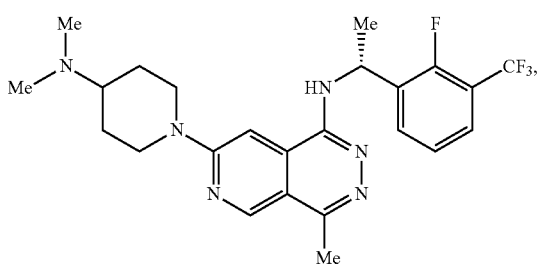
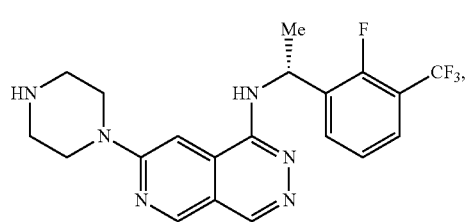
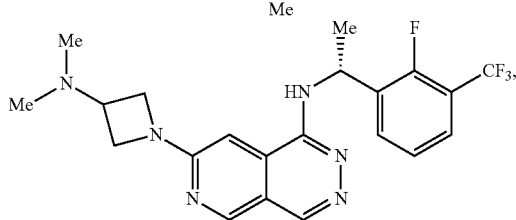
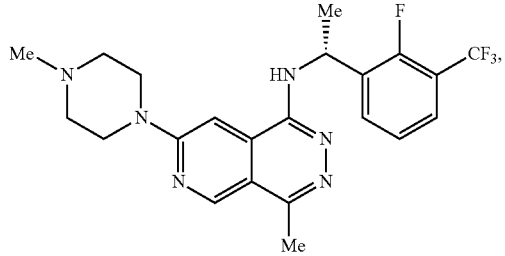
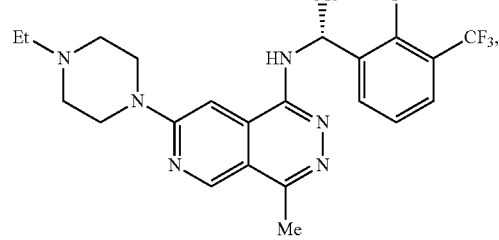

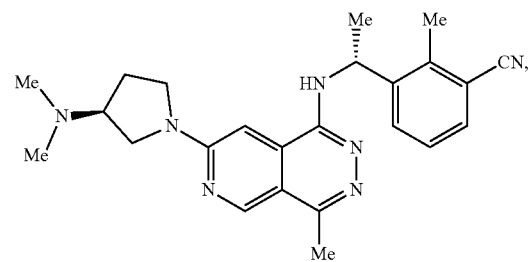
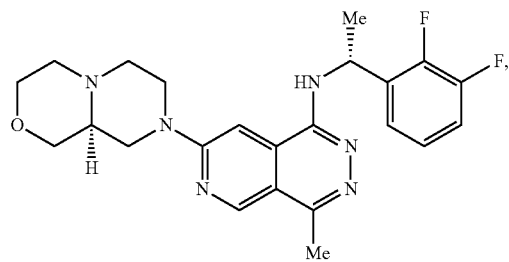
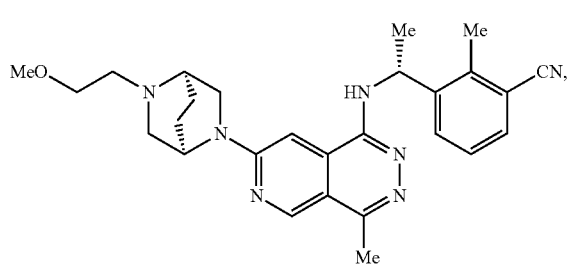
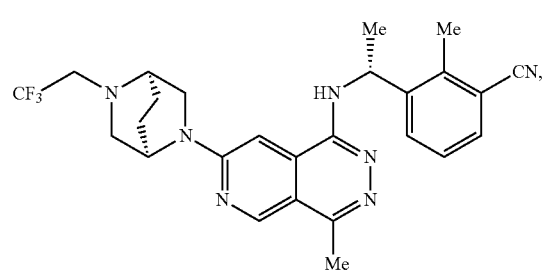
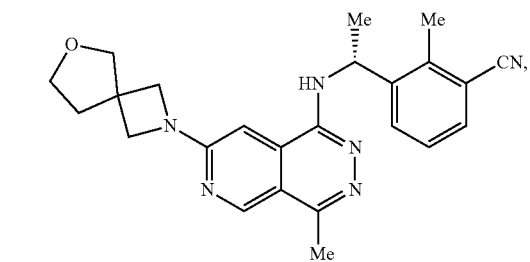
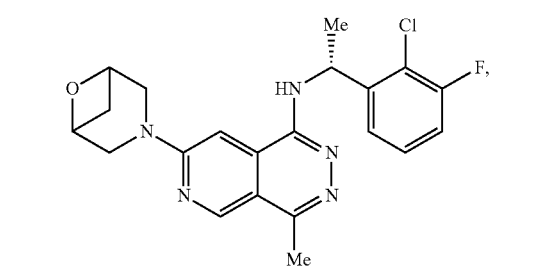
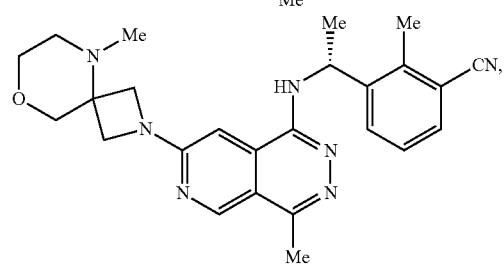
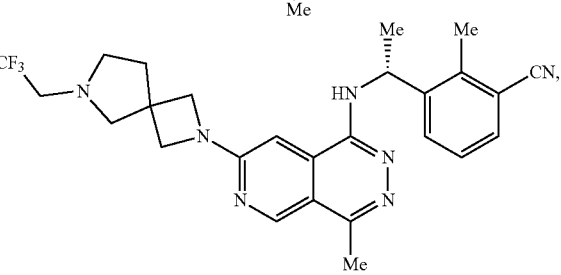
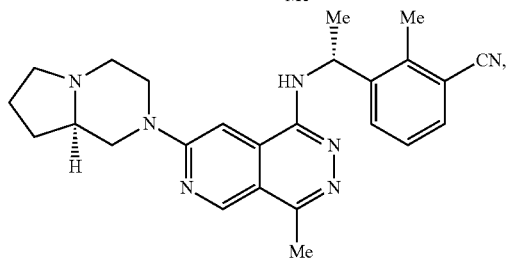
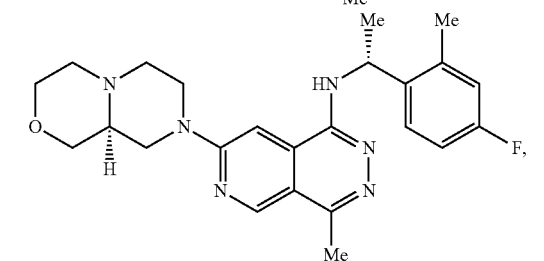
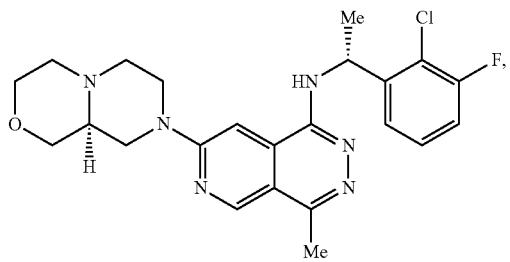
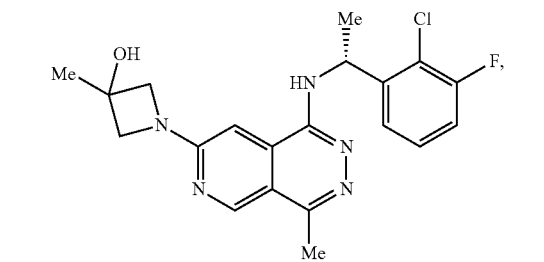

61
-continued
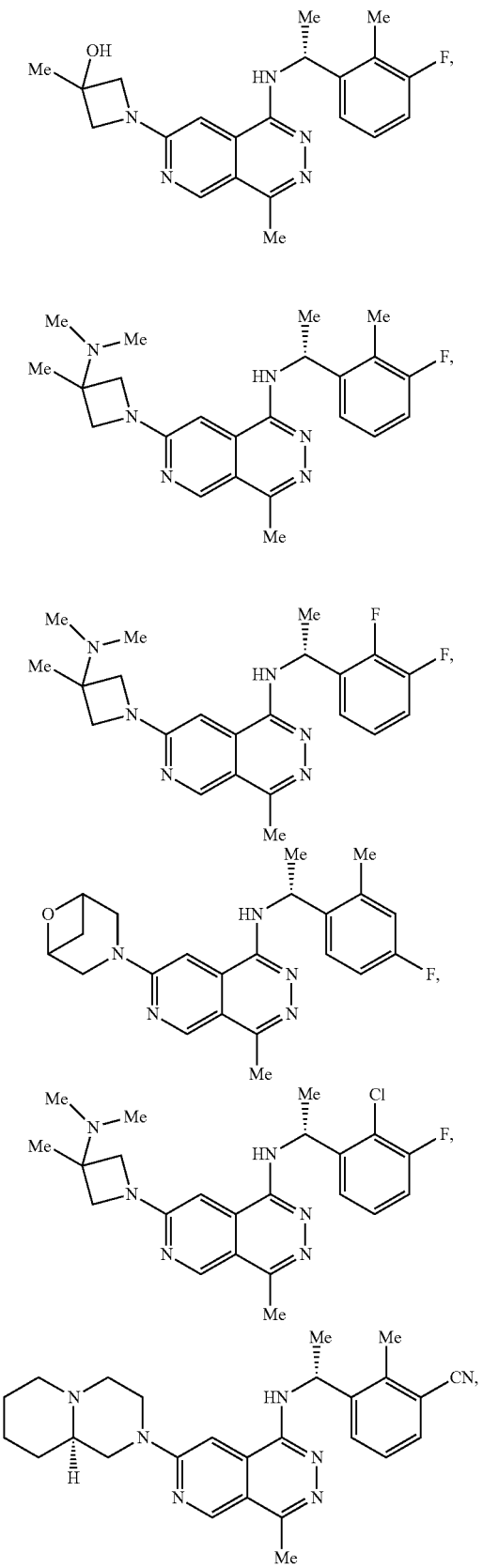
62
-continued
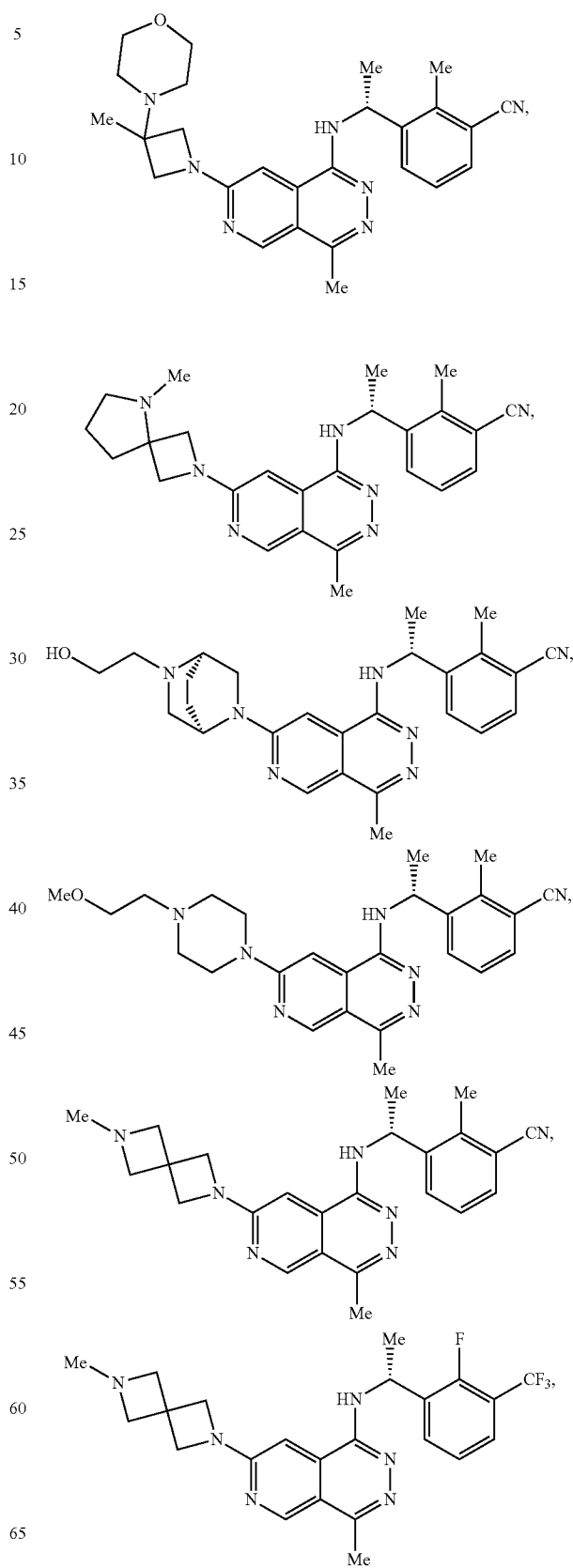

-continued
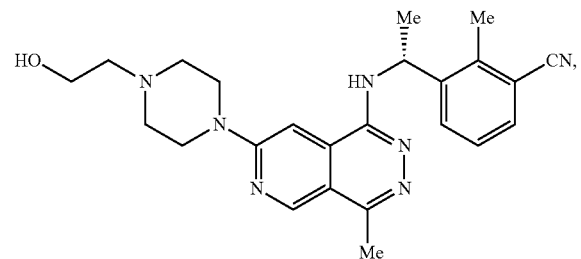
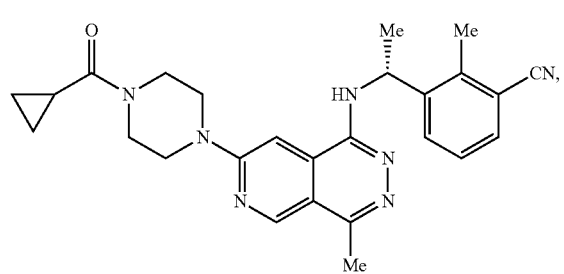
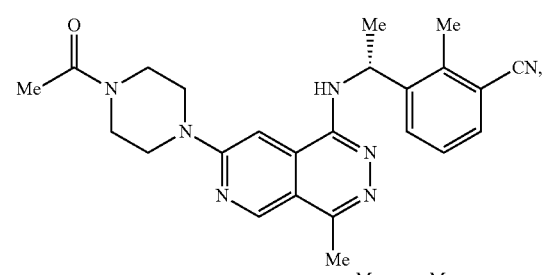
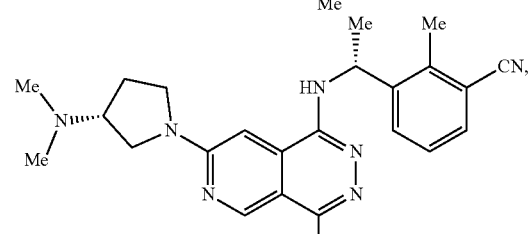
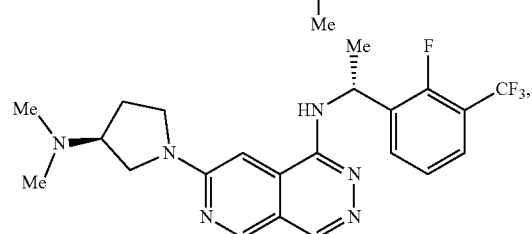
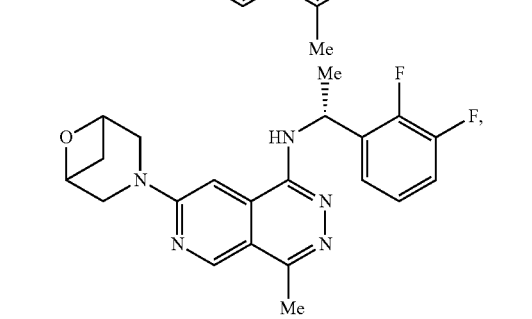
-continued
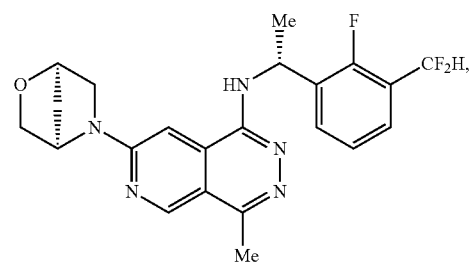
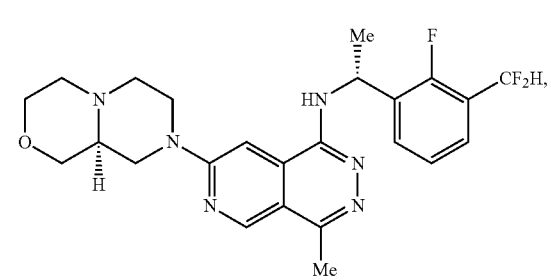
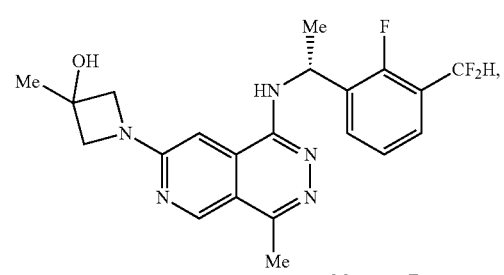
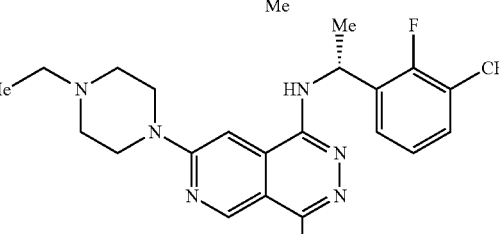
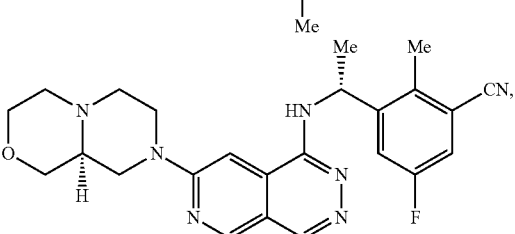
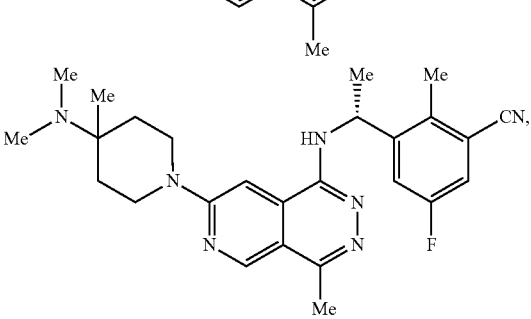

-continued
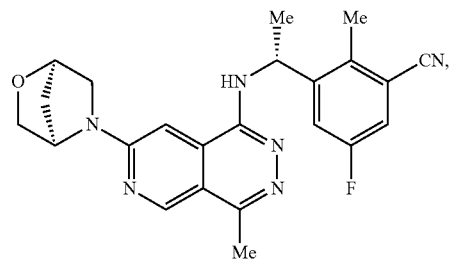
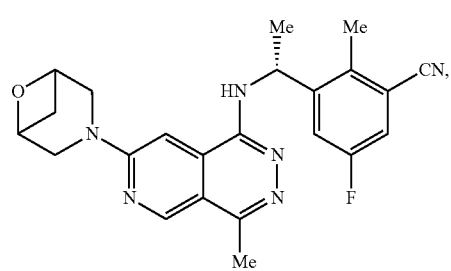
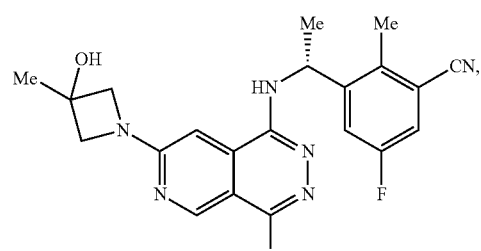
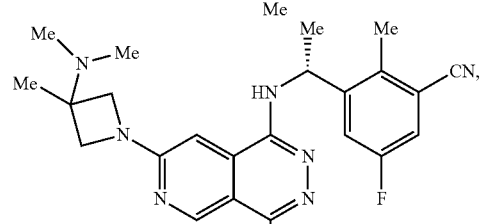
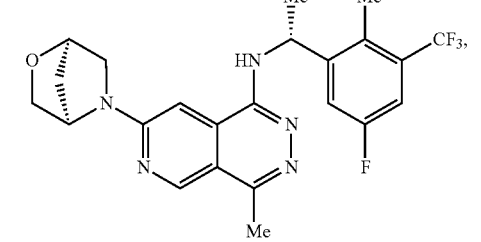
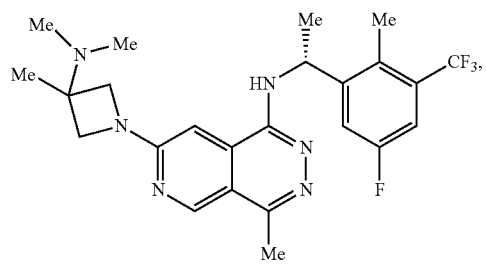
-continued
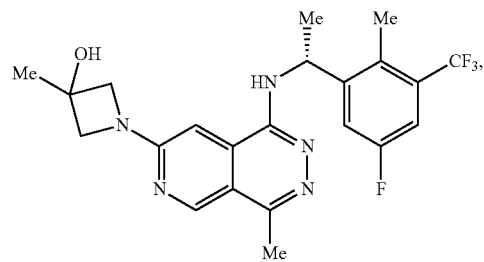
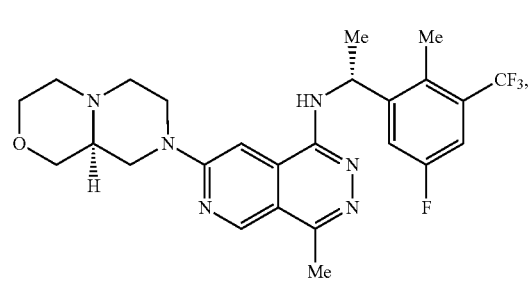
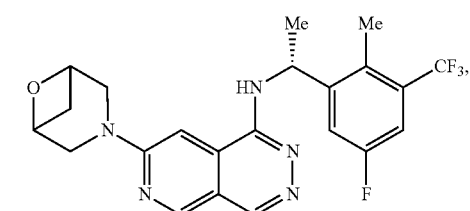
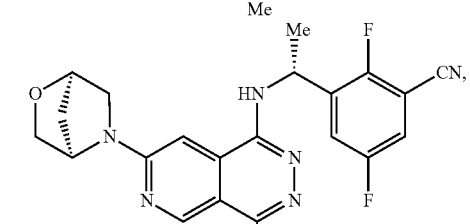
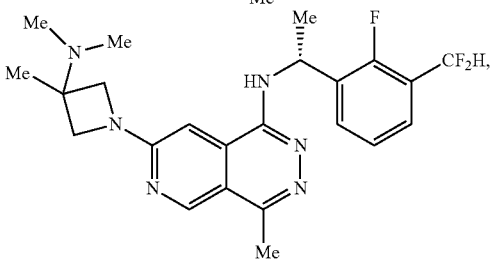
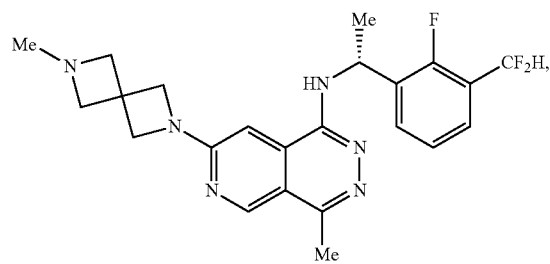

-continued
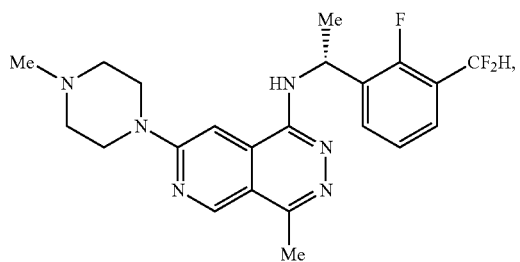
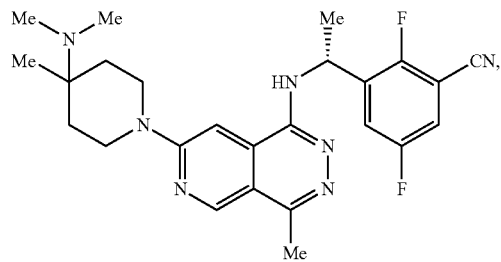
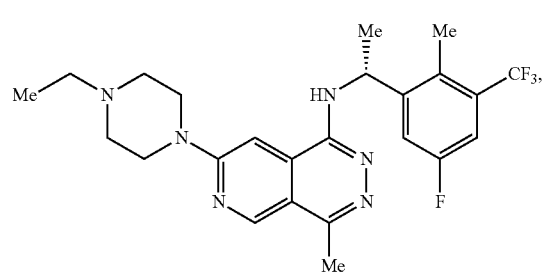
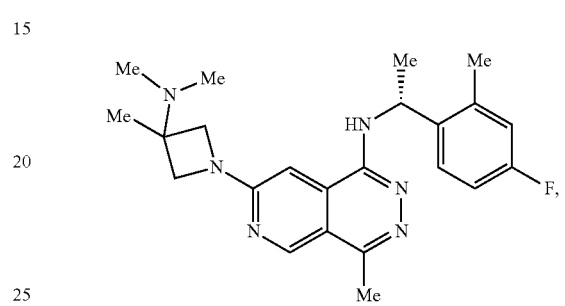
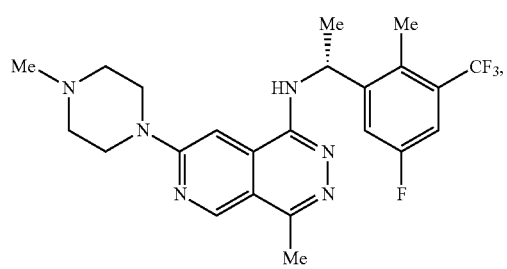
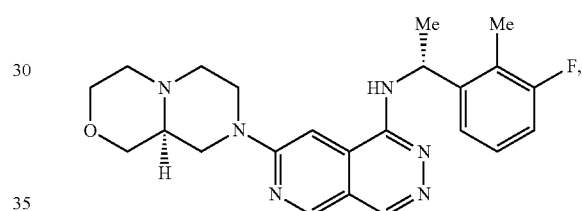
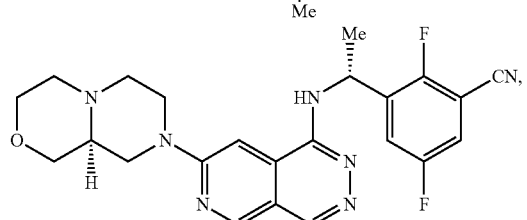
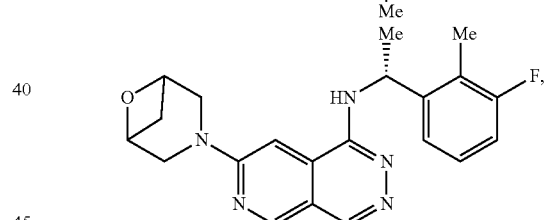
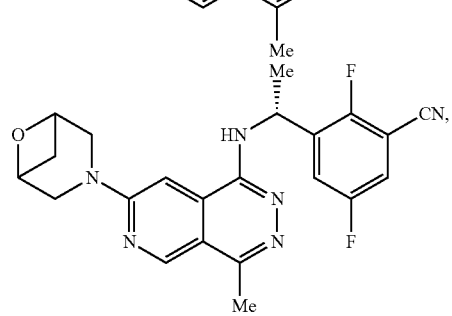
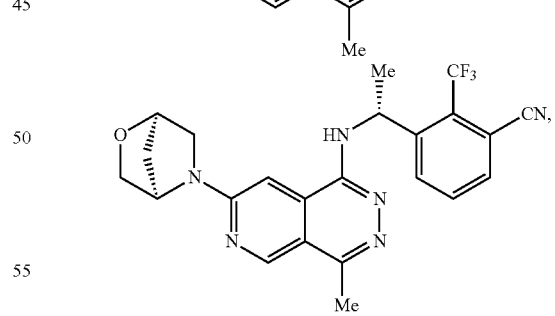
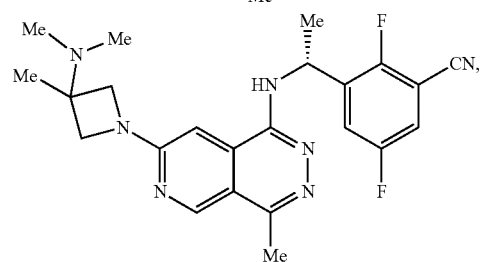
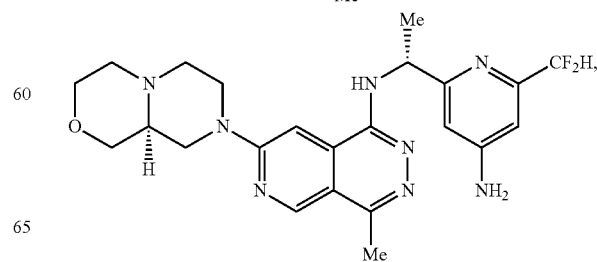

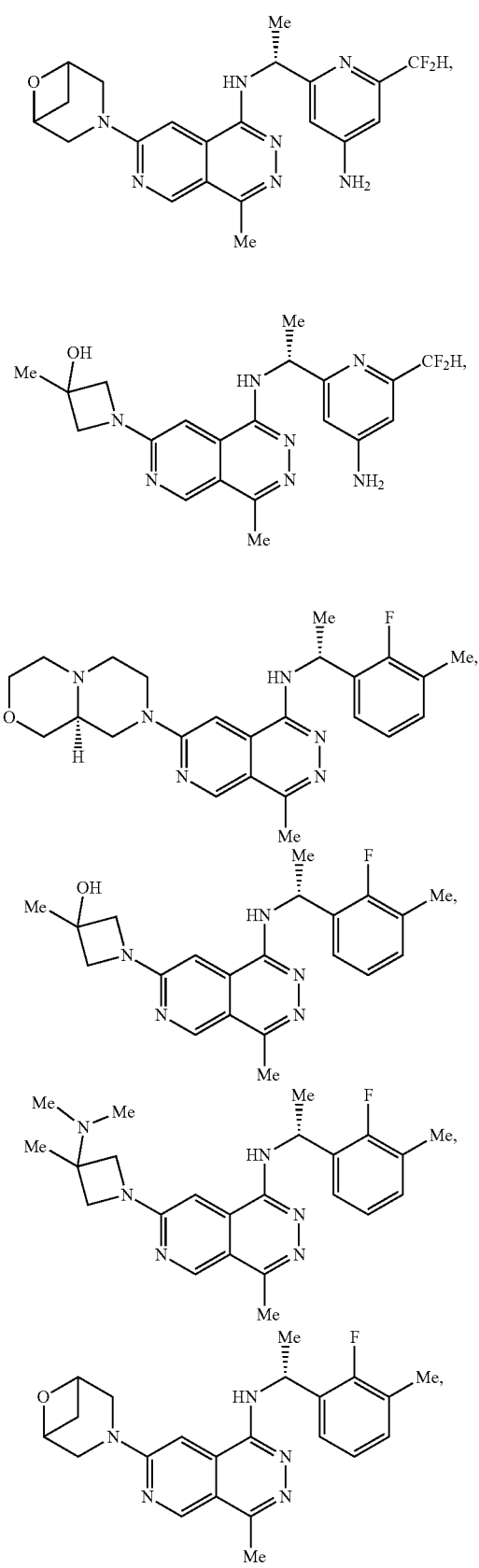
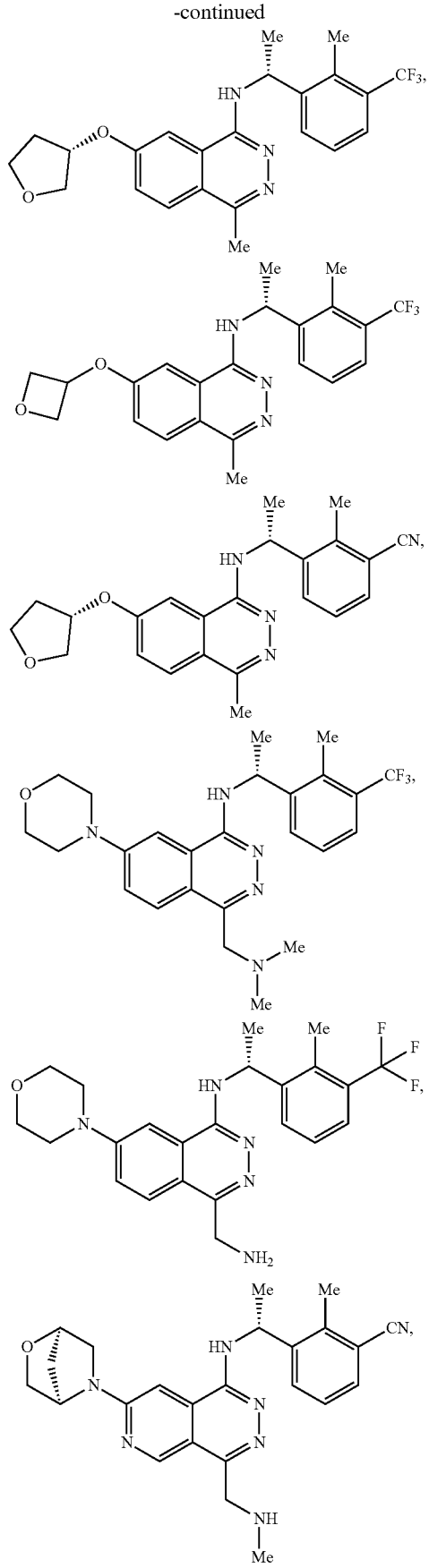

71
-continued
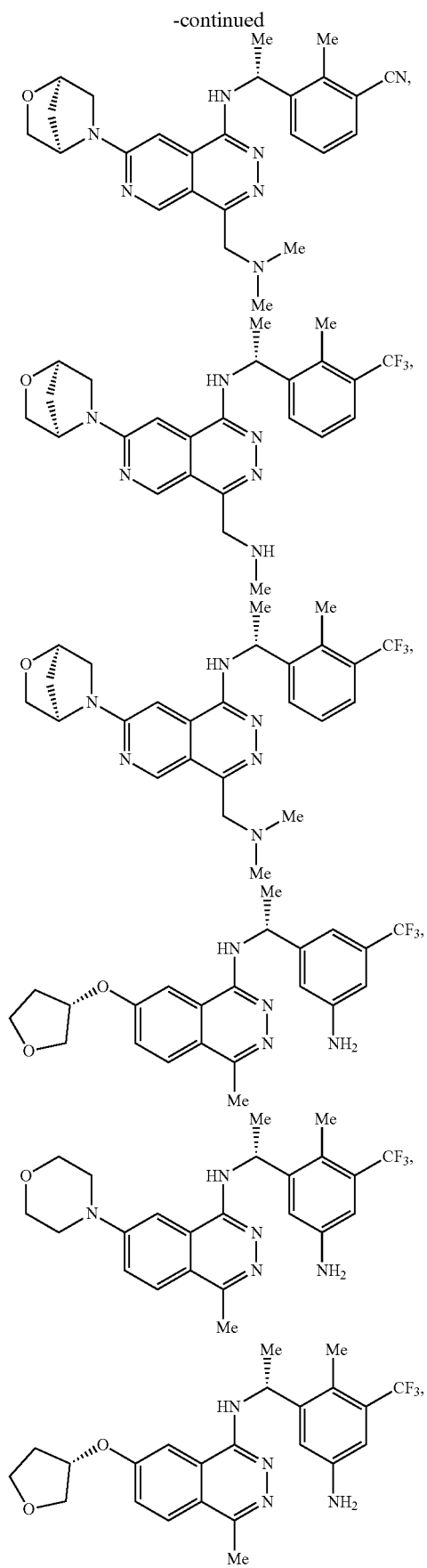
72
-continued
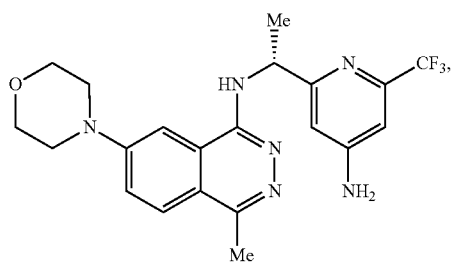
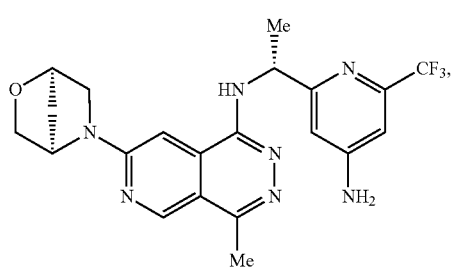
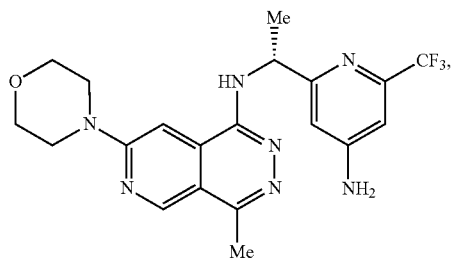
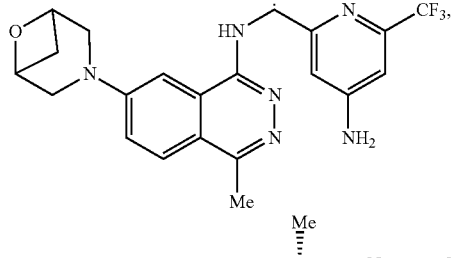
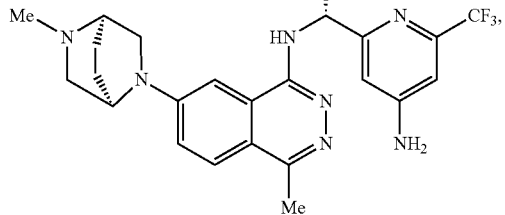
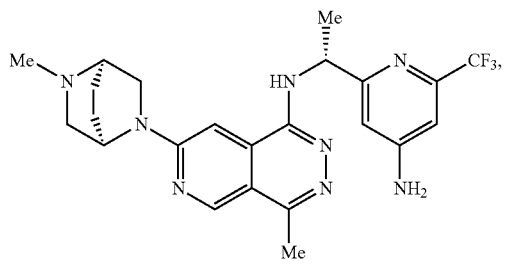

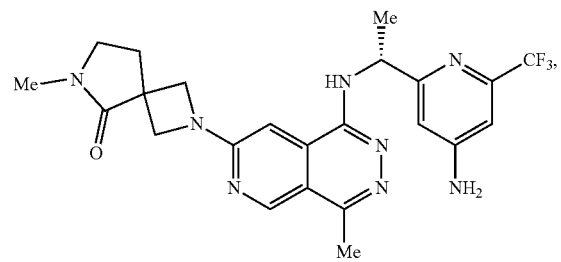
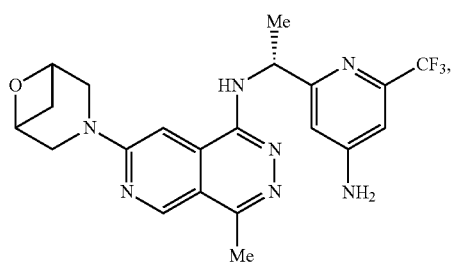
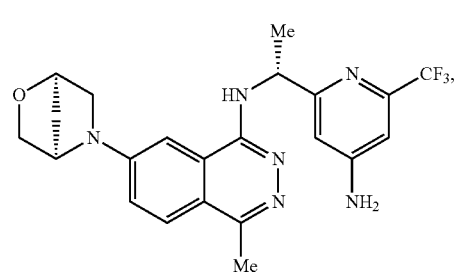
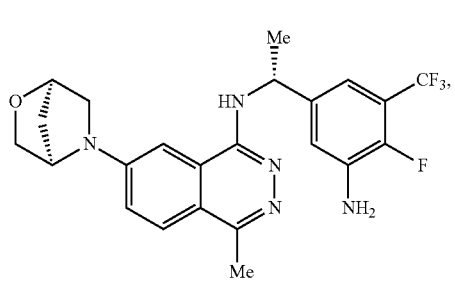
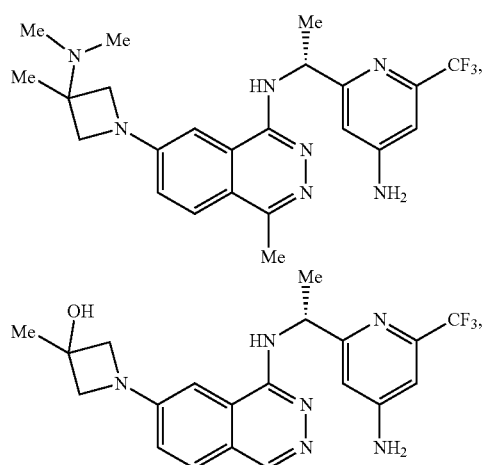
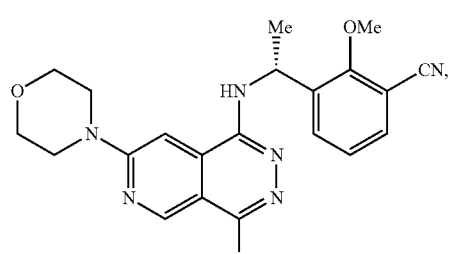
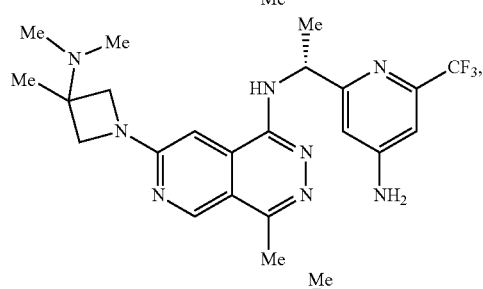
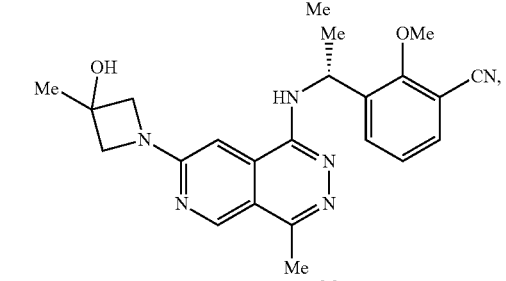
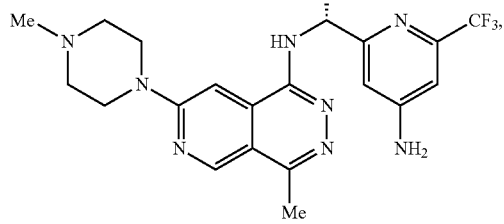
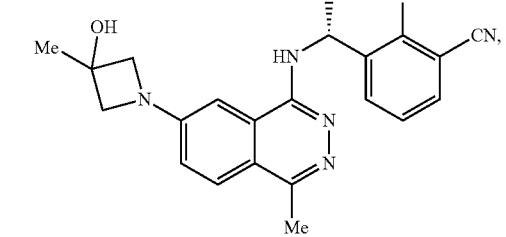

75
-continued
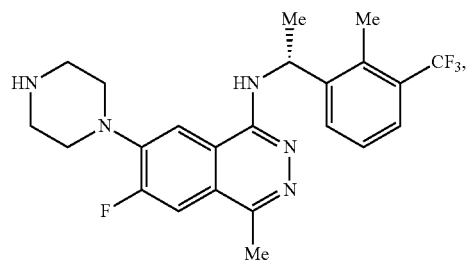
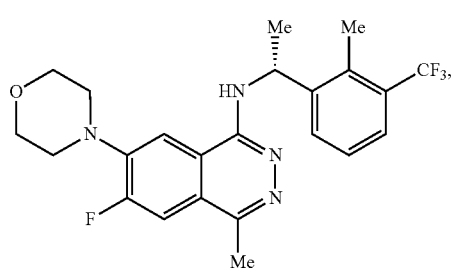
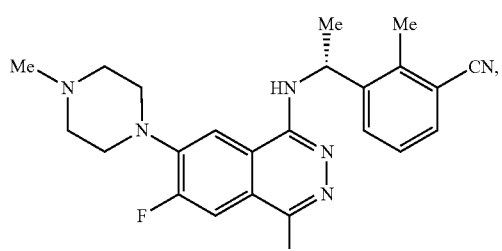
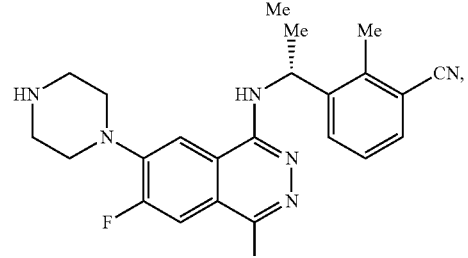
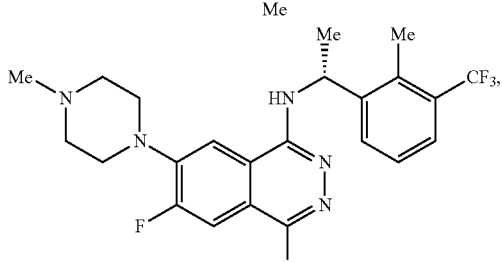
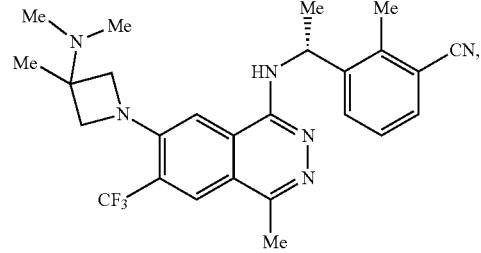
76
-continued
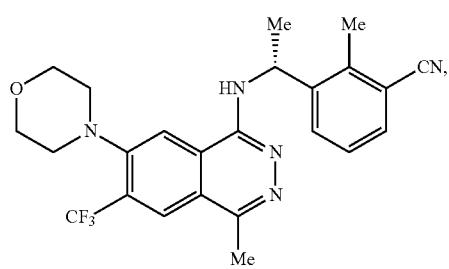
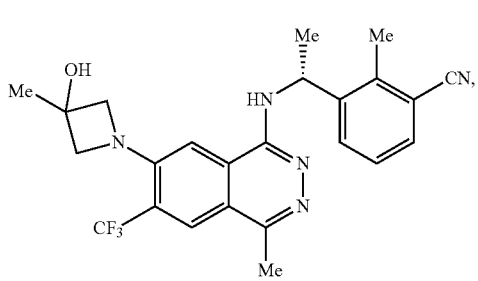
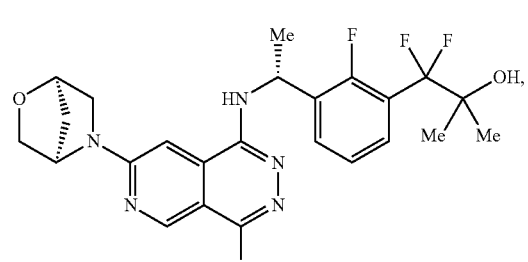
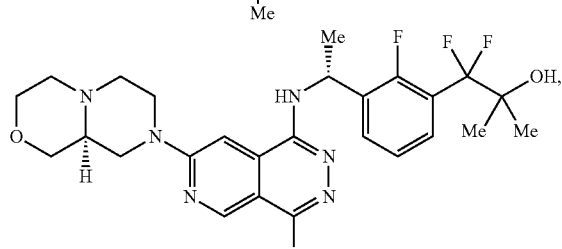
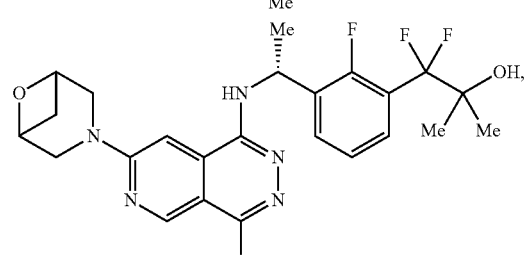
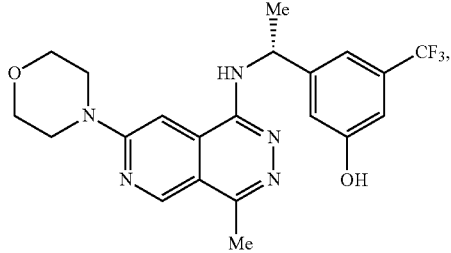

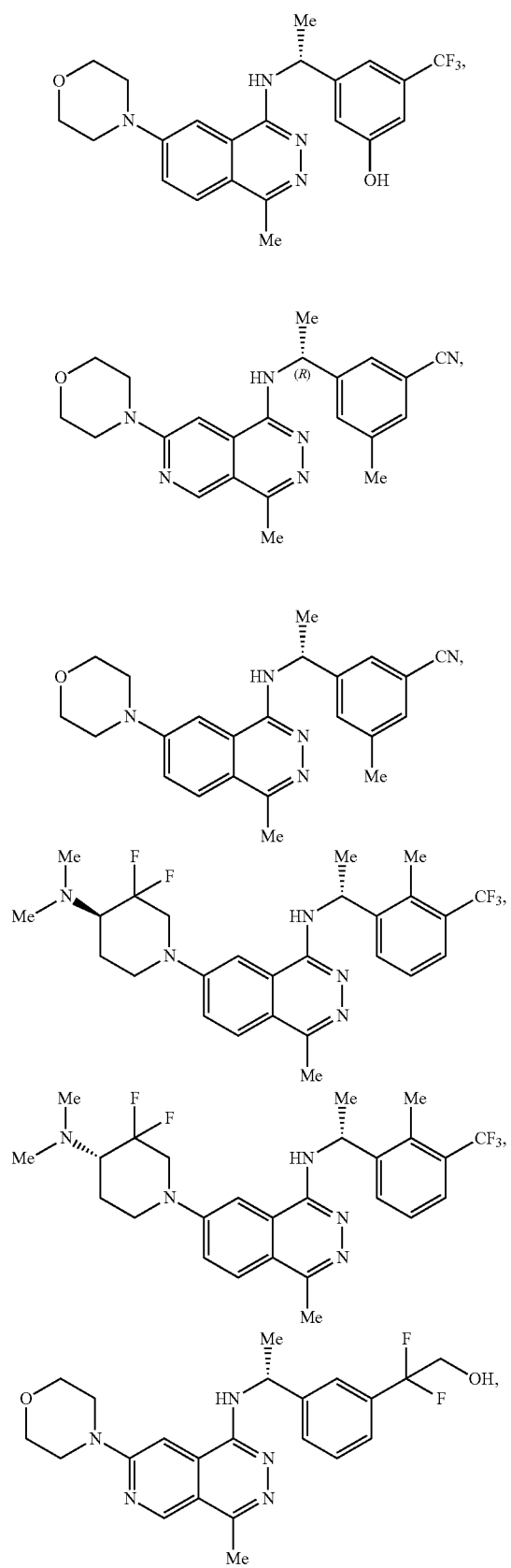
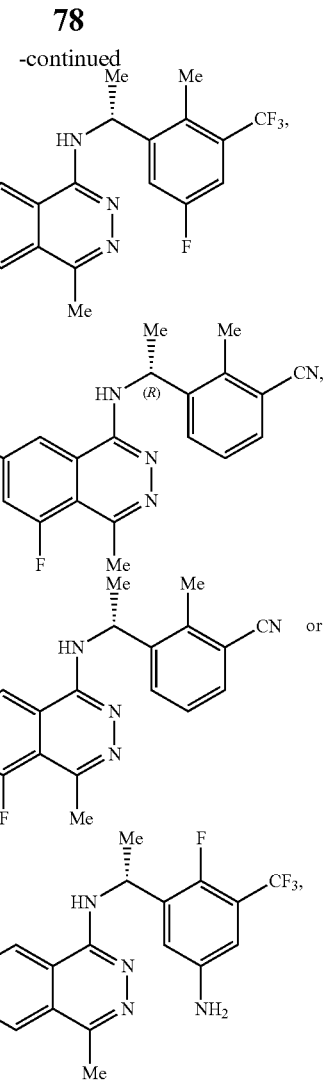

and pharmaceutically acceptable salts of the foregoing compounds.

The compounds of Formula (I) may be formulated into pharmaceutical compositions.

Pharmaceutical Compositions

In another aspect, the invention provides pharmaceutical compositions comprising a SOS1 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting SOS1 activity in a cell, comprising contacting the cell in which inhibition of SOS1 activity is desired in vitro with an effective amount of a compound of Formula (I), pharmaceutically acceptable salts thereof or pharmaceutical compositions containing the compound or pharmaceutically acceptable salt thereof.

The compositions and methods provided herein are particularly deemed useful for inhibiting SOS1 activity in a cell. In one embodiment, a cell in which inhibition of SOS1 activity is desired is contacted in vivo with a therapeutically effective amount of a compound of Formula (I) to negatively modulate the activity of SOS1. In other embodiments, a therapeutically effective amount of pharmaceutically acceptable salt or pharmaceutical compositions containing the compound of Formula (I) may be used. In one embodiment, the cell harbors an activating mutation in a Ras family member, such as KRas, HRas, or NRas. In one embodiment, the cell has aberrant SOS1 activity. In one embodiment, the aberrant SOS1 activity is the result of a SOS1 activating mutation. In one embodiment, the SOS1 activating mutation is a N233S or N233Y mutation. In one embodiment, the cell has aberrant NF-1 or NF-2 activity. In one embodiment, the aberrant NF-1 or NF-2 activity is the result of a NF-1 or NF-2 activating mutation.

By negatively modulating the activity of SOS1, the methods are designed to block the interaction between SOS1 and the Ras family member and increased GTP-loading of RAS proteins thereby decreasing or inhibiting the GTP nucleotide exchange and locking the Ras family member in the GDP-bound, inactive form resulting in the inhibition of downstream Ras-mediated signaling. The cells may be contacted in a single dose or multiple doses in accordance with a particular treatment regimen to affect the desired negative modulation of SOS1.

In another aspect, methods of treating cancer comprising administering to a patient having cancer a therapeutically effective amount of a compound of Formula (I), pharmaceutically acceptable salts thereof or pharmaceutical compositions comprising the compound or pharmaceutically acceptable salts thereof are provided. In one embodiment, the cancer is a Ras family-associated cancer. In one embodiment, the cancer is a SOS-1-associated cancer. In one embodiment, the cancer is a NF-1/NF-2-associated cancer.

The compositions and methods provided herein may be used for the treatment of a wide variety of cancer including tumors such as prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is diffuse large B-cell lymphoma (DLBCL).

In one embodiment, the cancer is a Ras family-associated cancer, such as a KRas, NRas or HRas-associated cancer. In certain embodiments, the Ras family-associated cancer is non-small cell lung cancer or pancreatic cancer. In one embodiment, the cancer is a SOS1-associated cancer. In certain embodiments, the SOS1-associated cancer is lung adenocarcinoma, embryonal rhabdomyosarcoma, Sertoli cell testis tumor and granular cell tumors of the skin. In one embodiment, the cancer is a NF-1-associated cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or postoperatively.

General Reaction Scheme, Intermediates and Examples

General Reaction Schemes

The compounds of the present invention may be prepared using commercially available reagents and intermediates in the synthetic methods and reaction schemes described herein, or may be prepared using other reagents and conventional methods well known to those skilled in the art.

For instance, intermediates for preparing compounds and compounds of Formula (I) of the present invention may be prepared according to General Reaction Schemes I-VI:

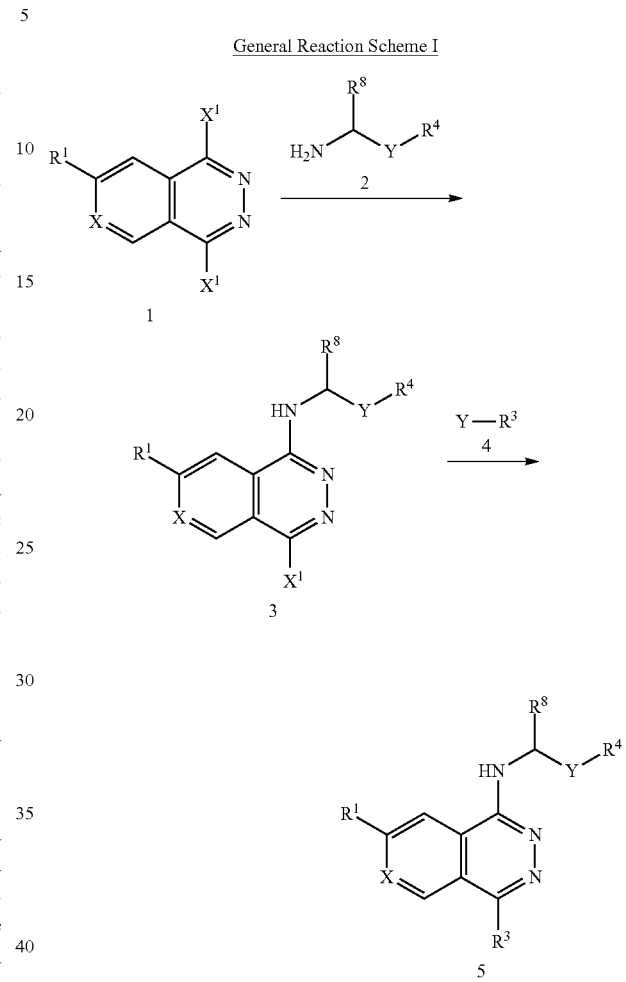

For General Reaction Scheme I, Compound 5 is an example of Formula (I). In this General Reaction Scheme I, 1 is reacted with an amine such as intermediate 2, this reaction could for example be a nucleophilic substitution or a metal catalyzed reaction, to yield Compound 3. Compound 3 can then undergo a metal catalyzed reaction with a coupling partner, such as a boronic acid derivative, Y—R³ 4 in the presence of a suitable base, e.g., sodium carbonate, to form title compound 5.

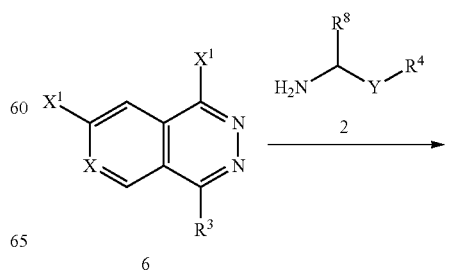

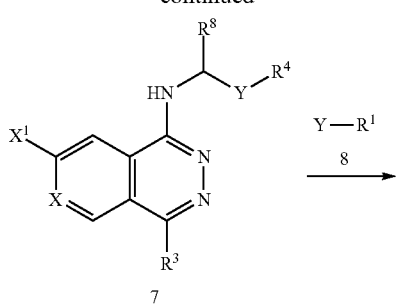

For General Reaction Scheme II, Compound 5 is an example of Formula (I). In this General Reaction Scheme II, 6 is reacted with an amine such as intermediate 2, this reaction could for example be a nucleophilic substitution or a metal catalyzed reaction, to yield Compound 7. Compound 7 can then undergo a metal catalyzed reaction with a coupling partner, such as a boronic acid derivative, Y—R¹ 8 in the presence of a suitable base, e.g., sodium carbonate, to form title compound 5.

For General Reaction Scheme III, Compound 5 is an example of Formula (I). In this General Reaction Scheme III, Compound 7 can either undergo a metal catalyzed reaction or a nucleophilic substitution with a coupling partner, such as an alcohol or amine, H—R¹ 9 in the presence of a suitable base, e.g., cesium carbonate, to form title compound 5.

For General Reaction Scheme IV, Compound 5 is an example of Formula (I). In this General Reaction Scheme IV, Compound 10 is reacted with an amine such as intermediate 2, this reaction could for example be a nucleophilic substitution or a metal catalyzed reaction, to form title compound 5.

-continued

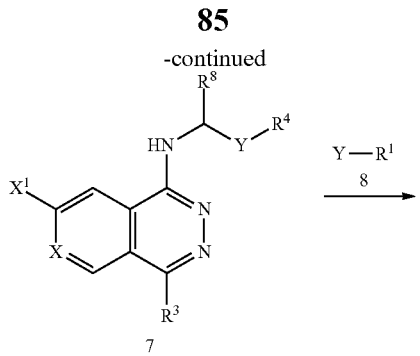

7

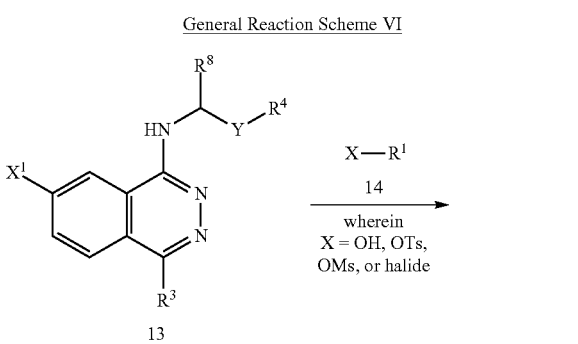

5

For General Reaction Scheme V, Compound 5 is an example of Formula (I). In this General Reaction Scheme V, 11 is reacted with an amine such as intermediate 2, this reaction could for example be a nucleophilic substitution or a metal catalyzed reaction, to yield Compound 12. Compound 12 can then undergo a metal catalyzed reaction with a coupling partner, such as a boronic acid derivative, Y—R³ 4 in the presence of a suitable base, e.g., sodium carbonate, to form compound 7. Compound 7 can then undergo a metal catalyzed reaction with a coupling partner, such as a boronic acid derivative, Y—R¹ 8 in the presence of a suitable base, e.g., sodium carbonate, to form title compound 5.

General Reaction Scheme VI

13

5

For General Reaction Scheme VI, Compound 5 is an example of Formula (I). In this General Reaction Scheme VI, Compound 13 can participate in a substitution reaction with a coupling partner, such as an alcohol, halide, tosylate, or mesylate X—R¹ 14 in the presence of a suitable base or coupling partner, e.g., cesium carbonate or diethyl azodicarboxylate, to form title compound 5.

The following intermediates may be used to prepare compounds of the present invention.

Intermediate A

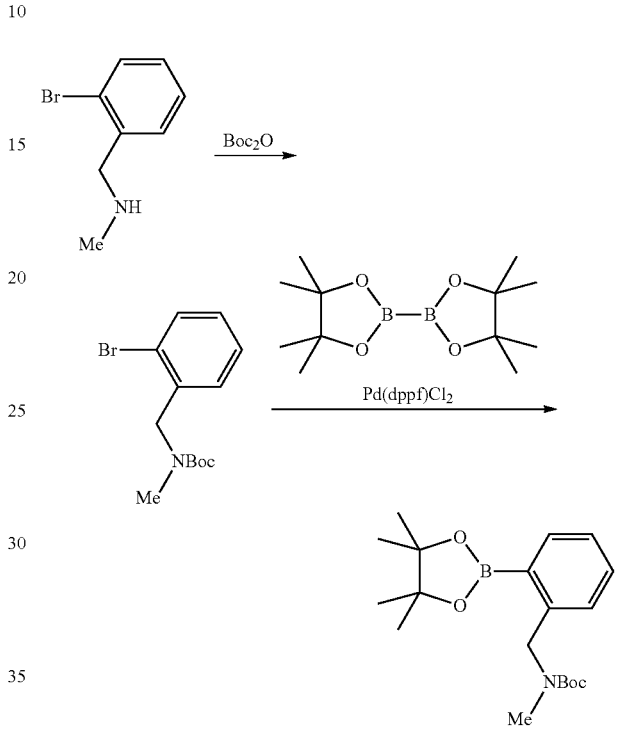

Step A: To a mixture of 1-(2-bromophenyl)-V-methyl-methanamine (6.50 g, 32.5 mmol, 1 eq.) in THF (70.0 mL) was added Boc₂O (7.80 g, 35.7 mmol, 8.21 mL, 1.10 eq.) dropwise at 25° C., and the mixture was stirred at 25° C. for 1 hour. The reaction mixture was directly concentrated in vacuo to give a residue. The residue was purified by column chromatography (SiO₂, petroleum ether/ethyl acetate=20/1 to 10/1) to give tert-butyl (2-bromobenzyl)(methyl)carbamate (7.50 g, 25.0 mmol, 76.9% yield) as a colorless oil.

¹H NMR (400 MHz, CDCl₃) δ 7.55 (br d, J=8.0 Hz, 1H), 7.34-7.28 (m, 1H), 7.22-7.08 (m, 2H), 4.61-4.42 (m, 2H), 2.94-2.78 (m, 3H), 1.60-1.33 (m, 9H).

Step B: A mixture of tert-butyl (2-bromobenzyl)(methyl) carbamate (7.00 g, 23.3 mmol, 1.00 eq.), bis(pinacolato) diboron (8.88 g, 35.0 mmol, 1.50 eq.), Pd(dppf)Cl₂ (1.71 g, 2.33 mmol, 0.10 eq.) and potassium acetate (5.72 g, 58.3 mmol, 2.50 eq.) in dioxane (80.0 mL) was degassed and purged with nitrogen for 3 times, and then the mixture was stirred at 110° C. for 12 hours under a nitrogen atmosphere. The reaction mixture was concentrated under reduced pressure to give a residue, and the residue was purified by column chromatography (SiO₂, petroleum ether/ethyl acetate=1/0 to 10/1) to give tert-butyl methyl(2-(4,4,5,5-tetramethyl-1,3,2-dioxaborolan-2-yl)benzyl)carbamate (8.00 g, 23.0 mmol, 98.8% yield) as a colorless oil.

¹H NMR (400 MHz, CDCl₃) δ 7.82 (br d, J=7.2 Hz, 1H), 7.48-7.37 (m, 1H), 7.27-7.21 (m, 2H), 4.85-4.63 (m, 2H), 2.92-2.73 (m 3H), 1.54-1.41 (m, 9H), 1.35 (s, 12H).

Intermediate B

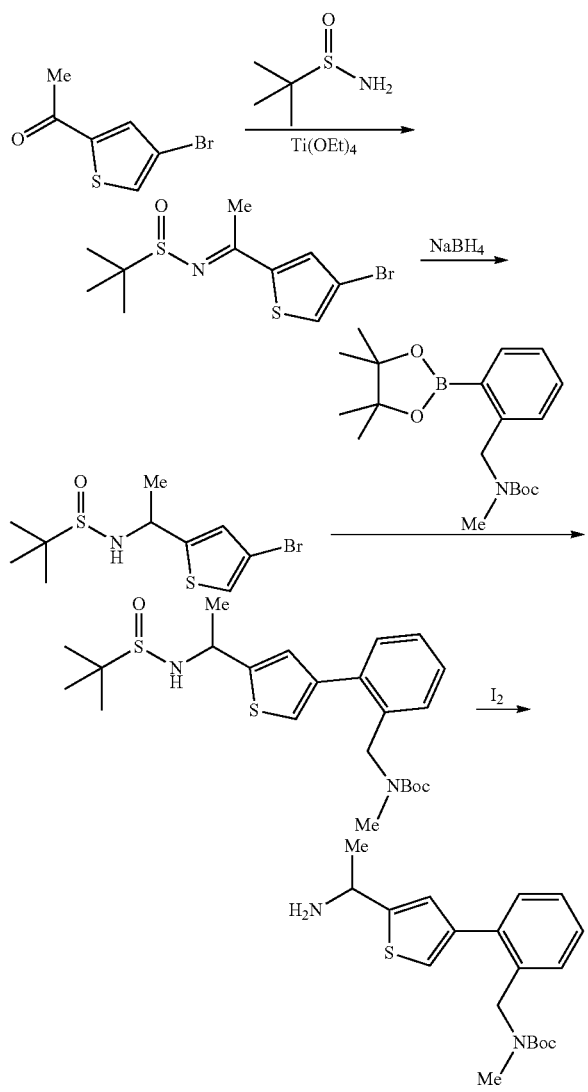

Step A: To a solution of 1-(4-bromothiophen-2-yl)ethan-1-one (4.00 g, 19.5 mmol, 1.10 eq.) and 2-methylpropane-2-sulfinamide (2.15 g, 17.7 mmol, 1.00 eq.) in THF (56.0 mL) was added Ti(OEt)$_4$ (8.09 g, 35.5 mmol, 7.35 mL, 2.00 eq.). The mixture was stirred at 70° C. for 2 hours. The mixture was poured into water (15.0 mL) and stirred for 5 minutes. The suspension was filtered, and filtrate was concentrated in vacuo to give a residue. The residue was washed with petroleum ether/ethyl acetate=5/1 (10 mL), filtered, and filter cake was collected and dried in vacuo to give N-(1-(4-bromothiophen-2-yl)ethylidene)-2-methylpropane-2-sulfinamide (3.00 g, 9.73 mmol, 54.9% yield) as a yellow solid.

$^1$H NMR (400 MHz, CDCl$_3$) δ 7.43 (d, J=1.2 Hz, 1H), 7.41 (d, J=1.2 Hz, 1H), 2.72 (s, 3H), 1.30 (s, 9H).

Step B: To a solution of N-(1-(4-bromothiophen-2-yl)ethylidene)-2-methylpropane-2-sulfinamide (3.70 g, 12.0 mmol, 1.00 eq.) in THF (40.0 mL) was added sodium borohydride (1.36 g, 36.0 mmol, 3.00 eq.) at 0° C. The reaction mixture was warmed slowly to 25° C. and stirred for 2 hours. The mixture was poured into ice-water (15.0 mL) and stirred for 5 minutes at 0° C. The aqueous phase was extracted with ethyl acetate (30.0 mL×3). The combined organic phases were washed with brine (30.0 mL×3), dried over anhydrous sodium sulfate, filtered, and concentrated in vacuo to give N-(1-(4-bromothiophen-2-yl)ethyl)-2-methylpropane-2-sulfinamide (3.60 g, 9.51 mmol, 79.3% yield, 82.0% purity) as yellow oil.

$^1$H NMR (400 MHz, CDCl$_3$) δ 7.15 (s, 1H), 6.98-6.96 (s, 1H), 4.81-4.75 (m, 1H), 3.55 (brd, J=3.6 Hz, 1H), 1.59 (d, J=6.4 Hz, 3H), 1.24 (s, 9H).

Step C: To a solution of N-(1-(4-bromothiophen-2-yl)ethyl)-2-methylpropane-2-sulfinamide (3.00 g, 9.67 mmol, 1.00 eq.) and tert-butyl methyl(2-(4,4,5,5-tetramethyl-1,3,2-dioxaborolan-2-yl)benzyl)carbamate (5.04 g, 14.5 mmol, 1.50 eq.) in dioxane (35.0 mL) and water (8.00 mL) was added Pd(PPh$_3$)$_4$ (1.12 g, 967 μmol, 0.10 eq.) and cesium carbonate (9.45 g, 29.01 mmol, 3.00 eq.) under a nitrogen atmosphere. The mixture was stirred at 110° C. for 2 hours under a nitrogen atmosphere. The mixture was filtered, and the filtrate was concentrated in vacuo to give a residue. The residue was purified by column chromatography (SiO$_2$, petroleum ether/ethyl acetate=10/1 to 1/1) to give tert-butyl (2-(5-(1-((tert-butylsulfinyl)amino)ethyl)thiophen-3-yl)benzyl)(methyl)carbamate (1.40 g, 3.11 mmol, 32.1% yield) as yellow oil. LCMS [M+1]: 451.2.

Step D: To a solution of tert-butyl (2-(5-(1-((tert-butylsulfinyl)amino)ethyl)thiophen-3-yl)benzyl)(methyl)carbamate (1.40 g, 4.88 mmol, 1.00 eq.) in THF (15.0 mL) and water (5.00 mL) was added iodine (232 mg, 1.46 mmol, 295 μL, 0.30 eq.). The mixture was stirred at 50° C. for 30 minutes. The residue was poured into saturated sodium sulfite aqueous solution (30.0 mL) and stirred for 5 minutes. The aqueous phase was extracted with ethyl acetate (15.0 mL×2). The combined organic phases were washed with brine (30.0 mL×2), dried over anhydrous sodium sulfate, filtered and concentrated in vacuo to give tert-butyl (2-(5-(1-aminoethyl)thiophen-3-yl)benzyl)(methyl)carbamate (1.20 g, crude) as yellow oil.

$^1$H NMR (400 MHz, CDCl$_3$) δ 7.36-7.28 (m, 3H), 7.26-7.22 (m, 1H), 7.01 (s, 1H), 6.91 (br s, 1H), 4.49 (br d, J=19.2 Hz, 2H), 4.40 (q, J=6.4 Hz, 1H), 2.72 (br d, J=19.2 Hz, 3H), 1.53 (d, J=6.4 Hz, 3H), 1.51-1.40 (m, 9H).

Intermediates C & D

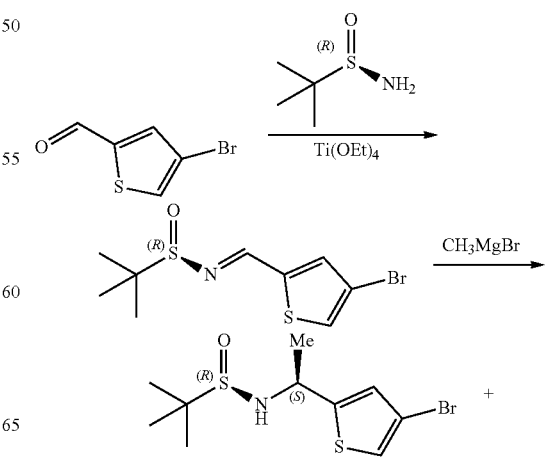

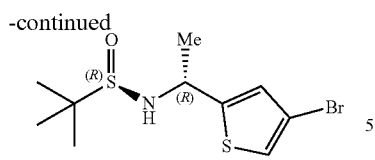

Step A: To a solution of 4-bromothiophene-2-carbaldehyde (20.0 g, 104 mmol, 1.00 eq.) and (R)-2-methylpropane-2-sulfinamide (12.1 g, 99.5 mmol, 0.95 eq.) in THF (200 mL) was added titanium (IV) ethoxide (47.8 g, 209 mmol, 43.4 mL, 2.00 eq.). The reaction mixture was stirred at 25° C. for 1 hour. The mixture was then poured into water (20.0 mL) and stirred for 5 minutes to give a suspension. The suspension was filtered and the filtered liquor was concentrated in vacuo to give (R,E)-N-((4-bromothiophen-2-yl)methylene)-2-methylpropane-2-sulfinamide (20.0 g, crude) as yellow oil. LCMS [M+1]: 295.8.

Step B: To a solution of (R,E)-N-((4-bromothiophen-2-yl)methylene)-2-methylpropane-2-sulfinamide (600 mg, 2.04 mmol, 1.00 eq.) in THF (200 mL) was added methyl magnesium bromide (3.00 M, 2.04 mL, 3.00 eq.) dropwise at 0° C. Then the reaction mixture was stirred at 25° C. for 1 hour. Saturated ammonium chloride aqueous solution (3.00 mL) was added to the reaction mixture and stirred for 5 minutes. The aqueous phase was extracted with ethyl acetate (3.00 mL×2), and the combined organic phases were washed with brine (3.00 mL×2), dried over anhydrous sodium sulfate, filtered and concentrated in vacuo to give a residue. The residue was purified by prep-TLC (SiO₂, petroleum ether/ethyl acetate=1/1) to give (R)—N—((S)-1-(4-bromothiophen-2-yl)ethyl)-2-methylpropane-2-sulfinamide (first eluting, Intermediate C) (120 mg, 19.0% yield) as yellow oil and (R)—N—((R)-1-(4-bromothiophen-2-yl)ethyl)-2-methylpropane-2-sulfinamide (2nd eluting, Intermediate D) (150 mg, 483 μmol, 23.7% yield) as yellow oil.

Intermediate C: ¹H NMR (400 MHz, CDCl₃) δ 7.15 (d, J=1.6 Hz, 1H), 6.97 (s, 1H), 4.81-4.75 (m, 1H), 3.51 (br d, J=3.2 Hz, 1H), 1.59 (d, J=6.8 Hz, 3H), 1.24 (s, 9H).

Intermediate D: ¹H NMR (400 MHz, CDCl₃) δ 7.14 (d, J=1.6 Hz, 1H), 6.89 (s, 1H), 4.81-4.74 (m, 1H), 3.39 (br d, J=5.6 Hz, 1H), 1.65 (d, J=6.8 Hz, 3H), 1.25 (s, 9H).

Intermediate E

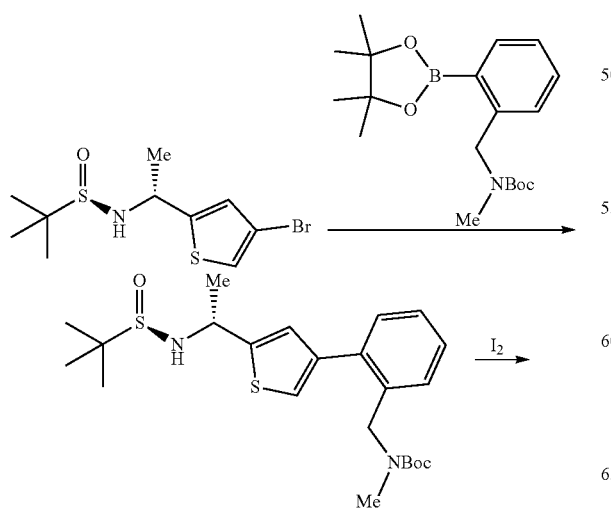

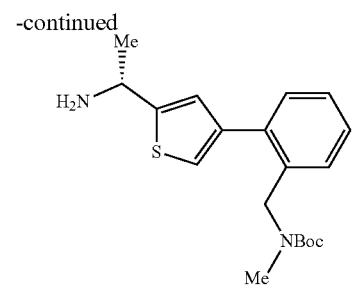

Step A: To a solution of (R)—N—((R)-1-(4-bromothiophen-2-yl)ethyl)-2-methylpropane-2-sulfinamide (150 mg, 483 μmol, 1.00 eq.) and tert-butyl methyl(2-(4,4,5,5-tetramethyl-1,3,2-dioxaborolan-2-yl)benzyl)carbamate (168 mg, 483 μmol, 1.00 eq.) in dioxane (1.00 mL) and water (0.20 mL) was added Pd(PPh₃)₄ (55.9 mg, 48.3 μmol, 0.10 eq.) and cesium carbonate (473 mg, 1.45 mmol, 3.00 eq.) under a nitrogen atmosphere. The reaction mixture was stirred at 110° C. for 2 hours under a nitrogen atmosphere, then to 25° C. and concentrated in vacuo to give a residue. The residue was purified by prep-TLC (SiO₂, petroleum ether/ethyl acetate=1/1) to give tert-butyl (2-(5-((R)-1-(((R)-tert-butylsulfinyl)amino)ethyl)thiophen-3-yl)benzyl)(methyl)carbamate (120 mg, 266 μmol, 55.1% yield) as a white solid. LCMS [M+1]=451.1.

¹H NMR (400 MHz, CDCl₃) δ 7.37-7.29 (m, 3H), 7.25 (s, 1H), 7.06 (s, 1H), 6.95 (br s, 1H), 4.88-4.81 (m, 1H), 4.48 (br d, J=16.0 Hz, 2H), 3.44 (br d, J=6.0 Hz, 1H), 2.73 (br d, J=12.8 Hz, 3H), 1.71 (d, J=6.4 Hz, 3H), 1.27 (s, 9H), 1.25 (s, 9H).

Step B: To a solution of tert-butyl (2-(5-((R)-1-(((R)-tert-butylsulfinyl)amino)ethyl)thiophen-3-yl)benzyl)(methyl) carbamate (120 mg, 266 μmol, 1.00 eq.) in THF (1.00 mL) and water (0.20 mL) was added iodine (20.3 mg, 79.9 μmol, 16.1 μL, 0.30 eq.), and the reaction mixture was stirred at 50° C. for 1 hour. The reaction mixture was then cooled to 25° C., poured into saturated sodium sulfite aqueous solution (2.00 mL) and stirred for 5 minutes. The aqueous phase was extracted with ethyl acetate (3.00 mL×3), and the combined organic phases were washed with brine (3.00 mL×3), dried over anhydrous sodium sulfate, filtered, and concentrated in vacuo to give a residue. The residue was purified by prep-HPLC (column: Phenomenex Gemini-NX C18 75×30 mm×3 um; mobile phase: [water (0.1% TFA)-ACN]; B %: 28%-38%) to give tert-butyl (R)-(2-(5-(1-aminoethyl)thiophen-3-yl)benzyl)(methyl)carbamate (40.0 mg, 113 μmol, 42.3% yield, 97.5% purity) as white oil.

¹H NMR (400 MHz, CD₃OD) δ 7.41-7.23 (m, 6H), 4.84-4.79 (m, 1H), 4.48 (s, 2H), 2.73 (s, 3H), 1.76 (d, J=6.8 Hz, 3H), 1.51-1.36 (m, 9H).

Intermediate F

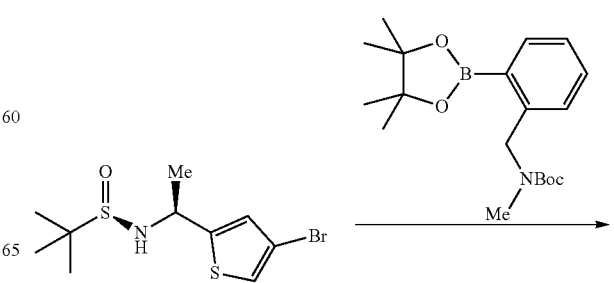

Intermediate G

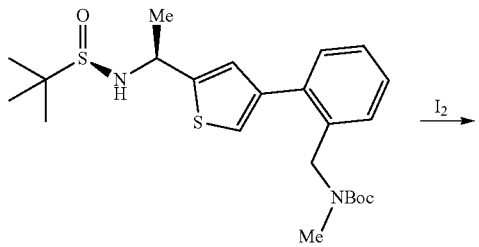

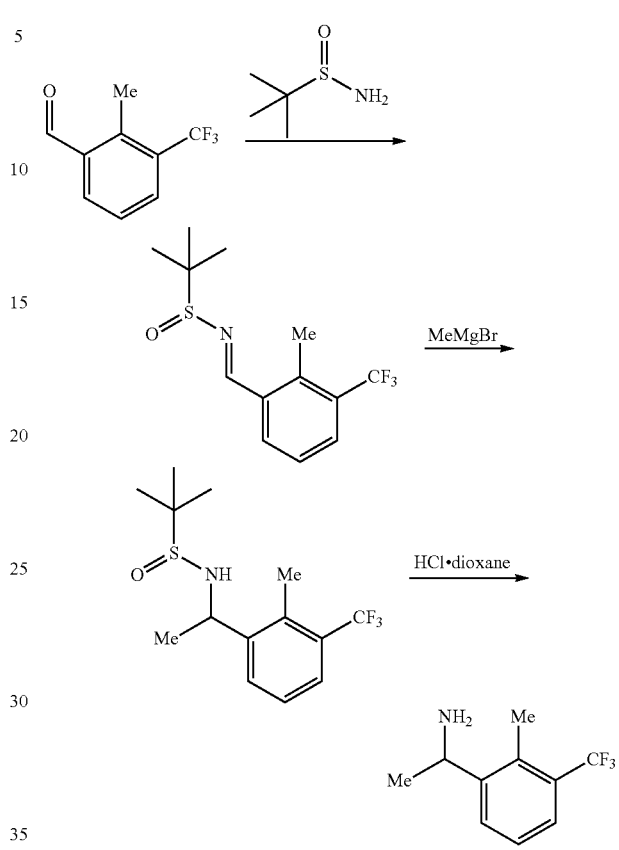

Step A: To a solution of (R)—N—((S)-1-(4-bromothiophen-2-yl)ethyl)-2-methylpropane-2-sulfinamide (100 mg, 322 µmol, 1.00 eq.) and tert-butyl methyl(2-(4,4,5,5-tetramethyl-1,3,2-dioxaborolan-2-yl)benzyl)carbamate (112 mg, 322 µmol, 1.00 eq.) in dioxane (1.00 mL) and water (0.20 mL) was added Pd(PPh$_3$)$_4$ (37.2 mg, 32.2 µmol, 0.10 eq.) and cesium carbonate (315 mg, 967 ummol, 3.00 eq.) under a nitrogen atmosphere. The reaction mixture was stirred at 110° C. for 2 hours, then cooled to 25° C. and concentrated in vacuo to give a residue. The residue was purified by prep-TLC (SiO$_2$, petroleum ether/ethyl acetate=1/1) to give tert-butyl (2-(5-((S)-1-(((R)-tert-butylsulfinyl)amino)ethyl)thiophen-3-yl)benzyl)(methyl)carbamate (100 mg, 266 µmol, 68.9% yield) as yellow oil. LCMS [M+1]=451.1.

$^1$H NMR (400 MHz, CDCl$_3$) δ 7.37-7.28 (m, 3H), 7.26-7.22 (m, 1H), 7.07 (d, J=1.2 Hz, 1H), 7.03 (br s, 1H), 4.90-4.83 (m, 1H), 4.55-4.41 (m, 2H), 3.71-3.55 (m, 1H), 2.80-2.65 (m, 3H), 1.64 (d, J=6.8 Hz, 3H), 1.52-1.41 (m, 9H), 1.26 (s, 9H).

Step B: To a solution of tert-butyl (2-(5-((S)-1-(((R)-tert-butylsulfinyl)amino)ethyl)thiophen-3-yl)benzyl)(methyl)carbamate (100 mg, 266 µmol, 1.00 eq.) in THF (1.00 mL) and water (0.20 mL) was added iodine (16.9 mg, 66.6 µmol, 13.4 µL, 0.30 eq.). The reaction mixture was stirred at 50° C. for 1 hour, thens cooled to 25° C. and poured into saturated aqueous sodium sulfite (2.00 mL) solution and stirred for 5 minutes. The aqueous phase was extracted with ethyl acetate (3.00 mL×3), and the combined organic phases were washed with brine (3.00 mL×3), dried over anhydrous sodium sulfate, filtered, and concentrated in vacuo to give a residue. The residue was purified by prep-HPLC (column: Phenomenex Luna C18 150×25 mm×10 um; mobile phase: [water(0.1% TFA)-ACN]; B %: 24%-54%) to give tert-butyl (S)-(2-(5-(1-aminoethyl)thiophen-3-yl)benzyl)(methyl)carbamate (45.0 mg, 97.7 µmol, 44.0% yield, TFA salt) as white oil. LCMS [M+1]=347.2.

$^1$H NMR (400 MHz, CD$_3$OD) δ 7.40 (d, J=1.2 Hz, 1H), 7.38-7.22 (m, 5H), 4.82-4.80 (br s, 1H), 4.48 (s, 2H), 2.73 (s, 3H), 1.75 (d, J=6.8 Hz, 3H), 1.50-1.35 (m, 9H).

Step A: To a solution of 2-methyl-3-(trifluoromethyl)benzaldehyde (300 mg, 1.59 mmol, 1.00 eq.) and 2-methylpropane-2-sulfinamide (213 mg, 1.75 mmol, 1.10 eq.) in THF (5.00 mL) was added titanium (IV) ethoxide (727 mg, 3.19 mmol, 661 µL, 2.00 eq.). The reaction mixture was stirred at 25° C. for 12 hours. The reaction mixture was poured into water (2.00 mL) and stirred for 5 minutes to give a suspension. The suspension was filtered and concentrated in vacuo to give 2-methyl-N-(2-methyl-3-(trifluoromethyl)benzylidene)propane-2-sulfinamide (360 mg, 1.24 mmol, 77.5% yield) as a white solid.

$^1$H NMR (400 MHz, CDCl$_3$) δ=8.98 (s, 1H), 8.13 (d, J=7.6 Hz, 1H), 7.78 (d, J=7.6 Hz, 1H), 7.40 (t, J=7.6 Hz, 1H), 2.70 (d, J=0.8 Hz, 3H), 1.29 (s, 9H).

Step B: To a solution of 2-methyl-N-(2-methyl-3-(trifluoromethyl)benzylidene)propane-2-sulfinamide (185 mg, 635 µmol, 1.00 eq.) in THF (5.00 mL) was added dropwise methyl magnesium bromide (227 mg, 3.00 M, 635 µL, 3.00 eq.) at 0° C. under a nitrogen atmosphere. The reaction mixture was stirred at 25° C. for 3 hours then treated with saturated ammonium chloride solution (10.0 mL) slowly. The organic layer and aqueous phase were separated, and the aqueous phase was extracted with ethyl acetate (5.00 mL×3). The combined organic layers were washed with brine (10.0 mL), dried over anhydrous sodium sulfate, filtered, and concentrated to give a residue. The residue was purified by column chromatography (SiO$_2$, petroleum ether/ethyl acetate=10/1 to 1/1) to give 2-methyl-N-(1-(2-methyl-3-(trifluoromethyl)phenyl)ethyl)propane-2-sulfinamide (150 mg, 488.0 µmol, 76.8% yield) as a yellow solid.

¹H NMR (400 MHz, CDCl₃) δ=7.65-7.54 (m, 4H), 7.35-7.28 (m, 2H), 5.00-4.87 (m, 2H), 2.49 (s, 6H), 1.54-1.50 (m, 6H), 1.26-1.24 (m, 9H), 1.22 (s, 9H).

Step C: To a solution of 2-methyl-N-(1-(2-methyl-3-(trifluoromethyl)phenyl)ethyl)propane-2-sulfinamide (150 mg, 488.0 μmol, 1.00 eq.) in HCl (4.0 M in dioxane, 1.00 mL) was stirred at 25° C. for 1 hour. The reaction mixture was filtered and filter cake was concentrated in vacuo to give 1-(2-methyl-3-(trifluoromethyl)phenyl)ethan-1-amine (45.0 mg, 38.5% yield) as a red solid. LCMS [M+1]=204.3.

¹H NMR (400 MHz, CD₃OD) δ=7.78-7.65 (m, 2H), 7.56-7.48 (m, 1H), 4.93-4.89 (m, 1H), 2.52 (d, J=0.8 Hz, 3H), 1.63 (d, J=6.8 Hz, 3H).

Intermediate H

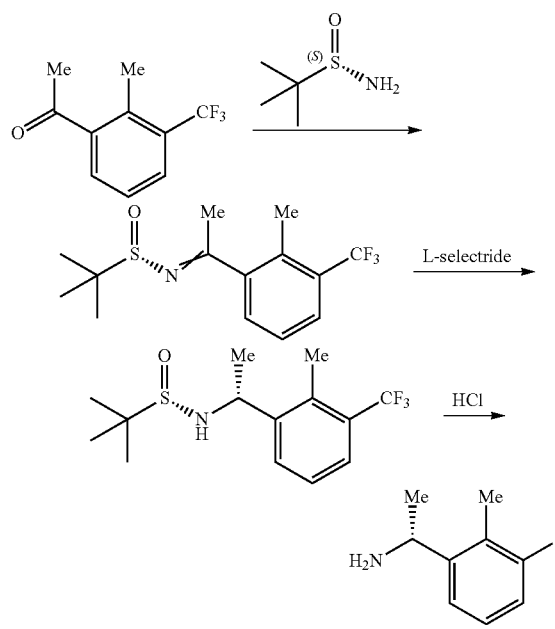

Step A: To a solution of 1-(2-methyl-3-(trifluoromethyl)phenyl)ethan-1-one (8.00 g, 39.6 mmol, 1.00 eq.) and (R)-2-methylpropane-2-sulfinamide (5.28 g, 43.5 mmol, 1.10 eq.) in THF (80.0 mL) was added titanium (IV) ethoxide (18.1 g, 79.1 mmol, 16.4 mL, 2.00 eq.). The reaction mixture was stirred at 70° C. for 2 hours. The reaction mixture was cooled at 25° C. and poured into ice-water (w/w=1/1) (80.0 mL) and stirred for 15 minutes to give a suspension. The suspension was filtered, the filtrate was extracted with ethyl acetate (50.0 mL×3). The combined organic phases were washed with brine (30.0 mL×3), dried over anhydrous sodium sulfate, filtered, and concentrated in vacuo to give a residue. The residue was purified by column chromatography (SiO₂, petroleum ether/ethyl acetate=20/1 to 3/1) to give tert-2-methyl-N-(1-(2-methyl-3-(trifluoromethyl)phenyl)ethylidene)propane-2-sulfinamide (8.00 g, 26.2 mmol, 66.2% yield) as yellow oil. LCMS [M+1]: 306.2.

¹H NMR (400 MHz, CD₃OD) δ 7.74 (br t, J=7.2 Hz, 2H), 7.57-7.51 (m, 1H), 7.46 (br t, J=7.6 Hz, 2H), 7.43-7.30 (m, 1H), 2.72 (s, 3H), 2.54 (J=6.8 Hz, 3H), 2.48 (s, 3H), 2.40 (br d, J=16.0 Hz, 3H), 1.31 (s, 9H), 1.24 (br d, J=12.4 Hz, 9H).

Step B: To a solution of S)-2-methyl-N-(1-(2-methyl-3-(trifluoromethyl)phenyl)ethylidene)propane-2-sulfinamide (8.00 g, 26.2 mmol, 1.00 eq.) in THF (80.0 mL) was added L-selectride (7.47 g, 39.3 mmol, 8.59 mL, 1.50 eq.) dropwise at −78° C. The reaction mixture was stirred at −78° C. for 2 hours. Water was added dropwise to the reaction mixture (10.0 mL) at 0° C. and the resulting mixture was stirred for 5 minutes. The aqueous phase was extracted with ethyl acetate (30.0 mL×3). The combined organic phases were washed with brine (30.0 mL×2), dried over anhydrous sodium sulfate, filtered, and concentrated in vacuo to give a residue. The residue was purified by column chromatography (SiO₂, petroleum ether/ethyl acetate=20/1 to 3/1) to give CV)-2-methyl-N—((R)-1-(2-methyl-3-(trifluoromethyl)phenyl)ethyl)propane-2-sulfinamide (3.50 g, 11.4 mmol, 43.5% yield) as yellow oil. LCMS [M+1]: 308.0.

¹H NMR (400 MHz, CD₃OD) δ=7.70 (d, J=8.0 Hz, 1H), 7.57 (d, J=1.6 Hz, 1H), 7.39-7.33 (m, 1H), 4.94-4.88 (m, 1H), 2.48 (d, J=1.2 Hz, 3H), 1.54 (d, J=6.4 Hz, 3H), 1.20 (s, 9H).

Step C: A solution of S)-2-methyl-N—((R)-1-(2-methyl-3-(trifluoromethyl)phenyl)ethyl)propane-2-sulfinamide (1.30 g, 4.23 mmol, 1.00 eq.) in HCl (4M in dioxane, 15.0 mL) was stirred at 25° C. for 30 minutes. The reaction mixture was filtered and filter cake dried in vacuo to give (R)-1-(2-methyl-3-(trifluoromethyl)phenyl)ethan-1-amine (700 mg, 2.89 mmol, 68.4% yield, 99.1% purity, hydrochloride) as a white solid. LCMS [M+H]: 204.0.

¹H NMR (400 MHz, CD₃OD) δ=7.73 (t, J=7.6 Hz, 2H), 7.54-7.49 (m, 1H), 4.92-4.88 (m, 1H), 2.52 (d, J=0.8 Hz, 3H), 1.62 (d, J=6.8 Hz, 3H).

Intermediate I

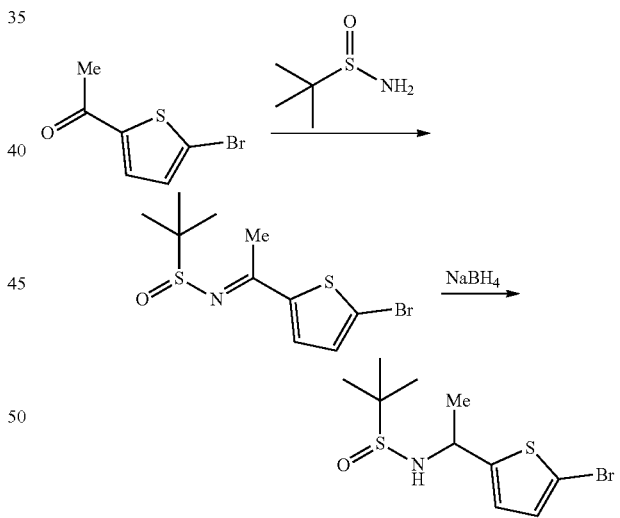

Step A: To a solution of 1-(5-bromothiophen-2-yl)ethan-1-one (11.0 g, 53.6 mmol, 1.00 eq.) in THF (120 mL) was added 2-methylpropane-2-sulfinamide (8.45 g, 69.7 mmol, 1.30 eq.) and titanium (IV) ethoxide (24.5 g, 107 mmol, 22.3 mL, 2.00 eq.), the reaction mixture was stirred at 75° C. for 12 hours under a nitrogen atmosphere. The reaction mixture was cooled to 25° C. and concentrated in vacuo to give a residue, the residue was diluted with water (200 mL) and ethyl acetate (200 mL), filtered, and the filtrate was extracted with ethyl acetate (100 mL×3). The combined organic layers were washed with brine (300 mL), dried over anhydrous sodium sulfate, filtered, and concentrated under reduced pressured to give A-(1-(5-bromothiophen-2-yl)ethylidene)-2-methylpropane-2-sulfinamide (16.0 g, crude) as a yellow solid. LCMS [M+1]: 308.0.

Step B: To a solution of A-(1-(5-bromothiophen-2-yl)ethylidene)-2-methylpropane-2-sulfinamide (16.0 g, 51.9 mmol, 1.00 eq.) in THF (150 mL) was added sodium borohydride (3.93 g, 104 mmol, 2.00 eq.) at 0° C., the reaction mixture was stirred at 20° C. for 1 hour. Saturated sodium bicarbonate aqueous solution (20.0 mL) was added to the reaction mixture dropwise, then the mixture was diluted with water (200 mL) and extracted with ethyl acetate (100 mL×3). The combined organic layers were dried over anhydrous sodium sulfate, filtered, and concentrated in vacuo to give a residue. The residue was purified by column chromatography (SiO$_2$, petroleum ether/ethyl acetate=30/1 to 2/1) to give N-(1-(5-bromothiophen-2-yl)ethyl)-2-methylpropane-2-sulfinamide (12.0 g, 38.7 mmol, 74.5% yield) as a yellow oil. LCMS [M+1]: 309.9.

Intermediate J

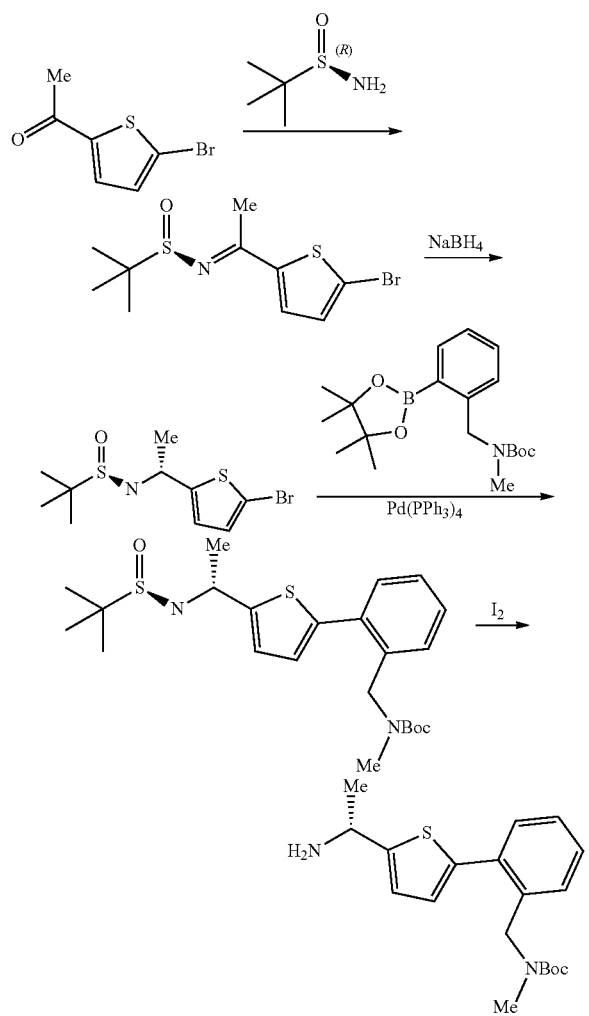

Step A: To a solution of 1-(5-bromothiophen-2-yl)ethan-1-one (10.0 g, 48.8 mmol, 1.00 eq.) and (R)-2-methylpropane-2-sulfinamide (7.68 g, 63.4 mmol, 1.30 eq.) in THF (120 mL) was added titanium (IV) ethoxide (22.3 g, 97.5 mmol, 20.2 mL, 2.00 eq.), the reaction mixture was stirred at 70° C. for 12 hours under a nitrogen atmosphere. The reaction mixture was cooled to 25° C., diluted with water (200 mL) and ethyl acetate (100 mL) to give a suspension, the suspension was filtered and the filtrate was extracted with ethyl acetate (100 mL×3). The combined organic layers were dried over sodium sulfate, filtered, and concentrated under reduced pressure to give (R, E)-N-(1-(5-bromothiophen-2-yl)ethylidene)-2-methylpropane-2-sulfinamide (13.0 g, crude) as a brown oil. LCMS [M+1]: 308.2.

$^1$H NMR (400 MHz, CDCl$_3$) δ=7.23 (d, J=4.0 Hz, 1H), 7.04 (d, J=4.0 Hz, 1H), 2.67 (s, 3H), 1.28 (s, 9H).

Step B: To a solution of (R,E)-N-(1-(5-bromothiophen-2-yl)ethylidene)-2-methylpropane-2-sulfinamide (13.0 g, 42.2 mmol, 1.00 eq.) in THF (150 mL) was added sodium borohydride (4.79 g, 127 mmol, 3.00 eq.) at 0° C. The reaction mixture was stirred at 20° C. for 2 hours under a nitrogen atmosphere. Saturate sodium bicarbonate aqueous solution (20.0 mL) was added to the mixture dropwise and diluted with water (200 mL), the resulting aqueous solution was extracted with ethyl acetate (100 mL×3), the combined organic layers were dried over sodium sulfate, filtered, and concentrated under vacuum to give a residue. The residue was purified by column chromatography (SiO$_2$, petroleum ether/ethyl acetate=30/1 to 2/1) to give (R)—N—((R)-1-(5-bromothiophen-2-yl)ethyl)-2-methylpropane-2-sulfinamide (6.00 g, 17.4 mmol, 41.3% yield, 90.0% purity) as a brown solid. LCMS [M+1]: 309.9.

$^1$H NMR (400 MHz, CDCl$_3$) δ=6.90 (d, J=3.6 Hz, 1H), 6.80 (d, J=3.6 Hz, 1H), 4.84-4.66 (m, 1H), 3.50 (d, J=2.8 Hz, 1H), 1.57 (d, J=6.4 Hz, 3H), 1.23 (s, 9H).

Step C: To a solution of (R)—N—((R)-1-(5-bromothiophen-2-yl)ethyl)-2-methylpropane-2-sulfinamide (2.00 g, 6.45 mmol, 1.00 eq.) and tert-butyl methyl(2-(4,4,5,5-tetramethyl-1,3,2-dioxaborolan-2-yl)benzyl)carbamate (2.69 g, 7.74 mmol, 1.20 eq.) in dioxane (20.0 mL) and water (2.00 mL) was added cesium carbonate (6.30 g, 19.3 mmol, 3.00 eq.) and Pd(PPh$_3$)$_4$ (745 mg, 645 µmol, 0.10 eq.) under a nitrogen atmosphere. The reaction mixture was stirred at 110° C. for 2 hours under a nitrogen atmosphere. The reaction mixture was then cooled to 25° C., diluted with water (100 mL), and extracted with ethyl acetate (50.0 mL×3). The combined organic layers were dried over sodium sulfate, filtered, and concentrated under reduced pressure to give a residue. The residue was purified by column chromatography (SiO$_2$, petroleum ether/ethyl acetate=20/1 to 1/1) to give tert-butyl (2-(5-((R)-1-(((R)-tert-butylsulfinyl)amino)ethyl)thiophen-2-yl)benzyl)(methyl)carbamate (2.60 g, 5.19 mmol, 80.6% yield, 90.0% purity) as a yellow oil. LCMS [M+1]: 451.4.

$^1$H NMR (400 MHz, CDCl$_3$) δ=7.40-7.32 (m, 2H), 7.31-7.27 (m, 1H), 7.26-7.22 (m, 1H), 7.01 (s, 1H), 6.83 (s, 1H), 4.95-4.79 (m, 1H), 4.67-4.44 (m, 2H), 3.56 (d, J=3.2 Hz, 1H), 2.93-2.56 (m, 3H), 1.64 (d, J=6.4 Hz, 3H), 1.56-1.36 (m, 9H), 1.26 (s, 9H).

Step D: To a solution of tert-butyl (2-(5-((R)-1-(((R)-tert-butylsulfinyl)amino)ethyl)thiophen-2-yl)benzyl)(methyl)carbamate (2.60 g, 5.77 mmol, 1.00 eq.) in THF (20.0 mL) and water (4.00 mL) was added iodine (439 mg, 1.73 mmol, 349 µL, 0.30 eq.), the reaction mixture was stirred at 50° C. for 2 hours. The reaction mixture was cooled to 25° C., diluted with saturate sodium bicarbonate (50.0 mL) and extracted with ethyl acetate (20.0 mL×3). The combined organic layers were dried over sodium sulfate, filtered, and concentrated under reduced pressure to give a residue. The residue was purified by column chromatography (SiO$_2$, petroleum ether/ethyl acetate=10/1 to 0/1) to give (R)-tertbutyl (R)-(2-(5-(1-aminoethyl)thiophen-2-yl)benzyl)(methyl)carbamate (1.50 g, 3.68 mmol, 63.8% yield, 85.0% purity) as a yellow oil. LCMS [2M+1]: 693.3.

$^1$H NMR (400 MHz, CDCl$_3$) δ=7.39-7.31 (m, 2H), 7.30-7.20 (m, 2H), 7.01 (d, J=2.8 Hz, 1H), 6.81 (d, J=3.2 Hz, 1H), 4.61-4.48 (m, 3H), 4.04 (s, 2H), 2.73 (s, 3H), 1.64 (d, J=6.4 Hz, 3H), 1.57-1.33 (m, 9H).

Intermediate K

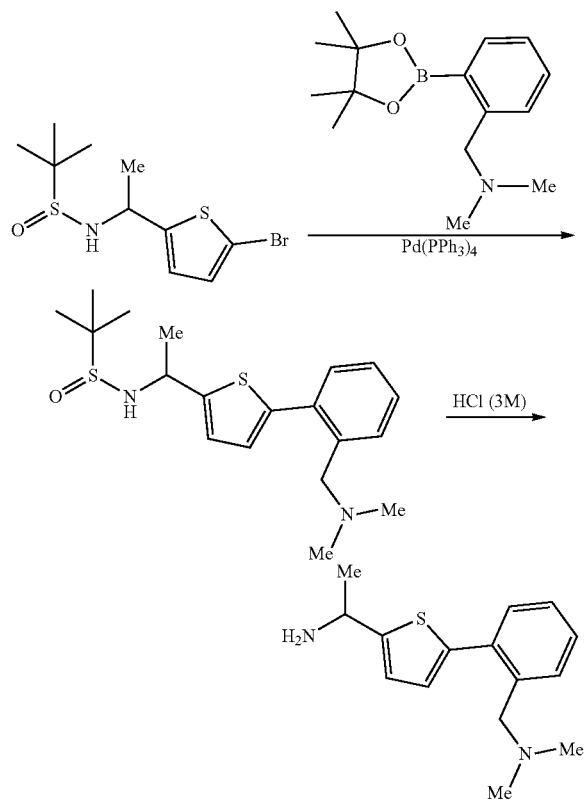

Step A: To a solution of A-(1-(5-bromothiophen-2-yl)ethyl)-2-methylpropane-2-sulfinamide (0.50 g, 1.61 mmol, 1.00 eq.) and N, N-dimethyl-1-(2-(4,4,5,5-tetramethyl-1,3,2-dioxaborolan-2-yl)phenyl)methanamine (505 mg, 1.93 mmol, 1.20 eq.) in dioxane (5.00 mL) and water (0.50 mL) was added cesium carbonate (1.58 g, 4.83 mmol, 3.00 eq.) and Pd(PPh$_3$)$_4$ (186 mg, 161 μmol, 0.10 eq.), then degassed and purged with nitrogen 3 times. The reaction mixture was stirred at 110° C. for 2 hours under a nitrogen atmosphere. Upon completion, the reaction mixture was cooled to 25° C., diluted with water (50.0 mL) and extracted with ethyl acetate (20.0 mL×3). The combined organic layers were dried over anhydrous sodium sulfate, filtered, and concentrated under reduced pressure to give a residue. The residue was purified by column chromatography (SiO$_2$, petroleum ether/ethyl acetate=20/1 to 0/1) to give N-(1-(5-(2-((dimethylamino)methyl)phenyl)thiophen-2-yl)ethyl)-2-methylpropane-2-sulfinamide (450 mg, 1.15 mmol, 71.3% yield, 93.0% purity) as a brown oil. LCMS [M+1]: 365.2.

Step B: To a solution of N-(1-(5-(2-((dimethylamino)methyl)phenyl)thiophen-2-yl)ethyl)-2-methylpropane-2-sulfinamide (410 mg, 1.12 mmol, 1.00 eq.) in THF (4.00 mL) was added hydrochloric acid (3.00 M, 375 μL, 1.00 eq.), the reaction mixture was stirred at 20° C. for 2 hours. Upon completion, the reaction mixture was diluted with saturated sodium bicarbonate (50.0 mL) and extracted with ethyl acetate (20.0 mL×3). The combined organic layers were dried over anhydrous sodium sulfate, filtered, and concentrated under reduced pressure to give a residue. The residue was purified by column chromatography (SiO$_2$, petroleum ether/ethyl acetate=10/1 to dichloromethane/methanol=10/1) to give 1-(5-(2-((dimethylamino)methyl)phenyl)thiophen-2-yl)ethanamine (200 mg, 691 μmol, 61.5% yield, 90.0% purity) as a yellow oil.

$^1$H NMR (400 MHz, DMSO-d$_6$) δ=7.48-7.42 (m, 1H), 7.41-7.36 (m, 1H), 7.34-7.28 (m, 2H), 7.13 (d, J=3.6 Hz, 1H), 6.96-6.92 (m, 1H), 4.29-4.21 (m, 1H), 3.39 (s, 2H), 2.14 (s, 6H), 1.38 (d, J=6.4 Hz, 3H).

Intermediate L

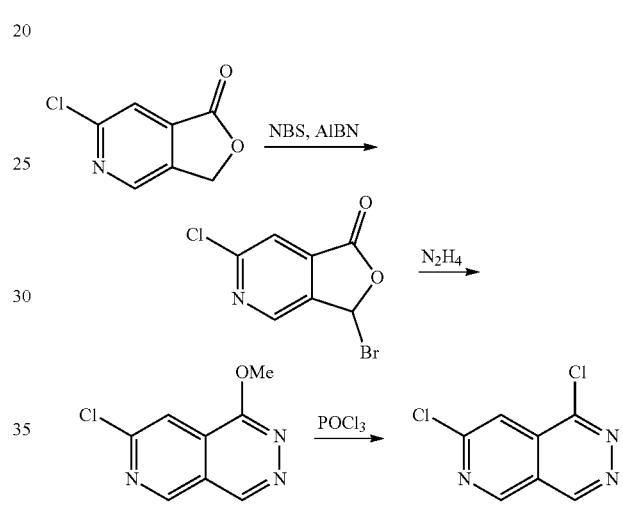

Step A: To a solution of 6-chlorofuro[3,4-c]pyridin-1(3H)-one (1.50 g, 8.85 mmol, 1.00 eq.) in carbon tetrachloride (10.0 mL) was added AIBN (145 mg, 884 μmol, 0.10 eq.) and NBS (1.42 g, 7.96 mmol, 0.9 eq.). The reaction mixture was stirred at 80° C. for 12 hours. The reaction was filtered and the filtrate was concentrated under vacuum to give a residue. The residue was purified by column chromatography (SiO$_2$, petroleum ether/ethyl acetate=50/1 to 10/1) to give 3-bromo-6-chlorofuro[3,4-c]pyridin-1(3H)-one (1.20 g, 4.83 mmol, 54.6% yield) as yellow oil. LCMS [M+3]: 249.8.

$^1$H NMR (400 MHz, CDCl$_3$) δ=8.84-8.80 (m, 1H), 7.84 (s, 1H), 7.47 (s, 1H).

Step B: To a solution of 3-bromo-6-chlorofuro[3,4-c]pyridin-1(3H)-one (1.20 g, 4.83 mmol, 1.00 eq.) in ethanol (20.0 mL) was added hydrazine hydrate (370 mg, 7.24 mmol, 359 μL, 1.50 eq.) at 0° C. The reaction mixture was stirred at 80° C. for 30 minutes. The reaction was cooled to 25° C., poured into ice water (1.00 mL) to give a suspension. The suspension was filtered, and the filter cake was collected and dried under vacuum to give 7-chloropyrido[3,4-d]pyridazin-1-ol (800 mg, 4.41 mmol, 91.2% yield) as a yellow solid. LCMS [M+1]$^+$: 182.0.

$^1$H NMR (400 MHz, DMSO-d$_6$) δ=13.08 (br s, 1H), 9.20 (s, 1H), 8.53 (s, 1H), 8.10 (s, 1H).

Step C: To a solution of 7-chloropyrido[3,4-d]pyridazin-1-ol (78.0 mg, 430 μmol, 1.00 eq.) in acetonitrile (2.00 mL) was added phosphorus (V) oxychloride (231 mg, 1.50 mmol, 139 μL, 3.50 eq.) at 25° C. The reaction mixture was stirred at 80° C. for 2 hours. The reaction was cooled at 25° C., poured into saturated sodium bicarbonate aqueous solution (2.00 mL) and stirred for 5 minutes at 0° C. The aqueous phase was extracted with ethyl acetate (3.00 mL×3). The combined organic phases were washed with brine (2.00 mL×3), dried over anhydrous sodium sulfate, filtered, and concentrated in vacuo to give 1,7-dichloropyrido[3,4-d] pyridazine (65.0 mg, crude) as a red solid. LCMS [M+1]: 199.8.

Intermediate M

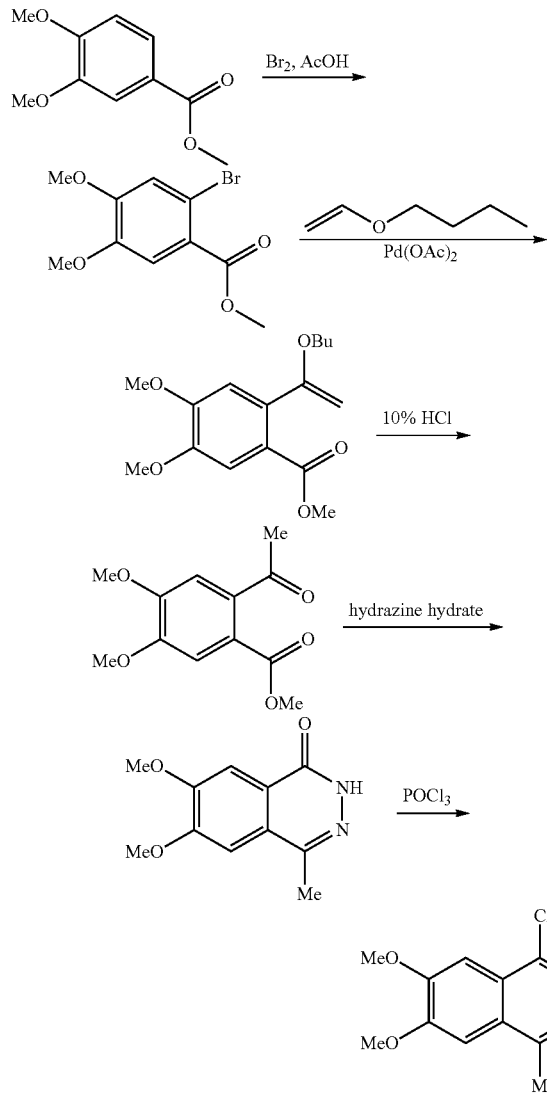

Step A: To a mixture of methyl 3,4-dimethoxybenzoate (10.0 g, 51.0 mmol, 1.00 eq.) in acetic acid (50.0 mL) was added bromine (8.96 g, 56.1 mmol, 2.89 mL, 1.10 eq.) in acetic acid (50.0 mL) at 0° C. over 1.5 hours. The mixture was then slowly brought to room temperature and stirred for 45 minutes. Upon completion, the reaction was quenched by pouring into water (700 mL) and stirred for 30 minutes, then stirring was stopped and the mixture was filtered after 1 hr of sitting. The collected solid was washed with water (100 mL) and washed with sodium sulfite aqueous solution (100 mL). The solid was partially dried, dissolved in hot methanol (300 mL), and the resultant solution was cooled. The cool methanolic solution was treated with water (200 mL) to give a suspension, the suspension was filtered, the filter cake was collected and dried in vacuo to give methyl 2-bromo-4,5-dimethoxybenzoate (9.00 g, 32.7 mmol, 64.2% yield) as a white powder. LCMS [M+1]: 275.3.

$^1$H NMR (400 MHz, DMSO-d$_6$) δ=7.36 (s, 1H), 7.24 (s, 1H), 3.84 (s, 3H), 3.82 (s, 3H), 3.79 (s, 3H).

Step B: A mixture of methyl 2-bromo-4,5-dimethoxybenzoate (6.00 g, 21.8 mmol, 1.00 eq.), 1-(vinyloxy)butane (10.9 g, 109 mmol, 14.0 mL, 5.00 eq.), Pd(OAc)$_2$ (490 mg, 2.18 mmol, 0.10 eq.), triphenylphosphine (1.14 g, 4.36 mmol, 0.20 eq.) and triethylamine (2.65 g, 26.2 mmol, 3.64 mL, 1.20 eq.) in acetonitrile (60.0 mL) was degassed and purged with nitrogen 3 times, and then the reaction mixture was stirred at 100° C. for 16 hours under a nitrogen atmosphere. The mixture was then cooled to 25° C., filtered, and the filtrate concentrated under reduced pressure to give methyl methyl 2-(1-butoxyvinyl)-4,5-dimethoxybenzoate (6.00 g, crude) was obtained as a yellow oil which was used in the next step directly.

Step C: A mixture of methyl 2-(1-butoxyvinyl)-4,5-dimethoxybenzoate (6.00 g, 20.4 mmol, 1.00 eq.) in hydrochloric acid (10% in water, 61.2 g, 168 mmol, 60.0 mL, 8.23 eq.) and THF (60.0 mL) was stirred at 20° C. for 1 hour. The reaction mixture was diluted with water (100 mL) and extracted with ethyl acetate (50.0 mL×3). The combined organic layers were brought to pH=7 with a saturated sodium bicarbonate aqueous solution, then the organic layers were washed with brine (100 mL), dried over anhydrous sodium sulfate, filtered, and concentrated under reduced pressure to give a residue. The residue was triturated with petroleum ether/ethyl acetate=5/1 (50.0 mL) at 20° C. for 20 minutes to give a suspension, the suspension was filtered, the filter cake was collected and dried in vacuo to give methyl 2-acetyl-4,5-dimethoxybenzoate (3.00 g, 12.6 mmol, 61.8% yield) as a white solid.

1H NMR (400 MHz, DMSO-d6) δ=7.26 (s, 1H), 7.17 (s, 1H), 3.86 (s, 3H), 3.84 (s, 3H), 3.77 (s, 3H), 2.46 (s, 3H).

Step D: To a solution of methyl 2-acetyl-4,5-dimethoxybenzoate (3.00 g, 12.6 mmol, 1.00 eq.) in ethanol (30.0 mL) was added hydrazine hydrate (2.22 g, 37.8 mmol, 2.16 mL, 3.00 eq.) at room temperature, and then the reaction mixture was stirred at 95° C. for 30 minutes. The reaction mixture was diluted with water (100 mL) and extracted with ethyl acetate several times. The combined organic layers were washed with brine (100 mL), dried over anhydrous sodium sulfate, filtered, and concentrated under reduced pressure to give a residue. The residue was triturated with ethyl acetate (50.0 mL) at 20° C. for 20 minutes to give a suspension, the suspension was filtered, the filter cake was collected and dried in vacuo to give 6,7-dimethoxy-4-methylphthalazin-1 (2H)-one (2.00 g, 9.08 mmol, 72.1% yield) as a off-white solid. LCMS [M+1]: 221.4.

1H NMR (400 MHz, DMSO-d6) δ=12.25 (s, 1H), 7.58 (s, 1H), 7.21 (s, 1H), 3.96 (s, 3H), 3.92 (s, 3H), 2.48 (s, 3H).

Step E: A mixture of 6,7-dimethoxy-4-methylphthalazin-1(2H)-one (1.30 g, 5.90 mmol, 1.00 eq.) in phosphorus (V) oxychloride (13.0 mL) was stirred at 120° C. for 12 hours. The reaction mixture was concentrated under reduced pressure to give 1-chloro-6,7-dimethoxy-4-methylphthalazine (1.20 g, crude) as a yellow solid. LCMS [M+1]: 239.0.

1H NMR (400 MHz, DMSO-d6) δ=7.80 (s, 1H), 7.64 (s, 1H), 4.13 (s, 3H), 4.12 (s, 3H), 3.08 (s, 3H).

Intermediate N

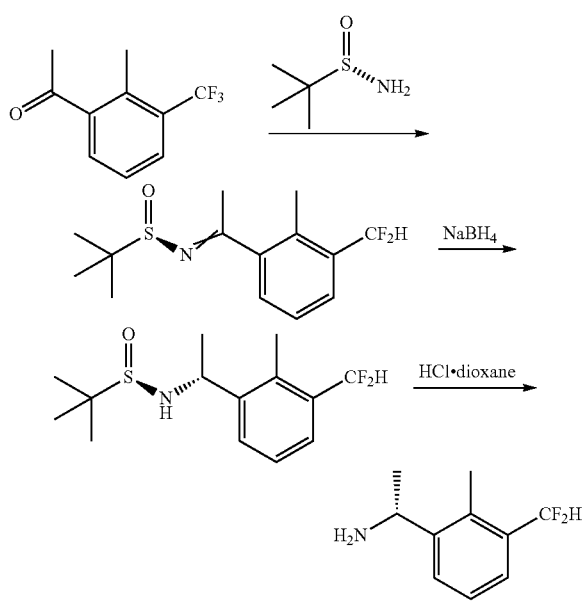

Step A: To a solution of 1-(3-(difluoromethyl)-2-methylphenyl)ethan-1-one (0.37 g, 1.99 mmol, 1.00 eq.) in tetrahydrofuran (10.0 mL) was added titanium(IV) ethoxide (2.27 g, 9.95 mmol, 2.06 mL, 5.00 eq.) and (R)-2-methylpropane-2-sulfinamide (724 mg, 5.97 mmol, 3.00 eq.). The mixture was stirred at 75° C. for 16 hours. The reaction mixture was quenched by addition saturated aqueous sodium bicarbonate 20.0 mL at 25° C. The mixture was filtered, and filtrate was extracted with ethyl acetate 45.0 mL (15.0 mL×3). The combined organic layers were washed with brine 20.0 mL (20.0 mL×1), dried over anhydrous sodium sulfate, filtered, and concentrated under reduced pressure to give a residue. The residue was purified by flash silica gel chromatography (0-12% Ethyl acetate/Petroleum ether) to give (R,E)-N-(1-(3-(difluoromethyl)-2-methylphenyl)ethylidene)-2-methylpropane-2-sulfinamide (0.36 g, 1.19 mmol, 59.8% yield, 95.0% purity) as a colorless oil.

¹H NMR (400 MHz, CD₃OD) δ=7.55-7.62 (m, 1H), 7.16-7.51 (m, 2H), 6.79-7.13 (m, 1H), 2.48-2.73 (m, 3H), 2.27-2.47 (m, 3H), 1.19-1.30 (m, 9H).

Step B: To a solution of (R,E)-N-(1-(3-(difluoromethyl)-2-methylphenyl)ethylidene)-2-methylpropane-2-sulfinamide (340 mg, 1.18 mmol, 1.00 eq.) in tetrahydrofuran (5.00 mL) was added sodium borohydride (89.5 mg, 2.37 mmol, 2.00 eq.). The mixture was stirred at 0° C. for 1 hour. The reaction mixture was quenched by addition water 10.0 mL at 25° C., and then extracted with ethyl acetate 30.0 mL (10.0 mL×3). The combined organic layers were washed with brine (10.0 mL×1) dried over anhydrous sodium sulfate, filtered, and concentrated under reduced pressure to give a residue. The residue was purified by flash silica gel chromatography (0-13% Ethyl acetate/Petroleum ether) to give (R)—N—((R)-1-(3-(difluoromethyl)-2-methylphenyl)ethyl)-2-methylpropane-2-sulfinamide (190 mg, 643 μmol, 54.4% yield, 98.0% purity) as a yellow oil. LCMS [M+1]⁺=290.1.

Step C: A mixture of (R)—N—((R)-1-(3-(difluoromethyl)-2-methyl phenyl)ethyl)-2-methylpropane-2-sulfinamide (140 mg, 484 μmol, 1.00 eq.) in dioxane hydrochloride (4.00 M, 7.00 mL, 57.9 eq) was stirred at 25° C. for 1 h. The reaction mixture was concentrated under reduced pressure to give crude product (R)-1-(3-(difluoromethyl)-2-methylphenyl)ethan-1-amine (110 mg, 475 μmol, 98.2% yield, 80.0% purity) as a white solid, which was used without further purification. LCMS [M+1]⁺=186.0.

Intermediate O

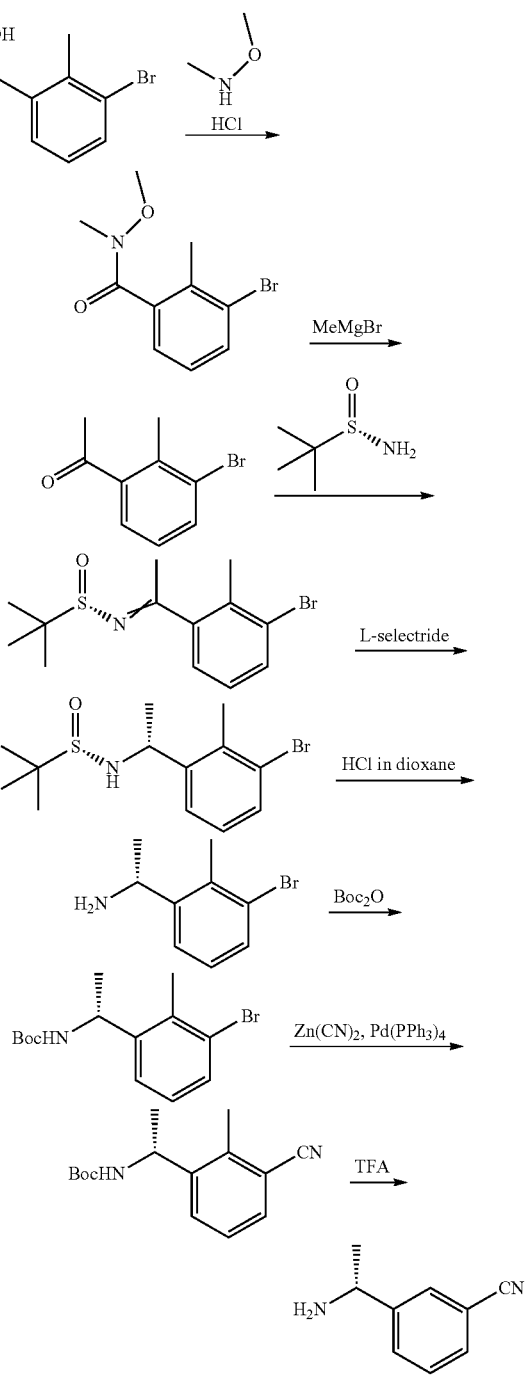

Step A: To a solution of 3-bromo-2-methylbenzoic acid (100 g, 465 mmol, 1.00 eq.) and N O-dimethylhydroxylamine hydrochloride (68.6 g, 512 mmol, 1.10 eq., HCl) in DMF (1000 mL) was added 1-[Bis(dimethylamino)methylene]-1H-1,2,3-triazolo[4,5-b]pyridinium 3-oxid hexafluorophosphate (195 g, 512 mmol, 1.10 eq.) and N,N-diisopropylethylamine (180 g, 1.40 mol, 243 mL, 3.00 eq.). The mixture was stirred at 25° C. for 2 hours, then poured into water (1000 mL) and stirred for 15 minutes. The aqueous phase was extracted with ethyl acetate (1000 mL×3). The combined organic phases were washed with brine (1000 mL×5), dried over anhydrous sodium sulfate, filtered and concentrated in vacuo to give 3 3-bromo-N-methoxy-N,2-dimethylbenzamide (120 g, crude) as yellow oil. LCMS [M+1]$^+$: 258.0.

Step B: To a solution of 33-bromo-N-methoxy-N,2-dimethylbenzamide (120 g, 465 mmol, 1.00 eq.) in THF (100 mL) was added methyl magnesium bromide (3.0 M, 180 mL, 1.16 eq.) at 0° C. The mixture was stirred between 0-40° C. for 3 hours, then the mixture was cooled to 0° C. and hydrochloric acid (6.0 N) (450 mL) was added dropwise, and stirred for 2 hours between 40-45° C. Then the mixture was cooled to 25° C. and poured into a saturated ammonium chloride solution (9000 mL). The aqueous phase was extracted with ethyl acetate (1500 mL×3). The combined organic phase was washed with brine (1000 mL×3), dried over anhydrous sodium sulfate, filtered, and concentrated under vacuum to give 1-(3-bromo-2-methylphenyl)ethan-1-one (90.0 g, 422 mmol, 90.9% yield) as yellow oil.

$^1$H NMR (400 MHz, CD$_3$OD) δ=7.70 (dd, J=1.2, 8.0 Hz, 1H), 7.62 (dd, J=0.8, 7.6 Hz, 1H), 7.19 (t, J=8.0 Hz, 1H), 2.56 (s, 3H), 2.46 (s, 3H).

Step C: To a solution of 1-(3-bromo-2-methylphenyl)ethan-1-one (88.0 g, 413 mmol, 1.00 eq.) and (<S)-2-methylpropane-2-sulfinamide (60.1 g, 496 mmol, 1.20 eq.) in THF (100 mL) was added titanium (IV) ethoxide (471 g, 2.07 mol, 428 mL, 5.00 eq.) and diglyme (55.4 g, 413 mmol, 59.1 mL, 1.00 eq.). The mixture was stirred at 80° C. for 2 hours then poured into water (300 mL) and stirred for 15 minutes. The mixture was then filtered and concentrated in vacuo to give a residue. The residue was purified by column chromatography (SiO$_2$, petroleum ether/ethyl acetate=100/1 to 40/1) to give (S)—N-(1-(3-bromo-2-methylphenyl)ethylidene)-2-methylpropane-2-sulfinamide (110 g, 348 mmol, 84.2% yield) as yellow oil.

$^1$H NMR (400 MHz, CD$_3$OD) δ=7.63 (br t, J=6.8 Hz, 2H), 7.28 (br d, J=7.6 Hz, 1H), 7.17 (t, J=8.0 Hz, 2H), 7.14-7.02 (m, 1H), 2.67 (s, 3H), 2.50 (br d, J=4.8 Hz, 3H), 2.42 (s, 3H), 2.31 (br d, J=17.2 Hz, 3H), 1.31-1.26 (m, 9H), 1.24-1.16 (m, 9H)

Step D: To a solution of (S)—N-(1-(3-bromo-2-methylphenyl)ethylidene)-2-methylpropane-2-sulfinamide (109 g, 345 mmol, 1.00 eq.) in THF (1100 mL) was added L-selectride (1.0 M, 689 mL, 2.00 eq.) at −78° C. The mixture was stirred at −78° C. for 2 hours then poured into a saturated aqueous solution of ammonium chloride (1000 mL) and stirred for 60 minutes at 25° C. The aqueous phase was extracted with ethyl acetate (1000 mL×3). The combined organic phase were washed with brine (500 mL×3), dried over anhydrous sodium sulfate, filtered, and concentrated under vacuum to give a residue. The residue was purified by column chromatography (SiO$_2$, petroleum ether/ethyl acetate=100/1 to 2/1) to give a residue. The residue was further washed with petroleum ether to give (S)—N—((R)-1-(3-bromo-2-methylphenyl)ethyl)-2-methylpropane-2-sulfinamide (70.0 g, 220 mmol, 63.8% yield) as a white solid. LCMS [M+1]$^+$: 318.1.

Step E: To a solution of (R)—N—((R)-1-(3-bromo-2-methylphenyl)ethyl)-2-methylpropane-2-sulfinamide (71.0 g, 223 mmol, 1.00 eq.) in an HCl/dioxane solution (300 mL) and MeOH (300 mL) was stirred at 0° C. for 30 minutes. The mixture was concentrated in vacuo to give a (R)-1-(3-bromo-2-methylphenyl)ethan-1-amine (55.0 g, crude, HCl) as a white solid. LCMS [M+1]$^+$: 214.1.

Step F: To a solution of (R)-1-(3-bromo-2-methylphenyl)ethan-1-amine (55.0 g, 220 mmol, 1.00 eq., HCl) and Boc$_2$O (48.4 g, 222 mmol, 50.9 mL, 1.01 eq.) in dichloromethane (500 mL) was added N,N-diisopropylethylamine (56.7 g, 439 mmol, 76.5 mL, 2.00 eq.). The mixture was stirred between 0-25° C. for 30 minutes, then concentrated under vacuum to give a residue. The residue was purified by column chromatography (SiO$_2$, petroleum ether/ethyl acetate=1/0 to 100/1) to give a residue. The residue was further washed with petroleum ether to give tert-butyl (R)-(1-(3-bromo-2-methylphenyl)ethyl)carbamate (51.0 g, 162 mmol, 73.9% yield) as a white solid. LCMS [M−55]$^+$: 258.0.

$^1$H NMR (400 MHz, CD$_3$OD) δ=7.43 (d, J=8.0 Hz, 1H), 7.32 (d, J=8.0 Hz, 1H), 7.10-7.03 (m, 1H), 4.93 (br d, J=6.4 Hz, 2H), 2.45 (s, 3H), 1.41 (br s, 9H), 1.33 (d, J=6.8 Hz, 3H).

Step G: To a solution of tert-butyl (R)-(1-(3-bromo-2-methylphenyl)ethyl)carbamate (51.0 g, 162 mmol, 1.00 eq.) in DMF (540 mL) was added zinc cyanide (22.9 g, 195 mmol, 12.4 mL, 1.20 eq.) and Pd(PPh$_3$)$_4$ (18.8 g, 16.2 mmol, 0.10 eq.). The mixture was stirred at 110° C. for 3 hours, then cooled to 25° C. and poured into water (500 mL). The aqueous phase was extracted with ethyl acetate (100 mL×3). The combined organic phases were washed with brine (1000 mL×3), dried over anhydrous sodium sulfate, filtered, and concentrated under vacuum to give a residue. The residue was purified by column chromatography (SiO$_2$, petroleum ether/ethyl acetate=100/1 to 5/1) to give tert-butyl (R)-(1-(3-cyano-2-methylphenyl)ethyl)carbamate (37.0 g, 142.1 mmol, 87.6% yield) as a white solid. LCMS [M−55]$^+$: 205.0.

$^1$H NMR (400 MHz, CD$_3$OD) δ=7.63 (d, J=7.6 Hz, 1H), 7.54 (d, J=7.2 Hz, 1H), 7.39-7.30 (m, 1H), 4.93 (br d, J=6.8 Hz, 1H), 2.58 (s, 3H), 1.40 (br s, 9H), 1.34 (d, J=7.2 Hz, 3H).

Step H: To a solution of tert-butyl (R)-(1-(3-cyano-2-methylphenyl)ethyl)carbamate (49.0 g, 188 mmol, 1.00 eq.) in dichloromethane (400 mL) was added TFA (133 mL). The mixture was stirred at 0° C. for 30 minutes then poured into saturated sodium bicarbonate solution (200 mL) and stirred for and additional 30 minutes. The aqueous phase was extracted with ethyl acetate (1000 mL×3). The combined organic phases were washed with brine (200 mL×3), dried over anhydrous sodium sulfate, filtered, and concentrated under vacuum to give (R)-3-(1-aminoethyl)-2-methylbenzonitrile (26.0 g, 162 mmol, 86.2% yield) as yellow oil. LCMS [M−16]$^+$: 144.1.

$^1$H NMR (400 MHz, DMSO-d$_6$) δ=8.36 (br s, 2H), 7.86 (d, J=8.0 Hz, 1H), 7.80 (dd, J=0.8, 7.6 Hz, 1H), 7.51 (t, J=8.0 Hz, 1H), 4.68 (q, J=6.8 Hz, 1H), 2.55 (s, 3H), 1.48 (d, J=6.8 Hz, 3H).

SFC conditions: Column: Chiralpak IC-3 50×4.6 mm I.D., 3 μm Mobile phase: Phase A for CO$_2$, and Phase B for MeOH (0.05% DEA); Gradient elution: MeOH (0.05% DEA) in CO$_2$ from 5% to 40% Flow rate: 3 mL/min; Detector: PDA Column Temp: 35° C.; Back Pressure: 100 Bar.

Intermediate P

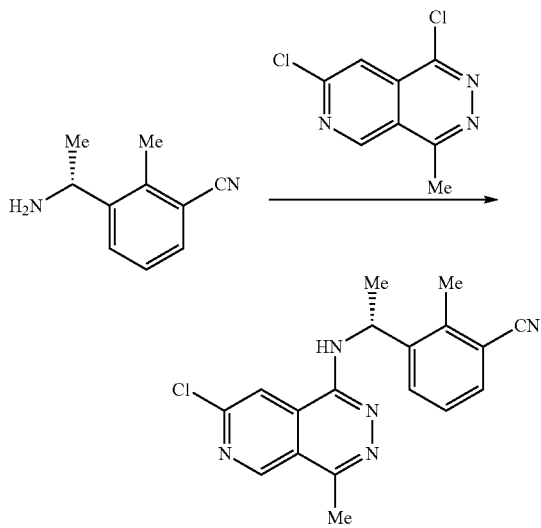

To a solution of (R)-3-(1-aminoethyl)-2-methylbenzonitrile (16.0 g, 99.9 mmol, 1.00 eq.) and 1,7-dichloro-4-methylpyrido[3,4-d]pyridazine (21.4 g, 99.9 mmol, 1.00 eq.) in DMSO (130 mL) was added cesium fluoride (22.8 g, 150 mmol, 5.52 mL, 1.50 eq.), and the mixture was stirred at 130° C. for 2 hours. The mixture was then cooled to 25° C., diluted with water (200 mL), and extracted with ethyl acetate (200 mL×3). The combined organic phases were washed with brine (100 mL×3), dried over anhydrous sodium sulfate, filtered, and concentrated under reduced pressure. The residue was purified by prep-HPLC [column: Kromasil Eternity XT 250×80 mm×10 um; mobile phase: phase A: water (0.1% TFA), phase B: acetonitrile; B %: 25%-55%]. To the combined fractions were combined and the pH was adjusted to pH=8 using aqueous sodium bicarbonate. The suspension was extracted with ethyl acetate (1000 mL×3), and the combined organic phases were washed with brine (100 mL×3), dried over anhydrous sodium sulfate, filtered, and concentrated under reduced pressure to give (R)-3-(1-((7-chloro-4-methylpyrido[3,4-d]pyridazin-1-yl)amino)ethyl)-2-methylbenzonitrile (14.5 g, 42.9 mmol, 43.0% yield) as a yellow solid.

$^1$H NMR (400 MHz, CDCl$_3$) δ=9.19 (d, J=0.4 Hz, 1H), 7.74 (s, 1H), 7.63 (d, J=8.0 Hz, 1H), 7.50 (dd, J=1.2, 7.6 Hz, 1H), 7.23 (t, J=7.6 Hz, 1H), 5.72 (quin, J=6.8 Hz, 1H), 5.40 (br d, J=6.0 Hz, 1H), 2.86 (s, 3H), 2.69 (s, 3H), 1.63 (s, 3H).

Intermediate Q

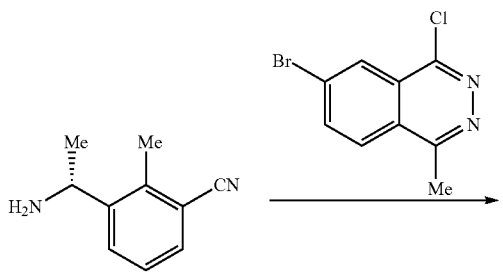

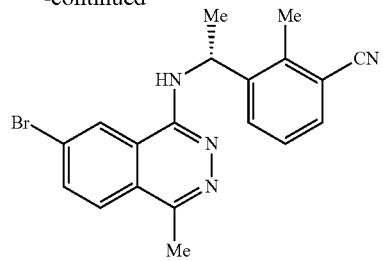

To a solution of (R)-3-(1-aminoethyl)-2-methylbenzonitrile (5.32 g, 19.4 mmol, 1.00 eq., TFA) and 6-bromo-4-chloro-1-methylphthalazine (5.00 g, 19.4 mmol, 1.00 eq.) in DMSO (30.0 mL) was added cesium fluoride (5.90 g, 38.8 mmol, 1.43 mL, 2.00 eq.) and N,N-diisopropylethylamine (5.02 g, 38.8 mmol, 6.76 mL, 2.00 eq.) and the mixture was stirred at 130° C. for 2 hours. The mixture was then cooled to 25° C., diluted with water (10.0 mL), and the aqueous phase was extracted with ethyl acetate (100 mL×3). The combined organic phases were washed with brine (100 mL×3), dried over anhydrous sodium sulfate, filtered, and concentrated under reduced pressure. The residue was purified by column chromatography (SiO$_2$, petroleum ether/ethyl acetate=20/1 to 2/1) to give (R)-3-(1-((7-bromo-4-methylphthalazin-1-yl)amino)ethyl)-2-methylbenzonitrile (5.20 g, 13.6 mmol, 70.2% yield) as a yellow solid. LCMS [M+1]$^+$: 381.1.

Intermediate R

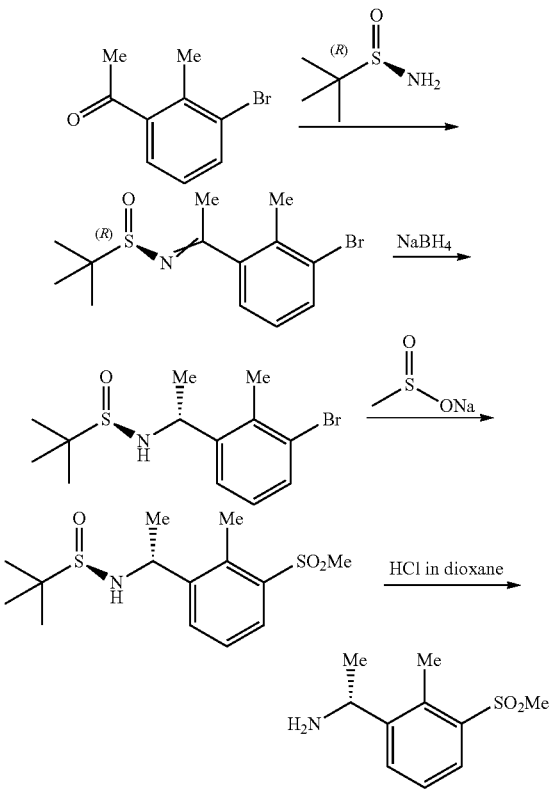

Step A: A mixture of (R)-2-methylpropane-2-sulfinamide (5.12 g, 42.2 mmol, 1.00 eq.), 1-(3-bromo-2-methylphenyl)

ethan-1-one (9.00 g, 42.2 mmol, 1.00 eq.), titanium (IV) isopropoxide (60.0 g, 211 mmol, 62.3 mL, 5.00 eq.) in THF (90.0 mL) was degassed and purged with nitrogen 3 times, and stirred at 80° C. for 12 hours. The mixture was cooled to 25° C., quenched by addition of water (100 mL), filtered, and the filtrate was partitioned between ethyl acetate (300 mL) and water (300 mL). The organic phase was dried over sodium sulfate, filtered, and concentrated under reduced pressure to give a residue. The residue was purified by column chromatography (SiO$_2$, petroleum ether/ethyl acetate=1/0 to 5/1) (R)—N-(1-(3-bromo-2-methylphenyl)ethylidene)-2-methylpropane-2-sulfinamide (7.23 g, 22.8 mmol, 54.1% yield) as a yellow solid. LCMS [M+3]$^+$: 318.0.

$^1$H NMR (400 MHz, CD$_3$OD) δ=7.67-7.58 (m, 2H), 7.28 (br d, J=7.6 Hz, 1H), 7.17 (t, J=8.0 Hz, 2H), 7.14-7.01 (m, 1H), 2.67 (s, 3H), 2.50 (br d, J=4.0 Hz, 3H), 2.42 (s, 3H), 2.31 (br d, J=17.2 Hz, 3H), 1.28 (s, 9H), 1.21 (br d, J=11.2 Hz, 9H). (the ratio of E/Z isomers was ~1/1).

Step B: To a solution of (R)—N-(1-(3-bromo-2-methylphenyl)ethylidene)-2-methylpropane-2-sulfinamide (400 mg, 1.26 mmol, 1.00 eq.) in THF (5.00 mL) was added sodium borohydride (239 mg, 6.32 mmol, 5.00 eq.) at 0° C. portionwise, then the reaction was stirred at 25° C. for 1 hour. The reaction mixture was poured into water (30.0 mL) and stirred for 5 minutes. The resulting aqueous phase was extracted with ethyl acetate (150 mL×3), and the combined organic phases were washed with brine (150 mL×3), dried over anhydrous sodium sulfate, filtered, and concentrated under reduced pressure. The residue was purified by column chromatography (SiO$_2$, petroleum ether/ethyl acetate=10/l to 1/1) to give (R)—N—((R)-1-(3-bromo-2-methylphenyl)ethyl)-2-methylpropane-2-sulfinamide (200 mg, 628 µmol, 49.7% yield) as a brown oil.

Step C: To a mixture of (R)—N—((R)-1-(3-bromo-2-methylphenyl)ethyl)-2-methylpropane-2-sulfinamide (250 mg, 786 µmol, 1.00 eq), sodium methanesulfinate (176 mg, 1.73 mmol, 2.20 eq.), potassium carbonate (326 mg, 2.36 mmol, 3.00 eq.) and L-proline (18.1 mg, 157 µmol, 0.20 eq.) in dimethyl sulfoxide (3.00 mL) was added copper (I) iodide (15.0 mg, 78.6 µmol, 0.10 eq.) at 20° C., the mixture was stirred at 130° C. for 3 hours under a nitrogen atmosphere. To the mixture was added water (15.0 mL), and the mixture was extracted with ethyl acetate (20.0 mL×3). The combined organic phases were washed with brine (30.0 mL×3), dried over anhydrous sodium sulfate, filtered, and concentrated under reduced pressure to give a residue. The residue was purified by prep-TLC (silica gel plate, petroleum ether/ethyl acetate=1/1) to give (R)-2-methyl-N—((R)-1-(2-methyl-3-(methylsulfonyl)phenyl)ethyl)propane-2-sulfinamide (120 mg, 378 µmol, 48.1% yield) as a yellow oil. LCMS [M+1]$^+$: 318.1.

$^1$H NMR (400 MHz, DMSO-d$_6$) δ=7.85 (dd, J=8.0, 1.2 Hz, 1H), 7.78 (d, J=7.6 Hz, 1H), 7.46 (t, J=8.0 Hz, 1H), 5.42-5.50 (m, 1H), 4.71-4.80 (m, 1H), 3.22 (s, 3H), 2.65 (s, 3H), 1.46 (d, J=6.8 Hz, 3H), 1.09 (s, 9H).

Step D: A mixture of (R)-2-methyl-N—((R)-1-(2-methyl-3-(methylsulfonyl)phenyl)ethyl)propane-2-sulfinamide (120 mg, 378 µmol, 1.00 eq.) in hydrochloric acid (4.0 M in dioxane, 2.00 mL, 21.2 eq.) was stirred at 20° C. for 1 hour. The mixture was concentrated under reduced pressure to give (R)-1-(2-methyl-3-(methylsulfonyl)phenyl)ethan-1-amine (91.0 mg, crude, HCl) as a white solid.

Intermediate S

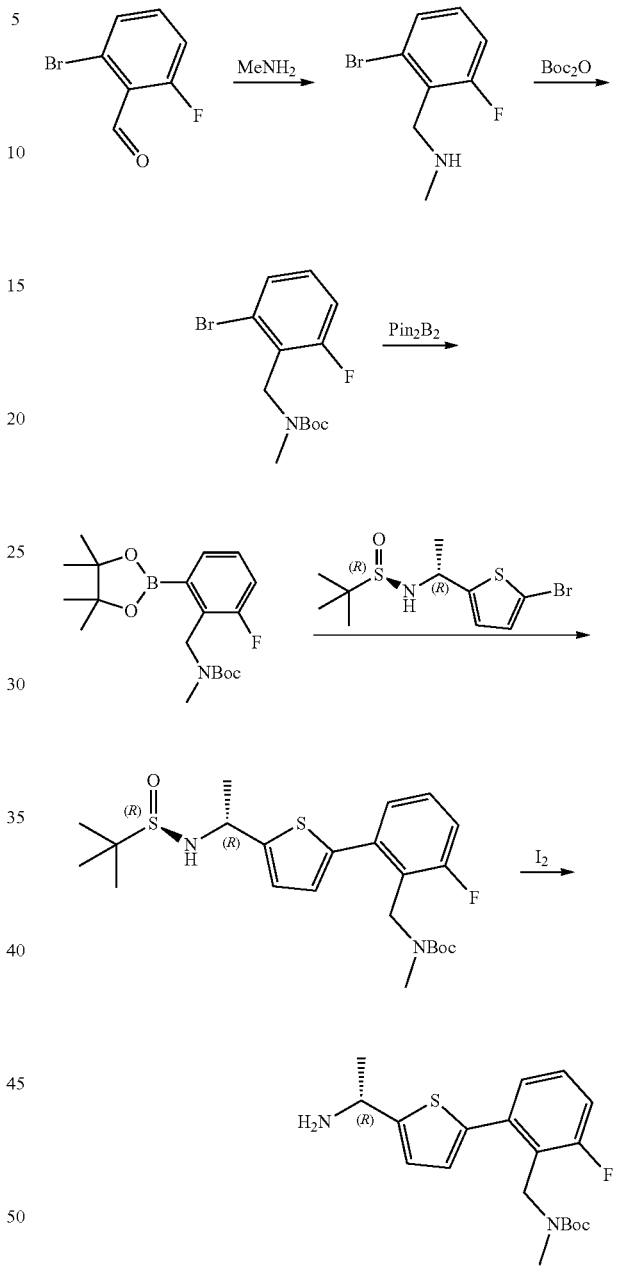

Step A: To a solution of methyl amine (100 g, 1.48 mol, 3.01 eq. HCl salt) in THF (1.00 L) was added N, N-diisopropylethylamine (237 g, 1.84 mol, 3.73 eq.), 2-bromo-6-fluorobenzaldehyde (100 g, 493 mmol, 1.00 eq.), acetic acid (9.00 g, 150 mmol, 0.30 eq.) and sodium cyanoborohydride (62.0 g, 987 mmol, 2.00 eq.). The reaction mixture was stirred at 25° C. for 3 hours, then diluted with water (500 mL) and extracted with ethyl acetate (1.00 L×2). The combined organic phases were washed with brine (500 mL), dried over sodium sulfate, filtered, and concentrated under vacuum to give 1-(2-bromo-6-fluorophenyl)-N-methylmethanamine (120 g, 484 mmol, 88% purity) as off white solid which was used in the next step directly. LCMS [M+1]$^+$: 218.0.

Step B: To a solution of 1-(2-bromo-6-fluorophenyl)-N-methylmethanamine (120 g, 484 mmol, 88% purity, 1.00 eq.) in THF (1.00 L) was added di-tert-butyl dicarbonate (211 g, 968 mmol, 2.00 eq.), and the mixture was stirred at 25° C. for 2 hours. The mixture was then concentrated in vacuo to give a residue. The residue was purified by column chromatography (SiO$_2$, petroleum ether/ethyl acetate=1/0 to 100/1) to give tert-butyl A-[(2-bromo-6-fluoro-phenyl)methyl]-N-methyl-carbamate (70.0 g, 220 mmol) as a brown oil. LCMS [M−55]+: 261.9

$^1$H NMR (400 MHz, DMSO-d6) δ=7.49 (d, J=7.6 Hz, 1H), 7.33-7.26 (m, 2H), 4.57 (s, 2H), 2.64 (s, 3H), 1.38 (s, 9H).

Step C: To a solution of tert-butyl (2-bromo-6-fluorobenzyl)(methyl)carbamate (60.0 g, 189 mmol, 1.00 eq.) and 4,4,4',4',5,5,5',5'-octamethyl-2,2'-bi(1,3,2-dioxaborolane) (60.0 g, 236 mmol, 1.25 eq.) in dioxane (600 mL) was added Pd(dppf)Cl$_2$—CH$_2$Cl$_2$ (15.0 g, 18.4 mmol, 0.10 eq.) and potassium acetate (72.0 g, 734 mmol, 3.89 eq.). The reaction mixture was degassed with nitrogen (3 times) and stirred at 100° C. for 12 hours under a nitrogen atmosphere. The mixture was cooled to 25° C. and concentrated under vacuum to give a residue. The residue was purified by column chromatography (SiO$_2$, petroleum ether/ethyl acetate=1/0 to 100/1) to give tert-butyl (2-fluoro-6-(4,4,5,5-tetramethyl-1,3,2-dioxaborolan-2-yl)benzyl)(methyl)carbamate (80.0 g, 160 mmol, 73% purity) as a yellow oil. LCMS [M−55]$^+$: 266.1.

Step D: To a solution of tert-butyl (2-fluoro-6-(4,4,5,5-tetramethyl-1,3,2-dioxaborolan-2-yl)benzyl)(methyl)carbamate (80.0 g, 160 mmol, 73% purity, 1.00 eq.) and (R)—N-[(1R)-1-(5-bromo-2-thienyl)ethyl]-2-methyl-propane-2-sulfinamide (56.0 g, 180 mmol, 1.13 eq.) in dioxane (500 mL) and water (100 mL) was added cesium carbonate (150 g, 460 mmol, 2.88 eq.) and Pd(PPh$_3$)$_4$ (20.0 g, 17.3 mmol, 0.10 eq.) under a nitrogen atmosphere and the mixture was stirred at 100° C. for 3 hours under a nitrogen atmosphere. The mixture was diluted with water (500 mL), extracted with ethyl acetate (1.00 L×2), the organic phase was washed with brine (200 mL), dried over sodium sulfate, filtered and concentrated in vacuo to give a residue. The residue was purified by column chromatography (SiO$_2$, petroleum ether/ethyl acetate=0/1 to 5/1) to give tert-butyl (2-(5-((R)-1-(((R)-tert-butylsulfinyl)amino)ethyl)thiophen-2-yl)-6-fluorobenzyl)(methyl)carbamate (84.0 g, 152 mmol, 85% purity) as a yellow oil. LCMS [M−100]$^+$: 369.1.

$^1$H NMR (400 MHz, DMSO-d$_6$) δ=7.44-7.36 (m, 1H), 7.27-7.17 (m, 2H), 7.08 (br d, J=2.8 Hz, 1H), 6.96 (d, J=3.6 Hz, 1H), 5.88 (br d, J=6.8 Hz, 1H), 4.65 (quin, J=6.4 Hz, 1H), 4.56 (s, 2H), 2.48 (s, 3H), 1.55 (br d, J=6.8 Hz, 3H), 1.33 (br s, 9H), 1.13 (s, 9H).

Step E: To a solution of tert-butyl (2-(5-((R)-1-(((R)-tert-butylsulfinyl)amino)ethyl)thiophen-2-yl)-6-fluorobenzyl)(methyl)carbamate (80.0 g, 145 mmol, 85% purity, 1.00 eq.) in THF (240 mL) and water (48.0 mL) was added iodine (6.80 g, 26.8 mmol, 0.19 eq.). The reaction was heated 50° C. for 2 hours, then diluted with water (500 mL) and extracted with ethyl acetate (500 mL×2). The organic phases were washed with brine (200 mL), dried over sodium sulfate, filtered and concentrated in vacuo to give a residue. The residue was purified by column chromatography (SiO$_2$, dichloromethane/methanol=300/1 to 10/1) to give tert-butyl (R)-(2-(5-(1-aminoethyl)thiophen-2-yl)-6-fluorobenzyl)(methyl)carbamate (40.0 g, 110 mmol) as yellow oil. LCMS [M−16]$^+$: 348.1.

Intermediate T

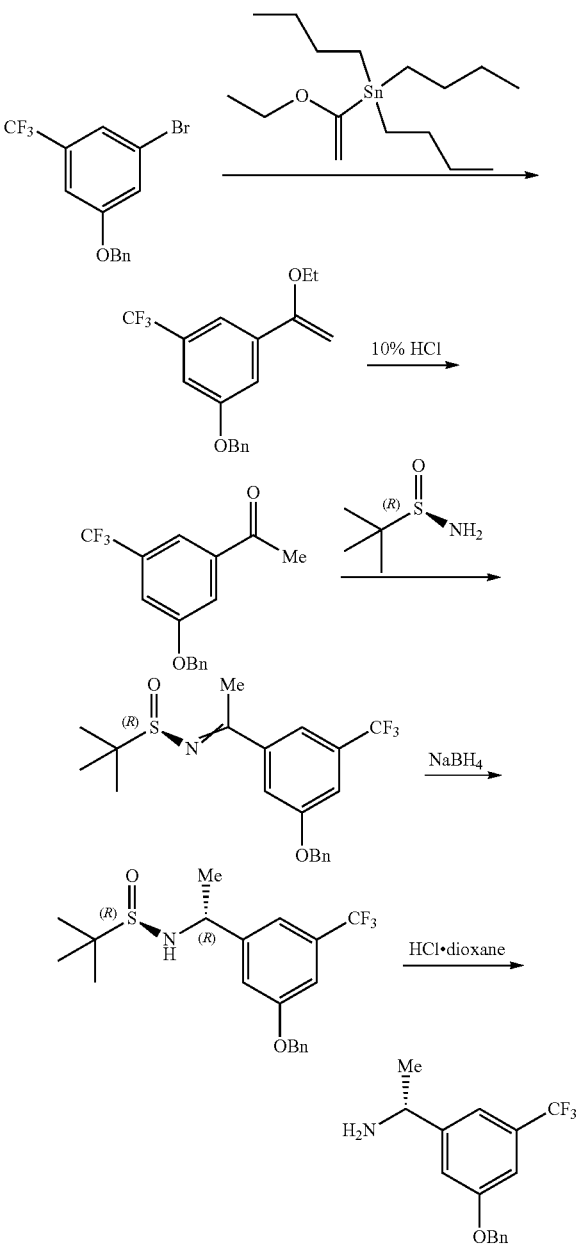

Step A: To a mixture of 1-(benzyloxy)-3-bromo-5-(trifluoromethyl)benzene (3.00 g, 9.06 mmol, 1.00 eq.) and Pd(dppf)Cl2 (663 mg, 906 μmol, 0.10 eq.) in dioxane (50.0 mL) was added tributyl(1-ethoxyvinyl)tin (5.00 g, 13.8 mmol, 4.67 mL, 1.53 eq.) at 20° C., and the mixture was stirred at 80° C. for 12 hours under a nitrogen atmosphere. To this mixture was then added saturated potassium fluoride solution (100 mL) and the solution was stirred at 20° C. for 1 hour. The mixture was extracted with ethyl acetate (100 mL×3), and the combined organic phases were washed with brine (100 mL×3), dried over anhydrous sodium sulfate, filtered, and concentrated under reduced pressure to give a crude 1-(benzyloxy)-3-(1-ethoxyvinyl)-5-(trifluoromethyl)benzene (2.90 g, crude) as a yellow oil. This crude oil was used in the next step without further purification.

Step B: To a solution of 1-(benzyloxy)-3-(1-ethoxyvinyl)-5-(trifluoromethyl)benzene (2.90 g, 9.00 mmol, crude, 1.00 eq.) in tetrahydrofuran (30.0 mL) was added hydrochloric acid (3.0 M in THF, 10.0 mL, 3.33 eq.), and the solution was stirred at 20° C. for 1 hour. The mixture was then diluted with water (60.0 mL), extracted with ethyl acetate (20.0 mL×3), dried over anhydrous sodium sulfate, filtered, and concentrated under reduced pressure. The residue was purified by column chromatography (silica gel, petroleum ether/ethyl acetate=50/1 to 10/1) to give 1-(3-(benzyloxy)-5-(trifluoromethyl)phenyl)ethan-1-one (2.60 g, 8.84 mmol, 98.2% yield) as a yellow oil.

$^1$H NMR (400 MHz, CDCl$_3$) δ=7.79 (s, 1H), 7.74 (s, 1H), 7.45-7.39 (m, 6H), 5.16 (s, 2H), 2.63 (s, 3H).

Step C: To a solution of 1-(3-(benzyloxy)-5-(trifluoromethyl)phenyl)ethan-1-one (2.60 g, 8.84 mmol, 1.00 eq.) and (R)-2-methylpropane-2-sulfinamide (1.39 g, 11.5 mmol, 1.30 eq.) in tetrahydrofuran (40.0 mL) was added titanium (IV) ethoxide (5.02 g, 17.7 mmol, 5.22 mL, 2.00 eq.) under a nitrogen atmosphere, and the solution was stirred at 70° C. for 12 hours. The mixture was then concentrated under reduced pressure, and the residue was purified by column chromatography (silica gel, petroleum ether/ethyl acetate=20/1 to 10/1) to give (R)—N-(1-(3-(benzyloxy)-5-(trifluoromethyl)phenyl)ethylidene)-2-methylpropane-2-sulfinamide (2.20 g, 5.03 mmol, 57.0% yield) as a yellow oil.

$^1$H NMR (400 MHz, CDCl3) δ=7.45 (d, J=10.0 Hz, 2H), 7.24-7.13 (m, 6H), 4.94 (s, 2H), 2.56 (s, 3H), 1.10 (s, 9H).

Step D: To a mixture of (R)—N-(1-(3-(benzyloxy)-5-(trifluoromethyl)phenyl)ethylidene)-2-methylpropane-2-sulfinamide (2.20 g, 5.54 mmol, 1.00 eq.) in tetrahydrofuran (30.0 mL) was added sodium borohydride (270 mg, 7.14 mmol, 1.29 eq.) at 0° C., and the mixture was stirred at 20° C. for 3 hours. To the mixture was added saturated aqueous ammonium chloride solution (80.0 mL) and the resulting mixture was stirred at 20° C. for 30 minutes. The mixture was then extracted with ethyl acetate (80.0 mL×3), and the combined organic phases were washed with brine (80.0 mL×3), dried over anhydrous sodium sulfate, filtered, and concentrated under reduced pressure. The residue was purified by column chromatography on silica gel (petroleum ether/ethyl acetate=50/1 to 3/1) to give (R)—N—((R) 1-(3-(benzyloxy)-5-(trifluoromethyl)phenyl)ethyl)-2-methylpropane-2-sulfinamide (1.20 g, 3.00 mmol, 54.3% yield) as a yellow oil.

$^1$H NMR (400 MHz, CDCl$_3$) δ=7.53-7.32 (m, 5H), 7.23-7.12 (m, 3H), 5.12 (s, 2H), 4.62-4.53 (m, 1H), 3.43 (d, J=2.8 Hz, 1H), 1.53 (d, J=6.4 Hz, 3H), 1.25 (s, 9H).

Step E: To a solution of (R)—N—((R)-1-(3-(benzyloxy)-5-(trifluoromethyl)phenyl)ethyl)-2-methylpropane-2-sulfinamide (1.20 g, 3.00 mmol, 1.00 eq.) was added hydrochloric acid (4.0 M in dioxane, 751 μL, 1.00 eq.), and the solution was stirred at 20° C. for 20 minutes. The mixture was concentrated under reduced pressure to remove to give (R)-1-(3-(benzyloxy)-5-(trifluoromethyl)phenyl)ethan-1-amine (1.20 g, crude, HCl) as a white solid, which was used without further purification.

$^1$H NMR (400 MHz, CDCl$_3$) δ=8.82 (s, 2H), 7.44-7.31 (m, 8H), 5.09 (s, 2H), 4.42 (s, 1H), 1.43 (s, 3H).

Intermediate U

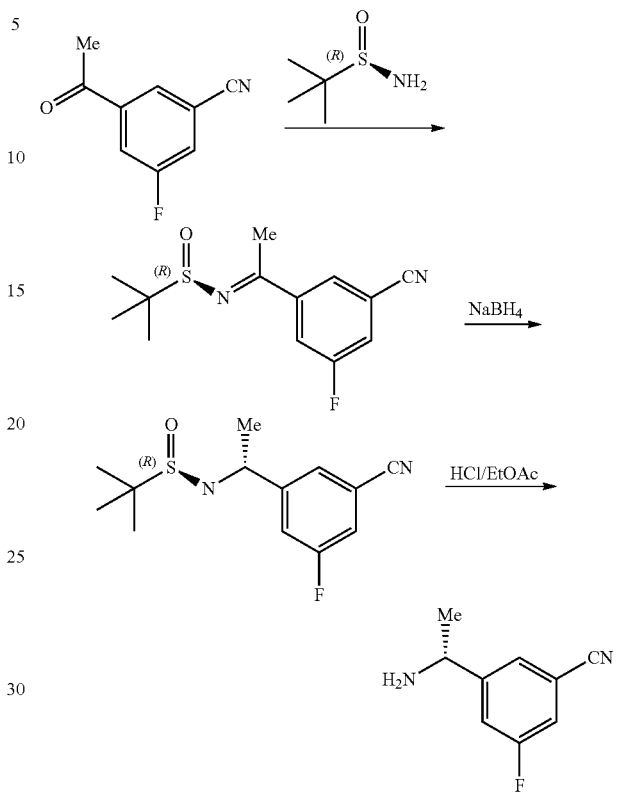

Step A: To a solution of 3-acetyl-5-fluorobenzonitrile (2.00 g, 12.3 mmol, 1.00 eq.) in tetrahydrofuran (20.0 mL) was added titanium ethoxide (5.59 g, 24.5 mmol, 5.08 mL, 2.00 eq.) and (R)-2-methylpropane-2-sulfinamide (1.93 g, 15.9 mmol, 1.30 eq.). The mixture was degassed and purged with nitrogen 3 times, then t stirred at 70° C. for 12 hours under a nitrogen atmosphere. The mixture was diluted with water (20.0 mL) and filtered. The filtrate was extracted with ethyl acetate (30.0 mL×3), dried over anhydrous sodium sulfate, filtered, and concentrated under reduced pressure to give a residue. The residue was purified by column chromatography (SiO$_2$, petroleum ether/ethyl acetate=50/1 to 1/1) to give (R,E)-N-(1-(3-cyano-5-fluorophenyl)ethylidene)-2-methylpropane-2-sulfinamide (1.01 g, 3.68 mmol, 30.0% yield, 97.5% purity) as a yellow oil. LCMS [M+1]$^+$: 267.1.

$^1$H NMR (400 MHz, CDCl$_3$) δ=7.93 (s, 1H), 7.82-7.79 (m, 1H), 7.45-7.52 (m, 1H), 2.79 (s, 3H), 1.35 (s, 9H).

Step B: To a solution of (R,E)-N-(1-(3-cyano-5-fluorophenyl)ethylidene)-2-methylpropane-2-sulfinamide (900 mg, 3.38 mmol, 1.00 eq.) in tetrahydrofuran (10.0 mL) was added sodium borohydride (383 mg, 10.1 mmol, 3.00 eq.) at 0° C. Then the mixture was warmed to 20° C. and stirred for 2 hours. The mixture was quenched with saturated ammonium chloride aqueous solution (20.0 mL) at 25° C., extracted with ethyl acetate (20.0 mL×3), dried over anhydrous sodium sulfate, filtered, and concentrated under reduced pressure to give a residue. The residue was purified by column chromatography (SiO$_2$, petroleum ether/ethyl acetate=20/1 to 0/1) to give (R)—N—((R)-1-(3-cyano-5-fluorophenyl)ethyl)-2-methylpropane-2-sulfinamide (711 mg, 2.52 mmol, 74.5% yield, 95.3% purity) as a yellow oil. LCMS [M+1]$^+$: 269.1.

¹H NMR (400 MHz, CDCl₃) δ=7.46 (t, J=1.2 Hz, 1H), 7.46-7.33 (m, 1H), 7.31-7.29 (m, 1H), 4.60-4.55 (m, 1H), 3.47 (d, J=3.6 Hz, 1H), 1.54 (d, J=6.8 Hz, 3H), 1.25 (s, 9H).

Step C: To a solution of (R)—N—((R)-1-(3-cyano-5-fluorophenyl)ethyl)-2-methylpropane-2-sulfinamide (711 mg, 2.65 mmol, 1.00 eq.) in dioxane (3.00 mL) was added hydrochloric acid in ethyl acetate (4.0 M, 9.94 mL, 15.0 eq.). The mixture was stirred at 20° C. for 2 hours. The mixture was neutralized with saturated sodium bicarbonate solution (10.0 mL), extracted with ethyl acetate (10.0 mL×3), dried over anhydrous sodium sulfate, filtered, and concentrated under reduced pressure to give (R)-3-(1-aminoethyl)-5-fluorobenzonitrile (330 mg, crude) as a yellow oil.

¹H NMR (400 MHz, CD₃OD) δ=7.72-7.71 (m, 1H), 7.67-7.66 (m, 1H), 7.65-7.62 (m, 1H), 4.59 (q, J=6.8 Hz, 1H), 1.65 (d, J=6.8 Hz, 3H).

Intermediate V

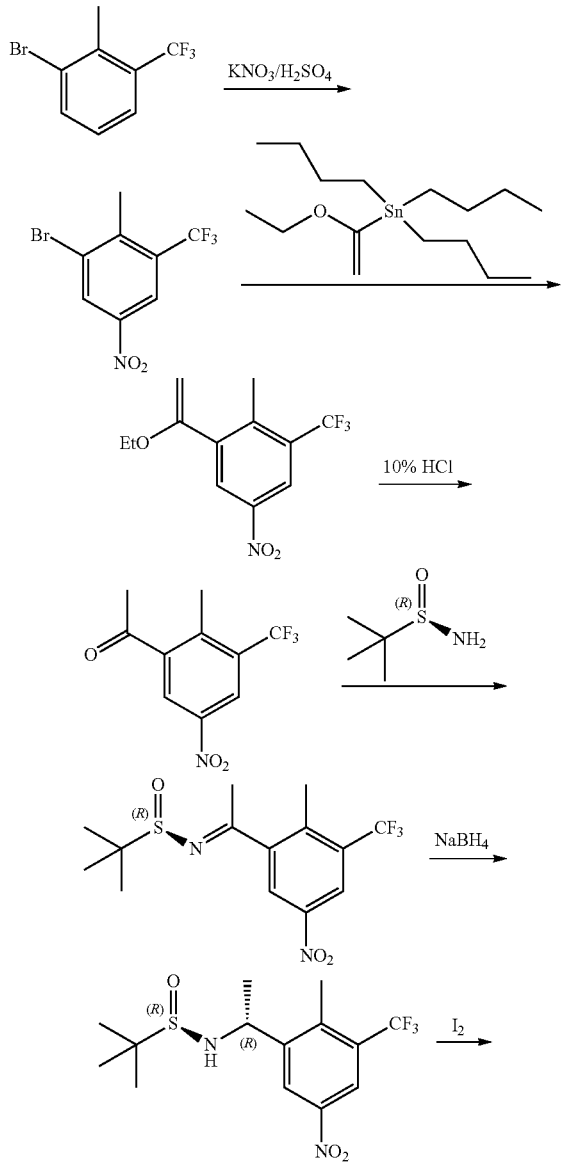

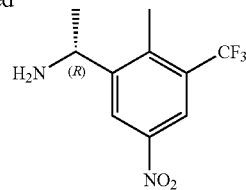

Step A: 1-bromo-2-methyl-3-(trifluoromethyl)benzene (10.0 g, 41.8 mmol, 1.00 eq.) was added the ice-cooled concentrated sulfuric acid (100 mL), then potassium nitrate (12.7 g, 125 mmol, 3.00 eq.) was added slowly at 0° C., then the mixture was stirred at 100° C. for 1 hour. The mixture was then cooled to 25° C., poured into ice-water (500 mL), and extracted with ethyl acetate (300 mL×3). The combined organic layers were washed with brine (400 mL), dried over sodium sulfate, filtered, and concentrated under reduced pressure to give a residue. The residue was purified by column chromatography (SiO₂, petroleum ether/ethyl acetate=1/0 to 1/1) to give 1-bromo-2-methyl-5-nitro-3-(trifluoromethyl)benzene (5.20 g, 16.9 mmol, 40.4% yield) as a white oil.

¹H NMR (400 MHz, DMSO-d₆) δ=8.72 (d, J=2.0 Hz, 1H), 8.40 (d, J=2.4 Hz, 1H), 2.58-2.62 (m, 3H).

Step B: A mixture of 1-bromo-2-methyl-5-nitro-3-(trifluoromethyl)benzene (5.20 g, 18.3 mmol, 1.00 eq.) tributyl (1-ethoxyvinyl)tin (8.60 g, 23.8 mmol, 8.03 mL, 1.30 eq.) and Pd(PPh₃)₂Cl₂ (385 mg, 549 μmol, 0.03 eq.) in dioxane (60.0 mL) was degassed and purged with nitrogen for 3 times, and then the mixture was stirred at 80° C. for 10 hours under a nitrogen atmosphere. The reaction mixture was quenched with saturated potassium fluoride solution (300 mL) and stirred at 25° C. for 2 hours. Then the suspension extracted with ethyl acetate (180 mL×3). The combined organic layers were washed with brine (200 mL×3), dried over sodium sulfate, filtered, and concentrated under reduced pressure to give 1-(1-ethoxyvinyl)-2-methyl-5-nitro-3-(trifluoromethyl)benzene (6.00 g, crude) as black oil.

¹H NMR (400 MHz, CD₃OD) δ=8.47 (d, J=2.0 Hz, 1H), 8.32 (d, J=2.0 Hz, 1H), 4.58 (d, J=2.8 Hz, 1H), 4.32 (d, J=2.4 Hz, 1H), 4.00-3.95 (m, 2H), 2.56 (d, J=1.2 Hz, 3H), 1.37 (t, J=7.0 Hz, 3H).

Step C: A mixture of 1-(1-ethoxyvinyl)-2-methyl-5-nitro-3-(trifluoromethyl)benzene (6.00 g, 21.8 mmol, 1.00 eq) and hydrochloric acid (3.0 M, 20.7 mL, 2.85 eq.) in THF (80.0 mL) was stirred at 20° C. for 1 hour under a nitrogen atmosphere. The reaction mixture was quenched by addition water (100 mL), and then extracted with ethyl acetate (60.0 mL×3). The combined organic layers were washed with brine (70.0 mL), dried over sodium sulfate, filtered, and concentrated under reduced pressure to give a residue. The residue was purified by column chromatography (SiO₂, petroleum ether/ethyl acetate=1/0 to 10/1) to give 1-(2-methyl-5-nitro-3-(trifluoromethyl)phenyl)ethan-1-one (4.10 g, 16.5 mmol, 76.0% yield) as yellow oil.

¹H NMR (400 MHz, CD₃OD) δ=8.67 (s, 1H), 8.57 (s, 1H), 2.66 (s, 3H), 2.60 (s, 3H).

Step D: To a solution of 1-(2-methyl-5-nitro-3-(trifluoromethyl)phenyl)ethan-1-one (2.00 g, 8.09 mmol, 1.00 eq.) and (R)-2-methylpropane-2-sulfinamide (1.27 g, 10.5 mmol, 1.30 eq.) in THF (20.0 mL) was added Ti(OEt)₄ (3.69 g, 16.1 mmol, 3.36 mL, 2.00 eq.), the mixture was stirred at 70° C. for 12 hours under a nitrogen atmosphere. The reaction mixture was diluted with water (70.0 mL) and ethyl acetate (60.0 mL), filtered, and the filtrate was extracted with ethyl acetate (50.0 mL×3). The combined organic layers were dried over sodium sulfate, filtered, and concentrated under reduced pressure to give a residue. The residue was purified by column chromatography (SiO$_2$, petroleum ether/ethyl acetate=1/0 to 5/1) to give (RJ)-2-methyl-N-(1-(2-methyl-5-nitro-3-(trifluoromethyl)phenyl)ethylidene)propane-2-sulfinamide (2.00 g, 5.71 mmol, 70.5% yield) as yellow oil.

$^1$H NMR (400 MHz, CD$_3$OD) δ=8.43 (s, 1H), 8.30 (s, 1H), 2.75 (s, 3H), 2.58 (s, 3H), 1.30 (m, 9H).

Step E: To a solution of (R,E)-2-methyl-N-(1-(2-methyl-5-nitro-3-(trifluoromethyl)phenyl)ethylidene)propane-2-sulfinamide (2.00 g, 5.71 mmol, 1.00 eq) in THF (23.0 mL) was added sodium borohydride (647 mg, 17.1 mmol, 3.00 eq) at 0° C. The mixture was then stirred at 20° C. for 2 hours, and saturated sodium bicarbonate was added, then diluted with water (100 mL). The mixture was extracted with ethyl acetate (60.0 mL×3), the combined organic layers were dried over sodium sulfate, filtered, and concentrated under reduced pressure to give a residue. The residue was purified by column chromatography (SiO$_2$, petroleum ether/ethyl acetate=1/0 to 0/1) to give (R)-2-methyl-N—((R)-1-(2-methyl-5-nitro-3-(trifluoromethyl)phenyl)ethyl)propane-2-sulfinamide (700 mg, 1.75 mmol, 30.6% yield) as black brown oil. LCMS [M+1]$^+$: 353.0.

$^1$H NMR (400 MHz, DMSO-d$_6$) δ=8.67 (d, J=2.4 Hz, 1H), 8.31 (d, J=2.0 Hz, 1H), 6.09 (d, J=7.2 Hz, 1H), 4.83-4.79 (m, 1H), 2.54 (s, 3H), 1.43 (d, J=6.8 Hz, 1H), 1.11 (m, 9H).

Step F: A mixture of (R)-2-methyl-N—((R)-1-(2-methyl-5-nitro-3-(trifluoromethyl)phenyl)ethyl)propane-2-sulfinamide (700 mg, 1.99 mmol, 1.00 eq) and iodine (151 mg, 595 μmol, 120 μL, 0.30 eq) in tetrahydrofuran (8.00 mL) and water (2.00 mL) was degassed and purged with nitrogen 3 times, and then the mixture was stirred at 50° C. for 2 hour under nitrogen atmosphere. The reaction was quenched saturated sodium bicarbonate (50.0 mL) and then extracted with ethyl acetate (30.0 mL×3). The combined organic phases were washed with brine (20.0 mL), dried over anhydrous sodium sulfate, filtered, and concentrated under reduced pressure to give a residue. The residue was purified by column chromatography (SiO$_2$, petroleum ether/ethyl acetate=10/1 to 0/1) to give (R)-1-(2-methyl-5-nitro-3-(trifluoromethyl)phenyl)ethan-1-amine (250 mg, 1.01 mmol, 50.7% yield) as a yellow solid.

$^1$H NMR (400 MHz, DMSO-d$_6$) δ=8.76 (d, J=2.4 Hz, 1H), 8.30 (d, J=2.4 Hz, 1H), 4.54-4.49 (m, 1H), 2.57 (s, 3H), 1.46 (d, J=6.4 Hz, 1H).

Intermediate W

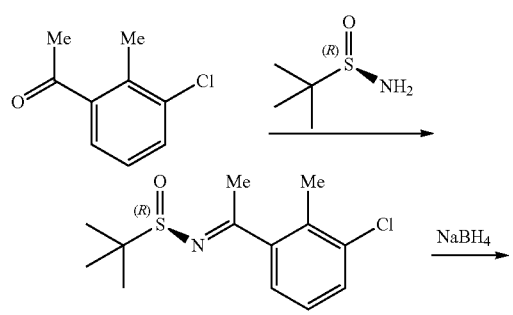

Step A: To a solution of 1-(3-chloro-2-methylphenyl)ethan-1-one (1.50 g, 8.90 mmol, 1.00 eq) in tetrahydrofuran (30.0 mL) was added titanium ethoxide (6.09 g, 26.7 mmol, 5.53 mL, 3.00 eq) and (R)-2-methylpropane-2-sulfinamide (1.40 g, 11.6 mmol, 1.30 eq). The mixture was stirred at 70° C. for 10 hours. The reaction mixture was quenched by sodium bicarbonate (50.0 mL) at 20° C., and then stirred for 10 minutes. The solid was filtered, and the filtrate was extracted with ethyl acetate (20.0 mL×3). The combined organic layers were washed with brine, dried over anhydrous sodium sulfate, filtered, and concentrated under reduced pressure to give (R,E)-N-(1-(3-chloro-2-methyl phenyl)ethylidene)-2-methyl propane-2-sulfinamide (2.40 g, crude) as a yellow oil. LCMS [M+1]$^+$: 272.0.

Step B: To a solution of (RJ)-N-(1-(3-chloro-2-methyl phenyl)ethylidene)-2-methylpropane-2-sulfinamide (2.30 g, 8.46 mmol, 1.00 eq) in tetrahydrofuran (30.0 mL) was added sodium borohydride (850 mg, 22.5 mmol, 2.66 eq) at −40° C., the mixture was stirred at −40° C. for 2 hours. The reaction mixture was quenched with saturated ammonium chloride solution (50.0 mL) at 20° C., and then stirred for 10 mins. The solid was filtered off, the filtration was extracted with ethyl acetate (20.0 mL×3). The combined organic layers were washed with brine, dried over anhydrous sodium sulfate, filtered, and concentrated under reduced pressure to give a residue. The residue was purified by column chromatography (SiO$_2$, petroleum ether/ethyl acetate=1/0 to 1/1) to give (R)—N—((R)-1-(3-chloro-2-methyl phenyl)ethyl)-2-methylpropane-2-sulfinamide (1.50 g, 5.48 mmol, 64.7% yield) as a colourless oil. LCMS [M+1]$^+$: 274.1.

Step C: To a solution of (R)—N—((R)-1-(3-chloro-2-methyl phenyl)ethyl)-2-methylpropane-2-sulfinamide (1.10 g, 4.02 mmol, 1.00 eq) in ethyl acetate (20.0 mL) was added hydrochloride in ethyl acetate (4.0 M, 30.0 mL) at 0° C., the mixture was stirred at 20° C. for 2 hours. The reaction mixture was concentrated under reduced pressure to give (R)-1-(3-chloro-2-methylphenyl)ethan-1-amine (700 mg, crude) as a white solid. LCMS [M+1]$^+$: 170.1.

Intermediate X

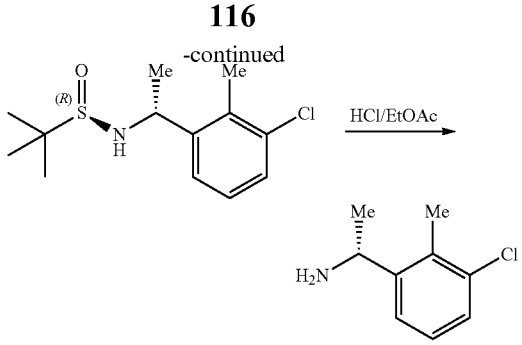

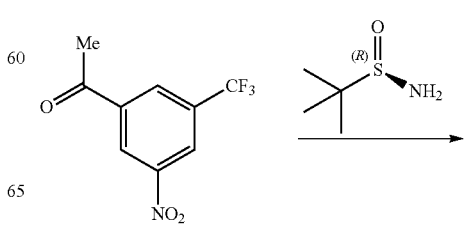

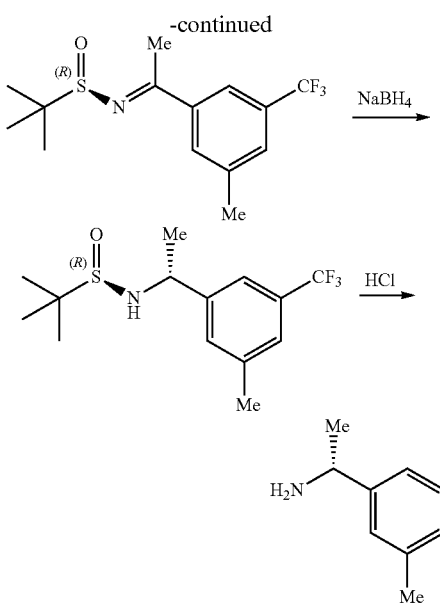

Step A: To a solution of 1-(3-methyl-5-(trifluoromethyl) phenyl)ethan-1-one (500 mg, 2.47 mmol, 1.00 eq.) and (R)-2-methylpropane-2-sulfinamide (689 mg, 5.69 mmol, 2.30 eq.) in THF (7.00 mL) was added Ti(OEt)$_4$ (1.30 g, 5.69 mmol, 1.18 mL, 2.30 eq.), the mixture was stirred at 70° C. for 12 hours under a nitrogen atmosphere. The reaction mixture was diluted with water (30.0 mL) and ethyl acetate (20.0 mL), filtered and the filtrate was extracted with ethyl acetate (3×20.0 mL). The combined organic layers were dried over sodium sulfate, filtered, and concentrated under reduced pressure to give a residue. The residue was purified by column chromatography (SiO$_2$, petroleum ether/ethyl acetate=10/1) to give (R,E)-2-methyl-N-(1-(3-methyl-5-(trifluoromethyl)phenyl)ethylidene)propane-2-sulfinamide (750 mg, 2.46 mmol, 99.3% yield) as a yellow oil. LCMS [M+1]$^+$: 306.1.

$^1$H NMR (400 MHz, DMSO-d$_6$) δ=7.99 (s, 1H), 7.95 (s, 1H), 7.75 (s, 1H), 5.75 (s, 1H), 2.76 (s, 3H), 2.46 (s, 3H), 1.22 (s, 9H).

Step B: To a solution of (R,E)-2-methyl-N-(1-(3-methyl-5-(trifluoromethyl)phenyl)ethylidene)propane-2-sulfinamide (650 mg, 2.13 mmol, 1.00 eq.) in THF (15.0 mL) was added sodium borohydride (253 mg, 6.69 mmol, 3.14 eq.) at −40° C. The mixture was stirred at −40° C. for 2 hours. The mixture was added saturated sodium bicarbonate solution and diluted by water (50.0 mL). The mixture was extracted with ethyl acetate (3×50.0 mL), the combined organic layers were dried over sodium sulfate, filtered, and concentrated under reduced pressure to give a residue. The residue was purified by column chromatography (SiO$_2$, petroleum ether/ethyl acetate=5/1 to 2/1) to give (R)-2-methyl-N—((R)-1-(3-methyl-5-(trifluoromethyl)phenyl)ethyl)propane-2-sulfinamide (320 mg, 1.04 mmol, 48.9% yield) as a light yellow solid. LCMS [M+1]$^+$: 308.1.

$^1$H NMR (400 MHz, CD$_3$OD) δ=7.52 (s, 1H), 7.50 (s, 1H), 7.39 (s, 1H), 4.56-4.51 (m, 1H), 2.44 (s, 1H), 1.54-1.53 (d, 3H), 1.25 (s, 9H).

Step C: A solution of (R)-2-methyl-N—((R)-1-(3-methyl-5-(trifluoromethyl)phenyl)ethyl)propane-2-sulfinamide (305 mg, 992 μmol, 1.00 eq.) in hydrochloric acid (4.0 M in ethyl acetate, 10.0 mL), resulting mixture was stirred at 25° C. for 1 hr. Concentrated under reduced pressure to give (R)-1-(3-methyl-5-(trifluoromethyl)phenyl)ethan-1-amine (200 mg, crude) as a light yellow solid. The crude was used directly into next step without further purification. LCMS [M+1]$^+$: 204.0.

Intermediate Y

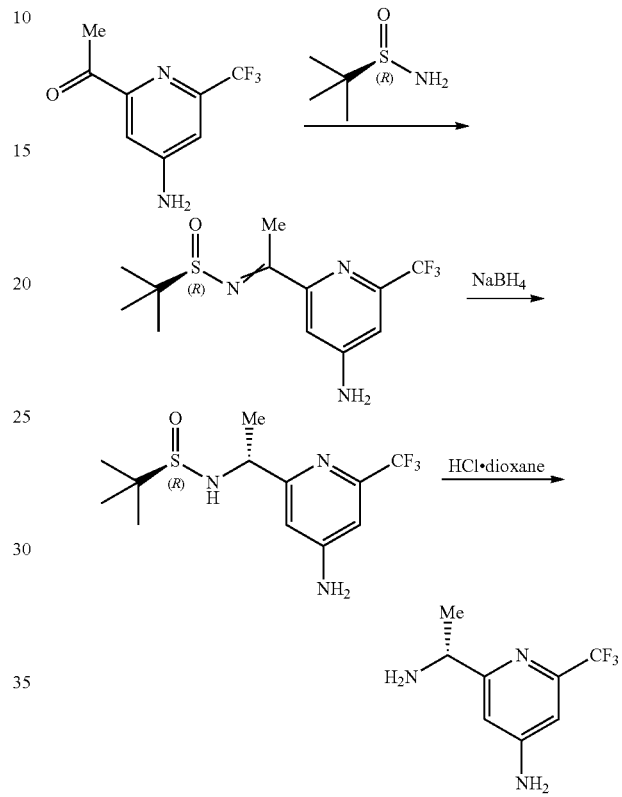

Step A: To a solution of 1-(4-amino-6-(trifluoromethyl) pyridin-2-yl)ethan-1-one (35.6 g, 175 mmol, 1.00 eq.) and (R)-2-methylpropane-2-sulfinamide (25.4 g, 209 mmol, 1.20 eq.) in THF (350 mL) was added titanium (IV) isopropoxide (149 g, 524 mmol, 155 mL, 3.00 eq.), and 1,2-dimethoxyethane (15.7 g, 175 mmol, 18.1 mL, 1.00 eq.). The reaction mixture was stirred at 80° C. for 12 hours, after which point was added water (50.0 mL) to give a suspension. The suspension was filtered, the filtrate was concentrated under reduced pressure to give a residue, the residue was purified by silica gel chromatography(petroleum ether/ethyl acetate=10/1 to 1/1) to give (R)—N-(1-(4-amino-6-(trifluoromethyl)pyridin-2-yl)ethylidene)-2-methylpropane-2-sulfinamide (44.0 g, 143 mmol, 82.0% yield) as brown oil.

$^1$H NMR (400 MHz, CDCl$_3$) δ=7.45 (d, J=2.0 Hz, 1H), 6.97 (d, J=2.0 Hz, 1H), 4.56 (br s, 2H), 2.82 (s, 3H), 1.33 (s, 9H).

Step B: To a solution of (R)—N-(1-(4-amino-6-(trifluoromethyl)pyridin-2-yl)ethylidene)-2-methylpropane-2-sulfinamide (44.0 g, 143 mmol, 1.00 eq.) in THF (400 mL) was added sodium borohydride (16.3 g, 430 mmol, 3.00 eq.) at 0° C. in portionwise, then the reaction was stirred at 0° C. for 1 hour. The mixture was slowly poured into water (200 mL) and stirred for 5 minutes, then extracted with ethyl acetate (300 mL×3). The combined organic phases were washed with brine (200 mL×3), dried with anhydrous sodium sulfate, filtered and concentrated under reduced pressure to give a residue. The residue was purified by column chromatography (SiO₂, petroleum ether/ethyl acetate=10/1 to 1/1) to give (R)—N—((R)-1-(4-amino-6-(trifluoromethyl)pyridin-2-yl)ethyl)-2-methylpropane-2-sulfinamide (24.0 g, 76.2 mmol, 53.2% yield, 98.2% purity) as a brown oil.

$^1$H NMR (400 MHz, CDCl$_3$) δ=6.63 (d, J=2.0 Hz, 1H), 6.56 (d, J=2.0 Hz, 1H), 5.06 (d, J=6.0 Hz, 1H), 4.69 (s, 2H), 4.46-4.39 (m, 1H), 1.45 (d, J=6.8 Hz, 3H), 1.27 (s, 9H).

Step C: To a solution of (R)—N—((R)-1-(4-amino-6-(trifluoromethyl)pyridin-2-yl)ethyl)-2-methylpropane-2-sulfinamide (23.5 g, 76.0 mmol, 1.00 eq) in HCl/dioxane (200 mL) was stirred at 25° C. for 2 hours. The mixture was filtered, and the filter cake was washed with ethyl acetate (100 mL), then the filter cake was collected and dried under vacuum to give (R)-2-(1-aminoethyl)-6-(trifluoromethyl)pyridin-4-amine (hydrochloride salt) as a white solid.

$^1$H NMR (400 MHz, DMSO-d$_6$) δ=8.43 (br s, 3H), 6.93 (br d, J=2.0 Hz, 2H), 6.74 (d, J=1.6 Hz, 1H), 4.34-4.27 (m, 1H), 1.45 (d, J=6.8 Hz, 3H).

Intermediate Z

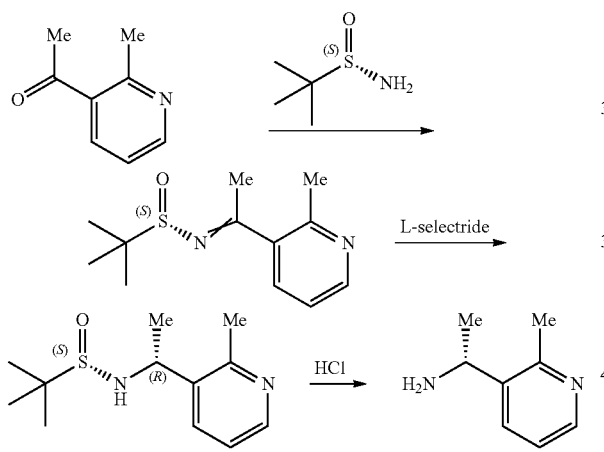

Step A: To a solution of 1-(2-methylpyridin-3-yl)ethan-1-one (800 mg, 5.92 mmol, 1.00 eq.) and (S)-2-methylpropane-2-sulfinamide (933 mg, 7.69 mmol, 1.30 eq.) in tetrahydrofuran (8.00 mL) was added titanium (IV) ethoxide (2.70 g, 11.8 mmol, 2.45 mL, 2.00 eq.) and 1,2-dimethoxyethane (533 mg, 5.92 mmol, 615 μL, 1.00 eq.), and the mixture was stirred at 70° C. for 16 hours. After cooling to 25° C. the mixture was concentrated under reduced pressure and purified by column chromatography (SiO₂, petroleum ether/ethyl acetate=5/1 to 1/1) to give (S)-2-methyl-N-(1-(2-methylpyridin-3-yl)ethylidene)propane-2-sulfinamide (1.25 g, 5.24 mmol, 88.6% yield) as a yellow oil. LCMS [M+1]$^+$: 239.2.

Step B: To a solution of (S)-2-methyl-N-(1-(2-methylpyridin-3-yl)ethylidene)propane-2-sulfinamide (1.25 g, 5.24 mmol, 1.00 eq.) in tetrahydrofuran (7.00 mL) was added dropwise L-selectride (1.0 M in THF, 7.87 mL, 1.50 eq.) at −78° C. over 30 minutes, then stirred for an additional 1 hour at −78° C. The reaction mixture was then quenched by addition saturated ammonium chloride solution (in water, 30.0 mL) at 0° C., and stirred for another 1 hour at 25° C. The solution was then extracted with ethyl acetate (50.0 mL×3), and the combined organic layers were washed with brine (30.0 mL×2), dried over anhydrous sodium sulfate, filtered, and concentrated under reduced pressure. The residue was purified twice by column chromatography (SiO₂, petroleum ether/ethyl acetate=5/1 to 0/1) to give (S)-2-methyl-N—((R)-1-(2-methylpyridin-3-yl)ethyl)propane-2-sulfinamide (600 mg, 2.50 mmol, 47.6% yield) as a white solid. LCMS [M+1]$^+$: 432.3.

$^1$H NMR (400 MHz, CDCl$_3$) δ=8.36 (dd, J=1.2, 3.6 Hz, 1H), 7.64 (dd, J=1.6, 8.0 Hz, 1H), 7.12 (dd, J=4.8, 7.6 Hz, 1H), 4.81-4.70 (m, 1H), 2.58 (s, 3H), 1.47 (d, J=6.8 Hz, 3H), 1.14 (s, 9H).

SFC conditions: Column: Chiralpak AD-3 50×4.6 mm I.D., 3 um Mobile phase: Phase A: CO₂, and Phase B: for MeOH (0.05% diethylamine); Gradient elution: MeOH (0.05% diethylamine) in C02 from 5% to 40% f Flow rate: 3 mL/min; Detector: PDA Column Temp: 35° C.; Back Pressure: 100 Bar.

Step C: A mixture of (S)-2-methyl-N—((R)-1-(2-methyl pyri din-3-yl)ethyl)propane-2-sulfinamide (600 mg, 2.50 mmol, 1.00 eq.) in HCl.dioxane (3.00 mL) was was stirred at 0° C. for 30 minutes under a nitrogen atmosphere. After this time, a white precipitate was formed, and the suspension was filtered. The cake was collected and dried under vacuum, and the residue was further purified by prep-HPLC [column: Waters Xbridge 150×25 mm×5 um; mobile phase: phase A: water (0.05% ammonium hydroxide v/v), phase B: MeCN; B %: 3%-33%] to give (R)-1-(2-methylpyridin-3-yl)ethan-1-amine (370 mg, 2.23 mmol, 89.2% yield, 82% purity) as an colorless oil. LCMS [M−16]$^+$: 120.3.

Intermediate AA

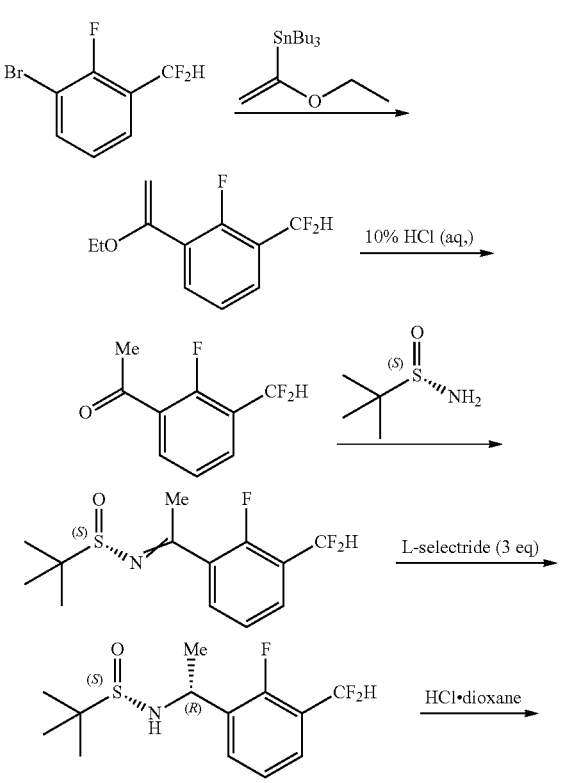

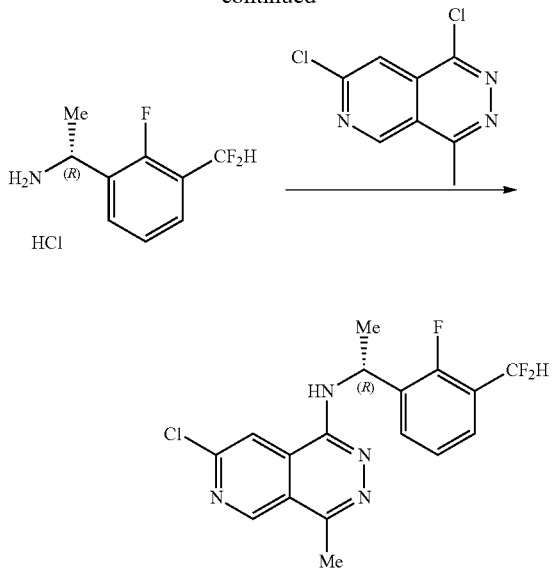

Step A: To a solution of 1-bromo-3-(difluoromethyl)-2-fluorobenzene (commercially available, 4.50 g, 20.0 mmol, 1.00 eq.) in 1,4-dioxane (50.0 mL) was added PdCl$_2$(PPh$_3$)$_2$ (1.40 g, 2.00 mmol, 0.10 eq.) and tributyl(1-ethoxyvinyl)tin (21.7 g, 60.0 mmol, 20.3 mL, 3.00 eq.), and the mixture was degassed and purged with nitrogen (3 times) then stirred at 100° C. for 3 hours under a nitrogen atmosphere. The mixture was cooled to room temperature, concentrated under reduced pressure, and added potassium fluoride aqueous solution (2.0 M, 100 mL) was added to the residue. The mixture was extracted with ethyl acetate (100 mL×3), dried over anhydrous sodium sulfate, and filtered. The filtrate was concentrated under reduced pressure to give 1-(difluoromethyl)-3-(1-ethoxyvinyl)-2-fluorobenzene (7.50 g, crude) as a brown oil, which was used without further purification.

Step B: To a solution of 1-(difluoromethyl)-3-(1-ethoxyvinyl)-2-fluorobenzene (7.50 g, 34.7 mmol, 1.00 eq.) in tetrahydrofuran (50.0 mL) was added hydrochloric aqueous solution (30.0 mL, 10% purity), and the mixture was stirred at 25° C. for 1 hour. After this time, the pH of the mixture was adjusted to ~pH to 6-8 with sodium bicarbonate aqueous solution and the mixture was extracted with ethyl acetate (100 mL×3). The combined organic layers were dried over anhydrous sodium sulfate, filtered, and concentrated under reduced pressure. The residue was purified by column chromatography (silica gel, petroleum ether/ethyl acetate=1/0 to 5/1) to give 1-(3-(difluoromethyl)-2-fluorophenyl)ethan-1-one (6.01 g, 31.3 mmol, 90.2% yield, 98.0% purity) as a colorless oil. LCMS [M+1]$^+$: 189.1.

$^1$H NMR (400 MHz, CDCl$_3$) δ=8.02-7.97 (m, 1H), 7.80-7.76 (m, 1H), 7.34 (t, J=8.0 Hz, 1H), 6.94 (t, J=14.8 Hz, 1H), 2.66 (d, J=5.2 Hz, 3H).

Step C: A mixture of (S)-2-methylpropane-2-sulfinamide (2.32 g, 19.1 mmol, 1.20 eq.), 1-(3-(difluoromethyl)-2-fluorophenyl)ethan-1-one (3.00 g, 16.0 mmol, 1.00 eq.) and titanium (IV) ethoxide(7.27 g, 31.9 mmol, 6.60 mL, 2.00 eq.) in 2-methyl tetrahydrofuran (30.0 mL) was degassed and purged with nitrogen (3 times), and then stirred at 75° C. for 4 hours under a nitrogen atmosphere. The reaction mixture was then cooled, diluted with water (50.0 mL), extracted with ethyl acetate (50.0 mL×3), and the combined organic layers were washed with brine (100 mL×2), dried over anhydrous sodium sulfate, and filtered. The filtrate was concentrated under reduced pressure, and the residue was purified by column chromatography (silica gel, petroleum ether/ethyl acetate=20/1 to 1/1) to give (S)—N-(1-(3-(difluoromethyl)-2-fluorophenyl)ethylidene)-2-methylpropane-2-sulfinamide (1.80 g, 6.18 mmol, 38.8% yield). LCMS [M+1]$^+$: 292.2.

Step D: To a mixture of (R)—N-(1-(3-(difluoromethyl)-2-fluorophenyl)ethylidene)-2-methylpropane-2-sulfinamide (1.80 g, 6.18 mmol, 1.00 eq.) in 2-methyl tetrahydrofuran (30.0 mL) was added L-selectride (3.52 g, 18.5 mmol, 4.10 mL, 3.00 eq.) under a nitrogen atmosphere at −78° C., and then the mixture was stirred at −78° C. for 3 hours under a nitrogen atmosphere. After this time, additional L-selectride (1.76 g, 9.30 mmol, 2.00 mL, 1.50 eq.) was added and the solution was degassed and purged with nitrogen (3 times) and stirred at −78° C. for 9 hours under a nitrogen atmosphere. The mixture was cooled to room temperature, diluted with water (30.0 mL), and extracted with ethyl acetate (30.0 mL×3). The combined organic layers were washed with brine (30.0 mL×2), dried over anhydrous sodium sulfate, filtered, and concentrated under reduced pressure. The residue was purified by column chromatography (silica gel, petroleum ether/ethyl acetate=20/1 to 1/1) to give (S)—N—((R)-1-(3-(difluoromethyl)-2-fluorophenyl)ethyl)-2-methylpropane-2-sulfinamide (1.30 g, 4.34 mmol, 70.3% yield, 98% purity) as a colorless oil. LCMS [M+1]$^+$: 294.2.

Step E: To a solution of (S)—N—((R)-1-(3-(difluoromethyl)-2-fluorophenyl)ethyl)-2-methylpropane-2-sulfinamide (1.29 g, 4.43 mmol, 1.00 eq.) was added hydrochloric acid (4.00 M in 1,4-dioxane, 15.0 mL, 14.0 eq.), and the mixture was stirred at 25° C. for 30 minutes. The mixture was then diluted with water (30.0 mL), extracted with ethyl acetate (30.0 mL %), and the combined organic layers were washed with brine (30.0 mL×2), dried over anhydrous sodium sulfate, and filtered. The filtrate was concentrated under reduced pressure to (R)-1-(3-(difluoromethyl)-2-fluorophenyl)ethan-1-amine (480 mg, 2.13 mmol, 48.0% yield, HCl salt) as a yellow oil, which was used without further purification.

$^1$H NMR (400 MHz, CDCl$_3$) δ=7.52-7.47 (m, 2H), 7.24-7.19 (m, 1H), 6.88 (t, J=14.8 Hz, 1H), 4.85-4.92 (m, 1H), 1.57 (d, J=6.8 Hz, 3H).

Step F: A mixture of (R)-1-(3-(difluoromethyl)-2-fluorophenyl)ethan-1-amine (300 mg, 1.59 mmol, 1.00 eq.), 1,7-dichloro-4-methylpyrido[3,4-d]pyridazine (339 mg, 1.59 mmol, 1.00 eq.) and potassium fluoride (461 mg, 7.93 mmol, 186 μL, 5.00 eq.) in dimethyl sulfoxide (6.00 mL) was degassed and purged with nitrogen (3 times), and the mixture was stirred at 130° C. for 12 hours under a nitrogen atmosphere. The mixture was then cooled to 25° C., diluted with water (30.0 mL), and extracted with ethyl acetate (30.0 mL×3). The combined organic layers were washed with brine (30.0 mL×3), dried over sodium sulfate, filtered, and concentrated under reduced pressure. The residue was purified by column chromatography (silica gel, petroleum ether/ethyl acetate=10/1 to 1/1) and prep-HPLC [column: Phenomenex luna C18 150×25 mm×10 um; mobile phase: phase A: water(0.225% formic acid), phase B: acetonitrile; B %: 20%-50%] to give (R)-7-chloro-N-(1-(3-(difluoromethyl)-2-fluorophenyl)ethyl)-4-methylpyrido[3,4-d]pyridazin-1-amine (250 mg, 629 μmol, 39.7% yield, 92.3% purity) as a yellow solid. LCMS [M+1]$^+$: 367.2.

123

Intermediate AB

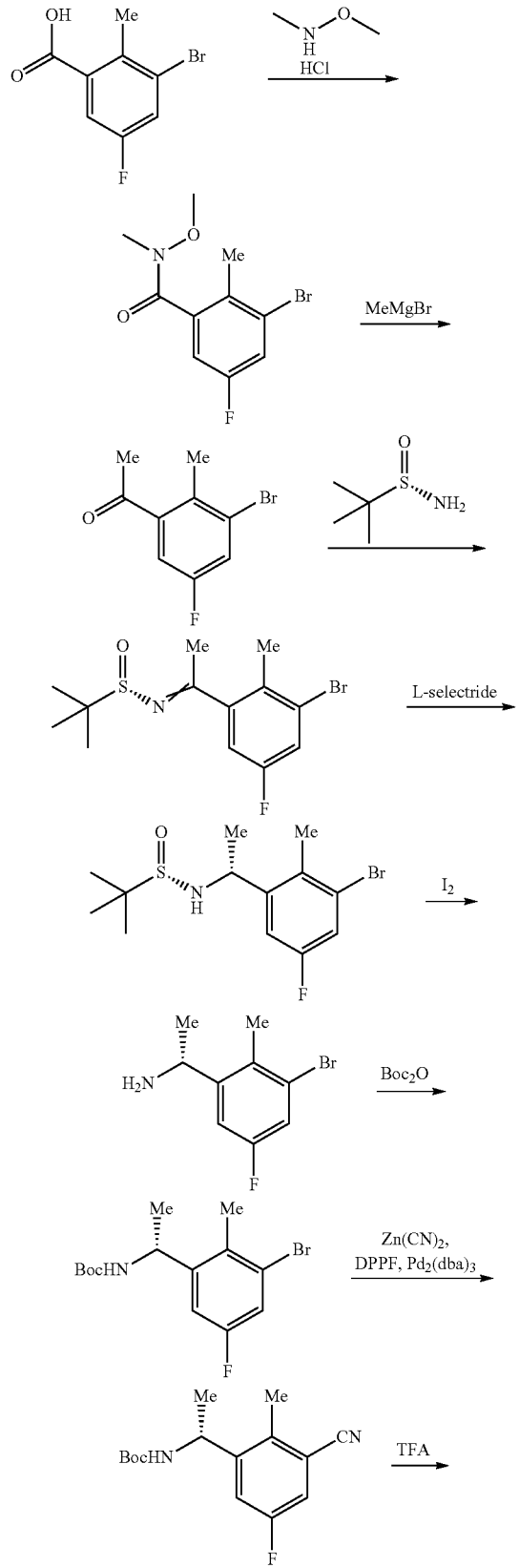

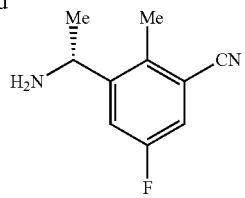

Step A: To a solution of 3-bromo-5-fluoro-2-methylbenzoic acid (4.00 g, 17.2 mmol, 1.00 eq.) and N,O-dimethylhydroxylamine (1.84 g, 18.9 mmol, 1.10 eq., HCl salt) in DMF (50.0 mL) was added N,N-diisopropylethylamine (6.66 g, 51.5 mmol, 8.97 mL, 3.00 eq.) and HATU (7.83 g, 20.6 mmol, 1.20 eq.), and the reaction mixture was stirred at 20° C. for 2 hours. The reaction mixture was diluted with ethyl acetate (50.0 mL), washed with brine (30.0 mL×3), and the combined organic phases were collected, dried over sodium sulfate, filtered, and concentrated under reduced pressure. The residue was purified by column chromatography (SiO$_2$, petroleum ether/ethyl acetate=5/1 to 2/1) to give 3-bromo-5-fluoro-N-methoxy-N,2-dimethylbenzamide (4.70 g, 17.0 mmol, 99.2% yield) as a white solid.

Step B: To a solution of 3-bromo-5-fluoro-N-methoxy-N,2-dimethyl-benzamide (4.70 g, 17.0 mmol, 1.00 eq.) in THF (100 mL) was added methylmagnesium bromide (3.0 M, 34.1 mL, 6.00 eq.) dropwise at 0° C. After dropwise addition was completed, the reaction mixture was warmed to 45° C. and stirred for 5 hours. The mixture was then cooled to 25° C., quenched by water (20.0 mL), and extracted with ethyl acetate (50.0 mL×3). The combined organic phases were dried over sodium sulfate, filtered, and concentrated under reduced pressure. The residue was purified by column chromatography (SiO$_2$, petroleum ether/ethyl acetate=5/1) to give 1-(3-bromo-5-fluoro-2-methylphenyl)ethan-1-one (3.80 g, 16.5 mmol, 96.6% yield) as a light yellow solid.

$^1$H NMR (400 MHz, CDCl$_3$) δ=7.43 (dd, J=2.8, 7.6 Hz, 1H), 7.19 (dd, J=2.8, 8.4 Hz, 1H), 2.55 (s, 3H), 2.45 (d, J=0.4 Hz, 3H).

Step C: To a solution of 1-(3-bromo-5-fluoro-2-methylphenyl)ethan-1-one (3.80 g, 16.5 mmol, 1.00 eq.) and (S)-2-methylpropane-2-sulfinamide (2.79 g, 23.0 mmol, 1.40 eq.) in THF (60.0 mL) was added titanium (IV) ethoxide (7.50 g, 32.9 mmol, 6.82 mL, 2.00 eq.) and 1,2-dimethoxyethane (1.48 g, 16.5 mmol, 1.71 mL, 1.00 eq.), and the mixture was stirred at 70° C. for 12 hours. The reaction mixture was then cooled to 25° C., diluted with ethyl acetate (100 mL) and water (10.0 mL) to give a suspension. The suspension was filtered, and the filtrate was concentrated under reduced pressure to remove all volatiles. The residue was purified by column chromatography (SiO$_2$, petroleum ether/ethyl acetate=30/1 to 20/1) to give (R)—N-(1-(3-bromo-5-fluoro-2-methylphenyl)ethylidene)-2-methylpropane-2-sulfinamide (4.70 g, 14.1 mmol, 85.5% yield) as yellow oil. LCMS [M+3]$^+$: 336.0.

$^1$H NMR (400 MHz, CDCl$_3$) δ=7.35 (br dd, J=2.4, 7.6 Hz, 1H), 6.92 (dd, J=2.4, 8.4 Hz, 1H), 2.66 (s, 3H), 2.37 (s, 3H), 1.30 (s, 9H).

Step D: To a solution of (S)—N-(1-(3-bromo-5-fluoro-2-methyl phenyl)ethylidene)-2-methylpropane-2-sulfinamide (5.50 g, 16.5 mmol, 1.00 eq.) in THF (80.0 mL) was added L-selectride (1.0 M, 24.7 mL, 1.50 eq.) dropwise at −78° C., and the reaction mixture was warmed to 0° C. and stirred for 2 hours. The mixture was then diluted with ammonium chloride aqueous solution (30.0 mL), and the resulting solution was extracted with ethyl acetate (50.0 mL×2). The combined organic phases were dried over sodium sulfate, filtered, and concentrated under reduced pressure. The residue was triturated with petroleum ether (20.0 mL), filtered, and the filter cake was dried under vacuum to give (S)—N—((R)-1-(3-bromo-5-fluoro-2-methylphenyl)ethyl)-2-methylpropane-2-sulfinamide (3.20 g, 9.52 mmol, 57.8% yield) as a white solid.

$^1$H NMR (400 MHz, CDCl$_3$) δ=7.24 (dd, J=2.4, 7.6 Hz, 1H), 7.10 (dd, J=2.8, 10.0 Hz, 1H), 4.90-4.82 (m, 1H), 3.30 (br d, J=2.8 Hz, 1H), 2.42 (s, 3H), 1.48 (d, J=6.8 Hz, 3H), 1.23 (s, 9H).

Step E: To a solution of (S)—N—((R)-1-(3-bromo-5-fluoro-2-methylphenyl)ethyl)-2-methylpropane-2-sulfinamide (1.60 g, 4.76 mmol, 1.00 eq.) in THF (20.0 mL) and water (5.00 mL) was added iodine (362 mg, 1.43 mmol, 288 µL, 0.30 eq.), and the mixture was stirred at 50° C. for 2 hours. The mixture was then cooled to 25° C., and the pH was adjusted to pH=7 with sodium bicarbonate aqueous solution. The resulting solution was extracted with DCM (20.0 mL×3), and the combined organic phases were dried over sodium sulfate, filtered, and concentrated under reduced pressure to give (R)-1-(3-bromo-5-fluoro-2-methylphenyl)ethan-1-amine (1.20 g, crude) as a light yellow oil. This crude oil was used without further purification.

Step F: To a solution of (R)-1-(3-bromo-5-fluoro-2-methylphenyl)ethan-1-amine (1.20 g, 5.17 mmol, 1.00 eq.) in THF (20.0 mL) was added di-tert-butyl dicarbonate (1.35 g, 6.20 mmol, 1.43 mL, 1.20 eq.) and the mixture was stirred at 20° C. for 3 hours. The mixture was then concentrated under reduced pressure, and the residue was purified by column chromatography (SiO$_2$, petroleum ether/ethyl acetate=150/1 to 70/1) to give tert-butyl (R)-(1-(3-bromo-5-fluoro-2-methylphenyl)ethyl)carbamate (1.45 g, 4.36 mmol, 84.4% yield) as a white solid.

Step G: A mixture of tert-butyl (R)-(1-(3-bromo-5-fluoro-2-methylphenyl)ethyl)carbamate (1.35 g, 4.06 mmol, 1.00 eq.), zinc cyanide (954 mg, 8.13 mmol, 516 µL, 2.00 eq.), DPPF (451 mg, 813 µmol, 0.20 eq.), zinc powder (26.6 mg, 406 µmol, 0.10 eq.) and Pd$_2$(dba)$_3$ (372 mg, 406 µmol, 0.10 eq.) in dimethylacetamide (20.0 mL) was degassed and purged with nitrogen (3 times), and the mixture was stirred at 120° C. for 6 hours under a nitrogen atmosphere. The mixture was then diluted with ethyl acetate (60.0 mL), filtered, and the filtrate was washed with brine (30.0 mL×3), dried over sodium sulfate, and concentrated under reduced pressure. The residue was purified by column chromatography (SiO$_2$, petroleum ether/ethyl acetate=100/1 to 30/1) to give tert-butyl (R)-(1-(3-cyano-5-fluoro-2-methylphenyl)ethyl)carbamate (1.10 g, 3.95 mmol, 97.3% yield) as a light yellow solid.

Step H: To a solution of tert-butyl (R)-(1-(3-cyano-5-fluoro-2-methylphenyl)ethyl)carbamate (1.10 g, 3.95 mmol, 1.00 eq.) in DCM (5.00 mL) was added TFA (1.88 g, 16.5 mmol, 1.22 mL, 4.18 eq.) and the mixture was stirred at 20° C. for 1 hour. The mixture was then concentrated under reduced pressure, and the residue was adjusted to pH=7 with saturated sodium bicarbonate aqueous solution. The resulting solution was extracted with DCM (50.0 mL), and the organic phase was dried over sodium sulfate, and concentrated in vacuum to give (R)-3-(1-aminoethyl)-5-fluoro-2-methylbenzonitrile (0.80 g, crude) as brown oil which was used without further purification.

Intermediate AC

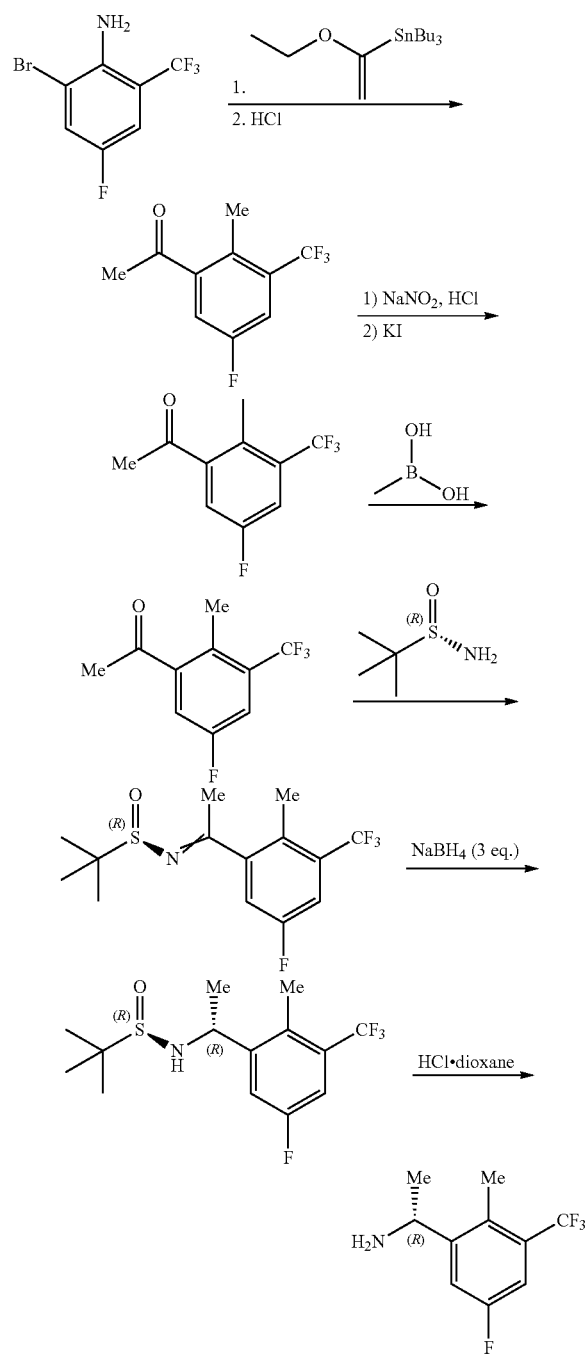

Step A: To a solution of 2-bromo-4-fluoro-6-(trifluoromethyl)aniline (2.00 g, 7.75 mmol, 1.00 eq.) and tributyl(1-ethoxyvinyl)tin (2.80 g, 7.75 mmol, 2.62 mL, 1.00 eq.) in dioxane (20.0 mL) was added PdCl$_2$(PPh$_3$)$_2$ (544 mg, 775 µmol, 0.10 eq.) under a nitrogen atmosphere, and the mixture was stirred at 80° C. for 12 hours. The reaction mixture was then cooled to 25° C., diluted with potassium fluoride aqueous solution (100 mL) and then extracted with ethyl acetate (100 mL×3). The combined organic layers were washed with brine (100 mL), dried over sodium sulfate, filtered, and concentrated under reduced pressure to give compound 2-(1-ethoxyvinyl)-4-fluoro-6-(trifluoromethyl)aniline (4.00 g, crude) as a yellow oil. To a solution of 2-(1-ethoxyvinyl)-4-fluoro-6-(trifluoromethyl)aniline (4.00 g, crude) in tetrahydrofuran (50.0 mL) was added hydrochloric acid aqueous solution (4.00 M, 20.0 mL, 1.33 eq.) dropwise. Then the mixture was stirred at 25° C. for 1 hour, diluted with water (100 mL) and extracted with ethyl acetate (300 mL×3). The combined organic layers were washed with brine (200 mL), dried over sodium sulfate, filtered, and concentrated under reduced pressure. The residue was purified by column chromatography (petroleum ether/ethyl acetate=30/1 to 3/1) to give compound 1-(2-amino-5-fluoro-3-(trifluoromethyl)phenyl)ethan-1-one (5.60 g, 25.3 mmol, 42.0% yield, 99.9% purity) as a yellow solid.

$^1$H NMR (400 MHz, DMSO-$d_6$) δ=7.99 (d, J=9.2 Hz, 1H), 7.65-7.61 (m, 1H), 7.33 (s, 2H), 2.59 (s, 3H).

Step B: To a solution of 1-(2-amino-5-fluoro-3-(trifluoromethyl)phenyl)ethan-1-one (5.60 g, 25.3 mmol, 1.00 eq.) in hydrochloric acid (50.0 mL) and water (100 mL) was added sodium nitrite (2.27 g, 32.9 mmol, 1.30 eq.) portionwise, then potassium iodide (8.41 g, 50.6 mmol, 2.00 eq.) was added to the mixture at 0° C. After the addition was finished, the reaction mixture was stirred at 25° C. for 12 hours then diluted with water (100 mL), and extracted with ethyl acetate (200 mL×3). The combined organic layers were washed with sodium sulfite (200 mL×3), dried over sodium sulfate, filtered, and concentrated under reduced pressure. The residue was purified by column chromatography (petroleum ether/ethyl acetate=50/1 to 10/1) to give compound 1-(5-fluoro-2-iodo-3-(trifluoromethyl)phenyl)ethan-1-one (5.60 g, 10.3 mmol, 40.8% yield, 61.2% purity) as a yellow solid.

$^1$H NMR (400 MHz, DMSO-$d_6$) δ=7.83-7.76 (m, 1H), 7.74-7.71 (m, 1H), 2.56 (s, 3H).

Step C: To a solution of methylboronic acid (1.62 g, 27.1 mmol, 2.50 eq.) and 1-(5-fluoro-2-iodo-3-(trifluoromethyl)phenyl)ethan-1-one (3.60 g, 10.8 mmol, 1.00 eq.) in dioxane (20.0 mL) was added Pd(dppf)Cl$_2$ (400 mg, 542 μmol, 0.05 eq.) and potassium carbonate (7.49 g, 54.2 mmol, 5.00 eq.) under a nitrogen atmosphere, and the mixture was stirred at 90° C. for 12 hours. The mixture was then cooled to 25° C., diluted with water (50.0 mL) and extracted with ethyl acetate (100 mL×3). The combined organic layers were washed with brine (100 mL), dried over sodium sulfate, filtered, and concentrated under reduced pressure. The residue was purified by column chromatography (petroleum ether/ethyl acetate=50/1 to 10/1) to give compound 1-(5-fluoro-2-methyl-3-(trifluoromethyl)phenyl)ethan-1-one (1.70 g, 7.72 mmol, 71.2% yield) as a yellow oil.

$^1$H NMR (400 MHz, CDCl$_3$) δ=7.47 (dd, J=2.8, 8.8 Hz, 1H), 7.36-7.30 (m, 1H), 2.58 (s, 3H), 2.47 (s, 3H).

Step D: To a solution of 1-(5-fluoro-2-methyl-3-(trifluoromethyl)phenyl)ethan-1-one (2.20 g, 9.99 mmol, 1.00 eq.) and (R)-2-methylpropane-2-sulfinamide (2.42 g, 20.0 mmol, 2.00 eq.) in tetrahydrofuran (15.0 mL) was added titanium (IV) isopropoxide (5.68 g, 20.0 mmol, 5.90 mL, 2.00 eq.) and 1-methoxy-2-(2-methoxyethoxy)ethane (4.12 g, 30.7 mmol, 4.40 mL, 3.08 eq), and the mixture was stirred at 75° C. for 12 hours. The mixture was then cooled to 25° C., diluted with water (50.0 mL) to give a suspension. The resulting suspension was filtered, and the filtrate was diluted with ethyl acetate (100 mL×3). The combined organic layers were washed with brine (50.0 mL), dried over sodium sulfate, filtered, and concentrated under reduced pressure. The residue was purified by column chromatography (petroleum ether/ethyl acetate=10/1 to 3/1) to give compound (R)—N-(1-(5-fluoro-2-methyl-3-(trifluoromethyl)phenyl)ethylidene)-2-methylpropane-2-sulfinamide (1.50 g, 4.64 mmol, 46.4% yield) as a yellow oil.

$^1$H NMR (400 MHz, CDCl$_3$) δ=7.39 (dd, J=2.2, 8.8 Hz, 1H), 7.10 (dd, J=2.4, 8.4 Hz, 1H), 2.68 (s, 3H), 2.41 (s, 3H), 1.30 (s, 9H).

Step E: To a solution of (R)—N-(1-(5-fluoro-2-methyl-3-(trifluoromethyl)phenyl)ethylidene)-2-methylpropane-2-sulfinamide (1.90 g, 5.88 mmol, 1.00 eq.) in tetrahydrofuran (20.0 mL) was added sodium borohydride (667 mg, 17.6 mmol, 3.00 eq.) portionwise at 0° C. The reaction mixture was stirred at 0° C. for 2 hours, then diluted slowly with saturated aqueous ammonium chloride (50.0 mL) and stirred for 30 minutes. The resulting mixture was extracted with ethyl acetate (100 mL×3), and the combined organic layers were dried over anhydrous sodium sulfate, filtered, and concentrated under reduced pressure. The residue was purified by column chromatography (petroleum ether/ethyl acetate=10/1 to 3/1) to afford (R)—N—((R)-1-(5-fluoro-2-methyl-3-(trifluoromethyl)phenyl)ethyl)-2-methylpropane-2-sulfinamide (1.30 g, 4.00 mmol, 68.0% yield) as a yellow oil.

$^1$H NMR (400 MHz, CDCl$_3$) δ=7.40-7.28 (m, 2H), 4.95-4.84 (m, 1H), 3.40-3.32 (m, 1H), 2.43 (s, 3H), 1.49 (d, J=6.4 Hz, 3H), 1.23 (s, 9H).

Step F: To a solution of (R)—N—((R)-1-(5-fluoro-2-methyl-3-(trifluoromethyl)phenyl)ethyl)-2-methylpropane-2-sulfinamide (1.30 g, 4.00 mmol, 1.00 eq.) in dichloromethane (5.00 mL) was added hydrochloric acid (4.00 M in 1,4-dioxane, 5.00 mL, 5.0 eq.), and the mixture was stirred at 25° C. for 1 hour. The mixture was then concentrated under reduced pressure to give compound (R)-1-(5-fluoro-2-methyl-3-(trifluoromethyl)phenyl)ethan-1-amine (700 mg, 2.81 mmol, 70.4% yield, 88.9% purity, HCl salt) as a yellow oil, which was used directly without further purification.

Intermediate AD

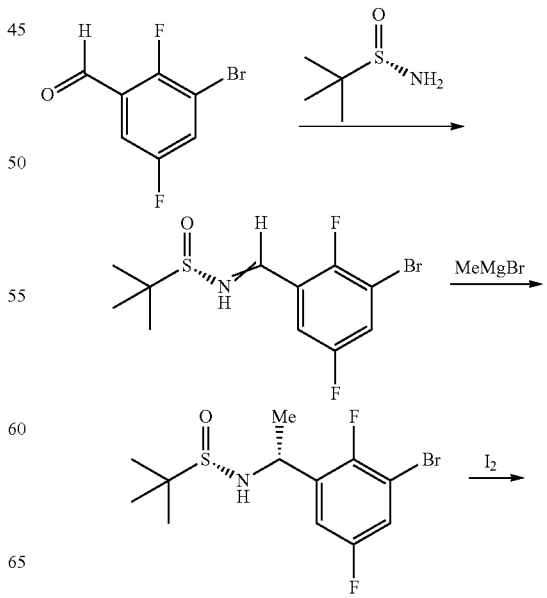

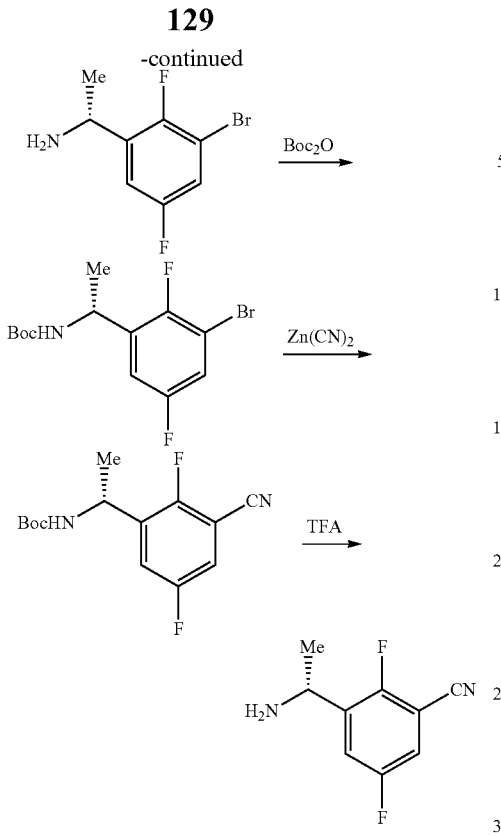

Step A: To a solution of 3-bromo-2,5-difluorobenzaldehyde (4.00 g, 18.1 mmol, 1.00 eq.) and (R)-2-methylpropane-2-sulfinamide (3.07 g, 25.3 mmol, 1.40 eq.) in THF (50.0 mL) was added titanium (IV) ethoxide (8.26 g, 36.2 mmol, 7.51 mL, 2.00 eq.) and 1,2-dimethoxyethane (1.63 g, 18.1 mmol, 1.88 mL, 1.00 eq.), and the mixture was stirred at 70° C. for 12 hours. The mixture was then cooled to 25° C., diluted with ethyl acetate (50.0 mL) and water (5.00 mL) slowly to give a suspension. The suspension was filtered, and the filtrate was concentrated under reduced pressure then purified by column chromatography (SiO₂, petroleum ether/ethyl acetate=20/1 to 10/1) to give (S)—N-(3-bromo-2,5-difluorobenzylidene)-2-methylpropane-2-sulfinamide (5.70 g, 17.6 mmol, 97.1% yield) as a white solid.

¹H NMR (400 MHz, CDCl₃) δ=8.81 (d, J=2.4 Hz, 1H), 7.74 (dd, J=6.0, 8.4 Hz, 1H), 7.44 (dd, J=5.2, 8.8 Hz, 1H), 1.28 (s, 9H).

Step B: To a solution of (R)—N-(3-bromo-2,5-difluorobenzylidene)-2-methylpropane-2-sulfinamide (5.50 g, 17.0 mmol, 1.00 eq.) in DCM (60.0 mL) was added methylmagnesium bromide (3.0 M, 17.0 mL, 3.00 eq.) dropwise at −60° C., and then the mixture was warmed to 0° C. and stirred for 1 hour. The mixture was diluted with ammonium chloride aqueous solution (50.0 mL), and the resulting aqueous solution was extracted with ethyl acetate (50.0 mL×3). The combined organic phases were dried over sodium sulfate, filtered, and concentrated under reduced pressure. The residue was purified by column chromatography (SiO₂, petroleum ether/ethyl acetate=5/1 to 2/1) to give (S)—N—((R)-1-(3-bromo-2,5-difluorophenyl)ethyl)-2-methylpropane-2-sulfinamide (3.50 g, 10.3 mmol, 60.6% yield) as a white solid.

¹H NMR (400 MHz, CDCl₃) δ=7.31-7.26 (m, 1H), 7.16 (dd, J=6.4, 8.8 Hz, 1H), 4.89-4.78 (m, 1H), 3.35 (br d, J=4.0 Hz, 1H), 1.56 (d, J=6.8 Hz, 3H), 1.23 (s, 9H).

Step C: To a solution of (S)—N—((R)-1-(3-bromo-2,5-difluorophenyl)ethyl)-2-methylpropane-2-sulfinamide (1.50 g, 4.41 mmol, 1.00 eq.) in THF (20.0 mL) and water (5.00 mL) was added iodine (336 mg, 1.32 mmol, 266 µL, 0.30 eq.), and the mixture was stirred at 50° C. for 2 hours. The mixture was then cooled to 25° C., and the pH was adjusted to pH=7 with sodium bicarbonate aqueous solution. The resulting aqueous solution was extracted with DCM (20.0 mL×3), and the combined organic phases were dried over sodium sulfate, filtered, and concentrated under reduced pressure to give (R)-1-(3-bromo-2,5-difluorophenyl)ethan-1-amine (1.20 g, crude) as a light yellow oil. This crude oil was used directly without further purification.

Step D: To a solution of (R)-1-(3-bromo-2,5-difluorophenyl)ethan-1-amine (1.20 g, 5.08 mmol, 1.00 eq.) in THF (20.0 mL) was added di-tert-butyl dicarbonate (1.22 g, 5.59 mmol, 1.28 mL, 1.10 eq.), and the mixture was stirred at 20° C. for 2 hours. The reaction mixture was concentrated under reduced pressure, and purified by column chromatography (SiO₂, petroleum ether/ethyl acetate=150/1 to 80/1) to give tert-butyl (R)-(1-(3-bromo-2,5-difluorophenyl)ethyl)carbamate (1.30 g, 3.87 mmol, 76.1% yield) as a white solid.

Step E: A mixture of tert-butyl (R)-(1-(3-bromo-2,5-difluorophenyl)ethyl)carbamate (1.20 g, 3.57 mmol, 1.00 eq.), zinc cyanide (838 mg, 7.14 mmol, 453 µL, 2.00 eq.), zinc (23.3 mg, 357 µmol, 0.10 eq.), DPPF (396 mg, 714 µmol, 0.20 eq.) and Pd₂(dba)₃ (327 mg, 357 µmol, 0.10 eq.) in dimethylacetamide (20.0 mL) was degassed and purged with nitrogen (3 times), and the mixture was stirred at 115° C. for 3 hours under a nitrogen atmosphere. The mixture was then cooled 25° C., diluted with ethyl acetate (100 mL), and the organic phase was washed with brine (50.0 mL×3), dried over sodium sulfate, filtered, and concentrated under reduced pressure. The residue was purified by column chromatography (SiO₂, petroleum ether/ethyl acetate=100/1 to 30/1) to give tert-butyl (R)-(1-(3-cyano-2,5-difluorophenyl)ethyl)carbamate (0.90 g, 3.19 mmol, 89.3% yield) as a light yellow solid.

Step F: To a solution of tert-butyl (R)-(1-(3-cyano-2,5-difluorophenyl)ethyl)carbamate (0.90 g, 3.19 mmol, 1.00 eq.) in DCM (10.0 mL) was added TFA (4.62 g, 40.5 mmol, 3.00 mL, 12.7 eq.), and the reaction mixture was stirred at 20° C. for 1 hour. The reaction mixture was then concentrated under reduced pressure, and the residue was diluted with water (10.0 mL). The pH of the solution was adjusted to pH=7 with sodium bicarbonate aqueous solution, and the resulting aqueous solution was extracted with DCM (20.0 mL×2). The combined organic phases were dried over sodium sulfate, filtered, and concentrated under reduced pressure to give (R)-3-(1-aminoethyl)-2,5-difluorobenzonitrile (700 mg, crude) as light-yellow oil. This compound was used directly without further purification.

Intermediate AE

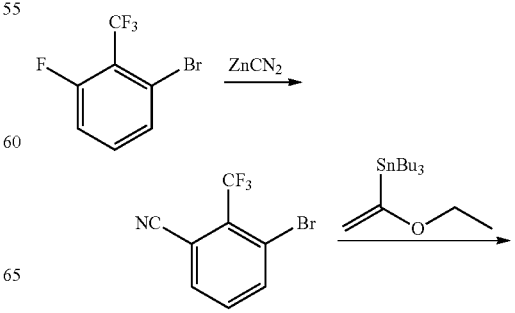

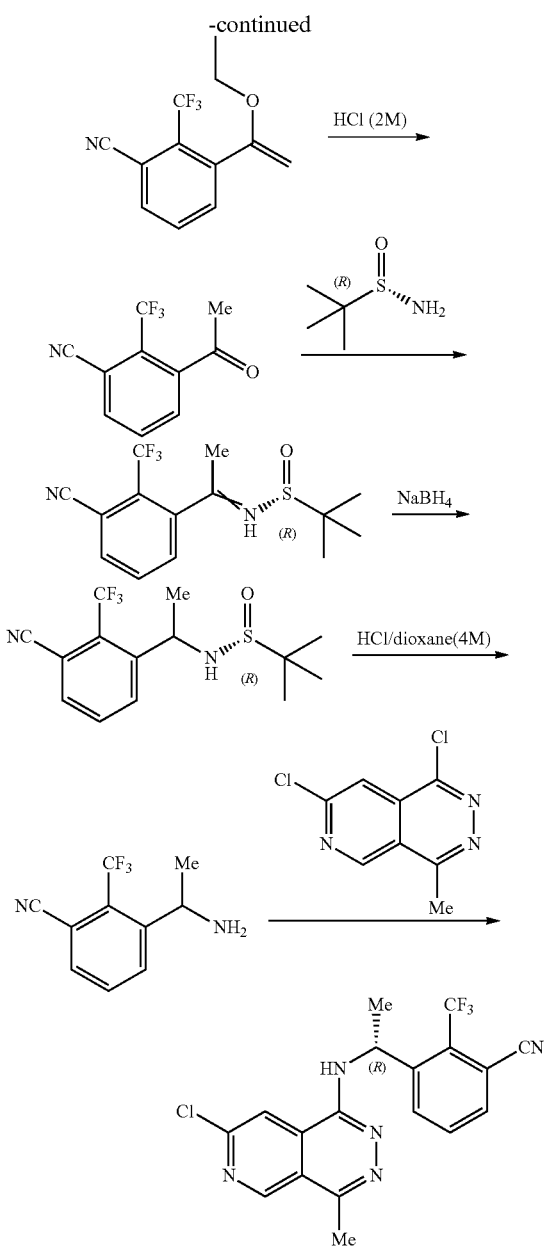

Step A: To a solution of 1-bromo-3-fluoro-2-(trifluoromethyl)benzene (39.0 g, 160 mmol, 1.00 eq) in dimethylsulfoxide (200 mL) was added zinc cyanide (11.5 g, 176 mmol, 7.56 mL, 1.10 eq), and the reaction mixture was stirred at 80° C. for 16 hours. The mixture was then cooled to 25° C., diluted with ethyl acetate (1.00 L), and the organic phase phase was separated, washed with water (500 mL×3), dried over sodium sulfate, filtered, and concentrated under reduced pressure. The residue was purified by silica gel chromatography (petroleum ether/ethyl acetate=1/0 to 2/1) to give 3-bromo-2-(trifluoromethyl)benzonitrile (29.0 g, 116 mmol, 72.3% yield) as a white solid.

$^1$H NMR (400 MHz, DMSO-$d_6$) δ=8.20 (d, J=8.0 Hz, 1H), 8.10 (d, J=7.6 Hz, 1H), 7.75 (t, J=8.0 Hz, 1H).

Step B: To a solution of 3-bromo-2-(trifluoromethyl)benzonitrile (29.0 g, 116 mmol, 1.00 eq) and tributyl(1-ethoxyvinyl)tin (50.3 g, 139 mmol, 47.0 mL, 1.20 eq) in toluene (250 mL) was added Pd(PPh$_3$)$_4$ (6.70 g, 5.80 mmol, 0.05 eq) under a nitrogen atmosphere, and the mixture was stirred at 100° C. for 16 hours. The reaction mixture was cooled to 25° C., diluted with water (500 mL) and ethyl acetate (200 mL), and finally followed by addition of potassium fluoride (50.0 g) solid. The mixture was stirred at 25° C. for 30 minutes, then the organic layer was separated, dried over sodium sulfate, filtered, and concentrated under reduced pressure. The residue was purified by column chromatography (SiO$_2$, petroleum ether/ethyl acetate=20/1 to 5/1) to afford a crude product. The crude product was triturated by petroleum ether (50.0 mL), filtered, and the filtrate was concentrated under reduced pressure to give 3-(1-ethoxyvinyl)-2-(trifluoromethyl)benzonitrile (8.00 g, 33.2 mmol, 23.0% yield) as light yellow oil.

$^1$H NMR (400 MHz, CDCl$_3$) δ=7.82 (d, J=7.2 Hz, 1H), 7.70 (d, J=7.2 Hz, 1H), 7.65-7.59 (t, J=7.6 Hz, 1H), 4.37 (d, J=2.8 Hz, 1H), 4.25 (d, J=2.8 Hz, 1H), 3.90 (q, J=7.2 Hz, 2H), 1.36 (t, J=6.8 Hz, 3H).

Step C: To a solution of 3-(1-ethoxyvinyl)-2-(trifluoromethyl)benzonitrile (7.00 g, 29.0 mmol, 1.00 eq.) in tetrahydrofuran (10.0 mL) was added hydrochloric acid (2.00 M, 29.0 mL, 2.00 eq.), and the reaction mixture was stirred at 20° C. for 2 hours. The pH of the mixture was then adjusted to pH=8 with sodium bicarbonate aqueous solution and further diluted with water (100 mL). The resulting solution was extracted with ethyl acetate (50.0 mL×3), and the combined organic organic phases were washed with brine (100 mL), dried over sodium sulfate, filtered, and concentrated under reduced pressure. The residue was purified by column chromatography (SiO$_2$, petroleum ether/ethyl acetate=20/1 to 5/1) to give 3-acetyl-2-(trifluoromethyl)benzonitrile (5.30 g, 24.8 mmol, 85.6% yield) as colorless oil.

$^1$H NMR (400 MHz, DMSO-$d_6$) δ=8.25 (dd, J=0.8, 7.6 Hz, 1H), 8.07-7.94 (m, 2H), 2.60 (s, 3H).

Step D: To a solution of 3-acetyl-2-(trifluoromethyl)benzonitrile (1.00 g, 4.69 mmol, 1.00 eq.) and (R)-2-methylpropane-2-sulfinamide (625 mg, 5.16 mmol, 1.10 eq.) in tetrahydrofuran (2.00 mL) was added 1,2-dimethoxyethane (423 mg, 4.69 mmol, 488 µL, 1.00 eq.) and titanium (IV) ethoxide (3.21 g, 14.1 mmol, 2.92 mL, 3.00 eq), and the reaction mixture was stirred at 80° C. for 16 hours. The mixture was concentrated under reduced pressure, and the residue was diluted with ethyl acetate (100 mL) and poured into a mixture of celatom (20.0 g) and saturated sodium bicarbonate (10.0 g) in water (100 mL). The mixture was stirred then filtered, and the filter cake was stirred with ethyl acetate (30.0 mL) and filtered, the procedure was repeated three times until the cake of product was washed away. The combined filtrate was separated, and the aqueous phase was extracted with ethyl acetate (100 mL). The combined organic layers were washed with brine (50.0 mL), dried over sodium sulfate, filtered, and concentrated under reduced pressure. The residue was purified by flash silica gel chromatography (ethyl acetate/petroleum ether, 0-30%) to afford (R)—N-(1-(3-cyano-2-(trifluoromethyl)phenyl)ethylidene)-2-methylpropane-2-sulfinamide (950 mg, 2.99 mmol, 63.7% yield, 99.5% purity) as light yellow oil. LCMS [M+1]$^+$: 317.1.

$^1$H NMR (400 MHz, CDCl$_3$) δ=7.92-7.80 (m, 1H), 7.77-7.65 (m, 1H), 7.61-7.37 (m, 1H), 2.74-2.38 (m, 3H), 1.29-1.24 (m, 9H).

Step E: To a solution of (R)—N-(1-(3-cyano-2-(trifluoromethyl)phenyl)ethylidene)-2-methylpropane-2-sulfinamide (1.70 g, 5.37 mmol, 1.00 eq.) in tetrahydrofuran (20.0 mL) was added sodium borohydride (610 mg, 16.0 mmol, 3.00 eq.) portionwise under a nitrogen atmosphere at 0° C.

After addition, the mixture was stirred at this temperature for 30 minutes, and then warmed to 25° C. and stirred for an additional 3 hours. The mixture was then diluted with saturated aqueous ammonium chloride (100 mL) dropwise under a nitrogen atmosphere while stirring at 25° C., then extracted with ethyl acetate (150 mL×2). The combined organic layers were dried over anhydrous sodium sulfate, filtered, and concentrated under reduced pressure. The residue was purified by column chromatography (SiO$_2$, petroleum ether/ethyl acetate=5/1 to 1/1) to give (R)—N-(1-(3-cyano-2-(trifluoromethyl)phenyl)ethyl)-2-methylpropane-2-sulfinamide (1.50 g, 4.71 mmol, 87.7% yield, mixture of diastereomers) as a white solid. LCMS [M+1]$^+$: 319.1.

Step F: A mixture of (R)—N-(1-(3-cyano-2-(trifluoromethyl)phenyl)ethyl)-2-methylpropane-2-sulfinamide (1.4 g, 4.40 mmol, 1.00 eq.) in HCL dioxane (10.0 mL) was was stirred at 5° C. for 30 minutes. After this time, a white precipitate was formed and the suspension was filtered. The filter cake was collected and dried under vacuum to give 3-(1-aminoethyl)-2-(trifluoromethyl)benzonitrile (850 mg, 3.39 mmol, 77.1% yield, HCl salt) as a white solid. LCMS [M+1]$^+$: 215.1.
$^1$H NMR (400 MHz, DMSO-d$_6$) δ=8.84 (s, 3H), 8.38 (br d, J=8.0 Hz, 1H), 8.19 (d, J=7.6 Hz, 1H), 8.12-7.95 (m, 1H), 4.64 (br d, J=6.0 Hz, 1H), 1.56 (d, J=6.0 Hz, 3H).

Step G: A mixture of 3-(1-aminoethyl)-2-(trifluoromethyl)benzonitrile (300 mg, 1.40 mmol, 1.00 eq., HCl salt), 1,7-dichloro-4-methylpyrido[3,4-d]pyridazine (300 mg, 1.40 mmol, 1.00 eq. diisopropylethylamine (499 mg, 3.86 mmol, 673 µL, 2.76 eq.) and cesium fluoride (400 mg, 2.63 mmol, 97.0 µL, 1.88 eq.) in dimethylsulfoxide (1.50 mL) was degassed and purged with nitrogen (3 times), and then the mixture was stirred at 130° C. for 1 hour under a nitrogen atmosphere. The mixture was then cooled to 25° C. and ethyl acetate (60.0 mL) was added, and the organic solution was washed with brine (30.0 mL×2), dried over anhydrous sodium sulfate, filtered and concentrated under reduced pressure. The residue was purified by column chromatography (SiO$_2$, petroleum ether/ethyl acetate=5/1 to 1/1) to give 3-(1-((7-chloro-4-methylpyrido[3,4-d]pyridazin-1-yl)amino)ethyl)-2-(trifluoromethyl)benzonitrile (160 mg, 408 µmol, 29.2% yield) as a white solid. LCMS [M+1]$^+$: 392.1.

3-(1-((7-chloro-4-methylpyrido[3,4-d]pyridazin-1-yl)amino)ethyl)-2-(trifluoromethyl)benzonitrile (160 mg) was further purified using SFC [column: DAICEL CHIRALPAK AD (250 mm×30 mm, 10 um); mobile phase: phase A: (0.1% NH$_4$OH) in MeOH, phase B: CO$_2$; B %: 20%-20%] to give the first eluting isomer as (R)-3-(1-((7-chloro-4-methyl pyrido[3,4-b]pyridazin-1-yl)amino)ethyl)-2-(trifluoromethyl)benzonitrile (62.0 mg, 158 µmol, 39.0% yield) as a white solid. LCMS [M+1]$^+$: 392.1.
$^1$H NMR (400 MHz, CD$_3$OD) δ=9.24 (d, J=0.8 Hz, 1H), 8.46 (d, J=0.8 Hz, 1H), 8.05 (d, J=8.4 Hz, 1H), 7.80 (d, J=7.2 Hz, 1H), 7.71-7.57 (m, 1H), 5.74 (q, J=6.8 Hz, 1H), 2.74 (s, 3H), 1.68 (d, J=6.8 Hz, 3H).

Intermediate AF

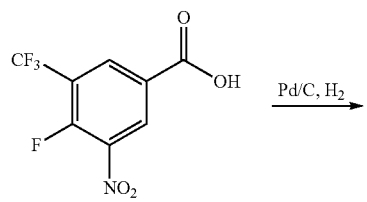

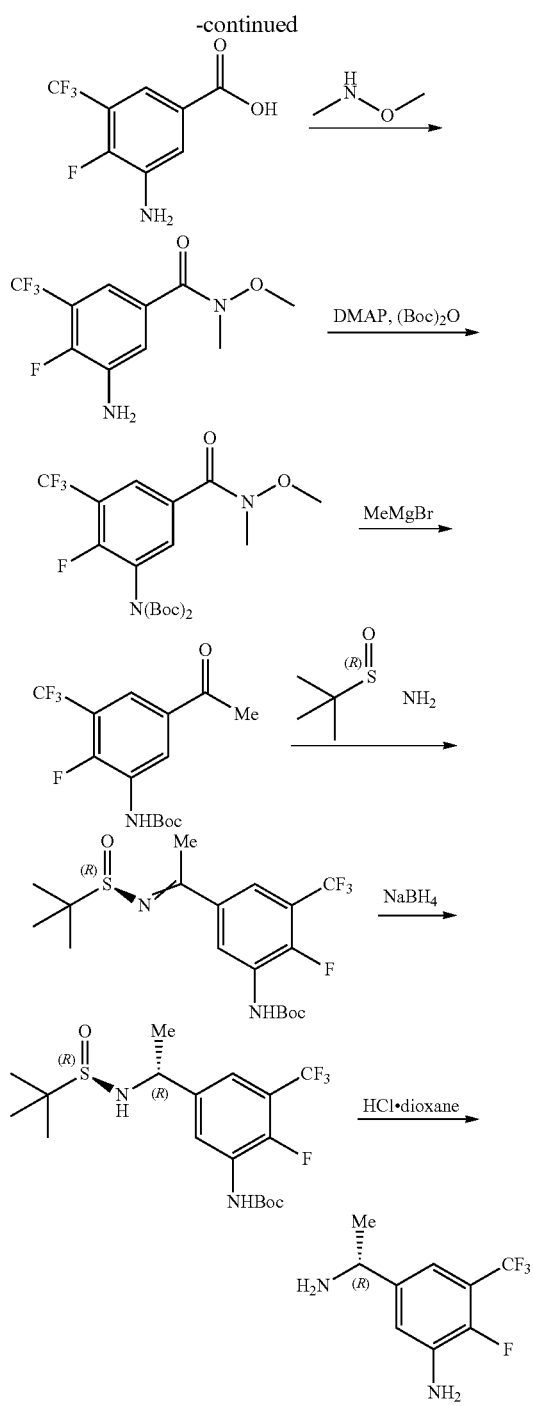

Step A: To a solution of 4-fluoro-3-nitro-5-(trifluoromethyl)benzoic acid (2.00 g, 7.90 mmol, 1.00 eq.) in tetrahydrofuran (15.0 mL) was added palladium on carbon (7.90 mmol, 10% purity, 1.00 eq.) under a nitrogen atmosphere, and the mixture was stirred at 25° C. for 2 hours under a hydrogen atmosphere (15 Psi). The mixture was then filtered and concentrated under reduced pressure to give compound 3-amino-4-fluoro-5-(trifluoromethyl)benzoic acid (1.60 g, 7.17 mmol, 90.8% yield) as a white solid.
$^1$H NMR (400 MHz, DMSO-d$_6$) δ=7.68-7.64 (m, 1H), 7.32-7.29 (m, 1H), 5.95-5.89 (m, 2H).

Step B: To a solution of 3-amino-4-fluoro-5-(trifluoromethyl)benzoic acid (1.50 g, 6.72 mmol, 1.00 eq.) and N,O- dimethylhydroxylamine (830 mg, 13.45 mmol, 2.00 eq.) in N,N-dimethylformamide (10.0 mL) was added HATU (5.11 g, 13.5 mmol, 2.00 eq.) and N,N-diisopropylethylamine (2.61 g, 20.2 mmol, 3.50 mL, 3.00 eq.) and the mixture was stirred at 25° C. for 12 hours. The mixture was diluted with water (50.0 mL) and then extracted with ethyl acetate (50.0 mL×3). The combined organic layers were washed with brine (50.0 mL×3), dried over sodium sulfate, filtered and concentrated under reduced pressure. The residue was purified by column chromatography (silica gel, petroleum ether/ethyl acetate=10/1 to 3/1) to give compound 3-amino-4-fluoro-N-methoxy-N-methyl-5-(trifluoromethyl)benzamide (1.50 g, 5.64 mmol, 83.9% yield) as a yellow oil.

$^1$H NMR (400 MHz, CDCl$_3$) δ=7.38-7.34 (m, 2H), 3.57 (s, 3H), 3.36 (s, 3H)

Step C: To a solution of 3-amino-4-fluoro-N-methoxy-N-methyl-5-(trifluoromethyl)benzamide (1.50 g, 5.64 mmol, 1.00 eq.) in dichloromethane (10.0 mL) was added di-tert-butyl dicarbonate (3.69 g, 16.9 mmol, 3.88 mL, 3.00 eq.) and 4-dimethylaminopyridine (688 mg, 5.64 mmol, 1.00 eq.), and the mixture was stirred at 25° C. for 12 hours. The reaction mixture was diluted with water (50.0 mL) and then extracted with ethyl acetate (50.0 mL×3). The combined organic layers were washed with brine (50.0 mL×3), dried over sodium sulfate, filtered, and concentrated under reduced pressure. The residue was purified by column chromatography (silica gel, petroleum ether/ethyl acetate=10/1 to 3/1) to give compound tert-butyl (tert-butoxycarbonyl)(2-fluoro-5-(methoxy(methyl)carbamoyl)-3-(trifluoromethyl)phenyl)carbamate (2.00 g, 4.29 mmol, 76.1% yield) as a yellow oil.

$^1$H NMR (400 MHz, CDCl$_3$) δ=8.05-8.01 (m, 1H), 7.87-7.84 (m, 1H), 3.55 (s, 3H), 3.39 (s, 3H), 1.42 (s, 18H).

Step D: To a solution of tert-butyl (tert-butoxycarbonyl)(2-fluoro-5-(methoxy(methyl)carbamoyl)-3-(trifluoromethyl)phenyl)carbamate (1.80 g, 3.86 mmol, 1.00 eq.) in tetrahydrofuran (20.0 mL) was added methylmagnesium bromide solution (3.00 M, 3.86 mL, 3.00 eq.) at 0° C., and the mixture was stirred at 0° C. for 12 hours. The reaction mixture was then diluted with water (100 mL), and the solution was extracted with ethyl acetate (100 mL×3). The combined organic layers were washed with brine (100 mL×3), dried over sodium sulfate, filtered, and concentrated under reduced pressure. The residue was purified by column chromatography (silica gel, petroleum ether/ethyl acetate=10/1 to 3/1) to give compound tert-butyl (5-acetyl-2-fluoro-3-(trifluoromethyl)phenyl)carbamate (1.10 g, 3.42 mmol, 88.7% yield) as a yellow oil.

$^1$H NMR (400 MHz, CDCl$_3$) δ=8.98 (d, J=6.4 Hz, 1H), 7.90-7.87 (m, 1H), 6.86 (s, 1H), 2.65 (s, 3H), 1.56 (s, 9H).

Step E: To a solution of tert-butyl (5-acetyl-2-fluoro-3-(trifluoromethyl)phenyl)carbamate (1.10 g, 2.61 mmol, 1.00 eq.) and (R)-2-methylpropane-2-sulfinamide (950 mg, 7.83 mmol, 3.00 eq.) in tetrahydrofuran (10.0 mL) were added titanium (IV) isopropoxide (1.48 g, 5.22 mmol, 1.54 mL, 2.00 eq.) and 1-methoxy-2-(2-methoxyethoxy)ethane (1.87 g, 13.97 mmol, 2.00 mL, 5.35 eq.), and the mixture was stirred at 70° C. for 12 hours. The mixture was then diluted with water (50.0 mL) and extracted with ethyl acetate (50.0 mL×3). The combined organic layers were washed with brine (50.0 mL×3), dried over sodium sulfate, filtered, and concentrated under reduced pressure. The residue was purified by column chromatography (petroleum ether/ethyl acetate=10/1 to 3/1) to give compound tert-butyl (R)-(5-(1-((tert-butylsulfinyl)imino)ethyl)-2-fluoro-3-(trifluoromethyl)phenyl)carbamate (1.00 g, 2.36 mmol, 90.1% yield) as a yellow oil.

$^1$H NMR (400 MHz, CDCl$_3$) δ=8.86 (d, J=6.4 Hz, 1H), 7.82 (d, J=6.0 Hz, 1H), 6.85 (s, 1H), 2.79 (s, 3H), 1.54 (s, 9H), 1.33 (s, 9H).

Step F: To a solution of tert-butyl (R)-(5-(1-((tert-butylsulfinyl)imino)ethyl)-2-fluoro-3-(trifluoromethyl)phenyl)carbamate (1.00 g, 2.36 mmol, 1.00 eq.) in tetrahydrofuran (10.0 mL) was added sodium borohydride (268 mg, 7.07 mmol, 3.00 eq.) at 0° C., and the mixture was stirred at 0° C. for 2 hours. The mixture was then diluted with water (50.0 mL) and extracted with ethyl acetate (50.0 mL×3). The combined organic layers were washed with brine (50.0 mL×3), dried over sodium sulfate, filtered, and concentrated under reduced pressure to give a residue. The residue was purified by column chromatography (silica gel, petroleum ether/ethyl acetate=10/1 to 3/1) to give compound tert-butyl (5-((R)-1-(((R)-tert-butylsulfinyl)amino)ethyl)-2-fluoro-3-(trifluoromethyl)phenyl)carbamate (620 mg, 1.45 mmol, 61.7% yield) as a white solid.

$^1$H NMR (400 MHz, CDCl$_3$) δ=8.34 (d, J=6.4 Hz, 1H), 7.23-7.20 (m, 1H), 6.80 (s, 1H), 4.56-5.53 (m, 1H), 1.54-1.52 (m, 12H), 1.24 (s, 9H).

Step G: To a solution of tert-butyl (5-((R)-1-(((R)-tert-butylsulfinyl)amino)ethyl)-2-fluoro-3-(trifluoromethyl)phenyl)carbamate (620 mg, 1.45 mmol, 1.00 eq.) in dichloromethane (5.00 mL) was added hydrochloride (4.00 M in 1,4-dioxane, 5.00 mL, 13.76 eq.), and the mixture was stirred at 25° C. for 1 hour. The mixture was then concentrated under reduced pressure to give compound (R)-5-(1-aminoethyl)-2-fluoro-3-(trifluoromethyl)aniline (280 mg, 1.24 mmol, 85.5% yield, 98.6% purity, HCl salt) as a yellow oil. This compounds was used directly without further purification.

Intermediate AG

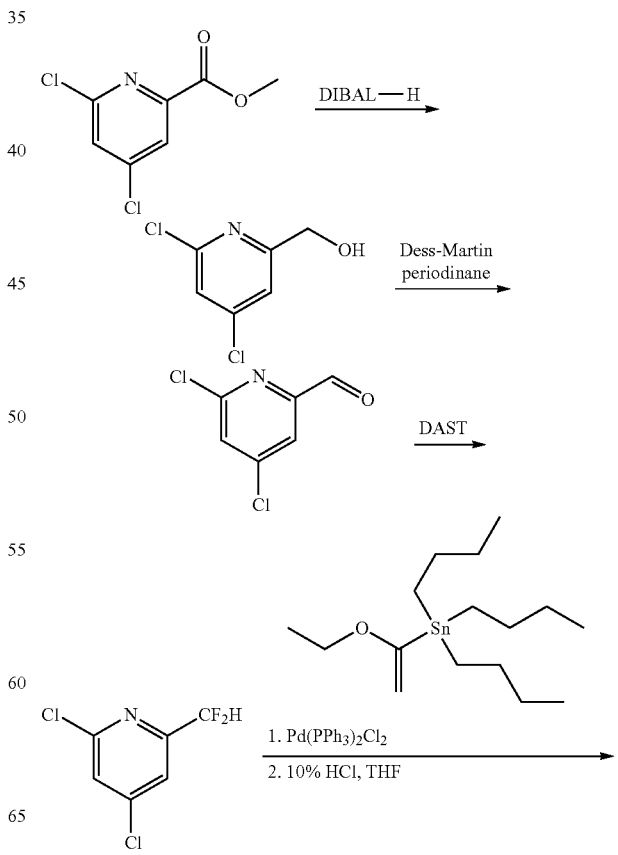

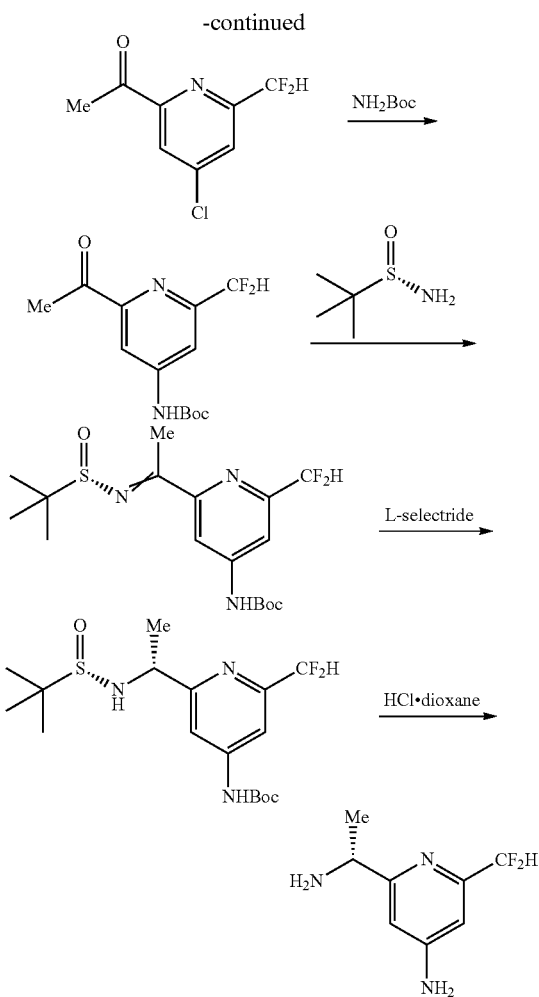

Step A: To a solution of methyl 4,6-dichloropicolinate (4.50 g, 21.8 mmol, 1.00 eq.) in dichloromethane (40.0 mL) was added DIBAL-H (1.0 M, 65.5 mL, 3.00 eq.) dropwise over 10 minutes at −78° C., and the reaction mixture was stirred at −78° C. for 2 hours. The mixture was then diluted with water (2.50 mL) dropwise at 0° C. under a nitrogen atmosphere, followed by addition of sodium hydroxide aqueous solution (2.50 mL, w/w=15%) and water (6.26 mL). The mixture was then stirred at 0° C. for 30 minutes to give a suspension, and the suspension was filtered and the filtrate was concentrated under reduced pressure. The residue was purified by column chromatography (SiO$_2$, petroleum ether/ethyl acetate=30/1 to 10/1) to give (4,6-dichloropyridin-2-yl)methanol (2.40 g, 13.5 mmol, 61.7% yield) as a yellow oil.

$^1$H NMR (400 MHz, DMSO-d$_6$) δ=7.65 (s, 1H), 7.52 (s, 1H), 5.69 (t, J=6.0 Hz, 1H), 4.53 (d, J=6.0 Hz, 2H).

Step B: To a solution of (4,6-dichloropyridin-2-yl)methanol (2.40 g, 13.5 mmol, 1.00 eq.) in dichloromethane (20.0 mL) was added Dess-Martin periodinane (11.4 g, 27.0 mmol, 8.35 mL, 2.00 eq.) portionwise at 0° C., and the mixture was stirred at 20° C. for 2 hours. The mixture was then poured into water (10.0 mL) and stirred for 15 minutes, then saturated sodium thiosulfate aqueous solution (20.0 mL) was slowly added and the mixture was stirred for an additional 15 minutes. The suspension was filtered, the layers were separated, and the aqueous phase was extracted with DCM (20.0 mL×2). The combined organic layers were washed with brine (20 mL), dried over anhydrous sodium sulfate, filtered, and concentrated under reduced pressure. The residue was purified by column chromatography (SiO$_2$, petroleum ether/ethyl acetate=50/1 to 10/1) to give 4,6-dichloropicolinaldehyde (1.60 g, 9.09 mmol, 67.4% yield) as a red oil.

$^1$H NMR (400 MHz, DMSO-d$_6$) δ=9.87 (s, 1H), 8.14 (d, J=1.6 Hz, 1H), 8.01 (d, J=1.6 Hz, 1H).

Step C: To a solution of 4,6-dichloropicolinaldehyde (1.10 g, 6.25 mmol, 1.00 eq.) in dichloromethane (10.0 mL) was added diethylaminosulfur trifluoride (2.01 g, 12.5 mmol, 1.65 mL, 2.00 eq.) dropwise at −20° C., and the mixture was stirred at 25° C. for 1 hour. The mixture was then slowly poured into saturated sodium bicarbonate aqueous solution (10.0 mL) at 25° C., and the resulting solution was extracted with ethyl acetate (10.0 mL×3). The combined organic phases were washed with brine (5.00 mL×3), dried over anhydrous sodium sulfate, filtered, and concentrated in under reduced pressure. The residue was purified by column chromatography (SiO$_2$, petroleum ether/ethyl acetate=100/1 to 20/1) to give 2,4-dichloro-6-(difluoromethyl)pyridine (1.00 g, 5.05 mmol, 80.8% yield) as yellow oil.

$^1$H NMR (400 MHz, CD$_3$OD) δ=7.75 (s, 1H), 7.74 (s, 1H), 6.82-6.55 (m, 1H).

Step D: To a solution of tributyl(1-ethoxyvinyl)tin (2.01 g, 5.56 mmol, 1.88 mL, 1.00 eq.) and 2,4-dichloro-6-(difluoromethyl)pyridine (1.10 g, 5.56 mmol, 1.00 eq.) in dioxane (10.0 mL) was added Pd(PPh$_3$)$_2$Cl$_2$ (390 mg, 556 μmol, 0.10 eq) under a nitrogen atmosphere, and the mixture was stirred at 110° C. for 12 hours. The reaction mixture was cooled to 25° C. and slowly poured into a saturated potassium fluoride aqueous solution (20.0 mL). The resulting aqueous solution was extracted with ethyl acetate (50.0 mL×3), and the combined organic layers were washed with brine (30.0 mL×2), dried over anhydrous sodium, filtered, and concentrated under reduced pressure. The residue was purified by column chromatography (SiO$_2$, petroleum ether/ethyl acetate=100/1 to 20/1) to give 4-chloro-2-(difluoromethyl)-6-(1-ethoxyvinyl)pyridine (1.20 g, 5.14 mmol, 92.5% yield) as a yellow oil which was used in the next step directly.

To a solution of 4-chloro-2-(difluoromethyl)-6-(1-ethoxyvinyl)pyridine (1.00 g, 4.28 mmol, 1.00 eq) in dioxane (5.00 mL) was added hydrochloric acid aqueous solution (2.00 M, 4.28 mL, 2.00 eq) at 20° C., and the mixture was stirred at 20° C. for 1 hour. The pH of the mixture was then adjusted to pH=8 by addition saturated sodium bicarbonate (15.0 mL), and extracted with ethyl acetate (30.0 mL×2). The combined organic phases were washed with brine (10.0 mL×2), dried over anhydrous sodium sulfate, filtered, and concentrated under reduced pressure. The residue was purified by column chromatography (SiO$_2$, petroleum ether/ethyl acetate=50/1 to 10/1) to give 1-(4-chloro-6-(difluoromethyl)pyridin-2-yl)ethan-1-one (800 mg, 3.89 mmol, 90.9% yield) as a white solid.

$^1$H NMR (400 MHz, CD$_3$OD) δ=8.10-8.16 (m, 1H), 7.95 (d, J=1.6 Hz, 1H), 6.67-6.95 (m, 1H), 2.69 (s, 3H).

Step E: To a solution of 1-(4-chloro-6-(difluoromethyl)pyridin-2-yl)ethan-1-one (0.85 g, 4.13 mmol, 1.00 eq.) and tert-butyl carbamate (1.45 g, 12.4 mmol, 3.00 eq.) in dioxane (6.00 mL) was added cesium carbonate (2.69 g, 8.27 mmol, 2.00 eq.), XPhos (394 mg, 827 μmol, 0.20 eq.), and palladium acetate (92.8 mg, 413 μmol, 0.10 eq.) under a nitrogen atmosphere, and the mixture was stirred at 90° C.

for 2 hours. The mixture was then cooled to 25° C. and concentrated under reduced pressure, and the residue was purified by column chromatography (SiO₂, petroleum ether/ethyl acetate=100/1 to 10/1) to give tert-butyl (2-acetyl-6-(difluoromethyl)pyridin-4-yl)carbamate (1.00 g, 3.49 mmol, 84.5% yield) as a white solid. LCMS [M+1]⁺: 287.1.

Step F: To a solution of tert-butyl (2-acetyl-6-(difluoromethyl)pyridin-4-yl)carbamate (1.00 g, 3.49 mmol, 1.00 eq.) and (<S)-2-methylpropane-2-sulfinamide (508 mg, 4.19 mmol, 1.20 eq.) in THF (10.0 mL) was added titanium (IV) ethoxide (7.97 g, 34.9 mmol, 7.24 mL, 10.0 eq.), and the mixture was stirred at 75° C. for 12 hours. The mixture was then cooled to 25° C. and poured into water (5.00 mL), then the suspension was filtered, and the filtrate was concentrated under reduced pressure. The residue was purified by column chromatography (SiO₂, petroleum ether/ethyl acetate=50/1 to 5/1) to give tert-butyl (S)-(2-(1-((tert-butylsulfinyl)imino)ethyl)-6-(difluoromethyl)pyridin-4-yl)carbamate (1.00 g, 2.57 mmol, 73.5% yield) as a yellow solid.

¹H NMR (400 MHz, CD₃OD) δ=8.30 (s, 1H), 7.94 (d, J=1.6 Hz, 1H), 6.52-6.82 (m, 1H), 2.81 (s, 3H), 1.54 (s, 9H), 1.35 (s, 9H).

Step G: To a solution of tert-butyl (S)-(2-(1-((tert-butylsulfinyl)imino)ethyl)-6-(difluoromethyl)pyridin-4-yl)carbamate (1.00 g, 2.57 mmol, 1.00 eq.) in THF (10.0 mL) was added L-selectride (1.0 M, 976 mg, 5.14 mmol, 1.12 mL, 2.00 eq.) dropwise at 0° C., and the mixture was stirred at 0-20° C. for 1 hour. The mixture was poured into saturated ammonium chloride aqueous solution (15.0 mL) and stirred for 10 minutes, then extracted with ethyl acetate (15.0 mL×3). The combined organic phases were washed with brine (15.0 mL×3), dried over anhydrous sodium sulfate, filtered, and filtrate concentrated under reduced pressure. The residue was purified by column chromatography (SiO₂, petroleum ether/ethyl acetate=100/1 to 5/1) to give tert-butyl (2-((R)-1-((S)-tert-butylsulfinyl)amino)ethyl)-6-(difluoromethyl)pyridin-4-yl)carbamate (550 mg, 1.26 mmol, 49.0% yield, 89.5% purity) as a white solid.

¹H NMR (400 MHz, CD₃OD) δ=7.70 (s, 1H), 7.61 (d, J=2.0 Hz, 1H), 6.41-6.77 (m, 1H), 4.55 (q, J=6.8 Hz, 1H), 1.58 (d, J=6.8 Hz, 3H), 1.53 (s, 9H), 1.23 (s, 9H).

SFC: Column: Chiralcel OD-3 50×4.6 mm I.D., 3 um Mobile phase: Phase A for CO₂, and Phase B for MeOH (0.05% DEA); Gradient elution: MeOH (0.05% DEA) in CO₂ from 5% to 40% Flow rate: 3 mL/min; Detector: PDA Column Temp: 35° C.; Back Pressure: 100 Bar.

Step H: A solution of tert-butyl (2-((R)-1-(((S)-tert-butylsulfinyl)amino)ethyl)-6-(difluoromethyl)pyridin-4-yl)carbamate (450 mg, 1.15 mmol, 1.00 eq.) in hydrochloric acid/dioxane (2.00 mL) was stirred at 0-20° C. for 1 hour. The mixture was then concentrated under reduced pressure to give a mixture of (R)-2-(1-aminoethyl)-6-(difluoromethyl)pyridin-4-amine and tert-butyl (2-((R)-1-(((S)-tert-butylsulfinyl)amino)ethyl)-6-(difluoromethyl)pyridin-4-yl)carbamate as a white solid which was used directly in the next step directly without purification. LCMS [M+1]⁺: 288.2.

¹H NMR (400 MHz, CD₃OD) δ=7.74 (s, 1H), 7.65 (d, J=1.6 Hz, 1H), 6.82-6.51 (m, 1H), 4.60-4.45 (m, 2H), 1.61 (d, J=6.8 Hz, 3H), 1.54 (s, 9H).

Intermediate AH

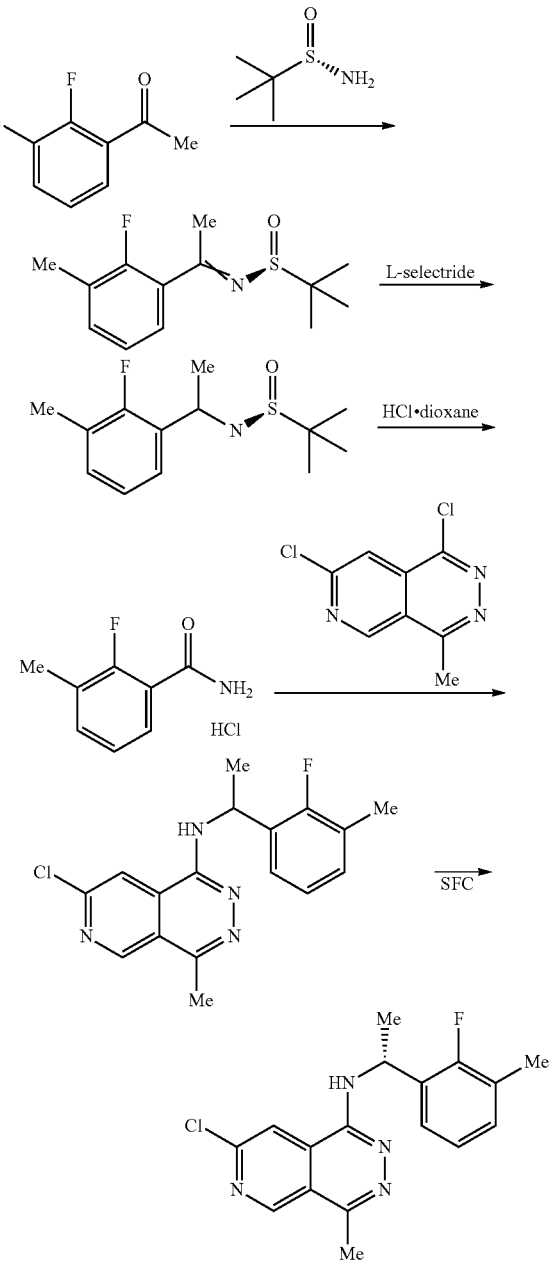

Step A: To a solution of 1-(2-fluoro-3-methylphenyl)ethan-1-one (1.00 g, 6.57 mmol, 1.00 eq.) and (S)-2-methylpropane-2-sulfinamide (1.04 g, 8.54 mmol, 1.30 eq.) in tetrahydrofuran (20.0 mL) were added titanium tetrisopropyloxide (3.73 g, 13.1 mmol, 3.88 mL, 2.00 eq.) under a nitrogen atmosphere, and the mixture was stirred at 70° C. for 12 hours under a nitrogen atmosphere. The reaction mixture was cooled to 25° C. and poured into water (40.0 mL) to give a suspension after stirring for 10 minutes, the suspension was filtered, the resulting aqueous solution was extracted with ethyl acetate (40.0 mL×3). The combined organic layers were washed with brine (30.0 mL), dried over sodium sulfate, filtered, and concentrated under reduced pressure. The residue was purified by column chromatography (silica gel, petroleum ether/ethyl acetate=50/1 to 2/1) to give (S)—N-(1-(2-fluoro-3-methyl phenyl)ethylidene)-2-methylpropane-2-sulfinamide (1.50 g, 5.87 mmol, 89.4% yield) as a yellow solid. LCMS [M+1]$^+$: 256.2.

$^1$H NMR (400 MHz, DMSO-d$_6$) δ=7.46 (br t, J=6.8 Hz, 1H), 7.30-7.24 (m, 1H), 7.09-7.04 (m, 1H), 2.76 (br d, J=2.8 Hz, 3H), 2.31 (d, J=2.4 Hz, 3H), 1.31 (s, 9H).

Step B: To a solution of (R)—N-(1-(2-fluoro-3-methylphenyl)ethylidene)-2-methylpropane-2-sulfinamide (1.50 g, 5.87 mmol, 1.00 eq.) in tetrahydrofuran (20.0 mL) was added L-selectride (1.0 M, 11.7 mmol, 11.8 mL, 2.00 eq.) at −78° C. under a nitrogen atmosphere, and the mixture was stirred at −78° C. for 2 hours. The reaction mixture was poured into water (10.0 mL) slowly and stirred for 10 minutes, and the resulting mixed solution was extracted with ethyl acetate (10.0 mL×3). The combined organic layers were washed with brine (10.0 mL), dried over sodium sulfate, filtered, and concentrated under reduced pressure. The residue was purified by column chromatography (silica gel, petroleum ether/ethyl acetate=50/1 to 1/1) to give (R)—N-(1-(2-fluoro-3-methylphenyl)ethyl)-2-methylpropane-2-sulfinamide (900 mg, 3.50 mmol, 59.5% yield) as a yellow oil. LCMS [M+1]$^+$: 258.4.

$^1$H NMR (400 MHz, DMSO-d$_6$) δ=7.16 (t, J=7.6 Hz, 1H), 7.13-7.08 (m, 1H), 7.04-6.99 (m, 1H), 4.85 (q, J=6.8 Hz, 1H), 2.28 (d, J=2.0 Hz, 3H), 1.58 (d, J=6.8 Hz, 3H), 1.20 (s, 9H).

Step C: To a solution of (S)—N-(1-(2-fluoro-3-methylphenyl)ethyl)-2-methylpropane-2-sulfinamide (900 mg, 3.50 mmol, 1.00 eq.) in dichloromethane (5.00 mL) was added HCl (4.00 M in 1,4-dioxane, 5.00 mL, 5.72 eq.) under nitrogen a atmosphere, and the mixture was stirred at 20° C. for 1 hour. The mixture was concentrated to give 1-(2-fluoro-3-methylphenyl)ethan-1-amine (390 mg, crude, hydrochloride salt) as a yellow solid which was used directly without further purification.

To a solution of 1-(2-fluoro-3-methylphenyl)ethan-1-amine (300 mg, 1.96 mmol, 1.00 eq., hydrochloride salt), 1,7-dichloro-4-methylpyrido[3,4-d]pyridazine (419 mg, 1.96 mmol, 1.00 eq.), N,N-diisopropylethylamine (506 mg, 3.92 mmol, 2.00 eq.) and potassium fluoride (341 mg, 5.87 mmol, 0.14 mL, 3.00 eq.) in dimethyl sulfoxide (5.00 mL) were stirred at 130° C. for 1 hour under a nitrogen atmosphere. The mixture was then cooled to 25° C., poured into water (20.0 mL), and extracted with ethyl acetate (20.0 mL×3). The combined organic layers were washed with brine (20.0 mL), dried over sodium sulfate, filtered, and concentrated under reduced pressure. The residue was purified by prep-HPLC [column: Welch Xtimate C18 150×25 mm×5 um; mobile phase: phase A: water(0.05% HCl), phase B: acetonitrile; B %: 14%-44%] to give 7-chloro-N-(1-(2-fluoro-3-methylphenyl)ethyl)-4-methylpyrido[3,4-d]pyridazin-1-amine (100 mg, 0.30 mmol, 23.2% yield) as a yellow solid. LCMS [M+1]$^+$: 331.2.

A racemic 7-chloro-N-(1-(2-fluoro-3-methyl phenyl)ethyl)-4-methylpyrido[3,4-d]pyridazin-1-amine (200 mg, 0.60 mmol, 1.00 eq.) was purified by SFC (column: DAICEL CHIRALPAK IG (250 mm×30 mm, 10 um); mobile phase: phase A: 0.1% NH$_4$OH in MeOH, phase B: CO$_2$; B %: 30%-30%] to give (R)-7-chloro-N-(1-(2-fluoro-3-methylphenyl)ethyl)-4-methylpyrido[3,4-d]pyridazin-1-amine as the first eluting isomer (80.0 mg, 0.24 mmol, 40.0% yield) as a yellow solid.

The following Examples are intended to illustrate further certain embodiments of the invention and are not intended to limit the scope of the invention.

Example 1-1

6,7-dimethoxy-N-(1-(4-(2-((methylamino)methyl)phenyl)thiophen-2-yl)ethyl)phthalazin-1-amine

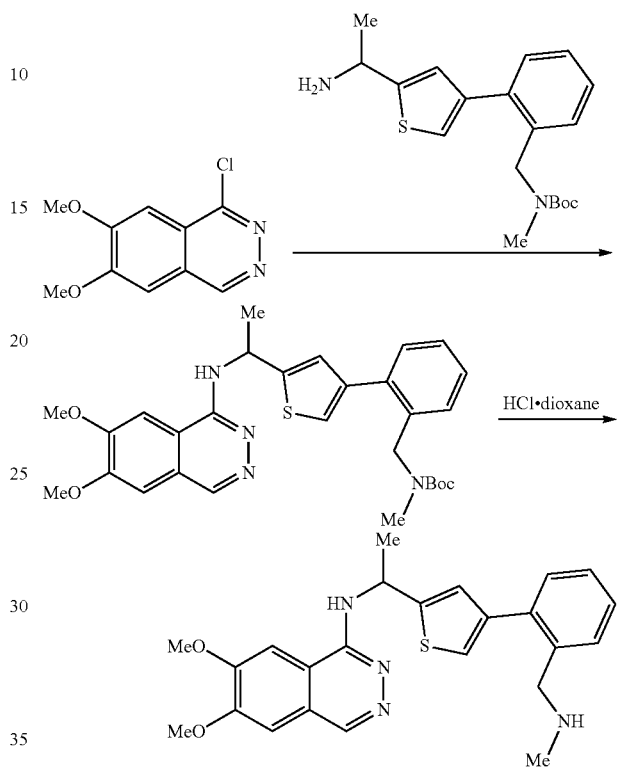

Step A: A mixture of 1-chloro-6,7-dimethoxyphthalazine (120 mg, 534 μmol, 1.00 eq.), tert-butyl (2-(5-(1-aminoethyl)thiophen-3-yl)benzyl)(methyl)carbamate (130 mg, 374 μmol, 0.70 eq.), BrettPhos Pd G$_3$ (48.4 mg, 53.4 μmol, 0.10 eq.) and potassium tert-butoxide (150 mg, 1.34 mmol, 2.50 eq.) in toluene (3.00 mL) was degassed and purged with nitrogen 3 times, then the reaction mixture was stirred at 100° C. for 1 hour under a nitrogen atmosphere. The reaction mixture was cooled to 25° C. and filtered, and the filtrate was concentrated under reduced pressure to give a residue. The residue was purified by prep-TLC (SiO$_2$, dichloromethane/methanol=10/1) to give tert-butyl (2-(5-(1-((6,7-dimethoxyphthalazin-1-yl)amino)ethyl)thiophen-3-yl)benzyl)(methyl)carbamate (70.0 mg, 24.5% yield) as a brown solid. LCMS [M+1]: 535.5.

Step B: To a solution of tert-butyl (2-(5-(1-((6,7-dimethoxyphthalazin-1-yl)amino)ethyl)thiophen-3-yl)benzyl)(methyl)carbamate (60.0 mg, 112 μmol, 1.00 eq.) in acetonitrile (1.00 mL) was added HCl (4.0 M in dioxane, 0.20 mL). The reaction mixture was stirred at 25° C. for 10 minutes, then the mixture was filtered and concentrated under reduced pressure at 25° C. to give a residue. The residue was dissolved in methanol (2.00 mL) and adjusted to pH=7 with solid sodium bicarbonate (around 30.0 mg) to give a suspension. The suspension was filtered, and the filtrate was purified by prep-HPLC (column: Waters Xbridge 150×25 mm×5 um; mobile phase: [water(10 mM NH$_4$HCO$_3$)-ACN]; B %: 19%-49%, 9 min) and lyophilization to give 6,7-dimethoxy-N-(1-(4-(2-((methylamino)methyl)phenyl)thiophen-2-yl)ethyl)phthalazin-1-amine (16.6 mg, 33.8% yield, 99.6% purity) as a white solid. LCMS [M+1]: 435.1.

$^1$H NMR (400 MHz, CD$_3$OD) δ 8.73 (d, J=2.4 Hz, 1H), 7.75 (s, 1H), 7.51-7.46 (m, 1H), 7.43-7.37 (m, 3H), 7.35 (d, J=5.2 Hz, 1H), 7.19 (d, J=1.2 Hz, 1H), 7.16 (s, 1H), 5.93-5.81 (m, 1H), 4.10 (s, 2H), 4.05 (s, 3H), 4.00 (s, 3H), 2.45 (s, 3H), 1.83 (d, J=6.8 Hz, 3H).

Example 1-2

(R)-7-(1-methyl-1H-pyrazol-4-yl)-N-(1-(4-(2-((methylamino)methyl)phenyl)thiophen-2-yl)ethyl)phthalazin-1-amine

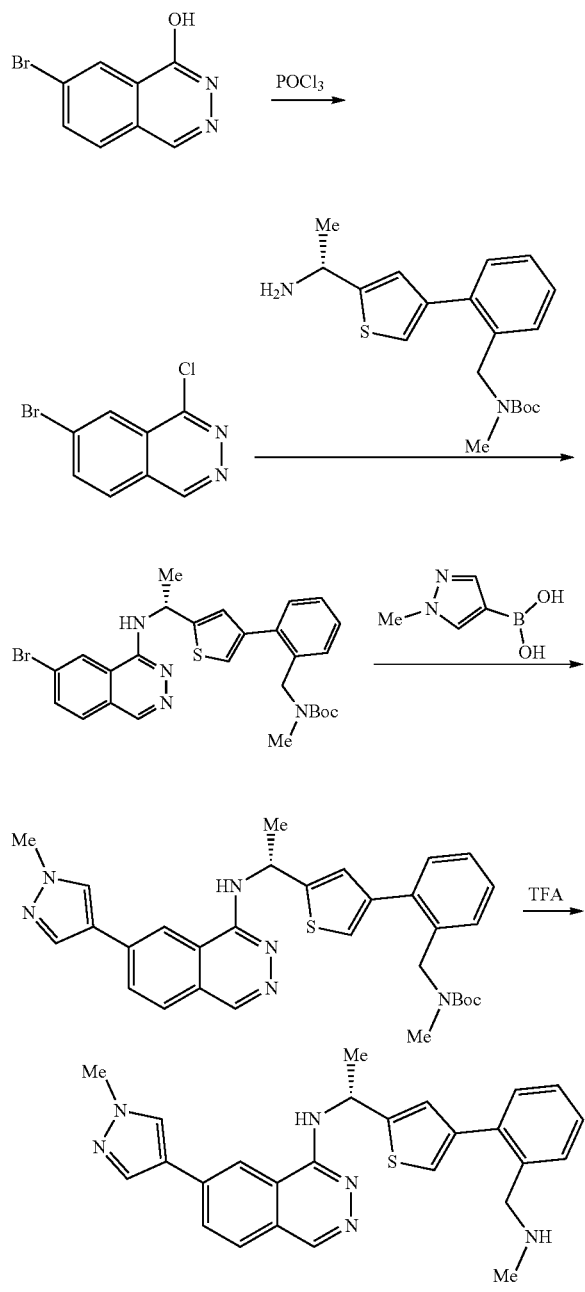

Step A: To a solution of 7-bromophthalazin-1-ol (950 mg, 4.22 mmol, 1.00 eq.) in acetonitrile (19.0 mL) was added phosphorus (V) oxychloride (2.27 g, 14.8 mmol, 1.37 mL, 3.50 eq.), the reaction mixture was stirred at 80° C. for 2 hours. The reaction mixture was cooled to 25° C. and concentrated in vacuo to remove the solvent. The remaining residue was diluted with DCM (50.0 mL) cooled to 0° C., and the organic layer was adjusted to pH=7 with saturated sodium bicarbonate aqueous solution (30.0 mL). The organic phase was separated, washed with brine (30.0 mL×2), dried over anhydrous sodium sulfate, filtered, and concentrated under reduced pressure to give 7-bromo-1-chlorophthalazine (900 mg, 3.70 mmol, 87.6% yield) as a brown solid. LCMS [M+3]: 244.8.

$^1$H NMR (400 MHz, CDCl$_3$) δ 9.44 (d, J=0.8 Hz, 1H), 8.52-8.49 (m, 1H), 8.10 (dd, J=2.0, 8.8 Hz, 1H), 7.90 (d, J=8.4 Hz, 1H).

Step B: To a solution of 7-bromo-1-chlorophthalazine (100 mg, 411 μmol, 1.00 eq.) in DMSO (2.00 mL) was added tert-butyl (R)-(2-(5-(1-aminoethyl)thiophen-3-yl)benzyl)(methyl)carbamate (129 mg, 370 μmol, 0.90 eq.), potassium fluoride (71.6 mg, 1.23 mmol, 28.8 μL, 3.00 eq.) and diisopropylethylamine (106 mg, 821 μmol, 143 μL, 2.00 eq.). The reaction mixture was stirred at 130° C. for 4 hours under a nitrogen atmosphere. After this time, the reaction mixture was cooled to 25° C. Ethyl acetate (10.0 mL) and water (8.00 mL) were added to the reaction mixture and layers were separated, then the aqueous phase was extracted with ethyl acetate (10.0 mL×2). Combined organic layers were washed with brine (10.0 mL×2), dried over sodium sulfate, filtered, and concentrated under reduced pressure to give a residue. The residue was purified by prep-TLC (SiO$_2$, petroleum ether/ethyl acetate=1/1) to give tert-butyl (R)-(2-(5-(1-((7-bromophthalazin-1-yl)amino)ethyl)thiophen-3-yl)benzyl)(methyl)carbamate (80.0 mg, 35.2% yield) as a yellow solid. LCMS [M+1]: 553.0.

$^1$H NMR (400 MHz, CD$_3$OD) δ 8.80 (s, 1H), 8.56 (s, 1H), 8.20 (s, 1H), 8.12-8.07 (m, 2H), 7.91 (br d, J=8.4 Hz, 1H), 7.33-7.25 (m, 3H), 7.19 (br d, J=7.2 Hz, 1H), 7.15-7.03 (m, 2H), 5.90-5.97 (m, 1H), 4.45 (br d, J=14.8 Hz, 2H), 3.97 (s, 3H), 2.66 (s, 3H), 1.84 (d, J=6.8 Hz, 3H), 1.46-1.29 (m, 9H).

Step D: To a solution of tert-butyl (R)-methyl(2-(5-(1-((7-(1-methyl-1H-pyrazol-4-yl)phthalazin-1-yl)amino)ethyl)thiophen-3-yl)benzyl)carbamate (18.0 mg, 32.5 μmol, 1.00 eq.) in DCM (1.00 mL) was added TFA (770 mg, 6.75 mmol, 0.50 mL, 208 eq.). The reaction mixture was stirred at 25° C. for 10 minutes. The reaction mixture was filtered and concentrated under reduced pressure to give a residue. The residue was purified by prep-HPLC (column: Phenomenex Luna C18 75×30 mm×3 um; mobile phase: [water (0.05% HCl)-ACN]; B %: 13%-33%) and lyophilization to give (R)-7-(1-methyl-1H-pyrazol-4-yl)-N-(1-(4-(2-((methylamino)methyl)phenyl)thiophen-2-yl)ethyl)phthalazin-1-amine (9.02 mg, 55.7% yield, 91.1% purity) as a off-white solid. LCMS [M+1]: 455.2.

$^1$H NMR (400 MHz, CD$_3$OD) δ 9.10 (br s, 1H), 8.49 (s, 1H), 8.39 (dd, J=1.2, 8.4 Hz, 1H), 8.29 (s, 1H), 8.23 (br d, J=8.4 Hz, 1H), 8.17 (s, 1H), 8.08 (s, 1H), 7.60-7.57 (m, 1H), 7.50-7.45 (m, 2H), 7.44-7.40 (m, 1H), 7.39-7.34 (m, 2H), 5.78 (q, J=6.4 Hz, 1H), 4.30 (s, 2H), 4.04 (s, 2H), 4.01 (s, 3H), 2.62 (s, 3H), 1.98 (br d, J=6.8 Hz, 3H).

Example 1-3

(R)—N-(1-(4-(2-((methylamino)methyl)phenyl)thiophen-2-yl)ethyl)-7-morpholinophthalazin-1-amine

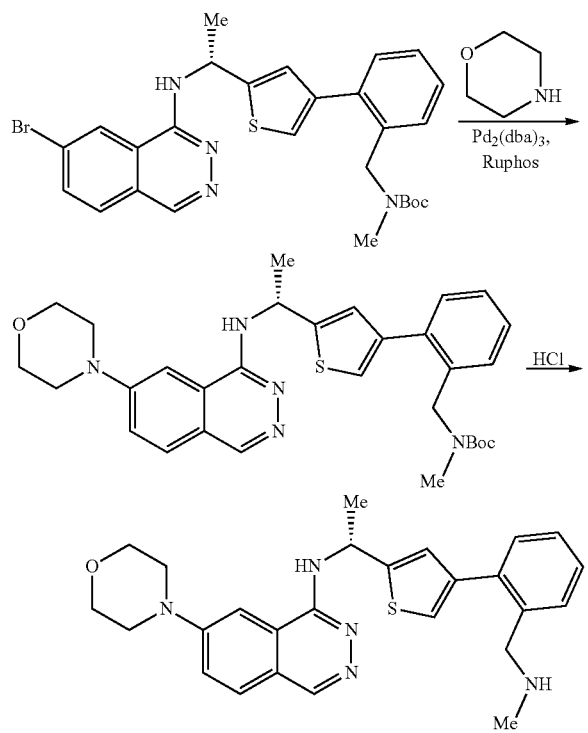

Step A: A mixture of tert-butyl (R)-(2-(5-(1-((7-bromophthalazin-1-yl)amino)ethyl)thiophen-3-yl)benzyl)(methyl)carbamate (45.0 mg, 81.3 μmol, 1.00 eq.), morpholine (10.6 mg, 122 μmol, 10.7 μL, 1.50 eq.), Pd₂(dba)₃ (7.44 mg, 8.13 μmol, 0.10 eq), RuPhos (7.59 mg, 16.3 μmol, 0.20 eq) and potassium tert-butoxide (1.00 M in THF, 163 μL, 2.00 eq.) in toluene (3.00 mL) was degassed and purged with nitrogen 3 times, then the reaction mixture was stirred at 110° C. for 1 hour under a nitrogen atmosphere. The reaction mixture was cooled to 25° C. and concentrated under reduced pressure to give a residue. The residue was purified by column chromatography (SiO₂, dichloromethane/methanol=100/1 to 20/1) to give tert-butyl (R)-methyl(2-(5-(1-((7-morpholinophthalazin-1-yl)amino)ethyl)thiophen-3-yl)benzyl)carbamate (40.0 mg, 57.2 μmol, 70.3% yield, 80.0% purity) as a yellow solid. LCMS [M+1]: 560.2.

¹H NMR (400 MHz, CDCl₃) δ 8.81 (s, 1H), 7.72 (d, J=8.8 Hz, 1H), 7.46-7.41 (m, 1H), 7.35-7.28 (m, 3H), 7.26-7.06 (m, 3H), 7.03 (d, J=1.2 Hz, 1H), 6.15-5.95 (m, 1H), 4.80-4.40 (m, 2H), 3.96-3.86 (m, 4H), 3.46-3.28 (m, 4H), 2.80-2.52 (m, 3H), 1.83 (d, J=6.8 Hz, 3H), 1.42 (s, 9H).

Step B: To a mixture of tert-butyl (R)-methyl(2-(5-(1-((7-morpholinophthalazin-1-yl)amino)ethyl)thiophen-3-yl)benzyl)carbamate (37.0 mg, 52.9 μmol, 1.00 eq) in acetonitrile (1.00 mL) was added HCl (4.00 M in dioxane, 0.50 mL) dropwise at 0° C., the reaction mixture was stirred at 0° C. for 30 minutes. The mixture was added methanol (2.00 mL) and adjusted to pH=7 with solid sodium bicarbonate (around 30.0 mg) to give a suspension, the suspension was filtered, the filtrate was concentrated in vacuo to give a residue. The residue was purified by prep-HPLC (column: Waters Xbridge 150×25 mm×5 um; mobile phase: [A: water(10 mM NH₄HCO₃)—B: ACN]; B %: 22%-52%] to give (R)—N-(1-(4-(2-((methylamino)methyl)phenyl)thiophen-2-yl)ethyl)-7-morpholinophthalazin-1-amine (18.3 mg, 38.5 μmol, 72.7% yield, 96.6% purity) as a white solid. LCMS [M+1]: 460.2.

¹H NMR (400 MHz, CD₃OD) δ 8.66 (s, 1H), 7.82 (dd, J=1.2, 8.8 Hz, 1H), 7.65-7.60 (m, 1H), 7.55 (d, J=2.0 Hz, 1H), 7.46-7.41 (m, 1H), 7.36-7.30 (m, 3H), 7.18 (d, J=5.2 Hz, 2H), 5.94 (q, J=6.8 Hz, 1H), 3.93-3.87 (m, 4H), 3.81 (s, 2H), 3.49-3.43 (m, 4H), 2.28 (s, 3H), 1.84 (d, J=6.8 Hz, 3H).

Example 1-4

(R)—N-(1-(2-methyl-3-(trifluoromethyl)phenyl)ethyl)-7-morpholinophthalazin-1-amine

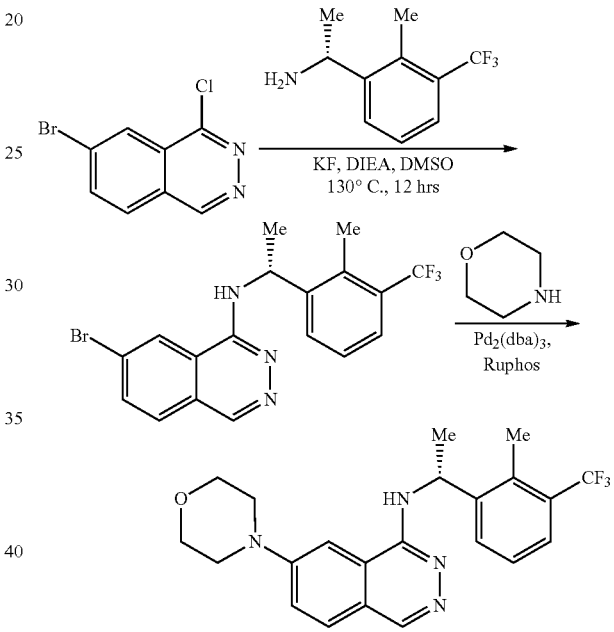

Step A: To a solution of 7-bromo-1-chlorophthalazine (244 mg, 1.00 mmol, 1.00 eq.) and (R)-1-(2-methyl-3-(trifluoromethyl)phenyl)ethan-1-amine (242 mg, 1.00 mmol, 1.00 eq., hydrochloride) in DMSO (3.00 mL) was added potassium fluoride (175 mg, 3.00 mmol, 70.4 μL, 3.00 eq.) and DIEA (259 mg, 2.00 mmol, 349 μL, 2.00 eq.), the reaction mixture was stirred at 130° C. for 12 hours under a nitrogen atmosphere. The reaction mixture was cooled to 25° C. and diluted with ethyl acetate (20.0 mL), the organic layer was washed with brine (20.0 mL×2), dried over anhydrous sodium sulfate, filtered and concentrated in vacuo to give a residue. The residue was purified by silica gel chromatography (petroleum ether/ethyl acetate=10/1 to 1/1) to give (R)-7-bromo-N-(1-(2-methyl-3-(trifluoromethyl)phenyl)ethyl)phthalazin-1-amine (280 mg, 683 μmol, 68.2% yield) as a brown solid. LCMS [M+1]: 409.9.

¹H NMR (400 MHz, CDCl₃) δ 8.92 (s, 1H), 7.94 (s, 1H), 7.91 (dd, J=1.6, 8.4 Hz, 1H), 7.71 (d, J=8.4 Hz, 1H), 7.68 (d, J=7.6 Hz, 1H), 7.58 (d, J=8.0 Hz, 1H), 7.32-7.28 (m, 1H), 6.02-5.94 (m, 1H), 5.14 (br d, J=6.4 Hz, 1H), 2.58 (s, 3H), 1.70 (d, J=6.8 Hz, 3H).

Step B: To a solution of (R)-7-bromo-N-(1-(2-methyl-3-(trifluoromethyl)phenyl)ethyl)phthalazin-1-amine (30.0 mg, 73.1 μmol, 1.00 eq.) and morpholine (12.7 mg, 146 μmol, 12.9 μL, 2.00 eq.) in dioxane (1.00 mL) was added Pd$_2$(dba)$_3$ (6.70 mg, 7.31 μmol, 0.10 eq.), RuPhos (6.82 mg, 14.6 μmol, 0.20 eq), and cesium carbonate (47.7 mg, 146 μmol, 2.00 eq.) under a nitrogen atmosphere. The reaction mixture was stirred at 110° C. for 1 hour under a nitrogen atmosphere. The reaction mixture was cooled to 25° C., filtered, and concentrated in vacuo to give a residue. The residue was purified by prep-TLC (dichloromethane/methanol=10/1) to give a crude product, the crude product was purified by prep-HPLC (column: Waters Xbridge C18 150× 50 mm×10 um; mobile phase: [A: water(10 mM NH$_4$HCO$_3$), B: ACN]; B %: 40%-70%) to give (R)—N-(1-(2-methyl-3-(trifluoromethyl)phenyl)ethyl)-7-morpholinophthalazin-1-amine (11.0 mg, 26.2 μmol, 35.8% yield, 99.2% purity) as a white solid. LCMS [M+1]: 417.1.

$^1$H NMR (400 MHz, CD$_3$OD) δ=8.56 (s, 1H), 7.79-7.75 (m, 1H), 7.72 (d, J=8.0 Hz, 1H), 7.62-7.57 (m, 2H), 7.49 (d, J=7.2 Hz, 1H), 7.25 (t, J=7.6 Hz, 1H), 5.77 (q, J=6.8 Hz, 1H), 3.94-3.84 (m, 4H), 3.51-3.42 (m, 4H), 2.61 (s, 3H), 1.64 (d, J=7.2 Hz, 3H).

Following the teachings of General Reaction Scheme III and the procedures described for the preparation of Examples 1-1-1-4, the following compounds of Formula (I), Examples 1-5 to 1-50 shown in Table 1 were prepared:

TABLE 1

| Ex. # | Structure | Spectral Data |
|---|---|---|
| 1-5 | 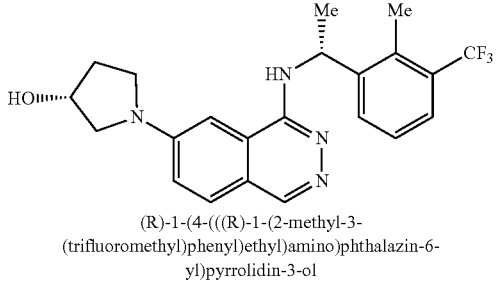<br>(R)-1-(4-(((R)-1-(2-methyl-3-(trifluoromethyl)phenyl)ethyl)amino)phthalazin-6-yl)pyrrolidin-3-ol | $^1$H NMR (400 MHz, CD$_3$OD) δ 8.69 (s, 1H), 7.89 (br d, J = 8.0 Hz, 1H), 7.71 (br d, J = 7.6 Hz, 1H), 7.52 (br d, J = 7.6 Hz, 1H), 7.38-7.30 (m, 2H), 7.30-7.23 (m, 1H), 5.69-5.58 (m, 1H), 4.64 (br s, 1H), 3.76-3.63 (m, 3H), 3.52 (br d, J = 11.2 Hz, 1H), 2.61 (s, 3H), 2.30-2.11 (m, 2H), 1.67 (br d, J = 6.4 Hz, 3H). LCMS [M + 1]: 417.0. |
| 1-6 | 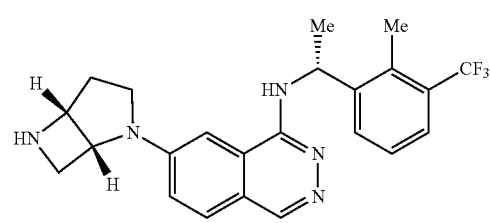 [SMILES: Cc1c([C@@H](C)Nc2nncc3ccc(N4CC[C@H]5NC[C@H]54)cc23)cccc1C(F)(F)F]<br>7-((1R,5R)-2,6-diazabicyclo[3.2.0]heptan-2-yl)-N-((R)-1-(2-methyl-3-(trifluoromethyl)phenyl)ethyl)phthalazin-1-amine | $^1$H NMR (400 MHz, CD$_3$OD) δ = 8.67 (s, 1H), 7.88 (d, J = 8.8 Hz, 1H), 7.74 (d, J = 8.0 Hz, 1H), 7.52 (d, J = 8.0 Hz, 1H), 7.41 (d, J = 1.6 Hz, 1H), 7.34 (dd, J = 2.0, 8.8 Hz, 1H), 7.30-7.24 (m, 1H), 5.72 (q, J = 6.8 Hz, 1H), 5.19 (t, J = 6.0 Hz, 1H), 4.98-4.93 (m, 1H), 4.36 (dd, J = 5.6, 10.8 Hz, 1H), 4.23-4.17 (m, 1H), 3.93-3.85 (m, 1H), 3.49 (dd, J = 2.8, 10.4 Hz, 1H), 2.61 (s, 3H), 2.51-2.35 (m, 2H), 1.67 (d, J = 6.8 Hz, 3H). LCMS [M + 1]: 428.0. |
| 1-7 | 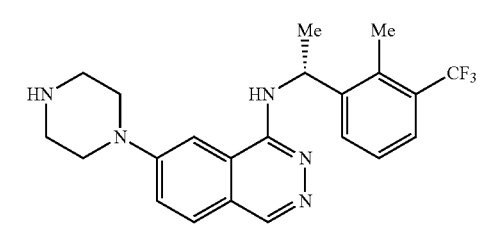 [SMILES: Cc1c([C@@H](C)Nc2nncc3ccc(N4CCNCC4)cc23)cccc1C(F)(F)F]<br>(R)-N-(1-(2-methyl-3-(trifluoromethyl)phenyl)ethyl)-7-(piperazin-1-yl)phthalazin-1-amine | $^1$H NMR (400 MHz, CD$_3$OD) δ 8.57 (s, 1H), 7.77 (d, J = 10.0 Hz, 1H), 7.73 (d, J = 7.6 Hz, 1H), 7.63-7.57 (m, 2H), 7.51 (d, J = 7.6 Hz, 1H), 7.26 (t, J = 7.6 Hz, 1H), 5.78 (q, J = 7.2 Hz, 1H), 3.56-3.44 (m, 4H), 3.11-2.97 (m, 4H), 2.63 (s, 3H), 1.66 (d, J = 6.8 Hz, 3H). LCMS [M + 1]: 416.2. |
| 1-8 | 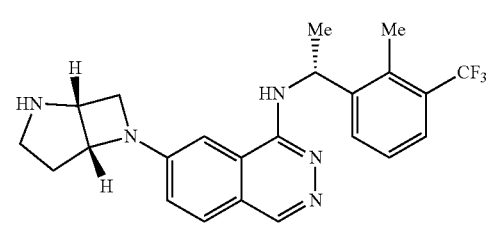 [SMILES: Cc1c([C@@H](C)Nc2nncc3ccc(N4C[C@H]5NCC[C@H]54)cc23)cccc1C(F)(F)F]<br>7-((1R,5R)-2,6-diazabicyclo[3.2.0]heptan-6-yl)-N-((R)-1-(2-methyl-3-(trifluoromethyl)phenyl)ethyl)phthalazin-1-amine | $^1$H NMR (400 MHz, CD$_3$OD) δ 8.48 (s, 1H), 7.73-7.66 (m, 2H), 7.51-7.46 (m, 1H), 7.27-7.21 (m, 1H), 7.10-7.07 (m, 1H), 7.06-7.00 (m, 1H), 5.74 (q, J = 6.9 Hz, 1H), 4.95-4.90 (m, 1H), 4.28-4.15 (m, 2H), 3.82-3.76 (m, 1H), 3.36-3.32f (m, 1H), 3.16-3.06 (m, 1H), 2.60 (s, 3H), 2.28-2.19 (m, 1H), 1.67-1.56 (m, 4H). LCMS [M + 1]: 428.0. |

TABLE 1-continued

| Ex. # | Structure | Spectral Data |
|---|---|---|
| 1-9 | 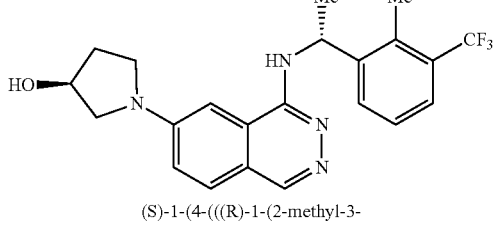<br>(S)-1-(4-(((R)-1-(2-methyl-3-(trifluoromethyl)phenyl)ethyl)amino)phthalazin-6-yl)pyrrolidin-3-ol | $^1$H NMR (400 MHz, CD$_3$OD) δ 8.48 (s, 1H), 7.75-7.67 (m, 2H), 7.51-7.46 (m, 1H), 7.27-7.18 (m, 2H), 7.17-7.14 (m, 1H), 5.76 (q, J = 6.9 Hz, 1H), 4.65-4.59 (m, 1H), 3.72-3.54 (m, 3H), 3.48-3.41 (m, 1H), 2.61 (s, 3H), 2.29-2.06 (m, 2H), 1.64 (d, J = 6.9 Hz, 3H). LCMS [M + 1]: 417.0. |
| 1-10 | 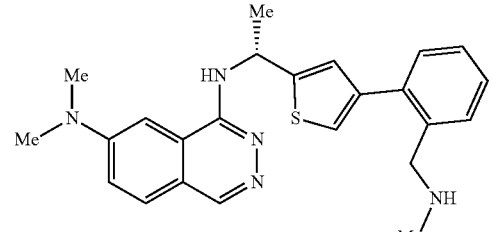<br>(R)-N$^7$,N$^7$-dimethyl-N$^1$-(1-(4-(2-((methylamino)methyl)phenyl)thiophen-2-yl)ethyl)phthalazine-1,7-diamine | $^1$H NMR (400 MHz, CD$_3$OD) δ 8.57 (s, 1H), 7.75 (d, J = 9.0 Hz, 1H), 7.42-7.36 (m, 2H), 7.33-7.26 (m, 3H), 7.24-7.22 (m, 1H), 7.17-7.13 (m, 2H), 5.95-5.89 (m, 1H), 3.72 (s, 2H), 3.17 (s, 6H), 2.21 (s, 3H), 1.82 (d, J = 6.9 Hz, 3H). LCMS [M + 1]: 418.2. |
| 1-11 | 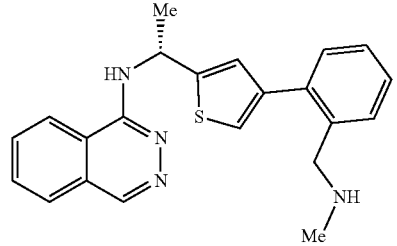 [SMILES: CNCc1ccccc1-c1csc([C@@H](C)Nc2nncc3ccccc23)c1]<br>(R)-N-(1-(4-(2-((methylamino)methyl)phenyl)thiophen-2-yl)ethyl)phthalazin-1-amine | $^1$H NMR (400 MHz, CD$_3$OD) δ 8.88 (s, 1H), 8.37-8.33 (m, 1H), 7.97-7.90 (m, 3H), 7.44-7.40 (m, 1H), 7.36-7.28 (m, 3H), 7.20-7.16 (m, 2H), 5.96 (q, J = 6.9 Hz, 1H), 3.75 (s, 2H), 2.24 (s, 3H), 1.83 (d, J = 6.9 Hz, 3H). LCMS [M + 1]: 375.1. |
| 1-12 | 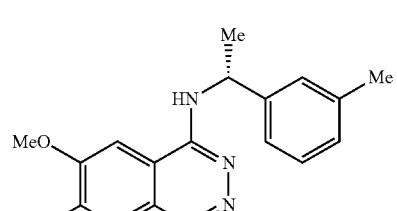<br>(R)-6,7-dimethoxy-N-(1-(m-tolyl)ethyl)phthalazin-1-amine | $^1$H NMR (400 MHz, CD$_3$OD) δ 8.65 (s, 1H), 7.77 (s, 1H), 7.34-7.13 (m, 4H), 7.04-6.98 (m, 1H), 5.52 (q, J = 7.0 Hz, 1H), 4.06 (s, 3H), 4.00 (s, 3H), 2.31 (s, 3H), 1.67 (d, J = 7.0 Hz, 3H). LCMS [M + 1]: 324.2 |
| 1-13 | 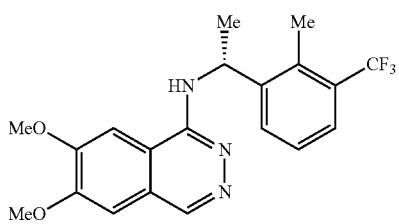 [SMILES: COc1cc2cnnc(N[C@H](C)c3cccc(C(F)(F)F)c3C)c2cc1OC]<br>(R)-6,7-dimethoxy-N-(1-(2-methyl-3-(trifluoromethyl)phenyl)ethyl)phthalazin-1-amine | $^1$H NMR (400 MHz, CDCl$_3$) δ 8.81 (s, 1H), 7.67 (d, J = 7.9 Hz, 1H), 7.55 (d, J = 7.9 Hz, 1H), 7.29-7.22 (m, 1H), 7.08 (s, 1H), 6.94 (s, 1H), 6.00-5.93 (m, 1H), 4.94 (d, J = 6.7 Hz, 1H), 4.04 (s, 3H), 4.02 (s, 3H), 2.56 (s, 3H), 1.68 (d, J = 6.7 Hz, 3H). LCMS [M + 1]: 392.1. |

TABLE 1-continued

| Ex. # | Structure | Spectral Data |
|---|---|---|
| 1-14 | 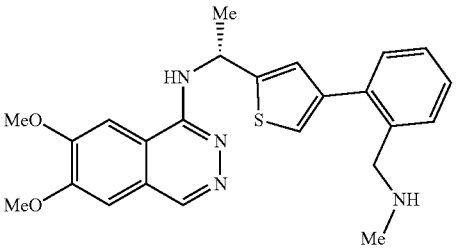 [SMILES: CNCc1ccccc1-c1csc([C@@H](C)Nc2nncc3cc(OC)c(OC)cc23)c1]<br>(R)-6,7-dimethoxy-N-(1-(4-(2-((methylamino)methyl)phenyl)thiophen-2-yl)ethyl)phthalazin-1-amine | $^1$H NMR (400 MHz, CDCl$_3$) δ 8.86 (s, 1H), 7.43-7.39 (m, 1H), 7.36-7.26 (m, 4H), 7.10 (s, 1H), 6.94 (s, 1H), 6.16-6.08 (m, 1H), 5.02 (d, J = 7.9 Hz, 1H), 4.06 (s, 3H), 4.05 (s, 4H), 3.73 (s, 2H), 2.38 (s, 3H), 1.84 (d, J = 6.6 Hz, 3H). LCMS [M + 1]: 435.2. |
| 1-15 | 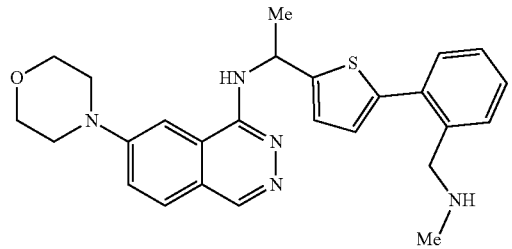<br>N-(1-(5-(2-((methylamino)methyl)phenyl)thiophen-2-yl)ethyl)-7-morpholinophthalazin-1-amine | $^1$H NMR (400 MHz, CD$_3$OD) δ 8.64 (s, 1H), 7.79 (d, J = 9.2 Hz, 1H), 7.59 (dd, J = 2.0, 8.8 Hz, 1H), 7.52 (d, J = 1.6 Hz, 1H), 7.41 (d, J = 7.2 Hz, 1H), 7.36-7.22 (m, 3H), 7.08 (d, J = 3.6 Hz, 1H), 6.92 (d, J = 3.6 Hz, 1H), 5.92 (q, J = 6.8 Hz, 1H), 3.94-3.83 (m, 4H), 3.77 (s, 2H), 3.50-3.38 (m, 4H), 2.24 (s, 3H), 1.81 (d, J = 7.2 Hz, 3H). LCMS [M + 1]: 460.2. |
| 1-16 | 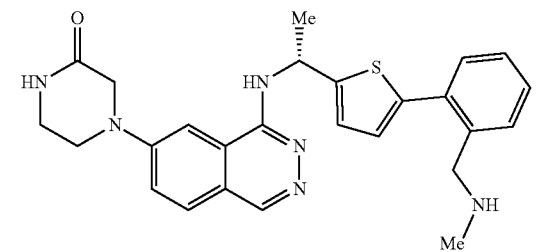 [SMILES: CNCc1ccccc1-c1ccc([C@@H](C)Nc2nncc3ccc(N4CCNC(=O)C4)cc23)s1]<br>(R)-4-(4-((1-(5-(2-((methylamino)methyl)phenyl)thiophen-2-yl)ethyl)amino)phthalazin-6-yl)piperazin-2-one | $^1$H NMR (400 MHz, CD$_3$OD) δ 9.00 (s, 1H), 8.14 (d, J = 9.2 Hz, 1H), 7.76 (dd, J = 2.4, 9.6 Hz, 1H), 7.65 (s, 1H), 7.60-7.54 (m, 1H), 7.53-7.43 (m, 3H), 7.21 (d, J = 3.2 Hz, 1H), 7.01 (d, J = 3.6 Hz, 1H), 5.83-5.72 (m, 1H), 4.34 (s, 2H), 4.26 (s, 2H), 3.97-3.87 (m, 2H), 3.62-3.53 (m, 2H), 2.64 (s, 3H), 1.88 (d, J = 6.8 Hz, 3H). LCMS [M + 1]: 473.2. |
| 1-17 | 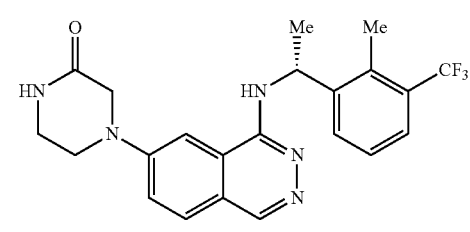 [SMILES: Cc1c([C@@H](C)Nc2nncc3ccc(N4CCNC(=O)C4)cc23)cccc1C(F)(F)F]<br>(R)-4-(4-((1-(2-methyl-3-(trifluoromethyl)phenyl)ethyl)amino)phthalazin-6-yl)piperazin-2-one | $^1$H NMR (400 MHz, CD$_3$OD) δ 8.93 (s, 1H), 8.10 (d, J = 9.2 Hz, 1H), 7.77-7.69 (m, 3H), 7.55 (d, J = 7.6 Hz, 1H), 7.30 (t, J = 8.8 Hz, 1H), 5.62-5.55 (m, 1H), 4.30 (s, 2H), 3.97-3.91 (m, 2H), 3.61-3.55 (m, 2H), 2.62 (s, 3H), 1.70 (d, J = 6.8 Hz, 3H). LCMS [M + 1]: 430.3. |
| 1-18 | 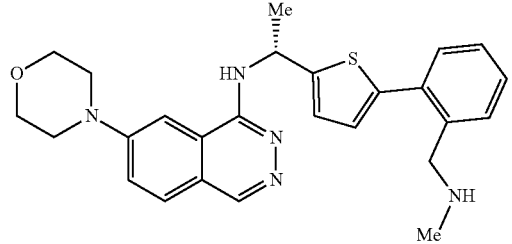 [SMILES: CNCc1ccccc1-c1ccc([C@@H](C)Nc2nncc3ccc(N4CCOCC4)cc23)s1]<br>(R)-N-(1-(5-(2-((methylamino)methyl)phenyl)thiophen-2-yl)ethyl)-7-morpholinophthalazin-1-amine | $^1$H NMR (400 MHz, CD$_3$OD) δ 8.64 (s, 1H), 7.80 (d, J = 8.8 Hz, 1H), 7.66-7.56 (m, 1H), 7.52 (s, 1H), 7.46-7.38 (m, 1H), 7.37-7.21 (m, 3H), 7.09 (d, J = 2.8 Hz, 1H), 6.92 (d, J = 2.8 Hz, 1H), 6.02-5.85 (m, 1H), 3.91-3.83 (m, 4H), 3.78 (s, 2H), 3.47-3.40 (m, 4H), 2.24 (s, 3H), 1.81 (d, J = 6.8 Hz, 3H). LCMS [M + 1]: 460.2. |

TABLE 1-continued

| Ex. # | Structure | Spectral Data |
|---|---|---|
| 1-19 | 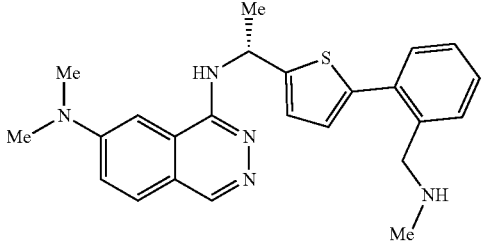 [SMILES: CNCc1ccccc1-c1ccc([C@@H](C)Nc2nncc3ccc(N(C)C)cc23)s1]<br>(R)-N⁷,N⁷-dimethyl-N¹-(1-(5-(2-((methylamino)methyl)phenyl)thiophen-2-yl)ethyl)phthalazine-1,7-diamine | $^1$H NMR (400 MHz, CD$_3$OD) δ = 8.92 (br s, 1H), 8.05 (d, J = 9.2 Hz, 1H), 7.59-7.53 (m, 2H), 7.52-7.43 (m, 4H), 7.19 (d, J = 3.2 Hz, 1H), 7.00 (d, J = 3.6 Hz, 1H), 5.82-5.71 (m, 1H), 4.34 (s, 2H), 3.30 (s, 6H), 2.63 (s, 3H), 1.86 (d, J = 6.8 Hz, 3H). LCMS [M + 1]: 418.2. |
| 1-20 | 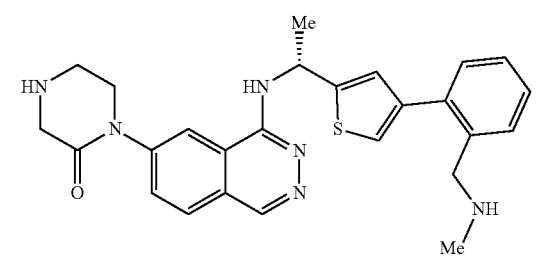 [SMILES: CNCc1ccccc1-c1csc([C@@H](C)Nc2nncc3ccc(N4CCNCC4=O)cc23)c1]<br>(R)-1-(4-((1-(4-(2-((methylamino)methyl)phenyl)thiophen-2-yl)ethyl)amino)phthalazin-6-yl)piperazin-2-one | $^1$H NMR (400 MHz, CD$_3$OD) δ = 9.10 (s, 1H), 8.79 (d, J = 3.2 Hz, 1H), 8.31-8.27 (m, 1H), 8.27-8.22 (m, 1H), 7.58-7.53 (m, 1H), 7.49-7.44 (m, 2H), 7.42-7.39 (m, 1H), 7.37 (d, J = 1.2 Hz, 1H), 7.28 (s, 1H), 5.79-5.71 (m, 1H), 4.26 (s, 2H), 4.24-4.18 (m, 2H), 4.12 (s, 2H), 3.79-3.73 (m, 2H), 2.59 (s, 3H), 1.92 (d, J = 6.8 Hz, 3H); LCMS [M + 1]: 473.4. |
| 1-21 | 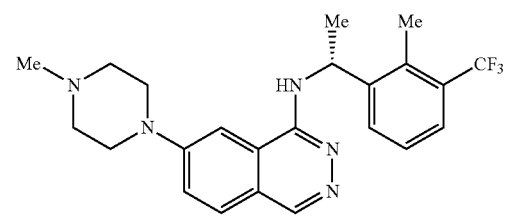 [SMILES: Cc1c([C@@H](C)Nc2nncc3ccc(N4CCN(C)CC4)cc23)cccc1C(F)(F)F]<br>(R)-N-(1-(2-methyl-3-(trifluoromethyl)phenyl)ethyl)-7-(4-methylpiperazin-1-yl)phthalazin-1-amine | $^1$H NMR (400 MHz, CD$_3$OD) δ = 8.55 (s, 1H), 7.75 (d, J = 9.6 Hz, 1H), 7.71 (d, J = 8.0 Hz, 1H), 7.61-7.55 (m, 2H), 7.49 (d, J = 7.2 Hz, 1H), 7.24 (t, J = 8.0 Hz, 1H), 5.76 (q, J = 6.8 Hz, 1H), 3.61-3.46 (m, 4H), 2.72-2.63 (m, 4H), 2.61 (s, 3H), 2.39 (s, 3H), 1.64 (d, J = 6.8 Hz, 3H). LCMS [M + 1]: 430.2. |
| 1-22 | 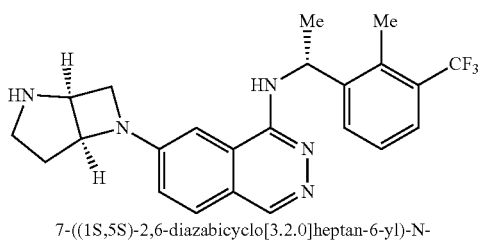<br>7-((1S,5S)-2,6-diazabicyclo[3.2.0]heptan-6-yl)-N-((R)-1-(2-methyl-3-(trifluoromethyl)phenyl)ethyl)phthalazin-1-amine | $^1$H NMR (400 MHz, CD$_3$OD) δ = 8.59 (s, 1H), 7.78 (d, J = 8.8 Hz, 1H), 7.70 (d, J = 7.6 Hz, 1H), 7.51 (d, J = 8.0 Hz, 1H), 7.25 (t, J = 8.0 Hz, 1H), 7.18 (d, J = 2.0 Hz, 1H), 7.10 (dd, J = 2.4, 8.8 Hz, 1H), 5.68 (q, J = 6.8 Hz, 1H), 4.99 (t, J = 4.8 Hz, 1H), 4.35-4.29 (m, 1H), 4.28-4.22 (m, 1H), 3.85 (dd, J = 2.8, 9.2 Hz, 1H), 3.38 (dd, J = 6.8, 11.6 Hz, 1H), 3.21-3.09 (m, 1H), 2.60 (s, 3H), 2.27 (dd, J = 5.2, 13.6 Hz, 1H), 1.73-1.67 (m, 1H), 1.65 (d, J = 6.8 Hz, 3H). LCMS [M + 1]$^+$: 428.0. |
| 1-23 | 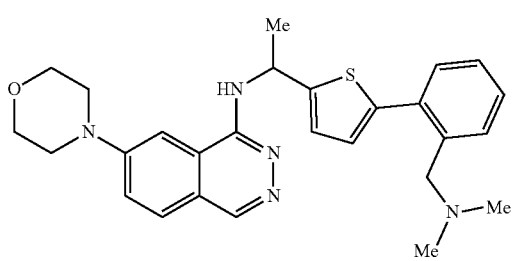 [SMILES: CC(Nc1nncc2ccc(N3CCOCC3)cc12)c1ccc(-c2ccccc2CN(C)C)s1]<br>N-(1-(5-(2-((dimethylamino)methyl)phenyl)thiophen-2-yl)ethyl)-7-morpholinophthalazin-1-amine | $^1$H NMR (400 MHz, CDCl$_3$) δ = 11.63 (s, 1H), 8.84-8.83 (m, 2H), 7.98 (s, 1H), 7.75 (d, J = 9.2 Hz, 1H), 7.46-7.39 (m, 5H), 7.08 (d, J = 3.6 Hz, 1H), 6.86 (d, J = 3.6 Hz, 1H), 5.66-5.63 (m, 1H), 4.72 (d, J = 13.6 Hz, 1H), 4.27 (d, J = 13.6 Hz, 1H), 3.82 (t, J = 4.8 Hz, 3H), 3.55 (t, J = 4.8 Hz, 3H), 2.68-2.64 (m, 6H), 1.77 (d, J = 6.8 Hz, 3H). LCMS [M + 1]: 474.2. |

TABLE 1-continued

| Ex. # | Structure | Spectral Data |
|---|---|---|
| 1-24 | 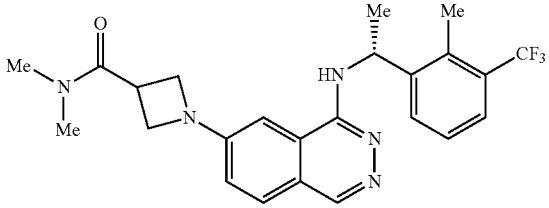 [SMILES: Cc1c([C@@H](C)Nc2nncc3ccc(N4CC(C(=O)N(C)C)C4)cc23)cccc1C(F)(F)F]<br>(R)-N,N-dimethyl-1-(4-((1-(2-methyl-3-(trifluoromethyl)phenyl)ethyl)amino)phthalazin-6-yl)azetidine-3-carboxamide | LCMS [M + 1]: 458.0. |
| 1-25 | 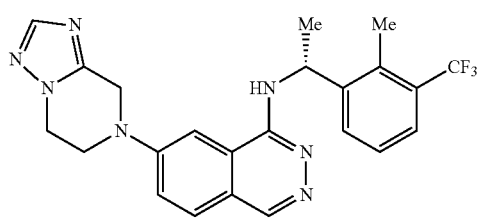 [SMILES: Cc1c([C@@H](C)Nc2nncc3ccc(N4CCn5ncnc5C4)cc23)cccc1C(F)(F)F]<br>(R)-7-(5,6-dihydro-[1,2,4]triazolo[1,5-a]pyrazin-7(8H)-yl)-N-(1-(2-methyl-3-(trifluoromethyl)phenyl)ethyl)phthalazin-1-amine | LCMS [M + 1]: 454.2. |
| 1-26 | 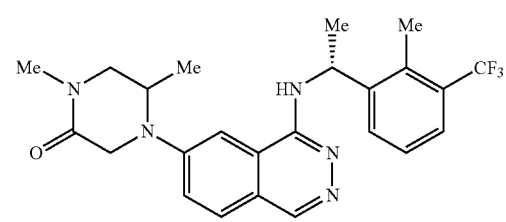 [SMILES: Cc1c([C@@H](C)Nc2nncc3ccc(N4CC(=O)N(C)CC4C)cc23)cccc1C(F)(F)F]<br>1,5-dimethyl-4-(4-(((R)-1-(2-methyl-3-(trifluoromethyl)phenyl)ethyl)amino)phthalazin-6-yl)piperazin-2-one | LCMS [M + 1]: 458.2. |
| 1-27 | 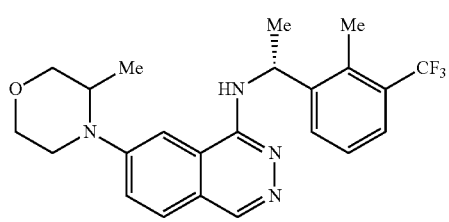 [SMILES: Cc1c([C@@H](C)Nc2nncc3ccc(N4CCOCC4C)cc23)cccc1C(F)(F)F]<br>N-((R)-1-(2-methyl-3-(trifluoromethyl)phenyl)ethyl)-7-(3-methylmorpholino)phthalazin-1-amine | LCMS [M + 1]: 431.2. |
| 1-28 | 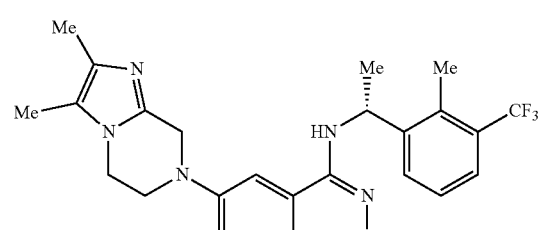<br>(R)-7-(2,3-dimethyl-5,6-dihydroimidazo[1,2-a]pyrazin-7(8H)-yl)-N-(1-(2-methyl-3-(trifluoromethyl)phenyl)ethyl)phthalazin-1-amine | LCMS [M + 1]: 481.2. |

TABLE 1-continued

| Ex. # | Structure | Spectral Data |
|---|---|---|
| 1-29 | (R)-7-(4-methyl-1,4-diazepan-1-yl)-N-(1-(2-methyl-3-(trifluoromethyl)phenyl)ethyl)phthalazin-1-amine | LCMS [M + 1]: 441.1. |
| 1-30 | (R)-1-methyl-4-(4-((1-(2-methyl-3-(trifluoromethyl)phenyl)ethyl)amino)phthalazin-6-yl)piperazin-2-one | LCMS [M + 1]: 444.0. |
| 1-31 | N-((R)-1-(2-methyl-3-(trifluoromethyl)phenyl)ethyl)-7-(5-methyloctahydro-2H-pyrrolo[3,4-c]pyridin-2-yl)phthalazin-1-amine | LCMS [M + 1]: 471.2. |
| 1-32 | (R)-7-(6-(dimethylamino)-2-azaspiro[3.3]heptan-2-yl)-N-(1-(2-methyl-3-(trifluoromethyl)phenyl)ethyl)phthalazin-1-amine | LCMS [M + 1]: 470.2. |
| 1-33 | N-((R)-1-(2-methyl-3-(trifluoromethyl)phenyl)ethyl)-7-(1-methyloctahydro-6H-pyrrolo[2,3-c]pyridin-6-yl)phthalazin-1-amine | LCMS [M + 1]: 470.1. |

TABLE 1-continued

| Ex. # | Structure | Spectral Data |
|---|---|---|
| 1-34 | 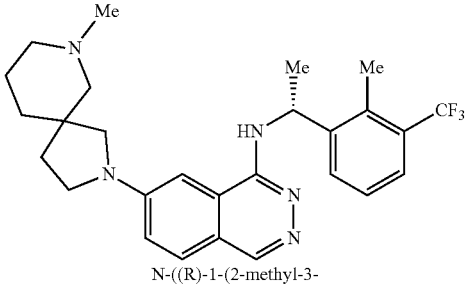 N-((R)-1-(2-methyl-3-(trifluoromethyl)phenyl)ethyl)-7-(7-methyl-2,7-diazaspiro[4.5]decan-2-yl)phthalazin-1-amine | LCMS [M + 1]: 485.2. |
| 1-35 | 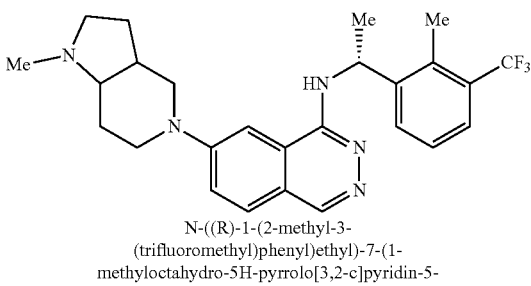 N-((R)-1-(2-methyl-3-(trifluoromethyl)phenyl)ethyl)-7-(1-methyloctahydro-5H-pyrrolo[3,2-c]pyridin-5-yl)phthalazin-1-amine | LCMS [M + 1]: 471.2. |
| 1-36 | 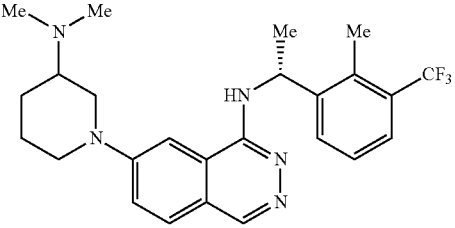 [SMILES: Cc1c([C@@H](C)Nc2nncc3ccc(N4CCCC(N(C)C)C4)cc23)cccc1C(F)(F)F] 7-(3-(dimethylamino)piperidin-1-yl)-N-((R)-1-(2-methyl-3-(trifluoromethyl)phenyl)ethyl)phthalazin-1-amine | LCMS [M + 1]: 458.2. |
| 1-37 | 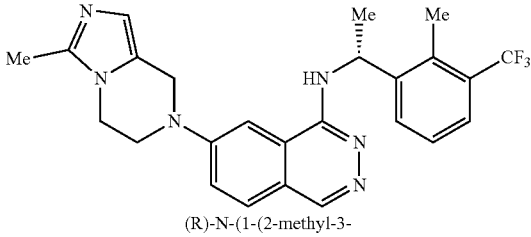 (R)-N-(1-(2-methyl-3-(trifluoromethyl)phenyl)ethyl)-7-(3-methyl-5,6-dihydroimidazo[1,5-a]pyrazin-7(8H)-yl)phthalazin-1-amine | LCMS [M + 1]: 467.2. |
| 1-38 | 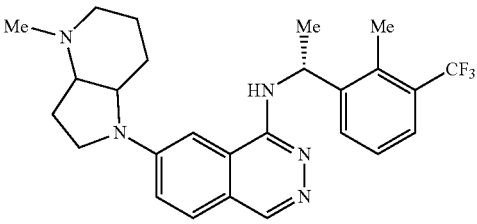 [SMILES: Cc1c([C@@H](C)Nc2nncc3ccc(N4CCC5C4CCCN5C)cc23)cccc1C(F)(F)F] N-((R)-1-(2-methyl-3-(trifluoromethyl)phenyl)ethyl)-7-(4-methyloctahydro-1H-pyrrolo[3,2-b]pyridin-1-yl)phthalazin-1-amine | LCMS [M + 1]: 470.2. |

TABLE 1-continued

| Ex. # | Structure | Spectral Data |
|---|---|---|
| 1-39 | 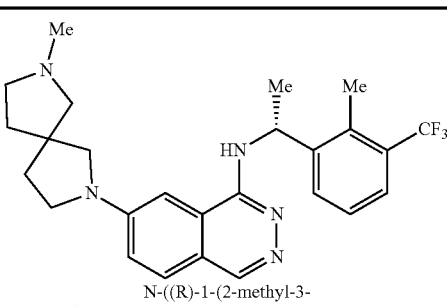<br>N-((R)-1-(2-methyl-3-(trifluoromethyl)phenyl)ethyl)-7-(7-methyl-2,7-diazaspiro[4.4]nonan-2-yl)phthalazin-1-amine | LCMS [M + 1]: 470.4. |
| 1-40 | 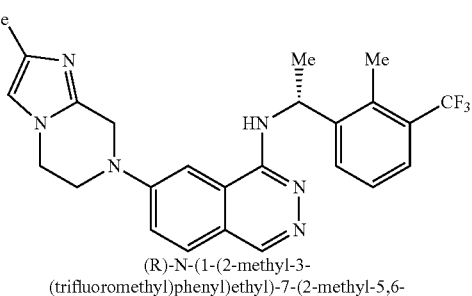<br>(R)-N-(1-(2-methyl-3-(trifluoromethyl)phenyl)ethyl)-7-(2-methyl-5,6-dihydroimidazo[1,2-a]pyrazin-7(8H)-yl)phthalazin-1-amine | LCMS [M + 1]: 467.2. |
| 1-41 | 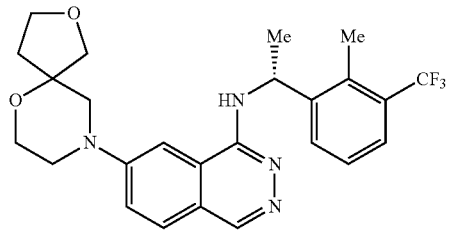 [SMILES: Cc1c([C@@H](C)Nc2nncc3ccc(N4CCOC5(CCOC5)C4)cc23)cccc1C(F)(F)F]<br>N-((R)-1-(2-methyl-3-(trifluoromethyl)phenyl)ethyl)-7-(2,6-dioxa-9-azaspiro[4.5]decan-9-yl)phthalazin-1-amine | LCMS [M + 1]: 473.0. |
| 1-42 | 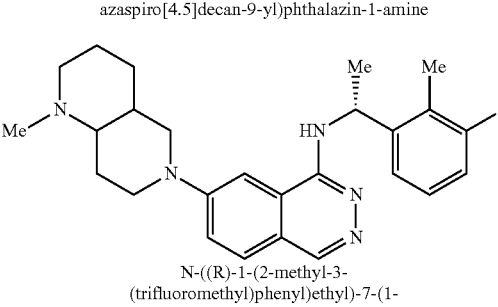<br>N-((R)-1-(2-methyl-3-(trifluoromethyl)phenyl)ethyl)-7-(1-methyloctahydro-1,6-naphthyridin-6(2H)-yl)phthalazin-1-amine | LCMS [M + 1]: 485.2. |
| 1-43 | 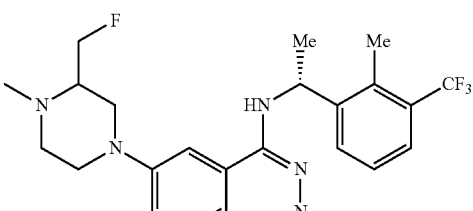<br>7-(3-(fluoromethyl)-4-methylpiperazin-1-yl)-N-((R)-1-(2-methyl-3-(trifluoromethyl)phenyl)ethyl)phthalazin-1-amine | LCMS [M + 1]: 462.1. |

TABLE 1-continued

| Ex. # | Structure | Spectral Data |
|---|---|---|
| 1-44 | 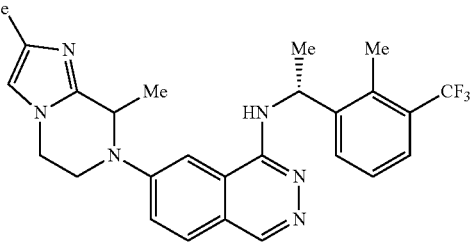 7-(2,8-dimethyl-5,6-dihydroimidazo[1,2-a]pyrazin-7(8H)-yl)-N-((R)-1-(2-methyl-3-(trifluoromethyl)phenyl)ethyl)phthalazin-1-amine | LCMS [M + 1]: 481.2. |
| 1-45 | 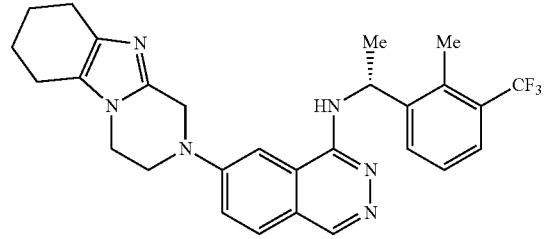 [SMILES: Cc1c([C@@H](C)Nc2nncc3ccc(N4CCn5c(nc6c5CCCC6)C4)cc23)cccc1C(F)(F)F] (R)-7-(3,4,6,7,8,9-hexahydrobenzo[4,5]imidazo[1,2-a]pyrazin-2(1H)-yl)-N-(1-(2-methyl-3-(trifluoromethyl)phenyl)ethyl)phthalazin-1-amine | LCMS [M + 1]: 508.2. |
| 1-46 | 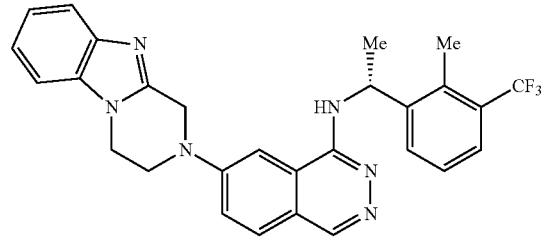 [SMILES: Cc1c([C@@H](C)Nc2nncc3ccc(N4CCn5c(nc6ccccc65)C4)cc23)cccc1C(F)(F)F] (R)-7-(3,4-dihydrobenzo[4,5]imidazo[1,2-a]pyrazin-2(1H)-yl)-N-(1-(2-methyl-3-(trifluoromethyl)phenyl)ethyl)phthalazin-1-amine | LCMS [M + 1]: 503.2. |
| 1-47 | 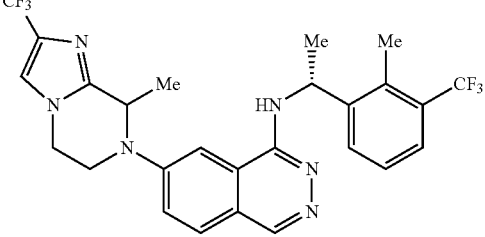 7-(8-methyl-2-(trifluoromethyl)-5,6-dihydroimidazo[1,2-a]pyrazin-7(8H)-yl)-N-((R)-1-(2-methyl-3-(trifluoromethyl)phenyl)ethyl)phthalazin-1-amine | LCMS [M + 1]: 535.0. |
| 1-48 | 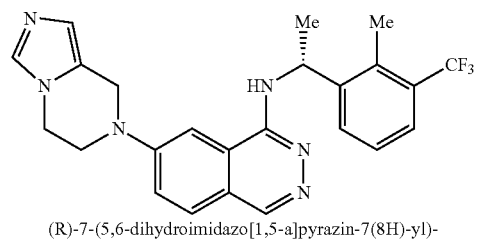 (R)-7-(5,6-dihydroimidazo[1,5-a]pyrazin-7(8H)-yl)-N-(1-(2-methyl-3-(trifluoromethyl)phenyl)ethyl)phthalazin-1-amine | LCMS [M + 1]: 453.2. |

TABLE 1-continued

| Ex. # | Structure | Spectral Data |
|---|---|---|
| 1-49 | 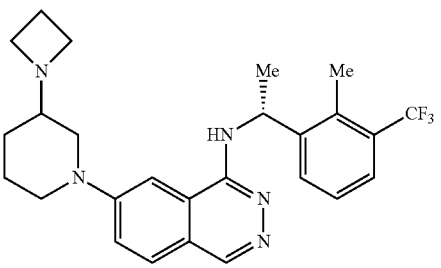 [SMILES: Cc1c([C@@H](C)Nc2nncc3ccc(N4CCCC(N5CCC5)C4)cc23)cccc1C(F)(F)F]<br>7-(3-(azetidin-1-yl)piperidin-1-yl)-N-((R)-1-(2-methyl-3-(trifluoromethyl)phenyl)ethyl)phthalazin-1-amine | LCMS [M + 1]: 470.2. |
| 1-50 | 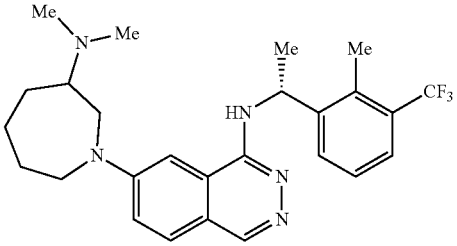 [SMILES: Cc1c([C@@H](C)Nc2nncc3ccc(N4CCCCC(N(C)C)C4)cc23)cccc1C(F)(F)F]<br>7-(3-(dimethylamino)azepan-1-yl)-N-((R)-1-(2-methyl-3-(trifluoromethyl)phenyl)ethyl)phthalazin-1-amine | LCMS [M + 1]: 472.2. |

Example 2-1

(R)—N-(1-(4-(2-((dimethylamino)methyl)phenyl)thiophen-2-yl)ethyl)-7-morpholinophthalazin-1-amine

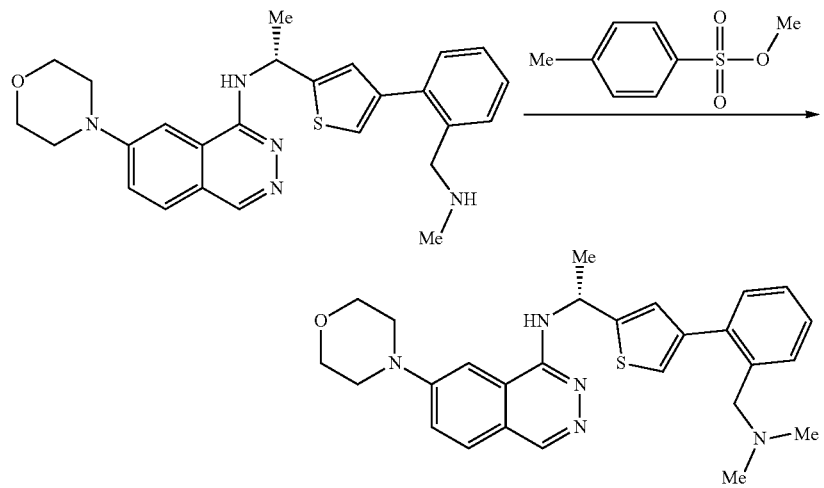

To a solution of (R)—N-(1-(4-(2-((methylamino)methyl)phenyl)thiophen-2-yl)ethyl)-7-morpholinophthalazin-1-amine (15.0 mg, 32.6 μmol, 1.00 eq.) in dimethyformamide (0.50 mL) was added potassium hydroxide (2.75 mg, 49.0 μmol, 1.50 eq.) at 15° C. and the reaction mixture was stirred at 15° C. for 1 hour. A solution of methyl 4-methylbenzenesulfonate (7.90 mg, 42.4 μmol, 1.3 eq) in dimethyformamide (0.20 mL) was added dropwise to the reaction mixture. After the dropwise addition had finished, the reaction mixture was heated to 50° C. and stirred for 2 hours. The reaction mixture was then cooled to 25° C., and ethyl acetate (3.00 mL) and water (3.00 mL) were added to the mixture. The layers were separated, and the organic phases were combined, washed twice with water (3.00 mL), and dried over anhydrous sodium sulfate to give a residue. The residue was purified by prep-HPLC (column: Waters Xbridge 150× 25 mm×5 um; mobile phase: [water (0.05% ammonia hydroxide v/v)—ACN]; B %: 32%-62%, 10 min) to give (R)—N-(1-(4-(2-((dimethylamino)methyl)phenyl)thiophen-2-yl)ethyl)-7-morpholinophthalazin-1-amine (1.61 mg, 3.39 μmol, 10.4% yield, 99.7% purity) as an off-white solid. LCMS [M+1]: 474.3.

$^1$H NMR (400 MHz, CD$_3$OD) δ 8.65 (s, 1H), 7.81 (d, J=8.8 Hz, 1H), 7.61 (dd, J=2.4, 9.2 Hz, 1H), 7.54 (d, J=2.4

Hz, 1H), 7.48-7.41 (m, 1H), 7.37-7.29 (m, 3H), 7.21 (d, J=1.2 Hz, 1H), 7.18-7.12 (m, 1H), 5.91 (q, J=6.8 Hz, 1H), 3.90-3.85 (m, 4H), 3.60 (s, 2H), 3.48-3.42 (m, 4H), 2.17 (s, 6H), 1.82 (d, J=6.8 Hz, 3H).

Example 2-2

N—((R)-1-(2-methyl-3-(trifluoromethyl)phenyl)ethyl)-7-(((S)-pyrrolidin-3-yl)oxy)phthalazin-1-amine

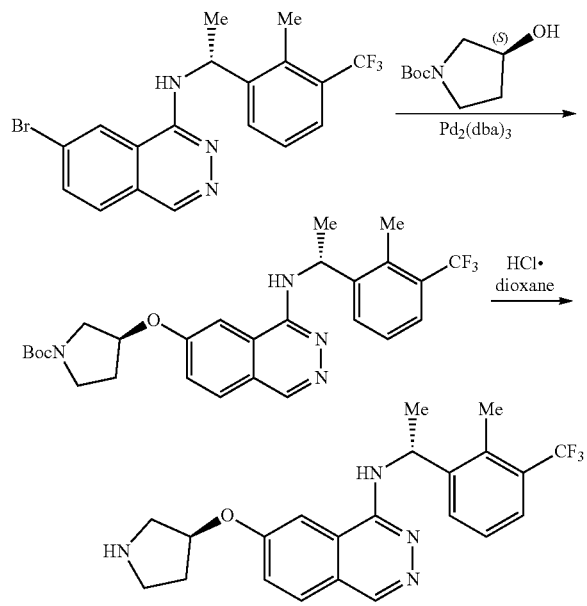

Step A: To a solution of (R)-7-bromo-N-(1-(2-methyl-3-(trifluoromethyl)phenyl)ethyl)phthalazin-1-amine (80.0 mg, 195 μmol, 1.00 eq.) in toluene (2.00 mL) was added sodium hydride (15.6 mg, 390 μmol, 60.0% purity, 2.00 eq.) at 0° C. under a nitrogen atmosphere. Then tert-butyl (S)-3-hydroxy-pyrrolidine-1-carboxylate (110 mg, 585 μmol, 3.00 eq.), Pd$_2$(dba)$_3$ (17.9 mg, 19.5 μmol, 0.10 eq.), and Tol-BINAP (132 mg, 195 μmol, 1.00 eq.) was added to the reaction mixture and the mixture was heated to 100° C. for 1 hour. The reaction mixture was cooled to 25° C., poured into water (20.0 mL) and extracted with ethyl acetate (20.0 mL×3). The combined organic phases were concentrated under vacuum to give a residue. The residue was purified by reversed-phase HPLC [water(0.1% TFA)—ACN] to give tert-butyl (S)-3-((4-(((R)-1-(2-methyl-3-(trifluoromethyl)phenyl)ethyl)amino)phthalazin-6-yl)oxy)pyrrolidine-1-carboxylate (35.0 mg, 44.0 μmol, 23.0% yield, 65.0% purity) as a yellow solid. LCMS [M+1]: 517.0.

Step B: To a solution of tert-butyl (S)-3-((4-(((R)-1-(2-methyl-3-(trifluoromethyl)phenyl)ethyl)amino)phthalazin-6-yl)oxy)pyrrolidine-1-carboxylate (35.0 mg, 44.0 μmol, 1.00 eq.) in acetonitrile (1.00 mL) was added HCl (4.00 M in dioxane, 11.0 μL, 1.00 eq.) dropwise at 0° C. under a nitrogen atmosphere. The reaction mixture was stirred at 0° C. for 30 minutes then concentrated under vacuum to give a residue. The residue was purified by reversed phase prep-HPLC (column: Phenomenex Gemini-NX C18 75×30 mm×3 um; mobile phase: [water(0.1% TFA)—ACN]; B %: 25%-35%) to afford N—(((R)-1-(2-methyl-3-(trifluoromethyl)phenyl)ethyl)-7-(((S)-pyrrolidin-3-yl)oxy)phthalazin-1-amine (8.01 mg, 18.2 μmol, 41.0% yield, 95% purity) as a yellow solid. LCMS [M+1]: 417.1.

$^1$H NMR (400 MHz, CD$_3$OD) δ=9.15 (s, 1H), 8.28-8.21 (m, 2H), 7.80-7.72 (m, 2H), 7.59 (d, J=7.6 Hz, 1H), 7.37-7.27 (t, J=7.6 Hz, 1H), 5.67-5.57 (m, 2H), 3.80-3.67 (m, 2H), 3.64-3.47 (m, 2H), 2.63 (s, 3H), 2.55-2.46 (m, 2H), 1.73 (d, J=6.8 Hz, 3H).

Following the teachings of General Reaction Scheme III and the procedures described for the preparation of Example 2-2, the following compounds of Formula (I), Examples 2-3 to 2-12 shown in Table 2 were prepared:

TABLE 2

| Ex. # | Structure | Spectral Data |
|---|---|---|
| 2-3 | (R)-N-(1-(2-methyl-3-(trifluoromethyl)phenyl)ethyl)-7-(piperidin-4-yloxy)phthalazin-1-amine | $^1$H NMR (400 MHz, CD$_3$OD) δ 9.14 (s, 1H), 8.28-2.11 (m, 2H), 7.83 (dd, J = 2.0, 8.8 Hz, 1H), 7.76 (br d, J = 8.0 Hz, 1H), 7.59 (br d, J = 7.6 Hz, 1H), 7.33 (t, J = 7.6 Hz, 1H), 5.62 (q, J = 6.8 Hz, 1H), 5.19-5.18 (m, 2H), 3.55-3.44 (m, 2H), 3.36-3.35 (m, 2H), 2.64 (s, 3H), 2.34-2.32 (m, 2H), 2.26-2.11 (m, 2H), 1.73 (d, J = 6.8 Hz, 3H). LCMS [M + 1]: 431.3. |
| 2-4 | N-((R)-1-(2-methyl-3-(trifluoromethyl)phenyl)ethyl)-7-(((S)-tetrahydrofuran-3-yl)oxy)phthalazin-1-amine | $^1$H NMR (400 MHz, CDCl$_3$) δ 8.92 (s, 1H), 8.58 (s, 1H), 8.09 (s, 1H), 7.75 (d, J = 8.8 Hz, 1H), 7.64 d, J = 8.0 Hz, 1H), 7.53-7.50 (m, 2H), 7.21 (t, J = 7.6 Hz, 1H), 5.43-5.40 (m, 1H), 5.33 (s, 1H), 4.11-4.04 (m, 3H), 3.96-3.93 (m, 1H), 2.52 (s, 3H), 2.50-2.44 (m, 1H), 2.16-2.11 (m, 1H), 1.69-1.67 (d, J = 7.2 Hz, 3H). LCMS [M + 1]: 418.2. |

TABLE 2-continued

| Ex. # | Structure | Spectral Data |
|---|---|---|
| 2-5 | 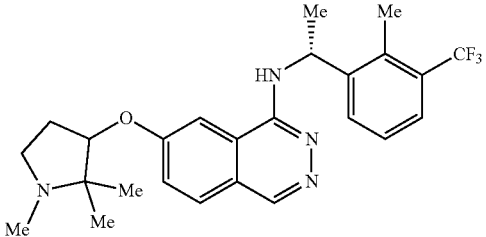 [SMILES: Cc1c([C@@H](C)Nc2nncc3ccc(OC4CCN(C)C4(C)C)cc23)cccc1C(F)(F)F] N-((R)-1-(2-methyl-3-(trifluoromethyl)phenyl)ethyl)-7-((1,2,2-trimethylpyrrolidin-3-yl)oxy)phthalazin-1-amine | LCMS [M + 1]: 459.1. |
| 2-6 | 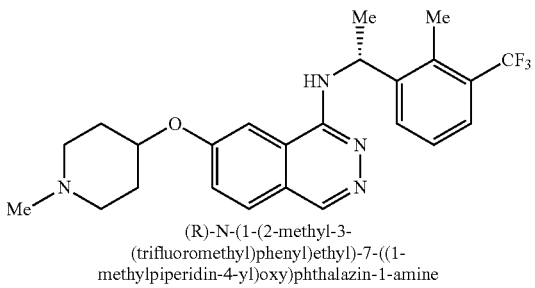 (R)-N-(1-(2-methyl-3-(trifluoromethyl)phenyl)ethyl)-7-((1-methylpiperidin-4-yl)oxy)phthalazin-1-amine | LCMS [M + 1]: 445.2. |
| 2-7 | 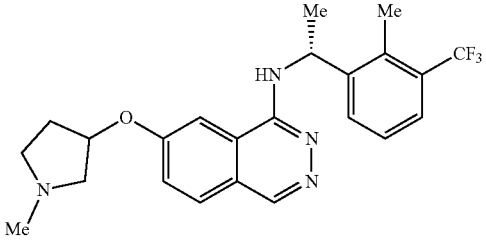 [SMILES: Cc1c([C@@H](C)Nc2nncc3ccc(OC4CCN(C)C4)cc23)cccc1C(F)(F)F] N-((R)-1-(2-methyl-3-(trifluoromethyl)phenyl)ethyl)-7-((1-methylpyrrolidin-3-yl)oxy)phthalazin-1-amine | LCMS [M + 1]: 431.2. |
| 2-8 | 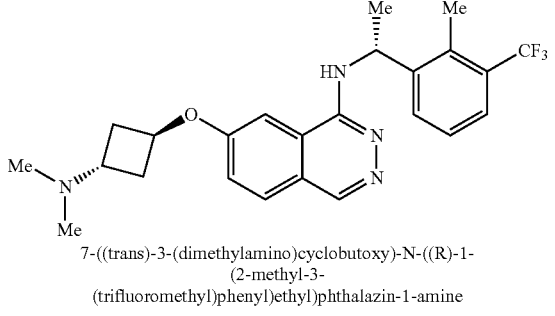 7-((trans)-3-(dimethylamino)cyclobutoxy)-N-((R)-1-(2-methyl-3-(trifluoromethyl)phenyl)ethyl)phthalazin-1-amine | LCMS [M + 1]: 445.2. |
| 2-9 | 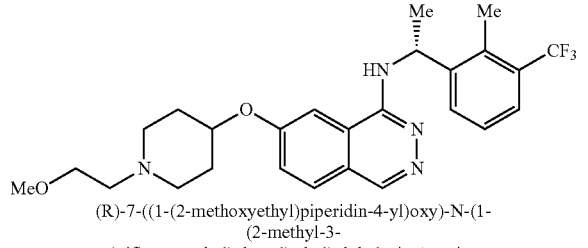 (R)-7-((1-(2-methoxyethyl)piperidin-4-yl)oxy)-N-(1-(2-methyl-3-(trifluoromethyl)phenyl)ethyl)phthalazin-1-amine | LCMS [M + 1]: 489.2. |

US 11,702,418 B2

171    172

TABLE 2-continued

| Ex. # | Structure | Spectral Data |
|---|---|---|
| 2-10 | 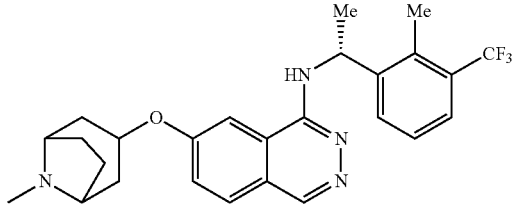 [SMILES: Cc1c([C@@H](C)Nc2nncc3ccc(OC4CC5CCC(C4)N5C)cc23)cccc1C(F)(F)F] N-((R)-1-(2-methyl-3-(trifluoromethyl)phenyl)ethyl)-7-((8-methyl-8-azabicyclo[3.2.1]octan-3-yl)oxy)phthalazin-1-amine | LCMS [M + 1]: 472.2. |
| 2-11 | 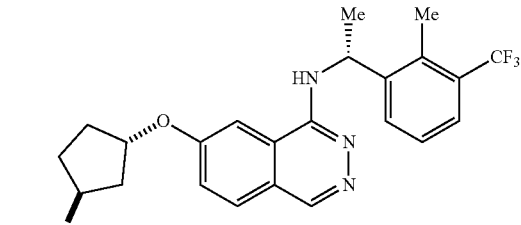 7-(((trans)-3-(dimethylamino)cyclopentyl)oxy)-N-((R)-1-(2-methyl-3-(trifluoromethyl)phenyl)ethyl)phthalazin-1-amine | LCMS [M + 1]: 459.1. |
| 2-12 | 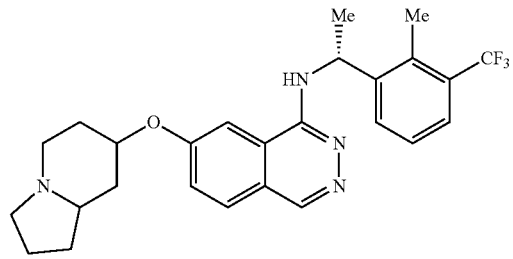 [SMILES: Cc1c([C@@H](C)Nc2nncc3ccc(OC4CCN5CCCC5C4)cc23)cccc1C(F)(F)F] N-((R)-1-(2-methyl-3-(trifluoromethyl)phenyl)ethyl)-7-((octahydroindolizin-7-yl)oxy)phthalazin-1-amine | LCMS [M + 1]: 471.1. |

Example 3-1

(R)—N-(1-(2-methyl-3-(trifluoromethyl)phenyl)ethyl)-7-(piperazin-1-yl)pyrido[3,4-b]pyridazin-1-amine

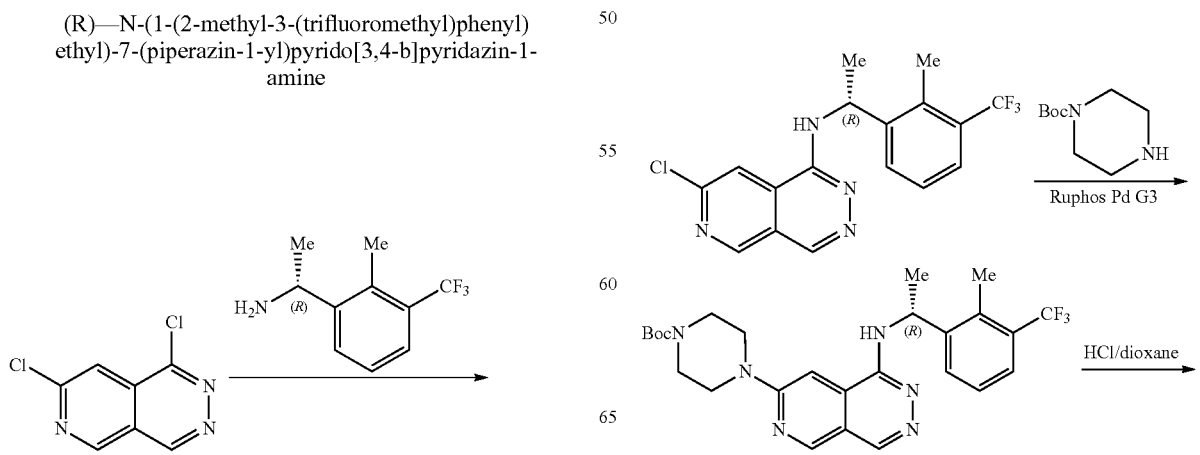

-continued

-continued

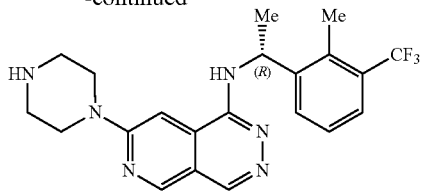

Step A: To a solution of 1,7-dichloropyrido[3,4-<7] pyridazine (40.0 mg, 200 µmol, 1.00 eq.) and (R)-1-(2-methyl-3-(trifluoromethyl)phenyl)ethan-1-amine (40.6 mg, 200 µmol, 1.00 eq.) in DMSO (1.00 mL) was added diisopropylethylamine (77.5 mg, 600 µmol, 105 µL, 3.00 eq.) and potassium fluoride (34.8 mg, 600 µmol, 14.05 µL, 3.00 eq.) under a nitrogen atmosphere. The reaction mixture was stirred at 130° C. for 1 hour under a nitrogen atmosphere, then cooled to 25° C., poured into water (3.00 mL) and stirred for 5 minutes. The aqueous phase was extracted with ethyl acetate (5.00 mL×3), and the combined organic phases were washed with brine (3.00 mL×2), dried over anhydrous sodium sulfate, filtered, and concentrated in vacuo to give a residue. The residue was purified by prep-TLC (SiO$_2$, petroleum ether/ethyl acetate=1/1) to give (R)-7-chloro-N-(1-(2-methyl-3-(trifluoromethyl)phenyl)ethyl)pyrido[3,4-d] pyridazin-1-amine (30.0 mg, 81.8 µmol, 40.9% yield) as a yellow solid. LCMS [M+1]: 367.2.

$^1$H NMR (400 MHz, CD$_3$OD) δ=9.14 (s, 1H), 8.95 (s, 1H), 8.49 (s, 1H), 7.69 (d, J=7.6 Hz, 1H), 7.51 (d, J=7.6 Hz, 1H), 7.26 (t, J=8.0 Hz, 1H), 5.76 (q, J=6.8 Hz, 1H), 2.63 (s, 3H), 1.64 (d, J=6.8 Hz, 3H).

Step B: To a solution of (R)-7-chloro-N-(1-(2-methyl-3-(trifluoromethyl)phenyl)ethyl)pyrido[3,4-d]pyridazin-1-amine (18.0 mg, 49.1 µmol, 1.00 eq.) and tert-butyl piperazine-1-carboxylate (13.7 mg, 73.6 µmol, 1.50 eq.) in dioxane (0.50 mL) was added potassium tert-butoxide (1.00 M, 98.2 µL, 2.00 eq.) and RuPhos-Pd-G3 (4.10 mg, 4.91 µmol, 0.10 eq.) under a nitrogen atmosphere. The reaction mixture was stirred at 100° C. for 1 hour then cooled to 25° C. and concentrated under vacuum to give a residue. The residue was purified by prep-TLC (SiO$_2$, petroleum ether/ethyl acetate=1/1) to give tert-butyl (R)-4-(1-((1-(2-methyl-3-(trifluoromethyl)phenyl)ethyl)amino)pyrido[3,4-b]pyridazin-7-yl)piperazine-1-carboxylate (18.0 mg, crude) as a yellow solid. LCMS [M+1]: 517.3.

Step C: To a solution of tert-butyl (R)-4-(1-((1-(2-methyl-3-(trifluoromethyl)phenyl)ethyl)amino)pyrido[3,4-d] pyridazin-7-yl)piperazine-1-carboxylate (11.0 mg, 21.3 µmol, 1.00 eq.) in acetonitrile (1.00 mL) was added HCl in dioxane (3M, 0.50 mL). The reaction mixture was stirred at 0° C. for 1 hour then concentrated in vacuo to give a residue. The residue was purified by prep-HPLC (column: Phenomenex luna C18 150×25 mm×10 um; mobile phase: [water (0.1% TFA)-ACN]; B %: 10%-40%) to give (R)—N-(1-(2-methyl-3-(trifluoromethyl)phenyl)ethyl)-7-(piperazin-1-yl) pyrido[3,4-d]pyridazin-1-amine (4.50 mg, 8.48 µmol, 39.8% yield, trifluoroacetic acid salt) as a white solid. LCMS [M+1]=417.1.

1H NMR (400 MHz, CD3OD) δ=9.18 (s, 1H), 9.05 (s, 1H), 7.76 (s, 1H), 7.71 (d, J=8.0 Hz, 1H), 7.56 (d, J=7.2 Hz, 1H), 7.36-7.27 (m, 1H), 5.58 (q, J=6.8 Hz, 1H), 4.30-4.21 (m, 4H), 3.50-3.38 (m, 4H), 2.61 (s, 3H), 1.69 (d, J=6.8 Hz, 3H).

SFC: Chiralpak OJ-3 (50×4.6 mm I.D., 3 um); Mobile phase: Phase A for C02, and Phase B for MeOH (0.05% DEA); Gradient elution: 50% MeOH (0.05% DEA) in C02 from 5% to 40%. Flow rate: 3 mL/min; Detector: PDA; Column Temp: 35° C.; Back Pressure: 100 Bar.

Following the teachings of General Reaction Scheme III and the procedures described for the preparation of Example 3-1, the following compounds of Formula (I), Examples 3-2-3-6 shown in Table 3 were prepared:

TABLE 3

| Ex. # | Structure | Spectral Data |
|---|---|---|
| 3-2 | ![structure] (R)-N-(1-(4-(2-((methylamino)methyl)phenyl)thiophen-2-yl)ethyl)-7-morpholinopyrido[3,4-d]pyridazin-1-amine | $^1$H NMR (400 MHz, CD$_3$OD) δ 8.93 (d, J = 0.8 Hz, 1H), 8.70 (s, 1H), 7.44 (d, J = 6.4 Hz, 1H), 7.37-7.29 (m, 4H), 7.22-7.15 (m, 2H), 5.91 (q, J = 6.8 Hz, 1H), 3.87-3.82 (m, 4H), 3.80-3.74 (m, 6H), 2.27 (s, 3H), 1.83 (d, J = 7.2 Hz, 3H). LCMS [M + 1]: 461.3. |
| 3-3 | ![structure] (R)-N-(1-(5-(2-((methylamino)methyl)phenyl)thiophen-2-yl)ethyl)-7-morpholinopyrido[3,4-d]pyridazin-1-amine | $^1$H NMR (400 MHz, CD$_3$OD) δ = 9.14 (s, 1H), 9.04 (s, 1H), 7.60-7.55 (m, 1H), 7.53-7.49 (m, 2H), 7.48-7.44 (m, 2H), 7.20 (d, J = 4.0 Hz, 1H), 7.01 (d, J = 4.0 Hz, 1H), 5.73 (q, J = 6.8 Hz, 1H), 4.34 (s, 2H), 4.01-3.89 (m, 4H), 3.88-3.77 (m, 4H), 2.64 (s, 3H), 1.85 (d, J = 7.2 Hz, 3H). LCMS [M + 1]: 461.2. |

TABLE 3-continued

| Ex. # | Structure | Spectral Data |
|---|---|---|
| 3-4 | 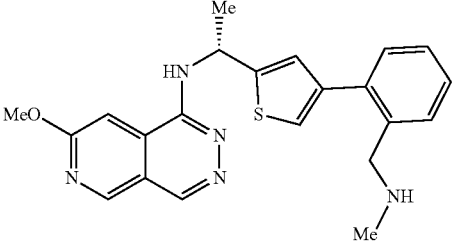 [SMILES: CNCc1ccccc1-c1csc([C@@H](C)Nc2nncc3cnc(OC)cc23)c1]<br>(R)-7-methoxy-N-(1-(4-(2-((methylamino)methyl)phenyl)thiophen-2-yl)ethyl)pyrido[3,4-d]pyridazin-1-amine | $^1$H NMR (400 MHz, CD$_3$OD) δ 9.32-9.30 (m, 1H), 9.25-9.22 (m, 1H), 7.91-7.89 (m, 1H), 7.59-7.55 (m, 1H), 7.51-7.45 (m, 2H), 7.45-7.39 (m, 1H), 7.37-7.34 (m, 1H), 7.27-7.25 (m, 1H), 5.80-5.73 (m, 1H), 4.28 (s, 2H), 4.19 (s, 3H), 2.60 (s, 3H), 1.88 (d, J = 6.9 Hz, 3H). LCMS [M + 1]: 406.1. |
| 3-5 | 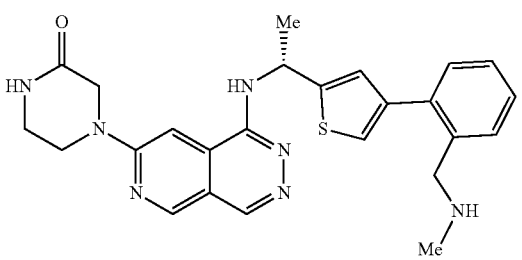 [SMILES: CNCc1ccccc1-c1csc([C@@H](C)Nc2nncc3cnc(N4CCNC(=O)C4)cc23)c1]<br>(R)-4-(1-((1-(4-(2-((methylamino)methyl)phenyl)thiophen-2-yl)ethyl)amino)pyrido[3,4-d]pyridazin-7-yl)piperazin-2-one | $^1$H NMR (400 MHz, CD$_3$OD) δ 9.20 (s, 1H), 9.09 (s, 1H), 7.59-7.55 (m, 1H), 7.53-7.46 (m, 3H), 7.45-7.39 (m, 1H), 7.33 (d, J = 1.5 Hz, 1H), 7.25-7.23 (m, 1H), 5.77 (q, J = 6.8 Hz, 1H), 4.42 (s, 2H), 4.29 (s, 2H), 4.23-4.16 (m, 2H), 3.54 (t, J = 5.4 Hz, 2H), 2.61 (s, 3H), 1.88 (d, J = 6.9 Hz, 3H). LCMS [M + 1]: 474.2. |
| 3-6 | 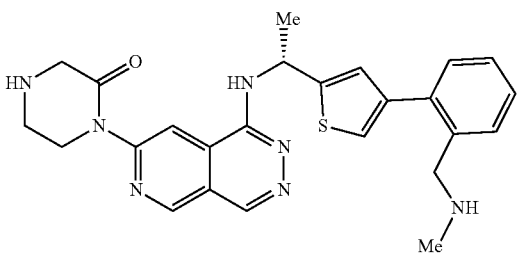 [SMILES: CNCc1ccccc1-c1csc([C@@H](C)Nc2nncc3cnc(N4CCNCC4=O)cc23)c1]<br>(R)-1-(1-((1-(4-(2-((methylamino)methyl)phenyl)thiophen-2-yl)ethyl)amino)pyrido[3,4-d]pyridazin-7-yl)piperazin-2-one | $^1$H NMR (400 MHz, CD$_3$OD) δ 9.43 (d, J = 0.9 Hz, 1H), 9.19 (d, J = 0.9 Hz, 1H), 9.07-9.05 (m, 1H), 7.57-7.51 (m, 1H), 7.48-7.42 (m, 2H), 7.41-7.36 (m, 1H), 7.34 (d, J = 1.5 Hz, 1H), 7.27-7.25 (m, 1H), 5.80-5.74 (m, 1H), 4.47-4.41 (m, 2H), 4.25 (s, 2H), 4.17 (s, 2H), 3.76-3.72 (m, 2H), 2.58 (s, 3H), 1.89 (d, J = 6.8 Hz, 3H). LCMS [M + 1]: 474.4. |

Example 4-1

(R)-6,7-dimethoxy-4-methyl-N-(1-(2-methyl-3-(trifluoromethyl)phenyl)ethyl)phthalazin-1-amine

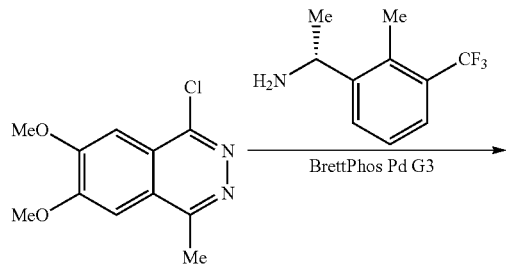

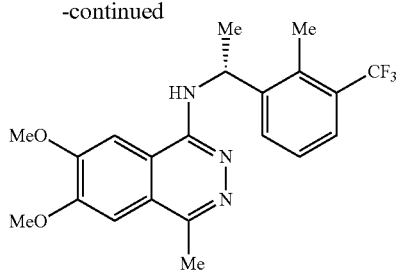

A mixture of 1-chloro-6,7-dimethoxy-4-methylphthalazine (100 mg, 419 μmol, 1.00 eq.), (R)-1-(2-methyl-3-(trifluoromethyl)phenyl)ethan-1-amine (85.1 mg, 419 μmol, 1.00 eq.), BrettPhos Pd G3 (38.0 mg, 41.9 μmol, 0.10 eq.) and potassium tert-butoxide (1.00 M, 1.26 mL, 3.00 eq.) in toluene (2.00 mL) was degassed and purged with nitrogen 3 times. The reaction mixture was stirred at 100° C. for 1 hour under a nitrogen atmosphere, then cooled to 25° C., filtered, and the filtrate was concentrated under reduced pressure to give a residue. The residue was purified by prep-HPLC (column: Waters Xbridge BEH C18 100×25 mm×5 um;

mobile phase: [water (10 mM NH₃HCO₃)—ACN]; B %: 35%-65%) to give (R)-6,7-dimethoxy-4-methyl-N-(1-(2-methyl-3-(trifluoromethyl)phenyl)ethyl)phthalazin-1-amine (8.24 mg, 20.3 µmol, 4.84% yield, 99.8% purity) as a white solid. LCMS [M+1]: 406.2.

¹H NMR (400 MHz, DMSO-d₆) δ=7.83 (s, 1H), 7.76 (d, J=7.6 Hz, 1H), 7.51 (d, J=8.0 Hz, 1H), 7.39 (d, J=6.8 Hz, 1H), 7.33-7.27 (m, 1H), 7.22 (s, 1H), 5.73-5.64 (m, 1H), 4.01 (s, 3H), 3.95 (s, 3H), 2.58 (s, 6H), 1.55 (d, J=7.2 Hz, 3H).

Following the teachings of General Reaction Scheme IV and the procedure described for the preparation of Example 4-1, the following compounds of Formula (I), Examples 4-2-4-4 shown in Table 4 were prepared:

TABLE 4

| Ex. # | Structure | Spectral Data |
|---|---|---|
| 4-2 | 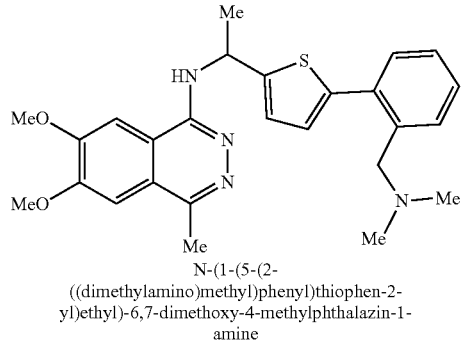<br>N-(1-(5-(2-((dimethylamino)methyl)phenyl)thiophen-2-yl)ethyl)-6,7-dimethoxy-4-methylphthalazin-1-amine | ¹H NMR (400 MHz, DMSO-d₆) δ 7.74 (s, 1H), 7.44-7.40 (m, 1H), 7.40-7.33 (m, 2H), 7.31-7.27 (m, 2H), 7.26 (s, 1H), 7.16 (d, J = 4.0 Hz, 1H), 7.06 (d, J = 3.6 Hz, 1H), 5.96-5.87 (m, 1H), 3.96 (s, 3H), 3.95 (s, 3H), 3.37 (s, 2H), 2.66 (s, 3H), 2.10 (s, 6H), 1.72 (d, J = 6.8 Hz, 3H). LCMS [M + 1]⁺: 463.2. |
| 4-3 | 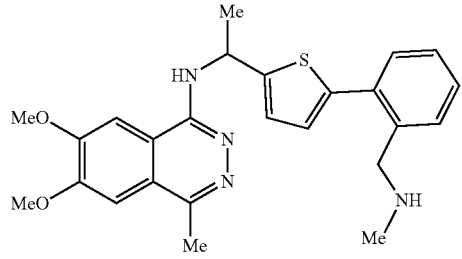 [SMILES: CNCc1ccccc1-c1ccc(C(C)Nc2nnc(C)c3cc(OC)c(OC)cc23)s1]<br>6,7-dimethoxy-4-methyl-N-(1-(5-(2-((methylamino)methyl)phenyl)thiophen-2-yl)ethyl)phthalazin-1-amine | ¹H NMR (400 MHz, CDCl₃) δ 7.44 (d, J = 7.2 Hz, 1H), 7.39 (dd, J = 0.8, 7.2 Hz, 1H), 7.33-7.29 (m, 2H), 7.17 (s, 1H), 7.11 (d, J = 3.2 Hz, 1H), 7.01 (d, J = 3.6 Hz, 1H), 6.98 (s, 1H), 6.06-6.02 (m, 1H), 4.98-4.96 (m, 1H), 4.06 (s, 6H), 3.85 (s, 2H), 2.80 (s, 3H), 2.41 (s, 3H), 1.83 (d, J = 6.8 Hz, 3H). LCMS [M + 1]: 449.2. |
| 4-4 | 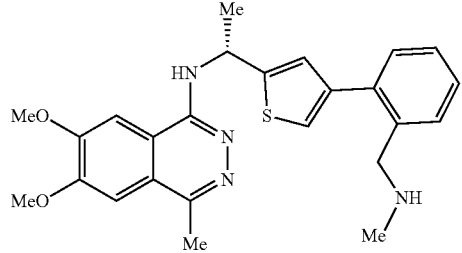 [SMILES: CNCc1ccccc1-c1csc([C@@H](C)Nc2nnc(C)c3cc(OC)c(OC)cc23)c1]<br>(R)-6,7-dimethoxy-4-methyl-N-(1-(4-(2-((methylamino)methyl)phenyl)thiophen-2-yl)ethyl)phthalazin-1-amine | ¹H NMR (400 MHz, DMSO-d₆) δ = 7.74 (s, 1H), 7.47-7.42 (m, 1H), 7.42 (d, J = 1.6 Hz, 1H), 7.34 (d, J = 8.4 Hz, 1H), 7.32-7.24 (m, 5H), 5.97-5.87 (m, 1H), 3.97 (s, 3H), 3.96 (s, 3H) 3.57 (s, 2H), 2.66 (s, 3H), 2.22 (s, 3H), 1.73 (d, J = 6.8 Hz, 3H). LCMS [M + 1]: 449.2. |

Example 5-1

(R)—N-(1-(5-(2-((dimethylamino)methyl)phenyl)thiophen-2-yl)ethyl)-4-isopropyl-6,7-dimethoxyphthalazin-1-amine

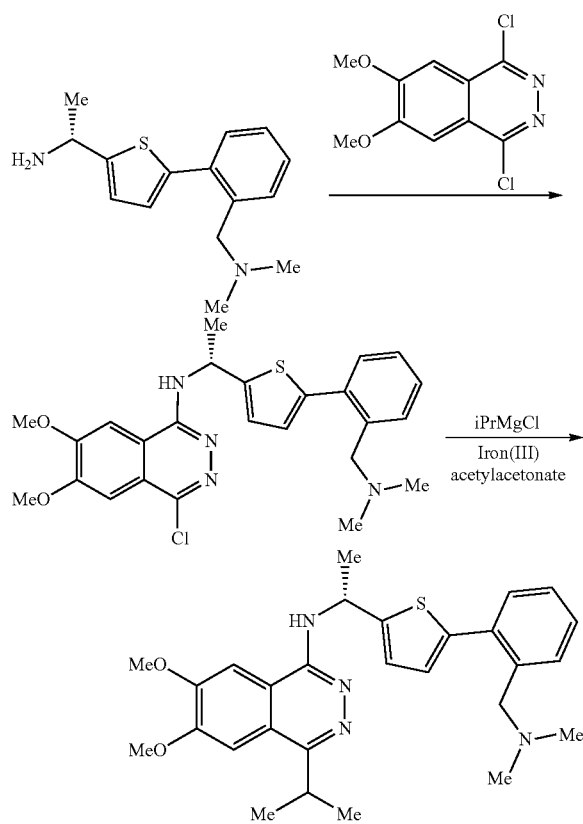

Step A: A mixture of (R)-1-(5-(2-((dimethylamino)methyl)phenyl)thiophen-2-yl)ethan-1-amine (200 mg, 768 μmol, 0.90 eq.), 1,4-dichloro-6,7-dimethoxy-phthalazine (221 mg, 853 μmol, 1.00 eq.), N, N-diisopropylethylamine (331 mg, 2.56 mmol, 446 μL, 3.00 eq.) and potassium fluoride (149 mg, 2.56 mmol, 60.0 μL, 3.00 eq.) in DMSO (3.00 mL) was stirred at 130° C. for 12 hours. The reaction mixture was then cooled to 25° C., then ethyl acetate (5.00 mL) and water (8.00 mL) were added and the layers were separated. The aqueous phase was extracted with ethyl acetate (10.0 mL×2) and the combined organic layers were washed with brine (10.0 mL×2), dried over sodium sulfate, filtered, and concentrated under reduced pressure to give a residue. The residue was purified by prep-TLC (SiO$_2$, petroleum ether/ethyl acetate=1/1) to give (R)-4-chloro-N-(1-(5-(2-((dimethylamino)methyl)phenyl)thiophen-2-yl)ethyl)-6,7-dimethoxyphthalazin-1-amine (100 mg, 24.3% yield) as a yellow solid. LCMS [M+1]: 483.0.

$^1$H NMR (400 MHz, CDCl$_3$) δ=7.53-7.49 (m, 1H), 7.44 (s, 1H), 7.44-7.40 (m, 1H), 7.34-7.29 (m, 2H), 7.13-7.05 (m, 2H), 6.99 (s, 1H), 6.06-5.96 (m, 1H), 4.09 (s, 3H), 4.07 (s, 3H), 3.60 (s, 2H), 2.27 (s, 6H), 1.84 (d, J=6.4 Hz, 3H).

Step B: To a solution of (R)-4-chloro-N-(1-(5-(2-((dimethylamino)methyl)phenyl)thiophen-2-yl)ethyl)-6,7-dimethoxyphthalazin-1-amine (40.0 mg, 82.8 μmol, 1.00 eq.) and iron (III) acetylacetonate (80.0 mg, 226 μmol, 2.74 eq.) in THF (1.00 mL) and 1-methyl-2-pyrrolidinone (0.01 mL) was added isopropylmagnesium chloride (3.00 M in THF, 600 μL, 21.7 eq.) dropwise at 0° C. After addition the mixture reaction was stirred at 25° C. for 10 minutes. The reaction mixture was quenched by addition saturated ammonium chloride solution (5.00 mL), and extracted with ethyl acetate (1.00 mL×3). The combined organic layers were washed with brine (2.00 mL×2), dried over sodium sulfate, filtered and concentrated under reduced pressure to give a residue. The residue was purified by prep-HPLC (column: Phenomenex luna C18 150×25 mm×10 um; mobile phase: [water (0.1% TFA)-ACN]; B %: 16%-46%) and lyophilized to give (R)—N-(1-(5-(2-((dimethylamino)methyl)phenyl)thiophen-2-yl)ethyl)-4-isopropyl-6,7-dimethoxyphthalazin-1-amine (10.3 mg, 20.4% yield, 99.0% purity, trifluoroacetic acid salt) as a off-white solid. LCMS [M+1]: 491.3.

$^1$H NMR (400 MHz, CD$_3$OD) δ=8.11 (s, 1H), 7.68 (s, 1H), 7.66-7.63 (m, 1H), 7.56-7.47 (m, 3H), 7.26-7.21 (m, 1H), 7.04 (d, J=3.6 Hz, 1H), 5.73-5.60 (m, 1H), 4.52 (s, 2H), 4.12 (s, 3H), 4.11 (s, 3H), 3.97-3.88 (m, 1H), 2.73 (s, 6H), 1.91 (d, J=6.8 Hz, 3H), 1.53-1.42 (m, 6H).

SFC Conditions: Column: Chiralcel OD-3 50×4.6 mm I.D., 3 um Mobile phase: Phase A for CO2, and Phase B for MeOH (0.05% DEA); Gradient elution: MeOH (0.05% DEA) in CO2 from 5% to 40% Flow rate: 3 mL/min; Detector: PDA Column Temp: 35C; Back Pressure: 100 Bar.

Following the teachings of General Reaction Scheme I and the procedure described for the preparation of Example 5-1, the following compounds of Formula (I), Examples 5-2-5-3 shown in Table 5 were prepared:

TABLE 5

| Ex. # | Structure | Spectral Data |
|---|---|---|
| 5-2 | ![structure] N-(1-(5-(2-((dimethylamino)methyl)phenyl)thiophen-2-yl)ethyl)-4-ethyl-6,7-dimethoxyphthalazin-1-amine | $^1$H NMR (400 MHz, CD$_3$OD) δ 8.08 (s, 1H), 7.69-7.64 (m, 2H), 7.58-7.48 (m, 3H), 7.25-7.23 (m, 1H), 7.06-7.02 (m, 1H), 5.73 (q, J = 6.8 Hz, 1H), 4.53 (s, 2H), 4.15 (s, 3H), 4.13 (s, 3H), 3.39-3.34 (m, 3H), 2.75 (s, 6H), 1.90 (d, J = 6.9 Hz, 3H), 1.48 (t, J = 7.5 Hz, 3H). LCMS [M + 1]: 477.3. |

TABLE 5-continued

| Ex. # | Structure | Spectral Data |
|---|---|---|
| 5-3 | 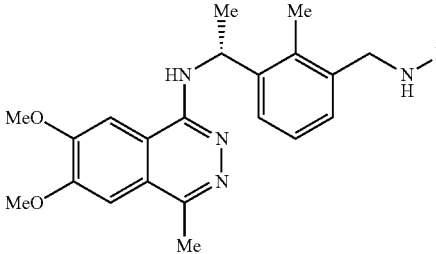<br>(R)-6,7-dimethoxy-4-methyl-N-(1-(2-methyl-3-((methylamino)methyl)phenyl)ethyl)phthalazin-1-amine | $^1$H NMR (400 MHz, CD$_3$OD) δ = 8.08 (s, 1H), 7.56-7.62 (m, 2H), 7.22-7.35 (m, 2H), 5.50-5.61 (m, 1H), 4.34-4.42 (m, 1H), 4.21-4.28 (m, 1H), 4.16 (s, 3 H), 4.09 (s, 3H), 2.85 (s, 3 H), 2.79 (s, 3H), 2.55 (s, 3H), 1.69 (d, J = 6.8 Hz, 3H). LCMS [M + 1]$^+$ = 381.2. |

Example 5-4

(R)—N-(1-(5-(2-((dimethylamino)methyl)phenyl)thiophen-2-yl)ethyl)-6,7-dimethoxy-4-(trifluoromethyl)phthalazin-1-amine

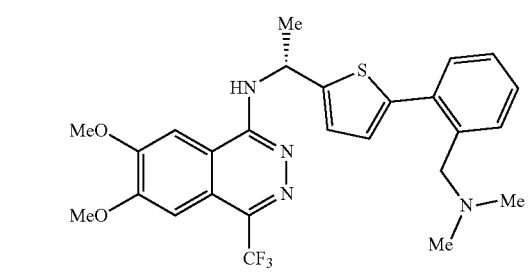

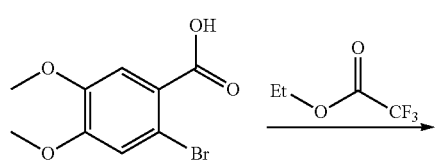

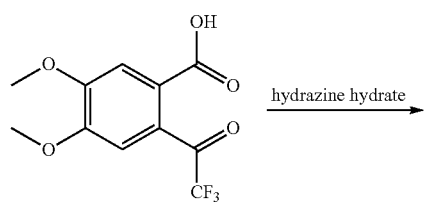

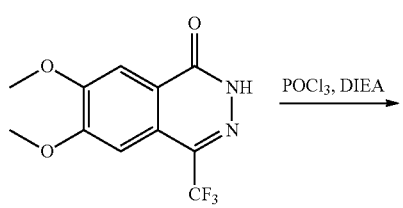

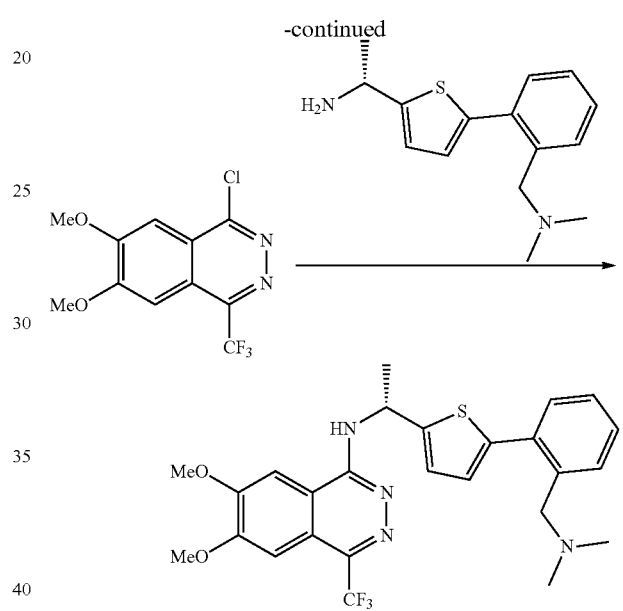

Step A: To a solution of 2-bromo-4,5-dimethoxybenzoic acid (0.30 g, 1.15 mmol, 1.00 eq.) in tetrahydrofuran (20.0 mL) was added n-BuLi (1.60 M, 1.72 mL, 2.40 eq.) at −78° C. under a nitrogen atmosphere. After stirring at −78° C. for 1 hour, ethyl 2,2,2-trifluoroacetate (163 mg, 1.15 mmol, 159 µL, 1.00 eq.) was added dropwise at the same temperature. The mixture was stirred at −78° C. for 1 hour, warmed to 20° C., and stirred at 20° C. for 3 hours. The reaction mixture was poured into ice water (20.0 mL) and extracted with ethyl acetate (20.0 mL×3). The combined organic phases were washed with brine (20.0 mL×3), dried over anhydrous sodium sulfate, filtered, and concentrated under reduced pressure to give a residue. The residue was purified by column chromatography (SiO$_2$, petroleum ether/ethyl acetate=5/1 to 0/1) to give 4,5-dimethoxy-2-(2,2,2-trifluoroacetyl)benzoic acid (0.10 g, 30.9% yield) as a yellow oil. LCMS [M+1]$^+$=279.0.

$^1$H NMR (400 MHz, CDCl$_3$) δ=7.30 (s, 1H), 7.11 (s, 1H), 4.03 (s, 3H), 3.98 (s, 3H).

Step B: To a suspension of 4,5-dimethoxy-2-(2,2,2-trifluoroacetyl)benzoic acid (0.10 g, 359 µmol, 1.00 eq.) in ethanol (10.0 mL) was added NH$_2$NH$_2$.H$_2$O (180 mg, 3.59 mmol, 175 µL, 10.0 eq.). The mixture was stirred at 100° C. for 3 hours. After completion, the reaction was concentrated under reduced pressure to give 6,7-dimethoxy- 4-(trifluoromethyl)phthalazin-1(2H)-one (80.0 mg, crude) as a yellow solid. LCMS [M+1]⁺=316.1.

¹H NMR (400 MHz, DMSO-d₆) δ=7.70 (s, 1H), 7.15 (s, 1H), 3.98 (s, 3H), 3.96 (s, 3H).

Step C: To a solution of 6,7-dimethoxy-4-(trifluoromethyl)phthalazin-1 (2H)-one (300 mg, 1.09 mmol, 1.00 eq.) in POCl₃ (4.95 g, 32.3 mmol, 3.00 mL, 29.5 eq.) was added N, N-diisopropylethylamine (707 mg, 5.47 mmol, 953 µL, 5.00 eq.) at 25° C. The mixture was stirred at 100° C. for 30 minutes. The reaction mixture was concentrated under reduced pressure to give a residue. Then diluted with ethyl acetate (10.0 mL) and poured into ice water (10.0 mL), extracted with ethyl acetate (10.0 mL×3). The combined organic layers were dried over anhydrous sodium sulfate, filtered, and concentrated under reduced pressure to give a residue. The residue was purified by column chromatography (SiO₂, petroleum ether/ethyl acetate=10/1 to 1/1) to give 1-chloro-6,7-dimethoxy-4-(trifluoromethyl)phthalazine (50.2 mg, 171 µmol, 15.7% yield) as a yellow solid. LCMS [M+1]⁺=293.0.

¹H NMR (500 MHz, CDCl₃) δ=7.60 (s, 1H), 7.44 (d, J=1.0 Hz, 1H), 4.15 (s, 3H), 4.12 (s, 3H).

Step D: To a solution of (R)-1-(5-(2-((dimethylamino)methyl)phenyl)thiophen-2-yl)ethan-1-amine (50.0 mg, 168 µmol, 1.00 eq., HCl) and 1-chloro-6,7-dimethoxy-4-(trifluoromethyl)phthalazine (49.3 mg, 168 µmol, 1.00 eq.) in DMSO (1.00 mL) and was added N A-diisopropylethylamine (87.1 mg, 674 µmol, 117 µL, 4.00 eq.) and potassium fluoride (2.94 mg, 50.5 µmol, 1.18 µL, 0.30 eq.). After completion, the reaction mixture was filtered and the residue was purified by prep-HPLC (Column: Agela DuraShell C18 150×25 mm×5 um; mobile phase: phase A: [water(0.05% NH₃H₂O+10 mM NH₄HCO₃)], phase B: acetonitrile; B %: 60%-90%) to give (R)—N-(1-(5-(2-((dimethylamino)methyl)phenyl)thiophen-2-yl)ethyl)-6,7-dimethoxy-4-(trifluoromethyl)phthalazin-1-amine (4.51 mg, 8.72 µmol, 5.18% yield, 99.9% purity) as a white solid. LCMS [M+1]⁺=517.1.

¹H NMR (500 MHz, CDCl₃) δ=7.51-7.46 (m, 1H), 7.43 (dd, J=1.5, 7.0 Hz, 1H), 7.36 (d, J=1.5 Hz, 1H), 7.35-7.28 (m, 2H), 7.13 (s, 2H), 6.99 (br s, 1H), 6.20-6.13 (m, 1H), 5.39 (br s, 1H), 4.08 (s, 3H), 4.07 (s, 3H), 3.53 (br s, 2H), 2.25 (br s, 6H), 1.87 (d, J=6.5 Hz, 3H).

Example 6-1

(R)-4-methyl-N-(1-(2-methyl-3-(trifluoromethyl)phenyl)ethyl)-7-(4-methylpiperazin-1-yl)phthalazin-1-amine

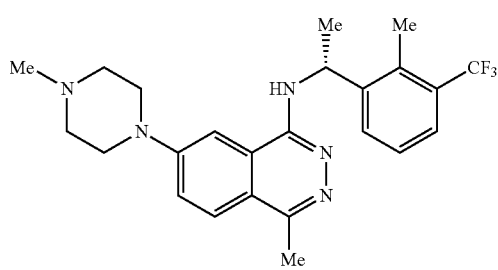

Step A: A mixture of methyl 5-bromo-2-iodobenzoate (5.00 g, 14.7 mmol, 1.00 eq.), tributyl(1-ethoxyvinyl)stannane (5.60 g, 15.4 mmol, 5.20 mL, 1.05 eq.) and Pd(PPh₃)₂Cl₂ (309 mg, 440 µmol, 0.03 eq.) in dioxane (50.0 mL) was degassed and purged with nitrogen for 3 times, and then the reaction mixture was stirred at 80° C. for 10 hours under a nitrogen atmosphere. The reaction mixture was cooled to 25° C., quenched by addition water (50.0 mL), and then extracted with ethyl acetate (50.0 mL×3). The combined organic layers were washed with brine (20.0 mL×3), dried over sodium sulfate, filtered, and concentrated under

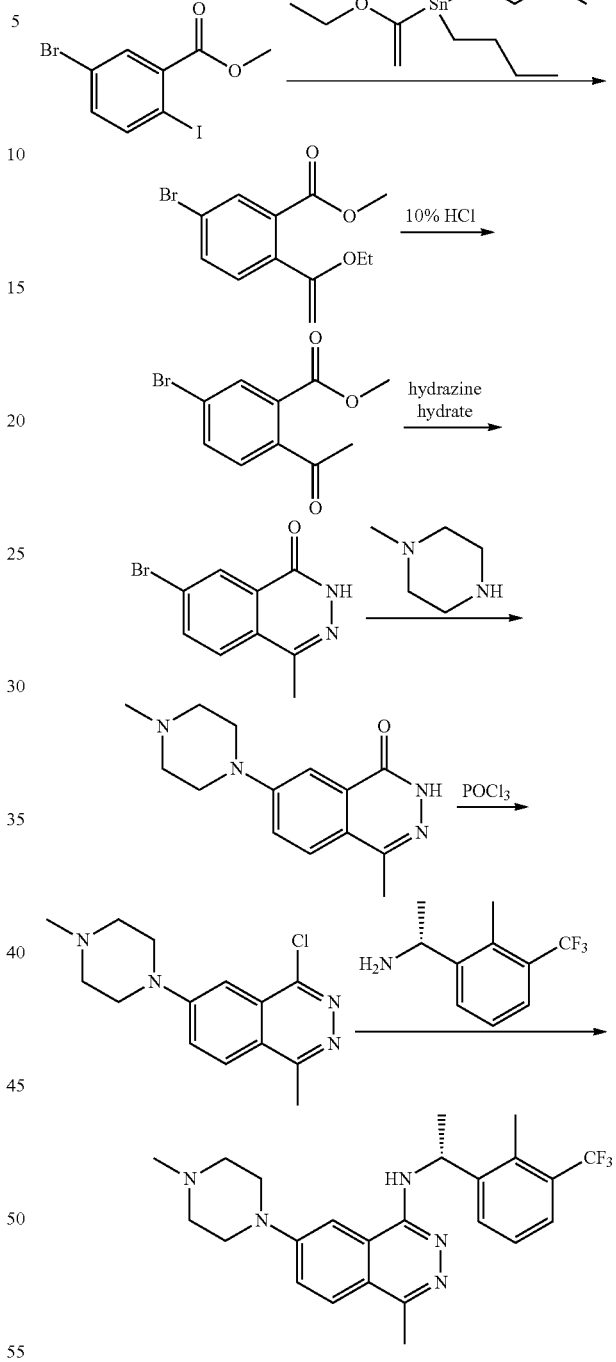
-continued reduced pressure to give methyl 5-bromo-2-(1-ethoxyvinyl) benzoate (6.00 g, crude) as a yellow oil which was used in the next step directly.

Step B: To a solution of methyl 5-bromo-2-(1-ethoxyvinyl)benzoate (6.00 g, crude) in THF (50.0 mL) was added hydrochloric acid aqueous solution (10%, 25.0 mL). The reaction mixture was stirred at 20° C. for 1 hour. To the reaction mixture was added water (50.0 mL), and the aqueous layer was extracted with ethyl acetate (100 mL×3). The combined organic layers were washed with brine (30.0 mL×2), dried over sodium sulfate, filtered, and concentrated under reduced pressure to give a residue. The residue was purified by column chromatography (SiO$_2$, petroleum ether/ethyl acetate=1/0 to 50/1) to give methyl 2-acetyl-5-bromobenzoate (2.50 g, 67.0% yield) as a yellow oil.

$^1$H NMR (400 MHz, CDCl$_3$) δ=7.97 (d, J=2.0 Hz, 1H), 7.70 (dd, J=2.0, 8.2 Hz, 1H), 7.32 (d, J=8.4 Hz, 1H), 3.91 (s, 3H), 2.53 (s, 3H).

Step C: To a solution of methyl 2-acetyl-5-bromobenzoate (1.50 g, 5.83 mmol, 1.00 eq.) in ethanol (30.0 mL) was added hydrazine hydrate (876 mg, 17.5 mmol, 851 μL, 3.00 eq.). The reaction mixture was stirred at 95° C. for 30 minutes. The reaction mixture was then cooled to 25° C., and concentrated under reduced pressure to give a residue. The residue was triturated with ethanol for 10 minutes to give a suspension, the suspension was filtered, and the filter cake was collected and dried under vacuum to give 7-bromo-4-methylphthalazin-1(2H)-one (0.70 g, 2.93 mmol, 50.2% yield) as a white solid. LCMS [M+1]$^+$: 239.0.

$^1$H NMR (400 MHz, DMSO-d$_6$) δ=12.57 (br s, 1H), 8.32 (d, J=2.0 Hz, 1H), 8.11 (dd, J=2.0, 8.4 Hz, 1H), 7.88 (d, J=8.4 Hz, 1H), 2.50 (s, 3H).

Step D: A mixture of 7-bromo-4-methyl-phthalazin-1-ol (1.00 g, 4.18 mmol, 1.00 eq), 1-methylpiperazine (628 mg, 6.27 mmol, 696 μL, 1.50 eq), RuPhos (195 mg, 418 μmol, 0.10 eq), Pd$_2$(dba)$_3$ (192 mg, 209 μmol, 0.05 eq) and t-BuOK (1M in THF, 8.37 mL, 2.00 eq) in dioxane (10.0 mL) was degassed and purged with N$_2$ 3 times, and then the mixture was stirred at 110° C. for 1.5 hours under a N$_2$ atmosphere. The reaction mixture was quenched by addition of water (20 mL), and then extracted with EtOAc (10 mL×3). The combined organic layers were washed with brine (5 mL×2), dried over Na$_2$SO$_4$, filtered, and concentrated under reduced pressure to give a residue. The crude product was triturated with EtOAc (3 mL) for 10 min to give 4-methyl-7-(4-methylpiperazin-1-yl)phthalazin-1(2H)-one (800 mg, 3.10 mmol, 74.0% yield) as a yellow solid. LCMS [M+1]$^+$: 259.1.

$^1$H NMR (400 MHz, DMSO-d$_6$) δ=12.13 (s, 1H), 7.74 (d, J=8.8 Hz, 1H), 7.56 (dd, J=2.8, 9.0 Hz, 1H), 7.50 (d, J=2.6 Hz, 1H), 3.40-3.34 (m, 4H), 2.49-2.45 (m, 4H), 2.43 (s, 3H), 2.23 (s, 3H).

Step E: To a solution of 4-methyl-7-(4-methylpiperazin-1-yl)phthalazin-1(2H)-one (100 mg, 387 μmol, 1.00 eq) in phosphorus oxychloride (1.61 g, 10.5 mmol, 976 μL, 27.1 eq.). The mixture was stirred at 110° C. for 16 hours. The reaction mixture was then cooled to 25° C., and concentrated under vacuum to give a residue. The residue was dissolved in water (10.0 mL) and adjust to pH=9 with saturated sodium sulfate, and extracted with ethyl acetate (5.00 mL×2). The organic layer was dried over anhydrous sodium sulfate and concentrated under vacuum to give 4-chloro-1-methyl-6-(4-methylpiperazin-1-yl)phthalazine (70.0 mg, crude) as brown solid which used directly without purification. LCMS [M+1]$^+$: 277.1.

Step F: To a solution of 7-chloro-1-methyl-6-(4-methylpiperazin-1-yl)phthalazine (60.0 mg, 217 μmol, 1.00 eq.)

and (R)-1-(2-methyl-3-(trifluoromethyl)phenyl)ethan-1-amine (48.5 mg, 238 μmol, 1.10 eq.) in dimethyl sulfoxide (3.00 mL) was added cesium fluoride (98.8 mg, 650 μmol, 24.0 μL, 3.00 eq.) and N, N-diisopropylethylamine (140 mg, 1.08 mmol, 189 μL, 5.00 eq.). Then the mixture was stirred at 120° C. for 16 hours. The reaction mixture was then poured into water (1.50 ml) and purified by prep-HPLC (column: Boston Green ODS 150×30 mm×5 um; mobile phase: [water(0.1% TFA)-ACN]; B %: 25%-45%, 10 min). The product was further purified by prep-HPLC (column: Agela DuraShell C18 150×25 mm×5 um; mobile phase: [water (0.05% NH$_3$H$_2$O+10 mM NH$_4$HCO$_3$)-ACN]; B %: 38%-68%, 10 min) to give (R)-4-methyl-N-(1-(2-methyl-3-(trifluoromethyl)phenyl)ethyl)-7-(4-methylpiperazin-1-yl) phthalazin-1-amine (17.0 mg, 3.83 μmol, 17.6% yield, 99.9% purity) as a white solid. LCMS [M+1]$^+$: 444.1.

$^1$H NMR (500 MHz, CD$_3$OD) δ=7.91 (d, J=9.50 Hz, 1H), 7.70 (d, J=8.50 Hz, 1H), 7.55-7.63 (m, 2H), 7.48 (d, J=8.00 Hz, 1H), 7.23 (t, J=7.50 Hz, 1H), 5.75-5.70 (m, 1H), 3.55 (br s, 4H), 2.68 (br t, J=5.00 Hz, 4H), 2.59-2.63 (m, 6H), 2.40 (s, 3H), 1.63 (d, J=7.00 Hz, 3H).

Example 6-2

(R)-4-methyl-N-(1-(5-(2-((methylamino)methyl) phenyl)thiophen-2-yl)ethyl)-7-morpholinopyrido[3, 4-d]pyridazin-1-amine

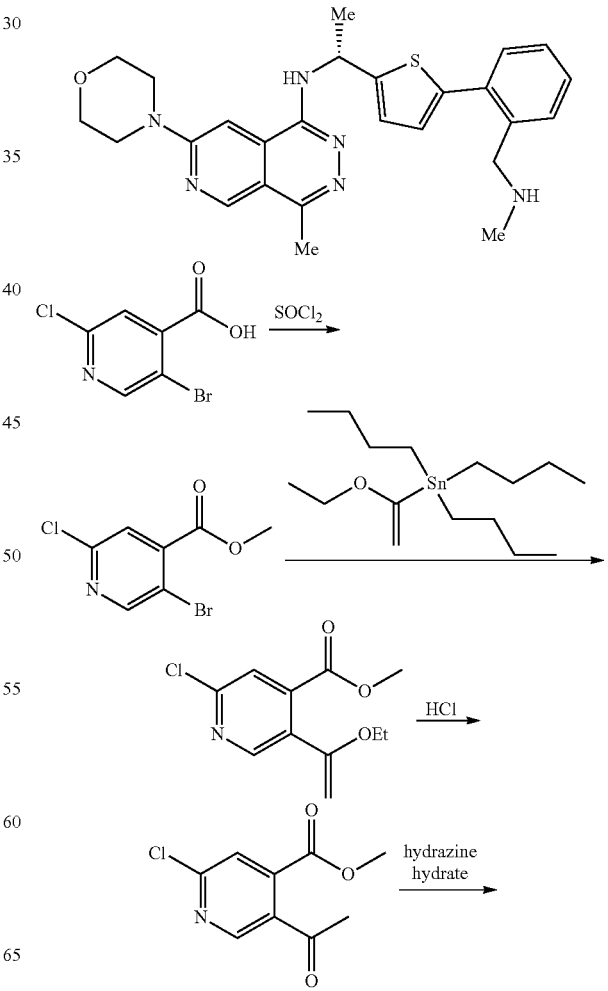

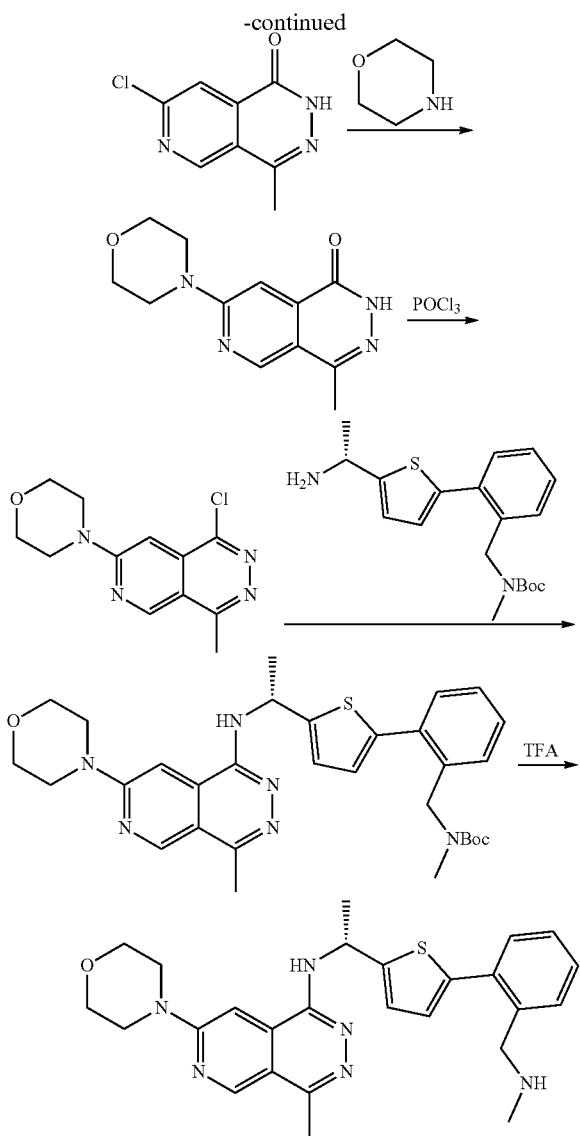

Step A: To a solution of 5-bromo-2-chloroisonicotinic acid (12.0 g, 50.6 mmol, 1.00 eq) in MeOH (100 mL) was added SOCl$_2$ (7.25 g, 60.9 mmol, 4.42 mL, 1.20 eq) dropwise, then the mixture was heated to 75° C. and stirred for 8 hours. The reaction mixture was then concentrated under reduced pressure to give a residue. The residue was diluted with EtOAc (100 mL), washed with saturated NaHCO$_3$ (100 mL), dried over Na$_2$SO$_4$, filtered, and concentrated under reduced pressure to give methyl 5-bromo-2-chloroisonicotinate (12.0 g, crude) as a yellow oil. LCMS [M+1]$^+$: 252.0.

$^1$H NMR (400 MHz, DMSO-d$_6$) δ=8.78 (s, 1H), 7.89 (s, 1H), 3.91 (s, 3H).

Step B: A solution of methyl 5-bromo-2-chloroisonicotinate (11.0 g, 43.92 mmol, 1.00 eq), tributyl(1-ethoxyvinyl)stannane (16.7 g, 46.1 mmol, 15.6 mL, 1.05 eq) and Pd(PPh$_3$)$_2$Cl$_2$ (1.23 g, 1.76 mmol, 0.04 eq) in dioxane (110 mL) was degassed and purged with N$_2$ 3 times, and then the mixture was heated at 80° C. for 16 hours under a N$_2$ atmosphere. The reaction mixture was then quenched by addition water (400 mL), and then extracted with EtOAc (150 mL×3). The combined organic layers were washed with brine (200 mL), dried over Na$_2$SO$_4$, filtered, and concentrated under reduced pressure to give methyl 2-chloro-5-(1-ethoxyvinyl)isonicotinate (10.6 g, crude) was obtained as a yellow oil.

Step C: To a solution of methyl 2-chloro-5-(1-ethoxyvinyl)isonicotinate (10.6 g, 43.9 mmol, 1.00 eq) in THF (100 mL) was added HCl (102 g, 280 mmol, 100 mL, 10% purity in water, 6.38 eq) dropwise, and the mixture was stirred at 20° C. for 16 hours. The reaction mixture was then quenched by addition of NaHCO$_3$ (300 mL) at 0° C., and then extracted with EtOAc (100 mL×3). The combined organic layers were washed with brine (100 mL), dried over Na$_2$SO$_4$, filtered, and concentrated under reduced pressure to give a residue. The residue was purified by column chromatography (SiO$_2$, Petroleum ether/Ethyl acetate=1/0 to 3/1) to give methyl 5-acetyl-2-chloroisonicotinate (4.50 g, 21.1 mmol, 48.0% yield) was obtained as a white solid.

$^1$H NMR (400 MHz, DMSO-d$_6$) δ=8.98 (s, 1H), 7.85 (s, 1H), 3.84 (s, 3H), 2.61 (s, 3H).

Step D: To a solution of methyl 5-acetyl-2-chloroisonicotinate (1.00 g, 4.68 mmol, 1.00 eq) in EtOH (15.0 mL) was added hydrazine hydrate (703 mg, 14.0 mmol, 683 µL, 3.00 eq), the mixture was stirred at 95° C. for 30 minutes. The reaction mixture was then filtered and the filter cake was concentrated under reduced pressure to give a residue to give 7-chloro-4-methylpyrido[3,4-d]pyridazin-1(2H)-one (0.85 g, crude) was obtained as a white solid. LCMS [M+1]$^+$: 196.1.

$^1$H NMR (400 MHz, DMSO-d$_6$) δ=9.20 (s, 1H), 8.10 (s, 1H), 2.58 (s, 3H).

Step E: A solution of 7-chloro-4-methylpyrido[3,4-d]pyridazin-1(2H)-one (750 mg, 3.83 mmol, 1.00 eq), morpholine (668 mg, 7.67 mmol, 675 µL, 2.00 eq) in dioxane (10.0 mL), tBuOK (1.00 M in THF, 11.5 mL, 3.00 eq), RuPhos (179 mg, 383 µmol, 0.10 eq), Pd$_2$(dba)$_3$ (176 mg, 192 µmol, 0.05 eq) was degassed and purged with nitrogen 3 times, and the mixture was stirred at 110° C. for 3 hours under a nitrogen atmosphere. The reaction mixture was filtered, and the filtrate was concentrated under reduced pressure to give a residue. The residue was purified by prep-HPLC (column: Phenomenex luna C18 (250*70 mm, 15 um); mobile phase: [water(0.05% HCl)-ACN]; B %: 10%-40%) to give 4-methyl-7-morpholinopyrido[3,4-d]pyridazin-1(2H)-one (500 mg, 2.03 mmol, 49.2% yield) was obtained as a white solid. LCMS [M+1]$^+$: 247.0.

$^1$H NMR (400 MHz, DMSO-d$_6$) δ=12.26 (s, 1H), 8.89 (s, 1H), 7.23 (s, 1H), 3.75-3.70 (m, 4H), 3.68-3.63 (m, 4H), 2.46 (s, 3H).

Step F: A solution of 7-methyl-7-morpholinopyrido[3,4-d]pyridazin-1(2H)-one (500 mg, 2.03 mmol, 1.00 eq) in POCl$_3$ (6.23 g, 40.6 mmol, 3.77 mL, 20.0 eq), was stirred at 110° C. for 3 hours. The reaction mixture was then concentrated under reduced pressure to remove POCl$_3$. The residue was diluted with H$_2$O (100 mL), and then adjusted to pH=8 using NaHCO$_3$ solid, and then extracted with ethyl acetate (50.0 mL×3). The combined organic layers were washed with brine (50.0 mL), dried over Na$_2$SO$_4$, filtered, and concentrated under reduced pressure to give 4-(1-chloro-4-methylpyrido[3,4-d]pyridazin-7-yl)morpholine (500 mg, crude) was obtained as a yellow solid. LCMS [M+1]$^+$: 264.9.

$^1$H NMR (400 MHz, CDCl$_3$) δ=9.13 (s, 1H), 6.89 (s, 1H), 3.92-3.86 (m, 4H), 3.81-3.75 (m, 4H), 2.91 (s, 3H).

Step G: To a mixture of 4-(1-chloro-4-methylpyrido[3,4-d]pyridazin-7-yl)morpholine (50.0 mg, 189 µmol, 1.00 eq.) and tert-butyl (R)-(2-(5-(1-aminoethyl)thiophen-2-yl)benzyl)(methyl)carbamate (65.5 mg, 189 µmol, 1.00 eq.) in dimethyl sulfoxide (2.00 mL) was added cesium fluoride (57.4 mg, 378 μmol, 13.9 μL, 2.00 eq.) and N, N-diisopropylethylamine (48.8 mg, 378 μmol, 65.8 μL, 2.00 eq.) in a glove box. The mixture was stirred at 130° C. for 3 hours then cooled to the room temperature, and water (30.0 mL) was added to the reaction mixture and extracted with ethyl acetate (3×20 mL). The combined organic layers were washed with brine (20.0 mL), dried over sodium sulfate, filtered, and concentrated under reduced pressure to give a residue. The residue was purified by prep-HPLC (column: Agela DuraShell C18 150×25 mm×5 um using water (0.04% NH$_4$OH+10 mM NH$_4$HCO$_3$) and acetonitrile as the eluents. Mobile phase A: water (0.04% NH$_3$H$_2$O+10 mM NH$_4$HCO$_3$)-ACN, mobile phase B: acetonitrile. Gradient: 24%-54% B) to give tert-butyl (R)-methyl(2-(5-(1-((4-methyl-7-morpholinopyrido[3,4-b]pyridazin-1-yl)amino)ethyl)thiophen-2-yl)benzyl)carbamate (20.0 mg, 34.8 μmol, 18.4% yield) as a yellow solid. LCMS [M+1]$^+$: 575.4.

$^1$H NMR (400 MHz, CD$_3$OD) δ=9.25 (s, 1H), 7.42 (s, 1H), 7.17-7.37 (m, 5H), 7.10 (d, J=3.6 Hz, 1H), 6.86 (br s, 1H), 5.59-5.68 (m, 1H), 4.46-4.52 (m, 2H), 3.92 (br s, 4H), 3.76-3.84 (m, 4H), 2.84 (s, 3H), 2.70 (s, 3H), 1.80 (d, J=7.2 Hz, 3H), 1.45 (br s, 9H).

Step H: To a mixture of tert-butyl (R)-methyl(2-(5-(1-((4-methyl-7-morpholinopyrido[3,4-b]pyridazin-1-yl)amino)ethyl)thiophen-2-yl)benzyl)carbamate (20.0 mg, 34.8 μmol, 1.00 eq.) in dichloromethane (1.00 mL) was added trifluoroacetic acid (0.20 mL). After completion, the mixture was concentrated and the residue was purified by prep-HPLC (column: Agela DuraShell C18 150×25 mm×5 um using water (0.04% NH$_3$H$_2$O+10 mM NH$_4$HCO$_3$) and acetonitrile as the eluents. Mobile phase A: water (0.04% NH$_4$OH+10 mM NH$_4$HCO$_3$), mobile phase B: acetonitrile. Gradient: 35%-65% B) to (R)-4-methyl-N-(1-(5-(2-((methylamino)methyl)phenyl)thiophen-2-yl)ethyl)-7-morpholinopyrido[3,4-b]pyridazin-1-amine (4 mg, 8.43 μmol, 24.2% yield) as a white solid. LCMS [M+1]$^+$: 475.3.

$^1$H NMR (400 MHz, CD$_3$OD) δ=9.04 (s, 1H), 7.43 (br d, J=6.4 Hz, 1H), 7.25-7.36 (m, 4H), 7.08 (d, J=2.8 Hz, 1H), 6.92 (d, J=3.2 Hz, 1H), 5.83 (br d, J=6.8 Hz, 1H), 3.80-3.86 (m, 6H), 3.70-3.77 (m, 4H), 2.69 (s, 3H), 2.28 (s, 3H), 1.79 (d, J=6.8 Hz, 3H).

Following the teachings of the General Reaction Schemes II & IV, and the procedure described for the preparation of Examples 6-1, 6-2, 10-1 & 10-2, the following compounds of Formula (I), Examples 6-3 to 6-19 shown in Table 6 were prepared:

TABLE 6

| Ex. # | Structure | Spectral Data |
|---|---|---|
| 6-3 | 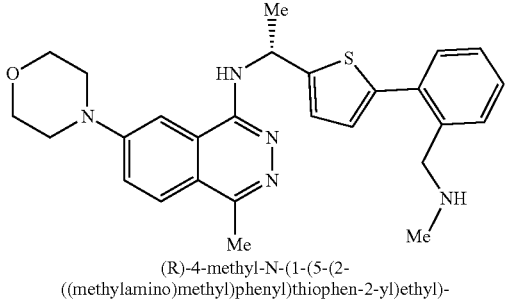<br>(R)-4-methyl-N-(1-(5-(2-((methylamino)methyl)phenyl)thiophen-2-yl)ethyl)-7-morpholinophthalazin-1-amine | 1H NMR (400 MHz, CD$_3$OD) δ = 7.93 (d, J = 9.2 Hz, 1H), 7.58 (dd, J = 2.8, 9.2 Hz, 1H), 7.51 (d, J = 2.0 Hz, 1H), 7.44-7.39 (m, 1H), 7.35-7.24 (m, 3H), 7.08 (dd, J = 0.8, 3.2 Hz, 1H), 6.91 (d, J = 3.6 Hz, 1H), 5.88 (q, J = 7.2 Hz, 1H), 3.90-3.85 (m, 4H), 3.80 (s, 2H), 3.46-3.40 (m, 4H), 2.67 (s, 3H), 2.25 (s, 3H), 1.80 (d, J = 7.2 Hz, 3H). LCMS [M + 1]$^+$: 474.2. |
| 6-4 | 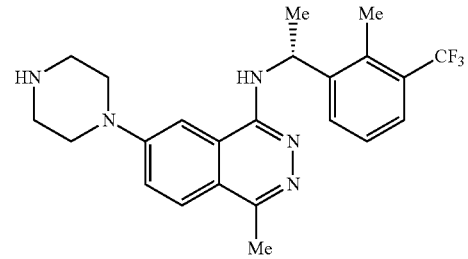 [SMILES: Cc1c([C@@H](C)Nc2nnc(C)c3ccc(N4CCNCC4)cc23)cccc1C(F)(F)F]<br>(R)-4-methyl-N-(1-(2-methyl-3-(trifluoromethyl)phenyl)ethyl)-7-(piperazin-1-yl)phthalazin-1-amine | $^1$H NMR (400 MHz, CD$_3$OD) δ 7.82-7.94 (m, 1H), 7.69 (d, J = 8.0 Hz, 1H), 7.55-7.62 (m, 2H), 7.47 (d, J = 7.6 Hz, 1H), 7.22 (t, J = 7.6 Hz, 1H), 5.70 (q, J = 6.8 Hz, 1H), 3.49-3.42 (m, 4H), 3.05-2.98 (m, 4H), 2.59 (s, 3H), 2.58 (s, 3H), 1.62 (d, J = 7.2 Hz, 3H). LCMS [M + 1]$^+$: 430.3. |
| 6-5 | 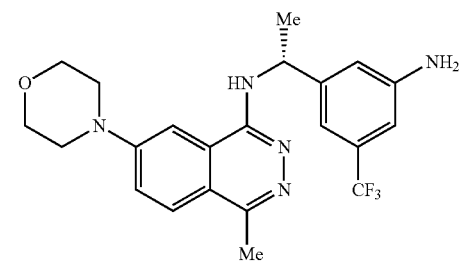 [SMILES: Cc1nnc(N[C@H](C)c2cc(N)cc(C(F)(F)F)c2)c2cc(N3CCOCC3)ccc12]<br>(R)-N-(1-(3-amino-5-(trifluoromethyl)phenyl)ethyl)-4-methyl-7-morpholinophthalazin-1-amine | $^1$H NMR (400 MHz, CD$_3$OD) δ = 8.18 (d, J = 9.2 Hz, 1H), 7.85 (br s, 3H), 7.73 (d, J = 8.4 Hz, 1H), 7.54 (s, 1H), 5.38 (q, J = 6.4 Hz, 1H), 3.91-3.86 (m, 4H), 3.73 (br s, 4H), 2.79 (s, 3H), 1.78 (d, J = 7.2 Hz, 3H). LCMS [M + 1]$^+$: 432.2. |

TABLE 6-continued

| Ex. # | Structure | Spectral Data |
|---|---|---|
| 6-6 | 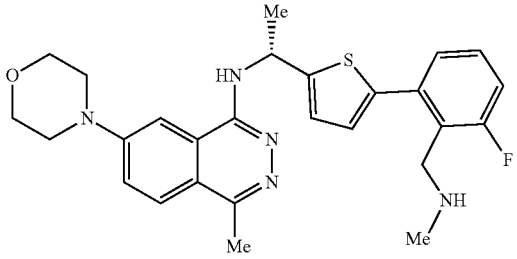 [SMILES: CNCc1c(F)cccc1-c1ccc([C@@H](C)Nc2nnc(C)c3ccc(N4CCOCC4)cc23)s1]<br>(R)-N-(1-(5-(3-fluoro-2-((methylamino)methyl)phenyl)thiophen-2-yl)ethyl)-4-methyl-7-morpholinophthalazin-1-amine | $^1$H NMR (400 MHz, CD$_3$OD) δ = 7.93 (dd, J = 2.0, 9.2 Hz, 1H), 7.61-7.56 (m, 1H), 7.51 (d, J = 2.0 Hz, 1H), 7.32-7.26 (m, 1H), 7.18 (d, J = 7.6 Hz, 1H), 7.12-7.06 (m, 2H), 6.98 (d, J = 3.6 Hz, 1H), 5.89 (q, J = 6.8 Hz, 1H), 3.91-3.85 (m, 4H), 3.80 (s, 2H), 3.47-3.40 (m, 4H), 2.67 (s, 3H), 2.21 (s, 3H), 1.80 (d, J = 6.8 Hz, 3H). LCMS [M + 1]$^+$: 492.0. |
| 6-7 | 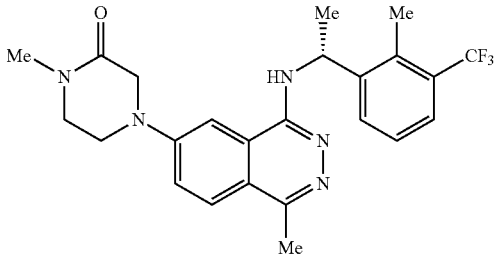 [SMILES: Cc1c([C@@H](C)Nc2nnc(C)c3ccc(N4CCN(C)C(=O)C4)cc23)cccc1C(F)(F)F]<br>(R)-1-methyl-4-(1-methyl-4-((1-(2-methyl-3-(trifluoromethyl)phenyl)ethyl)amino)phthalazin-6-yl)piperazin-2-one | $^1$H NMR (400 MHz, CD$_3$OD) δ 8.40 (d, J = 8.8 Hz, 1H), 7.87-7.97 (m, 3H), 7.73 (d, J = 7.6 Hz, 1H), 7.44-7.52 (m, 1H), 5.74 (q, J = 6.8 Hz, 1H), 4.51 (s, 2H), 4.14-4.25 (m, 2H), 3.87 (t, J = 5.2 Hz, 2H), 3.30 (s, 3H), 2.97 (s, 3H), 2.83 (s, 3H), 1.88 (d, J = 7.2 Hz, 3H); LCMS [M + 1]$^+$: 458.2. |
| 6-8 | 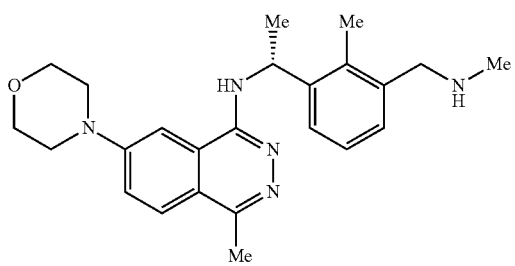 [SMILES: CNCc1cccc([C@@H](C)Nc2nnc(C)c3ccc(N4CCOCC4)cc23)c1C]<br>(R)-4-methyl-N-(1-(2-methyl-3-((methylamino)methyl)phenyl)ethyl)-7-morpholinophthalazin-1-amine | $^1$H NMR (500 MHz, CD$_3$OD) δ = 8.17 (d, J = 9.5 Hz, 1H), 7.69-7.78 (m, 2H), 7.57 (dd, J = 6.5, 1.0 Hz, 1H), 7.28-7.31 (m, 1H), 7.22-7.27 (m, 1H), 5.55 (q, J = 7.0 Hz, 1H), 4.40-4.36 (m, 1H), 4.20-4.28 (m, 1H), 3.86-3.93 (m, 4H), 3.64-3.72 (m, 4H), 2.78 (d, J = 4.5 Hz, 6H), 2.55 (s, 3 H), 1.66 (d, J = 7.0 Hz, 3H). LCMS [M + 1]$^+$ = 406.1 |
| 6-9 | 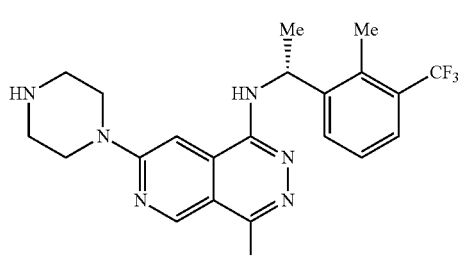<br>(R)-4-methyl-N-(1-(2-methyl-3-(trifluoromethyl)phenyl)ethyl)-7-(piperazin-1-yl)pyrido[3,4-d]pyridazin-1-amine | $^1$H NMR (400 MHz, CD$_3$OD) δ = 9.30 (s, 1H), 7.74 (s, 1H), 7.69 (d, J = 8.0 Hz, 1H), 7.54 (d, J = 8.0 Hz, 1H), 7.28 (t, J = 7.6 Hz, 1H), 5.51 (q, J = 7.2 Hz, 1H), 4.20-4.28 (m, 4H), 3.40-3.46 (m, 4H), 2.81 (s, 3H), 2.61 (s, 3H), 1.66 (d, J = 6.8 Hz, 3H); LCMS [M + 1]$^+$: 431.3. |

TABLE 6-continued

| Ex. # | Structure | Spectral Data |
|---|---|---|
| 6-10 | 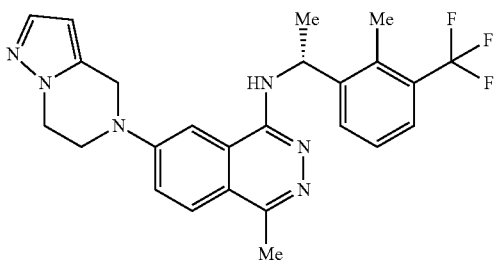 [SMILES: Cc1c([C@@H](C)Nc2nnc(C)c3ccc(N4CCn5nccc5C4)cc23)cccc1C(F)(F)F]<br>(R)-7-(6,7-dihydropyrazolo[1,5-a]pyrazin-5(4H)-yl)-4-methyl-N-(1-(2-methyl-3-(trifluoromethyl)phenyl)ethyl)phthalazin-1-amine | $^1$H NMR (400 MHz, CD$_3$OD) δ 8.22 (d, J = 9.2 Hz, 1H), 7.90-7.81 (m, 2H), 7.70 (d, J = 7.6 Hz, 1H), 7.56-7.50 (m, 2H), 7.32-7.23 (m, 1H), 6.29 (d, J = 2.0 Hz, 1H), 5.54 (q, J = 6.8 Hz, 1H), 5.01 (s, 2H), 4.44-4.37 (m, 2H), 4.31-4.24 (m, 2H), 2.77 (s, 3H), 2.63 (s, 3H), 1.68 (d, J = 7.2 Hz, 3H). LCMS [M + 1]$^+$: 467.2. |
| 6-11 | 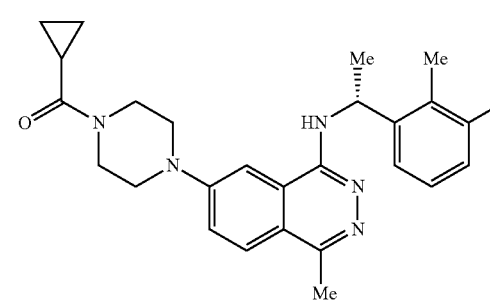<br>(R)-cyclopropyl(4-(1-methyl-4-((1-(2-methyl-3-(trifluoromethyl)phenyl)ethyl)amino)phthalazin-6-yl)piperazin-1-yl)methanone | $^1$H NMR (400 MHz, CD$_3$OD) δ 8.17 (d, J = 9.2 Hz, 1H), 7.78-7.65 (m, 3H), 7.52 (d, J = 7.6 Hz, 1H), 7.31-7.22 (m, 1H), 5.52 (q, J = 6.8 Hz, 1H), 4.05 (br s, 2H), 3.90-3.76 (m, 6H), 2.75 (s, 3H), 2.62 (s, 3H), 2.08-1.97 (m, 1H), 1.66 (d, J = 6.8 Hz, 3H), 0.97-0.84 (m, 4H). LCMS [M + 1]$^+$: 498.2. |
| 6-12 | 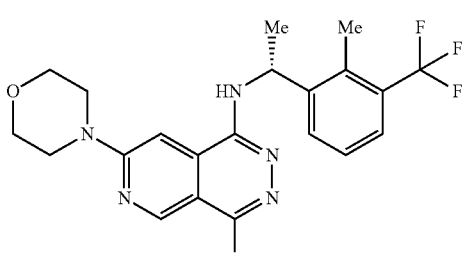<br>(R)-4-methyl-N-(1-(2-methyl-3-(trifluoromethyl)phenyl)ethyl)-7-morpholinopyrido[3,4-d]pyridazin-1-amine | $^1$H NMR (400 MHz, CD$_3$OD) δ = 9.00 (s, 1H), 7.67 (br d, J = 7.6 Hz, 1H), 7.48 (br d, J = 7.2 Hz, 1H), 7.33 (s, 1H), 7.23 (br t, J = 8.0 Hz, 1H), 5.67 (q, J = 6.8 Hz, 1H), 3.89-3.81 (m, 4H), 3.80-3.71 (m, 4H), 2.63-2.58 (m, 6H), 1.61 (d, J = 6.8 Hz, 3H). LCMS [M + 1]$^+$: 432.2. |
| 6-13 | 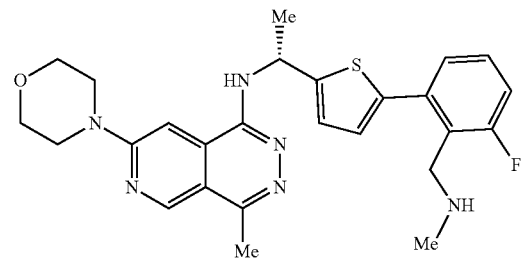<br>(R)-N-(1-(5-(3-fluoro-2-((methylamino)methyl)phenyl)thiophen-2-yl)ethyl)-4-methyl-7-morpholinopyrido[3,4-d]pyridazin-1-amine | $^1$H NMR (400 MHz, CD$_3$OD) δ = 9.03 (d, J = 0.4 Hz, 1H), 7.33-7.26 (m, 1H), 7.25 (s, 1H), 7.19-7.16 (m, 1H), 7.13-7.06 (m, 2H), 6.99 (d, J = 3.6 Hz, 1H), 5.85 (q, J = 6.8 Hz, 1H), 3.84-3.79 (m, 6H), 3.76-3.72 (m, 4H), 2.69 (s, 3H), 2.23 (s, 3H), 1.79 (d, J = 7.2 Hz, 3H). LCMS [M + 1]$^+$: 493.2. |

TABLE 6-continued

| Ex. # | Structure | Spectral Data |
|---|---|---|
| 6-14 | 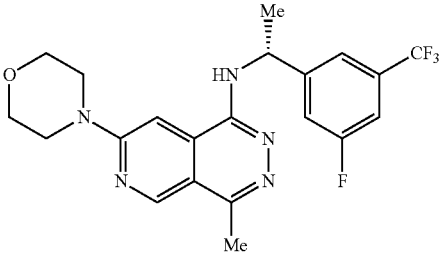<br>(R)-N-(1-(3-fluoro-5-(trifluoromethyl)phenyl)ethyl)-4-methyl-7-morpholinopyrido[3,4-d]pyridazin-1-amine | $^1$H NMR (400 MHz, DMSO-d$_6$) δ = 9.03 (s, 1H), 7.63 (s, 1H), 7.59-7.48 (m, 3H), 7.39 (s, 1H), 5.48 (t, J = 6.8 Hz, 1H), 3.86-3.76 (m, 4H), 3.75-3.66 (m, 4H), 2.58 (s, 3H), 1.61 (d, J = 6.8 Hz, 3H). LCMS [M + 1]$^+$: 436.3. |
| 6-15 | 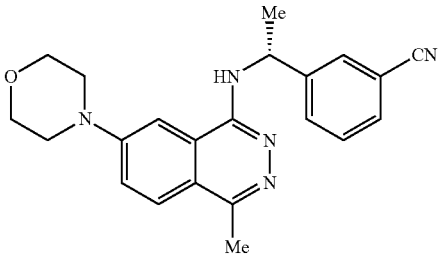 [SMILES: Cc1nnc(N[C@H](C)c2cccc(C#N)c2)c2cc(N3CCOCC3)ccc12]<br>(R)-3-(1-((4-methyl-7-morpholinophthalazin-1-yl)amino)ethyl)benzonitrile | $^1$H NMR (400 MHz, CD$_3$OD) δ = 8.20-8.14 (m, 1H), 7.84-7.77 (m, 1H), 7.82-7.69 (m, 3H), 7.60 (br d, J = 7.6 Hz, 1H), 7.54-7.47 (m, 1H), 5.29 (q, J = 7.2 Hz, 1H), 3.92-3.88 (m, 4H), 3.73-3.65 (m, 4H), 2.78 (s, 3H), 1.72 (d, J = 7.2 Hz, 3H). LCMS [M + 1]$^+$: 374.2. |
| 6-16 | 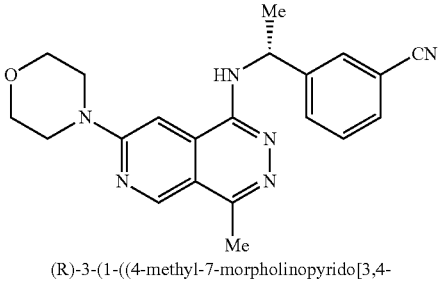<br>(R)-3-(1-((4-methyl-7-morpholinopyrido[3,4-d]pyridazin-1-yl)amino)ethyl)benzonitrile | $^1$H NMR (400 MHz, MeOD-d$_4$) δ = 9.25 (s, 1H), 7.84-7.73 (m, 2H), 7.61 (d, J = 7.6 Hz, 1H), 7.55-7.46 (m, 2H), 5.26 (q, J = 6.8 Hz, 1H), 4.00-3.94 (m, 1H), 4.04-3.93 (m, 3H), 3.88-3.83 (m, 2H), 3.88-3.81 (m, 1H), 3.88-3.80 (m, 1H), 2.80 (s, 3H), 1.71 (d, J = 7.2 Hz, 3H). LCMS [M + 1]$^+$: 375.1. |
| 6-17 | 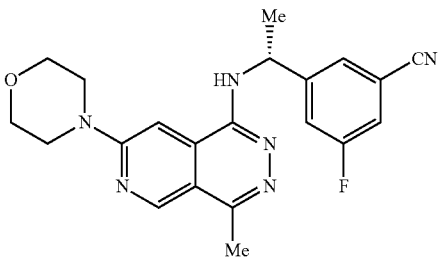 [SMILES: Cc1nnc(N[C@H](C)c2cc(F)cc(C#N)c2)c2cc(N3CCOCC3)ncc12]<br>(R)-3-fluoro-5-(1-((4-methyl-7-morpholinopyrido[3,4-d]pyridazin-1-yl)amino)ethyl)benzonitrile | $^1$H NMR (400 MHz, CD$_3$OD) δ = 9.01 (d, J = 0.8 Hz, 1H), 7.63 (t, J = 1.2 Hz, 1H), 7.51 (dt, J = 9.6, 2.0 Hz, 1H), 7.32-7.37 (m, 1H), 7.29 (d, J = 0.4 Hz, 1H), 5.39 (q, J = 7.2 Hz, 1H), 3.81-3.86 (m, 4H), 3.74-3.79 (m, 4H), 2.64 (s, 3H), 1.66 (d, J = 7.2 Hz, 3H). LCMS [M + 1]$^+$: 393.2. |
| 6-18 | 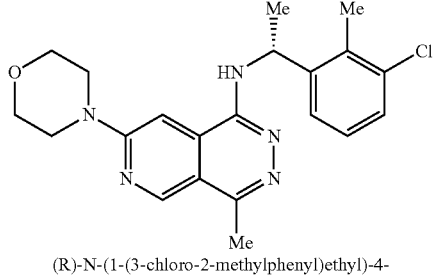<br>(R)-N-(1-(3-chloro-2-methylphenyl)ethyl)-4-methyl-7-morpholinopyrido[3,4-d]pyridazin-1-amine | $^1$H NMR (400 MHz, CD$_3$OD) δ = 9.23 (s, 1H), 7.53 (s, 1H), 7.35 (d, J = 8.0 Hz, 1H), 7.25 (d, J = 7.6 Hz, 1H), 7.13-7.06 (m, 1H), 5.43 (q, J = 6.8 Hz, 1H), 3.99-3.93 (m, 4H), 3.89-3.80 (m, 4H), 2.78 (s, 3H), 2.54 (s, 3H), 1.64 (d, J = 6.8 Hz, 3H). LCMS [M + 1]$^+$: 398.2. |

TABLE 6-continued
| Ex. # | Structure | Spectral Data |
|---|---|---|
| 6-19 | 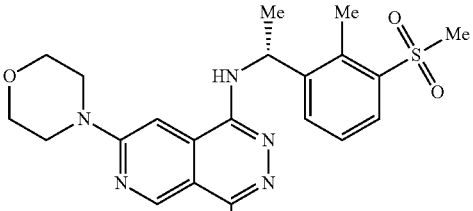
(R)-4-methyl-N-(1-(2-methyl-3-(methylsulfonyl)phenyl)ethyl)-7-morpholinopyrido[3,4-d]pyridazin-1-amine | $^1$H NMR (400 MHz, DMSO-$d_6$) δ = 9.01 (s, 1H), 7.79 (dd, J = 12.4, 8.0 Hz, 2H), 7.55 (d, J = 6.8 Hz, 1H), 7.45-7.36 (m, 2H), 5.71-5.61 (m, 1H), 3.82-3.77 (m, 4H), 3.76-3.67 (m, 4H), 3.26 (s, 3H), 2.80 (s, 3H), 2.57 (s, 3H), 1.56 (d, J = 6.8 Hz, 3H). LCMS [M + 1]$^+$: 442.1. |
Example 7-1
4-methyl-N—((R)-1-(5-(2-((methylamino)methyl(phenyl)thiophen-2-yl)ethyl)-7-(((S)-tetrahydrofuran-3-yl)oxy)phthalazin-1-amine
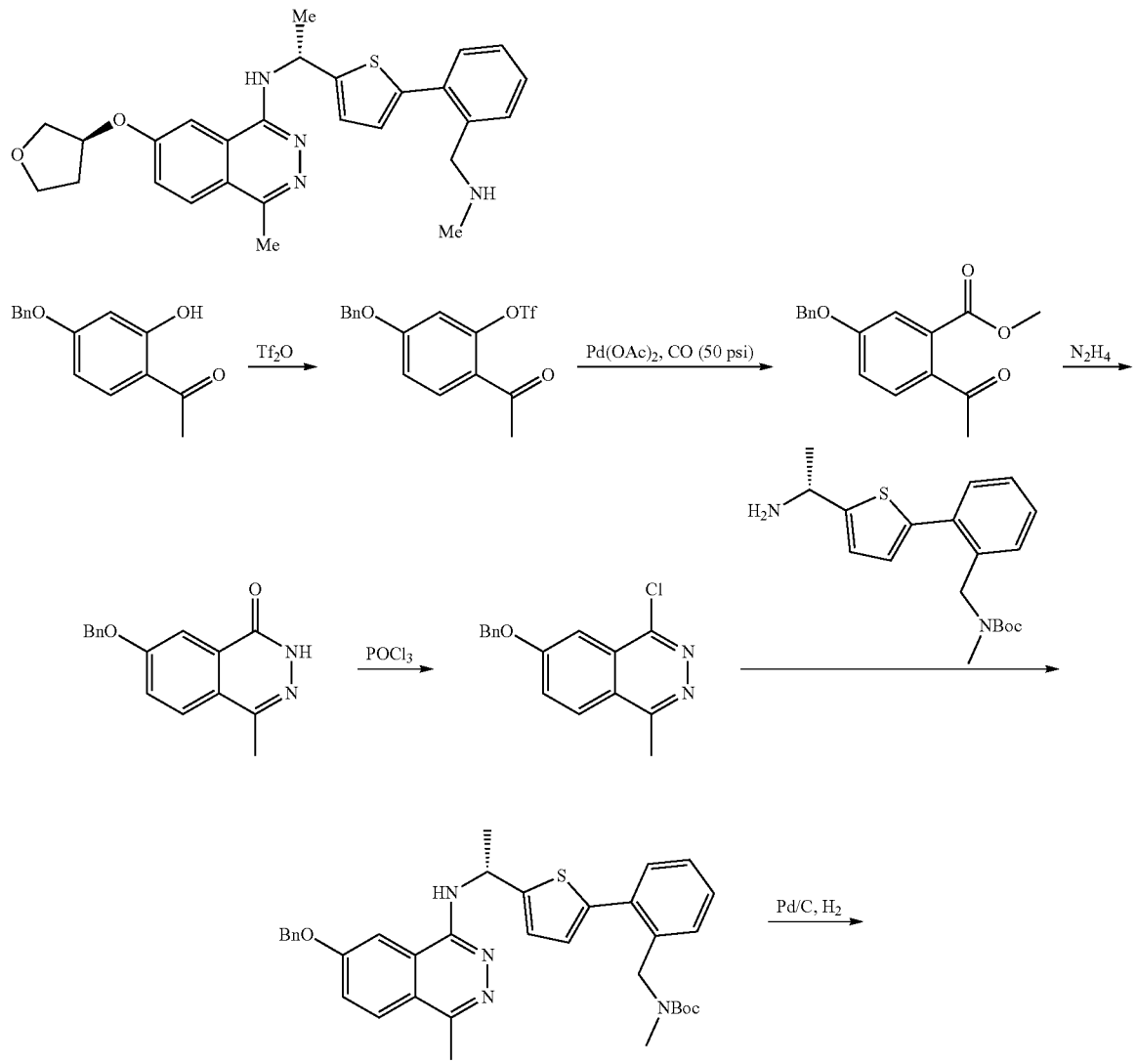

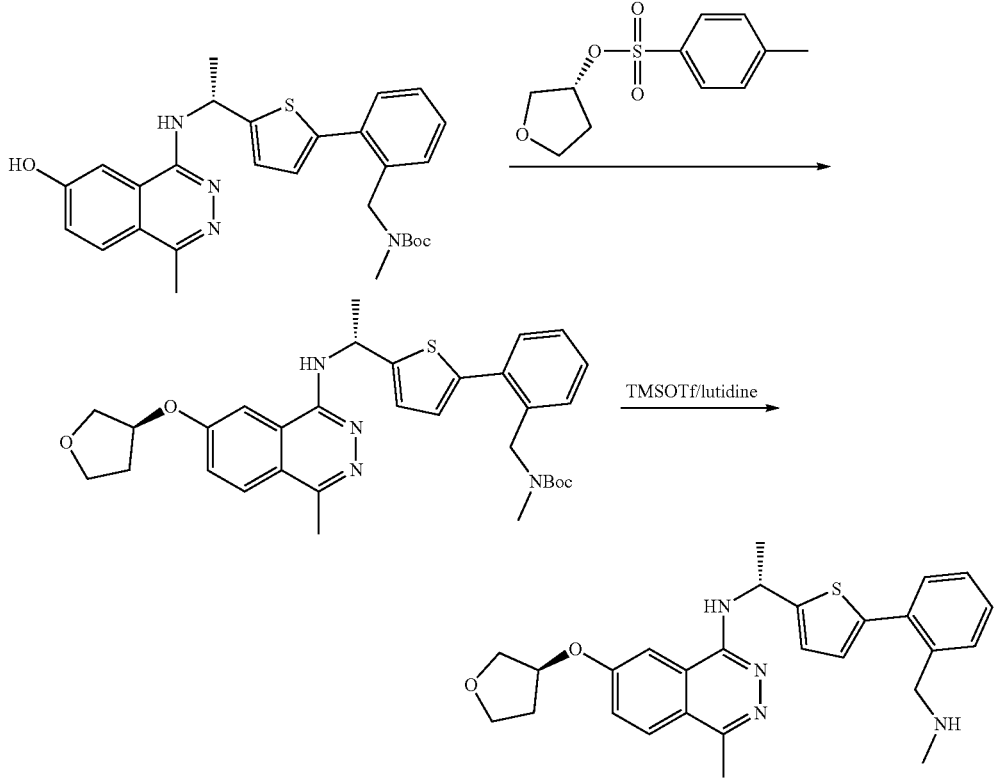

Step A: To a mixture of 1-(4-(benzyloxy)-2-hydroxyphenyl)ethan-1-one (5.00 g, 20.6 mmol, 1.00 eq.) and pyridine (4.90 g, 61.9 mmol, 5.00 mL, 3.00 eq.) in DCM (100 mL) was added trifluoromethylsulfonyl trifluoromethanesulfonate (11.7 g, 41.3 mmol, 6.81 mL, 2.00 eg) dropwise slowly at 0° C. under a nitrogen atmosphere. Then the reaction mixture was stirred at 20° C. for 16 hours. The reaction mixture was poured into water (100 mL) and stirred for 5 minutes. The aqueous phase was extracted with DCM (50.0 mL×3). The combined organic phases were washed with brine (50.0 mL), dried over anhydrous sodium sulfate, filtered, and concentrated under vacuum to give a residue. The residue was purified by silica gel chromatography (SiO$_2$, petroleum ether/ethyl acetate=10/1 to 3/1) to give 2-acetyl-5-(benzyloxy)phenyl trifluoromethanesulfonate (7.40 g, 17.8 mmol, 86.2% yield, 90% purity) as a yellow solid. LCMS [M+1]$^+$: 374.8.

$^1$H NMR (400 MHz, CDCl$_3$) δ=7.85 (d, J=8.8 Hz, 1H), 7.44-7.36 (m, 5H), 7.03 (dd, J=2.4, 8.8 Hz, 1H), 6.90 (d, J=2.4 Hz, 1H), 5.14 (s, 2H), 2.60 (s, 3H).

Step B: To a mixture of 2-acetyl-5-(benzyloxy)phenyl trifluoromethanesulfonate (13.0 g, 34.7 mmol, 1.00 eq.) and 1,1-bis(diphenylphosphino)ferrocene (1.93 g, 3.47 mmol, 0.10 eq.) in DMF (100 mL) and methanol (10.0 mL) was added triethylamine (17.6 g, 174 mmol, 24.2 mL, 5.00 eq.) and palladium (II) acetate (780 mg, 3.47 mmol, 0.10 eq.) in one portion at 20° C. under a nitrogen atmosphere. The reaction mixture was heated to 80° C. stirred for 16 hours under an atmosphere of carbon monoxide (50 Psi). The mixture was then cooled to 15° C. and concentrated under reduced pressure at 40° C. to give a residue. The residue was poured into water (100 mL) and stirred for 5 minutes. The aqueous phase was extracted with ethyl acetate (50.0 mL×3). The combined organic phases were washed with brine (50.0 mL), dried over anhydrous sodium sulfate, filtered, and concentrated under reduced pressure to give a residue. The residue was purified by silica gel chromatography (SiO$_2$, petroleum ether/ethyl acetate=5/1 to 4/1) to afford methyl 2-acetyl-5-(benzyloxy)benzoate (5.60 g, 16.9 mmol, 48.8% yield, 86% purity) as a yellow solid. LCMS [M+1]$^+$: 285.0.

$^1$H NMR (400 MHz, CDCl$_3$) δ=7.58 (d, J=8.8 Hz, 1H), 7.44-7.35 (m, 5H), 7.26 (d, J=2.8 Hz, 1H), 7.08 (dd, J=2.4, 8.4 Hz, 1H), 5.14 (s, 2H), 3.91 (s, 3H), 2.53 (s, 3H).

Step C: To a solution of methyl 2-acetyl-5-(benzyloxy)benzoate (4.60 g, 16.2 mmol, 1.00 eq) in ethanol (50.0 mL) was added hydrazine hydrate (2.48 g, 48.5 mmol, 2.41 mL, 98% purity, 3.00 eq) dropwise slowly at 25° C., then the reaction mixture was stirred at 95° C. for 30 minutes. The reaction mixture was cooled to 15° C. and poured into ice-water (w/w=1/1) (100 mL) and stirred for 5 minutes to give a suspension. The resulting suspension was filtered, and the filter cake was collected and dried under reduced pressure to afford 7-(benzyloxy)-4-methylphthalazin-1(2H)-one (4.00 g, crude) as a yellow solid. LCMS [M+1]$^+$: 267.0.

Step D: 7-(benzyloxy)-4-methylphthalazin-1(2H)-one (860 mg, 3.23 mmol, 1.00 eq) was added to phosphorus oxychloride (14.2 g, 92.6 mmol, 8.60 mL, 28.7 eq) in portions at 25° C., then the reaction mixture was stirred at 120° C. for 3 hours. The mixture was cooled to 25° C. and concentrated under reduced pressure to give a residue. The residue was poured into ice-water (50.0 mL) slowly and adjusted to pH=8 with saturated sodium bicarbonate aqueous solution (50.0 mL) and stirred for 5 minutes. The aqueous phase was extracted with ethyl acetate (50.0 mL×3). The combined organic phases were washed with brine (50.0 mL), dried over anhydrous sodium sulfate, filtered, and concentrated under reduced pressure to give 6 6-(benzyloxy)-4-chloro-1-methylphthalazine (740 mg, crude) as a white solid. LCMS [M+1]$^+$: 284.9.

Step E: To a solution of 6-(benzyloxy)-4-chloro-1-methylphthalazine (120 mg, 421 µmol, 1.00 eq.) and tert-butyl (R)-(2-(5-(1-aminoethyl)thiophen-2-yl)benzyl)(methyl)carbamate (102 mg, 295 µmol, 0.70 eq.) in dimethyl sulfoxide (1.00 mL) was added cesium fluoride (192 mg, 1.26 mmol, 46.6 µL, 3.00 eq.). Then the mixture was stirred at 130° C. for 16 hours and the mixture diluted with ethyl acetate (30.0 mL). The combined organic fractions were washed with brine (3×8 mL), dried over sodium sulfate, filtered, and the solvent was evaporated under reduced pressure to give a residue. The residue was purified by silica gel column flash chromatography 12 g, eluting with petroleum ether/ethyl acetate=0-100% to give tert-butyl (R)-(2-(5-(1-((7-(benzyloxy)-4-methylphthalazin-1-yl)amino)ethyl)thiophen-2-yl) benzyl)(methyl)carbamate (60.0 mg, 44.2 µmol, 10.5% yield, 43.8% purity) as a brown solid. LCMS [M+1]+: 595.3.

Step F: To a solution of tert-butyl (R)-(2-(5-(1-((7-(benzyloxy)-4-methylphthalazin-1-yl)amino)ethyl)thiophen-2-yl)benzyl)(methyl)carbamate (60.0 mg, 100 µmol, 1.00 eq.) in methanol (3.00 mL) was added Pd/C (10.7 mg, 10.1 µmol, 10% purity, 0.10 eq.). Then the mixture was stirred at 30° C. for 3 hours. The mixture was then filtered and the filter cake was washed with methanol (5.00 mL) and dichloromethane (10.0 ml). The filtrate was concentrated to under reduced pressure. The crude product was purified by reversed-phase HPLC (column: Phenomenex Synergi C18 150×30 mm×4 um; mobile phase: phase A: [water (0.1% TFA)], phase B: acetonitrile; B %: 42%-62%) to give tert-butyl (R)-(2-(5-(1-((7-hydroxy-4-methylphthalazin-1-yl)amino)ethyl)thiophen-2-yl)benzyl)(methyl)carbamate (15.0 mg, 29.7 µmol, 29.5% yield) as a white solid. LCMS [M+1]$^+$: 505.3.

Step G: To a solution of tert-butyl (R)-(2-(5-(1-((7-hydroxy-4-methylphthalazin-1-yl)amino)ethyl)thiophen-2-yl)benzyl)(methyl)carbamate (13.0 mg, 25.8 µmol, 1.00 eq.) and (R)-tetrahydrofuran-3-yl 4-methylbenzenesulfonate (9.16 mg, 30.9 µmol, 1.20 eq.) in DMF (0.10 mL) was added cesium fluoride (15.0 mg, 98.8 µmol, 3.64 µL, 3.83 eq.). The mixture was stirred at 90° C. for 2 hours then poured into water (5.00 mL) and filtered. The filtrate was extracted with ethyl acetate (10 mL×2) and the combined organic layers were washed with brine (10.0 mL), dried over anhydrous sodium sulfate and concentrated under vacuum to give a residue tert-butyl methyl(2-(5-((R)-1-((4-methyl-7-(((S)-tetrahydrofuran-3-yl)oxy)phthalazin-1-yl)amino)ethyl)thiophen-2-yl)benzyl)carbamate (14.8 mg, 25.8 µmol, 100% yield) was obtained as a yellow oil which was used without further purification. LCMS [M+1]$^+$: 575.3.

Step H: To a solution of tert-butyl methyl (2-(5-((R)-1-((4-methyl-7-(((S)-tetrahydrofuran-3-yl)oxy)phthalazin-1-yl)amino)ethyl)thiophen-2-yl)benzyl)carbamate (10.0 mg, 17.4 µmol, 1.00 eq.) in dichloromethane (0.50 mL) was added 2,6-lutidine (18.6 mg, 173 µmol, 20.3 µL, 10.0 eq.) followed by TMSOTf (19.3 mg, 87.0 µmol, 15.7 µL, 5.00 eq.) was added to the mixture. The mixture was stirred at 20° C. for 1 hour, then the solvent was evaporated under a nitrogen atmosphere. The crude product was purified by reversed-phase HPLC (column: Agela DuraShell C18 150× 25 mm×5 um; mobile phase: phase A: [water (0.05% $NH_3H_2O$+10 mM $NH_4HCO_3$)], phase B: acetonitrile; B %: 36%-66%) to give 4-methyl-N-((R)-1-(5-(2-((methylamino)methyl)phenyl)thiophen-2-yl)ethyl)-7-(((S)-tetrahydrofuran-3-yl)oxy)phthalazin-1-amine (2.20 mg, 4.64 µmol, 26.6% yield) as a white solid. LCMS [M+1]$^+$: 475.2.

$^1$H NMR (400 MHz, $CD_3OD$) δ=8.02 (d, J=8.8 Hz, 1H), 7.70 (d, J=2.4 Hz, 1H), 7.39-7.52 (m, 2H), 7.25-7.38 (m, 3H), 7.09 (d, J=2.8 Hz, 1H), 6.92 (d, J=3.2 Hz, 1H), 5.90 (q, J=6.8 Hz, 1H), 5.30 (br s, 1H), 3.88-4.09 (m, 4H), 3.81 (s, 2H), 2.72 (s, 3H), 2.29-2.44 (m, 1H), 2.26 (s, 3H), 2.18 (br dd, J=5.6, 12.0 Hz, 1H), 1.81 (d, J=7.2 Hz, 3H).

Following the teachings of the General Reaction Scheme VI, and the procedure described for the preparation of Example 7-1, the following compounds of Formula (I), Examples 7-2 to 7-7 shown in Table 7 were prepared.

TABLE 7

| Ex. # | Structure | Spectral Data |
|---|---|---|
| 7-2 | 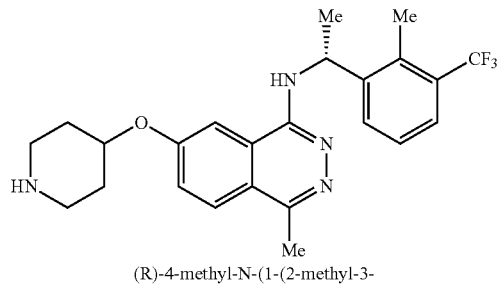<br>(R)-4-methyl-N-(1-(2-methyl-3-(trifluoromethyl)phenyl)ethyl)-7-(piperidin-4-yloxy)phthalazin-1-amine | $^1$H NMR (400 MHz, $CD_3OD$) δ = 8.35 (d, J = 9.2 Hz, 1H), 8.18 (br d, J = 2.0 Hz, 1H), 7.79 (dd, J = 2.4, 9.2 Hz, 1H), 7.70 (br d, J = 8.4 Hz, 1H), 7.54 (br d, J = 7.6 Hz, 1H), 7.28 (br t, J = 8.4 Hz, 1H), 5.57 (q, J = 7.2 Hz, 1H), 5.17 (br s, 1H), 3.47 (br d, J = 9.2 Hz, 2H), 2.83 (s, 3H), 2.64 (s, 3H), 2.33 (br s, 2H), 2.22 (br s, 2H), 1.68 (d, J = 7.2 Hz, 3H). LCMS [M + 1]$^+$: 445.2. |

TABLE 7-continued

| Ex. # | Structure | Spectral Data |
|---|---|---|
| 7-3 | 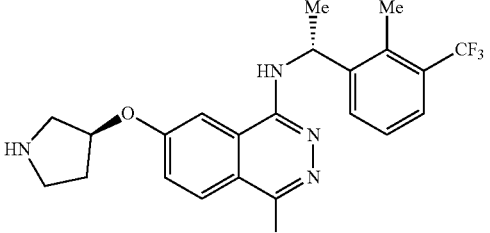<br>4-methyl-N-((R)-1-(2-methyl-3-(trifluoromethyl)phenyl)ethyl)-7-(((S)-pyrrolidin-3-yl)oxy)phthalazin-1-amine | $^1$H NMR (400 MHz, CD$_3$OD) δ = 8.44-8.22 (m, 2H), 7.85-7.68 (m, 2H), 7.53 (br d, J = 7.6 Hz, 1H), 7.28 (br t, J = 7.6 Hz, 1H), 5.73 (br s, 1H), 5.57 (q, J = 7.2 Hz, 1H), 3.81-3.67 (m, 2H), 3.65-3.51 (m, 2H), 2.85 (s, 3H), 2.65 (s, 2H), 2.62-2.41 (m, 2H), 1.73 (d, J = 6.8 Hz, 3H). LCMS [M + 1]$^+$: 431.3. |
| 7-4 | 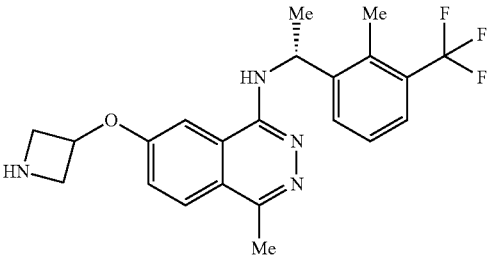 [SMILES: Cc1c([C@@H](C)Nc2nnc(C)c3ccc(OC4CNC4)cc23)cccc1C(F)(F)F]<br>(R)-7-(azetidin-3-yloxy)-4-methyl-N-(1-(2-methyl-3-(trifluoromethyl)phenyl)ethyl)phthalazin-1-amine | $^1$H NMR (500 MHz, CD$_3$OD) δ 8.38 (d, J = 9.0 Hz, 1H), 8.19 (s, 1H), 7.83 (d, J = 7.8 Hz, 1H), 7.76 (dd, J = 9.0, 2.4 Hz, 1H), 7.52 (d, J = 7.9 Hz, 1H), 7.27 (t, J = 8.0 Hz, 1H), 5.71-5.65 (m, 1H), 5.56 (q, J = 7.0 Hz, 1H), 4.85-4.77 (m, 2H), 4.34-4.26 (m, 2H), 2.84 (s, 3H), 2.63 (s, 3H), 1.73 (d, J = 7.0 Hz, 3H). LCMS [M + 1]$^+$: 417.2. |
| 7-5 | 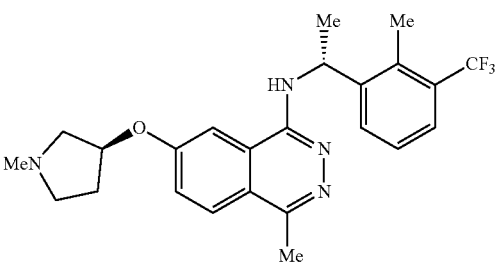 [SMILES: Cc1c([C@@H](C)Nc2nnc(C)c3ccc(O[C@H]4CCN(C)C4)cc23)cccc1C(F)(F)F]<br>4-methyl-N-((R)-1-(2-methyl-3-(trifluoromethyl)phenyl)ethyl)-7-(((S)-1-methylpyrrolidin-3-yl)oxy)phthalazin-1-amine | $^1$H NMR (400 MHz, CD$_3$OD) δ = 8.40 (br d, J = 8.8 Hz, 1H), 8.30 (br s, 1H), 7.85-7.74 (m, 2H), 7.56 (br d, J = 8.0 Hz, 1H), 7.30 (br t, J = 8.0 Hz, 1H), 5.79-5.67 (m, 1H), 5.59 (q, J = 6.8 Hz, 1H), 4.36-3.89 (m, 2H), 3.72-3.45 (m, 2H), 3.17-3.06 (m, 3H), 3.01-2.91 (m, 1H), 2.87 (s, 3H), 2.70-2.61 (m, 3H), 2.61-2.37 (m, 1H), 1.74 (br d, J = 6.8 Hz, 3H). LCMS [M + 1]$^+$: 445.2. |
| 7-6 | 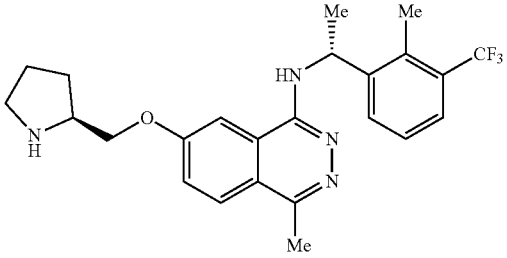 [SMILES: Cc1c([C@@H](C)Nc2nnc(C)c3ccc(OC[C@@H]4CCCN4)cc23)cccc1C(F)(F)F]<br>4-methyl-N-((R)-1-(2-methyl-3-(trifluoromethyl)phenyl)ethyl)-7-(((S)-pyrrolidin-2-yl)methoxy)phthalazin-1-amine | $^1$H NMR (400 MHz, CD$_3$OD) δ = 7.97 (d, J = 9.2 Hz, 1H), 7.80 (d, J = 2.4 Hz, 1H), 7.71 (d, J = 8.0 Hz, 1H), 7.52-7.46 (m, 2H), 7.23 (t, J = 7.6 Hz, 1H), 5.73 (q, J = 6.8 Hz, 1H), 4.28-4.22 (m, 1H), 4.13 (dd, J = 7.2, 9.2 Hz, 1H), 3.67-3.59 (m, 1H), 3.08-2.96 (m, 2H), 2.64 (s, 3H), 2.62 (s, 3H), 2.13-2.05 (m, 1H), 1.96-1.84 (m, 2H), 1.73-1.66 (m, 1H), 1.63 (d, J = 7.2 Hz, 3H). LCMS [M + 1]$^+$: 445.2. |

TABLE 7-continued

| Ex. # | Structure | Spectral Data |
|---|---|---|
| 7-7 | 4-methyl-N-((R)-1-(2-methyl-3-(trifluoromethyl)phenyl)ethyl)-7-(((R)-pyrrolidin-2-yl)methoxy)phthalazin-1-amine hydrochloride salt | $^1$H NMR (400 MHz, CD$_3$OD) δ = 8.40-8.38 (m, 2H), 7.91-7.78 (m, 2H), 7.55 (br d, J = 7.6 Hz, 1H), 7.30 (br t, J = 7.6 Hz, 1H), 5.60 (q, J = 7.2 Hz, 1H), 4.76 (dd, J = 3.2, 10.8 Hz, 1H), 4.70-4.59 (m, 1H), 4.23 (dq, J = 3.2, 8.0 Hz, 1H), 3.55-3.41 (m, 2H), 2.88 (s, 3H), 2.66 (s, 3H), 2.41 (dtd, J = 4.8, 7.6, 12.8 Hz, 1H), 2.33-2.11 (m, 2H), 2.11-2.00 (m, 1H), 1.75 (d, J = 6.8 Hz, 3H). LCMS [M + 1]$^+$: 445.2. |

Following the teachings of the General Reaction Scheme IV, and the procedure described for the preparation of Example 8-3 (below), the following compounds of Formula (I), Example 8-1 may be prepared and Example 8-2 shown in Table 8 was prepared:

Example 8-1

(R)-4,7-di methyl-N-(1-(5-(2-((methylamino)methyl)phenyl)thiophen-2-yl)ethyl)phthalazin-1-amine

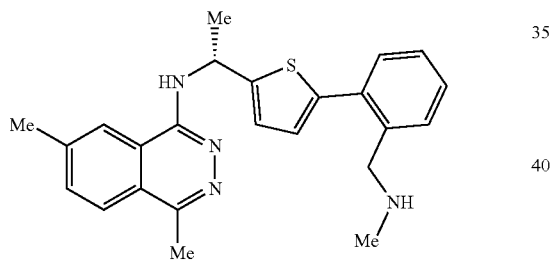

TABLE 8

| Ex. # | Structure | Spectral Data |
|---|---|---|
| 8-2 | (R)-7-ethyl-4-methyl-N-(1-(5-(2-((methylamino)methyl)phenyl)thiophen-2-yl)ethyl)phthalazin-1-amine | $^1$H NMR (400 MHz, CD$_3$OD) δ 8.17 (s, 1H), 8.00 (d, J = 8.4 Hz, 1H), 7.80 (d, J = 8.4 Hz, 1H), 7.42 (d, J = 7.4 Hz, 1H), 7.37-7.25 (m, 3H), 7.09 (d, J = 3.5 Hz, 1H), 6.92 (d, J = 3.6 Hz, 1H), 5.90 (q, J = 7.0 Hz, 1H), 3.80 (s, 2H), 2.92 (q, J = 7.6 Hz, 2H), 2.25 (s, 3H), 1.81 (d, J = 6.9 Hz, 3H), 1.37 (t, J = 7.6 Hz, 3H). LCMS [M + 1]$^+$: 417.2 |

Example 8-3

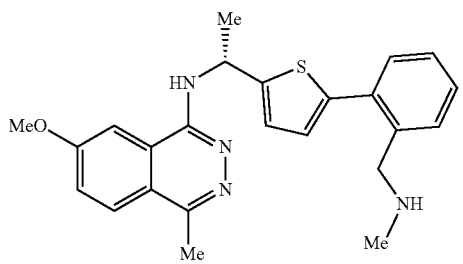 [SMILES: CNCc1ccccc1-c1ccc([C@@H](C)Nc2nnc(C)c3ccc(OC)cc23)s1]

(R)-7-methoxy-4-methyl-N-(1-(5-(2-((methylamino)methyl)phenyl)thiophen-2-yl)ethyl)phthalazin-1-amine

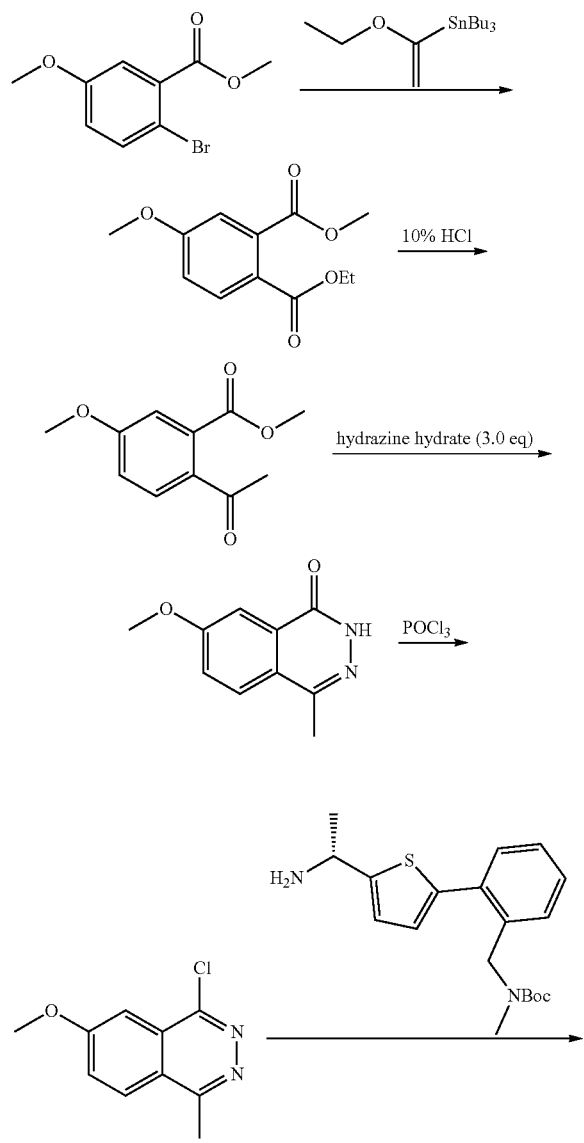

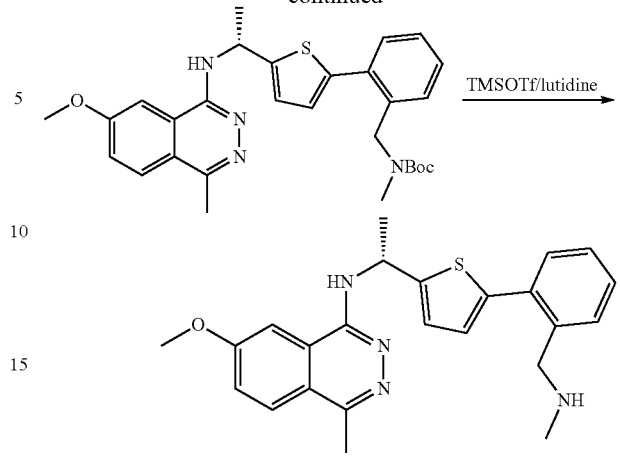

Step A: To a solution of methyl 2-bromo-5-methoxybenzoate (3.00 g, 12.2 mmol, 1.00 eq.) and tributyl(1-ethoxyvinyl)stannane (4.64 g, 12.9 mmol, 4.34 mL, 1.05 eq) in dioxane (30.0 mL) was added Pd(PPh$_3$)$_2$Cl$_2$ (258 mg, 367 µmol, 0.03 eq.). Then the mixture was stirred at 80° C. for 18 hours under a nitrogen atmosphere. The reaction mixture was then poured into water (30.0 mL) and extracted with ethyl acetate (30.0 mL×2). The organic layer was washed with brine (30.0 mL), dried over anhydrous sodium sulfate and concentrated under vacuum. The mixture was used directly without further purification to give methyl 2-(1-ethoxyvinyl)-5-methoxybenzoate (2.80 g, 11.9 mmol, 96.8% yield, assume 100% purity) as a brown oil. LCMS [M+1]$^+$: 237.1.

Step B: A mixture of methyl 2-(1-ethoxyvinyl)-5-methoxybenzoate (2.50 g, 10.6 mmol, 1.00 eq.) and 10% aqueous hydrogen chloride (386 mg, 10.6 mmol, 378 µL, 1.00 eq.) in THF (20.0 mL) was stirred at 20° C. for 1 hour. The reaction mixture was then poured into water (20.0 mL) and extracted with ethyl acetate (25.0 mL×3). The organic layer was washed with brine (50.0 mL), dried over anhydrous sodium sulfate and concentrated under vacuum to give a residue. The residue was purified by flash silica gel chromatography (0-20% ethyl acetate/petroleum ether) to give methyl 2-acetyl-5-methoxybenzoate (1.40 g, 5.72 mmol, 54.1% yield, 85.1% purity) as a yellow oil. LCMS [M+1]$^+$: 209.0.

$^1$H NMR (400 MHz, CD$_3$OD) δ=2.51 (s, 3H) 3.86 (d, J=10.0 Hz, 6H) 7.06-7.15 (m, 2H) 7.70-7.79 (m, 1H).

Step C: To a solution of methyl 2-acetyl-5-methoxybenzoate (1.30 g, 6.24 mmol, 1.00 eq.) in ethanol (15.0 mL) was added hydrazine hydrate (938 mg, 18.7 mmol, 910 µL, 98% purity, 3.00 eq.). Then the mixture was stirred at 80° C. for 1 hour under a nitrogen atmosphere. The reaction mixture was then poured into water (20.0 mL) and extracted with ethyl acetate (30.0 mL×2). The organic layer was washed with brine (30.0 mL), dried over anhydrous sodium sulfate, and concentrated under vacuum to give a residue. The crude product was used into the next step without purification to give 7-methoxy-4-methylphthalazin-1 (2H)-one (1.10 g, 5.74 mmol, 91.9% yield, 99.3% purity) as a white solid. LCMS [M+1]$^+$: 191.0.

Step D: A mixture of 7-methoxy-4-methylphthalazin-1 (2H)-one (0.90 g, 4.73 mmol, 1.00 eq.) and phosphorus oxychloride (15.2 g, 99.4 mmol, 9.23 mL, 21.0 eq.) was stirred at 115° C. for 18 hours. The mixture was then poured into water (25.0 mL). The saturated sodium carbonate solution was added until pH=9. The mixture was extracted with ethyl acetate (2×25.0 mL). The combined organic phases were washed with brine (saturated, 20.0 mL), dried over sodium sulfate, filtered, and the solvent was evaporated under reduced pressure. The residue was purified by column chromatography by prep-TLC (SiO$_2$, dichloromethane:methyl alcohol=10:1) to give 4-chloro-6-methoxy-1-methylphthalazine (240 mg, 1.14 mmol, 24.0% yield, 98.8% purity) as a white solid. LCMS [M+1]$^+$: 209.0.

Step E: A mixture of tert-butyl (R)-(2-(5-(1-aminoethyl) thiophen-2-yl)benzyl)(methyl)carbamate (49.3 mg, 142 µmol, 0.99 eq.), 4-chloro-6-methoxy-1-methylphthalazine (30.0 mg, 144 µmol, 1.00 eq.) and cesium fluoride (66.0 mg, 435 µmol, 16.0 µL, 3.02 eq.) in dimethyl sulfoxide (1.00 mL) was stirred at 130° C. for 18 hours. The mixture was then cooled to 25° C., diluted with ethyl acetate (5.00 mL), washed with brine (3.00×5 mL), dried over sodium sulfate, filtered, and the solvent was evaporated under reduced pressure to give a residue. The residue was purified by prep-HPLC (column: Boston Green ODS 150×30 mm×5 um; mobile phase: phase A: [water(0.1% TFA)], phase B: acetonitrile; B %: 38%-68%) to give tert-butyl (R)-(2-(5-(1-((7-methoxy-4-methylphthalazin-1-yl)amino)ethyl)thiophen-2-yl)benzyl)(methyl)carbamate (10.0 mg, 18.7 µmol, 13.0% yield, 96.8% purity) as a white solid. LCMS [M+1]$^+$: 519.2.

Step F: To a mixture of tert-butyl (R)-(2-(5-(1-((7-methoxy-4-methylphthalazin-1-yl)amino)ethyl)thiophen-2-yl)benzyl)(methyl)carbamate (8.00 mg, 15.4 µmol, 1.00 eq.) and 2,6-lutidine (16.5 mg, 154 µmol, 18.0 µL, 10.0 eq.) in dichloromethane (2.00 mL) was added TMSOTf (24.0 mg, 108 µmol, 19.5 µL, 7.00 eq.), then it was stirred at 20° C. for 2 hours under a nitrogen atmosphere. To the mixture was added N, N-diisopropyl ethyl amine (0.10 ml) and the mixture was concentrated under reduced pressure to give a residue. The residue was purified by prep-HPLC (column: Agela DuraShell C18 150×25 mm×5 um; mobile phase: phase A: [water (0.05% NH$_3$H$_2$O+10 mM NH$_4$HCO$_3$)], phase B: acetonitrile; B %: 38%-68%) to give (R)-7-m ethoxy-4-methyl-N-(1-(5-(2-((methylamino)methyl)phenyl) thiophen-2-yl)ethyl)phthalazin-1-amine (3.00 mg, 7.10 µmol, 46.0% yield, 99.0% purity) as a white solid. LCMS [M+1]$^+$: 419.2.

$^1$H NMR (500 MHz, CD$_3$OD) δ=8.01 (d, J=9.0 Hz, 1H), 7.73 (d, J=2.5 Hz, 1H), 7.49 (dd, J=9.0, 2.5 Hz, 1H), 7.44 (d, J=6.5 Hz, 1H), 7.33-7.37 (m, 2H), 7.26-7.34 (m, 1H), 7.10 (d, J=3.0 Hz, 1H), 6.93 (d, J=3.5 Hz, 1H), 5.85-5.96 (m, 1H), 4.02 (s, 3H), 3.86 (s, 2H), 2.73 (s, 3H), 2.29 (s, 3H), 1.82 (d, J=7.0 Hz, 3H).

Example 9-1

(R)-4-methoxy-N-(1-(2-methyl-3-(trifluoromethyl) phenyl)ethyl)-7-(piperazin-1-yl)phthalazin-1-amine

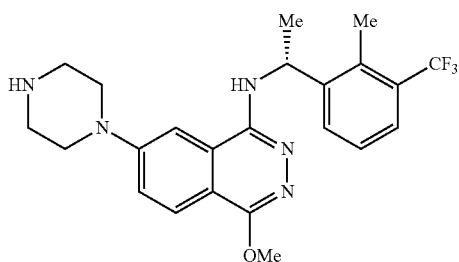

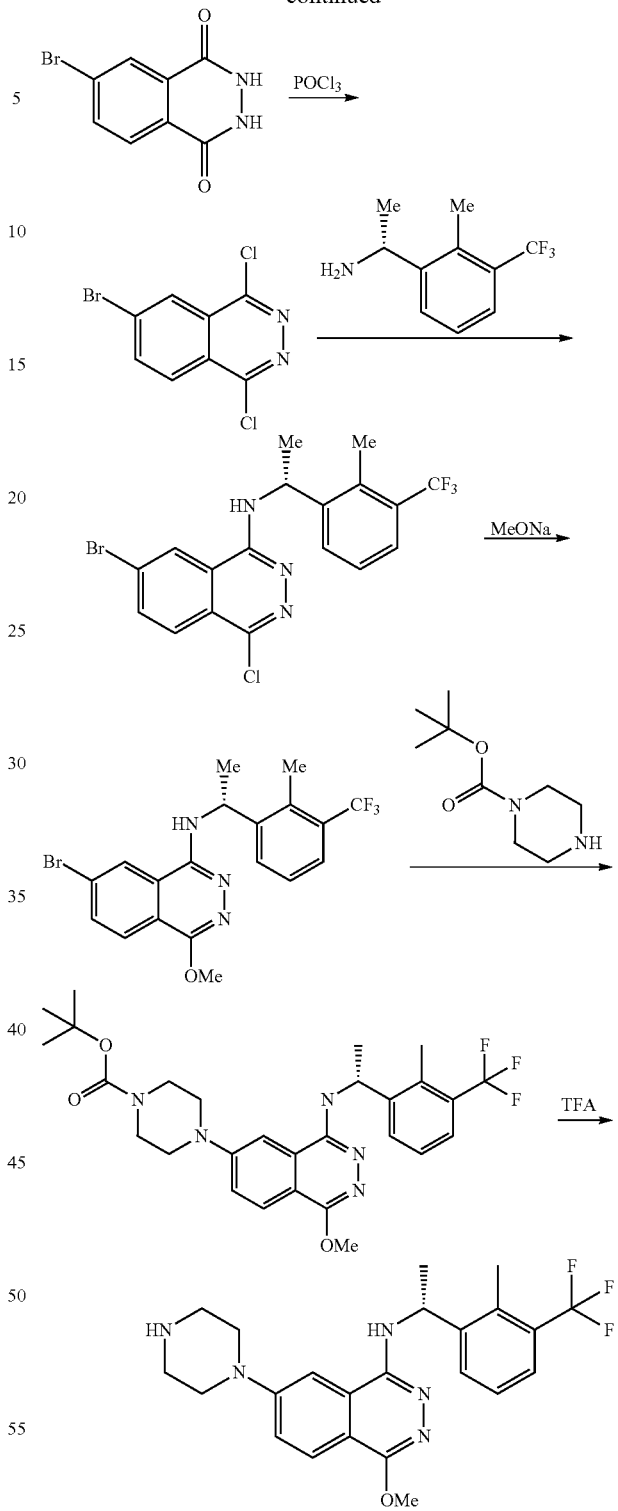

Step A: To a solution of 6-bromo-2,3-dihydrophthalazine-1,4-dione (3.00 g, 12.4 mmol, 1.00 eq.) in phosphorus oxychloride (40.0 mL) was added N A-diisopropylethylamine (4.02 g, 31.1 mmol, 5.42 mL, 2.50 eq.) dropwise at 25° C. The reaction was then stirred at 120° C. for 12 hours. The mixture was cooled to 25° C. and concentrated in vacuo to remove most of the phosphorus oxychloride and give a residue. The residue was poured into ice water (100 mL), and the resulting aqueous solution was adjusted to pH=7 with saturated sodium bicarbonate aqueous solution and then extracted with dichloromethane (50.0 mL×2). The combined organic phases were washed with brine (30.0 mL×2), dried over anhydrous sodium sulfate, filtered, and concentrated under vacuum to give 6-bromo-1,4-dichlorophthalazine (1.20 g, 4.32 mmol, crude) as a yellow solid without further purification. LCMS [M+3]⁺: 279.0.

Step B: To a mixture of 6-bromo-1,4-dichlorophthalazine (500 mg, 1.80 mmol, 1.00 eq.) and (R)-1-(2-methyl-3-(trifluoromethyl)phenyl)ethan-1-amine (365 mg, 1.80 mmol, 1.00 eq.) in DMSO (10.0 mL) was added potassium fluoride (313 mg, 5.40 mmol, 126 μL, 3.00 eq.), N N-diisopropylethylamine (465 mg, 3.60 mmol, 627 μL, 2.00 eq.) under a nitrogen atmosphere. The reaction mixture was then stirred at 130° C. for 3 hours. After this time, the reaction was cooled to 25° C., diluted with ethyl acetate (20.0 mL), washed with brine (5.00 mL×2), dried over anhydrous sodium sulfate, filtered, and concentrated under vacuum to give a residue. The residue was purified by preparative TLC (petroleum ether/ethyl acetate=3/1) to give (R)-7-bromo-4-chloro-N-(1-(2-methyl-3-(trifluoromethyl)phenyl)ethyl)phthalazin-1-amine (360 mg, 769 μmol, 42.7% yield) as a white solid. LCMS [M+3]⁺: 446.1.

¹H NMR (400 MHz, CDCl₃) δ=8.15-8.01 (m, 2H), 7.99-7.79 (m, 1H), 7.63 (d, J=8.0 Hz, 1H), 7.56-7.50 (m, 1H), 7.23 (s, 1H), 5.91-5.77 (m, 1H), 5.45 (br d, J=6.4 Hz, 1H), 2.55 (s, 3H), 1.65 (d, J=6.8 Hz, 3H).

Step C: To a mixture of (R)-7-bromo-4-chloro-N-(1-(2-methyl-3-(trifluoromethyl)phenyl)ethyl)phthalazin-1-amine (330 mg, 742 μmol, 1.00 eq.) in methanol (5.00 mL) was added sodium methoxide (200 mg, 3.71 mmol, 5.00 eq.) under nitrogen. The reaction mixture was stirred for 2 hours at 110° C. in a microwave reactor. The reaction mixture was then cooled to 25° C., and concentrated under reduced pressure to give a residue. The residue was purified by column chromatography (SiO₂, petroleum ether/ethyl acetate=50/1 to 1/1) to give (R)-7-bromo-4-methoxy-N-(1-(2-methyl-3-(trifluoromethyl)phenyl)ethyl)phthalazin-1-amine (281 mg, 638 μmol, 86.0% yield) as a white solid.

Step D: To a solution of (R)-7-bromo-4-methoxy-N-(1-(2-methyl-3-(trifluoromethyl)phenyl)ethyl)phthalazin-1-amine (240 mg, 545 μmol, 4.00 eq.) and tert-butyl piperazine-1-carboxylate (25.4 mg, 136 μmol, 1.00 eq.) in dioxane (5.00 mL) was added RuPhos Pd G3 (5.70 mg, 6.81 μmol, 0.05 eq.) and cesium carbonate (178 mg, 545 μmol, 4.00 eq.) in one portion at 20° C. under a nitrogen atmosphere. The mixture was stirred at 110° C. for 3 hours. LCMS showed the reaction was completed. The suspension was filtered through a pad of celite and the filter cake was washed with ethyl acetate (30.0 mL). The combined filtrates were concentrated to give a residue. The residue was purified by prep-HPLC (column: Phenomenex Synergi C18 150×30 mm×4 um, mobile phase A: water (0.1% TFA), mobile phase B: acetonitrile. Gradient: 49%69% B) to give tert-butyl (R)-4-(1-methoxy-4-((1-(2-methyl-3-(trifluoromethyl)phenyl)ethyl)amino)phthalazin-6-yl)piperazine-1-carboxylate (70.0 mg, 128 μmol, 94.1% yield) as a white solid. LCMS [M+1]⁺: 546.3.

Step E: To a mixture of tert-butyl (R)-4-(1-methoxy-4-((1-(2-methyl-3-(trifluoromethyl)phenyl)ethyl)amino)phthalazin-6-yl)piperazine-1-carboxylate (50.0 mg, 91.6 μmol, 1.00 eq.) in dichloromethane (1.00 mL) was added trifluoroacetic acid (0.20 mL). The mixture was stirred at 20° C. for 1 hour. LCMS showed the reaction was completed. The mixture was concentrated under reduced pressure to give a residue. The residue was purified by prep-HPLC (column: Phenomenex Synergi C18 100×21.2 mm×4 um using TFA water and acetonitrile as the eluents. Mobile phase A: water (0.1% TFA), mobile phase B: acetonitrile. Gradient: 14%44% B) to (R)-4-methoxy-N-(1-(2-methyl-3-(trifluoromethyl)phenyl)ethyl)-7-(piperazin-1-yl)phthalazin-1-amine (35.0 mg, 78.6 μmol, 85.7% yield) as a white solid. LCMS [M+1]⁺: 446.2.

¹H NMR (400 MHz, CD₃OD) δ=8.18 (d, J=9.2 Hz, 1H), 8.06 (d, J=2.8 Hz, 1H), 7.82 (dd, J=2.4, 9.2 Hz, 1H), 7.64-7.77 (m, 2H), 7.36-7.46 (m, 1H), 5.42 (q, J=6.4 Hz, 1H), 4.07 (s, 3H), 3.75-3.86 (m, 4H), 3.38-3.47 (m, 4H), 2.51 (s, 3H), 1.80 (d, J=6.8 Hz, 3H).

Following the teachings of the General Reaction Scheme III, and the procedure described for the preparation of Example 9-1, the following compound of Formula (I), Example 9-2 shown in Table 9 was prepared:

TABLE 9

| Ex. # | Structure | Spectral Data |
|---|---|---|
| 9-2 | 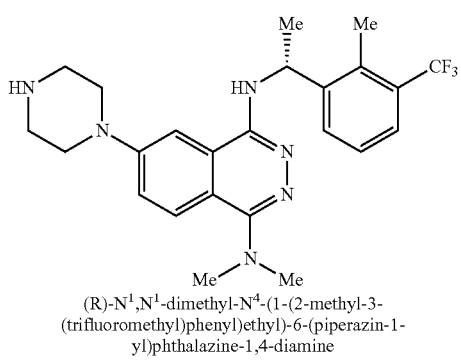<br>(R)-N¹,N¹-dimethyl-N⁴-(1-(2-methyl-3-(trifluoromethyl)phenyl)ethyl)-6-(piperazin-1-yl)phthalazine-1,4-diamine | 1H NMR (500 MHz, CD₃OD) δ = 8.26 (d, J = 9.0 Hz, 1H), 7.81 (br s, 1H), 7.67 (br d, J = 7.5 Hz, 2H), 7.52 (br d, J = 8.0 Hz, 1H), 7.17-7.32 (m, 1H), 5.43 (q, J = 7.5 Hz, 1H), 3.92 (br s, 4H), 3.44-3.48 (m, 4H), 3.23 (br s, 6H), 2.58 (s, 3H), 1.63 (br d, J = 7.0 Hz, 3H). LCMS [M + 1]⁺: 459.2 |

Example 10-1

(R)-4-methyl-N-(1-(2-methyl-3-(trifluoromethyl)phenyl)ethyl)-7-(piperidin-4-yl)phthalazin-1-amine

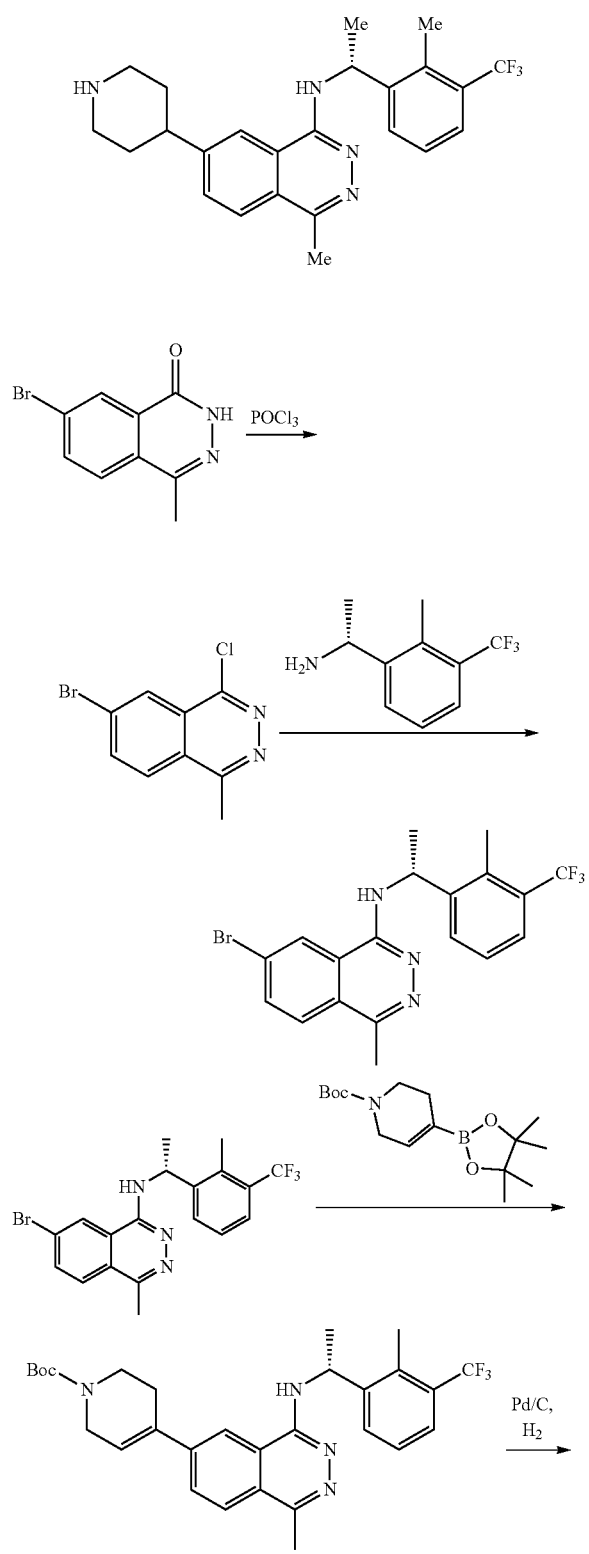

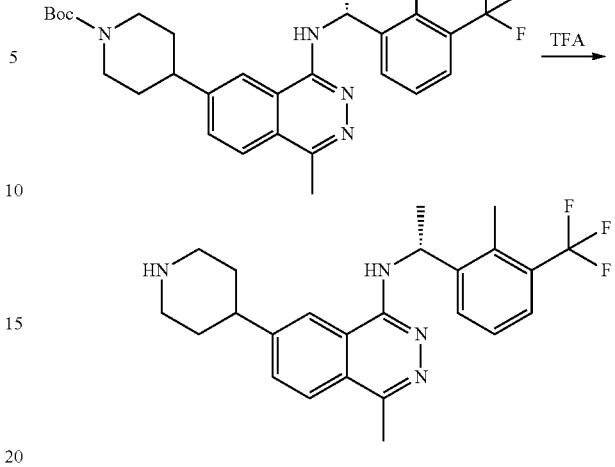

Step A: A mixture of 7-bromo-4-methylphthalazin-1(2H)-one (4 g, 16.73 mmol, 1.00 eq.) in $POCl_3$ (75.54 g, 492.66 mmol, 45.78 mL, 29.44 eq.) was stirred at 20° C. under a $N_2$ atmosphere then heat to 100° C. and stirred for 5 hours. The mixture was cooled to 20° C. and concentrated under reduced pressure. The residue was slowly poured into water and neutralized with sat. $NaHCO_3$ until pH=8. Then the ethyl acetate (100 mL) was added to the mixture and stirred for 30 minutes at 25° C. The mixture was filtered and the after cake was collected. The residue was purified using a silica gel column (0-55% petroleum ether/EtOAc) to give the 6-bromo-4-chloro-1-methylphthalazine (2.2 g, 8.54 mmol, 51.06% yield) as a yellow solid.

$^1$H NMR (500 MHz, DMSO-$d_6$) δ 8.41 (d, J=1.5 Hz, 1H), 8.29-8.34 (m, 1H), 8.24-8.28 (m, 1H), 2.89-2.93 (m, 3H).

Step B: To a mixture of 6-bromo-4-chloro-1-methylphthalazine (0.6 g, 2.32 mmol, 1.00 eq) and (R)-1-(2-methyl-3-(trifluoromethyl)phenyl)ethan-1-amine (472 mg, 2.32 mmol, 1.00 eq) in DMSO (4 mL) was added N, N-diisopropylethylamine (602 mg, 2.33 mmol, 810 μL, 2.00 eq) and CsF (706 mg, 4.66 mmol, 2.00 eq) in one portion at 20° C. under a $N_2$ atmosphere. The mixture was stirred at 130° C. for 3 hours. After this time the reaction was cooled to room temperature, water (50 mL) was added to the reaction mixture and extracted with ethyl acetate (3×30 mL). The combined organic layers were washed with brine (saturated, 20 mL), dried over $Na_2SO_4$, filtered, and concentrated to give a residue. The residue was purified using a preparative TLC plate eluting with 50% EtOAc/peteroleum ether to give (R)-7-bromo-4-methyl-N-(1-(2-methyl-3-(trifluoromethyl)phenyl)ethyl)phthalazin-1-amine (0.6 g, 1414 μmol, 60.70% yield) as a yellow oil.

Note: the reaction needed to be set up in glove box under a $N_2$ atmosphere to avoid moisture. All of reagents including solvent (DMSO) need to be dried.

$^1$H NMR (400 MHz, $CDCl_3$) δ 7.97 (s, 1H), 7.87-7.93 (m, 1H), 7.79-7.85 (m, 1H), 7.66 (d, J=7.6 Hz, 1H), 7.54 (d, J=7.6 Hz, 1H), 7.26-7.29 (m, 1H), 5.88 (quint, J=6.4 Hz, 1H), 5.12 (br s, 1H), 2.78 (s, 3H), 2.57 (s, 3H), 1.66 (d, J=6.8 Hz, 3H).

Step C: To a mixture of (R)-7-bromo-4-methyl-N-(1-(2-methyl-3-(trifluoromethyl)phenyl)ethyl)phthalazin-1-amine (35.0 mg, 82.5 μmol, 1.00 eq.) and tert-butyl 4-(4,4,5,5-tetramethyl-1,3,2-dioxaborolan-2-yl)-3,6-dihydropyridine-1(2H)-carboxylate (38.3 mg, 124 μmol, 1.50 eq.) in tetrahydrofuran (3.00 mL) and water (0.60 mL) was added sodium carbonate (26.2 mg, 247 μmol, 3.00 eq.) and Pd(dppf)Cl₂ (6.04 mg, 8.25 μmol, 0.10 eq.) in one portion at 20° C. under a nitrogen atmosphere. The mixture was stirred at 80° C. for 2 hours then cooled to the room temperature, and the mixture was diluted with ethyl acetate (30.0 mL), washed with water (10.0 mL×3). The combined organic layers were washed with brine (20.0 mL), dried over sodium sulfate and filtered. The filtrate was concentrated to give the crude product as yellow oil. The yellow oil was purified by prep-TLC (SiO₂, petroleum ether/ethyl acetate=2/1) to give tert-butyl (R)-4-(1-methyl-4-((1-(2-methyl-3-(trifluoromethyl)phenyl)ethyl)amino)phthalazin-6-yl)-3,6-dihydropyridine-1 (2H)-carboxylate (32.0 mg, 60.8 μmol, 73.7% yield) as a yellow oil. LCMS [M+1]⁺: 527.3.

Step D: To a solution of tert-butyl (R)-4-(1-methyl-4-((1-(2-methyl-3-(trifluoromethyl)phenyl)ethyl)amino)phthalazin-6-yl)-3,6-dihydropyridine-1 (2H)-carboxylate (14.0 mg, 26.6 μmol, 1.00 eq.) in methanol (3.00 mL) was added Pd/C (3.62 mg, 3.41 μmol, 10% purity, 0.13 eq.) under a nitrogen atmosphere. The suspension was degassed under vacuum and purged with hydrogen several times. The mixture was stirred under hydrogen (15.0 psi) at 25° C. for 2 hours then filtered through a pad of celite and the filter cake was washed with ethyl acetate (30.0 mL). The combined filtrates were concentrated to give tert-butyl (R)-4-(1-methyl-4-((1-(2-methyl-3-(trifluoromethyl)phenyl)ethyl)amino)phthalazin-6-yl)piperidine-1-carboxylate (14.0 mg, 26.5 μmol, 99.6% yield) as a yellow oil. The crude product was used directly in next step without further purification. LCMS [M+1]⁺: 529.3.

Step E: A mixture of tert-butyl (R)-4-(1-methyl-4-((1-(2-methyl-3-(trifluoromethyl)phenyl)ethyl)amino)phthalazin-6-yl)piperidine-1-carboxylate (14 mg, 26.5 μmol, 1.00 eq.) in dichloromethane (2.00 mL) and trifluoroacetic acid (0.40 mL) was stirred at 20° C. for 2 hours then concentrated to give a residue. The residue was purified by prep-HPLC (column: Phenomenex Synergi C18 150×30 mm×4 um using TFA water and acetonitrile as the eluents, mobile phase A: water (0.1% TFA), mobile phase B: acetonitrile. Gradient: 20%-50% B) to give (R)-4-methyl-N-(1-(2-methyl-3-(trifluoromethyl)phenyl)ethyl)-7-(piperidin-4-yl)phthalazin-1-amine (9.00 mg, 21.0 μmol, 79.3% yield) as a yellow solid. LCMS [M+1]⁺: 429.1.

¹H NMR (400 MHz, CD₃OD) δ=8.67 (s, 1H), 8.37 (d, J=8.8 Hz, 1H), 8.12 (d, J=8.4 Hz, 1H), 7.73 (d, J=8.4 Hz, 1H), 7.55 (d, J=8.0 Hz, 1H), 7.29 (t, J=7.6 Hz, 1H), 5.57 (q, J=6.8 Hz, 1H), 3.61 (br d, J=12.8 Hz, 2H), 3.20-3.30 (m, 3H), 2.87 (s, 3H), 2.63 (s, 3H), 2.21-2.32 (m, 2H), 2.05-2.20 (m, 2H), 1.71 (d, J=6.8 Hz, 3H).

Example 10-2

(R)—N-(1-(5-(2-((methylamino)methyl)phenyl)thiophen-2-yl)ethyl)-7-morpholino-4-(trifluoromethyl)phthalazin-1-amine

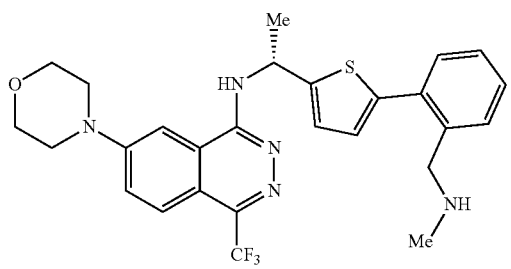

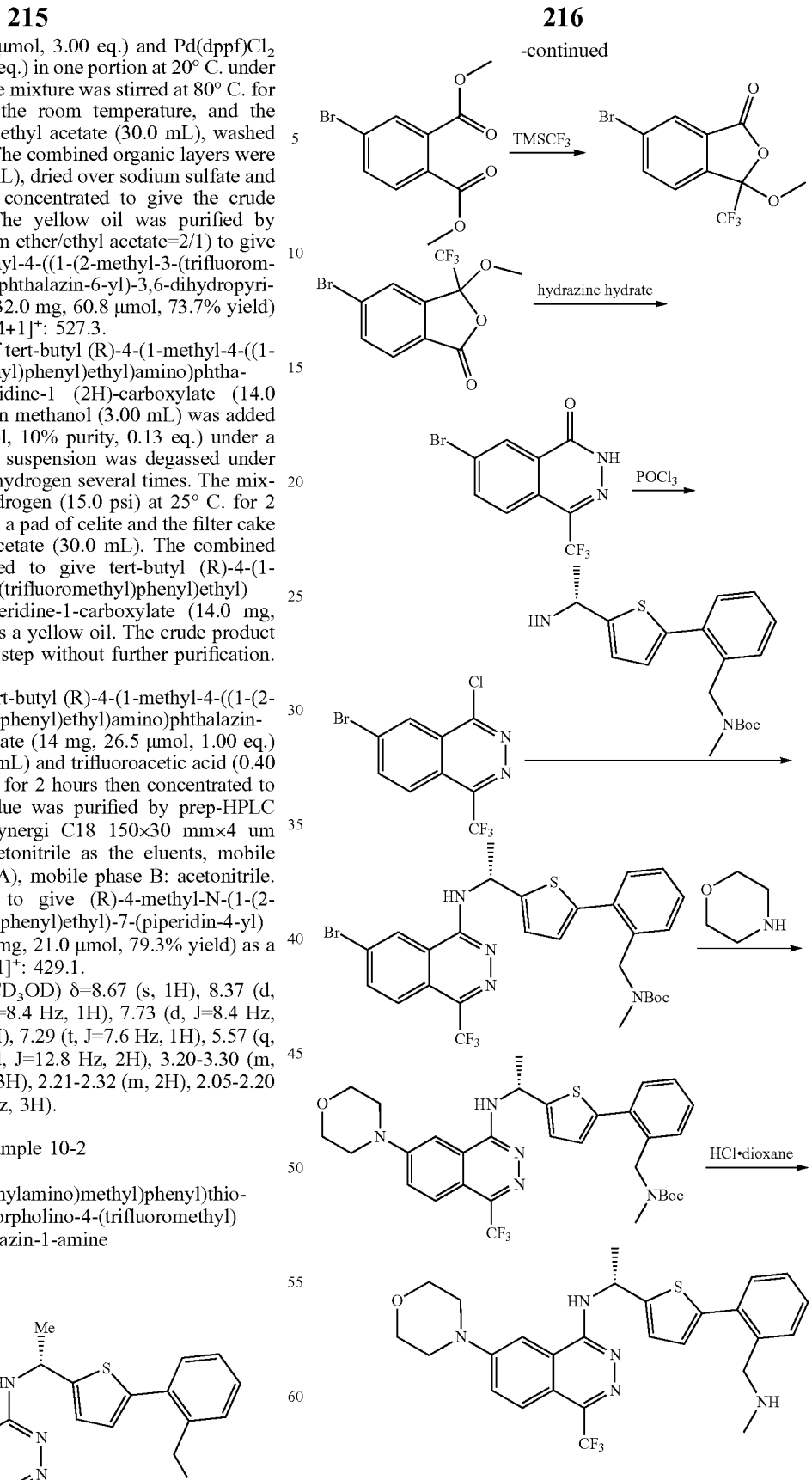

Step A: To a solution of dimethyl 4-bromophthalate (2.00 g, 7.32 mmol, 1.00 eq.) in 1,2-dimethoxyethane (25.0 mL) was added CsF (223 mg, 1.46 mmol, 54.0 μL, 0.20 eq.) and TMSCF$_3$ (1.25 g, 8.79 mmol, 1.20 eq.). The mixture was stirred between 0-25° C. for 1 hour. The mixture was then partitioned between ethyl acetate (1.00 mL) and water (15.0 mL). The organic phases were separated, washed with brine (15.0 mL×3), dried over anhydrous sodium sulfate, filtered, and concentrated under reduced pressure to give a mixture of 6-bromo-3-methoxy-3-(trifluoromethyl)isobenzofuran-1(3H)-one and 5-bromo-3-methoxy-3-(trifluoromethyl)isobenzofuran-1(3H)-one (2.20 g, crude) as a colorless oil.

Step B: To a solution of 6-bromo-3-methoxy-3-(trifluoromethyl)isobenzofuran-1(3H)-one and 5-bromo-3-methoxy-3-(trifluoromethyl)isobenzofuran-1 (3H)-one (2.20 g, 7.07 mmol, 1.00 eq.) in THF (25.0 mL) was added hydrazine hydrate (708 mg, 14.6 mmol, 688 μL, 2.00 eq.). The mixture was stirred at 75° C. for 18 hours then concentrated under reduced pressure to remove solvent. The residue was purified by flash silica gel chromatography (SiO$_2$, Petroleum ether/Ethyl acetate=10/1 to 8/1) to give 7-bromo-4-(trifluoromethyl)phthalazin-1 (2H)-one (680 mg, 2.32 mmol, 32.8% yield) as a white solid.

$^1$H NMR (400 MHz, CD$_3$OD) δ=8.54 (d, J=1.71 Hz, 1H), 8.15 (dd, J=8.68, 2.08 Hz, 1H), 7.91 (dd, J=8.80, 1.47 Hz, 1H).

Step C: To a solution of 7-bromo-4-(trifluoromethyl)phthalazin-1(2H)-one (200 mg, 683 μmol, 1.00 eq.) in POCl$_3$ (3.30 g, 21.5 mmol, 2.00 mL, 31.5 eq.) was added pyridine (108 mg, 1.37 mmol, 110 μL, 2.00 eq.) at 20° C. The mixture was stirred at 105° C. for 1.5 hours then concentrated under reduced pressure to give 6-bromo-4-chloro-1-(trifluoromethyl)phthalazine (210 mg, crude) as a white solid.

Step D: To a solution of 6-bromo-4-chloro-1-(trifluoromethyl)phthalazine (135 mg, 433 μmol, 1.50 eq.) in DMSO (2.00 mL) was added N, N-diisopropylethylamine (112 mg, 866 μmol, 151 μL, 3.00 eq.), KF (1.68 mg, 28.8 μmol, 6.76 μL, 0.10 eq.) and tert-butyl (R)-(2-(5-(1-aminoethyl)thiophen-2-yl)benzyl)(methyl)carbamate (0.10 g, 289 μmol, 100 eq.). The mixture was stirred at 130° C. for 45 minutes in the microwave. The mixture was diluted with water (2.00 mL) and extracted with ethyl acetate (2.00 mL×3). The combined organic layers were washed with water (2.00 mL×2), dried over anhydrous sodium sulfate, filtered and concentrated under reduced pressure to give a residue. The residue was purified by prep-TLC (SiO$_2$, Petroleum ether:Ethyl acetate=5:1) to give tert-butyl (R)-(2-(5-(1-((7-bromo-4-(trifluoromethyl)phthalazin-1-yl)amino)ethyl)thiophen-2-yl)benzyl)(methyl)carbamate (46.0 mg, 74.0 μmol, 25.6% yield) as a yellow oil.

Step E: A mixture of tert-butyl (R)-(2-(5-(1-((7-bromo-4-(trifluoromethyl)phthalazin-1-yl)amino)ethyl)thiophen-2-yl)benzyl)(methyl)carbamate (0.046 g, 74.0 μmol, 1.00 eq.), morpholine (7.74 mg, 88.8 μmol, 7.82 μL, 1.20 eq.), Cs$_2$CO$_3$ (72.3 mg, 222 μmol, 3.00 eq.), Pd$_2$(dba)$_3$ (6.78 mg, 7.40 μmol, 0.100 eq.) and RuPhos (6.91 mg, 14.8 μmol, 0.20 eq.) in dioxane (0.10 mL) was degassed and purged with nitrogen for 3 times, and then the mixture was stirred at 110° C. for 1 hour under a nitrogen atmosphere. After this time, the mixture was diluted with water (2.00 mL) and extracted with ethyl acetate (2.00 mL×3). The combined organic layers were washed with brine (2.00 mL×2), dried over anhydrous sodium sulfate, filtered and concentrated under reduced pressure to give a residue. The residue was purified by prep-TLC (SiO$_2$, Petroleum ether:Ethyl acetate=3:1) to give tert-butyl (R)-methyl(2-(5-(1-((7-morpholino-4-(trifluoromethyl)phthalazin-1-yl)amino)ethyl)thiophen-2-yl)benzyl)carbamate (43.0 mg, 68.5 μmol, 92.6% yield) as a yellow oil.

Step F: To a solution of tert-butyl (R)-methyl(2-(5-(1-((7-morpholino-4-(trifluoromethyl)phthalazin-1-yl)amino)ethyl)thiophen-2-yl)benzyl)carbamate (50.0 mg, 79.7 μmol, 1.00 eq.) in dichloromethane (1.00 mL) was added trifluoroacetic acid (770 mg, 6.75 mmol, 0.50 mL, 84.8 eq.). The mixture was stirred at 25° C. for 20 minutes, then filtered and concentrated under reduced pressure to give a residue. The residue was purified by prep-HPLC (Column: Phenomenex Synergi C18 100×21.2 mm×4 um; mobile phase: phase A: [water(0.1% TFA)], phase B: ACN; B %: 17%-47%) to give (R)—N-(1-(5-(2-((methylamino)methyl)phenyl)thiophen-2-yl)ethyl)-7-morpholino-4-(trifluoromethyl)phthalazin-1-amine (17.5 mg, 33.1 μmol, 41.6% yield) as a white solid.

$^1$H NMR (500 MHz, DMSO-d) δ 8.87 (s, 2H), 8.50 (s, 1H), 7.89-7.39 (m, 6H), 7.19 (s, 1H), 7.08 (s, 1H), 6.07-5.96 (m, 1H), 4.23 (s, 2H), 3.80 (s, 4H), 3.46 (s, 4H), 2.56 (s, 3H), 1.80 (d, J=6.9 Hz, 3H).

Following the teachings of the General Reaction Scheme III, and the procedure described for the preparation of Example 10-1 and 10-2, the following compounds of Formula (I), Examples 10-3 to 10-87 shown in Table 10 were prepared.

TABLE 10

| Ex. # | Structure | Spectral Data |
|---|---|---|
| 10-3 | 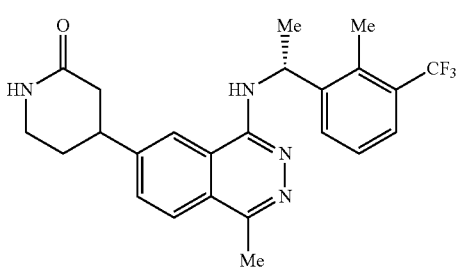 [SMILES: Cc1c([C@@H](C)Nc2nnc(C)c3ccc(C4CCNC(=O)C4)cc23)cccc1C(F)(F)F] 4-(1-methyl-4-(((R)-1-(2-methyl-3-(trifluoromethyl)phenyl)ethyl)amino)phthalazin-6-yl)piperidin-2-one | $^1$H NMR (400 MHz, CD$_3$OD) δ 8.70 (s, 1H), 8.39 (d, J = 8.5 Hz, 1H), 8.17 (dd, J = 8.5, 1.6 Hz, 1H), 7.74 (d, J = 7.9 Hz, 1H), 7.56 (s, 1H), 7.31 (s, 1H), 5.63-5.55 (m, 1H), 3.59-3.49 (m, 2H), 2.89 (s, 3H), 2.77-2.68 (m, 2H), 2.66 (s, 3H), 2.29-2.22 (m, 3H), 1.73 (d, J = 6.9 Hz, 3H). LCMS [M + 1]$^+$: 443.2 |

TABLE 10-continued

| Ex. # | Structure | Spectral Data |
|---|---|---|
| 10-4 | 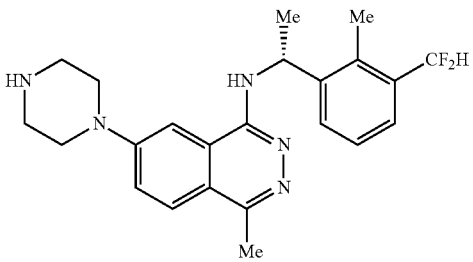 [SMILES: Cc1c(C(F)F)cccc1[C@@H](C)Nc1nnc(C)c2ccc(N3CCNCC3)cc12]<br>(R)-N-(1-(3-(difluoromethyl)-2-methylphenyl)ethyl)-4-methyl-7-(piperazin-1-yl)phthalazin-1-amine | $^1$H NMR (400 MHz, CD$_3$OD) δ = 8.25 (d, J = 9.2 Hz, 1H), 7.96 (s, 1H), 7.83 (dd, J = 2.4, 9.2 Hz, 1H), 7.65 (d, J = 8.0 Hz, 1H), 7.40 (br d, J = 7.2 Hz, 1H), 7.30-7.20 (m, 1H), 7.13-6.80 (m, 1H), 5.6 (q, J = 6.8 Hz, 1H), 4.17-3.93 (m, 4H), 3.58-3.43 (m, 4H), 2.80 (s, 3H), 2.59 (s, 3H), 1.71 (br d, J = 6.8 Hz, 3H). LCMS [M + 1]$^+$ = 412.3. |
| 10-5 | 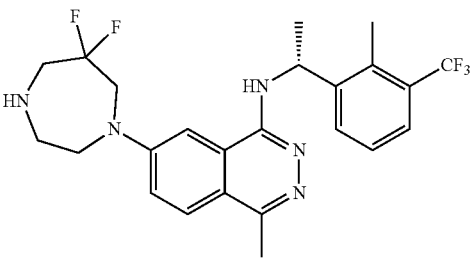 [SMILES: Cc1c([C@@H](C)Nc2nnc(C)c3ccc(N4CCNCC(F)(F)C4)cc23)cccc1C(F)(F)F]<br>(R)-7-(6,6-difluoro-1,4-diazepan-1-yl)-4-methyl-N-(1-(2-methyl-3-(trifluoromethyl)phenyl)ethyl)phthalazin-1-amine | $^1$H NMR (400 MHz, CD$_3$OD) δ = 7.89 (d, J = 8.8 Hz, 1H), 7.69 (d, J = 7.6 Hz, 1H), 7.56 (s, 1H), 7.53 (dd, J = 4.8, 8.8 Hz, 1H), 7.48 (d, J = 7.6 Hz, 1H), 7.22 (t, J = 8.0 Hz, 1H), 5.71 (br d, J = 6.8 Hz, 1H), 4.27 (dt, J = 2.0, 12.0 Hz, 2H), 3.89 (q, J = 4.8 Hz, 2H), 3.13 (t, J = 5.6 Hz, 2H), 3.07 (dt, J = 1.2, 14.8 Hz, 2H), 2.61 (s, 3H), 2.59 (s, 3H), 1.63 (d, J = 6.8 Hz, 3H). LCMS [M + 1]$^+$: 480.1. |
| 10-6 | 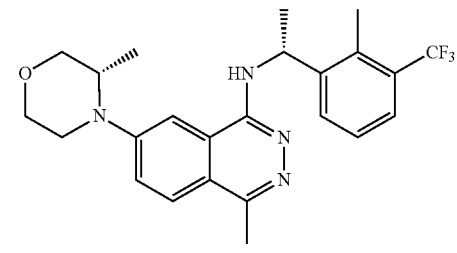 [SMILES: Cc1c([C@@H](C)Nc2nnc(C)c3ccc(N4CCOC[C@@H]4C)cc23)cccc1C(F)(F)F]<br>4-methyl-N-((R)-1-(2-methyl-3-(trifluoromethyl)phenyl)ethyl)-7-((S)-3-methylmorpholino)phthalazin-1-amine | $^1$H NMR (400 MHz, CD$_3$OD) δ = 8.16 (d, J = 10.0 Hz, 1H), 7.74-7.65 (m, 3H), 7.53 (br d, J = 7.8 Hz, 1H), 7.28 (s, 1H), 5.53 (d, J = 6.8 Hz, 1H), 5.49 (s, 1H), 4.46-4.36 (m, 1H), 4.12 (dd, J = 3.6, 11.2 Hz, 1H), 3.95-3.81 (m, 3H), 3.72 (dt, J = 2.8, 12.0 Hz, 1H), 3.51-3.40 (m, 1H), 3.35 (s, 1H), 2.75 (s, 3H), 2.63 (s, 3H), 1.66 (d, J = 6.8 Hz, 3H), 1.36 (d, J = 7.2 Hz, 3H). LCMS [M + 1]$^+$ = 445.2. |
| 10-7 | 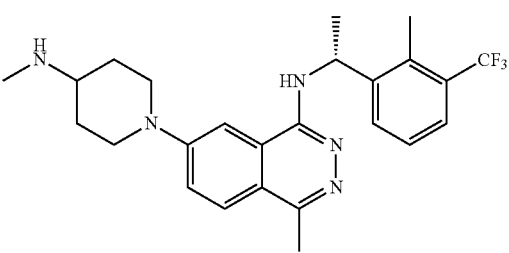 [SMILES: CNC1CCN(c2ccc3c(C)nnc(N[C@H](C)c4cccc(C(F)(F)F)c4C)c3c2)CC1]<br>(R)-4-methyl-N-(1-(2-methyl-3-(trifluoromethyl)phenyl)ethyl)-7-(4-(methylamino)piperidin-1-yl)phthalazin-1-amine | $^1$H NMR (400 MHz, CD$_3$OD) δ = 8.16 (d, J = 9.6 Hz, 1H), 7.84 (s, 1H), 7.78-7.71 (m, 2H), 7.52 (d, J = 7.6 Hz, 1H), 7.27 (t, J = 16.0 Hz, 1H), 5.55-5.50 (m, 1H), 4.54 (d, J = 13.6 Hz, 2H), 3.51-3.31 (m, 1H), 3.28-3.23 (m, 2H), 2.78 (s, 3H), 2.75 (s, 3H), 2.62 (s, 3H), 2.31 (d, J = 10.8 Hz, 2H), 1.78-1.72 (m, 2H), 1.68 (d, J = 7.6 Hz, 3H). LCMS [M + 1]$^+$: 458.2. |

TABLE 10-continued

| Ex. # | Structure | Spectral Data |
|---|---|---|
| 10-8 | 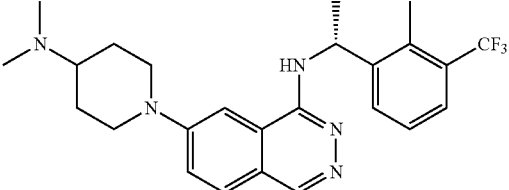<br>(R)-7-(4-(dimethylamino)piperidin-1-yl)-4-methyl-N-(1-(2-methyl-3-(trifluoromethyl)phenyl)ethyl)phthalazin-1-amine | $^1$H NMR (400 MHz, CD$_3$OD) δ = 8.17 (d, J = 9.6 Hz, 1H), 7.85 (s, 1H), 7.78-7.72 (m, 2H), 7.52 (d, J = 8.0 Hz, 1H), 7.27 (t, J = 8.0 Hz, 1H), 5.56-5.50 (m, 1H), 4.60 (d, J = 13.2 Hz, 2H), 3.66-3.63 (m, 1H), 3.30-3.22 (m, 2H), 2.93 (s, 6H), 2.75 (s, 3H), 2.32 (d, J = 9.6 Hz, 2H), 1.91-1.85 (m, 2H), 1.68 (d, J = 6.8 Hz, 3H). LCMS [M + 1]$^+$: 472.2. |
| 10-9 | 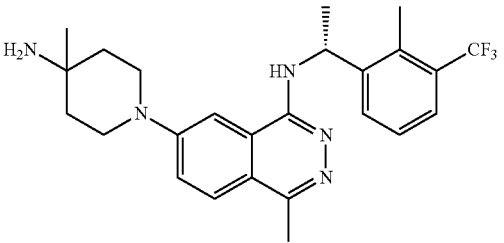 [SMILES: Cc1c([C@@H](C)Nc2nnc(C)c3ccc(N4CCC(C)(N)CC4)cc23)cccc1C(F)(F)F]<br>(R)-7-(4-amino-4-methylpiperidin-1-yl)-4-methyl-N-(1-(2-methyl-3-(trifluoromethyl)phenyl)ethyl)phthalazin-1-amine | $^1$H NMR (400 MHz, CD$_3$OD) δ 8.17 (d, J = 9.3 Hz, 1H), 7.85 (s, 1H), 7.79-7.71 (m, 2H), 7.53 (d, J = 7.8 Hz, 1H), 7.27 (t, J = 7.8 Hz, 1H), 5.54 (q, J = 6.9 Hz, 1H), 4.21 (d, J = 14.1 Hz, 2H), 3.58 (dd, J = 14.1, 6.9 Hz, 2H), 2.75 (s, 3H), 2.63 (s, 3H), 2.05-1.97 (m, 4H), 1.68 (d, J = 6.9 Hz, 3H), 1.57 (s, 3H). LCMS [M + 1]$^+$: 458.2. |
| 10-10 | 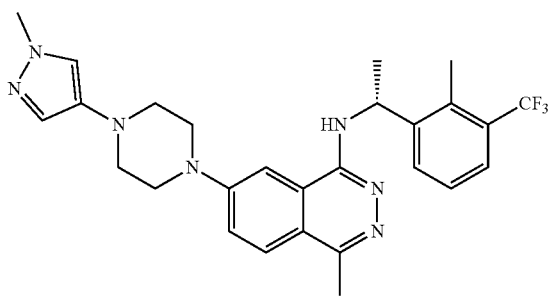 [SMILES: Cc1c([C@@H](C)Nc2nnc(C)c3ccc(N4CCN(c5cnn(C)c5)CC4)cc23)cccc1C(F)(F)F]<br>(R)-4-methyl-7-(4-(1-methyl-1H-pyrazol-4-yl)piperazin-1-yl)-N-(1-(2-methyl-3-(trifluoromethyl)phenyl)ethyl)phthalazin-1-amine | $^1$H NMR (400 MHz, DMSO-d$_6$) δ 14.83 (s, 1H), 8.76 (s, 1H), 8.16 (d, J = 9.3 Hz, 1H), 8.03 (s, 1H), 7.85-7.79 (m, 2H), 7.56 (d, J = 7.1 Hz, 2H), 7.36 (dd, J = 16.0, 8.2 Hz, 2H), 5.48 (q, J = 6.9 Hz, 1H), 3.92 (s, 4H), 3.78 (s, 3H), 3.17 (s, 5H), 2.73 (s, 3H), 2.59-2.56 (m, 3H), 1.64 (d, J = 6.9 Hz, 3H). LCMS [M + 1]$^+$: 510.2 |
| 10-11 | 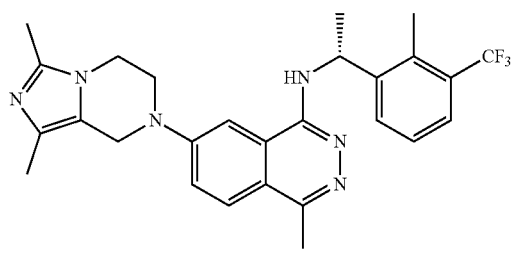 [SMILES: Cc1nc(C)n2c1CN(c1ccc3c(C)nnc(N[C@H](C)c4cccc(C(F)(F)F)c4C)c3c1)CC2]<br>(R)-7-(1,3-dimethyl-5,6-dihydroimidazo[1,5-a]pyrazin-7(8H)-yl)-4-methyl-N-(1-(2-methyl-3-(trifluoromethyl)phenyl)ethyl)phthalazin-1-amine | $^1$H NMR (400 MHz, CD$_3$OD) δ 8.30 (d, J = 9.3 Hz, 1H), 8.02 (d, J = 2.4 Hz, 1H), 7.92 (dd, J = 9.3, 2.5 Hz, 1H), 7.83 (d, J = 7.9 Hz, 1H), 7.57 (d, J = 7.8 Hz, 1H), 7.31 (t, J = 7.9 Hz, 1H), 5.61 (q, J = 6.9 Hz, 1H), 5.02 (d, J = 2.5 Hz, 2H), 4.43 (t, J = 5.4 Hz, 2H), 4.30 (t, J = 5.4 Hz, 2H), 2.83 (s, 3H), 2.69-2.65 (m, 6H), 2.43 (s, 3H), 1.76 (d, J = 7.0 Hz, 3H). LCMS [M + 1]$^+$: 495.2. |

TABLE 10-continued

| Ex. # | Structure | Spectral Data |
|---|---|---|
| 10-12 | 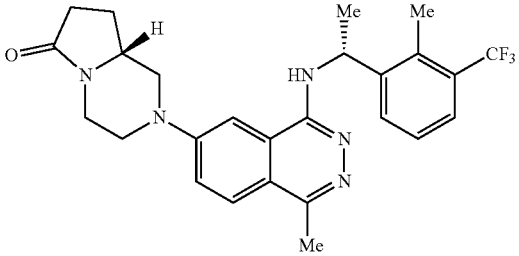 [SMILES: Cc1c([C@@H](C)Nc2nnc(C)c3ccc(N4CCN5C(=O)CC[C@@H]5C4)cc23)cccc1C(F)(F)F]<br>(R)-2-(1-methyl-4-(((R)-1-(2-methyl-3-(trifluoromethyl)phenyl)ethyl)amino)phthalazin-6-yl)hexahydropyrrolo[1,2-a]pyrazin-6(2H)-one | $^1$H NMR (400 MHz, DMSO-$d_6$) δ = 7.80 (d, J = 8.8 Hz, 1H), 7.75 (d, J = 7.6 Hz, 1H), 7.65-7.63 (m, 2H), 7.50 (d, J = 7.6 Hz, 1H), 7.36 (d, J = 6.8 Hz, 1H), 7.30 (t, J = 8.0 Hz, 1H), 5.70-5.66 (m, 1H), 4.24-4.23 (m, 1H), 4.12-3.96 (m, 1H), 3.94-3.93 (m, 1H), 3.72-3.71 (m, 1H), 3.09-3.20 (m, 1H), 2.91-3.02 (m, 1H), 2.60-2.71 (m, 1H), 2.57 (s, 3H), 2.52 (s, 3H), 2.32-2.28 (m, 2H), 2.26-2.14 (m, 1H), 1.70-1.68 (m, 1H), 1.55 (d, J = 6.8 Hz, 3H). LCMS [M + 1]$^+$: 484.1. |
| 10-13 | 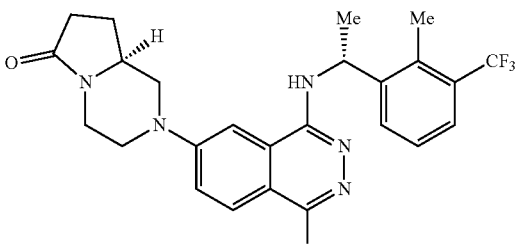<br>(S)-2-(1-methyl-4-(((R)-1-(2-methyl-3-(trifluoromethyl)phenyl)ethyl)amino)phthalazin-6-yl)hexahydropyrrolo[1,2-a]pyrazin-6(2H)-one | $^1$H NMR (400 MHz, DMSO-$d_6$) δ = 7.80 (d, J = 8.8 Hz, 1H), 7.73 (d, J = 8.0 Hz, 1H), 7.64-7.60 (m, 2H), 7.50 (d, J = 7.6 Hz, 1H), 7.29 (t, J = 8.0 Hz, 1H), 5.68-5.63 (m, 1H), 4.22 (d, J = 10.4 Hz, 1H), 4.13 (d, J = 12.4 Hz, 1H), 4.09-3.95 (m, 1H), 3.72-3.71 (m, 1H), 2.97 (t, J = 9.2 Hz, 1H), 2.81 (t, J = 12.0 Hz, 1H), 2.67-2.61 (m, 1H), 2.56 (s, 3H), 2.51 (s, 3H), 2.32-2.29 (m, 2H), 2.26-2.14 (m, 1H), 1.70-1.68 (m, 1H), 1.53 (d, J = 7.2 Hz, 3H). LCMS [M + 1]$^+$: 484.1. |
| 10-14 | 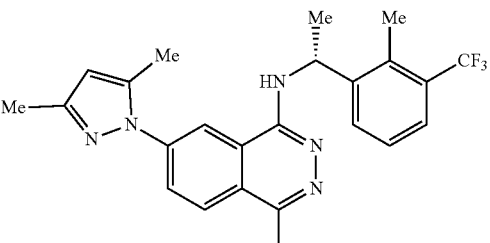<br>(R)-7-(3,5-dimethyl-1H-pyrazol-1-yl)-4-methyl-N-(1-(2-methyl-3-(trifluoromethyl)phenyl)ethyl)phthalazin-1-amine | $^1$H NMR (400 MHz, DMSO-$d_6$) δ = 9.01 (brs, 1H), 8.95 (s, 1H), 8.47 (d, J = 8.8 Hz, 1H), 8.31 (d, J = 8.0 Hz, 1H), 7.77 (d, J = 7.6 Hz, 1H), 7.58 (d, J = 8.0 Hz, 1H), 7.37 (m, 1H), 6.3 (s, 1H), 5.51 (m, 1H), 2.84 (s, 3H), 2.58 (s, 3H), 2.49 (s, 3H), 2.28 (s, 3H), 1.63 (d, J = 6.8 Hz, 3H). LCMS [M + H]$^+$: 440.6. |
| 10-15 | 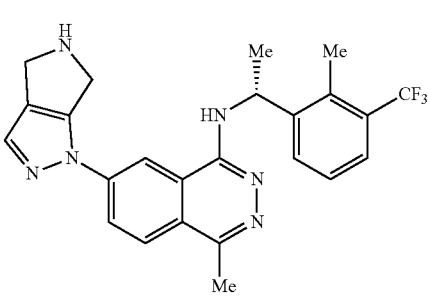 [SMILES: Cc1c([C@@H](C)Nc2nnc(C)c3ccc(-n4ncc5c4CNC5)cc23)cccc1C(F)(F)F]<br>(R)-7-(5,6-dihydropyrrolo[3,4-c]pyrazol-1(4H)-yl)-4-methyl-N-(1-(2-methyl-3-(trifluoromethyl)phenyl)ethyl)phthalazin-1-amine | $^1$H NMR (400 MHz, DMSO-$d_6$) δ = 8.77-8.71 (m, 1H), 8.13-8.08 (m, 1H), 8.03-7.98 (m, 1H), 7.93 (br d, J = 6.4 Hz, 1H), 7.79 (d, J = 8.0 Hz, 1H), 7.70 (s, 1H), 7.51 (d, J = 7.6 Hz, 1H), 7.30 (t, J = 6.8 Hz, 1H), 5.74-5.63 (m, 1H), 4.66-4.52 (m, 2H), 4.15-4.05 (m, 2H), 2.64 (s, 3H), 2.59 (br s, 3H), 1.56 (d, J = 6.8 Hz, 3H). LCMS [M + 1]$^+$: 453.3. |

TABLE 10-continued

| Ex. # | Structure | Spectral Data |
|---|---|---|
| 10-16 | 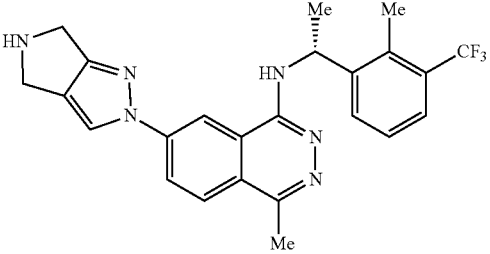 [SMILES: Cc1c([C@@H](C)Nc2nnc(C)c3ccc(-n4cc5c(n4)CNC5)cc23)cccc1C(F)(F)F]<br>(R)-7-(5,6-dihydropyrrolo[3,4-c]pyrazol-2(4H)-yl)-4-methyl-N-(1-(2-methyl-3-(trifluoromethyl)phenyl)ethyl)phthalazin-1-amine | $^1$H NMR (400 MHz, CD$_3$OD) δ = 8.75 (d, J = 2.0 Hz, 1H), 8.42-8.34 (m, 2H), 8.17 (d, J = 8.8 Hz, 1H), 7.75 (d, J = 8.0 Hz, 1H), 7.50 (d, J = 7.6 Hz, 1H), 7.25 (t, J = 8.0 Hz, 1H), 5.74 (q, J = 6.8 Hz, 1H), 4.42 (d, J = 7.2 Hz, 4H), 2.71 (s, 3H), 2.64 (s, 3H), 1.66 (d, J = 6.8 Hz, 3H). LCMS [M + 1]$^+$: 453.4. |
| 10-17 | 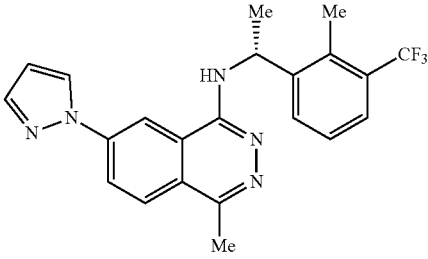 [SMILES: Cc1c([C@@H](C)Nc2nnc(C)c3ccc(-n4cccn4)cc23)cccc1C(F)(F)F]<br>(R)-4-methyl-N-(1-(2-methyl-3-(trifluoromethyl)phenyl)ethyl)-7-(1H-pyrazol-1-yl)phthalazin-1-amine | $^1$H NMR (400 MHz, DMSO-d$_6$) δ = 9.20 (s, 1H), 8.98 (br s, 1H), 8.87 (d, J = 2.8 Hz, 1H), 8.65 (dd, J = 9.2 Hz, J = 2.0 Hz 1H), 8.51 (d, J = 8.8 Hz, 1H), 8.03 (d, J = 1.6 Hz, 1H), 7.81 (d, J = 7.6 Hz, 1H), 7.59 (d, J = 7.6 Hz, 1H), 7.38 (m, 1H), 6.81 (m, 1H), 5.52 (m, 1H), 2.83 (s, 3H), 2.59 (s, 3H), 1.66 (d, J = 6.8 Hz, 3H). LCMS [M + H]$^+$: 412.3. |
| 10-18 | 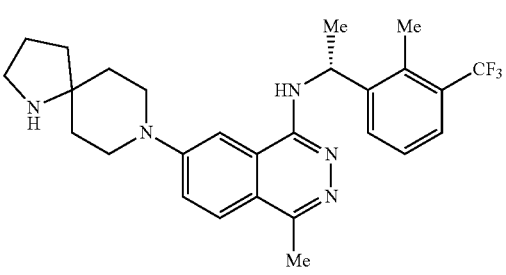 [SMILES: Cc1c([C@@H](C)Nc2nnc(C)c3ccc(N4CCC5(CCCN5)CC4)cc23)cccc1C(F)(F)F]<br>(R)-4-methyl-N-(1-(2-methyl-3-(trifluoromethyl)phenyl)ethyl)-7-(1,8-diazaspiro[4.5]decan-8-yl)phthalazin-1-amine | $^1$H NMR (400 MHz, CD$_3$OD) δ = 8.18 (d, J = 9.2 Hz, 1H), 7.89 (d, J = 2.4 Hz, 1H), 7.82-7.74 (m, 2H), 7.54 (d, J = 8.0 Hz, 1H), 7.29 (t, J = 7.6 Hz, 1H), 5.55 (q, J = 7.2 Hz, 1H), 4.28-4.16 (m, 2H), 3.70-3.57 (m, 2H), 3.47 (t, J = 6.8 Hz, 2H), 2.77 (s, 3H), 2.65 (s, 3H), 2.32-2.17 (m, 4H), 2.17-2.06 (m, 4H), 1.71 (d, J = 7.2 Hz, 3H). LCMS [M + 1]$^+$: 484.2. |
| 10-19 | 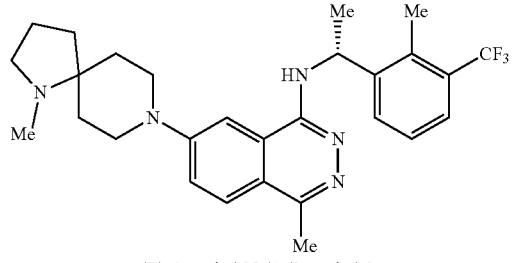<br>(R)-4-methyl-N-(1-(2-methyl-3-(trifluoromethyl)phenyl)ethyl)-7-(1-methyl-1,8-diazaspiro[4.5]decan-8-yl)phthalazin-1-amine | $^1$H NMR (400 MHz, CD$_3$OD) δ = 8.19 (d, J = 9.2 Hz, 1H), 7.91 (d, J = 2.0 Hz, 1H), 7.84-7.74 (m, 2H), 7.54 (d, J = 8.0 Hz, 1H), 7.29 (t, J = 7.6 Hz, 1H), 5.56 (q, J = 6.8 Hz, 1H), 4.62-4.50 (m, 2H), 3.83-3.71 (m, 1H), 3.42-3.33 (m, 3H), 2.85 (s, 3H), 2.77 (s, 3H), 2.65 (s, 3H), 2.62-2.53 (m, 1H), 2.35-2.14 (m, 4H), 2.13-1.93 (m, 3H), 1.71 (d, J = 7.2 Hz, 3H). LCMS [M + 1]$^+$: 498.3. |

TABLE 10-continued

| Ex. # | Structure | Spectral Data |
|---|---|---|
| 10-20 | 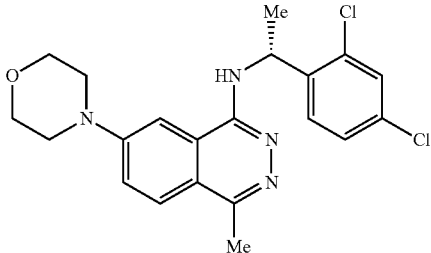 [SMILES: Cc1nnc(N[C@H](C)c2ccc(Cl)cc2Cl)c2cc(N3CCOCC3)ccc12] (R)-N-(1-(2,4-dichlorophenyl)ethyl)-4-methyl-7-morpholinophthalazin-1-amine | $^1$H NMR (400 MHz, DMSO-$d_6$) δ = 7.82 (d, J = 9.2 Hz, 1H), 7.63-7.62 (m, 1H), 7.57-7.56 (m, 2H), 7.44 (d, J = 8.0 Hz, 1H), 7.41-7.39 (m, 1H), 7.32-7.31 (m, 1H), 5.64-5.60 (m, 1H), 3.82 (t, J = 4.8 Hz, 4H), 3.41 (t, J = 4.4 Hz, 4H), 2.52 (s, 3H), 1.55 (d, J = 7.2 Hz, 3H). LCMS [M + 1]$^+$: 417.0. |
| 10-21 | 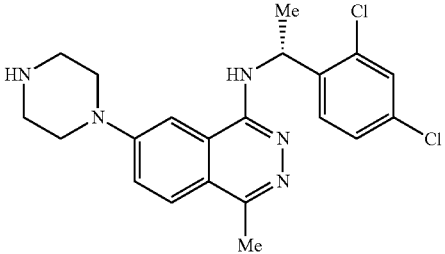 [SMILES: Cc1nnc(N[C@H](C)c2ccc(Cl)cc2Cl)c2cc(N3CCNCC3)ccc12] (R)-N-(1-(2,4-dichlorophenyl)ethyl)-4-methyl-7-(piperazin-1-yl)phthalazin-1-amine | $^1$H NMR (400 MHz, DMSO-$d_6$) δ = 14.96 (s, 1H), 9.60 (s, 2H), 9.05 (s, 1H), 8.22-8.21 (m, 2H), 7.82-7.77 (m, 1H), 7.65 (d, J = 8.4 Hz, 1H), 7.60 (d, J = 2.4 Hz, 1H), 7.37 (dd, J = 2.0 Hz, 8.4 Hz, 1H), 5.50-5.43 (m, 1H), 4.07-3.98 (m, 4H), 3.33-3.28 (m, 4H), 2.74 (s, 3H), 1.66 (d, J = 6.8 Hz, 3H). LCMS [M + 1]$^+$: 416.1. |
| 10-22 | 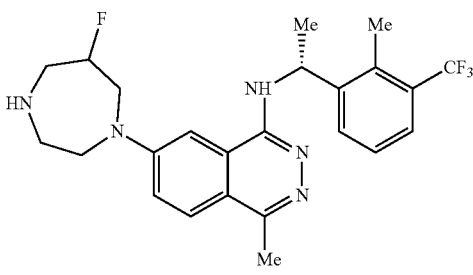 7-(6-fluoro-1,4-diazepan-1-yl)-4-methyl-N-((R)-1-(2-methyl-3-(trifluoromethyl)phenyl)ethyl)phthalazin-1-amine | $^1$H NMR (400 MHz, DMSO-$d_6$) δ = 7.88 (d, J = 9.2 Hz, 1H), 7.69 (d, J = 7.6 Hz, 1H), 7.51-7.47 (m, 3H), 7.22 (t, J = 8.0 Hz, 1H), 5.71-5.68 (m, 1H), 5.14-4.94 (m, 1H), 4.13-4.07 (m, 2H), 3.85-3.83 (m, 2H), 3.30-2.99 (m, 4H), 2.61-2.55 (m, 6H), 1.61 (d, J = 6.8 Hz, 3H). LCMS [M + 1]$^+$: 462.2. |
| 10-23 | 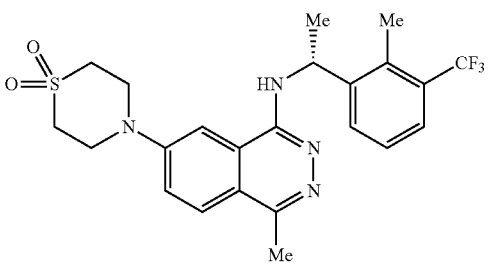 [SMILES: Cc1c([C@@H](C)Nc2nnc(C)c3ccc(N4CCS(=O)(=O)CC4)cc23)cccc1C(F)(F)F] (R)-4-(1-methyl-4-((1-(2-methyl-3-(trifluoromethyl)phenyl)ethyl)amino)phthalazin-6-yl)thiomorpholine 1,1-dioxide | $^1$H NMR (400 MHz, CD$_3$OD) δ = 7.95 (d, J = 8.8 Hz, 1H), 7.73-7.68 (m, 2H), 7.64 (dd, J = 2.4, 8.8 Hz, 1H), 7.48 (d, J = 7.6 Hz, 1H), 7.23 (t, J = 7.6 Hz, 1H), 5.72 (q, J = 6.8 Hz, 1H), 4.20-4.11 (m, 4H), 3.25-3.17 (m, 4H), 2.61 (s, 6H), 1.63 (d, J = 7.2 Hz, 3H). LCMS [M + 1]$^+$: 479.2. |

TABLE 10-continued

| Ex. # | Structure | Spectral Data |
|---|---|---|
| 10-24 | 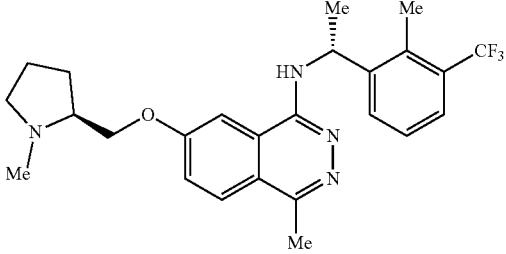 [SMILES: Cc1c([C@@H](C)Nc2nnc(C)c3ccc(OC[C@@H]4CCCN4C)cc23)cccc1C(F)(F)F]<br>4-methyl-N-((R)-1-(2-methyl-3-(trifluoromethyl)phenyl)ethyl)-7-(((S)-1-methylpyrrolidin-2-yl)methoxy)phthalazin-1-amine hydrochloride salt | $^1$H NMR (400 MHz, CD$_3$OD) δ = 8.40-8.36 (m, 2H), 7.88-7.77 (m, 2H), 7.54 (d, J = 8.0 Hz, 1H), 7.28 (t, J = 8.0 Hz, 1H), 5.58 (q, J = 6.8 Hz, 1H), 4.69 (br dd, J = 7.2, 11.2 Hz, 2H), 4.08 (br d, J = 3.6 Hz, 1H), 3.81 (br s, 1H), 3.15 (s, 3H), 2.86 (s, 3H), 2.64 (s, 3H), 2.51 (br dd, J = 6.0, 12.4 Hz, 1H), 2.45-2.04 (m, 4H), 1.73 (d, J = 6.8 Hz, 3H). LCMS [M + 1]$^+$: 459.2. |
| 10-25 | 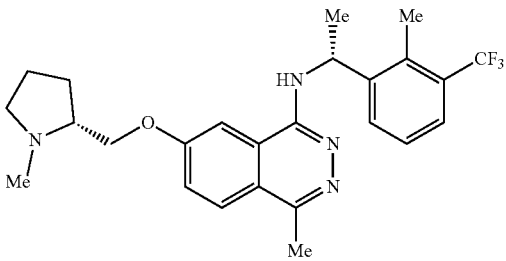 [SMILES: Cc1c([C@@H](C)Nc2nnc(C)c3ccc(OC[C@H]4CCCN4C)cc23)cccc1C(F)(F)F]<br>4-methyl-N-((R)-1-(2-methyl-3-(trifluoromethyl)phenyl)ethyl)-7-(((R)-1-methylpyrrolidin-2-yl)methoxy)phthalazin-1-amine hydrochloride salt | $^1$H NMR (400 MHz, CD$_3$OD) δ = 8.48-8.29 (m, 2H), 7.89-7.79 (m, 2H), 7.56 (br d, J = 7.6 Hz, 1H), 7.30 (br t, J = 8.0 Hz, 1H), 5.63-5.54 (m, 1H), 4.85-4.67 (m, 3H), 4.15-4.05 (m, 1H), 3.89-3.79 (m, 1H), 3.17 (s, 3H), 2.88 (s, 3H), 2.66 (s, 3H), 2.60-2.44 (m, 1H), 2.36-2.10 (m, 3H), 1.74 (br d, J = 6.8 Hz, 3H). LCMS [M + 1]$^+$: 459.2. |
| 10-26 | 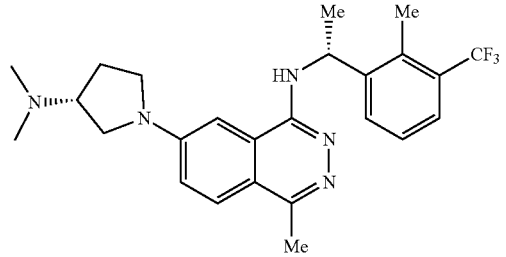 [SMILES: Cc1c([C@@H](C)Nc2nnc(C)c3ccc(N4CC[C@@H](N(C)C)C4)cc23)cccc1C(F)(F)F]<br>7-((R)-3-(dimethylamino)pyrrolidin-1-yl)-4-methyl-N-((R)-1-(2-methyl-3-(trifluoromethyl)phenyl)ethyl)phthalazin-1-amine hydrochloride salt | $^1$H NMR (400 MHz, CD$_3$OD) δ = 8.22 (d, J = 9.2 Hz, 1H), 7.79 (d, J = 7.6 Hz, 1H), 7.60 (d, J = 2.0 Hz, 1H), 7.54 (d, J = 8.0 Hz, 1H), 7.49 (dd, J = 2.4, 9.2 Hz, 1H), 7.29 (t, J = 8.0 Hz, 1H), 5.57 (q, J = 6.8 Hz, 1H), 4.26-4.17 (m, 2H), 4.06-3.96 (m, 1H), 3.95-3.85 (m, 1H), 3.78-3.67 (m, 1H), 3.09 (br d, J = 10.4 Hz, 6H), 2.78 (s, 3H), 2.77-2.70 (m, 1H), 2.65 (s, 3H), 2.47 (qd, J = 8.4, 12.4 Hz, 1H), 1.72 (d, J = 6.8 Hz, 3H). LCMS [M + 1]$^+$: 458.2. |
| 10-27 | 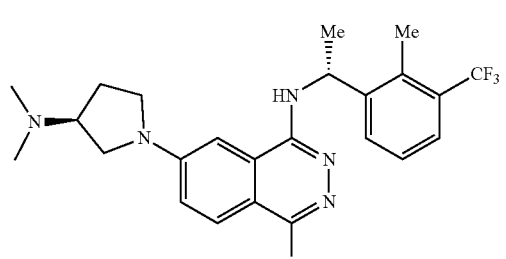<br>7-((R)-3-(dimethylamino)pyrrolidin-1-yl)-4-methyl-N-((R)-1-(2-methyl-3-(trifluoromethyl)phenyl)ethyl)phthalazin-1-amine hydrochloride salt | $^1$H NMR (400 MHz, CD$_3$OD) δ = 8.20 (d, J = 9.2 Hz, 1H), 7.77 (d, J = 7.6 Hz, 1H), 7.59 (d, J = 1.6 Hz, 1H), 7.52 (br d, J = 8.0 Hz, 1H), 7.47 (dd, J = 2.4, 9.2 Hz, 1H), 7.27 (t, J = 7.6 Hz, 1H), 5.55 (q, J = 6.8 Hz, 1H), 4.27-4.12 (m, 2H), 4.01-3.88 (m, 2H), 3.77-3.67 (m, 1H), 3.07 (br s, 6H), 2.76 (s, 3H), 2.74-2.69 (m, 1H), 2.63 (s, 3H), 2.46 (qd, J = 8.8, 12.8 Hz, 1H), 1.70 (d, J = 7.2 Hz, 3H). LCMS [M + 1]$^+$: 458.3. |

TABLE 10-continued

| Ex. # | Structure | Spectral Data |
|---|---|---|
| 10-28 | 4-methyl-N-((R)-1-(2-methyl-3-(trifluoromethyl)phenyl)ethyl)-7-(3-methyl-3,8-diazabicyclo[3.2.1]octan-8-yl)phthalazin-1-amine hydrochloride salt | $^1$H NMR (400 MHz, CD$_3$OD) δ = 8.25 (d, J = 9.2 Hz, 1H), 7.94 (d, J = 2.4 Hz, 1H), 7.80 (d, J = 8.0 Hz, 1H), 7.74 (dd, J = 2.4, 9.2 Hz, 1H), 7.54 (d, J = 7.6 Hz, 1H), 7.29 (t, J = 7.6 Hz, 1H), 5.56 (q, J = 6.8 Hz, 1H), 5.07 (br s, 2H), 3.60 (br d, J = 12.8 Hz, 2H), 3.40-3.34 (m, 2H), 2.87 (s, 3H), 2.79 (s, 3H), 2.65 (s, 3H), 2.47-2.24 (m, 4H), 1.72 (d, J = 6.8 Hz, 3H). LCMS [M + 1]$^+$: 470.2. |
| 10-29 | 4-methyl-N-((R)-1-(2-methyl-3-(trifluoromethyl)phenyl)ethyl)-7-(8-methyl-3,8-diazabicyclo[3.2.1]octan-3-yl)phthalazin-1-amine hydrochloride salt | $^1$H NMR (400 MHz, CD$_3$OD): δ = 8.28-8.21 (m, 1H), 7.94-7.90 (m, 1H), 7.81-7.73 (m, 2H), 7.55-7.50 (m, 1H), 7.31-7.24 (m, 1H), 5.60-5.51 (m, 1H), 4.43-4.32 (m, 2H), 4.28-4.21 (m, 2H), 3.84-3.58 (m, 2H), 3.01-2.91 (m, 3H), 2.83-2.76 (m, 3H), 2.65-2.60 (m, 3H), 2.49-2.33 (m, 2H), 2.25-2.12 (m, 2H), 1.74-1.66 (m, 3H). LCMS [M + 1]$^+$: 470.3. |
| 10-30 | (R)-7-(4-(azetidin-1-yl)piperidin-1-yl)-4-methyl-N-(1-(2-methyl-3-(trifluoromethyl)phenyl)ethyl)phthalazin-1-amine hydrochloride salt | $^1$H NMR (400 MHz, CD$_3$OD) δ = 8.17 (d, J = 9.6 Hz, 1H), 7.86 (d, J = 2.4 Hz, 1H), 7.81-7.72 (m, 2H), 7.54 (d, J = 7.6 Hz, 1H), 7.34-7.25 (m, 1H), 5.55 (q, J = 7.2 Hz, 1H), 4.54 (br d, J = 13.6 Hz, 2H), 4.39-4.13 (m, 4H), 3.65 (tt, J = 4.0, 11.2 Hz, 1H), 3.27 (br t, J = 12.4 Hz, 2H), 2.77 (s, 3H), 2.65 (s, 4H), 2.54-2.34 (m, 1H), 2.24 (br d, J = 11.6 Hz, 2H), 1.70 (d, J = 6.8 Hz, 3H), 1.67-1.52 (m, 2H). LCMS [M + 1]$^+$: 484.3. |
| 10-31 | 4-methyl-N-((R)-1-(2-methyl-3-(trifluoromethyl)phenyl)ethyl)-7-((1S,4S)-5-methyl-2,5-diazabicyclo[2.2.2]octan-2-yl)phthalazin-1-amine | $^1$H NMR (400 MHz, CD$_3$OD) δ = 8.04 (d, J = 9.2 Hz, 1H), 7.70 (d, J = 8.0 Hz, 1H), 7.51 (d, J = 7.6 Hz, 1H), 7.48-7.42 (m, 2H), 7.26 (t, J = 8.0 Hz, 1H), 5.57 (q, J = 6.8 Hz, 1H), 4.44 (br s, 1H), 4.02 (td, J = 2.4, 11.6 Hz, 1H), 3.52 (dd, J = 2.0, 11.6 Hz, 1H), 3.16-3.02 (m, 3H), 2.68 (s, 3H), 2.62 (s, 3H), 2.54 (s, 3H), 2.33-2.20 (m, 1H), 2.13-1.92 (m, 2H), 1.84-1.73 (m, 1H), 1.65 (d, J = 6.8 Hz, 3H). LCMS [M + 1]$^+$: 470.2. |

TABLE 10-continued

| Ex. # | Structure | Spectral Data |
|---|---|---|
| 10-32 | 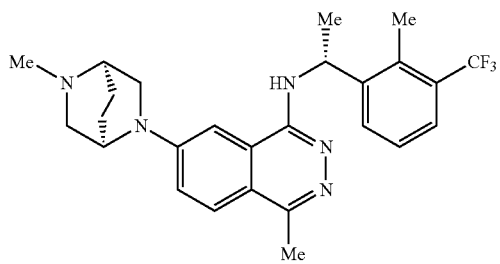 [SMILES: Cc1c([C@@H](C)Nc2nnc(C)c3ccc(N4C[C@H]5CC[C@@H]4CN5C)cc23)cccc1C(F)(F)F]<br>4-methyl-N-((R)-1-(2-methyl-3-(trifluoromethyl)phenyl)ethyl)-7-((1R,4R)-5-methyl-2,5-diazabicyclo[2.2.2]octan-2-yl)phthalazin-1-amine | $^1$H NMR (400 MHz, CD$_3$OD) δ = 7.85 (d, J = 8.8 Hz, 1H), 7.70 (d, J = 7.6 Hz, 1H), 7.47 (d, J = 7.6 Hz, 1H), 7.33 (dd, J = 2.4, 8.8 Hz, 1H), 7.28 (d, J = 2.4 Hz, 1H), 7.22 (t, J = 8.0 Hz, 1H), 5.71 (q, J = 6.8 Hz, 1H), 4.30 (br s, 1H), 3.96 (td, J = 2.4, 10.8 Hz, 1H), 3.43 (dd, J = 2.0, 10.8 Hz, 1H), 3.11-2.94 (m, 3H), 2.61 (s, 3H), 2.57 (s, 3H), 2.49 (s, 3H), 2.28-2.16 (m, 1H), 2.10-1.99 (m, 1H), 1.97-1.87 (m, 1H), 1.81-1.69 (m, 1H), 1.62 (d, J = 6.8 Hz, 3H). LCMS [M + 1]$^+$: 470.2. |
| 10-33 | 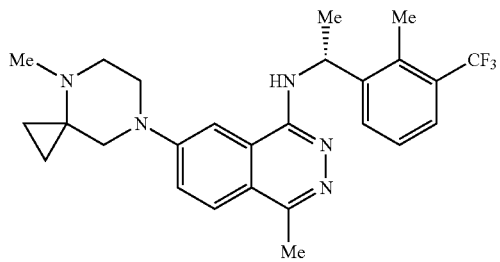 [SMILES: Cc1c([C@@H](C)Nc2nnc(C)c3ccc(N4CCN(C)C5(CC5)C4)cc23)cccc1C(F)(F)F]<br>(R)-4-methyl-N-(1-(2-methyl-3-(trifluoromethyl)phenyl)ethyl)-7-(4-methyl-4,7-diazaspiro[2.5]octan-7-yl)phthalazin-1-amine | $^1$H NMR (400 MHz, CD$_3$OD) δ = 7.88 (d, J = 8.8 Hz, 1H), 7.69 (d, J = 7.6 Hz, 1H), 7.58-7.52 (m, 2H), 7.47 (d, J = 7.6 Hz, 1H), 7.22 (t, J = 8.0 Hz, 1H), 5.72 (q, J = 6.8 Hz, 1H), 3.54 (dd, J = 4.8, 6.8 Hz, 2H), 3.35 (s, 2H), 3.18-3.11 (m, 2H), 2.64-2.57 (m, 6H), 2.48 (s, 3H), 1.62 (d, J = 6.8 Hz, 3H), 0.86-0.80 (m, 2H), 0.73-0.64 (m, 2H). LCMS [M + 1]$^+$: 470.3. |
| 10-34 | 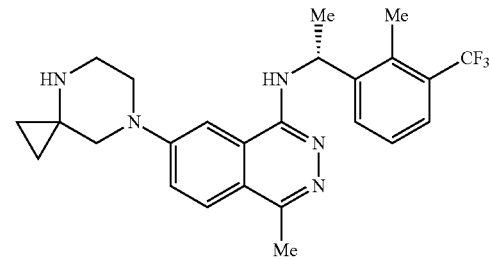 [SMILES: Cc1c([C@@H](C)Nc2nnc(C)c3ccc(N4CCNC5(CC5)C4)cc23)cccc1C(F)(F)F]<br>(R)-4-methyl-N-(1-(2-methyl-3-(trifluoromethyl)phenyl)ethyl)-7-(4,7-diazaspiro[2.5]octan-7-yl)phthalazin-1-amine | $^1$H NMR (400 MHz, DMSO-d$_6$) δ = 8.46 (br s, 1H), 8.06 (d, J = 9.2 Hz, 1H), 7.90 (br s, 1H), 7.81 (br d, J = 7.6 Hz, 1H), 7.72 (br d, J = 8.0 Hz, 1H), 7.54 (d, J = 7.6 Hz, 1H), 7.34 (br t, J = 8.0 Hz, 1H), 5.51 (br t, J = 6.8 Hz, 1H), 3.84 (br d, J = 4.8 Hz, 2H), 3.73 (br s, 2H), 3.25 (br s, 2H), 2.67 (s, 3H), 2.57 (s, 3H), 1.62 (br d, J = 6.8 Hz, 3H), 0.95-0.79 (m, 4H). LCMS [M + 1]$^+$: 456.2. |
| 10-35 | 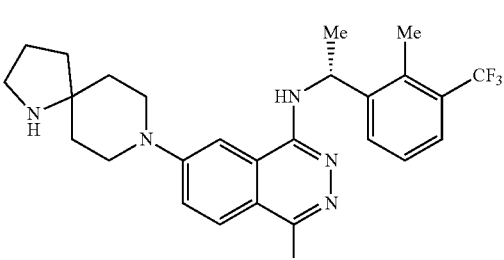<br>(R)-4-methyl-N-(1-(2-methyl-3-(trifluoromethyl)phenyl)ethyl)-7-(1,8-diazaspiro[4.5]decan-8-yl)phthalazin-1-amine | $^1$H NMR (400 MHz, CD$_3$OD) δ = 8.18 (d, J = 9.2 Hz, 1H), 7.89 (d, J = 2.4 Hz, 1H), 7.82-7.74 (m, 2H), 7.54 (d, J = 8.0 Hz, 1H), 7.29 (t, J = 7.6 Hz, 1H), 5.55 (q, J = 7.2 Hz, 1H), 4.28-4.16 (m, 2H), 3.70-3.57 (m, 2H), 3.47 (t, J = 6.8 Hz, 2H), 2.77 (s, 3H), 2.65 (s, 3H), 2.32-2.17 (m, 4H), 2.17-2.06 (m, 4H), 1.71 (d, J = 7.2 Hz, 3H). LCMS [M + 1]$^+$: 484.2. |

TABLE 10-continued

| Ex. # | Structure | Spectral Data |
|---|---|---|
| 10-36 | 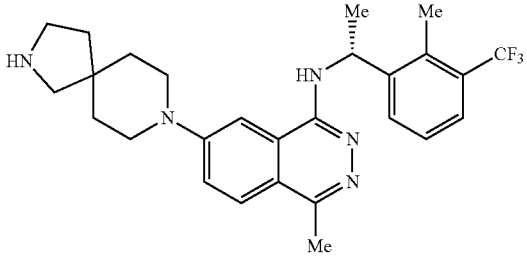 [SMILES: Cc1c([C@@H](C)Nc2nnc(C)c3ccc(N4CCC5(CCNC5)CC4)cc23)cccc1C(F)(F)F]<br>(R)-4-methyl-N-(1-(2-methyl-3-(trifluoromethyl)phenyl)ethyl)-7-(2,8-diazaspiro[4.5]decan-8-yl)phthalazin-1-amine hydrochloride salt | $^{1}$H NMR (400 MHz, CD$_3$OD) δ = 8.15 (d, J = 9.6 Hz, 1H), 7.83 (d, J = 2.4 Hz, 1H), 7.78-7.71 (m, 2H), 7.54 (d, J = 7.6 Hz, 1H), 7.29 (t, J = 8.0 Hz, 1H), 5.55 (q, J = 6.8 Hz, 1H), 3.95-3.75 (m, 4H), 3.50 (t, J = 7.2 Hz, 2H), 3.28 (s, 2H), 2.76 (s, 3H), 2.65 (s, 3H), 2.15-2.08 (m, 2H), 1.96-1.83 (m, 4H), 1.70 (d, J = 6.8 Hz, 3H). LCMS [M + 1]$^+$: 484.2. |
| 10-37 | 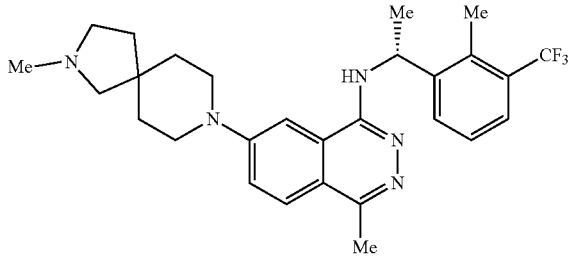 [SMILES: Cc1c([C@@H](C)Nc2nnc(C)c3ccc(N4CCC5(CCN(C)C5)CC4)cc23)cccc1C(F)(F)F]<br>(R)-4-methyl-N-(1-(2-methyl-3-(trifluoromethyl)phenyl)ethyl)-7-(2-methyl-2,8-diazaspiro[4.5]decan-8-yl)phthalazin-1-amine hydrochloride salt | $^{1}$H NMR (400 MHz, CD$_3$OD) δ = 8.15 (d, J = 9.2 Hz, 1H), 7.81 (d, J = 2.0 Hz, 1H), 7.77-7.69 (m, 2H), 7.54 (d, J = 7.6 Hz, 1H), 7.29 (t, J = 8.0 Hz, 1H), 5.55 (q, J = 6.8 Hz, 1H), 3.94-3.70 (m, 6H), 3.31-3.24 (m, 1H), 3.08 (d, J = 11.6 Hz, 1H), 3.01 (s, 3H), 2.76 (s, 3H), 2.64 (s, 3H), 2.33-2.21 (m, 1H), 2.17-2.08 (m, 1H), 2.01-1.87 (m, 4H), 1.69 (d, J = 6.8 Hz, 3H). LCMS [M + 1]$^+$: 498.3. |
| 10-38 | 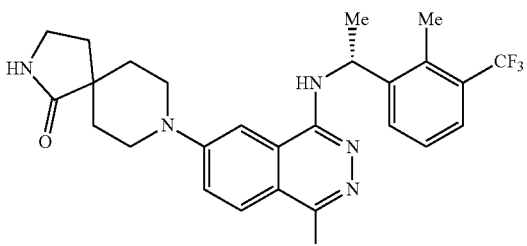<br>(R)-8-(1-methyl-4-((1-(2-methyl-3-(trifluoromethyl)phenyl)ethyl)amino)phthalazin-6-yl)-2,8-diazaspiro[4.5]decan-1-one | $^{1}$H NMR (400 MHz, DMSO-d$_6$) δ = 7.81-7.74 (m, 2H), 7.63-7.58 (m, 3H), 7.50 (d, J = 7.6 Hz, 1H), 7.55-7.44 (m, 1H), 7.32-7.29 (m, 1H), 5.68-5.64 (m, 1H), 4.05-4.01 (m, 2H), 3.21-3.23 (m, 1H), 3.08-3.13 (m, 3H), 2.57 (s, 3H), 2.53 (s, 3H), 2.06 (t, J = 6.8 Hz, 2H), 1.85-1.78 (m, 2H), 1.55 (d, J = 6.8 Hz, 3H), 1.50-1.52 (m, 2H). LCMS [M + 1]$^+$: 498.6. |
| 10-39 | 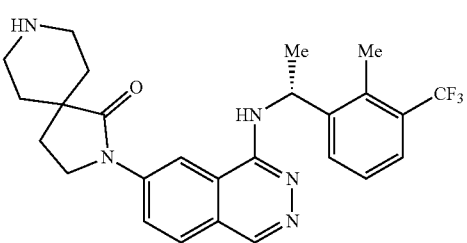<br>(R)-2-(1-methyl-4-((1-(2-methyl-3-(trifluoromethyl)phenyl)ethyl)amino)phthalazin-6-yl)-2,8-diazaspiro[4.5]decan-1-one hydrochloride salt | $^{1}$H NMR (400 MHz, DMSO-d$_6$) δ = 9.40 (br s, 1H), 9.17 (br s, 1H), 9.08-8.94 (m, 1H), 8.89 (dd, J = 1.2, 8.8 Hz, 1H), 8.70 (s, 1H), 8.39 (d, J = 9.2 Hz, 1H), 7.92 (d, J = 8.0 Hz, 1H), 7.54 (d, J = 7.6 Hz, 1H), 7.33 (t, J = 8.0 Hz, 1H), 5.50 (q, J = 6.4 Hz, 1H), 4.29-4.19 (m, 1H), 4.15-4.09 (m, 1H), 3.36-3.27 (m, 2H), 3.12-3.01 (m, 2H), 2.82 (s, 3H), 2.57 (s, 3H), 2.26 (br t, J = 6.8 Hz, 2H), 2.10-1.98 (m, 2H), 1.83 (br d, J = 12.8 Hz, 2H), 1.66 (d, J = 6.8 Hz, 3H). LCMS [M + 1]$^+$: 498.3. |

TABLE 10-continued

| Ex. # | Structure | Spectral Data |
|---|---|---|
| 10-40 | 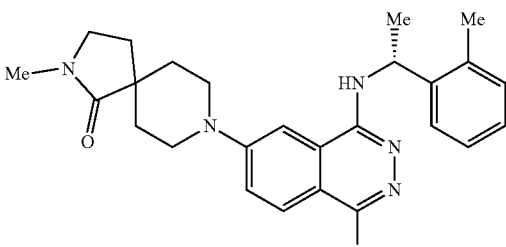<br>(R)-2-methyl-8-(1-methyl-4-((1-(2-methyl-3-(trifluoromethyl)phenyl)ethyl)amino)phthalazin-6-yl)-2,8-diazaspiro[4.5]decan-1-one | $^1$H NMR (400 MHz, CD$_3$OD) δ = 8.12 (br d, J = 9.2 Hz, 1H), 7.81-7.64 (m, 3H), 7.52 (br d, J = 7.6 Hz, 1H), 7.27 (br t, J = 7.6 Hz, 1H), 5.52 (q, J = 6.8 Hz, 1H), 4.31 (br d, J = 13.6 Hz, 2H), 3.55-3.39 (m, 4H), 2.88 (s, 3H), 2.73 (s, 3H), 2.63 (s, 3H), 2.20 (br t, J = 6.8 Hz, 2H), 1.98 (br t, J = 12.8 Hz, 2H), 1.66 (br d, J = 7.2 Hz, 5H). LCMS [M + 1]$^+$: 512.2. |
| 10-41 | 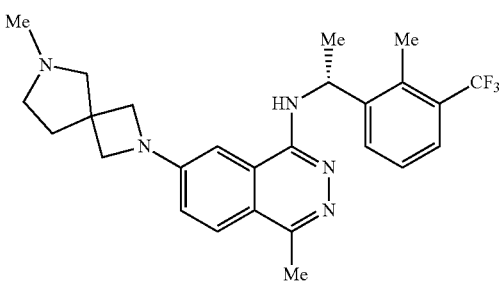 [SMILES: Cc1c([C@@H](C)Nc2nnc(C)c3ccc(N4CC5(CCN(C)C5)C4)cc23)cccc1C(F)(F)F]<br>(R)-4-methyl-N-(1-(2-methyl-3-(trifluoromethyl)phenyl)ethyl)-7-(6-methyl-2,6-diazaspiro[3.4]octan-2-yl)phthalazin-1-amine hydrochloride salt | $^1$H NMR (400 MHz, CD$_3$OD) δ = 8.14 (d, J = 9.2 Hz, 1H), 7.71 (d, J = 8.0 Hz, 1H), 7.55-7.49 (m, 1H), 7.55-7.47 (m, 1H), 7.43-7.40 (m, 1H), 7.43-7.38 (m, 1H), 7.27 (t, J = 7.6 Hz, 1H), 7.18 (d, J = 2.0, 8.8 Hz, 1H), 5.52 (q, J = 7.2 Hz, 1H), 4.44-4.32 (m, 2H), 4.32-4.23 (m, 1H), 4.19-4.04 (m, 1H), 3.85-3.69 (m, 1H), 3.52-3.43 (m, 1H), 3.01 (s, 2H), 2.77-2.71 (m, 3H), 2.70-2.59 (m, 4H), 2.57-2.49 (m, 1H), 2.57-2.49 (m, 1H), 1.73-1.63 (m, 3H). LCMS [M + 1]$^+$: 470.2. |
| 10-42 | 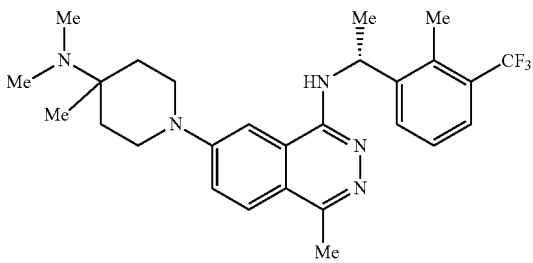 [SMILES: Cc1c([C@@H](C)Nc2nnc(C)c3ccc(N4CCC(C)(N(C)C)CC4)cc23)cccc1C(F)(F)F]<br>(R)-7-(4-(dimethylamino)-4-methylpiperidin-1-yl)-4-methyl-N-(1-(2-methyl-3-(trifluoromethyl)phenyl)ethyl)phthalazin-1-amine hydrochloride salt | $^1$H NMR (400 MHz, CD$_3$OD) δ = 8.17 (d, J = 9.2 Hz, 1H), 7.87 (d, J = 2.8 Hz, 1H), 7.78-7.73 (m, 2H), 7.52 (d, J = 7.6 Hz, 1H), 7.27 (t, J = 8.0 Hz, 1H), 5.54 (q, J = 6.8 Hz, 1H), 4.50-4.42 (m, 2H), 3.42-3.34 (m, 2H), 2.88 (s, 6H), 2.75 (s, 3H), 2.63 (s, 3H), 2.24-2.15 (m, 2H), 2.12-2.01 (m, 2H), 1.69 (d, J = 6.8 Hz, 3H), 1.57 (s, 3H). LCMS [M + 1]$^+$: 486.3. |
| 10-43 | 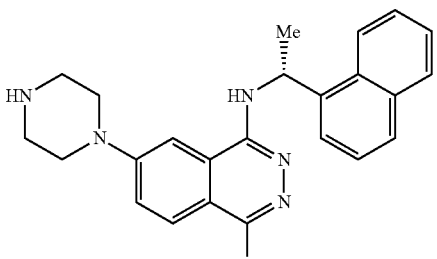<br>(R)-4-methyl-N-(1-(naphthalen-1-yl)ethyl)-7-(piperazin-1-yl)phthalazin-1-amine formate salt | $^1$H NMR (400 MHz, CD$_3$OD) δ = 8.49 (s, 1H), 8.19 (d, J = 8.0 Hz, 1H), 8.10 (d, J = 9.2 Hz, 1H), 7.92-7.83 (m, 1H), 7.78-7.73 (m, 2H), 7.71-7.67 (m, 1H), 7.63 (d, J = 7.2 Hz, 1H), 7.53-7.44 (m, 2H), 7.43-7.37 (m, 1H), 6.23-6.09 (m, 1H), 3.79-3.69 (m, 4H), 3.27-3.19 (m, 4H), 2.71 (s, 3H), 1.82 (d, J = 6.8 Hz, 3H). LCMS [M + 1]$^+$: 398.2. |

TABLE 10-continued

| Ex. # | Structure | Spectral Data |
|---|---|---|
| 10-44 | 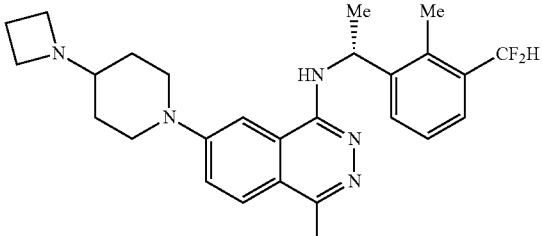<br>(R)-7-(4-(azetidin-1-yl)piperidin-1-yl)-N-(1-(3-(difluoromethyl)-2-methylphenyl)ethyl)-4-methylphthalazin-1-amine hydrochloride salt | $^1$H NMR (400 MHz, DMSO-$d_6$) δ = 8.69-8.52 (m, 1H), 8.11 (br d, J = 9.2 Hz, 1H), 7.95 (br s, 1H), 7.76 (br d, J = 9.6 Hz, 1H), 7.67 (br s, 1H), 7.40 (br d, J = 7.6 Hz, 1H), 7.36-7.07 (m, 2H), 5.45 (br t, J = 6.8 Hz, 1H), 4.49 (br d, J = 13.2 Hz, 2H), 4.18-3.93 (m, 4H), 3.55-3.48 (m, 1H), 3.19-3.10 (m, 2H), 2.70 (s, 3H), 2.51-2.51 (m, 3H), 2.40-2.15 (m, 2H), 2.07-2.02 (m, 2H), 1.62 (d, J = 7.2 Hz, 3H), 1.56-1.41 (m, 2H). LCMS [M + 1]$^+$: 466.2. |
| 10-45 | 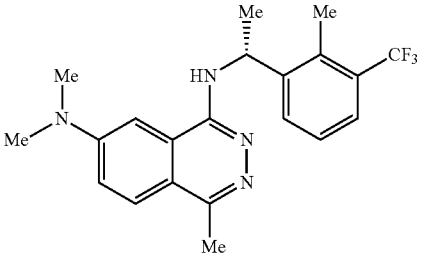 [SMILES: Cc1c([C@@H](C)Nc2nnc(C)c3ccc(N(C)C)cc23)cccc1C(F)(F)F]<br>(R)-N$^7$,N$^7$,4-trimethyl-N$^1$-(1-(2-methyl-3-(trifluoromethyl)phenyl)ethyl)phthalazine-1,7-diamine | $^1$H NMR (400 MHz, CD$_3$OD) δ = 8.12 (d, J = 8.8 Hz, 1H), 7.70 (d, J = 8.0 Hz, 1H), 7.57-7.44 (m, 3H), 7.27 (t, J = 8.0 Hz, 1H), 5.53 (q, J = 6.8 Hz, 1H), 3.34-3.32 (m, 6H), 2.80-2.71 (s, 3H), 2.63 (s, 3H), 1.67 (d, J = 7.2 Hz, 3H). LCMS [M + 1]$^+$: 389.2. |
| 10-46 | 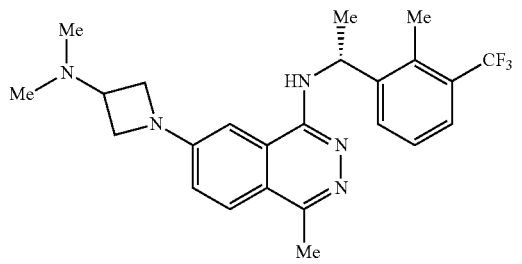<br>(R)-7-(3-(dimethylamino)azetidin-1-yl)-4-methyl-N-(1-(2-methyl-3-(trifluoromethyl)phenyl)ethyl)phthalazin-1-amine formate salt | $^1$H NMR (400 MHz, CDCl$_3$) δ = 8.56 (s, 1H), 7.92 (d, J = 8.8 Hz, 1H), 7.70 (d, J = 7.6 Hz, 1H), 7.49 (d, J = 7.6 Hz, 1H), 7.28-7.24 (m, 1H), 7.22 (d, J = 2.4 Hz, 1H), 7.11-7.03 (m, 1H), 5.68-5.55 (m, 1H), 4.25 (t, J = 8.0 Hz, 2H), 4.02-3.89 (m, 2H), 3.48-3.37 (m, 1H), 2.62 (s, 3H), 2.61 (s, 3H), 2.29 (s, 6H), 1.63 (d, J = 6.8 Hz, 3H). LCMS [M + 1]$^+$: 444.1. |
| 10-47 | 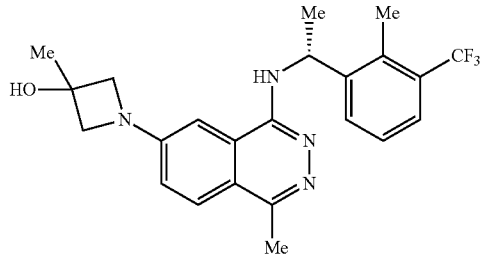 [SMILES: Cc1c([C@@H](C)Nc2nnc(C)c3ccc(N4CC(C)(O)C4)cc23)cccc1C(F)(F)F]<br>(R)-3-methyl-1-(1-methyl-4-((1-(2-methyl-3-(trifluoromethyl)phenyl)ethyl)amino)phthalazin-6-yl)azetidin-3-ol | $^1$H NMR (400 MHz, CD$_3$OD) δ = 7.83 (d, J = 8.8 Hz, 1H), 7.69 (d, J = 7.6 Hz, 1H), 7.47 (d, J = 7.6 Hz, 1H), 7.22 (t, J = 7.6 Hz, 1H), 7.15 (d, J = 2.0 Hz, 1H), 7.02 (dd, J = 2.4, 8.8 Hz, 1H), 5.70 (q, J = 6.8 Hz, 1H), 4.03 (dd, J = 4.0, 8.0 Hz, 2H), 3.94 (d, J = 8.0 Hz, 2H), 2.61 (s, 3H), 2.57 (s, 3H), 1.63-1.59 (m, 6H). LCMS [M + 1]$^+$: 431.3. |

TABLE 10-continued

| Ex. # | Structure | Spectral Data |
|---|---|---|
| 10-48 | 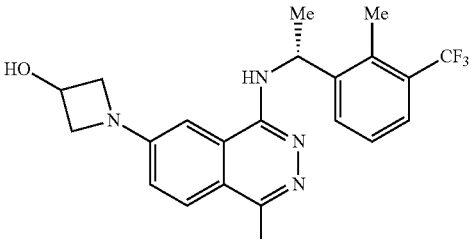<br>(R)-1-(1-methyl-4-((1-(2-methyl-3-(trifluoromethyl)phenyl)ethyl)amino)phthalazin-6-yl)azetidin-3-ol | $^1$H NMR (400 MHz, DMSO-$d_6$) δ = 14.61 (br s, 1H), 8.44 (br d, J = 6.4 Hz, 1H), 8.09 (d, J = 8.8 Hz, 1H), 7.77 (d, J = 8.0 Hz, 1H), 7.55 (d, J = 8.0 Hz, 1H), 7.46 (s, 1H), 7.34 (t, J = 7.6 Hz, 1H), 7.13 (dd, J = 2.0, 9.2 Hz, 1H), 5.96 (d, J = 6.0 Hz, 1H), 5.43 (br t, J = 6.8 Hz, 1H), 4.76-4.66 (m, 1H), 4.49-4.39 (m, 2H), 4.00-3.90 (m, 2H), 2.69 (s, 3H), 2.56 (s, 3H), 1.61 (d, J = 6.8 Hz, 3H). LCMS [M + 1]$^+$: 417.1. |
| 10-49 | 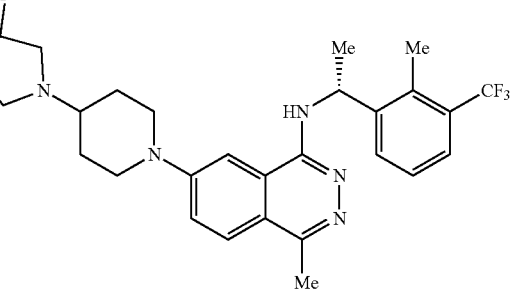<br>(R)-7-(4-(3,3-difluoropyrrolidin-1-yl)piperidin-1-yl)-4-methyl-N-(1-(2-methyl-3-(trifluoromethyl)phenyl)ethyl)phthalazin-1-amine<br>Formate salt | $^1$H NMR (400 MHz, DMSO-$d_6$) δ = 8.16 (s, 1H), 7.80-7.74 (m, 2H), 7.62-7.54 (m, 2H), 7.51 (d, J = 7.6 Hz, 1H), 7.42 (d, J = 6.4 Hz, 1H), 7.31 (t, J = 7.6 Hz, 1H), 5.71-5.62 (m, 1H), 4.02-3.98 (m, 2H), 3.04-2.96 (m, 5H), 2.80 (t, J = 7.2 Hz, 2H), 2.58 (s, 3H), 2.43-2.39 (m, 2H), 2.37-2.17 (m, 3H), 2.03-1.90 (m, 2H), 1.55 (d, J = 7.2 Hz, 3H), 1.54-1.45 (m, 2H). LCMS [M + 1]$^+$: 534.4. |
| 10-50 | 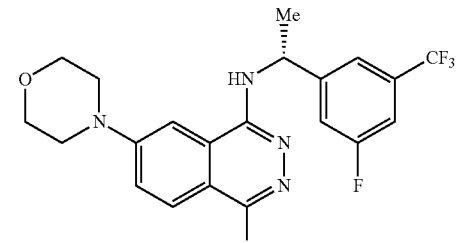<br>(R)-N-(1-(3-fluoro-5-(trifluoromethyl)phenyl)ethyl)-4-methyl-7-morpholinophthalazin-1-amine | $^1$H NMR (400 MHz, DMSO-$d_6$) δ = 7.84 (d, J = 8.8 Hz, 1H), 7.64 (s, 1H), 7.55-7.62 (m, 3H), 7.48 (d, J = 10.4 Hz, 1H), 7.36 (d, J = 7.6 Hz, 1H), 5.50-5.54 (m, 1H), 3.84-3.82 (m, 4H), 3.42-3.44 (m, 4H), 2.55 (s, 3H), 1.61 (d, J = 7.2 Hz, 3H). LCMS [M + 1]$^+$: 435.2. |
| 10-51 | 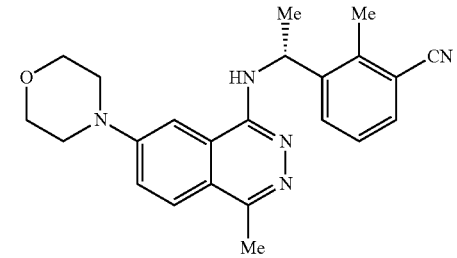<br>(R)-2-methyl-3-(1-((4-methyl-7-morpholinophthalazin-1-yl)amino)ethyl)benzonitrile | $^1$H NMR (400 MHz, CD$_3$OD) δ = 7.86 (d, J = 8.8 Hz, 1H), 7.77-7.68 (m, 1H), 7.58-7.52 (m, 2H), 7.46 (dd, J = 1.2, 7.6 Hz, 1H), 7.22 (t, J = 8.0 Hz, 1H), 5.61 (q, J = 7.2 Hz, 1H), 3.92-3.84 (m, 4H), 3.49-3.41 (m, 4H), 2.72 (s, 3H), 2.59 (s, 3H), 1.61 (d, J = 6.8 Hz, 3H). LCMS [M + 1]$^+$: 388.3. |

TABLE 10-continued

| Ex. # | Structure | Spectral Data |
|---|---|---|
| 10-52 | 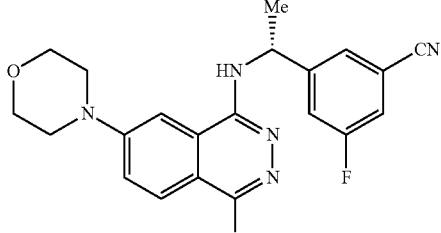<br>(R)-3-fluoro-5-(1-((4-methyl-7-morpholinophthalazin-1-yl)amino)ethyl)benzonitrile | $^1$H NMR (400 MHz, CD$_3$OD) δ = 7.89 (d, J = 9.2 Hz, 1H), 7.63 (t, J = 1.2 Hz, 1H), 7.58-7.49 (m, 3H), 7.33-7.28 (m, 1H), 5.42 (q, J = 6.8 Hz, 1H), 3.89-3.84 (m, 4H), 3.46-3.40 (m, 4H), 2.62 (s, 3H), 1.66 (d, J = 7.2 Hz, 3H). LCMS [M + 1]$^+$: 392.2. |
| 10-53 | 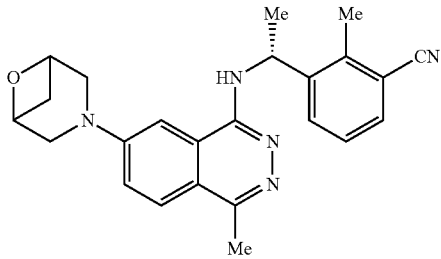 [SMILES: Cc1c(C#N)cccc1[C@@H](C)Nc1nnc(C)c2ccc(N3CC4CC(C3)O4)cc12]<br>3-((1R)-1-((7-(6-oxa-3-azabicyclo[3.1.1]heptan-3-yl)-4-methylphthalazin-1-yl)amino)ethyl)-2-methylbenzonitrile<br>Formate salt | $^1$H NMR (400 MHz, CDCl$_3$) δ = 7.66 (t, J = 8.4 Hz, 2H), 7.48-7.36 (m, 2H), 7.28-7.25 (m, 2H), 7.15 (t, J = 7.6 Hz, 1H), 5.52-5.36 (m, 1H), 4.88 (d, J = 6.4 Hz, 2H), 3.92-3.73 (m, 4H), 3.49-3.35 (m, 1H), 2.72 (s, 3H), 2.57 (s, 3H), 2.01 (d, J = 9.2 Hz, 1H), 1.65 (d, J = 6.8 Hz, 3H). LCMS [M + 1]$^+$: 400.2. |
| 10-54 | 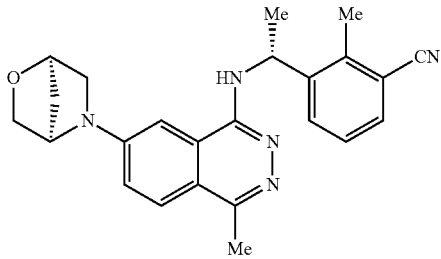 [SMILES: Cc1c(C#N)cccc1[C@@H](C)Nc1nnc(C)c2ccc(N3C[C@H]4C[C@@H]3CO4)cc12]<br>3-((R)-1-((7-((1R,4R)-2-oxa-5-azabicyclo[2.2.1]heptan-5-yl)-4-methylphthalazin-1-yl)amino)ethyl)-2-methylbenzonitrile<br>Formate salt | $^1$H NMR (400 MHz, CD$_3$OD) δ = 8.55 (br s, 1H), 8.04 (d, J = 8.8 Hz, 1H), 7.72 (d, J = 7.6 Hz, 1H), 7.52 (d, J = 7.6 Hz, 1H), 7.44-7.34 (m, 2H), 7.27 (t, J = 8.4 Hz, 1H), 5.47 (q, J = 6.8 Hz, 1H), 4.98 (s, 1H), 4.82 (s, 1H), 3.97 (d, J = 7.2 Hz, 1H), 3.88 (d, J = 7.6 Hz, 1H), 3.72 (d, J = 10.4 Hz, 1H), 3.43 (d, J = 10.4 Hz, 1H), 2.73 (s, 3H), 2.69 (s, 3H), 2.11 (s, 2H), 1.64 (d, J = 7.2 Hz, 3H). LCMS [M + 1]$^+$: 400.2. |
| 10-55 | 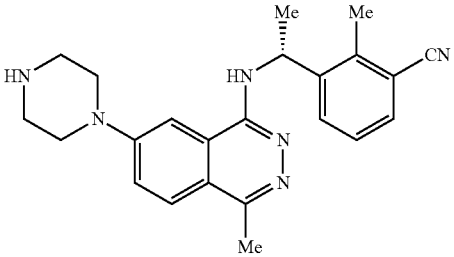<br>(R)-2-methyl-3-(1-((4-methyl-7-(piperazin-1-yl)phthalazin-1-yl)amino)ethyl)benzonitrile<br>Formate salt | $^1$H NMR (400 MHz, CD$_3$OD) δ = 8.49 (br s, 1H), 8.11 (d, J = 8.8 Hz, 1H), 7.79-7.69 (m, 3H), 7.52 (d, J = 7.2 Hz, 1H), 7.27 (t, J = 7.6 Hz, 1H), 5.50 (q, J = 6.8 Hz, 1H), 3.83-3.77 (m, 4H), 3.29-3.25 (m, 4H), 2.74 (s, 3H), 2.72 (s, 3H), 1.65 (d, J = 6.8 Hz, 3H). LCMS [M + 1]$^+$: 387.1. |

TABLE 10-continued

| Ex. # | Structure | Spectral Data |
|---|---|---|
| 10-56 | 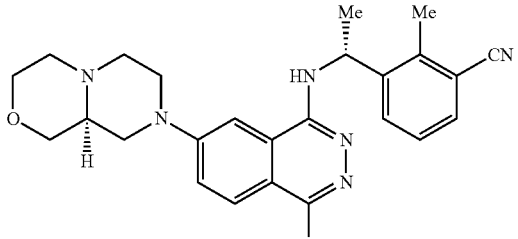<br>3-((R)-1-((7-((S)-hexahydropyrazino[2,1-c][1,4]oxazin-8(1H)-yl)-4-methylphthalazin-1-yl)amino)ethyl)-2-methylbenzonitrile<br>Formate salt | $^1$H NMR (400 MHz, CD$_3$OD) δ = 8.53 (s, 1H), 7.98 (d, J = 8.8 Hz, 1H), 7.72 (d, J = 8.0 Hz, 1H), 7.67-7.59 (m, 2H), 7.50 (d, J = 7.6 Hz, 1H), 7.25 (t, J = 7.6 Hz, 1H), 5.59-5.49 (m, 1H), 4.14 (d, J = 11.6 Hz, 1H), 3.98 (d, J = 12.0 Hz, 1H), 3.93-3.83 (m, 2H), 3.78-3.68 (m, 1H), 3.37 (d, J = 10.8 Hz 1H), 3.16 (dt, J = 2.8, 12.0 Hz, 1H), 2.99 (br d, J = 11.6 Hz, 1H), 2.81 (d, J = 11.2 Hz 1H), 2.73 (s, 3H), 2.71-2.67 (m, 1H), 2.66 (s, 3H), 2.53-2.37 (m, 3H), 1.63 (d, J = 6.8 Hz, 3H). LCMS [M + 1]$^+$: 443.2. |
| 10-57 | 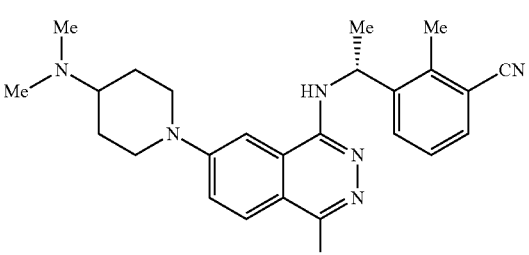<br>(R)-3-(1-((7-(4-(dimethylamino)piperidin-1-yl)-4-methylphthalazin-1-yl)amino)ethyl)-2-methylbenzonitrile<br>Formate salt | $^1$H NMR (400 MHz, CD$_3$OD) δ = 8.53 (br s, 1H), 8.03 (br d, J = 9.2 Hz, 1H), 7.76-7.62 (m, 3H), 7.52 (br d, J = 8.4 Hz, 1H), 7.27 (t, J = 7.6 Hz, 1H), 5.55-5.45 (m, 1H), 4.39 (br d, J = 12.8 Hz, 2H), 3.13 (t, J = 12.8 Hz, 2H), 3.03-2.94 (m, 1H), 2.73 (s, 3H), 2.68 (s, 3H), 2.62-2.54 (m, 6H), 2.16 (d, J = 11.6 H, 2H), 1.76-1.67 (m, 2H), 1.65 (d, J = 7.2 Hz, 3H). LCMS [M + 1]$^+$: 429.2. |
| 10-58 | 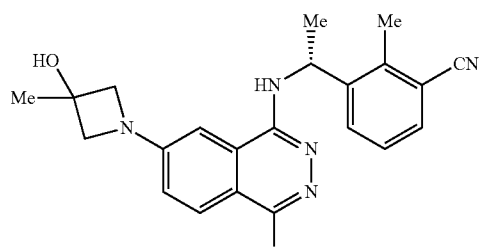<br>(R)-3-(1-((7-(3-hydroxy-3-methylazetidin-1-yl)-4-methylphthalazin-1-yl)amino)ethyl)-2-methylbenzonitrile | $^1$H NMR (400 MHz, CD$_3$OD) δ = 8.10 (d, J = 8.8 Hz, 1H), 7.73 (d, J = 7.6 Hz, 1H), 7.55-7.51 (m, 1H), 7.34-7.26 (m, 2H), 7.16 (dd, J = 2.0, 9.2 Hz, 1H), 5.42 (d, J = 6.8 Hz, 1H), 4.20-4.16 (m, 2H), 4.14-4.08 (m, 2H), 2.74 (s, 3H), 2.73 (s, 3H), 1.66 (d, J = 7.2 Hz, 3H), 1.62 (s, 3H). LCMS [M + 1]$^+$: 388.2. |
| 10-59 | 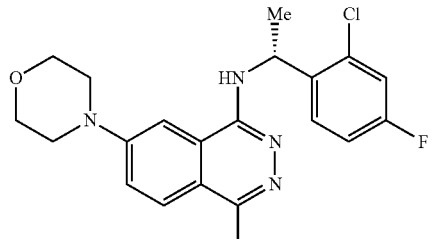<br>(R)-N-(1-(2-chloro-4-fluorophenyl)ethyl)-4-methyl-7-morpholinophthalazin-1-amine<br>Hydrochloride salt | $^1$H NMR (400 MHz, DMSO-d$_6$) δ = 14.8 (s, 1H), 8.60 (d, J = 6.4 Hz, 1H), 8.17 (d, J = 9.2 Hz, 1H), 7.92 (d, J = 0.8 Hz, 1H), 7.77 (dd, J = 2.4, 9.6 Hz, 1H), 7.58 (dd, J = 6.4, 8.8 Hz, 1H), 7.44 (dd, J = 2.8, 8.8 Hz, 1H), 7.22-7.15 (m, 1H), 5.47 (m, 1H), 3.79-3.86 (m, 4H), 3.74-3.66 (m, 4H), 2.73 (s, 3H), 1.63 (d, J = 6.8 Hz, 3H). LCMS [M + 1]$^+$: 401.1. |

TABLE 10-continued

| Ex. # | Structure | Spectral Data |
|---|---|---|
| 10-60 | 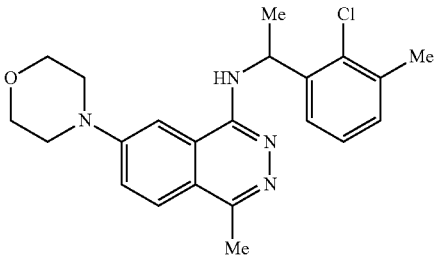 [SMILES: Cc1cccc(C(C)Nc2nnc(C)c3ccc(N4CCOCC4)cc23)c1Cl]<br>N-(1-(2-chloro-3-methylphenyl)ethyl)-4-methyl-7-morpholinophthalazin-1-amine | $^1$H NMR (400 MHz, DMSO-$d_6$) δ = 8.18 (s, 1H), 8.09-8.07 (m, 1H), 7.80-7.79 (m, 1H), 7.74-7.71 (m, 1H), 7.32-7.31 (m, 1H), 7.23-7.21 (m, 1H), 7.18-7.14 (m, 1H), 5.61-5.54 (m, 1H), 3.85-3.82 (m, 4H), 3.63-3.62 (m, 4H), 2.66 (s, 3H), 2.37 (s, 3H), 1.62-1.61 (m, 3H). LCMS [M + 1]$^+$: 397.1. |
| 10-61 | 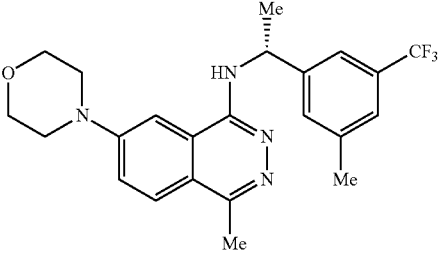 [SMILES: Cc1cc([C@@H](C)Nc2nnc(C)c3ccc(N4CCOCC4)cc23)cc(C(F)(F)F)c1]<br>(R)-4-methyl-N-(1-(3-methyl-5-(trifluoromethyl)phenyl)ethyl)-7-morpholinophthalazin-1-amine | $^1$H NMR (400 MHz, CD$_3$OD) δ = 8.19-8.16 (m, 1H), 7.74-7.73 (m, 2H) 7.53 (s, 2H), 7.34 (s, 1H), 5.29-5.27 (m, 1H), 3.91-3.89 (m, 4H), 3.71-3.69 (m, 4H), 2.77 (s, 3H), 2.39 (s, 3H), 1.71-1.69 (m, 3H). LCMS [M + 1]$^+$: 431.1. |
| 10-62 | 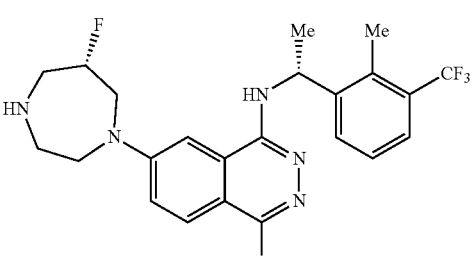<br>7-((S)-6-fluoro-1,4-diazepan-1-yl)-4-methyl-N-((R)-1-(2-methyl-3-(trifluoromethyl)phenyl)ethyl)phthalazin-1-amine Hydrochloride salt | $^1$H NMR (400 MHz, DMSO-$d_6$) δ = 14.77 (s, 1H), 9.84 (s, 1H), 8.92 (s, 1H), 8.78-8.77 (m, 1H), 8.19-8.16 (m, 1H), 7.89 (s, 1H), 7.83-7.82 (m, 1H), 7.73-7.71 (m, 1H), 7.59-7.55 (m, 1H), 7.37-7.33 (m, 1H), 5.49-5.37 (m, 2H), 4.61-4.55 (m, 1H), 4.25-4.21 (m, 1H), 4.09-3.97 (m, 2H), 3.62-3.58 (m, 2H), 3.48 (s, 2H), 2.73 (s, 3H), 2.56 (s, 3H), 1.86-1.84 (m, 3H). LCMS [M + 1]$^+$: 462.1. |
| 10-63 | 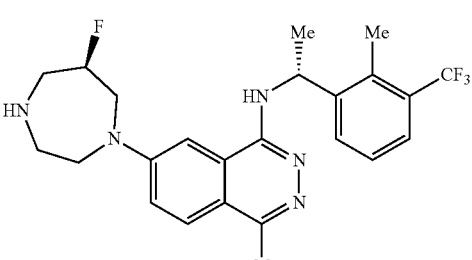<br>7-((R)-6-fluoro-1,4-diazepan-1-yl)-4-methyl-N-((R)-1-(2-methyl-3-(trifluoromethyl)phenyl)ethyl)phthalazin-1-amine Hydrochloride salt | $^1$H NMR (400 MHz, DMSO-$d_6$) δ = 14.75 (s, 1H), 9.76 (s, 1H), 8.92 (s, 1H), 8.69 (s, 1H), 8.19-8.16 (m, 1H), 7.85 (s, 1H), 7.79-7.77 (m, 1H), 7.73-7.71 (m, 1H), 7.57-7.55 (m, 1H), 7.37-7.33 (m, 1H), 5.51-5.34 (m, 2H), 4.56-4.50 (m, 1H), 4.20 (s, 1H), 4.10-4.00 (m, 2H), 3.55 (s, 2H), 3.49 (s, 2H), 2.73 (s, 3H), 2.58 (s, 3H), 1.85-1.84 (m, 3H). LCMS [M + 1]$^+$: 462.1. |

TABLE 10-continued

| Ex. # | Structure | Spectral Data |
|---|---|---|
| 10-64 | 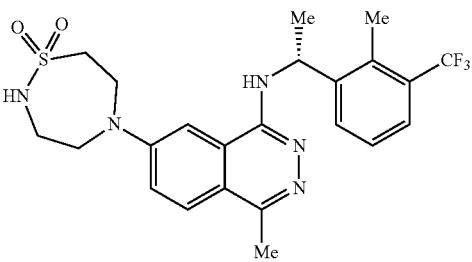 [SMILES: Cc1c([C@@H](C)Nc2nnc(C)c3ccc(N4CCNS(=O)(=O)CC4)cc23)cccc1C(F)(F)F]<br>(R)-5-(1-methyl-4-((1-(2-methyl-3-(trifluoromethyl)phenyl)ethyl)amino)phthalazin-6-yl)-1,2,5-thiadiazepane 1,1-dioxide | $^1$H NMR (400 MHz, Methanol-$d_4$) δ = 8.02 (d, J = 9.1 Hz, 1H), 7.69 (d, J = 7.8 Hz, 1H), 7.55-7.48 (m, 3H), 7.24 (t, J = 7.9 Hz, 1H), 5.64 (q, J = 6.9 Hz, 1H), 4.17-4.09 (m, 4H), 3.58-3.54 (m, 2H), 3.39 (t, J = 6.0 Hz, 2H), 2.66 (s, 3H), 2.61 (d, J = 1.6 Hz, 3H), 1.64 (d, J = 7.0 Hz, 3H). LCMS [M + 1]$^+$: 494.4 |
| 10-65 | 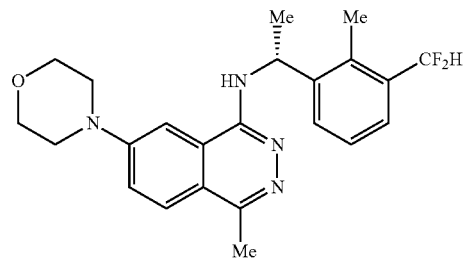 [SMILES: Cc1c(C(F)F)cccc1[C@@H](C)Nc1nnc(C)c2ccc(N3CCOCC3)cc12]<br>(R)-N-(1-(3-(difluoromethyl)-2-methylphenyl)ethyl)-4-methyl-7-morpholinophthalazin-1-amine<br>Hydrochloride salt | $^1$H NMR (400 MHz, CD$_3$OD) δ 8.16 (d, J = 9.3 Hz, 1H), 7.78-7.69 (m, 2H), 7.59 (d, J = 7.8 Hz, 1H), 7.38 (d, J = 7.6 Hz, 1H), 7.23 (t, J = 7.7 Hz, 1H), 6.94 (t, J = 55.3 Hz, 1H), 5.53 (q, J = 6.9 Hz, 1H), 4.61 (s, 3H), 3.93-3.87 (m, 4H), 3.73-3.64 (m, 4H), 2.75 (s, 3H), 2.56 (s, 3H), 1.66 (d, J = 6.9 Hz, 3H). LCMS [M + 1]$^+$: 413.2. |
| 10-66 | 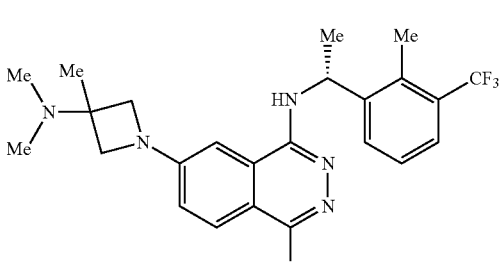<br>(R)-7-(3-(dimethylamino)-3-methylazetidin-1-yl)-4-methyl-N-(1-(2-methyl-3-(trifluoromethyl)phenyl)ethyl)phthalazin-1-amine | $^1$H NMR (400 MHz, CDCl$_3$) δ = 7.76 (d, J = 8.8 Hz, 1H), 7.67 (d, J = 7.8 Hz, 1H), 7.53 (d, J = 7.8 Hz, 1H), 7.25-7.19 (m, 1H), 6.90 (dd, J = 8.9, 2.2 Hz, 1H), 6.39 (d, J = 2.2 Hz, 1H), 5.85 (s, 1H), 4.88 (s, 1H), 3.87 (dd, J = 7.1, 3.5 Hz, 2H), 3.76 (dd, J = 7.1, 3.6 Hz, 2H), 2.68 (s, 3H), 2.56 (d, J = 1.7 Hz, 3H), 2.23 (s, 6H), 1.65 (d, J = 6.7 Hz, 3H), 1.39 (s, 3H). LCMS [M + 1]$^+$: 458.4. |
| 10-67 | 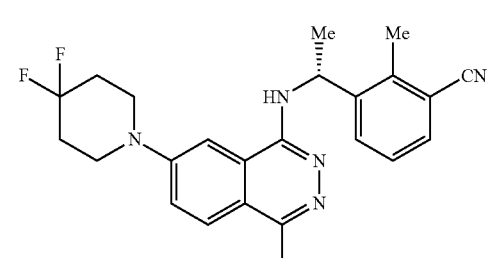<br>(R)-3-(1-((7-(4,4-difluoropiperidin-1-yl)-4-methylphthalazin-1-yl)amino)ethyl)-2-methylbenzonitrile | $^1$H NMR (400 MHz, CD$_3$OD) δ 7.96 (d, J = 9.1 Hz, 1H), 7.76-7.63 (m, 3H), 7.50 (dd, J = 7.7, 1.4 Hz, 1H), 7.25 (t, J = 7.8 Hz, 1H), 5.58 (q, J = 7.0 Hz, 1H), 3.75 (t, J = 5.8 Hz, 5H), 2.74 (s, 3H), 2.64 (s, 3H), 2.21-2.10 (m, 5H), 1.64 (d, J = 7.0 Hz, 3H). LCMS [M + 1]$^+$: 422.2. |

| Ex. # | Structure | Spectral Data |
|---|---|---|
| 10-68 | 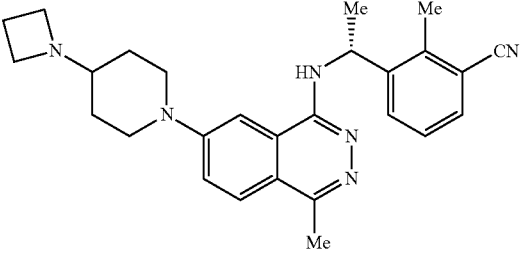<br>(R)-3-(1-((7-(4-(azetidin-1-yl)piperidin-1-yl)-4-methylphthalazin-1-yl)amino)ethyl)-2-methylbenzonitrile | ¹H NMR (400 MHz, CD₃OD) δ = 7.87-7.83 (m, 1H), 7.73 (dd, J = 8.0, 1.4 Hz, 1H), 7.57-7.53 (m, 2H), 7.48 (dd, J = 7.6, 1.3 Hz, 1H), 7.24 (t, J = 7.8 Hz, 1H), 5.62 (q, J = 6.9 Hz, 1H), 4.12 (d, J = 13.0 Hz, 2H), 2.98 (td, J = 12.7, 2.6 Hz, 2H), 2.74 (s, 3H), 2.59 (s, 3H), 2.45-2.34 (m, 1H), 2.12 (p, J = 7.1 Hz, 2H), 1.94-1.85 (m, 2H), 1.62 (d, J = 6.9 Hz, 3H), 1.37 (t, J = 12.1 Hz, 2H). LCMS [M + 1]⁺: 441.2. |
| 10-69 | 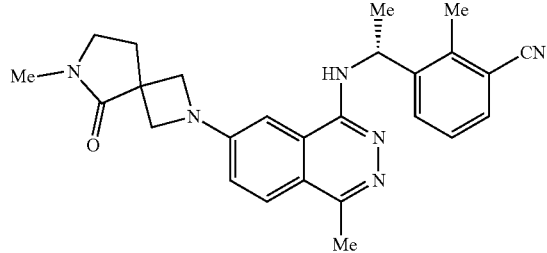 [SMILES: Cc1c(C#N)cccc1[C@@H](C)Nc1nnc(C)c2ccc(N3CC4(CCN(C)C4=O)C3)cc12]<br>(R)-2-methyl-3-(1-((4-methyl-7-(6-methyl-5-oxo-2,6-diazaspiro[3.4]octan-2-yl)phthalazin-1-yl)amino)ethyl)benzonitrile | ¹H NMR (400 MHz, DMSO-d₆) δ 7.80 (d, J = 8.9 Hz, 1H), 7.74 (dd, J = 7.9, 1.4 Hz, 1H), 7.59 (dd, J = 7.6, 1.4 Hz, 1H), 7.30 (dd, J = 9.2, 6.6 Hz, 2H), 7.19 (d, J = 2.3 Hz, 1H), 7.01 (dd, J = 8.9, 2.2 Hz, 1H), 5.58-5.49 (m, 1H), 4.11 (t, J = 8.2 Hz, 2H), 4.00 (dd, J = 7.7, 4.3 Hz, 2H), 2.79 (s, 3H), 2.66 (s, 3H), 2.44 (t, J = 6.9 Hz, 2H), 1.53 (d, J = 7.0 Hz, 3H). LCMS [M + 1]⁺: 441.4. |
| 10-70 | 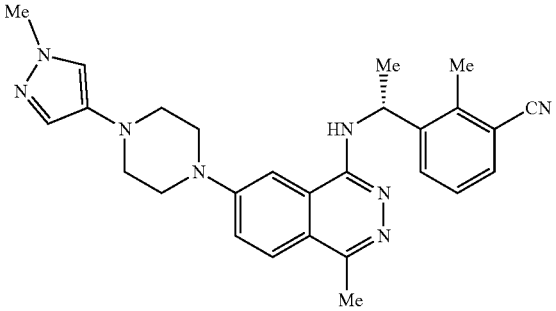 [SMILES: Cc1c(C#N)cccc1[C@@H](C)Nc1nnc(C)c2ccc(N3CCN(c4cnn(C)c4)CC3)cc12]<br>(R)-2-methyl-3-(1-((4-methyl-7-(4-(1-methyl-1H-pyrazol-4-yl)piperazin-1-yl)phthalazin-1-yl)amino)ethyl)benzonitrile | ¹H NMR (400 MHz, DMSO-d₆) δ 7.81 (d, J = 8.9 Hz, 1H), 7.75 (dd, J = 8.0, 1.4 Hz, 1H), 7.65-7.57 (m, 3H), 7.41 (d, J = 6.8 Hz, 1H), 7.36 (s, 1H), 7.30 (t, J = 7.8 Hz, 1H), 7.25 (s, 1H), 5.56 (q, J = 6.7 Hz, 1H), 3.75 (s, 3H), 3.59-3.53 (m, 4H), 3.05 (t, J = 5.1 Hz, 4H), 2.67 (s, 3H), 2.53 (s, 3H), 1.55 (d, J = 6.9 Hz, 3H). LCMS [M + 1]⁺: 467.2. |
| 10-71 | 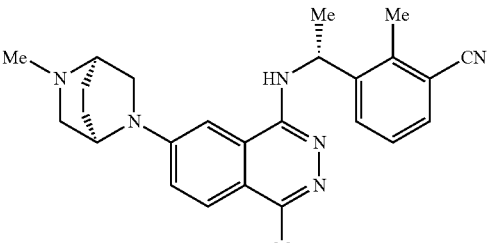<br>2-methyl-3-((R)-1-((4-methyl-7-((1R,4R)-5-methyl-2,5-diazabicyclo[2.2.2]octan-2-yl)phthalazin-1-yl)amino)ethyl)benzonitrile | ¹H NMR (400 MHz, CDCl₃) δ = 7.77 (d, J = 9.2 Hz, 1H), 7.67 (d, J = 7.2 Hz, 1H), 7.45 (dd, J = 1.2, 7.6 Hz, 1H), 7.26 (s, 1H), 7.22-7.14 (m, 2H), 6.56 (d, J = 2.4 Hz, 1H), 5.73 (br t, J = 6.4 Hz, 1H), 4.95 (br d, J = 4.8 Hz, 1H), 4.03 (br s, 1H), 3.90 (m, 1H), 3.31 (m, 1H), 3.10 (m, 1H), 2.96-2.87 (m, 2H), 2.68 (d, J = 7.2 Hz, 6H), 2.47 (s, 3H), 2.24-2.13 (m, 1H), 2.07-1.96 (m, 1H), 1.93 (m, 1H), 1.61 (d, J = 6.4 Hz, 3H). LCMS [M + 1]⁺: 427.2. |

TABLE 10-continued

| Ex. # | Structure | Spectral Data |
|---|---|---|
| 10-72 | 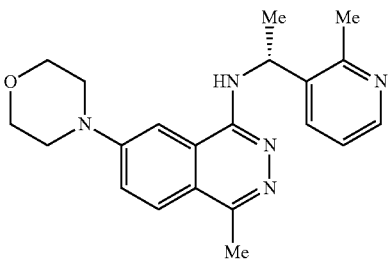<br>(R)-4-methyl-N-(1-(2-methylpyridin-3-yl)ethyl)-7-morpholinophthalazin-1-amine | $^1$H NMR (400 MHz, CD$_3$OD) δ = 8.21 (dd, J = 1.6, 4.8 Hz, 1H), 7.90 (br d, J = 8.4 Hz, 1H), 7.85 (dd, J = 1.6, 7.6 Hz, 1H), 7.62-7.53 (m, 2H), 7.16 (dd, J = 1.6, 7.6 Hz, 1H), 5.59 (q, J = 6.8 Hz, 1H), 3.96-3.84 (m, 4H), 3.50-3.40 (m, 4H), 2.73 (s, 3H), 2.61 (s, 3H), 1.64 (d, J = 6.8 Hz, 3H). LCMS [M + 1]$^+$: 364.2. |
| 10-73 | 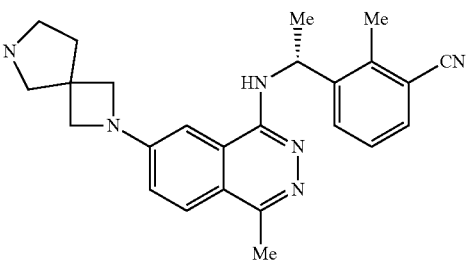<br>(R)-2-methyl-3-(1-((4-methyl-7-(6-methyl-2,6-diazaspiro[3.4]octan-2-yl)phthalazin-1-yl)amino)ethyl)benzonitrile<br>formate salt | $^1$H NMR (400 MHz, CD$_3$OD) δ = 8.55 (s, 1H), 8.01 (d, J = 9.2 Hz, 1H), 7.72 (d, J = 8.0 Hz, 1H), 7.55-7.50 (m, 1H), 7.30-7.26 (m, 1H), 7.25 (d, J = 2.0 Hz, 1H), 7.12-7.08 (m, 1H), 5.57-5.41 (m, 1H), 4.24-4.16 (m, 2H), 4.16-4.10 (m, 2H), 3.04 (s, 2H), 2.84 (t, J = 6.8 Hz, 2H), 2.74 (s, 3H), 2.68 (s, 3H), 2.52 (s, 3H), 2.32 (t, J = 6.8 Hz, 2H), 1.64 (d, J = 6.8 Hz, 3H). LCMS [M + 1]$^+$: 427.3. |
| 10-74 | 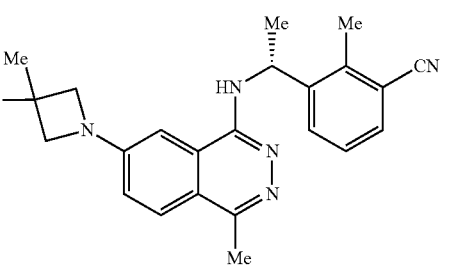<br>(R)-3-(1-((7-(3-(dimethylamino)-3-methylazetidin-1-yl)-4-methylphthalazin-1-yl)amino)ethyl)-2-methylbenzonitrile<br>Hydrochloride salt | $^1$H NMR (400 MHz, CD$_3$OD) δ = 8.19 (d, J = 9.2 Hz, 1H), 7.79 (d, J = 7.2 Hz, 1H), 7.61-7.49 (m, 2H), 7.34-7.19 (m, 2H), 5.44 (q, J = 7.2 Hz, 1H), 4.56 (dd, J = 5.6, 9.6 Hz, 2H), 4.29 (dd, J = 6.0, 10.0 Hz, 2H), 2.94 (s, 6H), 2.76 (d, J = 9.6 Hz, 6H), 1.83 (s, 3H), 1.69 (d, J = 7.2 Hz, 3H). LCMS [M + 1]$^+$: 415.3. |
| 10-75 | 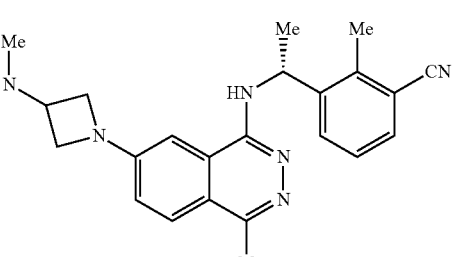<br>(R)-3-(1-((7-(3-(dimethylamino)azetidin-1-yl)-4-methylphthalazin-1-yl)amino)ethyl)-2-methylbenzonitrile<br>Hydrochloride salt | $^1$H NMR (400 MHz, CD$_3$OD) δ = 8.19 (d, J = 9.2 Hz, 1H), 7.79 (d, J = 8.0 Hz, 1H), 7.60-7.51 (m, 2H), 7.33-7.24 (m, 2H), 5.44 (q, J = 6.8 Hz, 1H), 4.67-4.57 (m, 2H), 4.51 (td, J = 5.2, 10.4 Hz, 2H), 4.47-4.38 (m, 1H), 3.01 (s, 6H), 2.76 (d, J = 7.2 Hz, 6H), 1.69 (d, J = 7.2 Hz, 3H). LCMS [M + 1]$^+$: 401.2. |

TABLE 10-continued

| Ex. # | Structure | Spectral Data |
|---|---|---|
| 10-76 | 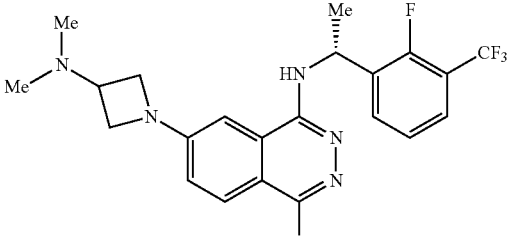

(R)-7-(3-(dimethylamino)azetidin-1-yl)-N-(1-(2-fluoro-3-(trifluoromethyl)phenyl)ethyl)-4-methylphthalazin-1-amine | $^1$H NMR (400 MHz, DMSO-d$_6$): δ = 7.79 (d, J = 8.8 Hz, 1H), 7.71 (t, J = 6.8 Hz, 1H), 7.60 (t, J = 6.8 Hz, 1H), 7.33-7.22 (m, 2H), 7.20 (s, 1H), 7.08-6.93 (m, 1H), 5.73-5.70 (m, 1H), 4.21-4.04 (m, 2H), 3.90-3.70 (m, 2H), 3.29-3.27 (m, 1H), 2.52-2.51 (m, 3H), 2.16 (s, 6H), 1.61 (d, J = 6.8 Hz, 3H). LCMS [M + 1]$^+$: 448.3. |
| 10-77 | 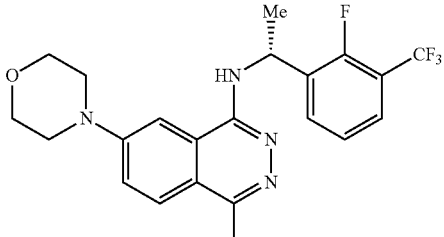

(R)-N-(1-(2-fluoro-3-(trifluoromethyl)phenyl)ethyl)-4-methyl-7-morpholinophthalazin-1-amine | $^1$H NMR (400 MHz, CD$_3$OD) δ 7.91 (dd, J = 13.0, 8.8 Hz, 1H), 7.71-7.55 (m, 3H), 7.48 (d, J = 7.5 Hz, 1H), 7.18 (t, J = 7.9 Hz, 1H), 5.72 (q, J = 7.0 Hz, 1H), 3.97-3.88 (m, 4H), 3.53-3.45 (m, 4H), 2.62-2.57 (m, 3H), 1.69 (d, J = 7.0 Hz, 3H). LCMS [M + 1]$^+$: 435.2. |
| 10-78 | 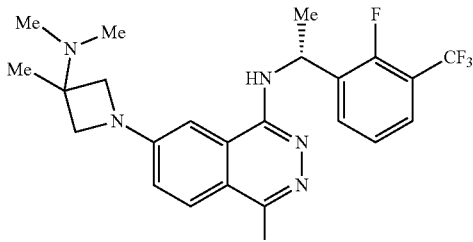

(R)-7-(3-(dimethylamino)-3-methylazetidin-1-yl)-N-(1-(2-fluoro-3-(trifluoromethyl)phenyl)ethyl)-4-methylphthalazin-1-amine | $^1$H NMR (400 MHz, DMSO-d$_6$) δ 7.79 (d, J = 8.9 Hz, 1H), 7.71 (t, J = 7.3 Hz, 1H), 7.60 (t, J = 7.3 Hz, 1H), 7.32-7.19 (m, 3H), 7.03 (dd, J = 8.8, 2.2 Hz, 1H), 3.83-3.74 (m, 4H), 3.29 (s, 3H), 2.15 (s, 6H), 1.61 (d, J = 7.1 Hz, 3H), 1.34 (s, 3H). LCMS [M + 1]$^+$: 462.1. |
| 10-79 | 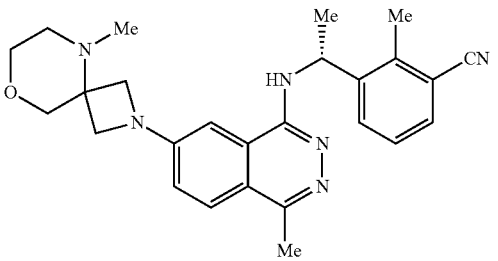 [SMILES: Cc1c(C#N)cccc1[C@@H](C)Nc1nnc(C)c2ccc(N3CC4(COCCN4C)C3)cc12]

(R)-2-methyl-3-(1-((4-methyl-7-(5-methyl-8-oxa-2,5-diazaspiro[3.5]nonan-2-yl)phthalazin-1-yl)amino)ethyl)benzonitrile
Formate salt | $^1$H NMR (400 MHz, CD$_3$OD) δ = 7.99 (d, J = 9.0 Hz, 1H), 7.73 (dd, J = 7.9, 1.3 Hz, 1H), 7.50 (dt, J = 7.7, 1.3 Hz, 1H), 7.29-7.23 (m, 2H), 7.16-7.12 (m, 1H), 5.51 (q, J = 7.0 Hz, 1H), 4.32 (d, J = 9.4 Hz, 2H), 3.86-3.75 (m, 6H), 2.73 (s, 3H), 2.66 (s, 3H), 2.63-2.60 (m, 2H), 2.50 (s, 3H), 1.63 (d, J = 6.9 Hz, 3H). LCMS [M + 1]$^+$: 443.2. |

TABLE 10-continued

| Ex. # | Structure | Spectral Data |
|---|---|---|
| 10-80 | 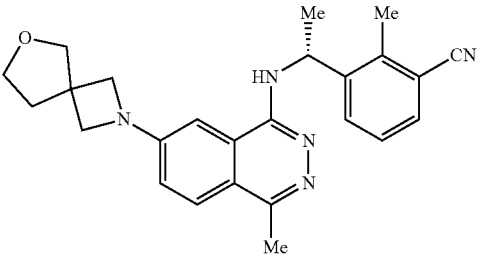 [SMILES: Cc1c(C#N)cccc1[C@@H](C)Nc1nnc(C)c2ccc(N3CC4(CCOC4)C3)cc12]<br>(R)-2-methyl-3-(1-((4-methyl-7-(6-oxa-2-azaspiro[3.4]octan-2-yl)phthalazin-1-yl)amino)ethyl)benzonitrile<br>Hydrochloride salt | $^1$H NMR (400 MHz, DMSO-d$_6$) δ 14.65 (s, 1H), 8.47 (s, 1H), 8.11 (d, J = 9.0 Hz, 1H), 7.77 (d, J = 8.0 Hz, 1H), 7.64 (d, J = 7.5 Hz, 1H), 7.48 (s, 1H), 7.34 (t, J = 7.8 Hz, 1H), 7.18-7.11 (m, 1H), 5.37-5.29 (m, 1H), 4.25-4.15 (m, 4H), 3.91-3.86 (m, 2H), 3.78 (t, J = 6.9 Hz, 2H), 2.69 (s, 3H), 2.66 (s, 3H), 2.24 (t, J = 6.9 Hz, 2H), 1.60 (d, J = 7.0 Hz, 3H). LCMS [M + 1]$^+$: 414.2. |
| 10-81 | 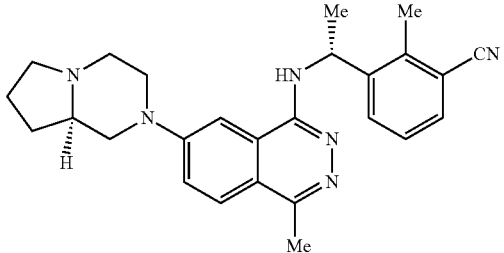 [SMILES: Cc1c(C#N)cccc1[C@@H](C)Nc1nnc(C)c2ccc(N3CCN4CCC[C@@H]4C3)cc12]<br>3-((R)-1-((7-((R)-hexahydropyrrolo[1,2-a]pyrazin-2(1H)-yl)-4-methylphthalazin-1-yl)amino)ethyl)-2-methylbenzonitrile | $^1$H NMR (400 MHz, CD$_3$OD) δ 7.87 (d, J = 9.8 Hz, 1H), 7.73 (dd, J = 7.9, 1.4 Hz, 1H), 7.63-7.56 (m, 2H), 7.47 (d, J = 7.6 Hz, 1H), 7.23 (t, J = 7.8 Hz, 1H), 5.61 (q, J = 6.9 Hz, 1H), 4.20 (d, J = 11.9 Hz, 1H), 4.05 (d, J = 12.5 Hz, 1H), 3.26-3.02 (m, 3H), 2.73 (s, 3H), 2.59 (s, 3H), 2.45 (td, J = 11.4, 3.4 Hz, 1H), 2.28 (q, J = 9.1 Hz, 2H), 2.06-1.83 (m, 4H), 1.62 (d, J = 6.9 Hz, 3H), 1.60-1.51 (m, 1H). LCMS [M + 1]$^+$: 427.3. |
| 10-82 | 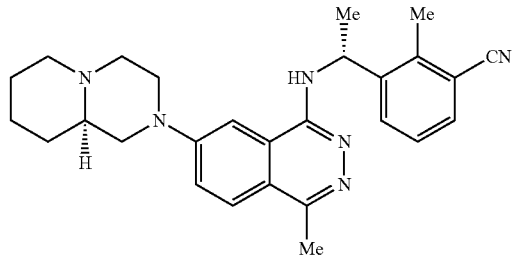 [SMILES: Cc1c(C#N)cccc1[C@@H](C)Nc1nnc(C)c2ccc(N3CCN4CCCC[C@@H]4C3)cc12]<br>2-methyl-3-((R)-1-((4-methyl-7-((R)-octahydro-2H-pyrido[1,2-a]pyrazin-2-yl)phthalazin-1-yl)amino)ethyl)benzonitrile<br>Hydrochloride salt | $^1$H NMR (400 MHz, Methanol-d$_4$) δ 8.25 (d, J = 9.3 Hz, 1H), 7.97 (d, J = 2.4 Hz, 1H), 7.89-7.77 (m, 2H), 7.56 (d, J = 7.6 Hz, 1H), 7.30 (t, J = 7.8 Hz, 1H), 5.47 (q, J = 7.0 Hz, 1H), 4.60 (t, J = 11.8 Hz, 2H), 3.67 (d, J = 12.5 Hz, 1H), 3.59 (t, J = 11.6 Hz, 2H), 3.49-3.35 (m, 1H), 3.33-3.26 (m, 1H), 3.18-3.07 (m, 1H), 2.80 (s, 3H), 2.76 (s, 3H), 2.21-2.13 (m, 1H), 2.05-2.00 (m, 3H), 2.00-1.92 (m, 1H), 1.84-1.68 (m, 5H). LCMS [M + 1]$^+$: 441.3. |
| 10-83 | 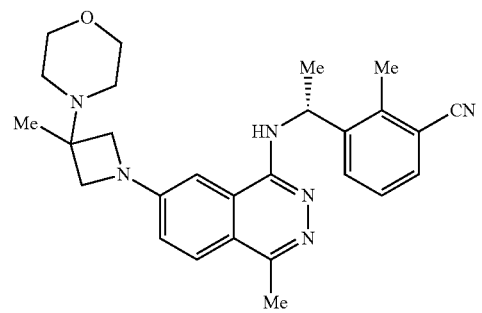 [SMILES: Cc1c(C#N)cccc1[C@@H](C)Nc1nnc(C)c2ccc(N3CC(C)(N4CCOCC4)C3)cc12]<br>(R)-2-methyl-3-(1-((4-methyl-7-(3-methyl-3-morpholinoazetidin-1-yl)phthalazin-1-yl)amino)ethyl)benzonitrile<br>Formate salt | $^1$H NMR (400 MHz, CD$_3$OD) δ = 8.55 (s, 1H), 8.02 (d, J = 9.0 Hz, 1H), 7.74 (dd, J = 7.9, 1.4 Hz, 1H), 7.52 (dd, J = 7.7, 1.4 Hz, 1H), 7.32-7.22 (m, 2H), 7.13 (dd, J = 9.0, 2.3 Hz, 1H), 5.50 (q, J = 6.9 Hz, 1H), 4.01 (t, J = 7.4 Hz, 2H), 3.88 (dd, J = 8.3, 5.9 Hz, 2H), 3.75 (t, J = 4.5 Hz, 3H), 2.72 (s, 3H), 2.69 (s, 3H), 2.59-2.54 (m, 4H), 1.64 (d, J = 7.0 Hz, 3H), 1.48 (s, 3H). LCMS [M + 1]$^+$: 457.3. |

TABLE 10-continued

| Ex. # | Structure | Spectral Data |
|---|---|---|
| 10-84 | 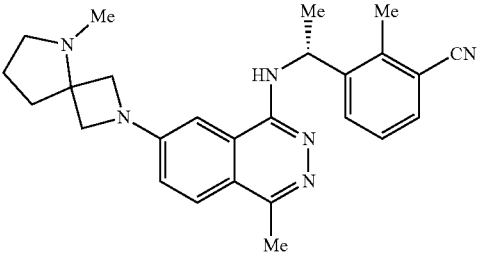 [SMILES: Cc1c(C#N)cccc1[C@@H](C)Nc1nnc(C)c2ccc(N3CC4(CCCN4C)C3)cc12]<br>(R)-2-methyl-3-(1-((4-methyl-7-(5-methyl-2,5-diazaspiro[3.4]octan-2-yl)phthalazin-1-yl)amino)ethyl)benzonitrile | $^1$H NMR (400 MHz, CD$_3$OD) δ 7.88 (d, J = 8.9 Hz, 1H), 7.76 (dd, J = 7.9, 1.4 Hz, 1H), 7.51 (dd, J = 7.7, 1.4 Hz, 1H), 7.26 (t, J = 7.8 Hz, 1H), 7.18 (d, J = 2.3 Hz, 1H), 7.09 (dd, J = 8.9, 2.3 Hz, 1H), 5.63 (q, J = 6.9 Hz, 1H), 4.27 (dd, J = 8.5, 2.6 Hz, 2H), 3.92 (d, J = 8.5 Hz, 2H), 2.84 (t, J = 7.3 Hz, 2H), 2.76 (s, 3H), 2.61 (s, 3H), 2.54 (s, 3H), 2.28-2.20 (m, 2H), 1.96-1.84 (m, 2H), 1.64 (d, J = 6.9 Hz, 3H). LCMS [M + 1]$^+$: 427.3. |
| 10-85 | 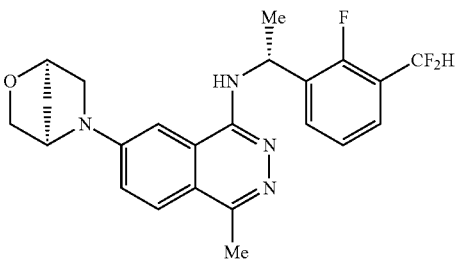<br>7-((1R,4R)-2-oxa-5-azabicyclo[2.2.1]heptan-5-yl)-N-((R)-1-(3-(difluoromethyl)-2-fluorophenyl)ethyl)-4-methylphthalazin-1-amine | $^1$H NMR (400 MHz, DMSO-d$_6$) δ 7.78 (d, J = 9.0 Hz, 1H), 7.57 (t, J = 7.4 Hz, 1H), 7.45 (t, J = 7.1 Hz, 1H), 7.33-7.15 (m, 4H), 5.73-5.65 (m, 1H), 4.92 (s, 1H), 4.75 (s, 1H), 3.91-3.84 (m, 1H), 3.75-3.69 (m, 1H), 3.67-3.60 (m, 1H), 3.27-3.21 (m, 1H), 2.04-1.93 (m, 2H), 1.60 (d, J = 7.1 Hz, 3H), 1.24 (s, 1H). LCMS [M + 1]$^+$: 429.3. |
| 10-86 | 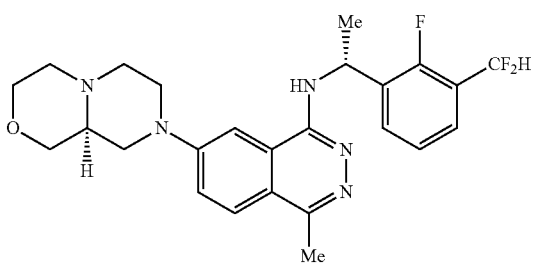<br>N-((R)-1-(3-(difluoromethyl)-2-fluorophenyl)ethyl)-7-((S)-hexahydropyrazino[2,1-c][1,4]oxazin-8(1H)-yl)-4-methylphthalazin-1-amine<br>Formate salt | $^1$H NMR (400 MHz, DMSO-d$_6$) δ 8.15 (s, 1H), 7.82 (d, J = 9.7 Hz, 1H), 7.64-7.54 (m, 2H), 7.46 (t, J = 7.1 Hz, 1H), 7.38-7.34 (m, 1H), 7.27-7.18 (m, 2H), 5.70 (t, J = 7.0 Hz, 1H), 4.12-4.04 (m, 1H), 3.92-3.77 (m, 3H), 3.64-3.53 (m, 1H), 3.27-3.20 (m, 1H), 3.03-2.90 (m, 2H), 2.78-2.71 (m, 1H), 2.70-2.67 (m, 1H), 2.54 (s, 3H), 2.42-2.34 (m, 1H), 2.32-2.22 (m, 2H), 1.62 (d, J = 7.1 Hz, 3H). LCMS [M + 1]$^+$: 472.4. |
| 10-87 | 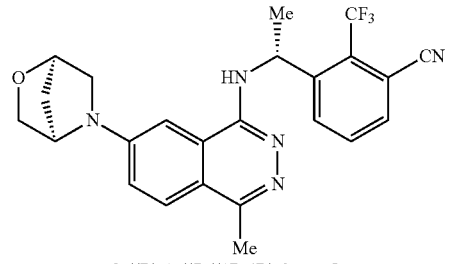<br>3-((R)-1-((7-((1R,4R)-2-oxa-5-azabicyclo[2.2.1]heptan-5-yl)-4-methylphthalazin-1-yl)amino)ethyl)-2-(trifluoromethyl)benzonitrile<br>Hydrochloride salt | $^1$H NMR (400 MHz, CD$_3$OD) δ = 8.42 (d, J = 9.2 Hz, 1H), 8.37 (d, J = 8.0 Hz, 1H), 8.13 (d, J = 7.6 Hz, 1H), 7.98 (t, J = 7.9 Hz, 1H), 7.82-7.77 (m, 1H), 7.75-7.71 (m, 1H), 5.90 (q, J = 7.0 Hz, 1H), 5.37 (s, 1H), 5.14 (s, 1H), 4.30 (d, J = 7.6 Hz, 1H), 4.19 (d, J = 7.7 Hz, 1H), 4.08-4.01 (m, 1H), 3.80 (d, J = 10.5 Hz, 1H), 3.02 (s, 2H), 2.43 (d, J = 3.0 Hz, 3H), 2.03 (d, J = 6.9 Hz, 3H). LCMS [M + 1]$^+$: 454.2. |

Example 11-1

(R)-(4-(1-methyl-4-((1-(2-methyl-3-(trifluoromethyl)phenyl)ethyl)amino)phthalazin-6-yl)piperazin-1-yl)(oxetan-3-yl)methanone

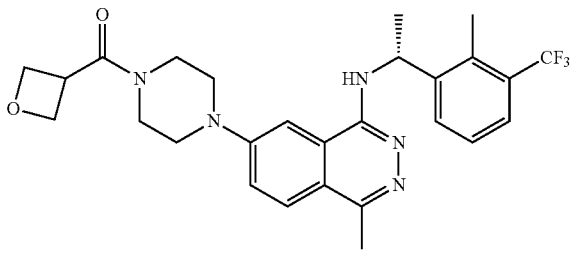

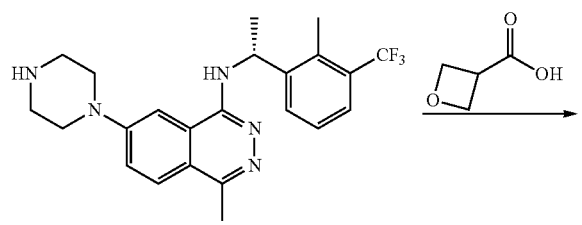 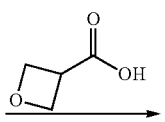

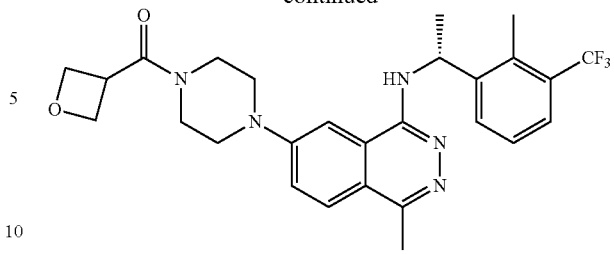

To a solution of (R)-4-methyl-N-(1-(2-methyl-3-(trifluoromethyl)phenyl)ethyl)-7-(piperazin-1-yl)phthalazin-1-amine (20.0 mg, 46.6 μmol, 1.00 eq.) and oxetane-3-carboxylic acid (5.70 mg, 55.9 μmol, 1.20 eq.) in DMF (0.50 mL) was added HATU (21.3 mg, 55.9 μmol, 1.20 eq.) and N,N-diisopropylethylamine (18.1 mg, 140 μmol, 24.3 μL, 3.00 eq.). The mixture was stirred at 25° C. for 1 hour then purified by prep-HPLC (Waters Xbridge 150×25 mm×5 um; mobile phase: mobile phase A: [water (10 mM NH$_4$HCO$_3$), mobile phase B: acetonitrile]; B %: 27%-57%) to give (R)-(4-(1-methyl-4-((1-(2-methyl-3-(trifluoromethyl)phenyl)ethyl)amino)phthalazin-6-yl)piperazin-1-yl)(oxetan-3-yl)methanone (9.00 mg, 17.4 μmol, 37.4% yield, 99.4% purity) as a off-white solid. LCMS [M+1]$^+$: 514.3.

$^1$H NMR (400 MHz, CD$_3$OD) δ=8.02 (d, J=9.2 Hz, 1H), 7.73-7.63 (m, 3H), 7.50 (d, J=7.6 Hz, 1H), 7.25 (t, J=8.0 Hz, 1H), 5.63 (q, J=7.2 Hz, 1H), 4.89 (br s, 4H), 4.33-4.22 (m, 1H), 3.89-3.78 (m, 2H), 3.69-3.58 (m, 4H), 3.55-3.47 (m, 2H), 2.67 (s, 3H), 2.61 (s, 3H), 1.64 (d, J=6.8 Hz, 3H).

Following the teachings of the General Reaction Scheme III, and the procedure described for the preparation of Examples 11-1, the following compounds of Formula (I), Examples 11-2 to 11-6 shown in Table 11 were prepared.

TABLE 11

| Ex. # | Structure | Spectral Data |
|---|---|---|
| 11-2 | (R)-(4-(1-methyl-4-((1-(2-methyl-3-(trifluoromethyl)phenyl)ethyl)amino)phthalazin-6-yl)piperazin-1-yl)(tetrahydro-2H-pyran-4-yl)methanone | $^1$H NMR (400 MHz, CD$_3$OD) δ = 7.95-7.88 (m, 1H), 7.70 (d, J = 8.0 Hz, 1H), 7.63-7.57 (m, 2H), 7.48 (d, J = 7.6 Hz, 1H), 7.23 (t, J = 7.6 Hz, 1H), 5.72 (d, J = 6.8 Hz, 1H), 4.02-3.94 (m, 2H), 3.88-3.78 (m, 4H), 3.61-3.49 (m, 6H), 3.10-3.00 (m, 1H), 2.65-2.57 (m, 6H), 1.89-1.77 (m, 2H), 1.71-1.64 (m, 2H), 1.63 (d, J = 6.8 Hz, 3H). LCMS [M + 1]$^+$: 542.4. |
| 11-3 | 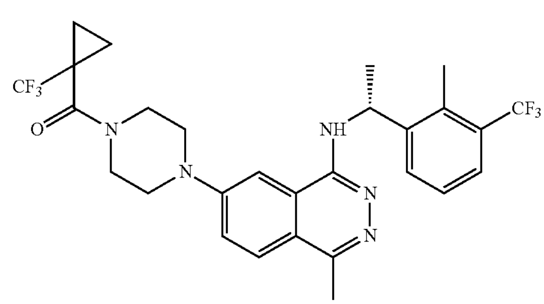 [SMILES: Cc1c([C@@H](C)Nc2nnc(C)c3ccc(N4CCN(C(=O)C5(C(F)(F)F)CC5)CC4)cc23)cccc1C(F)(F)F] | $^1$H NMR (400 MHz, CD$_3$OD) δ = 7.94-7.89 (m, 1H), 7.70 (d, J = 7.6 Hz, 1H), 7.65-7.59 (m, 2H), 7.48 (d, J = 7.6 Hz, 1H), 7.23 (t, J = 7.6 Hz, 1H), 5.72 (q, J = 6.8 Hz, 1H), 3.91 (br s, 4H), 3.60-3.52 (m, 4H), 2.65-2.58 (m, 6H), 1.63 (d, J = 6.8 Hz, 3H), 1.45-1.39 (m, 2H), 1.34-1.25 (m, 2H). LCMS [M + 1]$^+$: 566.4. |

TABLE 11-continued

| Ex. # | Structure | Spectral Data |
|---|---|---|
| | (R)-(4-(1-methyl-4-((1-(2-methyl-3-(trifluoromethyl)phenyl)ethyl)amino)phthalazin-6-yl)piperazin-1-yl)(1-(trifluoromethyl)cyclopropyl)methanone | |
| 11-4 | (structure) (4-(1-methyl-4-(((R)-1-(2-methyl-3-(trifluoromethyl)phenyl)ethyl)amino)phthalazin-6-yl)piperazin-1-yl)((R)-tetrahydrofuran-3-yl)methanone | $^1$H NMR (400 MHz, CD$_3$OD) δ 7.90 (d, J = 8.8 Hz, 1H), 7.70 (d, J = 7.8 Hz, 1H), 7.62-7.57 (m, 2H), 7.49-7.45 (m, 1H), 7.22 (t, J = 7.8 Hz, 1H), 5.71 (q, J = 6.9 Hz, 1H), 4.03-3.85 (m, 3H), 3.85-3.78 (m, 5H), 3.52 (tt, J = 11.6, 3.8 Hz, 6H), 2.24-2.09 (m, 2H), 1.62 (d, J = 6.9 Hz, 3H). LCMS [M + 1]$^+$: 528.3. |
| 11-5 | (structure) (4-(1-methyl-4-(((R)-1-(2-methyl-3-(trifluoromethyl)phenyl)ethyl)amino)phthalazin-6-yl)piperazin-1-yl)((S)-tetrahydrofuran-3-yl)methanone | $^1$H NMR (400 MHz, CD$_3$OD) δ 8.11 (d, J = 9.2 Hz, 1H), 7.75-7.68 (m, 4H), 7.52 (d, J = 7.8 Hz, 1H), 7.27 (t, J = 7.9 Hz, 1H), 5.61 (q, J = 6.9 Hz, 1H), 4.05-3.69 (m, 12H), 3.55 (tt, J = 8.3, 6.3 Hz, 1H), 2.72 (s, 3H), 2.63 (d, J = 1.8 Hz, 3H), 2.26-2.13 (m, 2H), 1.67 (d, J = 7.0 Hz, 3H). LCMS [M + 1]$^+$: 528.3. |
| 11-6 | (structure) (R)-3-(1-((7-(4-(cyclopropanecarbonyl)piperazin-1-yl)-4-methylpyrido[3,4-d]pyridazin-1-yl)amino)ethyl)-2-methylbenzonitrile | $^1$H NMR (400 MHz, CD$_3$OD) δ = 9.04 (s, 1H), 7.71 (d, J = 7.9 Hz, 1H), 7.50 (d, J = 7.6 Hz, 1H), 7.36 (s, 1H), 7.26 (t, J = 7.7 Hz, 1H), 5.59 (q, J = 6.8 Hz, 1H), 4.66-4.55 (m, 4H), 4.03-3.94 (m, 4H), 3.86-3.80 (m, 4H), 2.73 (s, 3H), 2.63 (s, 3H), 2.08-2.00 (m, 1H), 1.62 (d, J = 6.9 Hz, 3H), 0.97-0.85 (m, 4H). LCMS [M + 1]$^+$: 456.4. |

Example 12-1

(R)-4-methyl-7-(4-(1-methyl-1H-pyrazol-4-yl)piperazin-1-yl)-N-(1-(2-methyl-3-(trifluoromethyl)phenyl)ethyl)pyrido[3,4-d]pyridazin-1-amine

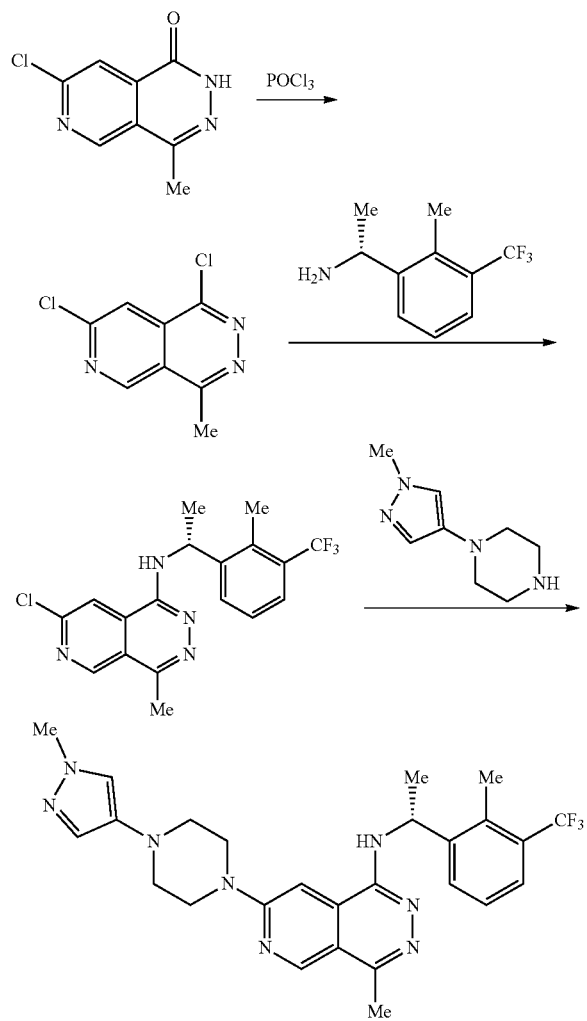

Step A: A solution of 7-chloro-4-methylpyrido[3,4-d]pyridazin-1(2H)-one (5.00 g, 25.6 mmol, 1.00 eq.) in POCl₃ (137 g, 893 mmol, 83.0 mL, 34.9 eq) was added N,N-diisopropylethylamine (9.91 g, 76.7 mmol, 13.4 mL, 3 eq.) dropwise at 25° C., then the reaction was stirred at 110° C. for 2 h. After this time the mixture was cooled to 25° C. and concentrated under vacuum to give a residue, the residue was diluted with ethyl acetate (300 mL) at 0° C., adjusted to pH=7 with slow addition of sodium bicarbonate saturated aqueous solution. The combined organic phases were washed with brine (200 mL×2), dried over anhydrous sodium sulfate, filtered, and concentrated under vacuum to give 1,7-dichloro-4-methylpyrido[3,4-d]pyridazine (4.10 g, 19.2 mmol, 74.9% yield) as a pink solid.

¹H NMR (400 MHz, DMSO-d₆) δ=9.65 (s, 1H), 8.22 (s, 1H), 3.02 (s, 3H).

Step B: To a solution of 1,7-dichloro-4-methylpyrido[3,4-d]pyridazine (300 mg, 1.40 mmol, 1.00 eq) and (R)-1-(2-methyl-3-(trifluoromethyl)phenyl)ethan-1-amine (285 mg, 1.40 mmol, 1.00 eq) in DMSO (5.00 mL) was added potassium fluoride (244 mg, 4.20 mmol, 98.5 μL, 3.00 eq) and N,N-diisopropylethylamine (543 mg, 4.20 mmol, 732 μL, 3.00 eq). The mixture was stirred at 130° C. for 12 hours, then cooled to room temperature and water (20.0 mL) was added. The mixture was extracted with ethyl acetate (10.0 mL×3), and the combined organic layers were washed with brine (5.00 mL×2), dried over sodium sulfate, filtered, and concentrated under reduced pressure to give a residue. The residue was purified by column chromatography (SiO₂, petroleum ether/ethyl acetate=1/0 to 5/1) to give (R)-7-chloro-4-methyl-N-(1-(2-methyl-3-(trifluoromethyl)phenyl)ethyl)pyrido[3,4-d]pyridazin-1-amine (320 mg, 840 μmol, 60.0% yield) as a yellow solid. LCMS [M+1]⁺: 381.0.

Step C: A mixture of (R)-7-chloro-4-methyl-N-(1-(2-methyl-3-(trifluoromethyl)phenyl)ethyl)pyrido[3,4-d]pyridazin-1-amine (40.0 mg, 105 μmol, 1.00 eq), 1-(1-methyl-1H-pyrazol-4-yl)piperazine (58.9 mg, 210 μmol, 2.00 eq., TFA salt), cesium carbonate (171 mg, 525 μmol, 5.00 eq), RuPhos Pd G3 (8.79 mg, 10.5 μmol, 0.10 eq) in dioxane (1.00 mL) was degassed and purged with nitrogen 3 times, and then the mixture was stirred at 80° C. for 10 hours under a nitrogen atmosphere. The reaction mixture was quenched by addition water (15.0 mL) at 20° C., and then extracted with ethyl acetate (5.00 mL×3). The combined organic layers were washed with brine (5.00 mL), dried over sodium sulfate, filtered, and concentrated under reduced pressure to give a residue. The residue was purified by prep-HPLC (column: Phenomenex Gemini-NX C18 75×30 mm×3 um; mobile phase: phase A: water (0.04% HCl), phase B: acetonitrile; gradient: B %: 30%-60%) to give (R)-4-methyl-7-(4-(1-methyl-1H-pyrazol-4-yl)piperazin-1-yl)-N-(1-(2-methyl-3-(trifluoromethyl)phenyl)ethyl)pyrido[3,4-d]pyridazin-1-amine (9.51 mg, 15.1% yield, HCl salt) as a light yellow solid. LCMS [M+1]⁺: 511.1.

¹H NMR (400 MHz, DMSO-d₆) δ=9.00 (s, 1H), 7.72 (d, J=7.6 Hz, 1H), 7.57 (d, J=6.4 Hz, 1H), 7.52 (d, J=7.6 Hz, 1H), 7.48 (s, 1H), 7.36 (s, 1H), 7.35-7.29 (m, 1H), 7.25 (s, 1H), 5.63 (quin, J=6.8 Hz, 1H), 3.88-3.83 (m, 4H), 3.75 (s, 2H), 3.78-3.72 (m, 1H), 3.04-2.98 (m, 4H), 2.56 (s, 6H), 1.55 (d, J=6.8 Hz, 3H).

Example 12-2

7-(6-oxa-3-azabicyclo[3.1.1]heptan-3-yl)-4-methyl-N—((R)-1-(2-methyl-3-(trifluoromethyl)phenyl)ethyl)pyrido[3,4-d]pyridazin-1-amine

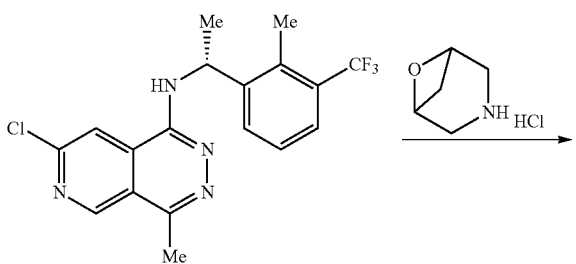

-continued

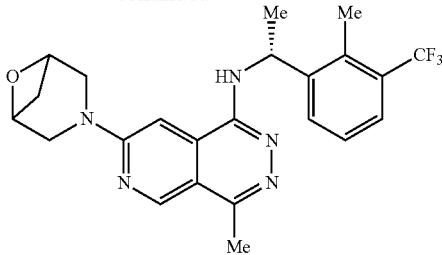

To a solution of (R)-7-chloro-4-methyl-N-(1-(2-methyl-3-(trifluoromethyl)phenyl)ethyl)pyrido[3,4-d]pyridazin-1-amine (50.0 mg, 131 μmol, 1.00 eq.) and 6-oxa-3-azabicyclo [3.1.1]heptane (35.6 mg, 263 μmol, 2.00 eq., HCl) in dioxane (2.00 mL) was added cesium carbonate (171 mg, 525 μmol, 4.00 eq.), RuPhos (6.10 mg, 13.1 μmol, 0.10 eq.) and Pd$_2$(dba)$_3$ (6.00 mg, 6.60 μmol, 0.05 eq.) under a nitrogen atmosphere. The mixture was stirred at 110° C. for 2 hours then cooled to 25° C., filtered, and the filtrate was quenched with water (10.0 mL), and then extracted with ethyl acetate (30.0 mL). The combined organic layers were washed with brine (10.0 mL), dried over anhydrous sodium sulfate, filtered, and concentrated under reduced pressure to give a residue. The residue was purified by prep-HPLC (column: Waters Xbridge BEH C18 100×25 mm×5 um; mobile phase: phase A: water (10 mM NH$_4$HCO$_3$), phase B: acetonitrile; gradient: B %: 30%-60%) to give 7-(6-oxa-3-azabicyclo[3.1.1]heptan-3-yl)-4-methyl-N—((R)-1-(2-methyl-3-(trifluoromethyl)phenyl)ethyl)pyrido[3,4-d]pyridazin-1-amine (8.64 mg, 18.9 μmol, 14.4% yield) as a yellow solid. LCMS [M+1]$^+$: 444.1.

$^1$H NMR (400 MHz, DMSO-dd) δ=9.03 (s, 1H), 7.74 (d, J=7.6 Hz, 1H), 7.57 (s, 1H), 7.52 (d, J=8.0 Hz, 1H), 7.31 (t, J=8.0 Hz, 1H), 7.27 (s, 1H), 5.66 (t, J=7.2 Hz, 1H), 4.80 (d, J=6.4 Hz, 2H), 3.91-3.90 (m, 2H), 3.75-3.68 (m, 2H), 3.23-3.16 (m, 1H), 2.57 (s, 6H), 1.95 (d, J=9.2 Hz, 1H), 1.55 (d, J=7.2 Hz, 3H).

SFC conditions: Chiralcel OD-3 3 μm, 0.46 cm id×5 cm L; Mobile phase: A for SFC C02 and B for MeOH (0.05% isopropylamine); Gradient: B in A from 10% to 40% in 3 minutes; Flow rate: 4.0 mL/min; Column temperature: 35° C.; Wavelength: 220 nm; System Back Pressure: 100 bar.

Following the teachings of the General Reaction Scheme III, and the procedure described for the preparation of Examples 12-1 and 12-2, the following compounds of Formula (I), Examples 12-3-12-134 shown in Table 12 were prepared.

TABLE 12

| Ex. # | Structure | Spectral Data |
|---|---|---|
| 12-3 | 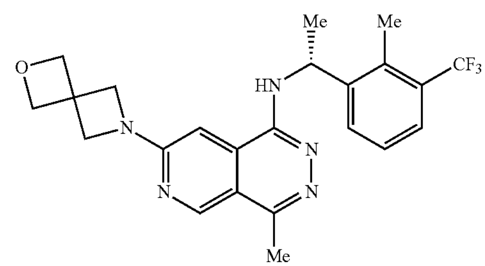 [SMILES: Cc1c([C@@H](C)Nc2nnc(C)c3cnc(N4CC5(COC5)C4)cc23)cccc1C(F)(F)F] | $^1$H NMR (400 MHz, DMSO-d$_6$) δ = 8.94 (s, 1H), 7.72 (d, J = 7.6 Hz, 1H), 7.52 (d, J = 7.6 Hz, 2H), 7.34-7.28 (m, 1H), 7.10 (s, 1H), 5.67-5.57 (m, 1H), 4.78 (s, 4H), 4.29 (s, 4H), 2.56-2.52 (m, 6H), 1.54 (d, J = 6.8 Hz, 3H). LCMS [M + 1] $^+$: 444.1. |
| 12-4 | 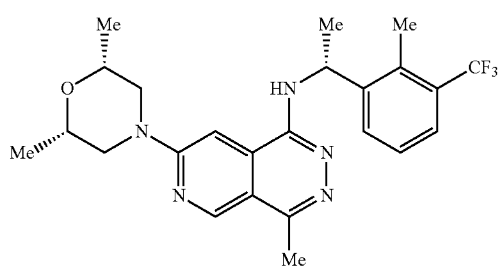 [SMILES: Cc1c([C@@H](C)Nc2nnc(C)c3cnc(N4C[C@@H](C)O[C@@H](C)C4)cc23)cccc1C(F)(F)F] | $^1$H NMR (400 MHz, DMSO-d$_6$) δ = 14.73 (s, 1H), 9.23 (s, 1H), 9.19 (br s, 1H), 8.04 (s, 1H), 7.89 (d, J = 7.6 Hz, 1H), 7.55 (d, J = 7.6 Hz, 1H), 7.37-7.35 (m, 1H), 5.45-5.41 (m, 1H), 4.76-4.73 (m, 2H), 3.67-3.63 (m, 2H), 2.78-2.74 (m, 5H), 2.56 (s, 3H), 1.64 (d, J = 6.8 Hz, 3H), 1.23 (d, J = 4.8 Hz, 6H). LCMS [M + 1] $^+$: 460.1. |
| 12-5 | 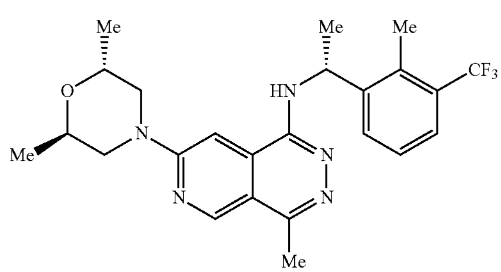 [SMILES: Cc1c([C@@H](C)Nc2nnc(C)c3cnc(N4C[C@@H](C)O[C@H](C)C4)cc23)cccc1C(F)(F)F] | $^1$H NMR (400 MHz, DMSO-d$_6$) δ = 14.66 (s, 1H), 9.23 (s, 1H), 9.00 (s, 1H), 7.90 (s, 1H), 7.83 (d, J = 7.6 Hz, 1H), 7.56 (d, 7.6 Hz, 1H), 7.36 (t, J = 8.0 Hz, 1H), 5.48-5.37 (m, 1H), 4.17-4.08 (m, 2H), 4.06-4.02 (m, 2H), 3.74-3.69 (m, 2H), 2.73 (s, 3H), 2.56 (s, 3H), 1.63 (d, J = 6.8 Hz, 3H), 1.19 (d, J = 6.4 Hz, 6H). LCMS [M + 1] $^+$: 460.1. |

TABLE 12-continued

| Ex. # | Structure | Spectral Data |
|---|---|---|
| 12-6 | 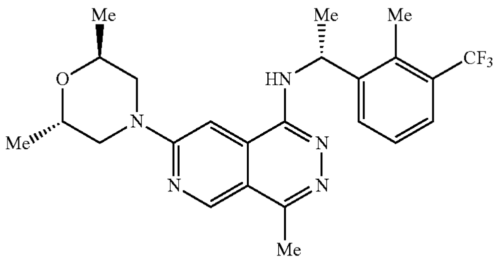 [SMILES: Cc1c([C@@H](C)Nc2nnc(C)c3cnc(N4C[C@H](C)O[C@@H](C)C4)cc23)cccc1C(F)(F)F] | ¹H NMR (400 MHz, DMSO-d₆) δ = 14.65 (s, 1H), 9.25 (s, 1H), 8.92 (s, 1H), 7.91-7.78 (m, 2H), 7.57 (d, J = 8.0 Hz, 1H), 7.41-7.32 (m, 1H), 5.49-5.37 (m, 1H), 4.18-4.09 (m, 2H), 4.09-4.00 (m, 2H), 3.76-3.63 (m, 2H), 2.73 (s, 3H), 2.56 (s, 3H), 1.63 (d, J = 7.2 Hz, 3H), 1.20 (d, J = 6.4 Hz, 6H). LCMS [M + 1]⁺: 460.1. |
| 12-7 | 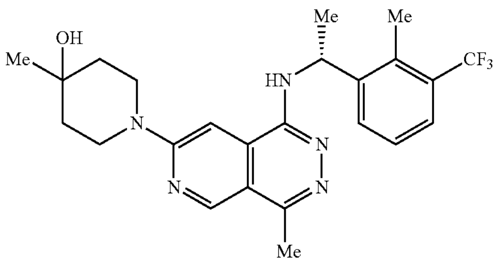 [SMILES: Cc1c([C@@H](C)Nc2nnc(C)c3cnc(N4CCC(C)(O)CC4)cc23)cccc1C(F)(F)F] | ¹H NMR (400 MHz, CD₃OD) δ = 9.19 (s, 1H), 7.68 (d, J = 8.0 Hz, 1H), 7.58-7.51 (m, 2H), 7.32-7.26 (m, 1H), 5.49 (q, J = 6.8 Hz, 1H), 4.46 (br s, 2H), 3.58-3.51 (m, 2H), 2.75 (s, 3H), 2.61 (s, 3H), 1.81-1.68 (m, 4H), 1.66 (d, J = 6.8 Hz, 3H), 1.31 (s, 3H). LCMS [M + 1]⁺: 460.1. |
| 12-8 | 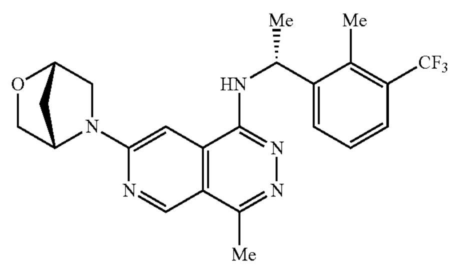 [SMILES: Cc1c([C@@H](C)Nc2nnc(C)c3cnc(N4C[C@@H]5C[C@H]4CO5)cc23)cccc1C(F)(F)F] | ¹H NMR (400 MHz, CD₃OD) δ = 8.96 (s, 1H), 7.68 (d, J = 8.0 Hz, 1H), 7.49 (d, J = 7.6 Hz, 1H), 7.29-7.19 (m, 1H), 7.10 (s, 1H), 5.74-5.61 (m, 1H), 5.15 (s, 1H), 4.80 (s, 1H), 3.95 (dd, J = 1.2, 7.6 Hz, 1H), 3.85 (d, J = 7.2 Hz, 1H), 3.66 (dd, J = 1.2, 10.4 Hz, 1H), 3.51 (d, J = 10.4 Hz, 1H), 2.61 (s, 6H), 2.14-1.99 (m, 2H), 1.61 (d, J = 6.8 Hz, 3H). LCMS [M + 1]⁺: 444.2. |
| 12-9 | 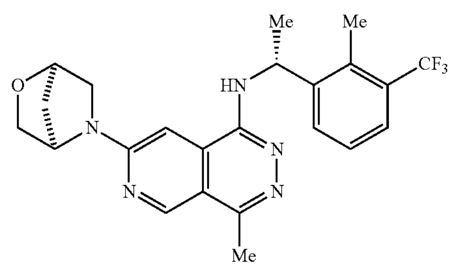 [SMILES: Cc1c([C@@H](C)Nc2nnc(C)c3cnc(N4C[C@H]5C[C@@H]4CO5)cc23)cccc1C(F)(F)F] | ¹H NMR (400 MHz, DMSO-d₆) δ = 8.96 (s, 1H), 7.67 (d, J = 8.0 Hz, 1H), 7.48 (d, J = 7.6 Hz, 1H), 7.25-7.22 (m, 1H), 7.09 (s, 1H), 5.68-5.66 (m, 1H), 5.15 (s, 1H), 4.79 (s, 1H), 3.96-3.93 (m, 1H), 3.86-3.84 (m, 1H), 3.68-3.65 (m, 1H), 3.51-3.49 (m, 1H), 2.61-2.60 (m, 6H), 2.06 (s, 2H), 1.61 (d, J = 7.2 Hz, 3H). LCMS [M + 1]⁺: 444.1. |
| 12-10 | 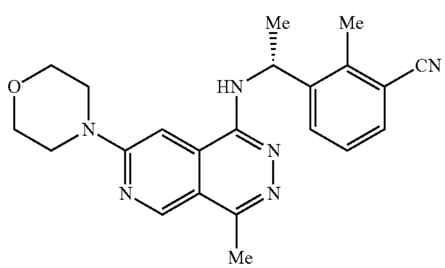 [SMILES: Cc1c(C#N)cccc1[C@@H](C)Nc1nnc(C)c2cnc(N3CCOCC3)cc12] | ¹H NMR (400 MHz, DMSO-d₆) δ = 9.00 (s, 1H), 7.71 (d, J = 8.0 Hz, 1H), 7.61 (d, J = 7.6 Hz, 1H), 7.53 (d, J = 6.8 Hz, 1H), 7.40 (s, 1H), 7.32 (t, J = 7.6 Hz, 1H), 5.53 (m, 1H), 3.74-3.83 (m, 4H), 3.63-3.73 (m, 4H), 2.66 (s, 3H), 2.56 (s, 3H), 1.54 (d, J = 6.8 Hz, 3H). LCMS [M + 1]⁺: 389.1 |

TABLE 12-continued

| Ex. # | Structure | Spectral Data |
|---|---|---|
| 12-11 | 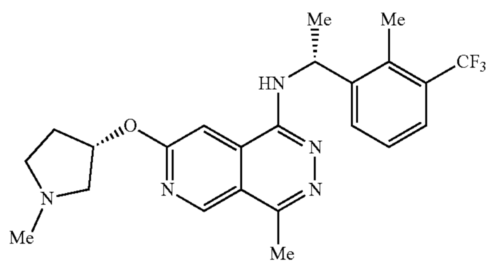 [SMILES: Cc1c([C@@H](C)Nc2nnc(C)c3cnc(O[C@H]4CCN(C)C4)cc23)cccc1C(F)(F)F] | $^1$H NMR (400 MHz, DMSO-$d_6$) δ = 9.44 (s, 1H), 8.25 (s, 1H), 7.75 (d, J = 7.6 Hz, 1H), 7.56 (d, J = 7.6 Hz, 1H), 7.37-7.33 (m, 1H), 5.81-5.77 (m, 1H), 5.48-5.43 (m, 1H), 4.12-3.73 (m, 3H), 3.41-3.23 (m, 2H), 2.93-2.83 (m, 6H), 2.66-2.57 (m, 1H), 2.55 (s, 3H), 2.33-2.22 (m, 1H), 1.58 (d, J = 6.8 Hz, 3H). LCMS [M + 1] $^+$: 446.1. |
| 12-12 | 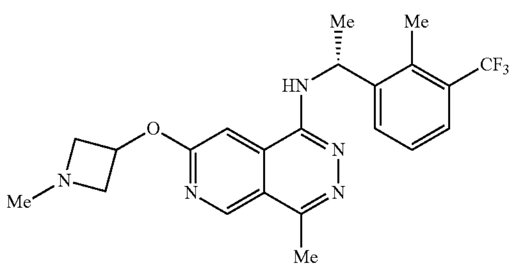 [SMILES: Cc1c([C@@H](C)Nc2nnc(C)c3cnc(OC4CN(C)C4)cc23)cccc1C(F)(F)F] | $^1$H NMR (400 MHz, DMSO-$d_6$) δ = 9.07 (s, 1H), 7.84 (s, 1H), 7.73-7.71 (m, 1H), 7.51 (d, J = 7.6 Hz, 1H), 7.32-7.30 (m, 1H), 5.64-5.59 (m, 1H), 5.27-5.24 (m, 1H), 3.79-3.75 (m, 2H), 3.06-3.01 (m, 2H), 2.61 (s, 3H), 2.56 (s, 3H), 2.31 (s, 3H), 1.52 (d, J = 6.8 Hz, 3H). LCMS [M + 1] $^+$: 432.1. |
| 12-13 | 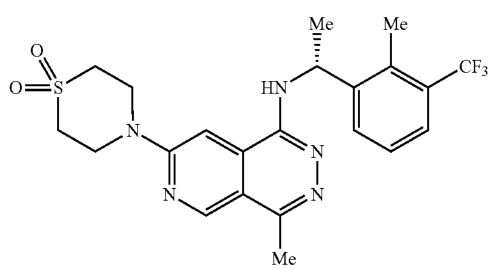 [SMILES: Cc1c([C@@H](C)Nc2nnc(C)c3cnc(N4CCS(=O)(=O)CC4)cc23)cccc1C(F)(F)F] | $^1$H NMR (400 MHz, CD$_3$OD) δ = 9.31 (s, 1H), 7.81 (s, 1H), 7.71 (d, J = 8.0 Hz, 1H), 7.54 (d, J = 8.0 Hz, 1H), 7.29 (t, J = 8.0 Hz, 1H), 5.53 (q, J = 6.8 Hz, 1H), 4.50 (br s, 4H), 3.30 (br s, 4H), 2.81 (s, 3H), 2.62 (s, 3H), 1.68 (d, J = 6.8 Hz, 3H). LCMS [M + 1] $^+$: 480.2. |
| 12-14 | 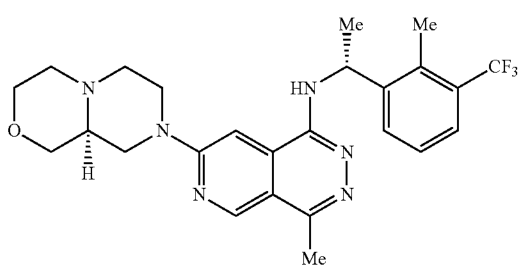 [SMILES: Cc1c([C@@H](C)Nc2nnc(C)c3cnc(N4CCN5CCOC[C@@H]5C4)cc23)cccc1C(F)(F)F] | $^1$H NMR (400 MHz, CD$_3$OD) δ = 9.32 (s, 1H), 7.90 (br s, 1H), 7.78 (d, J = 7.6 Hz, 1H), 7.55 (d, J = 8.0 Hz, 1H), 7.30 (t, J = 7.6 Hz, 1H), 5.55 (q, J = 6.8 Hz, 1H), 5.25-5.01 (m, 2H), 4.29-4.09 (m, 2H), 4.08-3.98 (m, 1H), 3.93-3.34 (m, 8H), 2.83 (s, 3H), 2.64 (s, 3H), 1.72 (d, J = 6.8 Hz, 3H). LCMS [M + 1] $^+$: 487.2. |
| 12-15 | 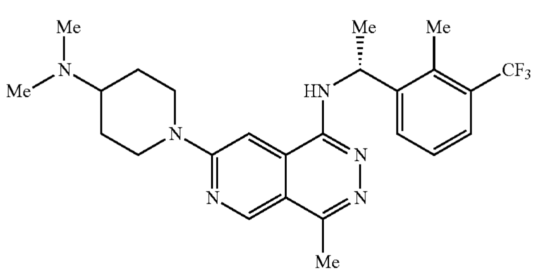 [SMILES: Cc1c([C@@H](C)Nc2nnc(C)c3cnc(N4CCC(N(C)C)CC4)cc23)cccc1C(F)(F)F] | $^1$H NMR (400 MHz, CD$_3$OD) δ = 8.94 (s, 1H), 7.68 (d, J = 8.0 Hz, 1H), 7.48 (d, J = 7.8 Hz, 1H), 7.32 (s, 1H), 7.23 (t, J = 7.6 Hz, 1H), 5.67 (q, J = 6.8 Hz, 1H), 4.77-4.65 (m, 2H), 3.05-2.94 (m, 2H), 2.61-2.58 (m, 6H), 2.57-2.48 (m, 1H), 2.03-1.97 (m, 2H), 1.60 (d, J = 6.8 Hz, 3H), 1.55-1.43 (m, 2H). LCMS [M + 1] $^+$: 473.3. |

TABLE 12-continued

| Ex. # | Structure | Spectral Data |
|---|---|---|
| 12-16 | 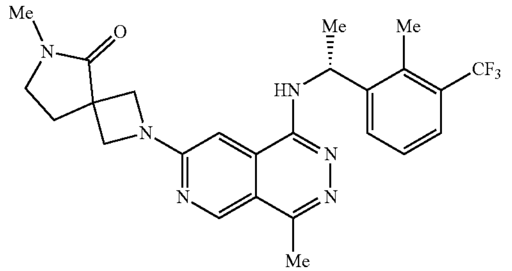 [SMILES: Cc1c([C@@H](C)Nc2nnc(C)c3cnc(N4CC5(CCN(C)C5=O)C4)cc23)cccc1C(F)(F)F] | $^1$H NMR (400 MHz, DMSO-$d_6$) δ = 9.15 (s, 1H), 7.68 (d, J = 8.0 Hz, 1H), 7.54 (d, J = 7.6 Hz, 1H), 7.32 (t, J = 8.0 Hz, 1H), 7.28 (s, 1H), 5.35 (q, J = 6.8 Hz, 1H), 4.30 (d, J = 8.4 Hz, 2H), 4.19 (d, J = 2.8, 9.2 Hz, 2H), 3.34 (t, J = 6.8 Hz, 2H), 2.78 (s, 3H), 2.69 (s, 3H), 2.52 (s, 3H), 2.41 (t, J = 6.8 Hz, 2H), 1.55 (d, J = 6.8 Hz, 3H). LCMS [M + 1]$^+$: 485.1. |
| 12-17 | 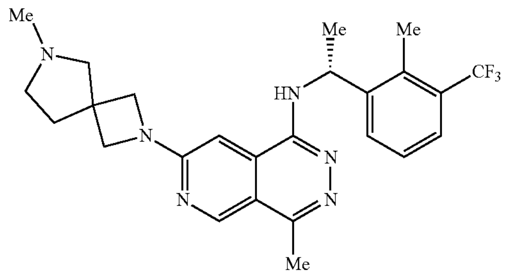 [SMILES: Cc1c([C@@H](C)Nc2nnc(C)c3cnc(N4CC5(CCN(C)C5)C4)cc23)cccc1C(F)(F)F] | $^1$H NMR (400 MHz, CD$_3$OD) δ = 9.25 (br s, 1H), 7.83-7.70 (m, 1H), 7.55 (br d, J = 7.6 Hz, 1H), 7.46-7.18 (m, 2H), 5.57-5.48 (m, 1H), 4.84-4.68 (m, 1H), 4.55-4.27 (m, 3H), 4.07-4.01 (m, 1H), 3.99-3.67 (m, 2H), 3.58-3.43 (m, 1H), 3.03 (s, 3H), 2.79 (s, 3H), 2.71-2.48 (m, 5H), 1.69 (d, J = 7.2 Hz, 3H). LCMS [M + 1]$^+$: 471.2. |
| 12-18 | 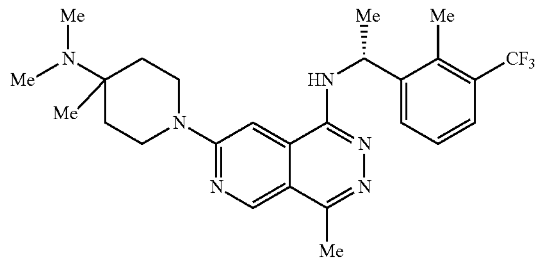 [SMILES: Cc1c([C@@H](C)Nc2nnc(C)c3cnc(N4CCC(C)(N(C)C)CC4)cc23)cccc1C(F)(F)F] | $^1$H NMR (400 MHz, CD$_3$OD) δ = 9.26 (s, 1H), 7.77 (t, J = 4.0 Hz, 2H), 7.55 (d, J = 7.6 Hz, 1H), 7.31 (t, J = 8.0 Hz, 1H), 5.53 (q, J = 6.8 Hz, 1H), 4.99-4.92 (m, 2H), 3.46-3.36 (m, 2H), 2.89 (s, 6H), 2.80 (s, 3H), 2.64 (s, 3H), 2.22 (br d, J = 12.4 Hz, 2H), 2.07-1.96 (m, 2H), 1.71 (d, J = 6.8 Hz, 3H), 1.61 (s, 3H). LCMS [M + 1]$^+$: 487.2. |
| 12-19 | 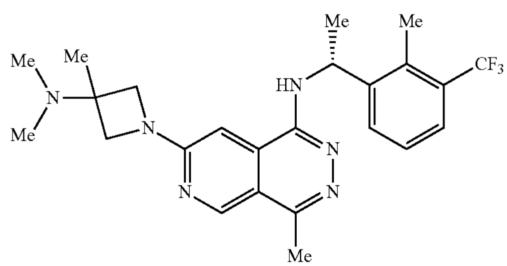 | $^1$H NMR (400 MHz, DMSO-$d_6$) δ = 8.93 (s, 1H), 7.72 (d, J = 7.6 Hz, 1H), 7.52 (d, J = 7.2 Hz, 1H), 7.45 (d, J = 6.8 Hz, 1H), 7.31 (t, J = 8.0 Hz, 1H), 7.09 (s, 1H), 5.68-5.57 (m, 1H), 3.94-3.86 (m, 2H), 3.80 (dd, J = 3.2, 8.0 Hz, 2H), 2.55 (br s, 3H), 2.54 (s, 3H), 2.15 (s, 6H), 1.53 (d, J = 7.2 Hz, 3H), 1.32 (s, 3H). LCMS [M + 1]$^+$: 459.4. |
| 12-20 | 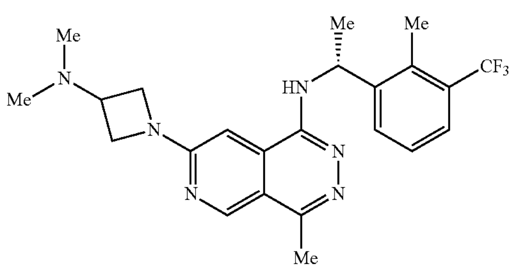 [SMILES: Cc1c([C@@H](C)Nc2nnc(C)c3cnc(N4CC(N(C)C)C4)cc23)cccc1C(F)(F)F] | $^1$H NMR (400 MHz, CD$_3$OD) δ = 9.27 (s, 1H), 7.71 (d, J = 7.2 Hz, 1H), 7.54 (d, J = 7.6 Hz, 1H), 7.44 (s, 1H), 7.32-7.27 (m, 1H), 5.52 (q, J = 7.2 Hz, 1H), 4.72-4.65 (m, 2H), 4.55 (m, 2H), 4.42 (br s, 1H), 3.01 (s, 6H), 2.80 (s, 3H), 2.62 (s, 3H), 1.68 (d, J = 7.2 Hz, 3H). LCMS [M + 1]$^+$: 445.2. |
| 12-21 | 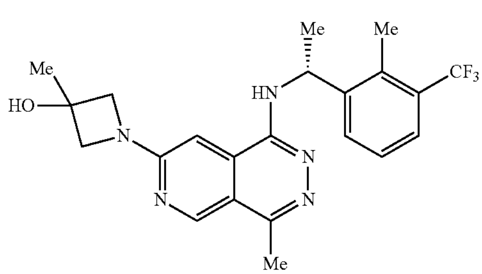 [SMILES: Cc1c([C@@H](C)Nc2nnc(C)c3cnc(N4CC(C)(O)C4)cc23)cccc1C(F)(F)F] | $^1$H NMR (400 MHz, DMSO-$d_6$) δ = 8.94 (s, 1H), 7.72 (d, J = 8.0 Hz, 1H), 7.49 (dd, J = 7.6, 18.8 Hz, 2H), 7.31 (t, J = 8.0 Hz, 1H), 7.08 (s, 1H), 5.71 (s, 1H), 5.62 (t, J = 6.8 Hz, 1H), 4.04-3.92 (m, 4H), 2.55 (s, 3H), 2.54 (s, 3H), 1.54 (d, J = 6.8 Hz, 3H), 1.49 (s, 3H). LCMS [M + 1]$^+$: 432.2. |

TABLE 12-continued

| Ex. # | Structure | Spectral Data |
|---|---|---|
| 12-22 | 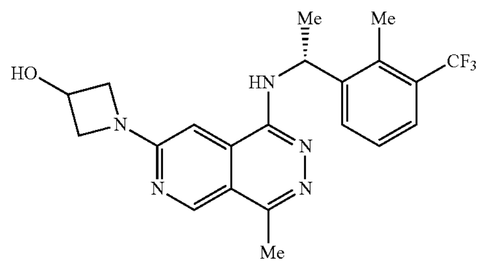 [SMILES: Cc1c([C@@H](C)Nc2nnc(C)c3cnc(N4CC(O)C4)cc23)cccc1C(F)(F)F] | ¹H NMR (400 MHz, DMSO-d₆) δ = 14.76 (br s, 1H), 9.19 (s, 1H), 8.97 (br d, J = 3.6 Hz, 1H), 7.85 (d, J = 8.0 Hz, 1H), 7.60-7.53 (m, 2H), 7.35 (t, J = 8.0 Hz, 1H), 5.42 (br t, J = 6.8 Hz, 1H), 4.76-4.68 (m, 1H), 4.55-4.44 (m, 1H), 4.08-3.98 (m, 2H), 2.74 (s, 3H), 2.56 (s, 3H), 1.62 (d, J = 7.2 Hz, 3H). LCMS [M + 1]⁺: 418.1. |
| 12-23 | 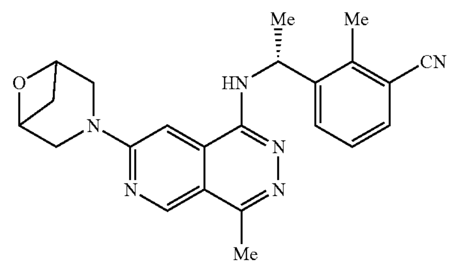 [SMILES: Cc1c(C#N)cccc1[C@@H](C)Nc1nnc(C)c2cnc(N3CC4CC(C3)O4)cc12] | ¹H NMR (400 MHz, DMSO-d₆) δ = 9.04 (s, 1H), 8.14 (s, 1H), 7.73 (d, J = 7.6 Hz, 1H), 7.64-7.57 (m, 2H), 7.31 (t, J = 7.6 Hz, 1H), 7.26 (s, 1H), 5.56-5.52 m, 1H), 4.80 (d, J = 6.0 Hz, 2H), 3.91-3.87 (m, 2H), 3.74-3.68 (m, 2H), 3.20 (d, J = 8.4 Hz, 2H), 2.66 (s, 3H), 2.57 (s, 3H), 1.95 (d, J = 9.2 Hz, 1H), 1.55 (d, J = 7.2 Hz, 3H). LCMS [M + 1]⁺: 401.3. |
| 12-24 | 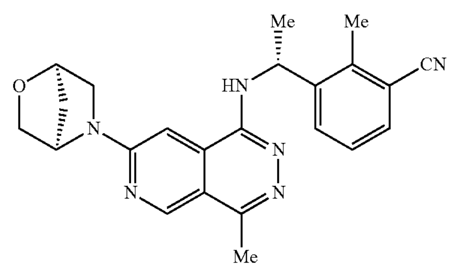 [SMILES: Cc1c(C#N)cccc1[C@@H](C)Nc1nnc(C)c2cnc(N3C[C@H]4C[C@@H]3CO4)cc12] | ¹H NMR (400 MHz, CD₃OD) δ = 9.10 (s, 1H), 8.47 (s, 1H), 7.70 (d, J = 7.6 Hz, 1H), 7.52 (d, J = 7.6 Hz, 1H), 7.28 (t, J = 7.6 Hz, 1H), 7.20 (s, 1H), 5.49-5.43 (m, 1H), 5.24 (s, 1H), 4.85-4.83 (m, 1H), 4.83 (s, 2H), 3.96 (d, J = 7.6 Hz, 1H), 3.85 (d, J = 7.6 Hz, 1H), 3.69 (d, J = 10.4 Hz, 1H), 3.55 (d, J = 10.8 Hz, 1H), 2.71 (s, 3H), 2.71 (s, 3H), 2.09 (s, 2H), 1.63 (d, J = 7.2 Hz, 3H). LCMS [M + 1]⁺: 401.3. |
| 12-25 | 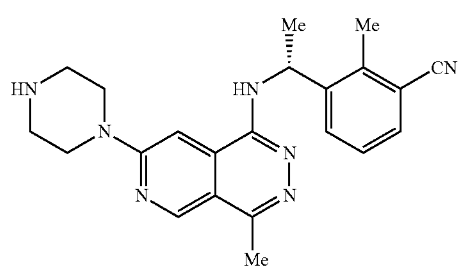 | ¹H NMR (400 MHz, CD₃OD) δ = 9.30 (s, 1H), 7.87 (s, 1H), 7.82 (d, J = 7.2 Hz, 1H), 7.55 (d, J = 6.8 Hz, 1H), 7.30 (t, J = 8.0 Hz, 1H), 7.34-7.26 (m, 1H), 5.44 (q, J = 6.8 Hz, 1H), 4.35-4.26 (m, 4H), 3.49-3.40 (m, 4H), 2.82 (s, 3H), 2.74 (s, 3H), 1.70 (d, J = 7.2 Hz, 3H). LCMS [M + 1]⁺: 388.2. |
| 12-26 | 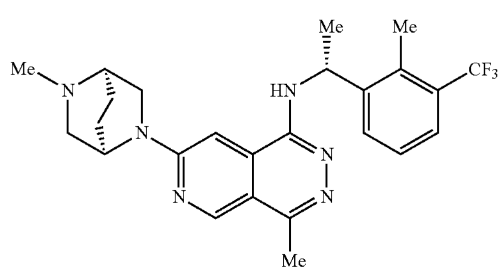 [SMILES: Cc1c([C@@H](C)Nc2nnc(C)c3cnc(N4C[C@H]5CC[C@@H]4CN5C)cc23)cccc1C(F)(F)F] | ¹H NMR (400 MHz, DMSO-d₆) δ = 8.94 (s, 1H), 8.17 (s, 1H), 7.73 (d, J = 8.0 Hz, 1H), 7.56-7.45 (m, 2H), 7.32 (t, J = 7.6 Hz, 1H), 7.11 (s, 1H), 5.70-5.58 (m, 1H), 4.88-4.69 (m, 1H), 3.86 (d, J = 11.2 Hz, 1H), 3.05-2.99 (m, 2H), 2.93-2.85 (m, 1H), 2.56 (s, 3H), 2.54 (s, 3H), 2.43 (s, 3H), 2.16-2.03 (m, 1H), 1.88-1.79 (m, 2H), 1.72-1.63 (m, 1H), 1.55 (d, J = 6.8 Hz, 3H). LCMS [M + 1]⁺: 471.2. |

TABLE 12-continued

| Ex. # | Structure | Spectral Data |
|---|---|---|
| 12-27 | 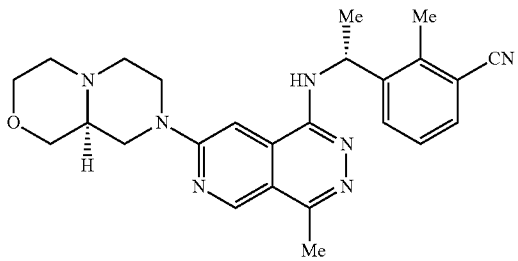 [SMILES: Cc1c(C#N)cccc1[C@@H](C)Nc1nnc(C)c2cnc(N3CCN4CCOC[C@@H]4C3)cc12] | $^1$H NMR (400 MHz, CD$_3$OD) δ = 9.02 (s, 1H), 7.72 (d, J = 7.6 Hz, 1H), 7.51 (dd, J = 1.2, 7.6 Hz, 1H), 7.34 (s, 1H), 7.27 (t, J = 8.0 Hz, 1H), 5.60 (q, J = 6.8 Hz, 1H), 4.63 (br d, J = 13.6 Hz, 1H), 4.42 (br d, J = 12.8 Hz, 1H), 3.94-3.83 (m, 2H), 3.75 (dt, J = 2.4, 11.6 Hz, 1H), 3.39 (t, J = 10.8 Hz, 1H), 3.18 (dt, J = 3.2, 12.8 Hz, 1H), 2.97 (br d, J = 11.6 Hz, 1H), 2.81 (br d, J = 11.6 Hz, 1H), 2.77-2.71 (m, 3H), 2.71-2.66 (m, 1H), 2.64 (s, 3H), 2.48-2.32 (m, 3H), 1.63 (d, J = 6.8 Hz, 3H). LCMS [M + 1]$^+$: 444.2. |
| 12-28 | 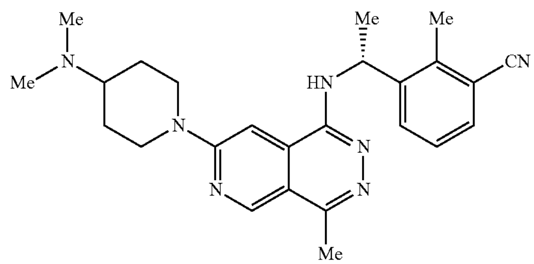 | $^1$H NMR (400 MHz, CD$_3$OD) δ = 9.25 (s, 1H), 7.77 (d, J = 8.0 Hz, 1H), 7.72 (s, 1H), 7.55 (d, J = 7.6 Hz, 1H), 7.33-7.27 (m, 1H), 5.43 (q, J = 6.8 Hz, 1H), 5.12-5.01 (m, 2H), 3.72-3.59 (m, 1H), 3.24 (br t, J = 12.4 Hz, 2H), 2.92 (s, 6H), 2.79 (s, 3H), 2.74 (s, 3H), 2.32 (br d, J = 11.6 Hz, 2H), 1.89-1.75 (m, 2H), 1.68 (d, J = 6.8 Hz, 3H). LCMS [M + 1]$^+$: 430.3. |
| 12-29 | 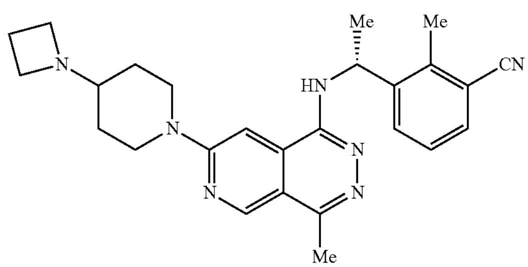 [SMILES: Cc1c(C#N)cccc1[C@@H](C)Nc1nnc(C)c2cnc(N3CCC(N4CCC4)CC3)cc12] | $^1$H NMR (400 MHz, DMSO-d$_6$) δ = 14.94-14.58 (m, 1H), 11.66-11.25 (m, 1H), 9.24 (s, 1H), 8.11 (s, 1H), 7.91 (d, J = 8.0 Hz, 1H), 7.65 (d, J = 7.6 Hz, 1H), 7.36 (t, J = 8.0 Hz, 1H), 5.33 (t, J = 6.8 Hz, 1H), 4.90 (br d, J = 13.2 Hz, 2H), 4.21-3.92 (m, 4H), 3.55 (br s, 1H), 3.18 (br t, J = 12.8 Hz, 2H), 2.74 (s, 3H), 2.67 (s, 3H), 2.44-2.19 (m, 2H), 2.08 (br d, J = 10 Hz, 2H), 1.64 (d, J = 6.8 Hz, 3H), 1.53-1.40 (m, 2H). LCMS [M + 1]$^+$: 442.3. |
| 12-30 | 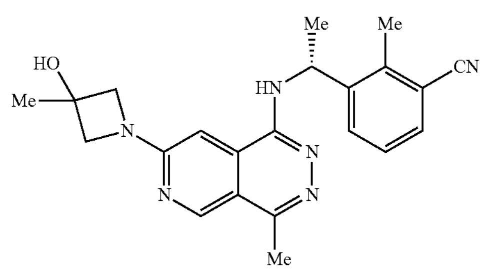 [SMILES: Cc1c(C#N)cccc1[C@@H](C)Nc1nnc(C)c2cnc(N3CC(C)(O)C3)cc12] | $^1$H NMR (400 MHz, DMSO-d$_6$) δ = 14.80 (br s, 1H), 9.19 (s, 1H), 9.04 (br d, J = 3.6 Hz, 1H), 7.87 (d, J = 8.0 Hz, 1H), 7.69-7.59 (m, 2H), 7.39-7.31 (m, 1H), 5.37-5.24 (m, 1H), 4.21-4.05 (m, 4H), 2.74 (s, 3H), 2.66 (s, 3H), 1.62 (br d, J = 7.2 Hz, 3H), 1.49 (s, 3H). LCMS [M + 1]$^+$: 389.2. |
| 12-31 | 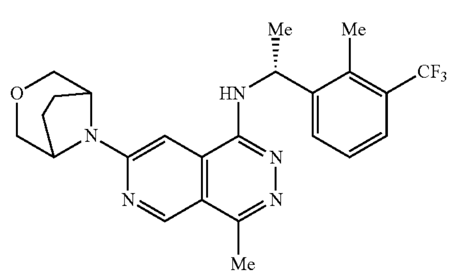 [SMILES: Cc1c([C@@H](C)Nc2nnc(C)c3cnc(N4C5CCC4COC5)cc23)cccc1C(F)(F)F] | $^1$H NMR (400 MHz, DMSO-d$_6$) δ = 14.65 (s, 1H), 9.26 (s, 1H), 8.88 (s, 1H), 7.88 (s, 1H), 7.82 (d, J = 8.0 Hz, 1H), 7.56 (d, J = 7.6 Hz, 1H), 7.36 (t, J = 7.6 Hz, 1H), 5.47-5.37 (m, 1H), 4.94 (s, 2H), 3.79-3.61 (m, 4H), 2.73 (s, 3H), 2.56 (s, 3H), 2.18-1.94 (m, 4H), 1.62 (d, J = 6.8 Hz, 3H). LCMS [M + 1]$^+$: 458.1. |

TABLE 12-continued

| Ex. # | Structure | Spectral Data |
|---|---|---|
| 12-32 | 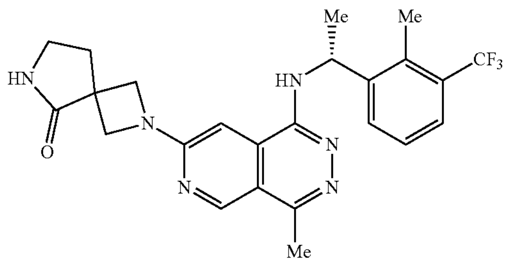 [SMILES: Cc1c([C@@H](C)Nc2nnc(C)c3cnc(N4CC5(CCNC5=O)C4)cc23)cccc1C(F)(F)F] | $^1$H NMR (400 MHz, DMSO-d$_6$) δ 9.24 (s, 1H), 8.78 (s, 1H), 7.94 (s, 1H), 7.76 (d, J = 7.9 Hz, 1H), 7.55 (d, J = 7.8 Hz, 1H), 7.49 (s, 1H), 7.34 (t, J = 7.8 Hz, 1H), 5.46-5.35 (m, 1H), 4.40-4.14 (m, 5H), 3.23 (t, J = 6.7 Hz, 2H), 2.72 (s, 3H), 2.54 (s, 3H), 1.59 (d, J = 6.9 Hz, 4H). LCMS [M + 1]$^+$: 471.1. |
| 12-33 | 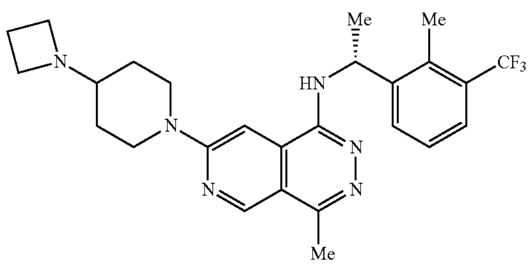 [SMILES: Cc1c([C@@H](C)Nc2nnc(C)c3cnc(N4CCC(N5CCC5)CC4)cc23)cccc1C(F)(F)F] | $^1$H NMR (400 MHz, Methanol-d$_4$) δ 9.23 (s, 1H), 7.77-7.70 (m, 2H), 7.53 (d, J = 7.8 Hz, 1H), 7.29 (t, J = 7.8 Hz, 1H), 5.51 (q, J = 6.9 Hz, 1H), 5.04-4.95 (m, 2H), 4.34-4.15 (m, 4H), 3.67 (d, J = 12.0 Hz, 1H), 3.25 (t, J = 13.1 Hz, 2H), 2.78 (s, 3H), 2.70-2.59 (m, 4H), 2.47-2.35 (m, 1H), 2.23 (d, J = 12.5 Hz, 2H), 1.68 (d, J = 6.9 Hz, 3H), 1.62-1.48 (m, 2H). LCMS [M + 1]$^+$: 485.2. |
| 12-34 | 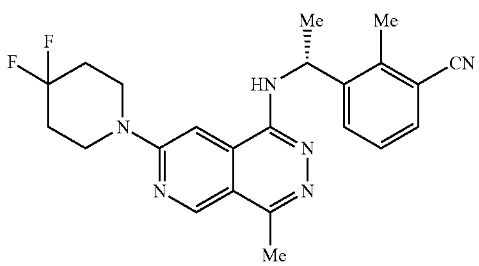 [SMILES: Cc1c(C#N)cccc1[C@@H](C)Nc1nnc(C)c2cnc(N3CCC(F)(F)CC3)cc12] | $^1$H NMR (400 MHz, Methanol-d$_4$) δ 9.06 (d, J = 0.8 Hz, 1H), 7.73 (dd, J = 7.9, 1.3 Hz, 1H), 7.52 (dd, J = 7.7, 1.3 Hz, 1H), 7.48 (d, J = 0.9 Hz, 1H), 7.28 (t, J = 7.8 Hz, 1H), 5.58 (q, J = 7.0 Hz, 1H), 4.03 (t, J = 5.8 Hz, 5H), 2.75 (s, 3H), 2.66 (s, 3H), 2.11 (ddt, J = 19.0, 13.5, 5.7 Hz, 5H), 1.64 (d, J = 7.0 Hz, 3H). LCMS [M + 1]$^+$: 423.2. |
| 12-35 | 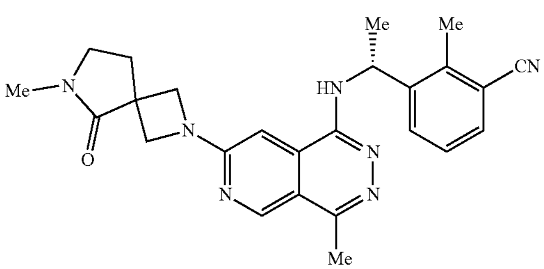 [SMILES: Cc1c(C#N)cccc1[C@@H](C)Nc1nnc(C)c2cnc(N3CC4(CCN(C)C4=O)C3)cc12] | $^1$H NMR (400 MHz, DMSO-d$_6$) δ 8.96 (s, 1H), 7.72 (d, J = 7.8 Hz, 1H), 7.60 (dd, J = 7.6, 1.3 Hz, 1H), 7.49 (d, J = 6.8 Hz, 1H), 7.31 (t, J = 7.8 Hz, 1H), 7.09 (s, 1H), 5.52 (q, J = 7.0 Hz, 1H), 4.19 (dd, J = 8.3, 5.1 Hz, 2H), 4.05 (dd, J = 8.0, 1.7 Hz, 2H), 2.79 (s, 3H), 2.68-2.64 (m, 4H), 2.55 (s, 3H), 2.43 (t, J = 6.8 Hz, 2H), 2.33 (p, J = 1.8 Hz, 1H), 1.53 (d, J = 7.0 Hz, 3H). LCMS [M + 1]$^+$: 442.2. |
| 12-36 | 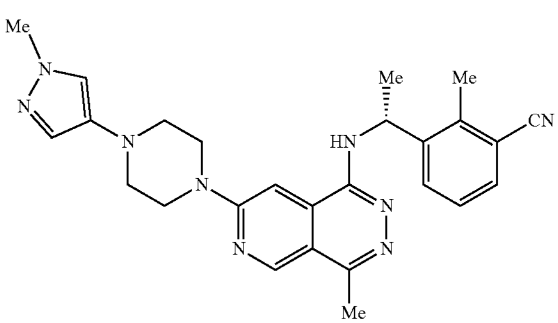 [SMILES: Cc1c(C#N)cccc1[C@@H](C)Nc1nnc(C)c2cnc(N3CCN(c4cnn(C)c4)CC3)cc12] | $^1$H NMR (400 MHz, DMSO-d$_6$) δ 9.00 (s, 1H), 7.71 (dd, J = 8.0, 1.4 Hz, 1H), 7.61 (dd, J = 7.6, 1.3 Hz, 1H), 7.55 (d, J = 6.8 Hz, 1H), 7.46 (s, 1H), 7.36 (s, 1H), 7.32 (t, J = 7.8 Hz, 1H), 7.24 (d, J = 0.9 Hz, 1H), 5.54 (q, J = 6.7 Hz, 1H), 3.85 (t, J = 5.2 Hz, 4H), 3.75 (s, 3H), 3.01 (t, J = 5.2 Hz, 4H), 2.65 (s, 3H), 2.55 (s, 3H), 1.55 (d, J = 7.0 Hz, 3H). LCMS [M + 1]$^+$: 468.3. |

TABLE 12-continued

| Ex. # | Structure | Spectral Data |
|---|---|---|
| 12-37 | 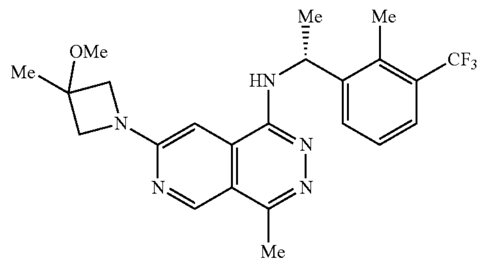 [SMILES: COC1(C)CN(c2cc3c(N[C@H](C)c4cccc(C(F)(F)F)c4C)nnc(C)c3cn2)C1] | $^1$H NMR (400 MHz, CDCl$_3$) δ 8.85 (s, 1H), 8.54 (s, 1H), 7.65 (d, J = 7.9 Hz, 1H), 7.49 (d, J = 7.8 Hz, 1H), 7.18 (t, J = 7.8 Hz, 1H), 6.75 (s, 1H), 5.57 (q, J = 6.8 Hz, 1H), 4.25-4.16 (m, 2H), 4.09-4.00 (m, 2H), 3.32 (s, 3H), 2.64 (s, 3H), 2.52 (s, 3H), 1.64 (d, J = 6.8 Hz, 3H), 1.59 (s, 3H). LCMS [M + 1]$^+$: 446.4. |
| 12-38 | 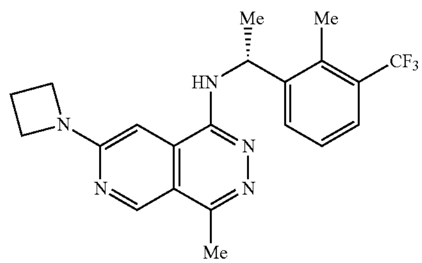 [SMILES: Cc1c([C@@H](C)Nc2nnc(C)c3cnc(N4CCC4)cc23)cccc1C(F)(F)F] | $^1$H NMR (400 MHz, CD$_3$OD) δ = 9.15 (s, 1H), 7.68 (d, J = 7.9 Hz, 1H), 7.54 (d, J = 7.8 Hz, 1H), 7.29 (t, J = 7.8 Hz, 1H), 7.16 (s, 1H), 5.49 (q, J = 7.0 Hz, 1H), 4.37 (t, J = 7.7 Hz, 5H), 2.75 (s, 3H), 2.68-2.50 (m, 5H), 1.65 (d, J = 7.0 Hz, 3H). LCMS [M + 1]$^+$: 402.2. |
| 12-39 | 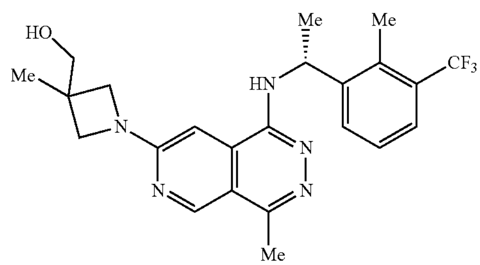 [SMILES: Cc1c([C@@H](C)Nc2nnc(C)c3cnc(N4CC(C)(CO)C4)cc23)cccc1C(F)(F)F] | $^1$H NMR (400 MHz, CD$_3$OD) δ = 9.15 (d, J = 0.8 Hz, 1H), 7.69-7.65 (m, 1H), 7.55-7.51 (m, 1H), 7.29 (t, J = 7.9 Hz, 1H), 7.17 (d, J = 0.8 Hz, 1H), 5.49 (q, J = 6.9 Hz, 1H), 4.24-4.17 (m, 2H), 3.93 (dd, J = 9.6, 3.7 Hz, 2H), 3.64 (s, 2H), 2.75 (s, 3H), 2.61 (d, J = 1.6 Hz, 3H), 1.65 (d, J = 7.0 Hz, 3H), 1.41 (s, 3H). LCMS [M + 1]$^+$: 446.2. |
| 12-40 | 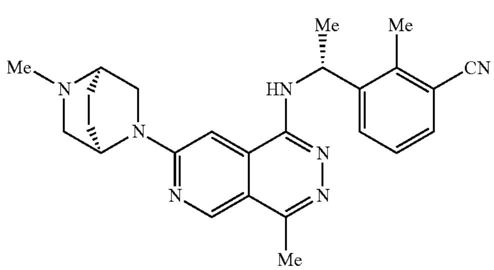 [SMILES: Cc1c(C#N)cccc1[C@@H](C)Nc1nnc(C)c2cnc(N3C[C@H]4CC[C@@H]3CN4C)cc12] | $^1$H NMR (400 MHz, DMSO-d$_6$) δ = 8.94 (s, 1H), 8.16 (s, 1H), 7.72 (d, J = 7.6 Hz, 1H), 7.62 (d, J = 7.6 Hz, 1H), 7.55-7.50 (m, 1H), 7.32 (t, J = 7.6 Hz, 1H), 7.09 (s, 1H), 5.55-5.51 (m, 1H), 4.81-4.76 (m, 1H), 3.86-3.83 (m, 1H), 3.47-3.44 (m, 1H), 3.02-3.00 (m, 2H), 2.90-2.85 (m, 1H), 2.66 (s, 3H), 2.54 (s, 3H), 2.41 (s, 3H), 2.12-2.07 (m, 1H), 1.90-1.82 (m, 2H), 1.71-1.64 (m, 1H), 1.54 (d, J = 6.8 Hz, 3H). LCMS [M + 1]$^+$: 428.4. |
| 12-41 | 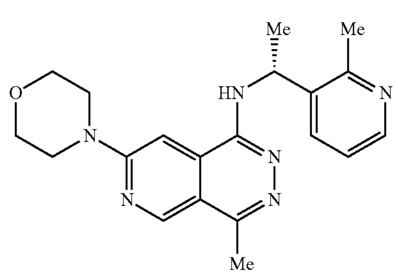 [SMILES: Cc1ncccc1[C@@H](C)Nc1nnc(C)c2cnc(N3CCOCC3)cc12] | $^1$H NMR (400 MHz, CD$_3$OD) δ 9.02 (d, J = 0.9 Hz, 1H), 8.22 (dd, J = 5.0, 1.7 Hz, 1H), 7.83 (dd, J = 7.9, 1.7 Hz, 1H), 7.31 (d, J = 1.0 Hz, 1H), 7.18 (dd, J = 7.9, 4.9 Hz, 1H), 5.59-5.53 (m, 1H), 3.86-3.81 (m, 4H), 3.79-3.73 (m, 4H), 2.72 (s, 3H), 2.63 (s, 3H), 1.63 (d, J = 7.0 Hz, 3H). LCMS [M + 1]$^+$: 365.3. |

TABLE 12-continued

| Ex. # | Structure | Spectral Data |
|---|---|---|
| 12-42 | 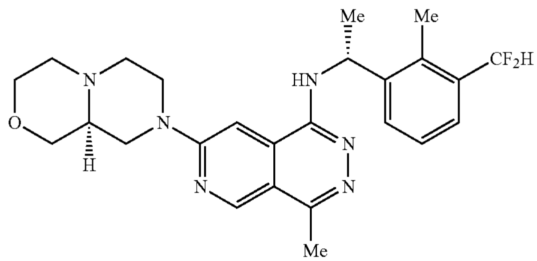 [SMILES: Cc1c(C(F)F)cccc1[C@@H](C)Nc1nnc(C)c2cnc(N3CCN4CCOC[C@@H]4C3)cc12] | ¹H NMR (400 MHz, DMSO-d₆): δ = 8.96 (s, 1H), 8.19 (s, 1H), 7.58 (d, J = 7.6 Hz, 1H), 7.45 (d, J = 7.2 Hz, 1H), 7.40 (s, 1H), 7.39-7.33 (m, 1H), 7.29-7.05 (m, 2H), 5.65-5.61 (m, 1H), 4.51-4.26 (m, 2H), 3.83-3.77 (m, 2H), 3.58-3.56 (m, 1H), 3.23 (t, J = 10.8, 1H), 3.06 (dt, J = 12.4, 2.8 Hz, 1H), 2.91 (d, J = 11.2 Hz, 1H), 2.72 (d, J = 11.2 Hz, 1H), 2.61-2.56 (m, 1H), 2.54 (s, 3H), 2.48 (s, 3H), 2.29-2.24 (m, 3H), 1.53 (d, J = 6.8 Hz, 3H). LCMS [M + 1]⁺: 469.2. |
| 12-43 | 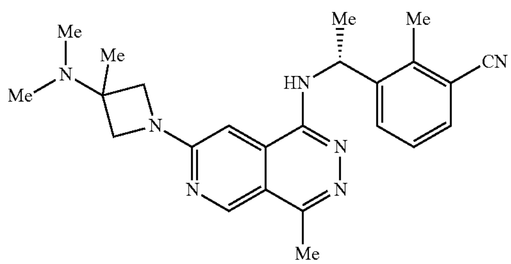 [SMILES: Cc1c(C#N)cccc1[C@@H](C)Nc1nnc(C)c2cnc(N3CC(C)(N(C)C)C3)cc12] | ¹H NMR (400 MHz, CD₃OD) δ = 9.26 (s, 1H), 7.79 (d, J = 8.0 Hz, 1H), 7.55 (d, J = 7.6 Hz, 1H), 7.49 (s, 1H), 7.30 (t, J = 8.0 Hz, 1H), 5.43 (q, J = 7.2 Hz, 1H), 4.64 (br dd, J = 4.4, 10.4 Hz, 2H), 4.35 (dd, J = 4.4, 10.4 Hz, 2H), 2.94 (s, 6H), 2.81 (s, 3H), 2.73 (s, 3H), 1.82 (s, 3H), 1.69 (d, J = 6.8 Hz, 3H). LCMS [M + 1]⁺: 416.2. |
| 12-44 | 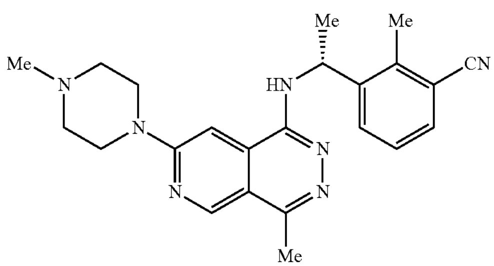 [SMILES: Cc1c(C#N)cccc1[C@@H](C)Nc1nnc(C)c2cnc(N3CCN(C)CC3)cc12] | ¹H NMR (400 MHz, CD₃OD) δ = 9.02 (s, 1H), 7.73 (d, J = 7.6 Hz, 1H), 7.51 (d, J = 8.0 Hz, 1H), 7.36 (s, 1H), 7.27 (t, J = 8.0 Hz, 1H), 5.59 (q, J = 7.2 Hz, 1H), 3.85 (s, 4H), 2.75 (s, 3H), 2.68-2.56 (m, 7H), 2.40 (s, 3H), 1.63 (d, J = 6.8 Hz, 3H). LCMS [M + 1]⁺: 402.3. |
| 12-45 | 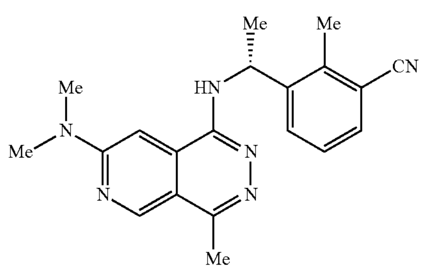 | ¹H NMR (400 MHz, CD₃OD) δ = 8.96 (s, 1H), 7.72 (d, J = 8.0 Hz, 1H), 7.49 (d, J = 7.6 Hz, 1H), 7.25 (t, J = 7.6 Hz, 1H), 7.12 (s, 1H), 5.58 (q, J = 7.2 Hz, 1H), 3.27 (s, 6H), 2.73 (s, 3H), 2.60 (br s, 3H), 1.62 (d, J = 6.8 Hz, 3H). LCMS [M + 1]⁺: 347.2. |
| 12-46 | 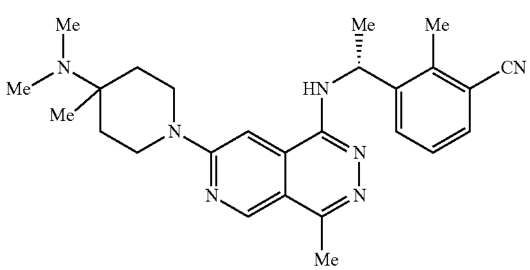 [SMILES: Cc1c(C#N)cccc1[C@@H](C)Nc1nnc(C)c2cnc(N3CCC(C)(N(C)C)CC3)cc12] | ¹H NMR (400 MHz, CD₃OD) δ = 8.99 (s, 1H), 7.73 (d, J = 7.6 Hz, 1H), 7.51 (d, J = 7.6 Hz, 1H), 7.33 (s, 1H), 7.27 (t, J = 7.6 Hz, 1H), 5.60 (q, J = 6.8 Hz, 1H), 4.27 (br d, J = 13.2 Hz, 2H), 3.45 (ddd, J = 4.4, 8.8, 13.2 Hz, 2H), 2.75 (s, 3H), 2.63 (s, 3H), 2.31 (s, 6H), 1.85-1.71 (m, 4H), 1.63 (d, J = 7.2 Hz, 3H), 1.15 (s, 3H). LCMS [M + 1]⁺: 444.5. |

TABLE 12-continued

| Ex. # | Structure | Spectral Data |
|---|---|---|
| 12-47 | 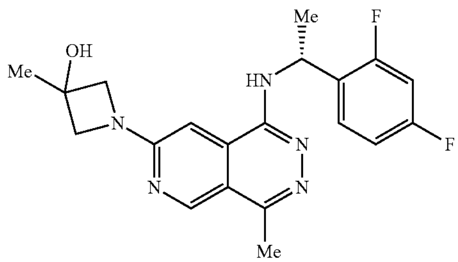 [SMILES: Cc1nnc(N[C@H](C)c2ccc(F)cc2F)c2cc(N3CC(C)(O)C3)ncc12] | $^1$H NMR (400 MHz, DMSO-$d_6$): δ = 8.95 (s, 1H), 7.44-7.38 (m, 1H), 7.36 (d, J = 7.6 Hz, 1H), 7.23-7.12 (m, 1H), 7.06 (s, 1H), 7.01-6.93 (m, 1H), 5.71 (s, 1H), 5.62-5.52 (m, 1H), 4.05-3.90 (m, 4H), 2.54 (s, 3H), 1.55 (d, J = 7.2 Hz, 3H), 1.49 (s, 3H). LCMS [M + 1]$^+$: 386.1. |
| 12-48 | 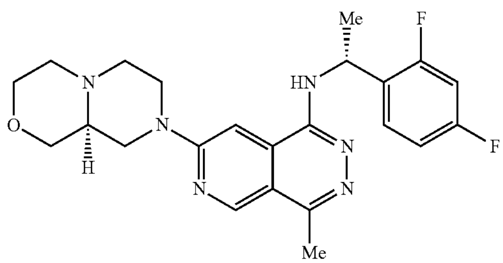 [SMILES: Cc1nnc(N[C@H](C)c2ccc(F)cc2F)c2cc(N3CCN4CCOC[C@@H]4C3)ncc12] | $^1$H NMR (400 MHz, DMSO-$d_6$): δ = 8.99 (s, 1H), 8.15 (s, 1H), 7.47-7.31 (m, 3H), 7.25-7.12 (m, 1H), 7.04-6.91 (m, 1H), 5.59 (t, J = 6.8 Hz, 1H), 4.49-4.31 (m, 2H), 3.88-3.74 (m, 2H), 3.61-3.54 (m, 1H), 3.24-3.21 (m, 1H), 3.12-3.04 (m, 1H), 2.92 (d, J = 10.8 Hz, 1H), 2.73 (d, J = 11.6 Hz, 1H), 2.63-2.57 (m, 1H), 2.57-2.53 (m, 3H), 2.29-2.15 (m, 3H), 1.57 (d, J = 7.2 Hz, 3H). LCMS [M + 1]$^+$: 441.4. |
| 12-49 | 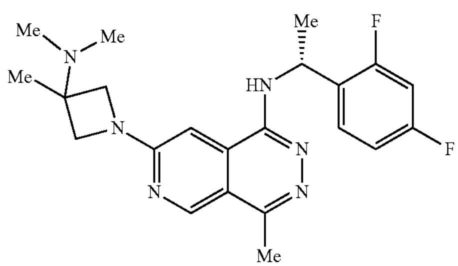 [SMILES: Cc1nnc(N[C@H](C)c2ccc(F)cc2F)c2cc(N3CC(C)(N(C)C)C3)ncc12] | $^1$H NMR (400 MHz, DMSO-$d_6$): δ = 8.95 (s, 1H), 8.16 (s, 1H), 7.45-7.32 (m, 2H), 7.22-7.14 (m, 1H), 7.08 (s, 1H), 7.01-6.93 (m, 1H), 5.57 (t, J = 6.8 Hz, 1H), 3.93-3.86 (m, 2H), 3.79 (d, J = 8.0 Hz, 2H), 2.55 (s, 3H), 2.15 (s, 6H), 1.56 (d, J = 7.2 Hz, 3H), 1.32 (s, 3H). LCMS [M + 1]$^+$: 413.4. |
| 12-50 | 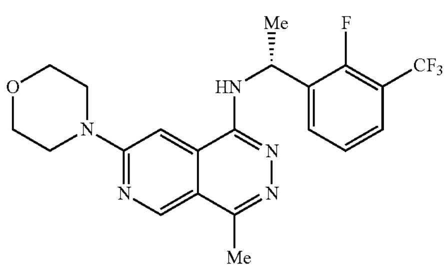 [SMILES: Cc1nnc(N[C@H](C)c2cccc(C(F)(F)F)c2F)c2cc(N3CCOCC3)ncc12] | $^1$H NMR (400 MHz, CD$_3$OD) δ = 9.03 (d, J = 0.8 Hz, 1H), 7.65 (t, J = 6.8 Hz, 1H), 7.51 (t, J = 7.2 Hz, 1H), 7.37 (s, 1H), 7.21 (t, J = 7.6 Hz, 1H), 5.68 (q, J = 7.2 Hz, 1H), 3.88-3.83 (m, 4H), 3.81-3.76 (m, 4H), 2.62 (s, 3H), 1.68 (d, J = 7.2 Hz, 3H). LCMS [M + 1]$^+$: 436.2. |
| 12-51 | 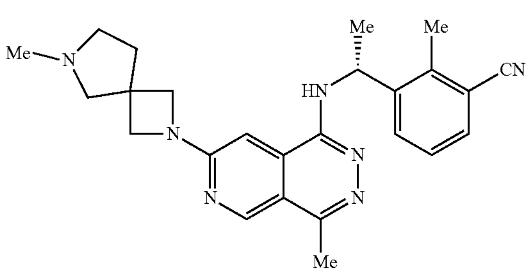 | $^1$H NMR (400 MHz, CD$_3$OD) δ = 8.92 (s, 1H), 7.70 (d, J = 8.0 Hz, 1H), 7.49 (d, J = 8.0 Hz, 1H), 7.29-7.21 (m, 1H), 7.00 (s, 1H), 5.57 (q, J = 6.8 Hz, 1H), 4.21-4.14 (m, 2H), 4.14-4.06 (m, 2H), 2.88 (s, 2H), 2.75 (s, 3H), 2.69 (t, J = 7.2 Hz, 2H), 2.61 (s, 3H), 2.41 (s, 3H), 2.25 (t, J = 7.2 Hz, 2H), 1.61 (d, J = 7.2 Hz, 3H). LCMS [M + 1]$^+$: 428.2. |

TABLE 12-continued

| Ex. # | Structure | Spectral Data |
|---|---|---|
| 12-52 | 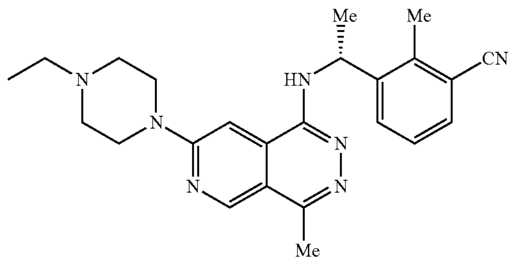 [SMILES: CCN1CCN(c2cc3c(N[C@H](C)c4cccc(C#N)c4C)nnc(C)c3cn2)CC1] | $^1$H NMR (400 MHz, CD$_3$OD) δ = 9.30 (s, 1H), 7.91 (s, 1H), 7.83 (d, J = 7.6 Hz, 1H), 7.55 (d, J = 7.6 Hz, 1H), 7.30 (t, J = 8.0 Hz, 1H), 5.44 (q, J = 6.8 Hz, 1H), 5.08 (br d, J = 14.4 Hz, 2H), 3.80 (br d, J = 12.0 Hz, 2H), 3.63 (br t, J = 12.8 Hz, 2H), 3.33 (s, 2H), 3.24 (br s, 2H), 2.82 (s, 3H), 2.74 (s, 3H), 1.70 (d, J = 6.8 Hz, 3H), 1.45 (t, J = 7.2 Hz, 3H). LCMS [M + 1]$^+$: 416.2. |
| 12-53 | 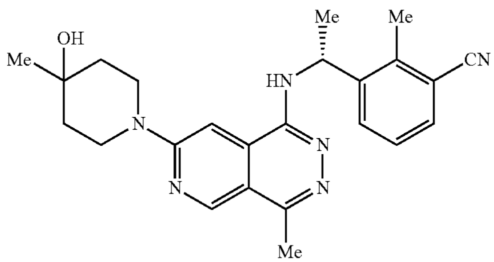 [SMILES: Cc1c(C#N)cccc1[C@@H](C)Nc1nnc(C)c2cnc(N3CCC(C)(O)CC3)cc12] | $^1$H NMR (400 MHz, CD$_3$OD) δ = 8.95 (s, 1H), 7.70 (d, J = 7.6 Hz, 1H), 7.48 (d, J = 6.8 Hz, 1H), 7.31 (s, 1H), 7.24 (t, J = 8.0 Hz, 1H), 5.61-5.49 (m, 1H), 4.23-4.13 (m, 2H), 3.63-3.52 (m, 2H), 2.72 (s, 3H), 2.59 (s, 3H), 1.73-1.64 (m, 4H), 1.60 (d, J = 6.8 Hz, 3H), 1.28 (s, 3H). LCMS [M + 1]$^+$: 417.3. |
| 12-54 | 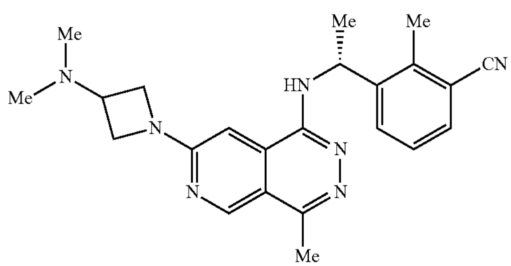 [SMILES: Cc1c(C#N)cccc1[C@@H](C)Nc1nnc(C)c2cnc(N3CC(N(C)C)C3)cc12] | $^1$H NMR (400 MHz, CD$_3$OD) δ = 9.26 (s, 1H), 7.80 (d, J = 7.2 Hz, 1H), 7.57-7.52 (m, 1H), 7.50 (s, 1H), 7.30 (t, J = 8.0 Hz, 1H), 5.43 (q, J = 6.8 Hz, 1H), 4.77-4.63 (m, 2H), 4.62-4.51 (m, 2H), 4.44 (tt, J = 4.8, 7.6 Hz, 1H), 3.00 (s, 6H), 2.81 (s, 3H), 2.73 (s, 3H), 1.69 (d, J = 6.8 Hz, 3H). LCMS [M + 1]$^+$: 402.2. |
| 12-55 | 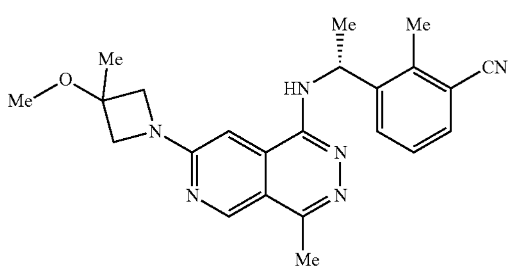 [SMILES: COC1(C)CN(c2cc3c(N[C@H](C)c4cccc(C#N)c4C)nnc(C)c3cn2)C1] | $^1$H NMR (400 MHz, CD$_3$OD) δ = 9.18 (s, 1H), 7.71 (d, J = 7.2 Hz, 1H), 7.55 (d, J = 6.8 Hz, 1H), 7.30 (t, J = 7.6 Hz, 1H), 7.21 (s, 1H), 5.40 (q, J = 6.8 Hz, 1H), 4.25 (dd, J = 2.8, 9.8 Hz, 2H), 4.13 (dd, J = 1.6, 10.0 Hz, 2H), 3.35 (s, 3H), 2.77 (s, 3H), 2.73 (s, 3H), 1.65 (d, J = 7.2 Hz, 3H), 1.62 (s, 3H). LCMS [M + 1]$^+$: 403.2. |
| 12-56 | 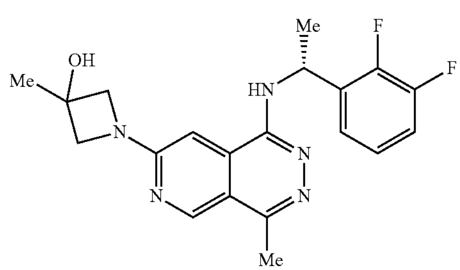 [SMILES: Cc1nnc(N[C@H](C)c2cccc(F)c2F)c2cc(N3CC(C)(O)C3)ncc12] | $^1$H NMR (400 MHz, DMSO-d$_6$) δ = 8.95 (s, 1H), 7.42 (d, J = 6.8 Hz, 1H), 7.27-7.17 (m, 2H), 7.14-7.05 (m, 2H), 5.71 (s, 1H), 5.65-5.58 (m, 1H), 4.05-3.94 (m, 4H), 2.55 (s, 3H), 1.60 (d, J = 6.8 Hz, 3H), 1.49 (s, 3H). LCMS [M + 1]$^+$: 386.0. |
| 12-57 | 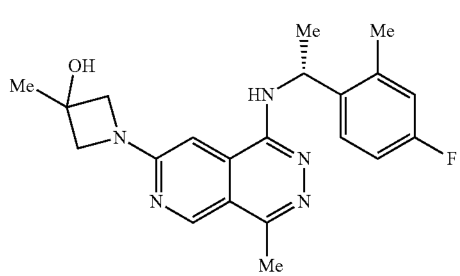 [SMILES: Cc1cc(F)ccc1[C@@H](C)Nc1nnc(C)c2cnc(N3CC(C)(O)C3)cc12] | $^1$H NMR (400 MHz, CD$_3$OD) δ = 8.92 (s, 1H), 7.41 (dd, J = 6.0, 8.4 Hz, 1H), 7.01 (s, 1H), 6.90-6.77 (m, 2H), 5.56 (q, J = 6.8 Hz, 1H), 4.12-3.98 (m, 4H), 2.63 (s, 3H), 2.47 (s, 3H), 1.62-1.55 (m, 6H). LCMS [M + 1]$^+$: 382.1. |

TABLE 12-continued

| Ex. # | Structure | Spectral Data |
|---|---|---|
| 12-58 | 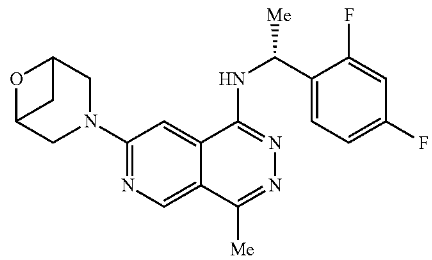 [SMILES: Cc1nnc(N[C@H](C)c2ccc(F)cc2F)c2cc(N3CC4CC(C3)O4)ncc12] | $^1$H NMR (400 MHz, DMSO-d$_6$) δ = 9.05 (s, 1H), 7.49-7.38 (m, 3H), 7.26 (s, 2H), 7.21-7.15 (m, 1H), 6.98 (t, J = 8.7 Hz, 1H), 5.62 (t, J = 7.0 Hz, 1H), 4.84-4.78 (m, 2H), 3.93-3.86 (m, 2H), 3.79-3.69 (m, 2H), 3.24-3.17 (m, 1H), 2.58 (s, 3H), 1.95 (d, J = 8.8 Hz, 1H), 1.58 (d, J = 7.1 Hz, 3H). LCMS [M + 1]$^+$: 398.1. |
| 12-59 | 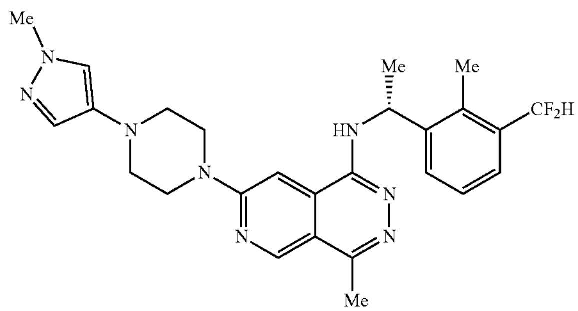 [SMILES: Cc1c(C(F)F)cccc1[C@@H](C)Nc1nnc(C)c2cnc(N3CCN(c4cnn(C)c4)CC3)cc12] | $^1$H NMR (400 MHz, DMSO-d$_6$) δ 8.99 (s, 1H), 7.62-7.18 (m, 7H), 5.64 (t, J = 6.9 Hz, 1H), 3.88-3.81 (m, 4H), 3.75 (s, 3H), 3.04-2.97 (m, 4H), 2.55 (s, 3H), 1.54 (d, J = 6.9 Hz, 3H). LCMS [M + 1]$^+$: 493.3. |
| 12-60 | 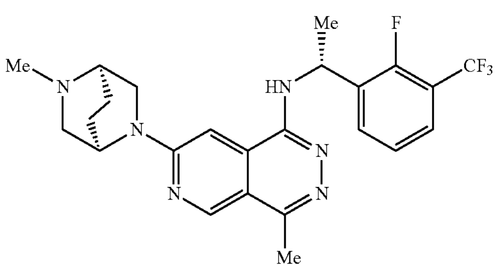 [SMILES: Cc1nnc(N[C@H](C)c2cccc(C(F)(F)F)c2F)c2cc(N3C[C@H]4CC[C@@H]3CN4C)ncc12] | $^1$H NMR (400 MHz, DMSO-d$_6$) δ = 8.94 (s, 1H), 7.69 (t, J = 7.2 Hz, 1H), 7.61 (t, J = 7.2 Hz, 1H), 7.47 (d, J = 7.0 Hz, 1H), 7.31 (t, J = 7.8 Hz, 1H), 7.11 (s, 1H), 5.70-5.59 (m, 1H), 3.84 (d, J = 11.2 Hz, 1H), 3.45 (d, J = 11.1 Hz, 1H), 3.00-2.77 (m, 4H), 2.37 (s, 3H), 2.13-1.96 (m, 2H), 1.87-1.79 (m, 2H), 1.61 (d, J = 7.0 Hz, 3H). LCMS [M + 1]$^+$: 475.0. |
| 12-61 | 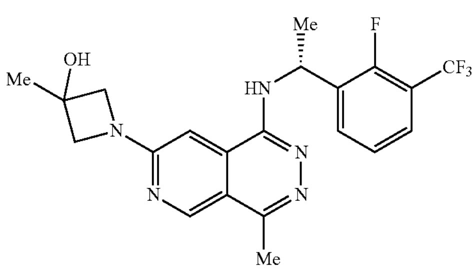 [SMILES: Cc1nnc(N[C@H](C)c2cccc(C(F)(F)F)c2F)c2cc(N3CC(C)(O)C3)ncc12] | $^1$H NMR (400 MHz, DMSO-d$_6$) δ = 8.96 (s, 1H), 7.69 (t, J = 7.3 Hz, 1H), 7.61 (t, J = 7.2 Hz, 1H), 7.48 (d, J = 7.0 Hz, 1H), 7.30 (t, J = 7.8 Hz, 1H), 7.08 (s, 1H), 5.67-5.59 (m, 1H), 4.05-3.93 (m, 4H), 2.54 (s, 3H), 1.60 (d, J = 7.0 Hz, 3H), 1.50 (s, 3H). LCMS [M + 1]$^+$: 436.1. |
| 12-62 | 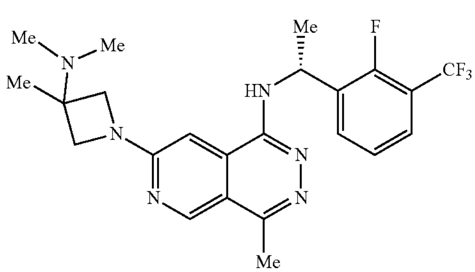 [SMILES: Cc1nnc(N[C@H](C)c2cccc(C(F)(F)F)c2F)c2cc(N3CC(C)(N(C)C)C3)ncc12] | $^1$H NMR (400 MHz, DMSO-d$_6$) δ 9.08 (s, 1H), 7.90 (s, 1H), 7.73 (t, J = 7.4 Hz, 1H), 7.64 (t, J = 7.3 Hz, 1H), 7.33 (t, J = 7.8 Hz, 1H), 7.21 (s, 1H), 5.63-5.54 (m, 1H), 4.06 (d, J = 9.0 Hz, 2H), 3.91 (d, J = 8.8 Hz, 2H), 2.62 (s, 3H), 2.29 (s, 6H), 1.63 (d, J = 7.0 Hz, 3H), 1.41 (s, 3H). LCMS [M + 1]$^+$: 463.3. |

TABLE 12-continued

| Ex. # | Structure | Spectral Data |
|---|---|---|
| 12-63 | 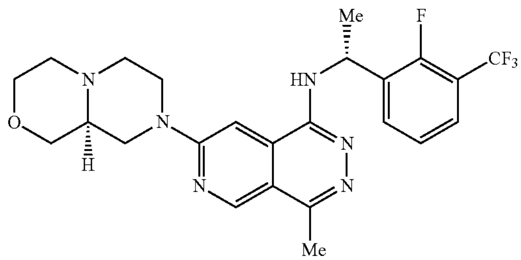 [SMILES: Cc1nnc(N[C@H](C)c2cccc(C(F)(F)F)c2F)c2cc(N3CCN4CCOC[C@@H]4C3)ncc12] | $^1$H NMR (400 MHz, Methanol-d$_4$) δ 9.02 (s, 1H), 7.65 (t, J = 7.4 Hz, 1H), 7.51 (t, J = 7.2 Hz, 1H), 7.37 (s, 1H), 7.21 (t, J = 7.8 Hz, 1H), 5.68 (q, J = 7.1 Hz, 1H), 4.63 (d, J = 13.3 Hz, 1H), 4.43 (d, J = 12.8 Hz, 1H), 3.93-3.71 (m, 3H), 3.38 (t, J = 10.7 Hz, 1H), 3.24-3.11 (m, 1H), 2.97 (d, J = 11.4 Hz, 1H), 2.80 (d, J = 11.6 Hz, 1H), 2.71 (t, J = 11.7 Hz, 1H), 2.62 (s, 3H), 2.47-2.33 (m, 3H), 1.68 (d, J = 7.0 Hz, 3H). LCMS [M + 1] $^+$: 491.4. |
| 12-64 | 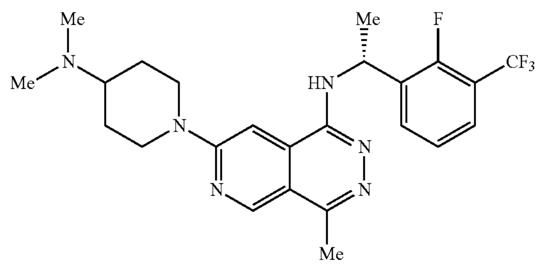 [SMILES: Cc1nnc(N[C@H](C)c2cccc(C(F)(F)F)c2F)c2cc(N3CCC(N(C)C)CC3)ncc12] | $^1$H NMR (400 MHz, DMSO-d$_6$) δ = 8.99 (s, 1H), 7.70 (t, J = 7.4 Hz, 1H), 7.62 (t, J = 7.3 Hz, 1H), 7.57 (d, J = 6.8 Hz, 1H), 7.47 (s, 1H), 7.31 (t, J = 7.7 Hz, 1H), 5.69-5.60 (m, 1H), 4.64 (d, J = 13.2 Hz, 2H), 3.02 (t, J = 12.6 Hz, 2H), 2.88-2.75 (m, 1H), 2.55 (s, 3H), 2.41 (s, 6H), 2.04-1.94 (m, 2H), 1.62 (d, J = 7.0 Hz, 3H), 1.49 (q, J = 12.4 Hz, 2H). LCMS [M + 1] $^+$: 477.3. |
| 12-65 | 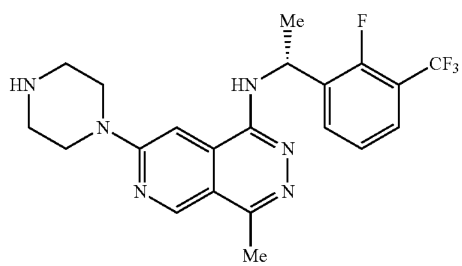 [SMILES: Cc1nnc(N[C@H](C)c2cccc(C(F)(F)F)c2F)c2cc(N3CCNCC3)ncc12] | $^1$H NMR (400 MHz, DMSO-d$_6$) δ 9.02 (s, 1H), 7.70 (t, J = 7.4 Hz, 1H), 7.62 (t, J = 7.2 Hz, 1H), 7.56 (s, 1H), 7.48 (s, 1H), 7.31 (t, J = 7.8 Hz, 1H), 5.69-5.60 (m, 1H), 3.85-3.77 (m, 4H), 3.10-3.02 (m, 4H), 2.56 (s, 3H), 1.62 (d, J = 7.0 Hz, 3H). LCMS [M + 1] $^+$: 435.3. |
| 12-66 | 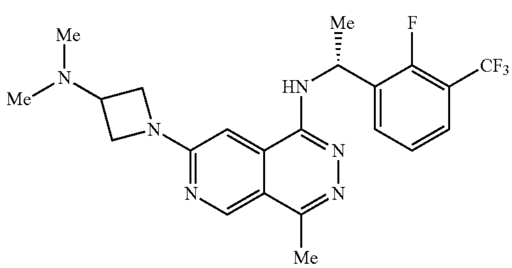 [SMILES: Cc1nnc(N[C@H](C)c2cccc(C(F)(F)F)c2F)c2cc(N3CC(N(C)C)C3)ncc12] | $^1$H NMR (400 MHz, DMSO-d$_6$) δ = 8.96 (s, 1H), 7.70 (t, J = 7.4 Hz, 1H), 7.61 (t, J = 7.3 Hz, 1H), 7.48 (d, J = 6.9 Hz, 1H), 7.30 (t, J = 7.8 Hz, 1H), 7.10 (s, 1H), 5.68-5.59 (m, 1H), 4.21-4.13 (m, 2H), 3.94-3.86 (m, 2H), 2.55 (s, 2H), 2.16 (s, 5H), 1.60 (d, J = 7.0 Hz, 3H). LCMS [M + 1] $^+$: 449.3. |
| 12-67 | 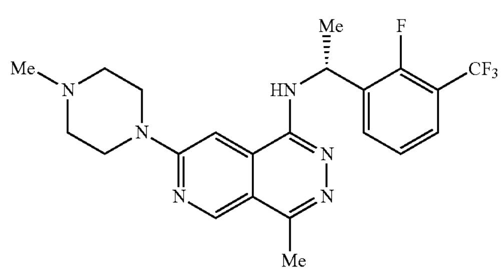 [SMILES: Cc1nnc(N[C@H](C)c2cccc(C(F)(F)F)c2F)c2cc(N3CCN(C)CC3)ncc12] | $^1$H NMR (400 MHz, CD$_3$OD) δ = 9.12 (s, 1H), 8.47 (s, 1H), 7.68 (t, J = 7.3 Hz, 1H), 7.54 (t, J = 7.3 Hz, 1H), 7.47 (s, 1H), 7.24 (t, J = 7.8 Hz, 1H), 5.61 (q, J = 7.0 Hz, 1H), 3.95 (t, J = 5.2 Hz, 4H), 2.69 (d, J = 2.9 Hz, 7H), 2.44 (s, 3H), 1.70 (d, J = 7.0 Hz, 3H). LCMS [M + 1] $^+$: 449.0. |

TABLE 12-continued

| Ex. # | Structure | Spectral Data |
|---|---|---|
| 12-68 | 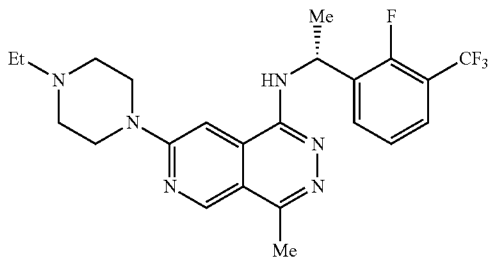 [SMILES: CCN1CCN(c2cc3c(N[C@H](C)c4cccc(C(F)(F)F)c4F)nnc(C)c3cn2)CC1] | ¹H NMR (400 MHz, CD₃OD) δ = 9.10 (s, 1H), 7.69 (t, J = 7.4 Hz, 1H), 7.55 (t, J = 7.2 Hz, 1H), 7.44 (s, 1H), 7.25 (t, J = 7.8 Hz, 1H), 5.66 (q, J = 7.0 Hz, 1H), 3.93 (t, J = 5.2 Hz, 4H), 2.73 (t, J = 5.2 Hz, 4H), 2.68 (s, 3H), 2.61 (q, J = 7.2 Hz, 2H), 1.71 (d, J = 7.0 Hz, 3H), 1.22 (t, J = 7.2 Hz, 3H). LCMS [M + 1]⁺: 463.0. |
| 12-69 | 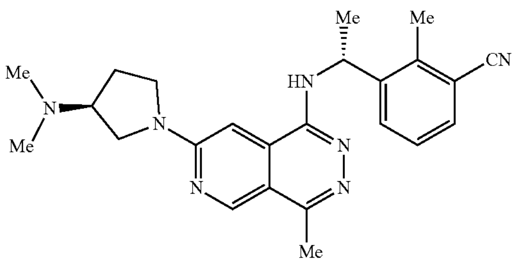 [SMILES: Cc1c(C#N)cccc1[C@@H](C)Nc1nnc(C)c2cnc(N3CC[C@H](N(C)C)C3)cc12] | ¹H NMR (400 MHz, CD₃OD) δ 8.95 (d, J = 0.8 Hz, 1H), 7.71 (dd, J = 8.0, 1.4 Hz, 1H), 7.50 (d, J = 1.4 Hz, 0H), 7.24 (t, J = 7.8 Hz, 1H), 7.01 (s, 1H), 5.58 (q, J = 6.9 Hz, 1H), 3.97-3.83 (m, 3H), 3.61-3.49 (m, 1H), 3.41-3.34 (m, 1H), 3.31 (s, 9H), 3.04-2.97 (m, 1H), 2.72 (s, 3H), 2.61 (s, 3H), 2.43-2.32 (m, 7H), 2.05-1.93 (m, 1H), 1.62 (d, J = 6.9 Hz, 4H). LCMS [M + 1]⁺: 416.3. |
| 12-70 | 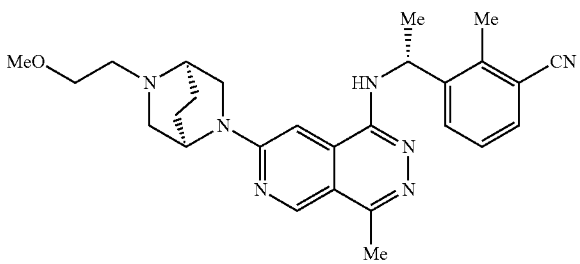 [SMILES: COCCN1C[C@H]2CC[C@@H]1CN2c1cc2c(N[C@H](C)c3cccc(C#N)c3C)nnc(C)c2cn1] | ¹H NMR (400 MHz, CD₃OD) δ = 9.17-9.14 (m, 1H), 7.74 (dd, J = 7.8, 1.3 Hz, 1H), 7.54 (dd, J = 7.7, 1.3 Hz, 1H), 7.31-7.25 (m, 2H), 5.47 (q, J = 6.9 Hz, 1H), 5.09 (s, 1H), 4.09 (d, J = 12.4 Hz, 1H), 3.71 (d, J = 12.4 Hz, 1H), 3.64 (t, J = 5.3 Hz, 2H), 3.57 (br s, 2H), 3.39 (s, 3H), 3.23-3.08 (m, 3H), 2.33 (d, J = 9.1 Hz, 1H), 2.03 (t, J = 8.3 Hz, 2H), 1.93-1.83 (m, 1H), 1.66 (d, J = 7.0 Hz, 3H). LCMS [M + 1]⁺: 472.3. |
| 12-71 | 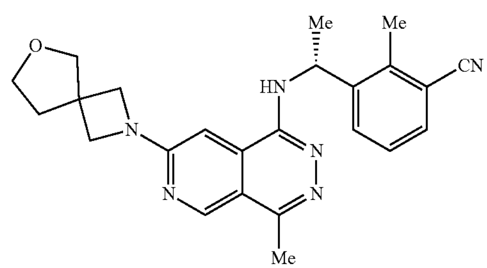 [SMILES: Cc1c(C#N)cccc1[C@@H](C)Nc1nnc(C)c2cnc(N3CC4(CCOC4)C3)cc12] | ¹H NMR (400 MHz, DMSO-d₆) δ = 14.73 (s, 1H), 9.24 (d, J = 2.7 Hz, 1H), 8.88 (s, 1H), 7.80 (d, J = 8.2 Hz, 1H), 7.66 (d, J = 7.6 Hz, 1H), 7.52 (s, 1H), 7.41-7.32 (m, 1H), 5.34-5.29 (m, 1H), 4.27 (s, 4H), 3.92-3.87 (m, 2H), 3.83-3.74 (m, 2H), 2.74 (s, 3H), 2.66 (s, 3H), 2.29-2.21 (m, 2H), 1.60 (d, J = 7.1, 3H). LCMS [M + 1]⁺: 415.2. |
| 12-72 | 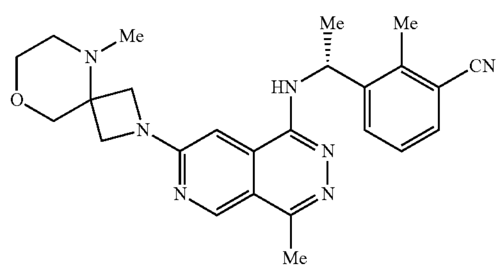 [SMILES: Cc1c(C#N)cccc1[C@@H](C)Nc1nnc(C)c2cnc(N3CC4(COCCN4C)C3)cc12] | ¹H NMR (400 MHz, CD₃OD) δ 9.06 (s, 1H), 8.49 (s, 1H), 7.72 (dd, J = 7.9, 1.3 Hz, 1H), 7.51 (dd, J = 7.7, 1.3 Hz, 1H), 7.27 (t, J = 7.8 Hz, 1H), 7.15 (s, 1H), 5.50 (q, J = 6.9 Hz, 1H), 4.38 (d, J = 10.0 Hz, 2H), 3.89 (dd, J = 10.0, 2.9 Hz, 2H), 3.82-3.73 (m, 4H), 2.71 (s, 3H), 2.69 (s, 3H), 2.65-2.58 (m, 2H), 2.50 (s, 3H), 1.63 (d, J = 7.0 Hz, 3H). LCMS [M + 1]⁺: 444.2. |

TABLE 12-continued

| Ex. # | Structure | Spectral Data |
|---|---|---|
| 12-73 | 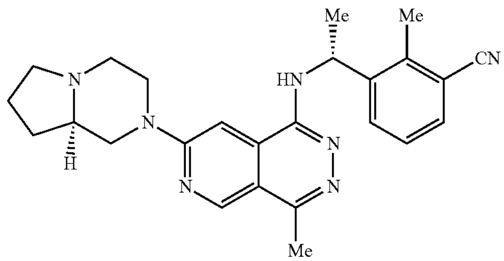 [SMILES: Cc1c(C#N)cccc1[C@@H](C)Nc1nnc(C)c2cnc(N3CCN4CCC[C@@H]4C3)cc12] | ¹H NMR (400 MHz, Methanol-d₄) δ 8.99 (d, J = 0.9 Hz, 1H), 7.70 (dd, J = 7.9, 1.4 Hz, 1H), 7.49 (dd, J = 7.7, 1.4 Hz, 1H), 7.34 (d, J = 1.0 Hz, 1H), 7.24 (t, J = 7.8 Hz, 1H), 5.57 (q, J = 6.9 Hz, 1H), 4.71 (d, J = 12.4 Hz, 1H), 4.62 (d, J = 13.4 Hz, 1H), 3.24-3.07 (m, 3H), 2.85-2.72 (m, 2H), 2.72 (s, 3H), 2.61 (s, 3H), 2.41-2.13 (m, 3H), 2.06-1.91 (m, 1H), 1.94-1.83. (m, 1H), 1.61 (d, J = 6.9 Hz, 3H), 1.61-1.48 (m, 1H). LCMS [M + 1] ⁺: 428.2. |
| 12-74 | 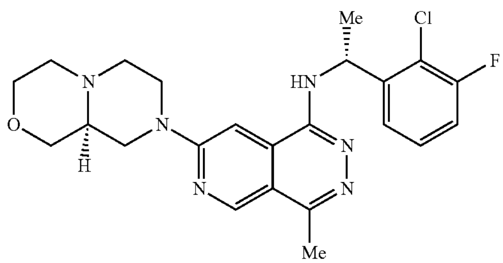 [SMILES: Cc1nnc(N[C@H](C)c2cccc(F)c2Cl)c2cc(N3CCN4CCOC[C@@H]4C3)ncc12] | ¹H NMR (400 MHz, CD₃OD) δ = 9.13 (s, 1H), 8.45 (s, 1H), 7.47 (s, 1H), 7.30-7.23 (m, 1H), 7.26-7.16 (m, 1H), 7.13-7.04 (m, 1H), 5.62 (q, J = 7.0 Hz, 1H), 4.72 (d, J = 13.3 Hz, 1H), 4.54-4.47 (m, 1H), 3.92-3.80 (m, 2H), 3.79-3.68 (m, 1H), 3.37 (t, J = 10.6 Hz, 1H), 3.31-3.20 (m, 1H), 3.02-2.93 (m, 1H), 2.83-2.72 (m, 2H), 2.70 (s, 3H), 2.46-2.35 (m, 2H), 2.39-2.28 (m, 1H), 1.65 (d, J = 7.0 Hz, 3H). LCMS [M + 1] ⁺: 457.2. |
| 12-75 | 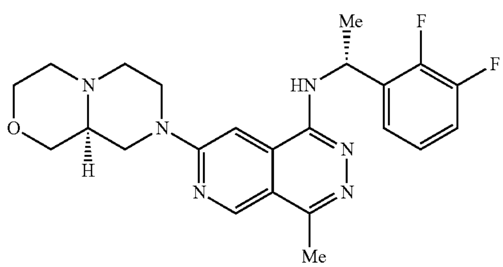 [SMILES: Cc1nnc(N[C@H](C)c2cccc(F)c2F)c2cc(N3CCN4CCOC[C@@H]4C3)ncc12] | ¹H NMR (400 MHz, DMSO-d₆) δ = 8.99 (s, 1H), 7.47 (d, J = 7.1 Hz, 1H), 7.41 (s, 1H), 7.30-7.15 (m, 2H), 7.14-7.04 (m, 1H), 5.67-5.59 (m, 1H), 4.44 (d, J = 12.5 Hz, 1H), 4.37 (d, J = 12.4 Hz, 1H), 3.86-3.76 (m, 2H), 3.63-3.52 (m, 1H), 3.29-3.19 (m, 1H), 3.14-3.02 (m, 1H), 2.92 (d, J = 11.5 Hz, 1H), 2.73 (d, J = 11.3 Hz, 1H), 2.64-2.57 (m, 1H), 2.56 (s, 3H), 2.36-2.18 (m, 3H), 1.60 (d, J = 7.0 Hz, 3H). LCMS [M + 1] ⁺: 441.1. |
| 12-76 | 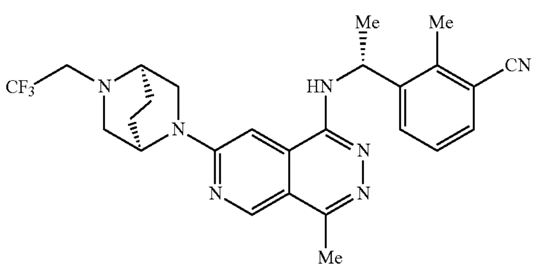 [SMILES: Cc1c(C#N)cccc1[C@@H](C)Nc1nnc(C)c2cnc(N3C[C@H]4CC[C@@H]3CN4CC(F)(F)F)cc12] | ¹H NMR (400 MHz, DMSO-d₆) δ = 8.93 (s, 1H), 7.72 (d, J = 8.0 Hz, 1H), 7.61 (d, J = 7.5 Hz, 1H), 7.47 (d, J = 6.8 Hz, 1H), 7.31 (t, J = 7.8 Hz, 1H), 7.08 (s, 1H), 5.57-5.46 (m, 1H), 3.78 (d, J = 11.2 Hz, 1H), 3.56-3.44 (m, 1H), 3.24-3.07 (m, 4H), 2.65 (s, 3H), 2.52 (s, 3H), 2.13-1.97 (m, 1H), 1.93-1.78 (m, 2H), 1.76-1.67 (m, 2H), 1.54 (d, J = 6.9 Hz, 3H). LCMS [M + 1] ⁺: 496.0. |
| 12-77 | 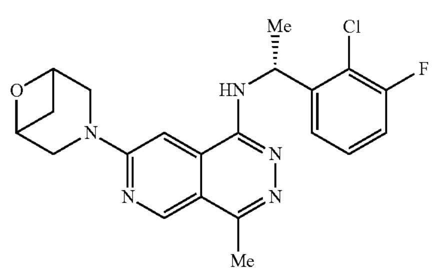 [SMILES: Cc1nnc(N[C@H](C)c2cccc(F)c2Cl)c2cc(N3CC4CC(C3)O4)ncc12] | ¹H NMR (400 MHz, CD₃OD) δ = 9.17 (s, 1H), 8.51 (s, 1H), 7.35 (s, 1H), 7.33-7.27 (m, 1H), 7.27-7.17 (m, 1H), 7.14-7.05 (m, 1H), 5.68 (q, J = 6.9 Hz, 1H), 4.87 (s, 2H), 4.02 (d, J = 13.0 Hz, 2H), 3.88 (d, J = 12.8 Hz, 2H), 3.42-3.34 (m, 1H), 2.72 (s, 3H), 2.07-2.00 (m, 1H), 1.68 (d, J = 7.0 Hz, 3H). LCMS [M + 1] ⁺: 414.2. |

| Ex. # | Structure | Spectral Data |
|---|---|---|
| 12-78 | 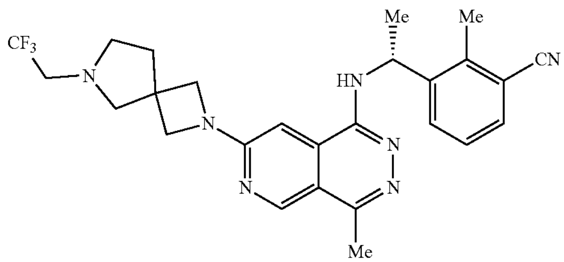 [SMILES: Cc1c(C#N)cccc1[C@@H](C)Nc1nnc(C)c2cnc(N3CC4(CCN(CC(F)(F)F)C4)C3)cc12] | ¹H NMR (400 MHz, DMSO-d₆) δ = 8.97 (s, 1H), 7.71 (d, J = 8.0 Hz, 1H), 7.61 (d, J = 7.7 Hz, 1H), 7.58-7.52 (m, 1H), 7.32 (t, J = 7.8 Hz, 1H), 7.08 (s, 1H), 5.48 (q, J = 6.9 Hz, 1H), 4.11-4.01 (m, 4H), 3.32-3.25 (m, 2H), 3.00 (s, 2H), 2.80 (t, J = 7.1 Hz, 2H), 2.64 (s, 3H), 2.55 (s, 3H), 2.13 (t, J = 7.0 Hz, 2H), 1.53 (d, J = 6.9 Hz, 3H). LCMS [M + 1]⁺: 496.4. |
| 12-79 | 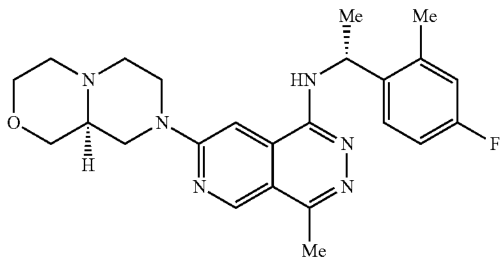 [SMILES: Cc1cc(F)ccc1[C@@H](C)Nc1nnc(C)c2cnc(N3CCN4CCOC[C@@H]4C3)cc12] | ¹H NMR (400 MHz, CD₃OD) δ = 9.25 (s, 1H), 7.59 (s, 1H), 7.43 (dd, J = 8.6, 5.8 Hz, 1H), 6.95-6.84 (m, 2H), 5.40 (q, J = 7.0 Hz, 1H), 3.98-3.69 (m, 3H), 3.51-3.37 (m, 4H), 3.22-2.86 (m, 3H), 2.81 (s, 3H), 2.68-2.53 (m, 3H), 2.50 (s, 3H), 1.65 (d, J = 6.9 Hz, 3H). LCMS [M + 1]⁺: 437.3. |
| 12-80 | 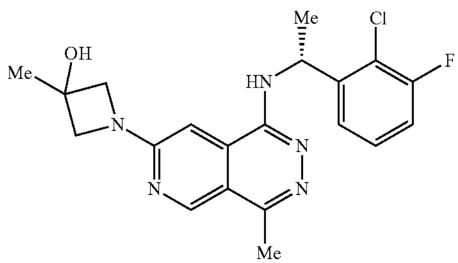 [SMILES: Cc1nnc(N[C@H](C)c2cccc(F)c2Cl)c2cc(N3CC(C)(O)C3)ncc12] | ¹H NMR (400 MHz, CD₃OD) δ = 9.06 (d, J = 0.8 Hz, 1H), 8.48 (s, 1H), 7.29-7.16 (m, 2H), 7.15-7.10 (m, 1H), 7.13-7.04 (m, 1H), 5.63 (q, J = 6.9 Hz, 1H), 4.21-4.14 (m, 2H), 4.14-4.08 (m, 2H), 2.68 (s, 3H), 1.65 (d, J = 7.0 Hz, 3H), 1.60 (s, 3H). LCMS [M + 1]⁺: 402.2. |
| 12-81 | 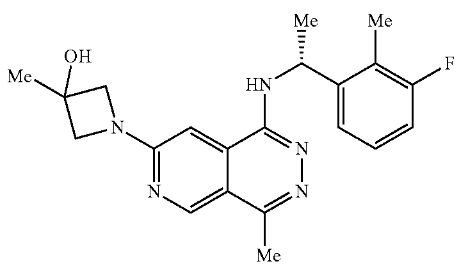 [SMILES: Cc1c(F)cccc1[C@@H](C)Nc1nnc(C)c2cnc(N3CC(C)(O)C3)cc12] | ¹H NMR (400 MHz, CD₃OD) δ = 8.94-8.89 (m, 1H), 7.22 (d, J = 7.7 Hz, 1H), 7.13-7.00 (m, 2H), 6.86 (t, J = 8.9 Hz, 1H), 5.58 (q, J = 6.9 Hz, 1H), 4.13-4.07 (m, 2H), 4.07-4.01 (m, 2H), 2.62 (s, 3H), 2.37 (s, 3H), 1.62-1.56 (m, 6H). LCMS [M + 1]⁺: 382.3. |
| 12-82 | 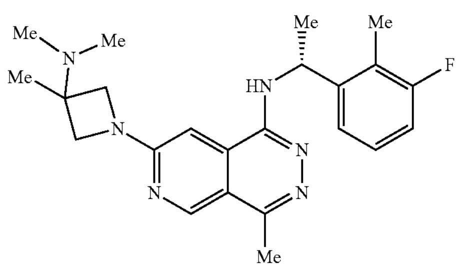 [SMILES: Cc1c(F)cccc1[C@@H](C)Nc1nnc(C)c2cnc(N3CC(C)(N(C)C)C3)cc12] | ¹H NMR (400 MHz, DMSO-d₆) δ = 14.91 (s, 1H), 12.41 (s, 1H), 9.12 (s, 1H), 8.90 (s, 1H), 7.67 (s, 1H), 7.22 (d, J = 7.8 Hz, 1H), 7.08-6.98 (m, 1H), 6.86 (t, J = 9.0 Hz, 1H), 5.23-5.11 (m, 1H), 4.54-4.46 (m, 2H), 4.06-4.01 (m, 2H), 2.64 (s, 3H), 2.57 (s, 6H), 2.20 (s, 3H), 1.56 (s, 3H), 1.47 (d, J = 6.9 Hz, 3H). LCMS [M + 1]⁺: 409.2. |
| 12-83 | 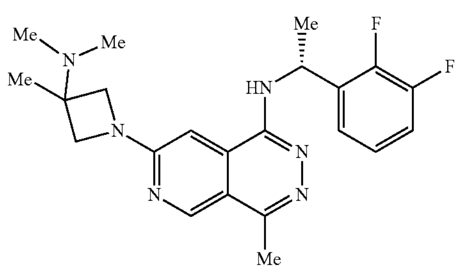 [SMILES: Cc1nnc(N[C@H](C)c2cccc(F)c2F)c2cc(N3CC(C)(N(C)C)C3)ncc12] | ¹H NMR (400 MHz, DMSO-d₆) δ = 8.97 (s, 1H), 8.14 (s, 1H), 7.45 (s, 1H), 7.30-7.16 (m, 2H), 7.13-7.06 (m, 2H), 5.63-5.59 (m, 1H), 3.91 (dd, J = 8.2, 4.3 Hz, 2H), 3.85-3.78 (m, 2H), 2.56 (s, 3H), 2.16 (s, 6H), 1.60 (d, J = 7.0 Hz, 3H), 1.33 (s, 3H). LCMS [M + 1]⁺: 413.1. |

TABLE 12-continued

| Ex. # | Structure | Spectral Data |
|---|---|---|
| 12-84 | 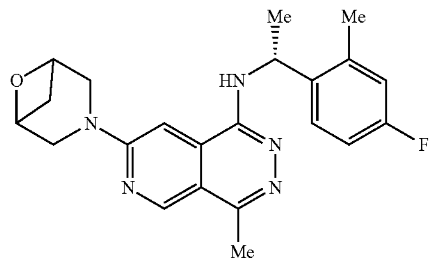 [SMILES: Cc1cc(F)ccc1[C@@H](C)Nc1nnc(C)c2cnc(N3CC4CC(C3)O4)cc12] | $^1$H NMR (400 MHz, CD$_3$OD) δ 9.19 (s, 1H), 7.44 (dd, J = 8.6, 5.9 Hz, 1H), 7.34 (s, 1H), 6.93-6.80 (m, 2H), 5.48 (q, J = 6.9 Hz, 1H), 4.85 (s, 2H), 4.02 (d, J = 13.0 Hz, 2H), 3.88 (d, J = 12.9 Hz, 2H), 3.41-3.33 (m, 1H), 2.76 (s, 3H), 2.49 (s, 3H), 2.02 (d, J = 9.1 Hz, 1H), 1.64 (d, J = 6.9 Hz, 3H). LCMS [M + 1]$^+$: 394.3. |
| 12-85 | 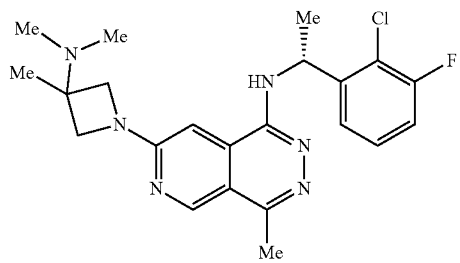 [SMILES: Cc1nnc(N[C@H](C)c2cccc(F)c2Cl)c2cc(N3CC(C)(N(C)C)C3)ncc12] | $^1$H NMR (400 MHz, CD$_3$OD) δ = 9.03 (d, J = 0.8 Hz, 1H), 7.30-7.23 (m, 1H), 7.25-7.15 (m, 1H), 7.12 (s, 1H), 7.12-7.03 (m, 1H), 5.65 (q, J = 7.0 Hz, 1H), 4.09 (d, J = 8.9 Hz, 2H), 3.95 (d, J = 8.8 Hz, 2H), 2.66 (s, 3H), 2.30 (s, 6H), 1.65 (d, J = 6.9 Hz, 3H), 1.47 (s, 3H). LCMS [M + 1]$^+$: 429.2. |
| 12-86 | 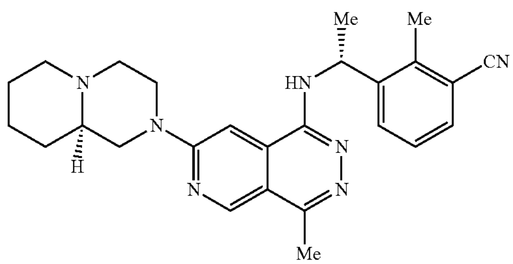 [SMILES: Cc1c(C#N)cccc1[C@@H](C)Nc1nnc(C)c2cnc(N3CCN4CCCC[C@@H]4C3)cc12] | $^1$H NMR (400 MHz, CD$_3$OD) δ = 9.09 (s, 1H), 7.72 (d, J = 8.0 Hz, 1H), 7.53 (d, J = 7.7 Hz, 1H), 7.41 (s, 1H), 7.28 (t, J = 7.8 Hz, 1H), 5.54 (q, J = 7.0 Hz, 1H), 4.70 (d, J = 13.2 Hz, 1H), 4.51 (d, J = 13.2 Hz, 1H), 3.28-3.16 (m, 1H), 3.04-2.96 (m, 2H), 2.84 (dd, J = 13.2, 10.7 Hz, 1H), 2.74 (s, 3H), 2.69 (s, 3H), 2.41 (td, J = 12.0, 3.3 Hz, 1H), 2.27-2.13 (m, 2H), 1.92-1.85 (m, 1H), 1.83-1.69 (m, 3H), 1.64 (d, J = 7.0 Hz, 3H), 1.50-1.33 (m, 2H). LCMS [M + 1]$^+$: 442.3. |
| 12-87 | 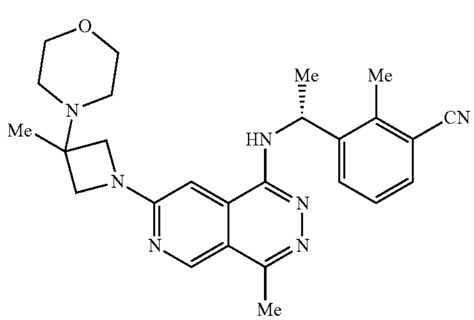 [SMILES: Cc1c(C#N)cccc1[C@@H](C)Nc1nnc(C)c2cnc(N3CC(C)(N4CCOCC4)C3)cc12] | $^1$H NMR (400 MHz, CD$_3$OD) δ = 9.04 (d, J = 0.9 Hz, 1H), 8.51 (s, 1H), 7.72 (dd, J = 7.9, 1.4 Hz, 1H), 7.52 (dd, J = 7.7, 1.4 Hz, 1H), 7.28 (t, J = 7.8 Hz, 1H), 7.08 (s, 1H), 5.52 (q, J = 6.9 Hz, 1H), 4.12-4.04 (m, 2H), 3.95-3.87 (m, 2H), 3.78-3.71 (m, 4H), 2.72 (s, 3H), 2.68 (s, 3H), 2.61-2.49 (m, 4H), 1.63 (d, J = 7.0 Hz, 3H), 1.47 (s, 3H). LCMS [M + 1]$^+$: 458.3. |
| 12-88 | 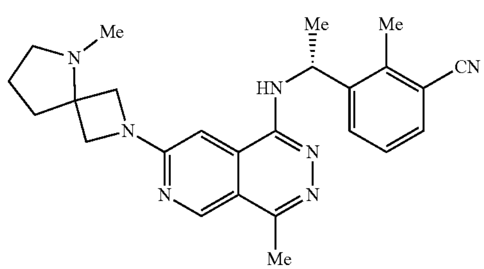 [SMILES: Cc1c(C#N)cccc1[C@@H](C)Nc1nnc(C)c2cnc(N3CC4(CCCN4C)C3)cc12] | $^1$H NMR (400 MHz, CD$_3$OD) δ = 8.95 (d, J = 0.9 Hz, 1H), 7.72 (dd, J = 7.9, 1.4 Hz, 1H), 7.50 (dd, J = 7.7, 1.3 Hz, 1H), 7.26 (t, J = 7.8 Hz, 1H), 7.05 (d, J = 0.9 Hz, 1H), 5.58 (q, J = 6.9 Hz, 1H), 4.34 (dd, J = 9.2, 3.3 Hz, 2H), 3.99 (d, J = 9.2 Hz, 2H), 2.82 (t, J = 7.3 Hz, 2H), 2.73 (s, 3H), 2.62 (s, 3H), 2.51 (s, 3H), 2.26-2.18 (m, 2H), 1.94-1.82 (m, 2H), 1.62 (d, J = 6.9 Hz, 3H). LCMS [M + 1]$^+$: 428.2. |

TABLE 12-continued

| Ex. # | Structure | Spectral Data |
|---|---|---|
| 12-89 | 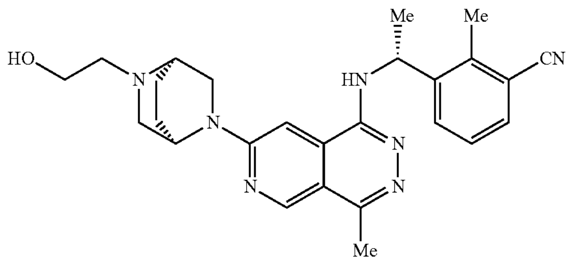 [SMILES: Cc1c(C#N)cccc1[C@@H](C)Nc1nnc(C)c2cnc(N3C[C@H]4CC[C@@H]3CN4CCO)cc12] | $^1$H NMR (400 MHz, CD$_3$OD) δ 9.19 (s, 1H), 7.76 (dd, J = 7.9, 1.4 Hz, 1H), 7.54 (dd, J = 7.8, 1.3 Hz, 1H), 7.35 (s, 1H), 7.29 (t, J = 7.8 Hz, 1H), 5.47 (q, J = 6.9 Hz, 1H), 5.15 (s, 1H), 4.14 (dt, J = 12.8, 2.7 Hz, 1H), 3.85-3.68 (m, 4H), 3.45-3.41 (m, 2H), 3.27-3.12 (m, 2H), 2.76 (s, 3H), 2.73 (s, 3H), 2.39-2.34 (m, 1H), 2.11-2.02 (m, 2H), 2.00-1.88 (m, 1H), 1.67 (d, J = 7.0 Hz, 3H). LCMS [M + 1]$^+$: 458.2. |
| 12-90 | 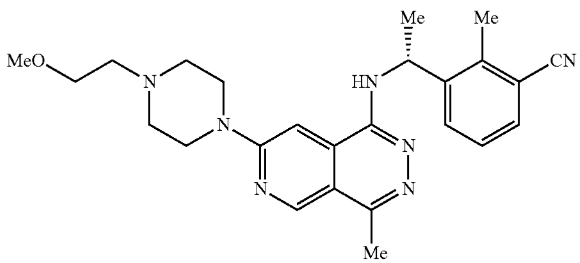 [SMILES: COCCN1CCN(c2cc3c(N[C@H](C)c4cccc(C#N)c4C)nnc(C)c3cn2)CC1] | $^1$H NMR (400 MHz, CD$_3$OD) δ = 8.97 (d, J = 0.8 Hz, 1H), 7.72 (dd, J = 8.0, 1.4 Hz, 1H), 7.48 (dd, J = 7.7, 1.4 Hz, 1H), 7.30 (d, J = 0.9 Hz, 1H), 7.24 (t, J = 7.8 Hz, 1H), 5.57 (q, J = 6.9 Hz, 1H), 3.84-3.77 (m, 4H), 3.60 (t, J = 5.5 Hz, 2H), 3.38 (s, 3H), 2.71 (s, 3H), 2.69-2.64 (m, 6H), 2.61 (s, 3H), 1.61 (d, J = 7.0 Hz, 3H). LCMS [M + 1]$^+$: 446.2. |
| 12-91 | 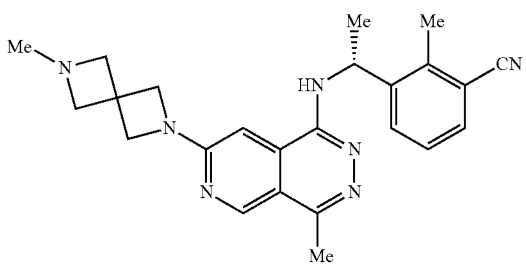 [SMILES: Cc1c(C#N)cccc1[C@@H](C)Nc1nnc(C)c2cnc(N3CC4(CN(C)C4)C3)cc12] | $^1$H NMR (400 MHz, CD$_3$OD) δ = 9.11 (s, 1H), 7.73 (d, J = 7.8 Hz, 1H), 7.54 (dd, J = 7.7, 1.3 Hz, 1H), 7.29 (t, J = 7.8 Hz, 1H), 7.20 (s, 1H), 5.47 (q, J = 6.8 Hz, 1H), 4.50 (s, 4H), 4.36 (s, 4H), 2.90 (s, 3H), 2.73 (s, 6H), 1.66 (d, J = 7.0 Hz, 3H). LCMS [M + 1]$^+$: 414.1. |
| 12-92 | 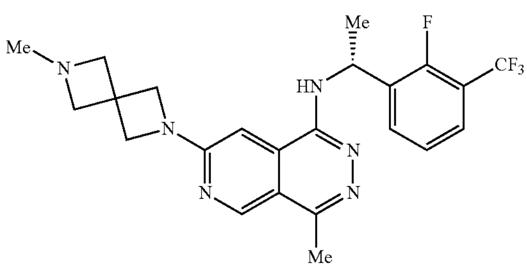 [SMILES: Cc1nnc(N[C@H](C)c2cccc(C(F)(F)F)c2F)c2cc(N3CC4(CN(C)C4)C3)ncc12] | $^1$H NMR (400 MHz, CD$_3$OD) δ 8.95 (s, 1H), 7.71-7.62 (m, 1H), 7.57-7.48 (m, 1H), 7.26-7.18 (m, 1H), 7.05 (s, 1H), 5.69 (q, J = 7.0 Hz, 1H), 4.29 (s, 4H), 3.54 (s, 4H), 2.61 (s, 3H), 2.39 (s, 3H), 1.69 (d, J = 7.0 Hz, 3H). LCMS [M + 1]$^+$: 461.6. |
| 12-93 | 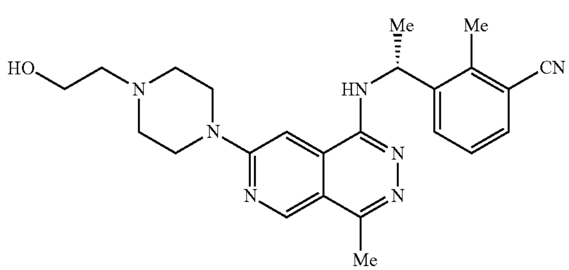 [SMILES: Cc1c(C#N)cccc1[C@@H](C)Nc1nnc(C)c2cnc(N3CCN(CCO)CC3)cc12] | $^1$H NMR (400 MHz, CD$_3$OD) δ = 8.98 (s, 1H), 7.72 (dd, J = 7.9, 1.3 Hz, 1H), 7.49 (dd, J = 7.7, 1.3 Hz, 1H), 7.31 (s, 1H), 7.25 (t, J = 7.8 Hz, 1H), 5.58 (q, J = 6.9 Hz, 1H), 3.86-3.79 (m, 4H), 3.76 (t, J = 5.9 Hz, 2H), 2.72 (s, 3H), 2.71-2.60 (m, 9H), 1.61 (d, J = 7.0 Hz, 3H). LCMS [M + 1]$^+$: 432.2. |

TABLE 12-continued

| Ex. # | Structure | Spectral Data |
|---|---|---|
| 12-94 | 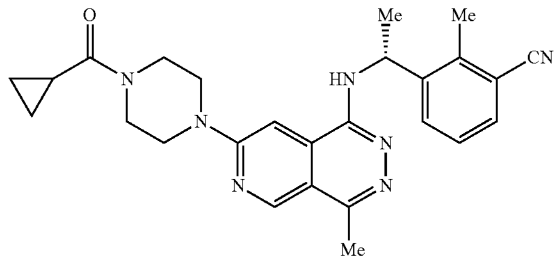 [SMILES: Cc1c(C#N)cccc1[C@@H](C)Nc1nnc(C)c2cnc(N3CCN(C(=O)C4CC4)CC3)cc12] | $^1$H NMR (400 MHz, CD$_3$OD) δ = 9.12 (s, 1H), 7.74 (dd, J = 8.0, 1.4 Hz, 1H), 7.53 (dd, J = 7.7, 1.4 Hz, 1H), 7.44 (s, 1H), 7.28 (t, J = 7.8 Hz, 1H), 5.54 (q, J = 6.9 Hz, 1H), 4.01 (d, J = 15.7 Hz, 4H), 3.84 (d, J = 24.5 Hz, 4H), 2.73 (s, 3H), 2.70 (s, 3H), 2.11-2.00 (m, 1H), 1.65 (d, J = 6.9 Hz, 3H), 1.00-0.91 (m, 2H), 0.94-0.85 (m, 2H). LCMS [M + 1]$^+$: 456.2. |
| 12-95 | 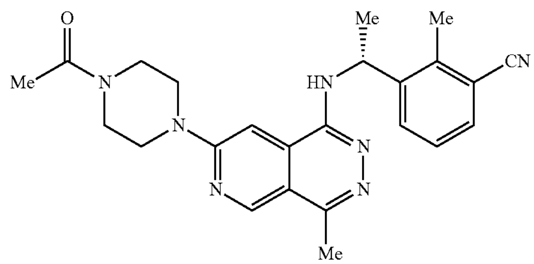 [SMILES: CC(=O)N1CCN(c2cc3c(N[C@H](C)c4cccc(C#N)c4C)nnc(C)c3cn2)CC1] | $^1$H NMR (400 MHz, CD$_3$OD) δ = 9.10 (d, J = 0.8 Hz, 1H), 7.71 (dd, J = 8.0, 1.4 Hz, 1H), 7.51 (dd, J = 7.6, 1.3 Hz, 1H), 7.42 (s, 1H), 7.26 (t, J = 7.8 Hz, 1H), 5.50 (q, J = 7.0 Hz, 1H), 4.01-3.94 (m, 2H), 3.90-3.81 (m, 2H), 3.81-3.69 (m, 4H), 2.71 (s, 3H), 2.68 (s, 3H), 2.18 (s, 3H), 1.63 (d, J = 6.9 Hz, 3H). LCMS [M + 1]$^+$: 430.1. |
| 12-96 | 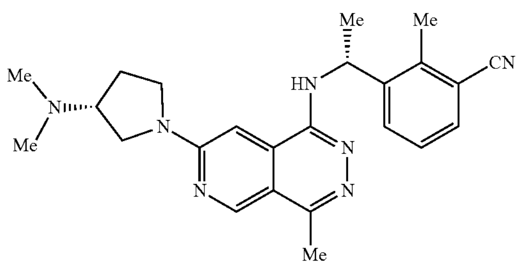 [SMILES: Cc1c(C#N)cccc1[C@@H](C)Nc1nnc(C)c2cnc(N3CC[C@@H](N(C)C)C3)cc12] | $^1$H NMR (400 MHz, CD$_3$OD) δ = 8.96 (d, J = 0.8 Hz, 1H), 7.73 (dd, J = 8.0, 1.3 Hz, 1H), 7.50 (dd, J = 7.5, 1.3 Hz, 1H), 7.25 (t, J = 7.8 Hz, 1H), 7.03 (s, 1H), 5.59 (q, J = 6.9 Hz, 1H), 3.94-3.84 (m, 2H), 3.63-3.51 (m, 1H), 3.41-3.34 (m, 1H), 3.06-2.96 (m, 1H), 2.73 (s, 3H), 2.62 (s, 3H), 2.39 (s, 7H), 2.07-1.91 (m, 1H), 1.63 (d, J = 6.9 Hz, 3H). LCMS [M + 1]$^+$: 416.2. |
| 12-97 | 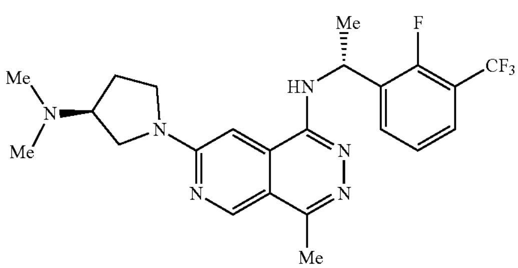 [SMILES: Cc1nnc(N[C@H](C)c2cccc(C(F)(F)F)c2F)c2cc(N3CC[C@H](N(C)C)C3)ncc12] | $^1$H NMR (400 MHz, DMSO-d$_6$) δ = 8.97 (s, 1H), 7.70 (t, J = 7.2 Hz, 1H), 7.61 (t, J = 12 Hz, 1H), 7.47 (d, J = 6.6 Hz, 1H), 7.30 (t, J = 7.8 Hz, 1H), 7.07 (s, 1H), 5.68-5.61 (m, 1H), 3.87-3.79 (m, 1H), 3.79-3.72 (m, 1H), 3.56-3.44 (m, 1H), 3.34-3.25 (m, 1H), 2.95-2.86 (m, 1H), 2.54 (s, 3H), 2.26 (s, 7H), 1.98-1.83 (m, 1H), 1.61 (d, J = 7.0 Hz, 3H). LCMS [M + 1]$^+$: 463.2. |
| 12-98 | 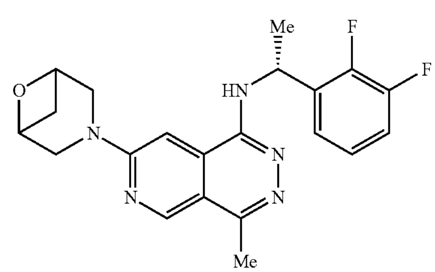 [SMILES: Cc1nnc(N[C@H](C)c2cccc(F)c2F)c2cc(N3CC4CC(C3)O4)ncc12] | $^1$H NMR (400 MHz, CD$_3$OD) δ = 9.08 (s, 1H), 7.24 (s, 1H), 7.20 (t, J = 7.0 Hz, 1H), 7.12-6.99 (m, 2H), 5.70 (q, J = 7.0 Hz, 1H), 3.99 (d, J = 12.7 Hz, 2H), 3.84 (d, J = 12.5 Hz, 2H), 3.41-3.34 (m, 2H), 2.66 (s, 3H), 2.08-2.01 (m, 2H), 1.70 (d, J = 7.0 Hz, 3H). LCMS [M + 1]$^+$: 398.0. |
| 12-99 | 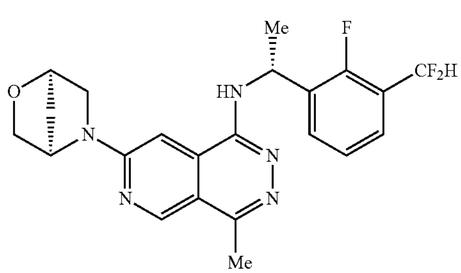 [SMILES: Cc1nnc(N[C@H](C)c2cccc(C(F)F)c2F)c2cc(N3C[C@H]4C[C@@H]3CO4)ncc12] | $^1$H NMR (400 MHz, DMSO-d$_6$) δ = 8.97 (s, 1H), 7.56 (t, J = 7.3 Hz, 1H), 7.43 (dt, J = 28.4, 8.1 Hz, 2H), 7.27-7.09 (m, 3H), 5.70-5.58 (m, 1H), 5.08 (s, 1H), 4.78 (s, 1H), 3.92-3.85 (m, 1H), 3.74-3.68 (m, 1H), 3.66-3.59 (m, 1H), 3.44-3.36 (m, 1H), 3.31-3.28 (m, 1H), 2.54 (s, 3H), 2.03-1.93 (m, 2H), 1.60 (d, J = 7.0 Hz, 3H). LCMS [M + 1]$^+$: 430.1. |

TABLE 12-continued

| Ex. # | Structure | Spectral Data |
|---|---|---|
| 12-100 | 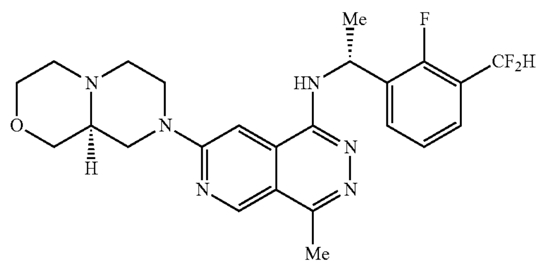 [SMILES: Cc1nnc(N[C@H](C)c2cccc(C(F)F)c2F)c2cc(N3CCN4CCOC[C@@H]4C3)ncc12] | $^1$H NMR (400 MHz, DMSO-d$_6$) δ 8.99 (s, 1H), 7.56 (t, J = 7.5 Hz, 2H), 7.50-7.08 (m, 4H), 5.70-5.59 (m, 1H), 4.49-4.34 (m, 2H), 3.86-3.76 (m, 2H), 3.63-3.55 (m, 1H), 3.27-3.22 (m, 1H), 3.11-3.06 (m, 1H), 2.96-2.89 (m, 1H), 2.77-2.69 (m, 1H), 2.64-2.57 (m, 1H), 2.55 (s, 3H), 2.35-2.17 (m, 3H), 1.60 (d, J = 7.0 Hz, 3H). LCMS [M + 1]$^+$: 473.3. |
| 12-101 | 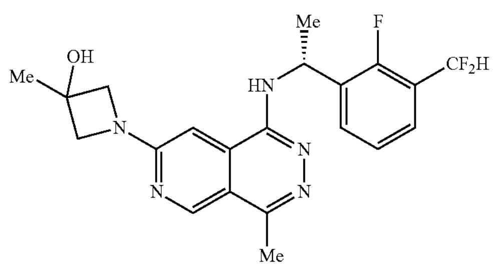 [SMILES: Cc1nnc(N[C@H](C)c2cccc(C(F)F)c2F)c2cc(N3CC(C)(O)C3)ncc12] | $^1$H NMR (400 MHz, DMSO-d$_6$) δ 8.96 (s, 1H), 7.57 (t, J = 7.5 Hz, 1H), 7.51-7.41 (m, 2H), 7.28-7.20 (m, 1H), 7.13-7.07 (m, 1H), 5.73 (s, 1H), 5.70-5.59 (m, 1H), 4.06-3.93 (m, 4H), 2.55 (s, 3H), 1.60 (d, J = 7.0 Hz, 3H), 1.50 (s, 3H). LCMS [M + 1]$^+$: 418.0. |
| 12-102 | 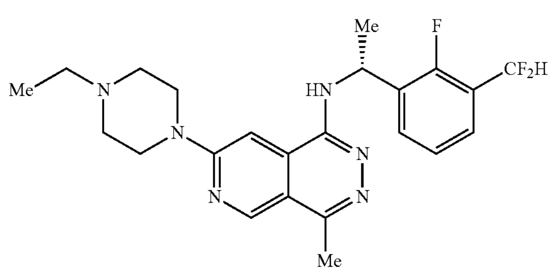 [SMILES: CCN1CCN(c2cc3c(N[C@H](C)c4cccc(C(F)F)c4F)nnc(C)c3cn2)CC1] | $^1$H NMR (400 MHz, DMSO-d$_6$) δ = 9.00 (s, 1H), 7.60-7.10 (m, 5H), 5.70-5.60 (m, 1H), 3.74 (t, J = 5.1 Hz, 4H), 2.57-2.53 (m, 7H), 2.42 (q, J = 7.2 Hz, 2H), 1.61 (d, J = 7.0 Hz, 3H), 1.08 (t, J = 7.1 Hz, 3H). LCMS [M + 1]$^+$: 445.7. |
| 12-103 | 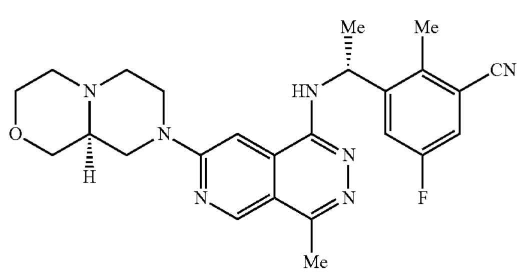 | $^1$H NMR (400 MHz, CD$_3$OD) δ = 9.18 (s, 1H), 8.33 (s, 1H), 7.50-7.43 (m, 2H), 7.35 (dd, J = 7.9, 2.8 Hz, 1H), 5.46-5.36 (m, 1H), 4.74 (d, J = 13.5 Hz, 1H), 4.54 (d, J = 13.0 Hz, 1H), 3.93-3.82 (m, 2H), 3.79-3.68 (m, 1H), 3.43-3.33 (m, 1H), 3.31-3.23 (m, 1H), 3.03-2.95 (m, 1H), 2.87-2.77 (m, 2H), 2.75 (s, 3H), 2.70 (s, 3H), 2.47-2.29 (m, 3H), 1.63 (d, J = 7.0 Hz, 3H). LCMS [M + 1]$^+$: 462.2. |
| 12-104 | 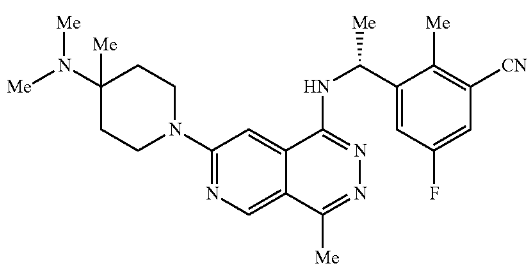 [SMILES: Cc1c(C#N)cc(F)cc1[C@@H](C)Nc1nnc(C)c2cnc(N3CCC(C)(N(C)C)CC3)cc12] | $^1$H NMR (400 MHz, CD$_3$OD) δ = 9.00 (d, J = 0.8 Hz, 1H), 7.47 (dd, 9.9, 2.8 Hz, 1H), 7.34-7.27 (m, 2H), 5.59-5.49 (m, 1H), 4.28-4.20 (m, 2H), 3.50-3.39 (m, 2H), 2.70 (s, 3H), 2.63 (s, 3H), 2.29 (s, 6H), 1.79-1.75 (m, 4H), 1.61 (d, J = 7.0 Hz, 3H), 1.13 (s, 3H). LCMS [M + 1]$^+$: 462.4. |

TABLE 12-continued

| Ex. # | Structure | Spectral Data |
|---|---|---|
| 12-105 | 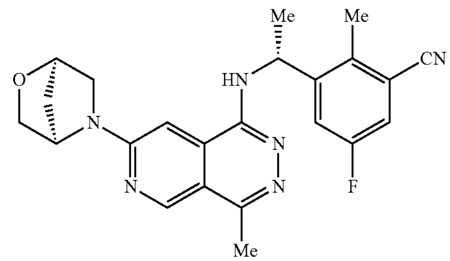 [SMILES: Cc1c(C#N)cc(F)cc1[C@@H](C)Nc1nnc(C)c2cnc(N3C[C@H]4C[C@@H]3CO4)cc12] | $^1$H NMR (400 MHz, CD$_3$OD) δ 8.98 (s, 1H), 7.46 (dd, J = 10.0, 2.8 Hz, 1H), 7.30 (dd, J = 7.9, 2.8 Hz, 1H), 7.07 (s, 1H), 5.58-5.48 (m, 1H), 5.17 (s, 1H), 4.81 (s, 1H), 4.00-3.93 (m, 1H), 3.87 (d, J = 7.4 Hz, 1H), 3.72-3.64 (m, 1H), 3.51 (d, J = 10.3 Hz, 1H), 2.70 (s, 3H), 2.64 (s, 3H), 2.10-2.05 (m, 2H), 1.61 (d, J = 7.0 Hz, 3H). LCMS [M + 1]$^+$: 419.3. |
| 12-106 | 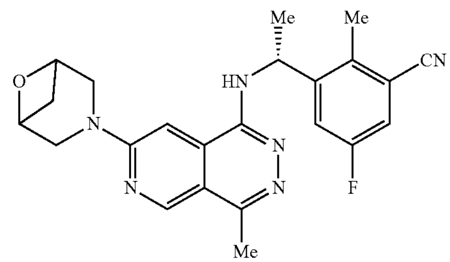 [SMILES: Cc1c(C#N)cc(F)cc1[C@@H](C)Nc1nnc(C)c2cnc(N3CC4CC(C3)O4)cc12] | $^1$H NMR (400 MHz, CD$_3$OD) δ = 9.17 (s, 1H), 7.50 (dd, J = 9.9, 2.8 Hz, 1H), 7.32 (dd, J = 7.9, 2.8 Hz, 1H), 7.30 (s, 1H), 5.53-5.43 (m, 1H), 4.88-4.82 (m, 2H), 4.03-3.95 (m, 2H), 3.90-3.82 (m, 2H), 3.41-3.32 (m, 1H), 2.74 (s, 3H), 2.69 (s, 3H), 2.02 (d, J = 9.1 Hz, 1H), 1.64 (d, J = 7.0 Hz, 3H). LCMS [M + 1]$^+$: 419.2. |
| 12-107 | 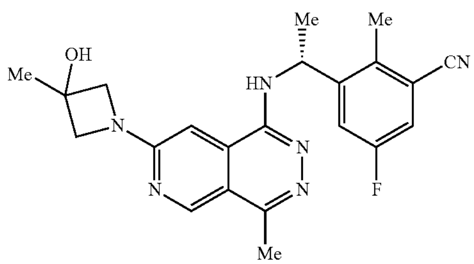 [SMILES: Cc1c(C#N)cc(F)cc1[C@@H](C)Nc1nnc(C)c2cnc(N3CC(C)(O)C3)cc12] | $^1$H NMR (400 MHz, CD$_3$OD) δ = 9.02 (s, 1H), 7.47 (dd, J = 9.8, 2.8 Hz, 1H), 7.33 (dd, J = 7.9, 2.9 Hz, 1H), 7.06 (s, 1H), 5.47 (q, J = 7.0 Hz, 1H), 4.19-4.06 (m, 4H), 2.69 (s, 3H), 2.68 (s, 3H), 1.63 (s, 3H), 1.61 (d, J = 1.7 Hz, 3H). LCMS [M + 1]$^+$: 407.2. |
| 12-108 | 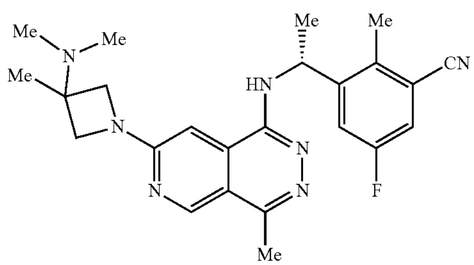 [SMILES: Cc1c(C#N)cc(F)cc1[C@@H](C)Nc1nnc(C)c2cnc(N3CC(C)(N(C)C)C3)cc12] | $^1$H NMR (400 MHz, CD$_3$OD) δ 8.95 (s, 1H), 7.47 (dd, J = 9.9, 2.8 Hz, 1H), 7.29 (dd, J = 7.9, 2.8 Hz, 1H), 7.02 (s, 1H), 5.58-5.48 (m, 1H), 4.06-3.98 (m, 2H), 3.93-3.84 (m, 2H), 2.68 (s, 3H), 2.64 (s, 3H), 2.27 (s, 6H), 1.60 (d, J = 7.0 Hz, 3H), 1.45 (s, 3H). LCMS [M + 1]$^+$: 434.2. |
| 12-109 | 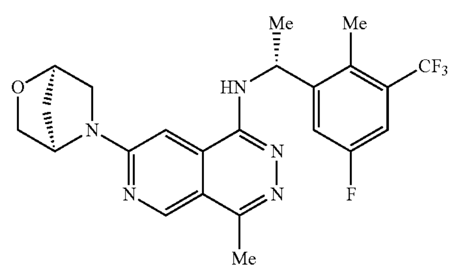 [SMILES: Cc1c([C@@H](C)Nc2nnc(C)c3cnc(N4C[C@H]5C[C@@H]4CO5)cc23)cc(F)cc1C(F)(F)F] | $^1$H NMR (400 MHz, CD$_3$OD) δ = 9.00 (s, 1H), 7.43 (dd, J = 9.9, 2.8 Hz, 1H), 7.25 (dd, J = 8.8, 2.8 Hz, 1H), 7.10 (s, 1H), 5.69-5.59 (m, 1H), 5.18 (s, 1H), 4.82 (s, 1H), 4.01-3.94 (m, 1H), 3.91-3.85 (m, 1H), 3.74-3.66 (m, 1H), 3.56-3.49 (m, 1H), 2.64 (s, 3H), 2.60 (s, 3H), 2.11-2.06 (m, 2H), 1.62 (d, J = 6.9 Hz, 3H). LCMS [M + 1]$^+$: 462.0. |
| 12-110 | 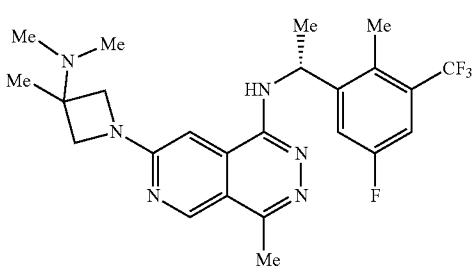 [SMILES: Cc1c([C@@H](C)Nc2nnc(C)c3cnc(N4CC(C)(N(C)C)C4)cc23)cc(F)cc1C(F)(F)F] | $^1$H NMR (400 MHz, CD$_3$OD) δ = 8.98 (s, 1H), 7.43 (dd, J = 9.8, 2.8 Hz, 1H), 7.26 (dd, J = 8.9, 2.8 Hz, 1H), 7.06 (s, 1H), 5.68-5.60 (m, 1H), 4.10-4.02 (m, 2H), 3.97-3.89 (m, 2H), 2.64 (s, 3H), 2.59 (s, 3H), 2.29 (s, 6H), 1.62 (d, J = 7.0 Hz, 3H), 1.47 (s, 3H). LCMS [M + 1]$^+$: 477.0. |

TABLE 12-continued

| Ex. # | Structure | Spectral Data |
|---|---|---|
| 12-111 | 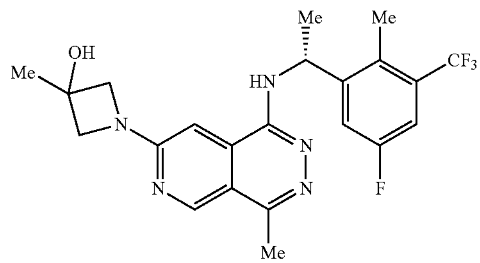 [SMILES: Cc1c([C@@H](C)Nc2nnc(C)c3cnc(N4CC(C)(O)C4)cc23)cc(F)cc1C(F)(F)F] | $^1$H NMR (400 MHz, CD$_3$OD) δ = 8.96 (s, 1H), 7.43 (dd, J = 9.9, 2.8 Hz, 1H), 7.26 (dd, J = 8.9, 2.8 Hz, 1H), 7.04 (s, 1H), 5.64 (q, J = 6.9 Hz, 1H), 4.14 (dd, J = 8.8, 3.4 Hz, 2H), 4.08 (dd, J = 8.8, 3.7 Hz, 2H), 2.63 (s, 3H), 2.60 (s, 3H), 1.65-1.59 (m, 6H). LCMS [M + 1]$^+$: 450.4. |
| 12-112 | 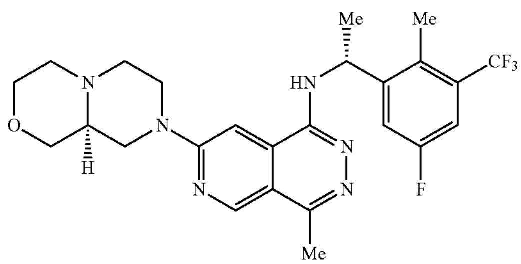 [SMILES: Cc1c([C@@H](C)Nc2nnc(C)c3cnc(N4CCN5CCOC[C@@H]5C4)cc23)cc(F)cc1C(F)(F)F] | $^1$H NMR (400 MHz, CD$_3$OD) δ = 9.04 (s, 1H), 7.46-7.39 (m, 1H), 7.36 (s, 1H), 7.29-7.22 (m, 1H), 5.69-5.61 (m, 1H), 4.68-4.57 (m, 1H), 4.48-4.40 (m, 1H), 3.94-3.85 (m, 2H), 3.81-3.70 (m, 1H), 3.45-3.35 (m, 1H), 3.25-3.15 (m, 1H), 3.02-2.94 (m, 1H), 2.85-2.78 (m, 1H), 2.77-2.67 (m, 1H), 2.65 (s, 3H), 2.60 (s, 3H), 2.48-2.32 (m, 3H), 1.62 (d, J = 6.9 Hz, 3H). LCMS [M + 1]$^+$: 505.5. |
| 12-113 | 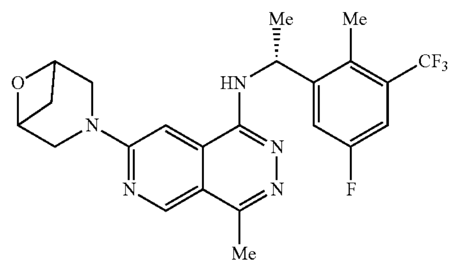 [SMILES: Cc1c([C@@H](C)Nc2nnc(C)c3cnc(N4CC5CC(C4)O5)cc23)cc(F)cc1C(F)(F)F] | $^1$H NMR (400 MHz, CD$_3$OD) δ = 9.08 (s, 1H), 7.45 (d, J = 9.9 Hz, H), 7.27-7.17 (m, H), 5.70-5.63 (m, 1H), 4.03-3.96 (m, 3H), 3.88-3.80 (m, 2H), 3.39-3.34 (m, 2H), 2.67 (s, 2H), 2.61 (s, 3H), 2.05 (d, J = 8.9 Hz, 1H), 1.64 (d, J = 6.9 Hz, 2H). LCMS [M + 1]$^+$: 462.0. |
| 12-114 | 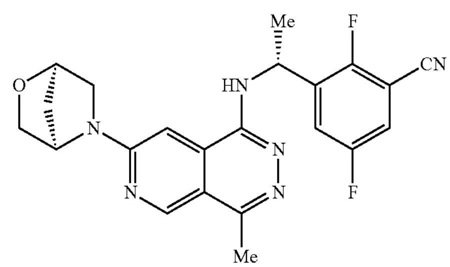 [SMILES: Cc1nnc(N[C@H](C)c2cc(F)cc(C#N)c2F)c2cc(N3C[C@H]4C[C@@H]3CO4)ncc12] | $^1$H NMR (400 MHz, CD$_3$OD) δ = 9.07 (s, 1H), 8.52 (s, 1H), 7.63-7.55 (m, 1H), 7.41-7.32 (m, 1H), 7.15 (s, 1H), 5.60-5.51 (m, 1H), 5.25-5.20 (m, 1H), 4.62-4.58 (m, 1H), 4.02-3.95 (m, 1H), 3.92-3.85 (m, 1H), 3.75-3.68 (m, 1H), 3.61-3.52 (m, 1H), 2.68 (s, 3H), 2.10 (s, 2H), 1.70 (d, J = 7.0 Hz, 3H). LCMS [M + 1]$^+$: 423.2. |
| 12-115 | 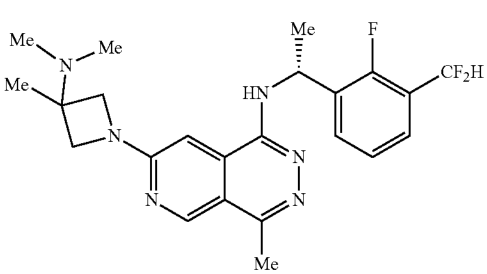 [SMILES: Cc1nnc(N[C@H](C)c2cccc(C(F)F)c2F)c2cc(N3CC(C)(N(C)C)C3)ncc12] | $^1$H NMR (400 MHz, DMSO-d$_6$) δ 8.96 (s, 1H), 7.57 (t, J = 7.5 Hz, 1H), 7.51-7.36 (m, 2H), 7.28-7.20 (m, 2H), 7.11 (s, 1H), 5.70-5.58 (m, 1H), 3.91 (dd, J = 8.2, 4.8 Hz, 2H), 3.81 (dd, J = 8.2, 2.1 Hz, 2H), 2.55 (s, 3H), 2.16 (s, 6H), 1.60 (d, J = 7.0 Hz, 3H), 1.33 (s, 3H). LCMS [M + 1]$^+$: 445.1. |

TABLE 12-continued

| Ex. # | Structure | Spectral Data |
|---|---|---|
| 12-116 | 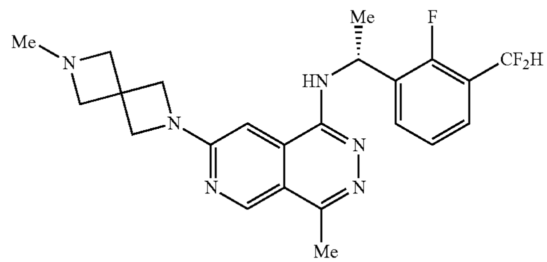 [SMILES: Cc1nnc(N[C@H](C)c2cccc(C(F)F)c2F)c2cc(N3CC4(CN(C)C4)C3)ncc12] | $^1$H NMR (400 MHz, CD$_3$OD) δ = 8.94 (s, 1H), 7.55 (t, J = 7.5 Hz, 1H), 7.44 (t, J = 7.1 Hz, 1H), 7.21-6.85 (m, 3H), 5.68 (q, J = 7.0 Hz, 1H), 4.28 (s, 4H), 3.53 (s, 4H), 2.62 (s, 3H), 2.38 (s, 3H), 1.69 (d, J = 7.0 Hz, 3H). LCMS [M + 1]$^+$: 443.5. |
| 12-117 | 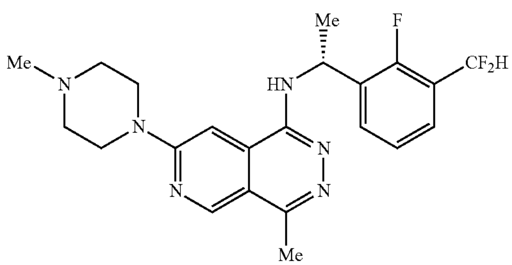 [SMILES: Cc1nnc(N[C@H](C)c2cccc(C(F)F)c2F)c2cc(N3CCN(C)CC3)ncc12] | $^1$H NMR (400 MHz, DMSO-d$_6$) δ = 8.99 (s, 1H), 7.61-7.08 (m, 7H), 5.70-5.60 (m, 1H), 3.74 (t, J = 5.0 Hz, 4H), 2.56 (s, 3H), 2.49-2.43 (m, 4H), 2.27 (s, 3H), 1.61 (d, J = 7.0 Hz, 3H). LCMS [M + 1]$^+$: 431.2. |
| 12-118 | 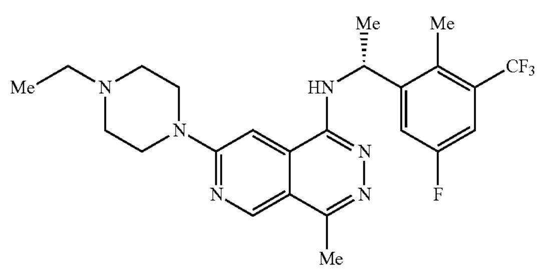 [SMILES: CCN1CCN(c2cc3c(N[C@H](C)c4cc(F)cc(C(F)(F)F)c4C)nnc(C)c3cn2)CC1] | $^1$H NMR (400 MHz, CD$_3$OD) δ = 9.03 (s, 1H), 7.47-7.40 (m, 1H), 7.35 (s, 1H), 7.25 (dd, J = 8.8, 2.8 Hz, 1H), 5.64 (q, J = 6.9 Hz, 1H), 3.90-3.83 (m, 4H), 2.70-2.65 (m, 4H), 2.64 (s, 3H), 2.60 (s, 3H), 2.55 (q, J = 7.2 Hz, 2H), 1.62 (d, J = 6.9 Hz, 3H), 1.20 (t, J = 7.2 Hz, 3H). LCMS [M + 1]$^+$: 477.6. |
| 12-119 | 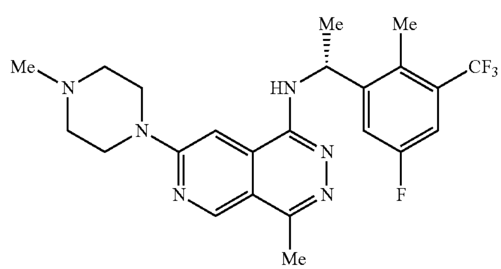 [SMILES: Cc1c([C@@H](C)Nc2nnc(C)c3cnc(N4CCN(C)CC4)cc23)cc(F)cc1C(F)(F)F] | $^1$H NMR (400 MHz, CD$_3$OD) δ = 9.04 (s, 1H), 7.43 (dd, 9.8, 2.7 Hz, 1H), 7.36 (s, 1H), 7.25 (dd, J = 8.9, 2.8 Hz, 1H), 5.64 (q, J = 7.1 Hz, 1H), 3.90-3.83 (m, 4H), 2.67-2.58 (m, 10H), 2.40 (s, 3H), 1.62 (d, J = 6.9 Hz, 3H). LCMS [M + 1]$^+$: 463.4. |
| 12-120 | 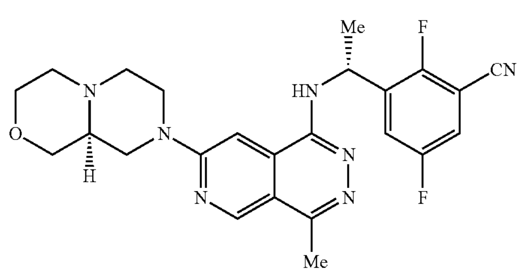 [SMILES: Cc1nnc(N[C@H](C)c2cc(F)cc(C#N)c2F)c2cc(N3CCN4CCOC[C@@H]4C3)ncc12] | $^1$H NMR (400 MHz, CD$_3$OD) δ = 9.20 (d, J = 0.8 Hz, 1H), 7.62 (dd, J = 9.3, 5.0 Hz, 1H), 7.50 (s, 1H), 7.41 (dd, J = 9.4, 5.7 Hz, 1H), 5.49 (q, J = 7.0 Hz, 1H), 4.77-4.72 (m, 2H), 4.57 (d, J = 13.4 Hz, 2H), 3.94-3.84 (m, 2H), 3.75 (td, J = 11.5, 2.4 Hz, 1H), 3.45-3.35 (m, 1H), 3.01 (d, J = 11.5 Hz, 1H), 2.88-2.78 (m, 2H), 2.76 (s, 3H), 2.47-2.38 (m, 1H), 2.42-2.31 (m, 1H), 1.71 (d, J = 7.1 Hz, 3H). LCMS [M + 1]$^+$: 466.3. |

TABLE 12-continued

| Ex. # | Structure | Spectral Data |
|---|---|---|
| 12-121 | 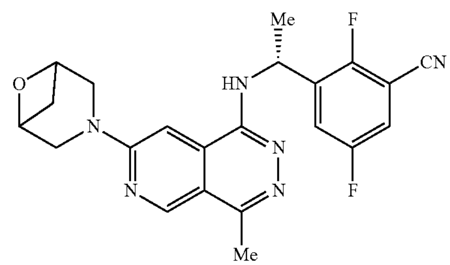 [SMILES: Cc1nnc(N[C@H](C)c2cc(F)cc(C#N)c2F)c2cc(N3CC4CC(C3)O4)ncc12] | $^1$H NMR (400 MHz, CD$_3$OD) δ 9.10 (s, 1H), 7.58 (dd, J = 9.2, 5.1 Hz, 1H), 7.37 (dd, J = 9.5, 5.7 Hz, 1H), 7.24 (s, 1H), 5.62 (q, J = 7.1 Hz, 1H), 4.89 (s, 1H), 4.00 (d, J = 12.8 Hz, 2H), 3.86 (d, J = 12.6 Hz, 2H), 3.42-3.34 (m, 2H), 2.68 (s, 3H), 2.06 (d, J = 9.0 Hz, 1H), 1.71 (d, J = 7.0 Hz, 3H). LCMS [M + 1]$^+$: 423.1. |
| 12-122 | 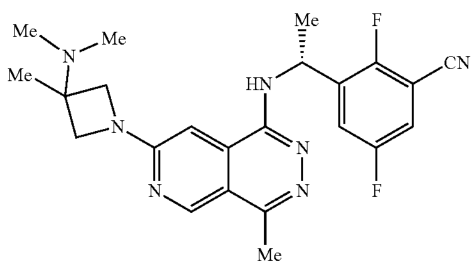 [SMILES: Cc1nnc(N[C@H](C)c2cc(F)cc(C#N)c2F)c2cc(N3CC(C)(N(C)C)C3)ncc12] | $^1$H NMR (400 MHz, CD$_3$OD) δ = 9.09 (d, J = 0.8 Hz, 1H), 8.45 (s, 1H), 7.60 (dd, J = 9.3, 5.1 Hz, 1H), 7.38 (dd, J = 9.5, 5.7 Hz, 1H), 7.12 (s, 1H), 5.52 (q, J = 7.0 Hz, 1H), 4.16-4.09 (m, 2H), 4.02-3.95 (m, 2H), 2.71 (s, 3H), 2.34 (s, 6H), 1.70 (d, J = 7.0 Hz, 3H), 1.49 (s, 3H). LCMS [M + 1]$^+$: 438.2. |
| 12-123 | 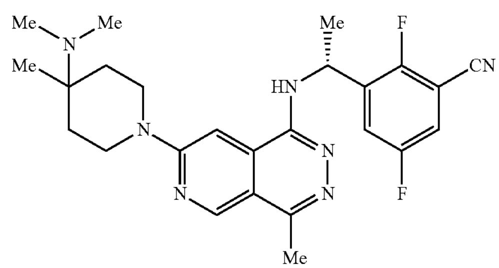 [SMILES: Cc1nnc(N[C@H](C)c2cc(F)cc(C#N)c2F)c2cc(N3CCC(C)(N(C)C)CC3)ncc12] | $^1$H NMR (400 MHz, CD$_3$OD) δ = 9.07 (s, 1H), 8.51 (s, 1H), 7.59 (dd, J = 9.2, 5.1 Hz, 1H), 7.41 (s, 1H), 7.35 (dd, J = 9.5, 5.7 Hz, 1H), 5.55 (q, J = 7.3 Hz, 1H), 4.68-4.59 (m, 5H), 2.75 (s, 6H), 2.66 (s, 3H), 2.11-2.03 (m, 2H), 1.96-1.85 (m, 1H), 1.70 (d, J = 7.1 Hz, 3H), 1.48 (s, 3H). LCMS [M + 1]$^+$: 466.3. |
| 12-124 | 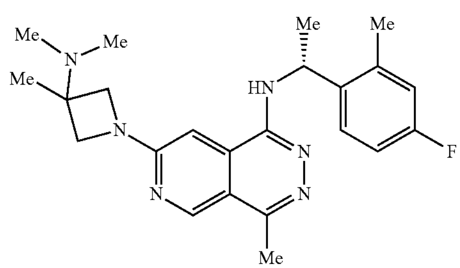 [SMILES: Cc1cc(F)ccc1[C@@H](C)Nc1nnc(C)c2cnc(N3CC(C)(N(C)C)C3)cc12] | $^1$H NMR (400 MHz, CD$_3$OD) δ = 8.94 (s, 1H), 7.41 (dd, J = 8.6, 5.9 Hz, 1H), 7.02 (s, 1H), 6.90-6.77 (m, 2H), 5.56 (q, J = 6.9 Hz, 1H), 4.01 (d, J = 8.4 Hz, 2H), 3.88 (d, J = 8.4 Hz, 2H), 2.63 (s, 3H), 2.47 (s, 3H), 2.26 (s, 6H), 1.59 (d, J = 6.9 Hz, 3H), 1.44 (s, 3H). LCMS [M + 1]$^+$: 409.4. |
| 12-125 | 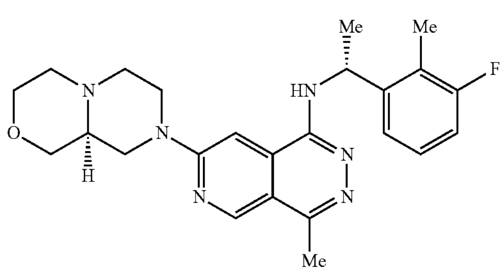 [SMILES: Cc1c(F)cccc1[C@@H](C)Nc1nnc(C)c2cnc(N3CCN4CCOC[C@@H]4C3)cc12] | $^1$H NMR (400 MHz, DMSO-d$_6$) δ = 15.02 (s, 1H), 12.35 (s, 1H), 9.48 (s, 1H), 9.30 (s, 1H), 8.48 (s, 1H), 7.47 (d, J = 7.8 Hz, 1H), 7.22-7.12 (m, 1H), 7.00 (t, J = 9.0 Hz, 1H), 5.39-5.31 (m, 1H), 5.15-5.03 (m, 2H), 4.27-4.20 (m, 1H), 4.03-3.95 (m, 2H), 3.79-3.71 (m, 3H), 3.35-3.06 (m, 2H), 3.59-3.55 (m, 2H), 2.80 (s, 3H), 2.37 (s, 3H), 1.66 (d, J = 7.0 Hz, 3H). LCMS [M + 1]$^+$: 473.3. |

TABLE 12-continued

| Ex. # | Structure | Spectral Data |
|---|---|---|
| 12-126 | 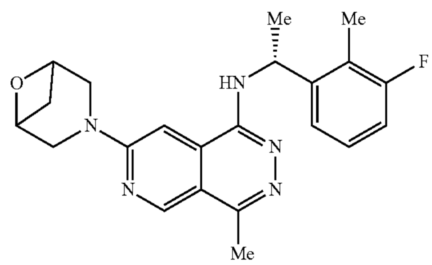 [SMILES: Cc1c(F)cccc1[C@@H](C)Nc1nnc(C)c2cnc(N3CC4CC(C3)O4)cc12] | ¹H NMR (400 MHz, CD₃OD) δ = 9.04 (s, 1H), 7.25 (d, J = 7.8 Hz, 1H), 7.20 (s, 1H), 7.13-7.03 (m, 1H), 6.91-6.82 (m, 1H), 5.62 (q, J = 6.9 Hz, 1H), 4.87-4.81 (m, 2H), 3.99-3.91 (m, 2H), 3.85-3.76 (m, 2H), 3.38-3.32 (m, 1H), 2.65 (s, 3H), 2.40-2.35 (m, 3H), 2.02 (d, 1H), 1.61 (d, J = 7.0 Hz, 3H). LCMS [M + 1]⁺: 394.3. |
| 12-127 | 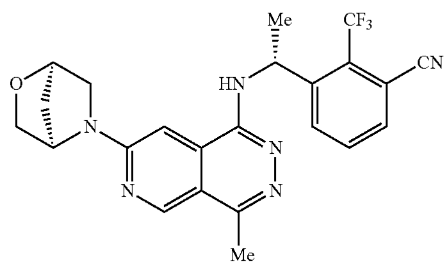 [SMILES: Cc1nnc(N[C@H](C)c2cccc(C#N)c2C(F)(F)F)c2cc(N3C[C@H]4C[C@@H]3CO4)ncc12] | ¹H NMR (400 MHz, CD₃OD) δ = 8.97 (s, 1H), 8.04 (d, J = 8.0 Hz, 1H), 7.79 (d, J = 7.6 Hz, 1H), 7.70-7.59 (m, 1H), 7.10 (s, 1H), 5.72 (q, J = 6.4 Hz, 1H), 5.16 (br s, 1H), 4.81 (s, 1H), 3.96 (dd, J = 1.2, 7.2 Hz, 1H), 3.87 (d, J = 7.2 Hz, 1H), 3.69 (dd, J = 1.2, 10.0 Hz, 1H), 3.52 (br d, J = 10.4 Hz, 1H), 2.59 (s, 3H), 2.07 (s, 2H), 1.67 (d, J = 6.8 Hz, 3H). LCMS [M + 1]⁺: 455.3. |
| 12-128 | 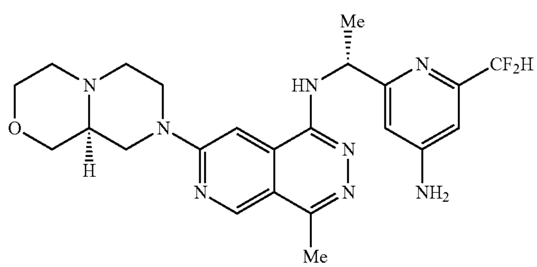 [SMILES: Cc1nnc(N[C@H](C)c2cc(N)cc(C(F)F)n2)c2cc(N3CCN4CCOC[C@@H]4C3)ncc12] | ¹H NMR (400 MHz, CD₃OD) δ = 8.99 (s, 1H), 7.28 (s, 1H), 6.67 (q, J = 2.2 Hz, 2H), 6.49 (t, J = 55.6 Hz, 1H), 5.28 (q, J = 6.9 Hz, 1H), 4.56 (d, J = 13.1 Hz, 1H), 4.41 (d, J = 12.7 Hz, 1H), 3.91-3.81 (m, 2H), 3.72 (td, J = 11.5, 2.3 Hz, 1H), 3.36 (t, J = 10.7 Hz, 1H), 3.15 (td, J = 12.6, 3.1 Hz, 1H), 2.94 (d, J = 11.5 Hz, 1H), 2.78 (d, J = 11.6 Hz, 1H), 2.71-2.64 (m, 1H), 2.63 (s, 3H), 2.46-2.29 (m, 3H), 1.62 (d, J = 7.0 Hz, 3H). LCMS [M + 1]⁺: 471.5. |
| 12-129 | 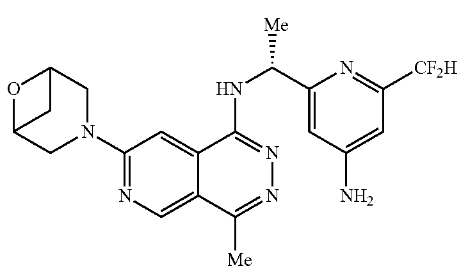 [SMILES: Cc1nnc(N[C@H](C)c2cc(N)cc(C(F)F)n2)c2cc(N3CC4CC(C3)O4)ncc12] | ¹H NMR (400 MHz, CD₃OD) δ = 9.06 (s, 1H), 7.15 (s, 1H), 6.73-6.68 (m, 2H), 6.52 (t, J = 55.7 Hz, 1H), 5.33 (q, J = 6.9 Hz, 1H), 4.85 (s, 2H), 3.96 (t, J = 11.6 Hz, 2H), 3.82 (dd, J = 12.7, 5.2 Hz, 2H), 3.40-3.33 (m, 1H), 2.67 (s, 3H), 2.05 (d, J = 9.0 Hz, 1H), 1.65 (d, J = 7.0 Hz, 3H). LCMS [M + 1]⁺: 428.4. |
| 12-130 | 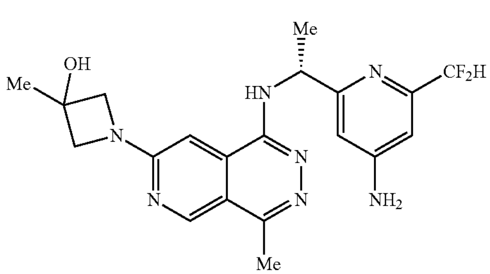 [SMILES: Cc1nnc(N[C@H](C)c2cc(N)cc(C(F)F)n2)c2cc(N3CC(C)(O)C3)ncc12] | ¹H NMR (400 MHz, CD₃OD) δ = 8.92 (s, 1H), 6.93 (s, 1H), 6.70 (s, 2H), 6.52 (t, J = 55.6 Hz, 1H), 5.29 (q, J = 6.9 Hz, 1H), 4.12-4.02 (m, 4H), 2.64 (s, 3H), 1.64 (d, J = 7.0 Hz, 3H), 1.60 (s, 3H). LCMS [M + 1]⁺: 416.4. |

TABLE 12-continued

| Ex. # | Structure | Spectral Data |
|---|---|---|
| 12-131 | 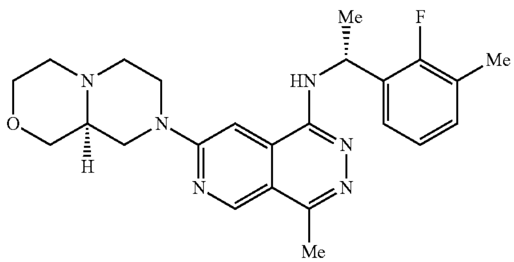 [SMILES: Cc1cccc([C@@H](C)Nc2nnc(C)c3cnc(N4CCN5CCOC[C@@H]5C4)cc23)c1F] | $^1$H NMR (400 MHz, DMSO-d$_6$) δ = 8.97 (s, 1H), 8.31 (s, 1H), 7.41 (s, 1H), 7.36 (d, J = 7.2 Hz, 1H), 7.18 (t, J = 7.2 Hz, 1H), 7.09-7.04 (m, 1H), 6.95 (t, J = 7.6 Hz, 1H), 5.66-5.62 (m, 1H), 4.44-4.36 (m, 2H), 3.89-3.75 (m, 2H), 3.58-3.54 (m, 1H), 3.21-3.20 (m, 1H), 3.11-3.05 (m, 1H), 2.91 (d, J = 11.2 Hz, 1H), 2.72 (d, J = 11.6 Hz, 1H), 2.57-2.56 (m, 1H), 2.55 (s, 3H), 2.30-2.26 (m, 1H), 2.24 (s, 3H), 2.22-2.15 (m, 2H), 1.56 (d, J = 7.2 Hz, 3H). LCMS [M + 1]$^+$: 437.1. |
| 12-132 | 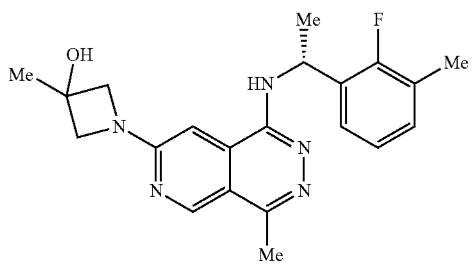 [SMILES: Cc1cccc([C@@H](C)Nc2nnc(C)c3cnc(N4CC(C)(O)C4)cc23)c1F] | $^1$H NMR (400 MHz, DMSO-d$_6$) δ 8.95 (s, 1H), 7.33 (d, J = 7.4 Hz, 1H), 7.18 (t, J = 7.2 Hz, 1H), 7.13-7.06 (m, 2H), 6.96 (t, J = 7.6 Hz, 1H), 5.71 (s, 1H), 5.64 (q, J = 7.0 Hz, 1H), 4.05-3.92 (m, 4H), 2.54 (s, 3H), 2.25 (s, 3H), 1.56 (d, J = 7.0 Hz, 3H), 1.49 (s, 3H). LCMS [M + 1]$^+$: 382.3. |
| 12-133 | 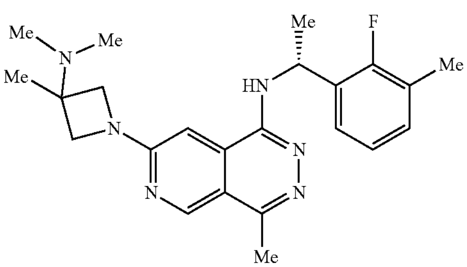 [SMILES: Cc1cccc([C@@H](C)Nc2nnc(C)c3cnc(N4CC(C)(N(C)C)C4)cc23)c1F] | $^1$H NMR (400 MHz, DMSO-d$_6$) δ 8.94 (s, 1H), 8.28 (s, 0H), 7.32 (d, J = 7.3 Hz, 1H), 7.19 (t, J = 7.6 Hz, 1H), 7.10 (d, J = 4.2 Hz, 2H), 6.96 (t, J = 7.5 Hz, 1H), 5.62 (q, J = 6.9 Hz, 1H), 3.89 (dd, J = 8.2, 5.2 Hz, 2H), 3.79 (dd, J = 8.1, 3.2 Hz, 2H), 2.54 (s, 3H), 2.24 (s, 3H), 2.15 (s, 6H), 1.56 (d, J = 7.0 Hz, 3H), 1.32 (s, 3H). LCMS [M + 1]$^+$: 409.4. |
| 12-134 | 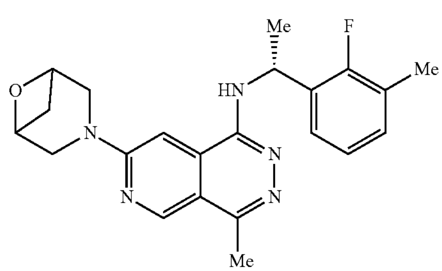 [SMILES: Cc1cccc([C@@H](C)Nc2nnc(C)c3cnc(N4CC5CC(C4)O5)cc23)c1F] | $^1$H NMR (400 MHz, DMSO-d$_6$) δ 9.04 (s, 1H), 7.45 (d, J = 7.4 Hz, 1H), 7.28 (s, 1H), 7.21 (t, J = 7.3 Hz, 1H), 7.09 (t, J = 7.2 Hz, 1H), 6.96 (t, J = 7.6 Hz, 1H), 5.67 (t, J = 7.1 Hz, 1H), 4.81 (d, J = 6.4 Hz, 2H), 3.95-3.85 (m, 2H), 3.77-3.67 (m, 2H), 2.57 (s, 3H), 2.25 (s, 3H), 1.95 (d, J = 8.8 Hz, 1H), 1.57 (d, J = 7.0 Hz, 3H). LCMS [M + 1]$^+$: 394.0. |

Example 13-1

4-methyl-N—((R)-1-(2-methyl-3-(trifluoromethyl)phenyl)ethyl)-7-(((S)-tetrahydrofuran-3-yl)oxy)phthalazin-1-amine

Example 13-2

(R)-4-methyl-N-(1-(2-methyl-3-(trifluoromethyl)phenyl)ethyl)-7-(oxetan-3-yloxy)phthalazin-1-amine

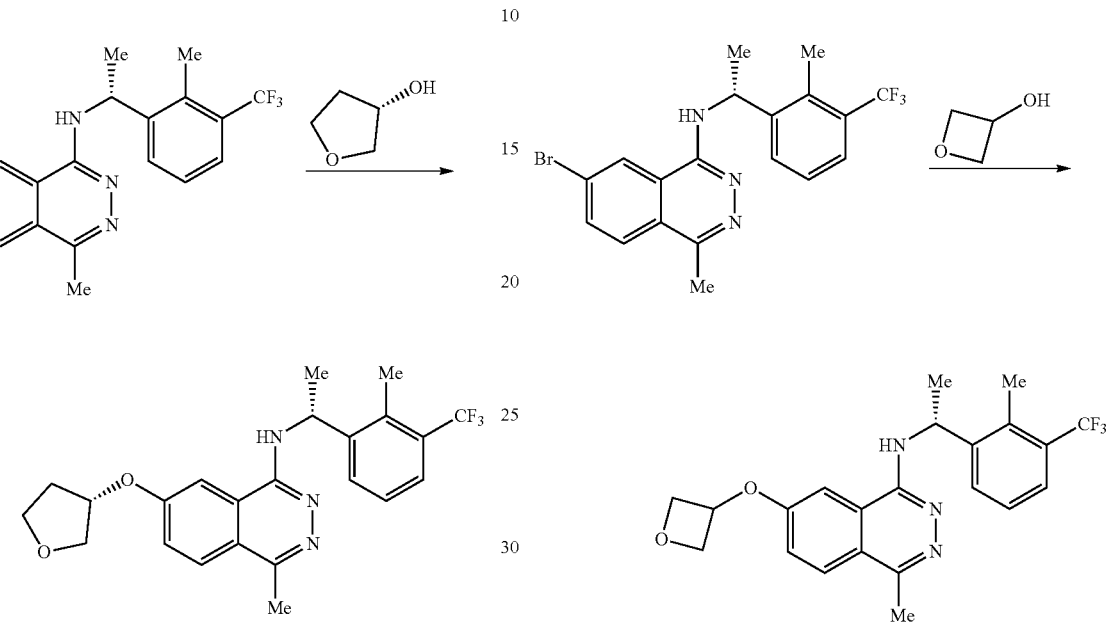

To a solution of (R)-7-bromo-4-methyl-N-(1-(2-methyl-3-(trifluoromethyl)phenyl)ethyl)phthalazin-1-amine (70.0 mg, 164 μmol, 1.00 eq) in toluene (1.00 mL) was added sodium hydride (13.2 mg, 329 μmol, 60.0% in mineral oil, 2.00 eq) at 0° C. under a nitrogen atmosphere, then (S)-tetrahydrofuran-3-ol (43.6 mg, 494 μmol, 3.00 eq), Pd$_2$(dba)$_3$ (15.1 mg, 16.5 μmol, 0.10 eq) and Tol-BINAP (22.4 mg, 33.0 μmol, 0.20 eq) was added the mixture. The reaction mixture was warmed to 100° C. and stirred 1 hour under a nitrogen atmosphere. After this time, the mixture was cooled to 25° C., slowly quenched with an aqueous saturated ammonium chloride (30.0 mL) then extracted with ethyl acetate (20.0 mL×3). The combined organic phases were washed with brine (30.0 mL), dried over anhydrous sodium sulfate, filtered, and concentrated under vacuum to give a residue. The residue was purified by prep-HPLC (column: Phenomenex luna C18 80×40 mm×3 μm; mobile phase: phase A: water with 0.04% HCl, phase B: acetonitrile; gradient of B %: 30%-52%) to give 4-methyl-N—((R)-1-(2-methyl-3-(trifluoromethyl)phenyl)ethyl)-7-(((S)-tetrahydrofuran-3-yl)oxy)phthalazin-1-amine (6.31 mg, 14.0 μmol, 8.5% yield, HCl salt) as a white solid. LCMS [M+1]$^+$: 432.1

$^1$H NMR (400 MHz, DMSO-d$_6$) δ=15.31 (s, 1H), 8.91 (s, 1H), 8.90-8.34 (m, 2H), 7.82-7.77 (m, 2H), 7.56 (d, J=8.0 Hz, 1H), 7.35 (t, J=8.0 Hz, 1H), 5.56 (s, 1H), 5.52-5.47 (m, 1H), 4.05-4.03 (m, 1H), 3.93-3.84 (m, 3H), 2.79 (s, 3H), 2.58 (s, 3H), 2.45-2.43 (m, 1H), 2.08-2.06 (m, 1H), 1.63 (d, J=7.2 Hz, 3H).

SFC conditions: Chiralcel OD-3 3 μm, 0.46 cm id×5 cm L; Mobile phase: MeOH (0.05% isopropylamine); Gradient: B in A from 10% to 40% in 3 minutes; Flow rate: 4.0 mL/min; Column temperature: 35° C.; Wavelength: 220 nm A mixture of (R)-7-bromo-4-methyl-N-(1-(2-methyl-3-(trifluoromethyl)phenyl)ethyl)phthalazin-1-amine (100 mg, 236 μmol, 1.00 eq.), oxetan-3-ol (26.2 mg, 354 μmol, 1.50 eq), sodium tert-butoxide (68.0 mg, 707 μmol, 3.00 eq.) and [2-(2-aminophenyl)phenyl]-methylsulfonyloxy-palladium; di-tert-butyl-[2-(2,4,6-triisopropyl phenyl)phenyl]phosphane (18.7 mg, 23.6 μmol, 0.10 eq.) in dioxane (2.00 mL) was degassed and purged with nitrogen 3 times, then the mixture was stirred at 100° C. for 1 hr under a nitrogen atmosphere. The mixture was filtered and concentrated under vacuum to give a residue. The residue was purified by prep-TLC (SiO$_2$, dichloromethane/methanol=20/1), then purified by prep-HPLC (column: Phenomenex luna C18 150×25 mm×10 um; mobile phases: phase A: water(0.225% TFA), phase B: acetonitrile; phase B gradient: 17%-47%) to give (R)-4-methyl-N-(1-(2-methyl-3-(trifluoromethyl)phenyl)ethyl)-7-(oxetan-3-yloxy)phthalazin-1-amine (5.20 mg, 12.4 μmol, 5.25% yield, 99.4% purity) as an off-white solid. LCMS [M+1]$^+$: 418.0.

$^1$H NMR (400 MHz, CD$_3$OD) δ=8.19 (d, J=8.8 Hz, 1H), 7.78-7.73 (m, 1H), 7.71 (d, J=8.0 Hz, 1H), 7.61-7.56 (m, 1H), 7.52 (d, J=7.6 Hz, 1H), 7.26 (t, J=8.0 Hz, 1H), 5.69-5.59 (m, 2H), 5.21-5.12 (m, 2H), 4.81-4.75 (m, 2H), 2.75 (s, 3H), 2.63 (s, 3H), 1.67 (d, J=7.2 Hz, 3H).

Following the teachings of the General Reaction Scheme III, and the procedure described for the preparation of Examples 13-1 and 13-2, the following compound of Formula (I), Example 13-3 shown in Table 13 was prepared.

TABLE 13

| Ex. # | Structure | Spectral Data |
|---|---|---|
| 13-3 | 2-methyl-3-((R)-1-(4-methyl-7-(((S)-tetrahydrofuran-3-yl)oxy)phthalazin-1-yl)amino)ethyl)benzonitrile | ¹H NMR (400 MHz, CD₃OD) = 8.04 (d, J = 9.2 Hz, 1H), 7.81 (d, J = 2.4 Hz, 1H), 7.73 (d, J = 7.6 Hz, 1H), 7.54-7.48 (m, 2H), 7.25 (t, J = 8.0 Hz, 1H), 5.66-5.55 (m, 1H), 5.38-5.33 (m, 1H), 4.12-4.05 (m, 1H), 4.04-3.99 (m, 2H), 3.98-3.91 (m, 1H), 2.75 (s, 3H), 2.67 (s, 3H), 2.46-2.35 (m, 1H), 2.25-2.17 (m, 1H), 1.63 (d, J = 7.2 Hz, 3H). LCMS [M + 1]⁺: 389.1. |

Example 14-1

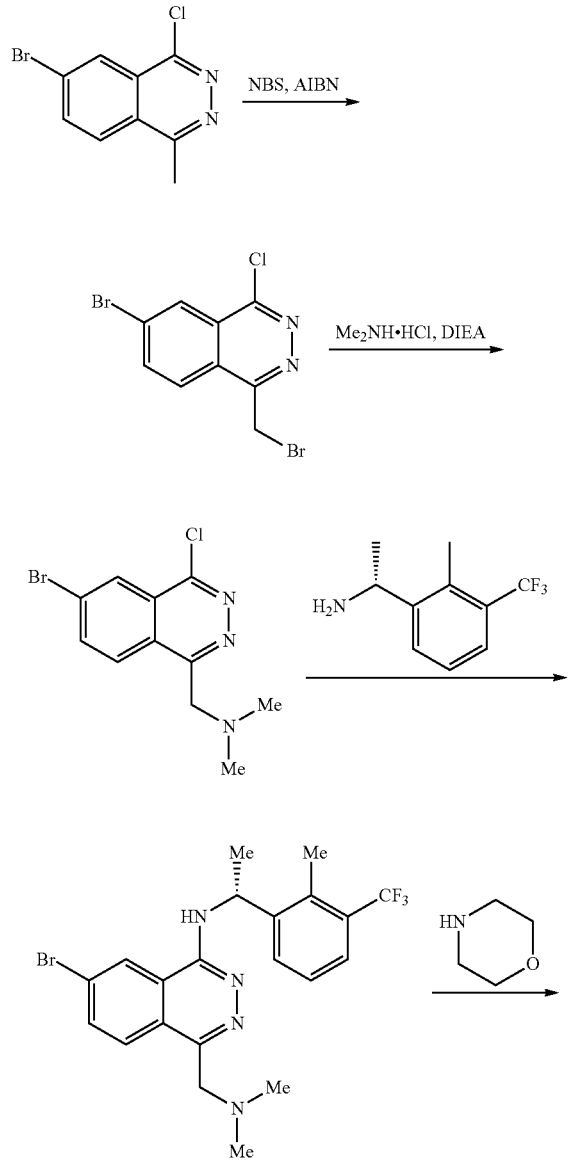

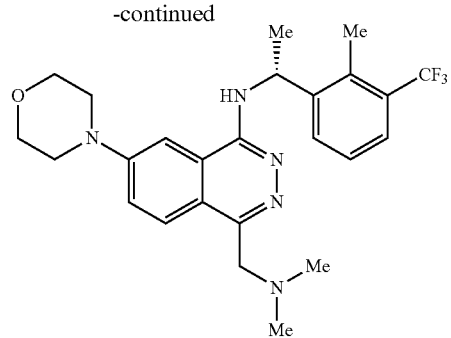

Step A: To a solution of 6 6-bromo-4-chloro-1-methylphthalazine (500 mg, 1.94 mmol, 1.00 eq.) in chloroform (8.00 mL) were added NBS (380 mg, 2.14 mmol, 1.10 eq.) and AIBN (48.0 mg, 0.29 mmol, 0.15 eq.), and the reaction mixture was stirred at 90° C. for 3 hours. The reaction mixture was then cooled to 25° C., quenched with water (20.0 mL) and extracted with ethyl acetate (30.0 mL×3). The combined organic layers were washed with brine (25.0 mL×2), dried over sodium sulfate, filtered, and concentrated under reduced pressure to give a residue. The residue was purified by column chromatography (SiO₂, petroleum ether/ethyl acetate=10/1 to 1/1) to give 6-bromo-1-(bromomethyl)-4-chlorophthalazine (180 mg, 535 µmol, 27.6% yield) as a yellow solid. LCMS [M+3]⁺: 336.6.

¹H NMR (400 MHz, DMSO-d₆) δ=8.52-8.50 (m, 1H), 8.41 (dd, J=1.2, 3.6 Hz, 2H), 5.42 (s, 1H), 5.31 (s, 1H).

Step B: To a solution of dimethylamine (48.2 mg, 1.07 mmol, 0.05 mL, 2.00 eq., HCl salt) in tetrahydrofuran (10.0 mL) was added N,N-diisopropyl ethyl amine (207 mg, 1.61 mmol, 0.28 mL, 3.00 eq.), then 6-bromo-1-(bromomethyl)-4-chlorophthalazine (180 mg, 0.54 mmol, 1.00 eq.) was added to the reaction mixture and the mixture was stirred at 25° C. for 12 hours. The mixture was diluted with water (30.0 mL) and extracted with ethyl acetate (30.0 mL×3). The combined organic layers were washed with brine (30.0 mL×2), dried over sodium sulfate, filtered, and concentrated under reduced pressure to give a residue. The residue was purified by prep-TLC (SiO₂, petroleum ether/ethyl acetate=1/1, Rf=0.4) to give 1-(6-bromo-4-chlorophthalazin-1-yl)-N,N-dimethylmethanamine (80.0 mg, 266 µmol, 49.7% yield) as a yellow solid. LCMS [M+3]⁺: 301.9

¹H NMR (400 MHz, DMSO-d₆) δ=8.51 (d, J=8.8 Hz, 1H), 8.44 (d, J=1.6 Hz, 1H), 8.30 (dd, J=2.0, 8.8 Hz, 1H), 4.02 (s, 2H), 2.22 (s, 6H).

Step C: To a solution of 1-(6-bromo-4-chlorophthalazin-1-yl)-N,N-dimethylmethanamine (120 mg, 0.40 mmol, 1.00 eq.) and (R)-1-(2-methyl-3-(trifluoromethyl)phenyl)ethan-1-amine (89.2 mg, 0.44 mmol, 1.10 eq.) in dimethylsulfoxide (3.00 mL) was added potassium fluoride (69.6 mg, 1.20 mmol, 0.03 mL, 3.00 eq.), then the reaction was stirred at 130° C. for 2 hours. The reaction was cooled to 25° C., quenched with water (20.0 mL) and extracted with ethyl acetate (20.0 mL×3). The combined organic layers were washed with brine (20.0 mL×2), dried over sodium sulfate, filtered, and concentrated under reduced pressure to give a residue. The residue was purified by prep-TLC (SiO$_2$, petroleum ether/ethyl acetate=1/1, Rf=0.2) to give (R)-7-bromo-4-((dimethylamino)methyl)-N-(1-(2-methyl-3-(trifluoromethyl)phenyl)ethyl)phthalazin-1-amine (90.0 mg, 192 μmol, 48.2% yield) as a yellow oil. LCMS [M+1]$^+$: 467.0.

Step D: To a solution of (R)-7-bromo-4-((dimethylamino)methyl)-N-(1-(2-methyl-3-(trifluoromethyl)phenyl)ethyl)phthalazin-1-amine (60.0 mg, 0.13 mmol, 1.00 eq.), morpholine (28.0 mg, 0.32 mmol, 0.03 mL, 2.50 eq.), cesium carbonate (125 mg, 0.39 mmol, 3.00 eq.) and RuPhos (12.0 mg, 0.03 mmol, 0.20 eq.) in dioxane (8.00 mL) was added Pd$_2$(dba)$_3$ (11.8 mg, 0.02 mmol, 0.10 eq.), then degassed and purged with nitrogen 3 times, and the reaction mixture was stirred at 100° C. for 2 hours under a nitrogen atmosphere. The reaction was cooled to 25° C., diluted with water (20.0 mL) and extracted with ethyl acetate (30.0 mL×3). The combined organic layers were washed with brine (25.0 mL×2), dried over sodium sulfate, filtered, and concentrated under reduced pressure to give a residue. The residue was purified by prep-TLC (SiO$_2$, petroleum ether/ethyl acetate=1/1) to give (R)-4-((dimethylamino)methyl)-N-(1-(2-methyl-3-(trifluoromethyl)phenyl)ethyl)-7-morpholinophthalazin-1-amine (5.75 mg, 12.1 μmol, 9.45% yield, 99.9% purity) as a yellow solid. LCMS [M+1]$^+$: 474.3.

$^1$H NMR (400 MHz, DMSO-d$_6$) δ=8.09 (d, J=8.8 Hz, 1H), 7.76 (d, J=8.0 Hz, 1H), 7.62 (s, 1H), 7.58 (dd, J=2.0, 8.8 Hz, 1H), 7.52 (br d, J=12 Hz, 2H), 7.32 (t, J=7.6 Hz, 1H), 5.77-5.67 (m, 1H), 3.86-3.80 (m, 4H), 3.45-3.40 (m, 4H), 3.31 (br s, 2H), 2.58 (s, 3H), 2.16 (br s, 6H), 1.56 (d, J=12 Hz, 3H).

SFC conditions: Chiralcel OD-3 50×4.6 mm I.D., 3 um Mobile phase: Phase A for CO$_2$, and Phase B for MeOH (0.05% DEA), Gradient elution: MeOH (0.05% DEA) in CO$_2$ from 5% to 40% Flow rate: 3 mL/min, Detector: PDA, Column Temp: 35° C., Back Pressure: 100 Bar.

Example 14-2

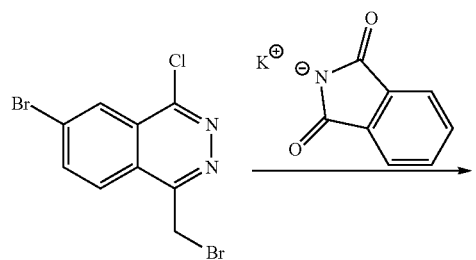

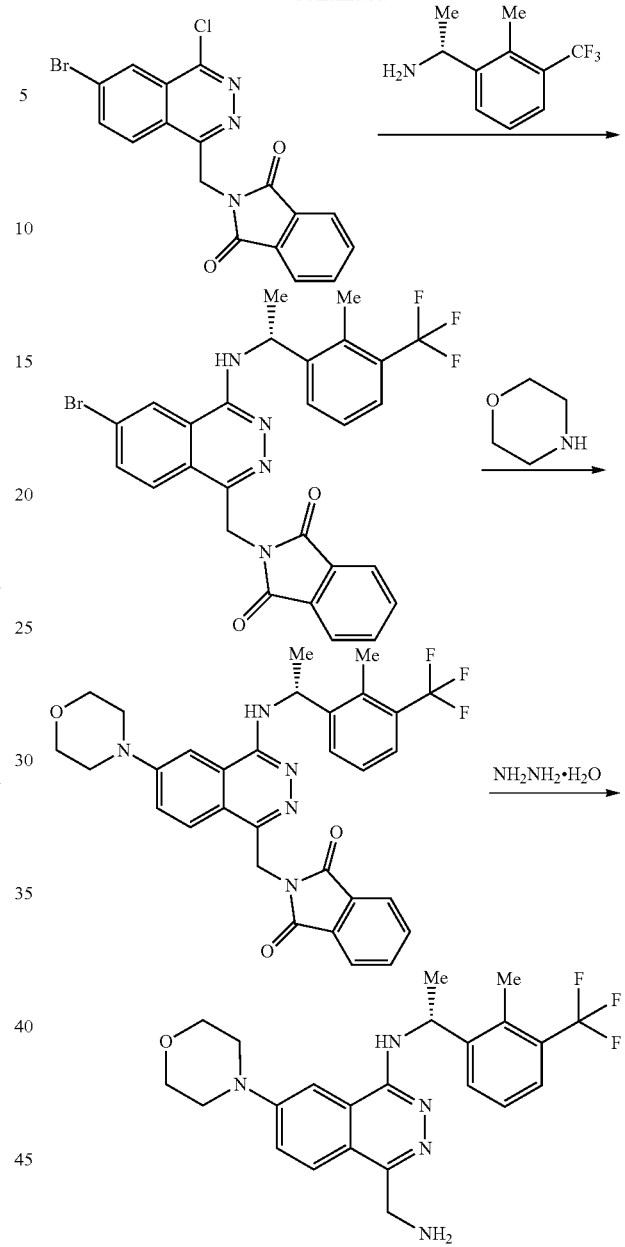

Step A: To a mixture of 6-bromo-1-(bromomethyl)-4-chlorophthalazine (150 mg, 446 μmol, 1.00 eq.) in dimethylformamide (15.0 mL) was added potassium phthalimide (116 mg, 624 μmol, 1.40 eq.) at 25° C. under a nitrogen atmosphere. The mixture was stirred at 85° C. for 2 hours then cooled to 25° C. Then the mixture was diluted with water (50.0 mL) and extracted with ethyl acetate (50.0 mL×3). The combined organic phases were washed with brine (100 mL), dried over anhydrous sodium sulfate, filtered, and concentrated under vacuum to give a residue. The residue was purified by column chromatography (SiO$_2$, petroleum ether/ethyl acetate=5/1) to give 2-((6-bromo-4-chlorophthalazin-1-yl)methyl)isoindoline-1,3-dione (150 mg, 373 μmol, 83.6% yield) as a yellow solid. LCMS [M+1]$^+$: 404.0.

$^1$H NMR (400 MHz, DMSO-d$_6$) δ=8.55 (m, 2H), 8.40 (m, 1H), 7.95 (m, 2H), 7.90 (m, 2H), 5.60 (s, 2H).

Step B: A solution of 2-((6-bromo-4-chlorophthalazin-1-yl)methyl)isoindoline-1,3-dione (130 mg, 323 μmol, 1.00 eq.) and (R)-1-(2-methyl-3-(trifluoromethyl)phenyl)ethan-1-amine (65.6 mg, 323 μmol, 1.00 eq.) in dimethyl sulfoxide (7.00 mL) was added NN-diisopropylethylamine (125 mg, 969 μmol, 169 μL, 3.00 eq.) and potassium fluoride (56.3 mg, 969 μmol, 22.7 μL, 3.00 eq.) was stirred at 130° C. for 12 hours in a sealed tube. The reaction was cooled to 25° C. and diluted with water (50.0 mL) and extracted with ethyl acetate (50.0 mL×3). The combined organic phases were washed with brine (100 mL), dried over sodium sulfate, filtered, and concentrated under reduced pressure to give a residue. The residue was purified by column chromatography (SiO$_2$, petroleum ether/ethyl acetate=5/1) to give (R)-2-((6-bromo-4-((1-(2-methyl-3-(trifluoromethyl)phenyl)ethyl)amino)phthalazin-1-yl)methyl)isoindoline-1,3-dione (130 mg, 228 μmol, 70.7% yield) as a yellow solid. LCMS [M+1]$^+$: 472.2.

$^1$H NMR (400 MHz, DMSO-d$_6$) δ=8.91 (s, 1H), 8.20-8.07 (m, 2H), 7.97-7.80 (m, 5H), 7.74 (d, J=8.0 Hz, 1H), 7.51 (d, J=8.0 Hz, 1H), 7.31 (t, J=8.0 Hz, 1H), 5.72-5.60 (m, 1H), 5.25 (s, 2H), 2.44 (s, 3H), 1.50 (d, J=12 Hz, 3H).

Step C: To a solution of (R)-2-((6-bromo-4-((1-(2-methyl-3-(trifluoromethyl)phenyl)ethyl)amino)phthalazin-1-yl)methyl)isoindoline-1,3-dione (100 mg, 176 μmol, 1.00 eq.) and morpholine (61.2 mg, 703 μmol, 61.8 μL, 4.00 eq.) in methylbenzene (10.0 mL) was added BINAP (21.9 mg, 35.1 μmol, 0.20 eq), cesium carbonate (172 mg, 527 μmol, 3.00 eq.) and Pd$_2$(dba)$_3$ (16.1 mg, 17.6 μmol, 0.10 eq.) at 25° C. under a nitrogen atmosphere. The mixture was stirred at 100° C. for 1 hour. The reaction was completed and cooled to 25° C. The reaction mixture was quenched with water (50.0 mL) and extracted with ethyl acetate (50.0 mL×3). The combined organic phases were washed with brine (100 mL), dried over sodium sulfate, filtered, and concentrated under reduced pressure to give a residue. The residue was purified by column chromatography (SiO$_2$, petroleum ether/ethyl acetate=1/1) to give (R)-2-((4-((1-(2-methyl-3-(trifluoromethyl)phenyl)ethyl)amino)-6-morpholinophthalazin-1-yl)methyl)isoindoline-1,3-dione (65.0 mg, 113 μmol, 64.3% yield) as a yellow solid. LCMS [M+1]$^+$: 576.3.

$^1$H NMR (400 MHz, DMSO-d$_6$) δ=8.03 (br d, J=10.0 Hz, 1H), 7.94-7.85 (m, 4H), 7.74 (br d, J=7.2 Hz, 1H), 7.65 (br s, 2H), 7.51 (br d, J=8.0 Hz, 1H), 7.43 (br d, J=7.2 Hz, 1H), 7.31 (br t, J=6.8 Hz, 1H), 5.72-5.67 (m, 1H), 5.18 (s, 2H), 3.83 (m, 4H), 3.45 (m, 4H), 2.44 (s, 3H), 1.51 (d, J=7.2 Hz, 3H).

Step D: To a solution of (R)-2-((4-((1-(2-methyl-3-(trifluoromethyl)phenyl)ethyl)amino)-6-morpholinophthalazin-1-yl)methyl)isoindoline-1,3-dione (60.0 mg, 104 μmol, 1.00 eq.) in ethanol (6.00 mL) was added hydrazine hydrate (47.0 mg, 938 μmol, 45.6 μL, 9.00 eq.) at 25° C. under a nitrogen atmosphere. The mixture was stirred at 25° C. for 1 hour, then quenched with water (10.0 mL) and extracted with ethyl acetate (10.0 mL×3). The combined organic layers were washed with brine (30.0 mL), dried over sodium sulfate, filtered, and concentrated under reduced pressure to give a residue. The crude product was purified by reverse-phase HPLC (water (0.04% HCl)/CH$_3$CN) to give (R)-4-(aminomethyl)-N-(1-(2-methyl-3-(trifluoromethyl)phenyl)ethyl)-7-morpholinophthalazin-1-amine (5.81 mg, 13.0 μmol, 12.5% yield, hydrochloride salt) as a yellow solid. LCMS [M+1]$^+$: 446.1.

$^1$H NMR (400 MHz, DMSO-d$_6$) δ=8.62 (br s, 3H), 8.12 (br s, 2H), 7.79 (br d, J=7.6 Hz, 2H), 7.61 (br d, J=8.0 Hz, 1H), 7.38 (br t, J=8.0 Hz, 1H), 5.66 (br d, J=6.4 Hz, 1H), 4.56 (br s, 2H), 3.81 (br t, J=4.8 Hz, 4H), 3.62 (br s, 4H), 2.53 (m, 3H), 1.70 (br d, J=5.6 Hz, 3H).

Example 14-3

3-((R)-1-((7-((1R,4R)-2-oxa-5-azabicyclo[2.2.1]heptan-5-yl)-4-((methylamino)methyl)pyrido[3,4-d]pyridazin-1-yl)amino)ethyl)-2-methylbenzonitrile

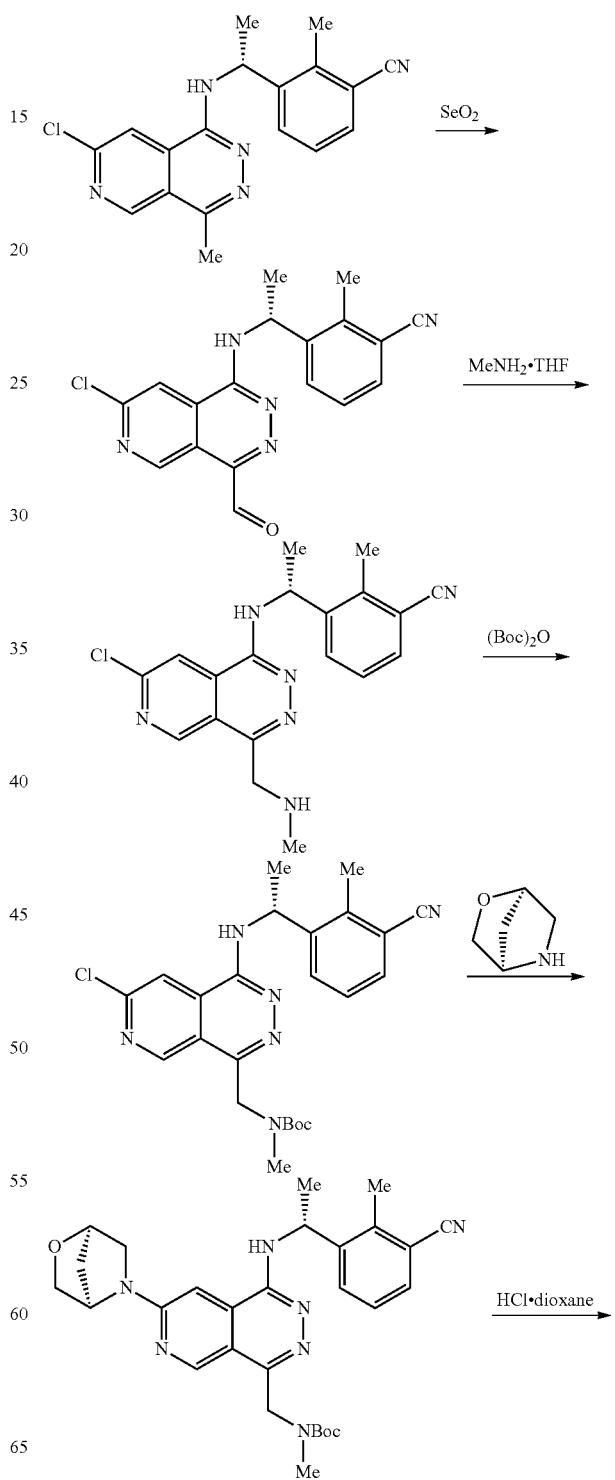

-continued

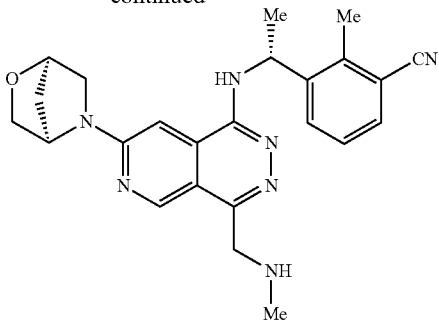

Step A: To a solution of (R)-3-(1-((7-chloro-4-methylpyrido[3,4-d]pyridazin-1-yl)amino)ethyl)-2-methylbenzonitrile (30.0 mg, 88.8 μmol, 1.00 eq.) in dioxane (1.00 mL) was added selenium dioxide (19.7 mg, 178 μmol, 19.3 μL, 2.00 eq.), and the mixture was stirred at 100° C. for 1 hour. The mixture was then concentrated under reduced pressure, and the residue was purified by column chromatography (SiO₂, petroleum ether/ethyl acetate=20/1 to 5/1) to give (R)-3-(1-((7-chloro-4-formylpyrido[3,4-b]pyridazin-1-yl)amino)ethyl)-2-methylbenzonitrile (16.0 mg, 45.5 μmol, 51.2% yield) as a yellow solid.

$^1$H NMR (400 MHz, DMSO-dis) δ=10.06 (s, 1H), 9.99 (s, 1H), 9.09 (br d, J=6.8 Hz, 1H), 8.76 (s, 1H), 7.78 (br d, J=8.0 Hz, 1H), 7.66 (br d, J=7.6 Hz, 1H), 7.36 (br t, J=8.0 Hz, 1H), 5.81 (br d, J=6.4 Hz, 1H), 2.69 (s, 3H), 1.63 (br d, J=6.8 Hz, 3H).

Step B: To a solution of (R)-3-(1-((7-chloro-4-formylpyrido[3,4-d]pyridazin-1-yl)amino)ethyl)-2-methylbenzonitrile (106 mg, 301 μmol, 1.00 eq.) and methylamine tetrahydrofuran solution (2.0 M, 360 μL, 2.39 eq.) in THF (3.00 mL) was added acetic acid (1.81 mg, 30.1 μmol, 1.72 μL, 0.10 eq.), and the mixture was stirred at 50° C. for 30 minutes. After this time was added sodium triacetoxyborohydride (192 mg, 904 μmol, 3.00 eq.), and shorly after the mixture was poured into water (5.00 mL). The aqueous phase was extracted with ethyl acetate (10.0 mL×3), and the combined organic phases were washed with brine (10.0 mL×2), dried over anhydrous sodium sulfate, filtered, and concentrated under reduced pressure to give (R)-3-(1-((7-chloro-4-((methylamino)methyl)pyrido[3,4-d]pyridazin-1-yl)amino)ethyl)-2-methylbenzonitrile (65.0 mg, 177 μmol, 58.8% yield) as a yellow solid. LCMS [M+1]⁺: 367.2.

Step C: To a solution of (R)-3-(1-((7-chloro-4-((methylamino)methyl)pyrido[3,4-d]pyridazin-1-yl)amino)ethyl)-2-methylbenzonitrile (34.0 mg, 92.7 μmol, 1.00 eq.) and (Boc)₂O (22.3 mg, 102 μmol, 23.4 μL, 1.10 eq.) in DCM (0.50 mL) was added DMAP (1.13 mg, 9.27 μmol, 0.10 eq.), and the mixture was stirred at 25° C. for 1 hour. The mixture was then concentrated under reduced pressure, and the residue was purified by prep-TLC (SiO₂, petroleum ether/ethyl acetate=2:1) to give tert-butyl (R)-((7-chloro-1-((1-(3-cyano-2-methyl phenyl)ethyl)amino)pyrido[3,4-b]pyridazin-4-yl)methyl)(methyl)carbamate (35.0 mg, 75.0 μmol, 80.9% yield) as a yellow solid.

$^1$H NMR (400 MHz, CD₃OD) δ=9.43 (br s, 1H), 8.50 (s, 1H), 7.72 (d, J=7.2 Hz, 1H), 7.52 (dd, J=1.2, 7.6 Hz, 1H), 7.29-7.24 (m, 1H), 5.68-5.62 (m, 1H), 2.78-2.75 (m, 5H), 1.63 (d, J=7.2 Hz, 3H), 1.49-1.41 (m, 9H), 1.22 (s, 3H).

Step D: To a solution of tert-butyl (R)-((7-chloro-1-((3-cyano-2-methyl phenyl)ethyl)amino)pyrido[3,4-b]pyridazin-4-yl)methyl)(methyl)carbamate (30.0 mg, 64.3 μmol, 1.00 eq.) and ((1R,4R)-2-oxa-5-azabicyclo[2.2.1]heptane (7.01 mg, 51.7 μmol, 0.8 eq., HCl) in DMSO (0.10 mL) was added cesium fluoride (19.5 mg, 128 μmol, 4.74 μL, 2.00 eq.) and N,N-diisopropylethylamine (16.6 mg, 128 μmol, 22.4 μL, 2.00 eq.), and the mixture was stirred at 130° C. for 1 hour. The solution was then cooled to 25° C., poured into water (10.0 mL), and the aqueous phase was extracted with ethyl acetate (10.0 mL×3). The combined organic phases were washed with brine (10.0 mL×3), dried over anhydrous sodium sulfate, filtered, and concentrated under reduced pressure to give tert-butyl ((7-((1R,4R)-2-oxa-5-azabicyclo[2.2.1]heptan-5-yl)-1-(((R)-1-(3-cyano-2-methylphenyl)ethyl)amino)pyrido[3,4-d]pyridazin-4-yl)methyl)(methyl)carbamate (30.0 mg, crude) as a yellow solid. LCMS [M+1]⁺: 530.2.

Step E: To a solution of tert-butyl ((7-((1R,4R)-2-oxa-5-azabicyclo[2.2.1]heptan-5-yl)-1-(((R)-1-(3-cyano-2-methyl phenyl)ethyl)amino)pyrido[3,4-b]pyridazin-4-yl)methyl)(methyl)carbamate (18.0 mg, 34.0 μmol, 1.00 eq.) in acetonitrile (1.50 mL) was added hydrochloric acid/dioxane (0.50 mL), and the mixture was stirred at 0° C. for 30 minutes. The mixture was then poured into water (5.00 mL), and the aqueous phase was extracted with ethyl acetate (5.00 mL×3). The combined organic phases were washed with brine (5.00 mL×3), dried over anhydrous sodium sulfate, filtered, and concentrated under reduced pressure. The residue was purified by prep-HPLC [column: 3_Phenomenex Luna C18 75×30 mm×3 um; mobile phase: phase A: water (0.05% HCl), phase B: acetonitrile; B %: 7%-27%] to give 3-((R)-1-((7-((1R,4R)-2-oxa-5-azabicyclo[2.2.1]heptan-5-yl)-4-((methylamino)methyl)pyrido[3,4-d]pyridazin-1-yl)amino)ethyl)-2-methylbenzonitrile (7.00 mg, 14.9 μmol, 43.8% yield, 99.1% purity, hydrochloride salt) as a yellow solid. LCMS [M+1]⁺: 430.3.

$^1$H NMR (400 MHz, CD₃OD) δ=9.09 (s, 1H), 7.83 (br d, J=7.6 Hz, 1H), 7.71 (d, J=7.6 Hz, 1H), 7.63-7.40 (m, 2H), 5.56 (q, J=6.4 Hz, 1H), 5.41 (br s, 1H), 4.83 (s, 3H), 3.96 (d, J=6.8 Hz, 1H), 3.84 (br s, 1H), 3.69 (br d, J=9.6 Hz, 1H), 3.49 (br d, J=3.2 Hz, 1H), 2.93 (s, 3H), 2.64 (s, 3H), 2.09 (br s, 2H), 1.84 (d, J=6.8 Hz, 3H).

Example 14-4

3-((R)-1-((7-((1R,4R)-2-oxa-5-azabicyclo[2.2.1]heptan-5-yl)-4-((di methyl amino)methyl)pyrido[3,4-b]pyridazin-1-yl)amino)ethyl)-2-methylbenzonitrile

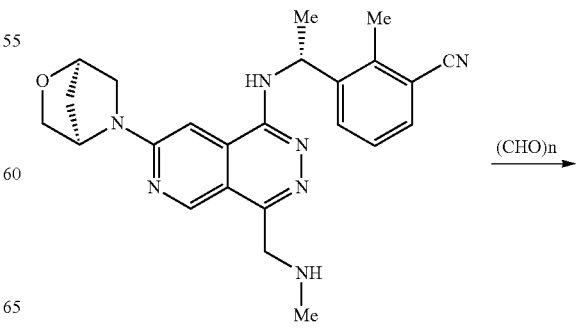

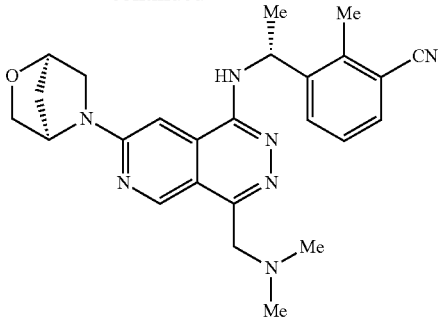 [SMILES: Cc1c([C@@H](C)Nc2nnc(CN(C)C)c3cnc(N4C[C@H]5C[C@@H]4CO5)cc23)cccc1C(F)(F)F]

To a solution of 3-((R)-1-((7-((1R,4R)-2-oxa-5-azabicyclo[2.2.1]heptan-5-yl)-4-((methylamino)methyl)pyrido[3,4-b]pyridazin-1-yl)amino)ethyl)-2-methylbenzonitrile (12.0 mg, 27.9 μmol, 1.00 eq.) and paraformaldehyde (1.68 mg) in methanol (1.00 mL) was added acetic acid (168 ug, 2.79 μmol, 0.16 μL, 0.10 eq.) and sodium cyanoborohydride (3.51 mg, 55.9 μmol, 2.00 eq.), and the mixture was stirred at 25° C. for 1 hour. The mixture was then poured into water (5.00 mL), and the aqueous phase was extracted with ethyl acetate (5.00 mL×3). The combined organic phases were washed with brine (5.00 mL×3), dried over anhydrous sodium, filtered, and concentrated under reduced pressure. The residue was purified by prep-HPLC [column: 3_Phenomenex Luna C18 75×30 mm×3 um; mobile phase: phase A: water (0.05% HCl), phase B: acetonitrile; B %: 9%-29%] to give 3-((R)-1-((7-((1R,4R)-2-oxa-5-azabicyclo[2.2.1]heptan-5-yl)-4-((dimethylamino)methyl)pyrido[3,4-d]pyridazin-1-yl)amino)ethyl)-2-methylbenzonitrile (5.20 mg, 11.4 μmol, 40.8% yield, 97.2% purity, hydrochloride salt) as a yellow solid. LCMS [M+1]$^+$: 444.3.

$^1$H NMR (400 MHz, CD$_3$OD) δ=9.11 (s, 1H), 7.83 (br d, J=7.6 Hz, 1H), 7.71 (d, J=7.6 Hz, 1H), 7.58-7.29 (m, 2H), 5.56 (q, J=6.4 Hz, 1H), 5.42 (br s, 1H), 5.04-4.93 (m, 2H), 4.83-4.81 (m, 1H), 3.95 (br d, J=7.6 Hz, 1H), 3.82 (br s, 1H), 3.67 (br s, 1H), 3.48 (br s, 1H), 3.11 (s, 6H), 2.64 (s, 3H), 2.08 (br s, 2H), 1.84 (br d, J=6.8 Hz, 3H).

Following the teachings of the General Reaction Scheme III, and the procedure described for the preparation of Examples 14-3-14-4, the following compounds of Formula (I), Examples 14-5 to 14-6 shown in Table 14 were prepared.

TABLE 14

| Ex. # | Structure | Spectral Data |
|---|---|---|
| 14-5 | ![structure] 7-((1R,4R)-2-oxa-5-azabicyclo[2.2.1]heptan-5-yl)-N-((R)-1-(2-methyl-3-(trifluoromethyl)phenyl)ethyl)-4-((methylamino)methyl)pyrido[3,4-d]pyridazin-1-amine Formate salt | $^1$H NMR (400 MHz, CD$_3$OD) δ = 8.94 (s, 1H), 8.53 (s, 1H), 7.67 (d, J = 7.6 Hz, 1H), 7.51 (d, J = 7.6 Hz, 1H), 7.25 (t, J = 8.0 Hz, 1H), 7.16 (s, 1H), 5.77-5.65 (m, 1H), 5.17 (br s, 1H), 4.81 (s, 1H), 4.57-4.43 (m, 2H), 3.99-3.92 (m, 1H), 3.85 (d, J = 7.6 Hz, 1H), 3.74-3.63 (m, 1H), 3.50 (br d, J = 10.4 Hz, 1H), 2.74 (s, 3H), 2.59 (s, 3H), 2.07 (s, 2H), 1.65 (d, J = 6.8 Hz, 3H). LCMS [M + 1]$^+$: 473.3. |
| 14-6 | ![structure] 7-((1R,4R)-2-oxa-5-azabicyclo[2.2.1]heptan-5-yl)-4-((dimethylamino)methyl)-N-((R)-1-(2-methyl-3-(trifluoromethyl)phenyl)ethyl)pyrido[3,4-d]pyridazin-1-amine | $^1$H NMR (400 MHz, CD$_3$OD) δ = 9.15 (s, 1H), 7.68 (d, J = 8.0 Hz, 1H), 7.50 (d, J = 7.6 Hz, 1H), 7.32-7.19 (m, 1H), 7.12 (s, 1H), 5.77-5.63 (m, 1H), 5.17 (br s, 1H), 4.80 (s, 1H), 4.07-4.01 (m, 1H), 3.99-3.93 (m, 2H), 3.85 (d, J = 7.2 Hz, 1H), 3.71-3.64 (m, 1H), 3.50 (br d, J = 10.4 Hz, 1H), 2.60 (s, 3H), 2.42 (s, 6H), 2.06 (s, 2H), 1.63 (d, J = 7.2 Hz, 3H). LCMS [M + 1]$^+$: 487.2. |

Example 15-1

N—((R)-1-(3-amino-5-(trifluoromethyl)phenyl)ethyl)-4-methyl-7-(((S)-tetrahydrofuran-3-yl)oxy)phthalazin-1-amine

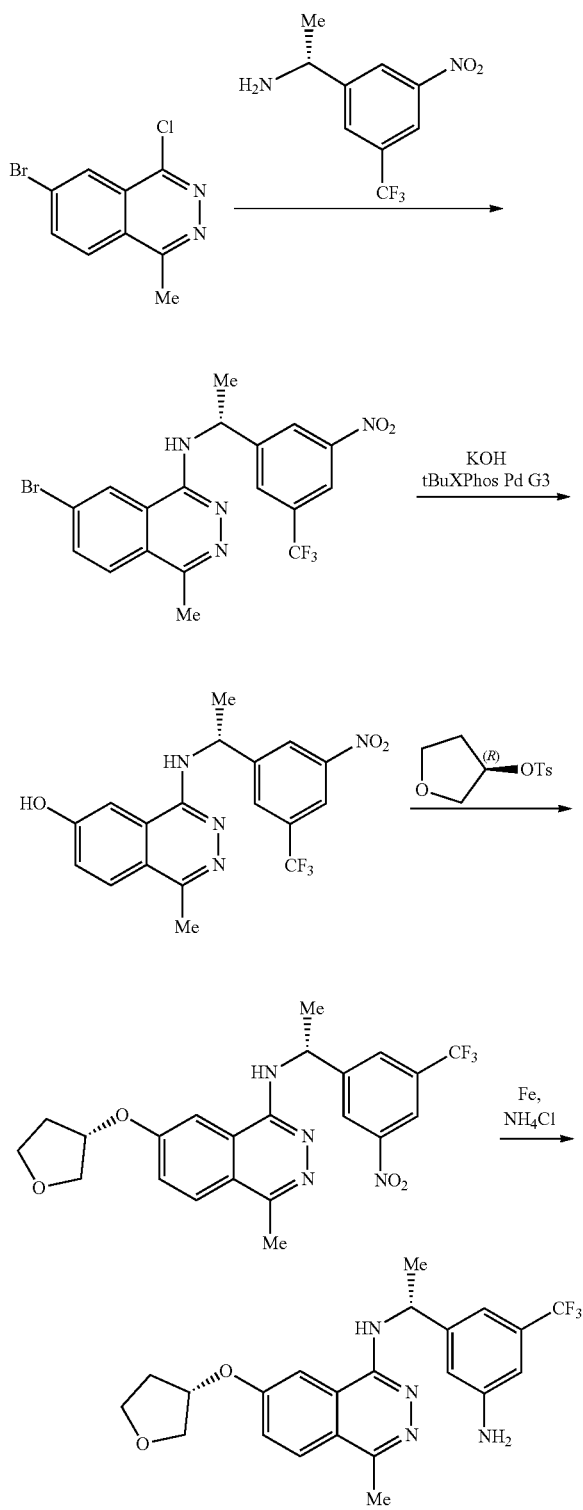

Step A: To a solution of 6-bromo-4-chloro-1-methylphthalazine (605 mg, 2.35 mmol, 1.10 eq.) in DMSO (1.50 mL) was added potassium fluoride (372 mg, 6.41 mmol, 150 µL, 3.00 eq.) and (R)-1-(3-nitro-5-(trifluoromethyl)phenyl)ethan-1-amine (commercially available, 500 mg, 2.14 mmol, 1.00 eq.). The mixture was stirred at 130° C. for 2 hours. The reaction mixture was quenched by addition water (3.00 mL) at 20° C., and then diluted with ethyl acetate (5.00 mL) and extracted with ethyl acetate (5.00 mL×3). The combined organic layers were washed with brine (5.00 mL×3), dried over sodium sulfate, filtered, and concentrated under reduced pressure to give a residue. The residue was purified by prep-TLC (SiO$_2$, petroleum ether:ethyl acetate, 1:1) to give (R)-7-bromo-4-methyl-N-(1-(3-nitro-5-(trifluoromethyl)phenyl)ethyl)phthalazin-1-amine (260 mg, 571 µmol, 26.8% yield) as a yellow oil. LCMS [M+1]$^+$: 455.0.

Step B: To a solution of (R)-7-bromo-4-methyl-N-(1-(3-nitro-5-(trifluoromethyl)phenyl)ethyl)phthalazin-1-amine (20.0 mg, 43.9 µmol, 1.00 eq.) in dioxane (0.50 mL) and water (0.30 mL) was added potassium hydroxide (4.93 mg, 87.9 µmol, 2.00 eq.) and t-BuXPhos Pd G3 (3.49 mg, 4.39 µmol, 0.10 eq.), The mixture was stirred at 80° C. for 2 hours. The mixture was diluted with water (3.00 mL) and extracted with ethyl acetate (3.00 mL×2). The combined organic layers were washed with brine (3.00 mL×3), dried over sodium sulfate, filtered, and concentrated under reduced pressure to give a crude product (R)-1-methyl-4-((1-(3-nitro-5-(trifluoromethyl)phenyl)ethyl)amino)phthalazin-6-ol (16.0 mg, 40.8 umol) as a brown oil used into the next step without further purification. LCMS [M+1]$^+$: 393.1.

Step C: To a solution of (R)-1-methyl-4-((1-(3-nitro-5-(trifluoromethyl)phenyl)ethyl)amino)phthalazin-6-ol (16.0 mg, 40.8 µmol, 1.00 eq.) in DMF (1.50 mL) was added cesium carbonate (39.9 mg, 122 µmol, 3.00 eq.) and (R)-tetrahydrofuran-3-yl 4-methylbenzenesulfonate (14.8 mg, 61.2 µmol, 1.50 eq.), The mixture was stirred at 80° C. for 12 hours. The residue was diluted with water (2.00 mL) and extracted with ethyl acetate (3.00 mL×3). The combined organic layers were washed with brine (5.00 mL×2), dried over sodium sulfate, filtered, and concentrated under reduced pressure to give a residue. The crude product 4-methyl-N—((R)-1-(3-nitro-5-(trifluoromethyl)phenyl)ethyl)-7-(((R)-tetrahydrofuran-3-yl)oxy)phthalazin-1-amine (18.0 mg, 38.93 µmol, crude) as a brown oil used into the next step without further purification. LCMS [M+1]$^+$: 463.1.

Step D: To a solution of 7-methyl-N—((R)-1-(3-nitro-5-(trifluoromethyl)phenyl)ethyl)-7-(((R)-tetrahydrofuran-3-yl)oxy)phthalazin-1-amine (18.0 mg, 38.9 µmol, 1.00 eq.) in ethanol (1.00 mL) and water (0.20 mL) was added iron powder (10.9 mg, 195 µmol, 5.00 eq.) and ammonium chloride (10.4 mg, 195 µmol, 5.00 eq). The mixture was stirred at 80° C. for 2 hours. The residue was diluted with methanol (3.00 mL), filtered, and concentrated under reduced pressure to give a residue. The residue was purified by prep-HPLC [Phenomenex Gemini-NX C18 75×30 mm×3 um; mobile phase: phase A: water(10 mM NH$_3$HCO$_3$), phase B: MeCN; B %: 25%-55%] to give N—((R)-1-(3-amino-5-(trifluoromethyl)phenyl)ethyl)-4-methyl-7-(((S)-tetrahydrofuran-3-yl)oxy)phthalazin-1-amine (7.00 mg, 16.2 µmol, 41.6% yield) as a off-white solid. LCMS [M+1]$^+$: 433.2.

$^1$H NMR (400 MHz, CD$_3$OD) δ=8.00 (d, J=8.8 Hz, 1H), 7.77 (d, J=2.4 Hz, 1H), 7.49 (dd, J=2.4, 9.2 Hz, 1H), 6.98 (br d, J=2.4 Hz, 2H), 6.76 (s, 1H), 5.42 (q, J=6.8 Hz, 1H), 5.34 (br dd, J=4.4, 6.0 Hz, 1H), 4.13-3.90 (m, 4H), 2.67 (s, 3H), 2.46-2.32 (m, 1H), 2.26-2.15 (m, 1H), 1.64 (d, J=7.2 Hz, 3H).

Example 15-2

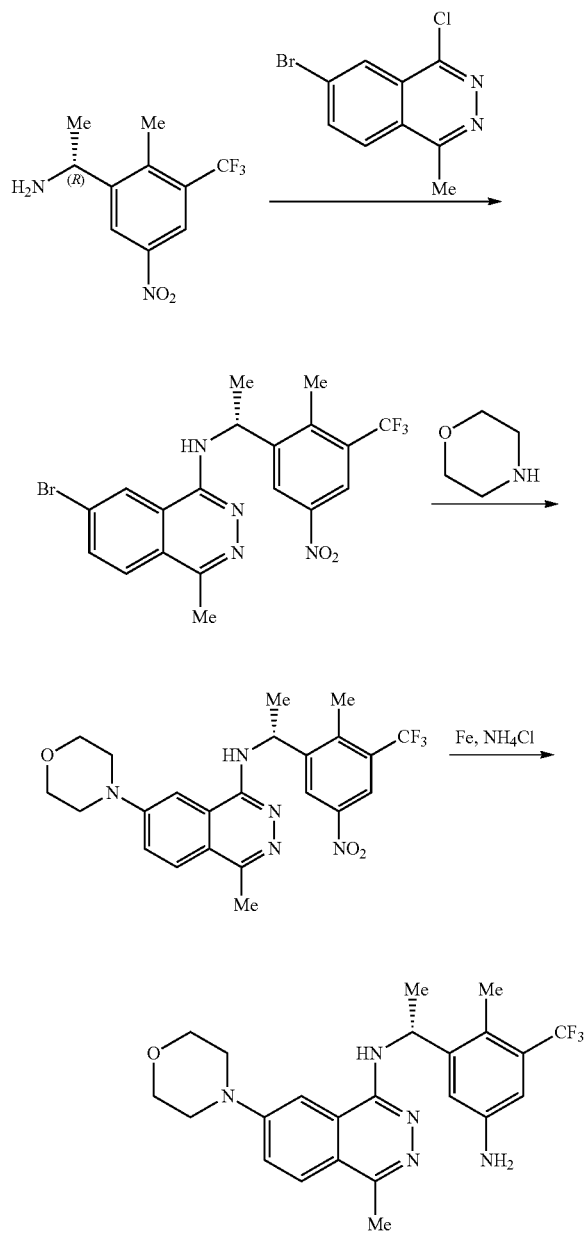

Step A: A solution of (R)-1-(2-methyl-5-nitro-3-(trifluoromethyl)phenyl)ethan-1-amine (250 mg, 1.01 mmol, 1.00 eq.) and 6-bromo-4-chloro-1-methylphthalazine (259 mg, 1.01 mmol, 1.00 eq.) in dimethyl sulfoxide (3.00 mL), N,N-diisopropylethylamine (390 mg, 3.02 mmol, 526 μL, 3.00 eq.) and potassium fluoride (175 mg, 3.02 mmol, 70.7 μL, 3.00 eq.) was stirred under a nitrogen atmosphere at 130° C. for 12 hours in a sealed tube. The reaction was cooled to 25° C. and the reaction was quenched with water (50.0 mL) and then extracted with ethyl acetate (30.0 mL×3). The combined organic phases were washed with brine (20.0 mL), dried over anhydrous sodium sulfate, filtered, and concentrated under reduced pressure to give a residue. The residue was purified by prep-TLC (SiO$_2$, petroleum ether/ethyl acetate=0/1) to give (R)-7-bromo-4-methyl-N-(1-(2-methyl-5-nitro-3-(trifluoromethyl)phenyl)ethyl)phthalazin-1-amine (200 mg, 426 μmol, 42.3% yield) as a yellow solid. LCMS [M+1]$^+$: 469.0.

$^1$H NMR (400 MHz, DMSO-d$_6$) δ=8.81 (s, 1H), 8.80 (s, 1H), 8.25 (s, 1H), 8.07-8.04 (m, 1H), 7.96-7.92 (m, 2H), 5.68-5.64 (m, 1H), 2.74 (s, 3H), 2.60 (s, 3H), 1.58 (d, J=6.8 Hz, 3H).

Step B: To a solution of morpholine (44.5 mg, 511 μmol, 45.0 μL, 3.00 eq.), (R)-7-bromo-4-methyl-N-(1-(2-methyl-5-nitro-3-(trifluoromethyl)phenyl)ethyl)phthalazin-1-amine (80.0 mg, 170 μmol, 1.00 eq) and cesium carbonate (166 mg, 511 μmol, 3.00 eq) in dioxane (2.00 mL) was added RuPhos (15.9 mg, 34.1 μmol, 0.20 eq) and Pd$_2$(dba)$_3$ (15.6 mg, 17.0 μmol, 0.10 eq) under a nitrogen atmosphere. The mixture was stirred at 110° C. for 1 hour, then cooled to 25° C., quenched with water (40.0 mL), and then extracted with ethyl acetate (20.0 mL×3). The combined organic phases were washed with brine (40.0 mL), dried over anhydrous sodium sulfate, filtered, and concentrated under reduced pressure to give a residue. The residue was purified by prep-TLC (SiO$_2$, dichloromethane:methanol=10/1) to give (R)-4-methyl-N-(1-(2-methyl-5-nitro-3-(trifluoromethyl)phenyl)ethyl)-7-morpholinophthalazin-1-amine (50.0 mg, 105 μmol, 61.6% yield) as a yellow solid.

$^1$H NMR (400 MHz, DMSO-d$_6$) δ=8.57 (d, J=2.4 Hz, 1H), 8.24 (d, J=2.4 Hz, 1H), 7.82 (d, J=8.8 Hz, 1H), 7.62-7.58 (m, 2H), 5.67-5.64 (m, 1H), 3.85-3.82 (m, 4H), 3.44-3.43 (m, 4H), 2.74 (s, 3H), 2.51 (s, 3H), 1.59 (d, J=7.2 Hz, 3H).

Step C: To a solution of (R)-4-methyl-N-(1-(2-methyl-5-nitro-3-(trifluoromethyl)phenyl)ethyl)-7-morpholinophthalazin-1-amine (45.0 mg, 94.6 μmol, 1.00 eq) and ammonium chloride (50.6 mg, 946 μmol, 10.0 eq) in ethanol (1.20 mL) and water (0.40 mL) was added iron powder (52.8 mg, 946.4 μmol, 10.0 eq) at 90° C. under a nitrogen atmosphere. The reaction mixture was stirred at 90° C. for 1 hour, then cooled to 25° C. The mixture was filtered and concentrated under reduced pressure to give a residue which was purified by prep-HPLC [column: Phenomenex luna C18 80×40 mm×3 um; mobile phase: phase A: water (0.04% HCl), phase B: acetonitrile; B %: 12%-38%] to give (R)—N-(1-(5-amino-2-methyl-3-(trifluoromethyl)phenyl)ethyl)-4-methyl-7-morpholinophthalazin-1-amine (20.0 mg, 44.8 μmol, 47.3% yield, hydrochloride salt) as a white solid. LCMS [M+1]$^+$: 446.1.

$^1$H NMR (400 MHz, DMSO-d$_6$) δ=14.85 (s, 1H), 8.62 (s, 1H), 8.16 (d, J=9.2 Hz, 1H), 7.93 (s, 1H), 7.77-7.74 (m, 1H), 7.23-7.22 (m, 1H), 7.08 (s, 1H), 5.37-5.34 (m, 1H), 3.83-3.81 (m, 4H), 3.70-3.68 (m, 4H), 2.73 (s, 3H), 2.43 (s, 3H), 1.59 (d, J=6.8 Hz, 3H).

SFC conditions: Chiralcel OD-3 3 μm, 0.46 cm id×5 cm L; Mobile phase: A for SFC CO$_2$ and B for MeOH (0.05% isopropylamine); Gradient: B in A from 10% to 40% in 3 minutes; Flowrate: 4.0 mL/min; Column temperature: 35° C.; Wavelength: 220 nm; System Back Pressure: 100 bar.

Following the teachings of the General Reaction Scheme VI, and the procedures described for the preparation of Examples 15-1-15-2, the following compound of Formula (I), Example 15-3 shown in Table 15 was prepared.

TABLE 15

| Ex. # | Structure | Spectral Data |
|---|---|---|
| 15-3 | 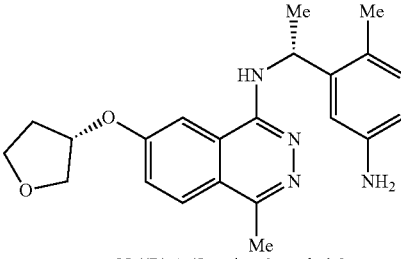<br>N-((R)-1-(5-amino-2-methyl-3-(trifluoromethyl)phenyl)ethyl)-4-methyl-7-(((S)-tetrahydrofuran-3-yl)oxy)phthalazin-1-amine<br>Hydrochloride salt | $^1$H NMR (400 MHz, CD$_3$OD) δ = 8.37-8.35 (m, 1H), 8.26 (d, J = 2.4 Hz, 1H), 7.79 (s, 1H), 7.75-7.72 (m, 1H), 7.47-7.46 (m, 1H), 5.58-5.54 (m, 2H), 4.15-4.12 (m, 1H), 4.05-4.03 (m, 2H), 3.99-3.96 (m, 1H), 2.85 (s, 3H), 2.66 (s, 3H), 2.52-2.48 (m, 1H), 2.25-2.25 (m, 1H), 1.73 (d, J = 7.2 Hz, 3H). LCMS [M + 1]$^+$: 447.1. |

Example 16-1

(R)—N-(1-(4-amino-6-(trifluoromethyl)pyridin-2-yl)ethyl)-4-methyl-7-morpholinophthalazin-1-amine

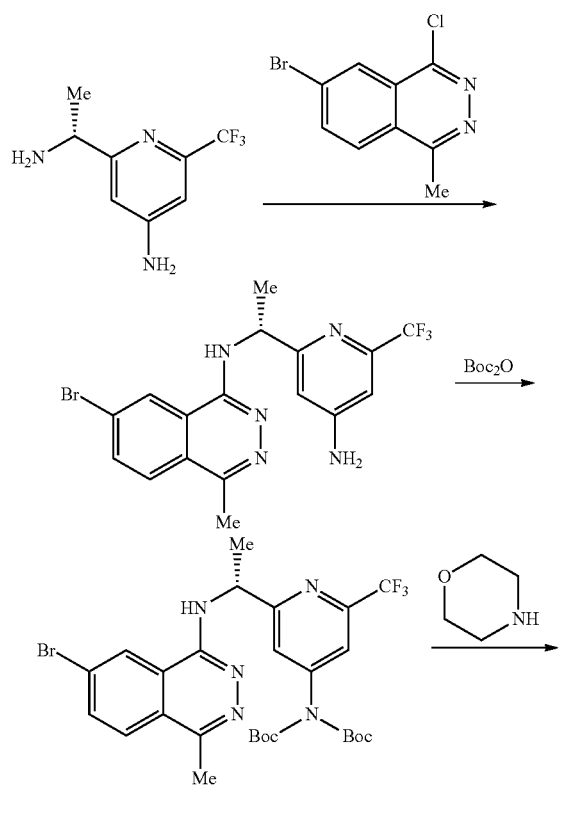

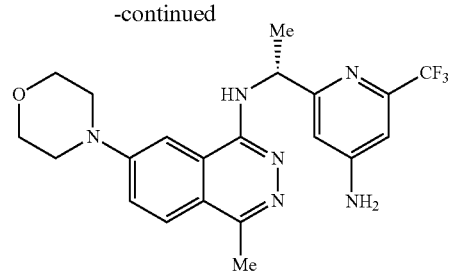

Step A: To a solution of (R)-2-(1-aminoethyl)-6-(trifluoromethyl)pyridin-4-amine (6.00 g, 24.8 mmol, 1.00 eq., hydrochloride), 6-bromo-4-chloro-1-methylphthalazine (7.03 g, 27.3 mmol, 1.10 eq.) and N,N-diisopropylethylamine (12.8 g, 99.3 mmol, 17.3 mL, 4.00 eq.) in DMSO (1.00 mL) was added cesium fluoride (5.66 g, 37.3 mmol, 1.37 mL, 1.50 eq.) and the mixture was stirred at 130° C. for 2 hour under a nitrogen atmosphere. The mixture was then cooled to 25° C., diluted with ethyl acetate (300 mL), washed with brine (200 mL×2), dried over anhydrous sodium sulfate, filtered, and concentrated under reduced pressure to give a residue, the residue was purified by silica gel chromatography (petroleum ether/ethyl acetate=10/1 to dichloromethane/methanol=10/1) to give (R)—N-(1-(4-amino-6-(trifluoromethyl)pyridin-2-yl)ethyl)-7-bromo-4-methylphthalazin-1-amine (9.00 g, 21.1 mmol, 85.0% yield) as a brown solid.

$^1$H NMR (400 MHz, CDCl$_3$) δ=8.11 (d, J=2.0 Hz, 1H), 7.89 (dd, J=1.6, 8.8 Hz, 1H), 7.78 (d, J=8.8 Hz, 1H), 6.94 (d, J=1.6 Hz, 1H), 6.87 (br s, 1H), 6.80 (d, J=2.0 Hz, 1H), 5.58-5.49 (m, 1H), 4.89 (br s, 2H), 2.77 (s, 3H), 1.68 (d, J=6.4 Hz, 3H).

Step B: To a solution of (R)—N-(1-(4-amino-6-(trifluoromethyl)pyridin-2-yl)ethyl)-7-bromo-4-methylphthalazin-1-amine (10.0 g, 23.5 mmol, 1.00 eq.) and DMAP (287 mg, 2.35 mmol, 0.10 eq.) in THF (100 mL) was added di-tert-butyl dicarbonate (10.5 g, 48.1 mmol, 11.1 mL, 2.05 eq.), the reaction mixture was stirred at 40° C. for 30 minutes, then concentrated under reduced pressure to give a residue. The residue was purified by silica gel chromatography (petroleum ether/ethyl acetate=10/1 to 1/1) to give tert-butyl (R)-(2-(1-((7-bromo-4-methylphthalazin-1-yl)amino)ethyl)-6-(trifluoromethyl)pyridin-4-yl)(tert-butoxycarbonyl)carbamate (7.45 g, 11.9 mmol, 50.7% yield) as a brown solid. LCMS [M+3]$^+$: 628.0.

Step C: To a solution of morpholine (4.09 g, 46.9 mmol, 4.13 mL, 4.00 eq.) and tert-butyl (R)-(2-(1-((7-bromo-4-methylphthalazin-1-yl)amino)ethyl)-6-(trifluoromethyl)pyridin-4-yl)(tert-butoxycarbonyl)carbamate (7.35 g, 11.7 mmol, 1.00 eq.) in dioxane (100 mL) was added Pd$_2$(dba)$_3$ (1.07 g, 1.17 mmol, 0.10 eq.), RuPhos (1.09 g, 2.35 mmol, 0.20 eq.) and cesium carbonate (11.5 g, 35.2 mmol, 3.00 eq.) under nitrogen, and the reaction mixture was stirred at 105° C. for 1 hour. The reaction mixture was cooled to 25° C., filtered, and the filter cake was washed with methanol (200 mL). The filtrate was concentrated under reduced pressure to give a residue which was purified by silica gel chromatography (petroleum ether/ethyl acetate=10/1 to DCM/methanol=10/1) to give tert-butyl (R)-(2-(1-((4-methyl-7-morpholinophthalazin-1-yl)amino)ethyl)-6-(trifluoromethyl)pyridin-4-yl)carbamate (4.75 g, 8.92 mmol, 76.0% yield) as a brown solid. LCMS [M+1]$^+$: 433.3.

Step D: To a solution of tert-butyl (R)-(2-(1-((4-methyl-7-morpholinophthalazin-1-yl)amino)ethyl)-6-(trifluoromethyl)pyridin-4-yl)carbamate (4.75 g, 8.92 mmol, 1.00 eq.) in acetonitrile (20.0 mL) was added HCl/dioxane (20.0 mL) at 0° C., the reaction was stirred at 0-25° C. for 3 hours. After this point, the pH of the mixture was adjusted to pH=7 by portionwise addition of solid sodium bicarbonate. The resulting mixture was concentrated under reduced pressure to give a residue, which was triturated with water (200 mL) then filtered. The filter cake was washed with water (30.0 mL×3), collected, and further triturated with acetonitrile (100 mL). The resulting suspension was filtered, and the filter cake was collected and dried under vacuum to give the product (R)—N-(1-(4-amino-6-(trifluoromethyl)pyridin-2-yl)ethyl)-4-methyl-7-morpholinophthalazin-1-amine (3.64 g, 7.99 mmol, 89.6% yield, 94.9% purity) as a off-white solid. LCMS [M+1]$^+$: 433.1.

$^1$H NMR (400 MHz, DMSO-d$_6$) δ=7.84 (d, J=9.2 Hz, 1H), 7.64 (d, J=2.0 Hz, 1H), 7.59 (dd, J=2.0, 8.8 Hz, 1H), 7.28 (d, J=6.8 Hz, 1H), 6.73 (d, J=2.0 Hz, 1H), 6.65 (d, J=1.6 Hz, 1H), 6.40 (s, 2H), 5.32-5.23 (m, 1H), 3.82 (t, J=4.8 Hz, 4H), 3.44-3.39 (m, 4H), 2.56 (s, 3H), 1.57 (d, J=7.2 Hz, 3H).

Example 16-2

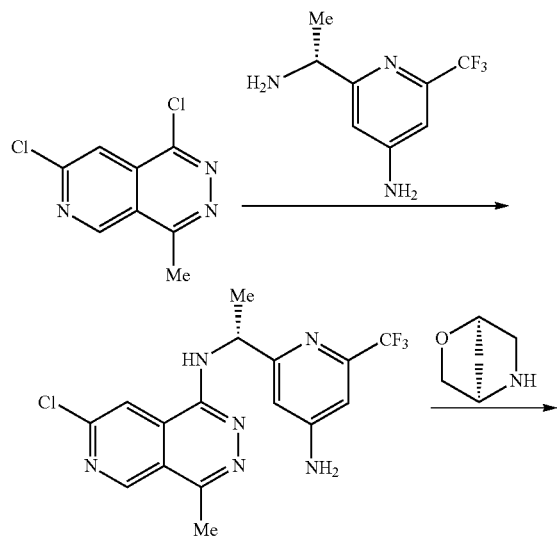

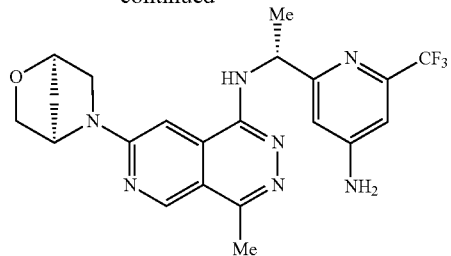

Step A: To a solution of 1,7-dichloro-4-methylpyrido[3,4-d]pyridazine (4.87 g, 22.8 mmol, 1.10 eq) and (R)-2-(1-aminoethyl)-6-(trifluoromethyl)pyridin-4-amine (5.00 g, 20.7 mmol, 1.00 eq., hydrochloride salt) in DMSO (40.0 mL) was added cesium fluoride (9.43 g, 62.1 mmol, 2.29 mL, 3.00 eq.) and N,N-diisopropylethylamine (8.02 g, 62.1 mmol, 10.8 mL, 3.00 eq.), and the mixture was stirred at 130° C. for 2 hours. After this time, the mixture was poured into water (50.0 mL), and extracted with ethyl acetate (150 mL×3). The combined organic phase were washed with brine (150 mL×3), dried over anhydrous sodium sulfate, filtered, and concentrated under reduced pressure. The residue was washed with petroleum ether:ethyl acetate=1:1 to give (R)—N-(1-(4-amino-6-(trifluoromethyl)pyridin-2-yl)ethyl)-7-chloro-4-methylpyrido[3,4-d]pyridazin-1-amine (5.00 g, 13.1 mmol, 63.1% yield) as a gray solid. LCMS [M+1]$^+$: 383.2.

Step B: To a solution of (R)—N-(1-(4-amino-6-(trifluoromethyl)pyridin-2-yl)ethyl)-7-chloro-4-methylpyrido[3,4-d]pyridazin-1-amine (115 mg, 300 μmol, 1.00 eq) and (1R,4R)-2-oxa-5-azabicyclo[2.2.1]heptane (61.1 mg, 451 μmol, 1.50 eq., hydrochloride salt) in DMSO (0.20 mL) was added N,N-diisopropylethylamine (77.7 mg, 601 μmol, 105 μL, 2.00 eq.) and cesium fluoride (274 mg, 1.80 mmol, 66.5 μL, 6.00 eq), and the mixture was stirred at 130° C. for 2 hours. The mixture was diluted with water (10.0 mL) and extracted with ethyl acetate (10.0 mL×3), and the combined organic layers were washed with brine (20.0 mL×3), dried over sodium sulfate, filtered, and concentrated under reduced pressure. The residue was purified by prep-HPLC [column: 3_Phenomenex Luna C18 75×30 mm×3 μm; mobile phase: phase A: water (0.05% HCl), phase B: acetonitrile; B %: 14%-34%] to give N—((R)-1-(4-amino-6-(trifluoromethyl)pyridin-2-yl)ethyl)-7-((1R,4R)-2-oxa-5-azabicyclo[2.2.1]heptan-5-yl)-4-methylpyrido[3,4-d]pyridazin-1-amine (93.9 mg, 211 μmol, 70.2% yield) as a yellow solid. LCMS [M+1]$^+$: 446.2.

$^1$H NMR (400 MHz, DMSO-d$_6$) δ=15.19-14.58 (m, 1H), 9.29 (s, 1H), 8.92-8.62 (m, 1H), 8.12-7.37 (m, 1H), 6.83 (d, J=2.0 Hz, 1H), 6.71 (br s, 1H), 5.41-5.18 (m, 1H), 5.15-5.03 (m, 1H), 4.94-4.76 (m, 1H), 4.02-3.81 (m, 2H), 3.80-3.65 (m, 3H), 2.05 (br d, J=4.8 Hz, 2H), 1.65 (br d, J=6.4 Hz, 3H).

$^1$H NMR (400 MHz, CD$_3$OD) δ=9.29 (s, 1H), 7.80-7.22 (m, 1H), 7.12 (d, J=2.0 Hz, 1H), 7.05 (br s, 1H), 5.53 (br s, 1H), 5.21 (q, J=6.4 Hz, 1H), 5.17-4.97 (m, 1H), 4.11-3.83 (m, 2H), 3.82-3.55 (m, 2H), 2.85 (s, 3H), 2.24-2.05 (m, 2H), 1.80 (br d, J=6.8 Hz, 3H).

Following the teachings of the General Reaction Scheme III, and the procedure described for the preparation of Examples 16-1-16-2, the following compounds of Formula (I), Examples 16-3-16-14 shown in Table 16 were prepared.

TABLE 16

| Ex. # | Structure | Spectral Data |
|---|---|---|
| 16-3 | 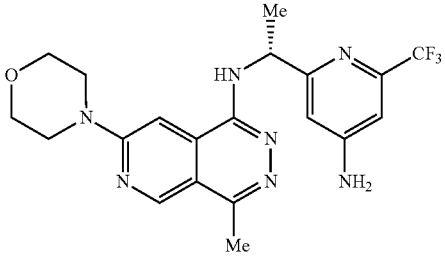 [SMILES: Cc1nnc(N[C@H](C)c2cc(N)cc(C(F)(F)F)n2)c2cc(N3CCOCC3)ncc12]<br>(R)-N-(1-(4-amino-6-(trifluoromethyl)pyridin-2-yl)ethyl)-4-methyl-7-morpholinopyrido[3,4-d]pyridazin-1-amine | $^1$H NMR (400 MHz, CD$_3$OD) δ 9.03 (s, 1H), 7.27 (s, 1H), 6.79-6.72 (m, 2H), 5.29 (q, J = 6.8 Hz, 1H), 3.86-3.79 (m, 4H), 3.75-3.70 (m, 4H), 1.63 (d, J = 6.8 Hz, 3H). LCMS [M + 1]$^+$: 434.2. |
| 16-4 | 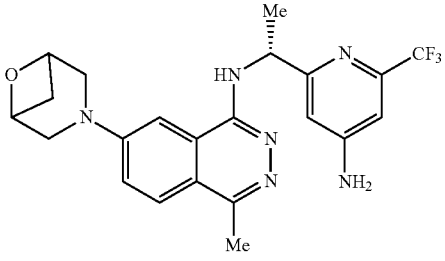 [SMILES: Cc1nnc(N[C@H](C)c2cc(N)cc(C(F)(F)F)n2)c2cc(N3CC4CC(C3)O4)ccc12]<br>N-((R)-1-(4-amino-6-(trifluoromethyl)pyridin-2-yl)ethyl)-7-(6-oxa-3-azabicyclo[3.1.1]heptan-3-yl)-4-methylphthalazin-1-amine | $^1$H NMR (400 MHz, CD$_3$OD) δ = 7.97 (d, J = 9.2 Hz, 1H), 7.48 (dd, J = 2.4, 9.2 Hz, 1H), 7.30 (d, J = 2.4 Hz, 1H), 6.78 (q, J = 2.0 Hz, 2H), 5.34 (q, J = 6.8 Hz, 1H), 4.90-4.87 (m, 2H), 3.87-3.78 (m, 2H), 3.76-3.68 (m, 2H), 3.35 (s, 1H), 2.65 (s, 3H), 2.06 (d, J = 9.2 Hz, 1H), 1.64 (d, J = 6.8 Hz, 3H). LCMS [M + 1] $^+$: 445.2. |
| 16-5 | 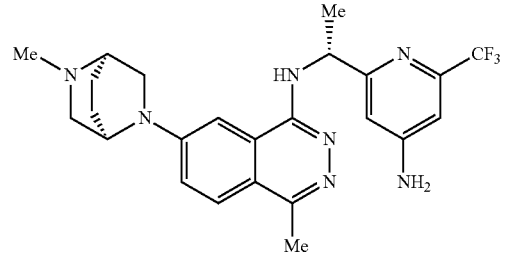 [SMILES: Cc1nnc(N[C@H](C)c2cc(N)cc(C(F)(F)F)n2)c2cc(N3C[C@H]4CC[C@@H]3CN4C)ccc12]<br>N-((R)-1-(4-amino-6-(trifluoromethyl)pyridin-2-yl)ethyl)-4-methyl-7-((1R, 4R)-5-methyl-2,5-diazabicyclo[2.2.2]octan-2-yl)phthalazin-1-amine<br>Hydrochloride salt | $^1$H NMR (400 MHz, CD$_3$OD) δ = 8.30 (d, J = 9.2 Hz, 1H), 7.87 (br s, 1H), 7.66 (br d, J = 9.2 Hz, 1H), 7.25 (br s, 1H), 7.17 (s, 1H), 5.46-5.18 (m, 1H), 4.98-4.94 (m, 1H), 4.45-4.19 (m, 1H), 4.16-3.83 (m, 3H), 3.56-3.36 (m, 1H), 3.11 (s, 3H), 2.85 (s, 3H), 2.62-2.38 (m, 1H), 2.36-2.04 (m, 3H), 1.87 (br d, J = 7.2 Hz, 3H). LCMS [M + 1] $^+$: 472.2. |
| 16-6 | 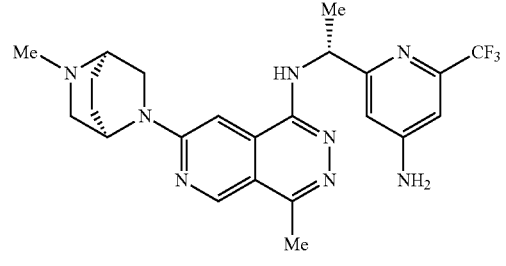 [SMILES: Cc1nnc(N[C@H](C)c2cc(N)cc(C(F)(F)F)n2)c2cc(N3C[C@H]4CC[C@@H]3CN4C)ncc12]<br>N-((R)-1-(4-amino-6-(trifluoromethyl)pyridin-2-yl)ethyl)-4-methyl-7-((1R, 4R)-5-methyl-2,5-diazabicyclo[2.2.2]octan-2-yl)pyrido[3,4-d]pyridazin-1-amine<br>Hydrochloride salt | $^1$H NMR (400 MHz, CD$_3$OD) δ = 9.37 (s, 1H), 8.18-7.44 (m, 1H), 7.31-7.23 (m, 1H), 7.19 (d, J = 2.0 Hz, 1H), 5.69-5.39 (m, 1H), 5.29 (br dd, J = 5.2, 6.8 Hz, 1H), 4.36 (br d, J = 13.6 Hz, 1H), 4.06 (br d, J = 11.6 Hz, 3H), 3.53-3.36 (m, 1H), 3.11 (s, 3H), 2.89 (s, 3H), 2.61-2.38 (m, 1H), 2.06-2.30 (m, 3H), 1.87 (br dd, J = 2.4, 6.8 Hz, 3H). LCMS [M + 1] $^+$: 473.2. |

TABLE 16-continued

| Ex. # | Structure | Spectral Data |
|---|---|---|
| 16-7 | 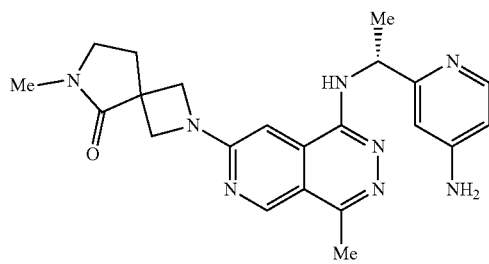<br>(R)-2-(1-((1-(4-amino-6-(trifluoromethyl)pyridin-2-yl)ethyl)amino)-4-methylpyrido[3,4-d]pyridazin-7-yl)-6-methyl-2,6-diazaspiro[3.4]octan-5-one<br>Hydrochloride salt | $^1$H NMR (400 MHz, CD$_3$OD) δ = 9.22 (s, 1H), 7.34 (s, 1H), 7.09 (d, J = 2.0 Hz, 1H), 7.04 (br s, 1H), 5.20 (q, J = 7.2 Hz, 1H), 4.48 (dd, J = 3.6, 9.6 Hz, 2H), 4.30 (br t, J = 9.6 Hz, 2H), 3.49 (t, J = 6.8 Hz, 2H), 2.93 (s, 3H), 2.83 (s, 3H), 2.55 (t, J = 6.8 Hz, 2H), 1.78 (d, J = 6.8 Hz, 3H). LCMS [M + 1]$^+$: 487.2. |
| 16-8 | 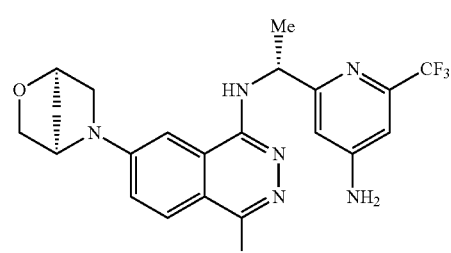<br>N-((R)-1-(4-amino-6-(trifluoromethyl)pyridin-2-yl)ethyl)-7-((1R, 4R)-2-oxa-5-azabicyclo[2.2.1]heptan-5-yl)-4-methylphthalazin-1-amine<br>Hydrochloride salt | $^1$H NMR (400 MHz, DMSO-d$_6$) δ 8.26 (s, 1H), 8.13 (d, J = 9.2 Hz, 1H), 7.62 (s, 1H), 7.45 (d, J = 9.1 Hz, 1H), 6.82 (s, 1H), 6.75 (s, 1H), 5.18-5.14 (m, 2H), 4.82 (s, 1H), 3.92 (d, J = 7.5 Hz, 1H), 3.75 (d, J = 7.6 Hz, 1H), 3.69 (d, J = 10.6 Hz, 1H), 3.46-3.39 (m, 1H), 2.75 (s, 3H), 2.04 (s, 2H), 1.67 (d, J = 7.0 Hz, 3H). LCMS [M + 1]$^+$: 445.2. |
| 16-9 | 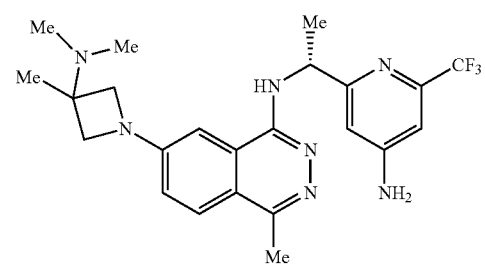 [SMILES: Cc1nnc(N[C@H](C)c2cc(N)cc(C(F)(F)F)n2)c2cc(N3CC(C)(N(C)C)C3)ccc12]<br>(R)-N-(1-(4-amino-6-(trifluoromethyl)pyridin-2-yl)ethyl)-7-(3-(dimethylamino)-3-methylazetidin-1-yl)-4-methylphthalazin-1-amine<br>Hydrochloride salt | $^1$H NMR (400 MHz, CD$_3$OD) δ = 8.26 (d, J = 9.1 Hz, 1H), 7.64 (d, J = 2.2 Hz, 1H), 7.33 (dd, J = 9.0, 2.2 Hz, 1H), 7.08 (q, J = 2.3 Hz, 2H), 5.25 (q, J = 7.0 Hz, 1H), 4.60 (dd, J = 14.5, 9.9 Hz, 2H), 4.34 (t, J = 10.2 Hz, 2H), 2.96 (s, 6H), 2.83 (s, 3H), 1.85 (s, 3H), 1.81 (d, J = 7.1 Hz, 3H). LCMS [M + 1]$^+$: 460.2. |
| 16-10 | 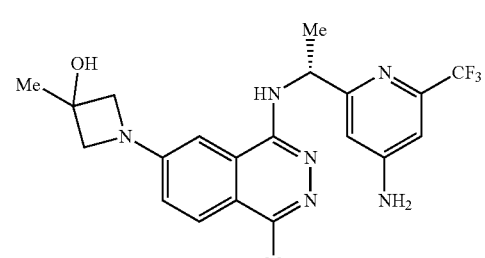<br>(R)-1-(4-((1-(4-amino-6-(trifluoromethyl)pyridin-2-yl)ethyl)amino)-1-methylphthalazin-6-yl)-3-methylazetidin-3-ol | $^1$H NMR (400 MHz, CD$_3$OD) δ 7.98 (d, J = 8.9 Hz, 1H), 7.15-7.07 (m, 2H), 6.83-6.74 (m, 2H), 5.25 (q, J = 6.9 Hz, 1H), 4.60 (s, 1H), 4.11 (dd, J = 8.5, 3.2 Hz, 2H), 4.02 (d, J = 8.5 Hz, 2H), 2.69 (s, 3H), 1.66 (d, J = 7.0 Hz, 3H), 1.63 (s, 3H). LCMS [M + 1]$^+$: 433.2. |

TABLE 16-continued

| Ex. # | Structure | Spectral Data |
|---|---|---|
| 16-11 | (R)-N-(1-(4-amino-6-(trifluoromethyl)pyridin-2-yl)ethyl)-7-(3-(dimethylamino)-3-methylazetidin-1-yl)-4-methylpyrido[3,4-d]pyridazin-1-amine dihydrochloride salt | $^1$H NMR (400 MHz, DMSO-$d_6$) δ = 15.06 (s, 1H), 12.63 (s, 1H), 9.31 (s, 1H), 9.01 (s, 1H), 7.78 (s, 1H), 6.90 (s, 1H), 6.81 (s, 1H), 6.76 (s, 1H), 5.17-5.09 (m, 1H), 4.65 (dd, J = 10.2, 6.0 Hz, 2H), 4.25 (s, 2H), 4.17 (d, J = 10.7 Hz, 2H), 2.81 (s, 3H), 2.71 (s, 6H), 1.70 (s, 3H), 1.66 (d, J = 7.0 Hz, 2H). LCMS [M + 1]$^+$: 461.2. |
| 16-12 | (R)-N-(1-(4-amino-6-(trifluoromethyl)pyridin-2-yl)ethyl)-4-methyl-7-(4-methylpiperazin-1-yl)pyrido[3,4-d]pyridazin-1-amine | $^1$H NMR (400 MHz, CD$_3$OD) δ = 9.02 (s, 1H), 7.29 (s, 1H), 6.79-6.71 (m, 2H), 5.29 (q, J = 6.9 Hz, 1H), 3.87-3.80 (m, 4H), 2.64 (s, 3H), 2.63-2.58 (m, 4H), 2.38 (s, 3H), 1.62 (d, J = 7.0 Hz, 3H). LCMS [M + 1]$^+$: 447.3. |
| 16-13 | N-((R)-1-(4-amino-6-(trifluoromethyl)pyridin-2-yl)ethyl)-7-(6-oxa-3-azabicyclo[3.1.1]heptan-3-yl)-4-methylpyrido[3,4-d]pyridazin-1-amine | $^1$H NMR (400 MHz, CD$_3$OD) δ = 9.08 (s, 1H), 7.16 (s, 1H), 6.82-6.75 (m, 2H), 5.34 (q, J = 7.0 Hz, 1H), 3.98 (d, J = 13.1 Hz, 2H), 3.83 (d, J = 12.6 Hz, 2H), 3.41-3.35 (m, 2H), 2.68 (s, 3H), 2.05 (d, J = 9.0 Hz, 1H), 1.66 (d, J = 7.0 Hz, 3H). LCMS [M + 1]$^+$: 446.2. |
| 16-14 | N-((R)-1-(3-amino-4-fluoro-5-(trifluoromethyl)phenyl)ethyl)-7-((1R,4R)-2-oxa-5-azabicyclo[2.2.1]heptan-5-yl)-4-methylphthalazin-1-amine | $^1$H NMR (400 MHz, DMSO-$d_6$) δ = 7.77 (d, J = 9.6 Hz, 1H), 7.26-7.24 (m, 2H), 7.08-7.06 (m, 2H), 6.85 (d, J = 6.0 Hz, 1H), 5.52 (s, 2H), 5.37-5.33 (m, 1H), 4.90 (s, 1H), 4.74 (s, 1H), 3.86 (d, J = 7.6 Hz, 1H), 3.71-3.60 (m, 2H), 3.22 (d, J = 9.6 Hz, 1H), 2.53 (s, 3H), 2.02-1.93 (m, 2H), 1.54 (d, J = 6.8 Hz, 3H). LCMS [M + 1]$^+$: 462.4. |

Example 17-1

(R)-2-methoxy-3-(1-((4-methyl-7-morpholinopyrido[3,4-d]pyridazin-1-yl)amino)ethyl)benzonitrile

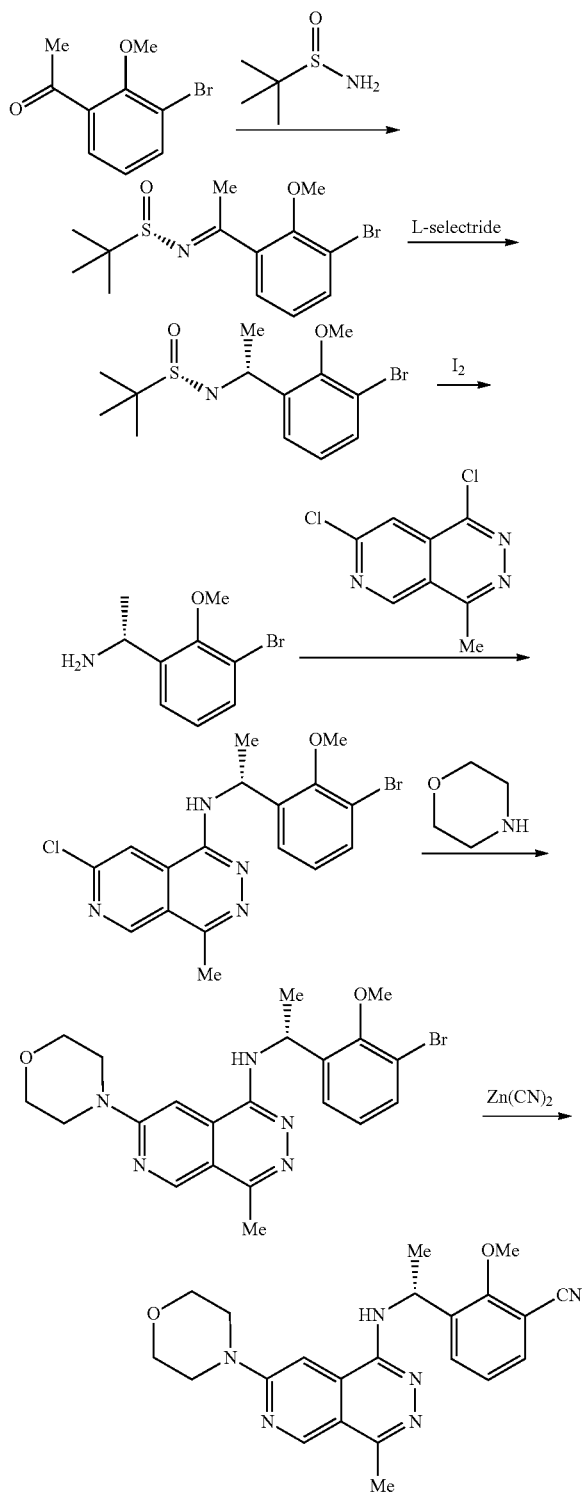

Step A: To a solution of 1-(3-bromo-2-methoxyphenyl)ethan-1-one (1.00 g, 4.37 mmol, 1.00 eq.) and (<S)-2-methylpropane-2-sulfinamide (688 mg, 5.68 mmol, 1.30 eq.) in THF (15.0 mL) was added titanium (IV) butoxide (1.99 g, 8.73 mmol, 1.81 mL, 2.00 eq.) and 1,2-dimethoxyethane (393 mg, 4.37 mmol, 454 µL, 1.00 eq.), and the mixture was stirred at 70° C. for 12 hours. The mixture was then diluted with ethyl acetate (50.0 mL) and water (5.00 mL), and filtered. The filtrate was concentrated under reduced pressure, and the residue was purified by column chromatography (SiO$_2$, petroleum ether/ethyl acetate=20/1 to 10/1) to give (S,E)-N-(1-(3-bromo-2-methoxyphenyl)ethylidene)-2-methylpropane-2-sulfinamide (1.25 g, 3.76 mmol, 86.2% yield) as yellow oil.

Step B: To a solution of (S,E)-N-(1-(3-bromo-2-methoxyphenyl)ethylidene)-2-methylpropane-2-sulfinamide (1.25 g, 3.76 mmol, 1.00 eq.) in THF (15.0 mL) was added L-selectride (1.0 M in THF, 5.64 mL, 1.50 eq.) dropwise at −60° C. After the addition was completed the mixture was warmed to 30° C. and stirred for 30 minutes, then diluted with water (5.00 mL) and extracted with ethyl acetate (30.0 mL×2). The combined organic phases were concentrated under reduced pressure, and the residue was purified by column chromatography (SiO$_2$, petroleum ether/ethyl acetate=5/1 to 3/1) to give (S)—N—((R)-1-(3-bromo-2-methoxyphenyl)ethyl)-2-methylpropane-2-sulfinamide (900 mg, 2.69 mmol, 71.6% yield) as yellow oil.

$^1$H NMR (400 MHz, CDCl$_3$) δ=7.52-7.44 (m, 1H), 7.34-7.29 (m, 1H), 7.01 (t, J=7.6 Hz, 1H), 5.05-4.95 (m, 1H), 3.92 (s, 3H), 1.50 (d, J=6.8 Hz, 3H), 1.21 (s, 9H).

Step C: To a solution of (S)—N—((R)-1-(3-bromo-2-methoxyphenyl)ethyl)-2-methylpropane-2-sulfinamide (900 mg, 2.69 mmol, 1.00 eq.) in THF (12.0 mL) and H$_2$O (3.00 mL) was added iodine (205 mg, 808 µmol, 163 µL, 0.30 eq.), and the mixture was stirred at 50° C. for 1 hour. The mixture was then diluted with ethyl acetate (30.0 mL), washed with sodium sulfite aqueous solution (20.0 mL), and further washed with brine (20.0 mL). The organic phase was dried and concentrated under reduced pressure, then purified by column chromatography (SiO$_2$, dichloromethane/methanol=1/0 to 40/1) to give (R)-1-(3-bromo-2-methoxyphenyl)ethan-1-amine (500 mg, 2.17 mmol, 80.7% yield) as yellow oil.

Step D: To a solution of 1,7-dichloro-4-methylpyrido[3,4-d]pyridazine (300 mg, 1.40 mmol, 1.00 eq.) in DMSO (5.00 mL) was added cesium fluoride (319 mg, 2.10 mmol, 77.5 µL, 1.50 eq.) and (R)-1-(3-bromo-2-methoxyphenyl)ethan-1-amine (322 mg, 1.40 mmol, 1.00 eq.), and the mixture was stirred at 130° C. for 30 minutes. The mixture was then diluted with ethyl acetate (50.0 mL) and washed with brine (30.0 mL×3). The separated organic phases were dried and concentrated under reduced pressure, and the residue was purified by column chromatography (SiO$_2$, petroleum ether/ethyl acetate=5/1 to 4/1) to give (R)—N-(1-(3-bromo-2-methoxyphenyl)ethyl)-7-chloro-4-methylpyrido[3,4-d]pyridazin-1-amine (250 mg, 613 µmol, 43.8% yield) as a yellow solid.

Step E: To a solution of (R)—N-(1-(3-bromo-2-methoxyphenyl)ethyl)-7-chloro-4-methylpyrido[3,4-d]pyridazin-1-amine (200 mg, 491 µmol, 1.00 eq.) in DMSO (0.80 mL) was added cesium fluoride (112 mg, 736 µmol, 27.1 µL, 1.50 eq.) and morpholine (192 mg, 2.21 mmol, 194 µL, 4.50 eq.). The mixture was stirred at 130° C. for 30 minutes, then diluted with water (20.0 mL) and filtered. The precipitate was dried in vacuum to give (R)—N-(1-(3-bromo-2-methoxyphenyl)ethyl)-4-methyl-7-morpholinopyrido[3,4-d]pyridazin-1-amine (200 mg, 436 µmol, 89.0% yield) as a yellow solid. LCMS [M+1]$^+$: 460.1.

Step F: A mixture of (R)—N-(1-(3-bromo-2-methoxyphenyl)ethyl)-4-methyl-7-morpholinopyrido[3,4-d]pyridazin-1-amine (180 mg, 393 µmol, 1.00 eq.), zinc cyanide (92.2 mg, 785 µmol, 49.9 µL, 2.00 eq.), DPPF (43.5 mg, 78.5 µmol, 0.20 eq.), zinc dust (2.57 mg, 39.3 µmol, 0.10 eq.) and Pd$_2$(dba)$_3$ (36.0 mg, 39.3 µmol, 0.10 eq.) in N,N-dimethylacetamide (4.00 mL) was degassed and purged with nitrogen (3 times), and the mixture was stirred at 120° C. for 6 hours under a nitrogen atmosphere. The reaction mixture was diluted with ethyl acetate (100 mL) and filtered. The filtrate was washed with brine (50.0 mL×3), dried, and concentrated under reduced pressure. The residue was purified by prep-HPLC [column: Phenomenex luna C18 150×25 mm×10 µm; mobile phase: phase A: water (0.225% formic acid), phase B: acetonitrile; B %: 11%-41%] to give (R)-2-methoxy-3-(1-((4-methyl-7-morpholinopyrido[3,4-d]pyridazin-1-yl)amino)ethyl)benzonitrile (93.0 mg, 226 µmol, 57.5% yield, 98.2% purity) as a yellow solid. LCMS [M+1]$^+$: 405.2.

$^1$H NMR (400 MHz, CD$_3$OD) δ=9.11 (s, 1H), 8.49 (s, 1H), 7.70-7.64 (m, 1H), 7.54-7.49 (m, 1H), 7.43 (s, 1H), 7.15 (t, J=7.6 Hz, 1H), 5.66-5.55 (m, 1H), 4.20 (s, 3H), 3.85 (s, 8H), 2.69 (s, 3H), 1.62 (d, J=6.8 Hz, 3H).

Example 17-2

3-((R)-1-((7-((R)-hexahydropyrazino[2,1-c][1,4]oxazin-8(1H)-yl)-4-methylpyrido[3,4-d]pyridazin-1-yl)amino)ethyl)-2-methoxybenzonitrile

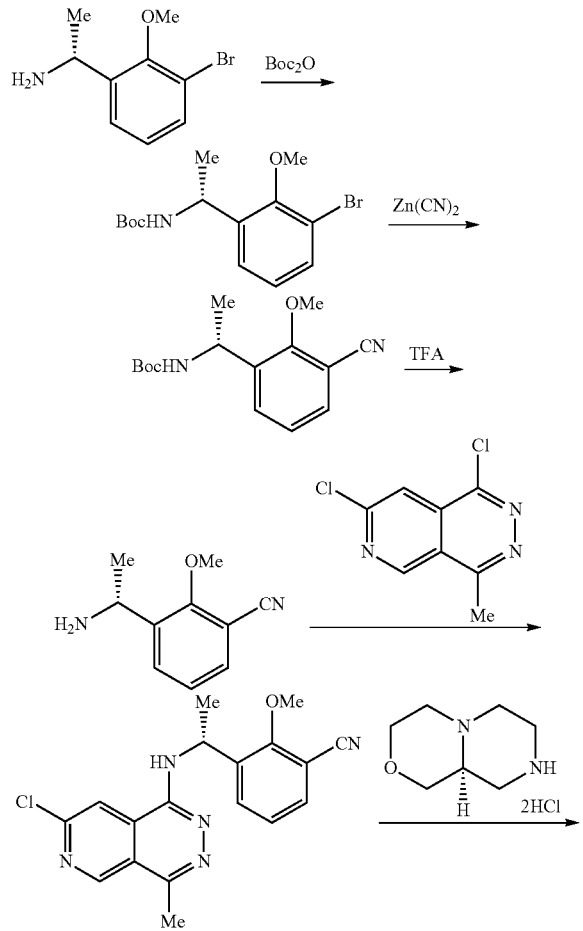

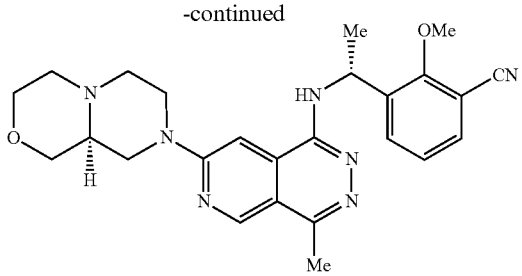

Step A: To a solution of (R)-1-(3-bromo-2-methoxyphenyl)ethan-1-amine (1.20 g, 5.22 mmol, 1.00 eq.) in THF (20.0 mL) was added Boc$_2$O (1.48 g, 6.78 mmol, 1.56 mL, 1.30 eq.), the mixture was stirred at 25° C. for 2 hours. The reaction mixture was concentrated under reduced pressure to give a residue. The residue was purified by column chromatography (SiO$_2$, petroleum ether/ethyl acetate=200/1 to 30/1) to give tert-butyl (R)-(1-(3-bromo-2-methoxyphenyl)ethyl)carbamate (1.50 g, 4.54 mmol, 87.1% yield) as light yellow oil.

$^1$H NMR (400 MHz, CDCl$_3$) δ=7.45 (dd, J=1.6, 8.0 Hz, 1H), 7.22 (d, J=6.8 Hz, 1H), 6.98 (t, J=7.6 Hz, 1H), 5.10-4.90 (m, 2H), 3.95 (s, 3H), 1.46-1.35 (m, 12H).

Step B: A mixture of tert-butyl (R)-(1-(3-bromo-2-methoxyphenyl)ethyl)carbamate (1.30 g, 3.94 mmol, 1.00 eq.), zinc cyanide (925 mg, 7.87 mmol, 500 µL, 2.00 eq.), zinc dust (25.7 mg, 394 µmol, 0.10 eq.), DPPF (437 mg, 787 µmol, 0.20 eq.) and Pd$_2$(dba)$_3$ (361 mg, 394 µmol, 0.10 eq.) in N,N-dimethylacetamide (15.0 mL) was degassed and purged with nitrogen (3 times), and the mixture was stirred at 130° C. for 5 hours under a nitrogen atmosphere. The mixture was then diluted with ethyl acetate (100 mL), filtered, and the filtrate was washed with brine (50.0 mL×3), dried and concentrated under reduced pressure. The residue was purified by column chromatography (SiO$_2$, petroleum ether/ethyl acetate=50/1 to 20/1) to give tert-butyl (R)-(1-(3-cyano-2-methoxyphenyl)ethyl)carbamate (0.90 g, 3.26 mmol, 82.7% yield) as yellow oil.

$^1$H NMR (400 MHz, CDCl$_3$) δ=7.50 (d, J=8.0 Hz, 2H), 7.14 (t, J=7.6 Hz, 1H), 5.09-4.91 (m, 2H), 4.15 (s, 3H), 1.54-1.32 (m, 12H).

Step C: To a solution of tert-butyl (R)-(1-(3-cyano-2-methoxyphenyl)ethyl)carbamate (0.90 g, 3.26 mmol, 1.00 eq.) in DCM (2.00 mL) was added TFA (6.93 g, 60.8 mmol, 4.50 mL, 18.7 eq. and the mixture was stirred at 20° C. for 30 minutes. The mixture was then concentrated under reduced pressure and the pH was adjusted to pH=7 with saturated sodium bicarbonate aqueous solution. The resulting mixture was extracted with a 10:1 solution of dichloromethane/methanol (50.0 mL), and the organic phases were dried and concentrated to give (R)-3-(1-aminoethyl)-2-methoxybenzonitrile (600 mg, crude) as brown oil.

$^1$H NMR (400 MHz, CDCl$_3$) δ=7.66 (dd, J=1.2, 7.6 Hz, 1H), 7.53 (dd, J=1.2, 7.6 Hz, 1H), 7.17 (t, J=8.0 Hz, 1H), 4.52 (q, J=6.8 Hz, 1H), 4.13 (s, 3H), 1.46 (d, J=6.4 Hz, 3H).

Step D: To a solution of 1,7-dichloro-4-methylpyrido[3,4-d]pyridazine (300 mg, 1.40 mmol, 1.00 eq.) in DMSO (5.00 mL) was added cesium fluoride (319 mg, 2.10 mmol, 77.5 µL, 1.50 eq.) and (R)-3-(1-aminoethyl)-2-methoxybenzonitrile (247 mg, 1.40 mmol, 1.00 eq. and the mixture was stirred at 130° C. for 30 minutes. The reaction mixture was diluted with ethyl acetate (50.0 mL), washed with brine (20.0 mL×3), and the separated organic phase was dried and concentrated under reduced pressure. The residue was purified by prep-HPLC [column: Phenomenex luna C18 150×40 mm×15 um; mobile phase: phase A: water (0.1% TFA), phase B: acetonitrile; B %: 14%-44%] to give (R)-3-(1-((7-chloro-4-methylpyrido[3,4-d]pyridazin-1-yl)amino)ethyl)-2-methoxybenzonitrile (200 mg, 565 μmol, 40.3% yield) as a yellow solid. LCMS [M+1]⁺: 354.1.

Step E: A mixture of (R)-3-(1-((7-chloro-4-methylpyrido[3,4-d]pyridazin-1-yl)amino)ethyl)-2-methoxybenzonitrile (30.0 mg, 84.8 μmol, 1.00 eq.), (S)-octahydropyrazino[2,1-c][1,4]oxazine (27.4 mg, 127 μmol, 1.50 eq., dihydrochloride salt), NN-diisopropylethylamine (32.9 mg, 254 μmol, 44.3 μL, 3.00 eq.) and cesium fluoride (19.3 mg, 127 μmol, 4.69 μL, 1.50 eq.) in DMSO (0.40 mL) was stirred at 130° C. for 2 hour under a nitrogen atmosphere. The mixture was then diluted with ethyl acetate (30.0 mL), washed with brine (10.0 mL×3), and the separated organic phase were dried and concentrated under reduced pressure. The residue was purified by prep-HPLC [column: 3_Phenomenex Luna C18 75×30 mm×3 um; mobile phase: phase A: water (0.05% HCl), phase B: acetonitrile; B %: 10%-30%] to give 3-((R)-1-((7-((S)-hexahydropyrazino[2,1-c][1,4]oxazin-8(1H)-yl)-4-methylpyrido[3,4-d]pyridazin-1-yl)amino)ethyl)-2-methoxybenzonitrile (13.9 mg, 27.8 μmol, 32.8% yield, 99.3% purity, HCl salt) as a yellow solid. LCMS [M+1]⁺: 460.2.

¹H NMR (400 MHz, CD₃OD) δ=9.35 (s, 1H), 7.91 (s, 1H), 7.79 (br d, J=7.6 Hz, 1H), 7.65-7.53 (m, 1H), 7.21 (t, J=8.0 Hz, 1H), 5.66-5.54 (m, 1H), 5.25-5.05 (m, 2H), 4.29-4.14 (m, 5H), 4.08-3.97 (m, 1H), 3.86-3.62 (m, 4H), 3.58 (br d, J=11.2 Hz, 1H), 3.52-3.35 (m, 3H), 2.86 (s, 3H), 1.71 (d, J=6.8 Hz, 3H).

Following the teachings of the General Reaction Scheme III, and the procedure described for the preparation of Examples 17-1-17-2, the following compounds of Formula (I), Examples 17-3-17-4 shown in Table 17 were prepared.

Example 18-1

(R)-6-fluoro-4-methyl-N-(1-(2-methyl-3-(trifluoromethyl)phenyl)ethyl)-7-(piperazin-1-yl)phthalazin-1-amine

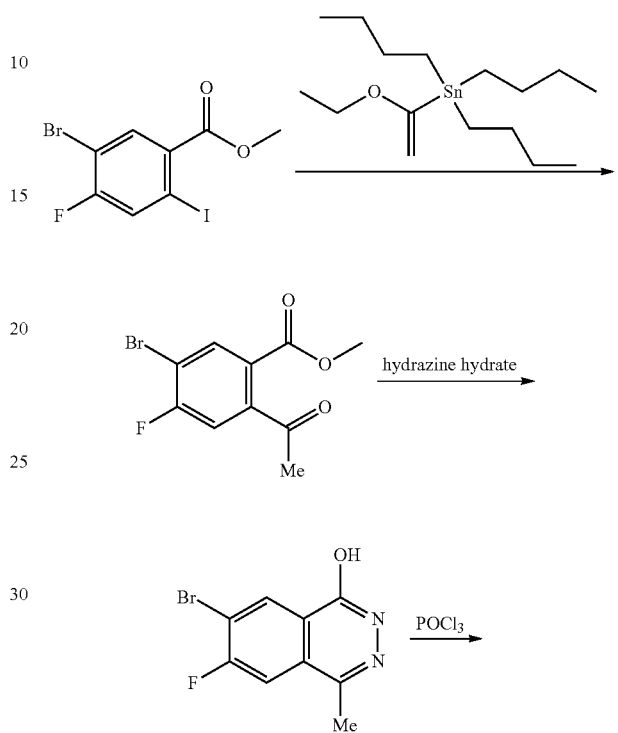

TABLE 17

| Ex. # | Structure | Spectral Data |
|---|---|---|
| 17-3 | 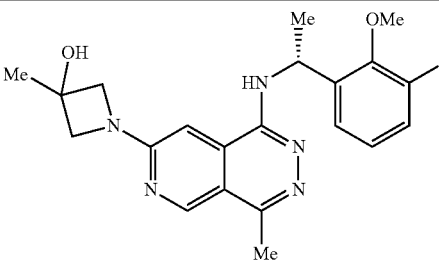<br>(R)-3-(1-((7-(3-hydroxy-3-methylazetidin-1-yl)-4-methylpyrido[3,4-d]pyridazin-1-yl)amino)ethyl)-2-methoxybenzonitrile | ¹H NMR (400 MHz, CD₃OD) δ = 8.96 (s, 1H), 7.67 (dd, J = 1.6, 8.0 Hz, 1H), 7.52 (dd, J = 1.6, 7.6 Hz, 1H), 7.15 (t, J = 8.0 Hz, 1H), 7.07 (s, 1H), 5.69 (q, J = 6.8 Hz, 1H), 4.24 (s, 3H), 4.17-4.05 (m, 4H), 2.63 (s, 3H), 1.66-1.59 (m, 6H). LCMS [M + 1]⁺: 405.2. |
| 17-4 | 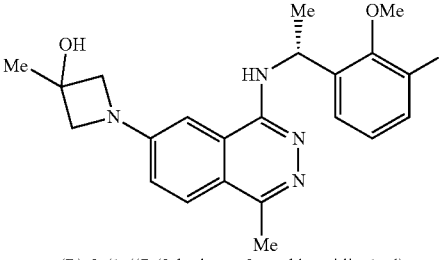<br>(R)-3-(1-((7-(3-hydroxy-3-methlazetidin-1-yl)-4-methylpyridazin-1-yl)amino)ethyl)-2-methoxybenzonitrile | ¹H NMR (400 MHz, CD₃OD) δ = 7.86 (br d, J = 9.2 Hz, 1H), 7.67 (dd, J = 1.6, 7.6 Hz, 1H), 7.48 (dd, J = 1.6, 7.6 Hz, 1H), 7.16 (s, 1H), 7.11 (t, J = 8.0 Hz, 1H), 7.08-7.03 (m, 1H), 5.70 (q, J = 6.8 Hz, 1H), 4.23 (s, 3H), 4.05 (br d, J = 8.0 Hz, 2H), 3.95 (br d, J = 8.4 Hz, 2H), 2.59 (s, 3H), 1.63-1.59 (m, 6H). LCMS [M + 1]⁺: 404.3. |

-continued

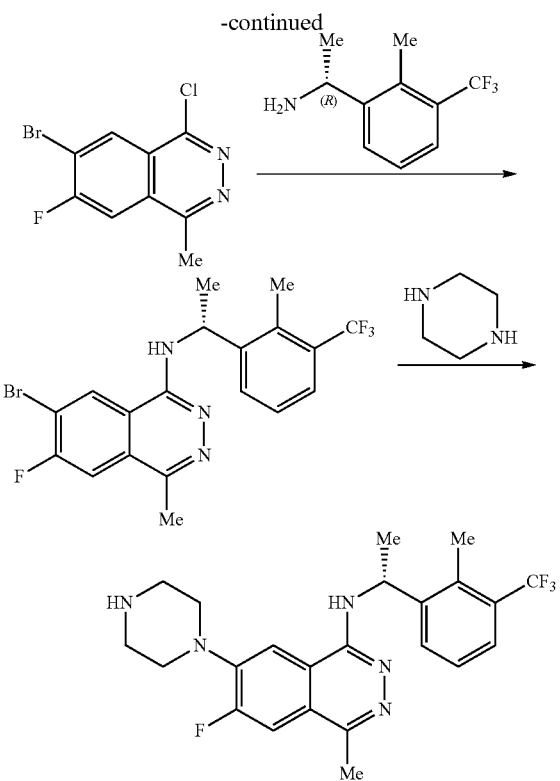

Step A: To a solution of methyl 5-bromo-4-fluoro-2-iodobenzoate (1.50 g, 4.18 mmol, 1.00 eq.) and tributyl(1-ethoxyvinyl)tin (1.52 g, 4.22 mmol, 1.42 mL, 1.01 eq.) in dioxane (20.0 mL) was added Pd(PPh$_3$)$_2$Cl$_2$ (60.0 mg, 0.08 mmol, 0.02 eq.) under a nitrogen atmosphere. The reaction mixture was stirred at 80° C. for 12 hours under a nitrogen atmosphere. The reaction mixture was cooled to 25° C., quenched by addition of saturated aqueous potassium fluoride (100 mL) and extracted with ethyl acetate (200 mL×3). The combined organic layers were washed with brine (200 mL×3), dried over sodium sulfate, filtered, and concentrated under reduced pressure to give compound methyl 5-bromo-2-(1-ethoxyvinyl)-4-fluorobenzoate (2.00 g, crude) as a brown oil which was used in next step directly.

To a solution of methyl 5-bromo-2-(1-ethoxyvinyl)-4-fluorobenzoate (2.00 g, crude) in THF (50.0 mL) was added hydrochloric acid aqueous solution (4.00 M, 10.0 mL, 6.06 eq). The mixture was stirred at 25° C. for 2 hours, then diluted with water (50.0 mL) and extracted with ethyl acetate (50.0 mL×3). The combined organic layers were washed with brine (20.0 mL), dried over sodium sulfate, filtered, and concentrated under reduced pressure to give a residue. The residue was purified by column chromatography (petroleum ether/ethyl acetate=10/1 to 1/1) to give compound methyl 2-acetyl-5-bromo-4-fluorobenzoate (700 mg, 2.54 mmol, 38.6% yield) as a yellow oil.

$^1$H NMR (400 MHz, CDCl$_3$) δ=8.14 (d, J=6.4 Hz, 1H), 7.12 (d, J=8.0 Hz, 1H), 3.91 (s, 3H), 2.52 (s, 3H).

Step B: To a solution of methyl 2-acetyl-5-bromo-4-fluorobenzoate (700 mg, 2.54 mmol, 1.00 eq.) in ethanol (10.0 mL) was added hydrazine hydrate (130 mg, 2.54 mmol, 98% purity, 1.00 eq.) dropwise. The reaction mixture was stirred at 95° C. for 30 minutes, then cooled to 25° C. and concentrated under reduced pressure to give 7-bromo-6-fluoro-4-methylphthalazin-1-ol (460 mg, 1.79 mmol, 70.3% yield) as a white solid.

$^1$H NMR (400 MHz, CDCl$_3$) δ=12.62 (s, 1H), 8.46 (d, J=7.2 Hz, 1H), 7.94 (d, J=9.6 Hz, 1H), 2.48 (s, 3H).

Step C: A mixture of 7-bromo-6-fluoro-4-methylphthalazin-1-ol (250 mg, 0.97 mmol, 1.00 eq.) in phosphorus (V) oxychloride (9.52 g, 62.1 mmol, 5.77 mL, 63.8 eq.) was stirred at 110° C. for 2 hours. The reaction mixture was cooled to 25° C. and concentrated under reduced pressure to give a residue. The residue was diluted with ethyl acetate (30.0 mL) and the pH was adjusted to pH=7 by slow addition of saturated sodium bicarbonate (aqueous solution). The organic phase was washed with brine (20.0 mL×2), dried over anhydrous sodium sulfate, filtered, and concentrated under reduced pressure. The crude product was purified by prep-TLC (petroleum ether/ethyl acetate=3/1) to give 6-bromo-4-chloro-7-fluoro-1-methylphthalazine (170 mg, 617 μmol, 63.5% yield) as a yellow solid. LCMS [M+3]$^+$: 276.7.

Step D: To a solution of 6-bromo-4-chloro-7-fluoro-1-methylphthalazine (170 mg, 0.62 mmol, 1.00 eq.) and (R)-1-(2-methyl-3-(trifluoromethyl)phenyl)ethan-1-amine (126 mg, 0.62 mmol, 1.00 eq.) in DMSO (5.00 mL) was added potassium fluoride (180 mg, 3.09 mmol, 5.00 eq.). The mixture was stirred at 130° C. for 12 hours then cooled to 25° C., quenched by addition water (10.0 mL), and extracted with ethyl acetate (20.0 mL×3). The combined organic layers were washed with brine (20.0 mL×3), dried over sodium sulfate, filtered, and concentrated under reduced pressure to give a residue. The residue was purified by prep-TLC (dichloromethane/methanol=20/1) to give compound (R)-7-bromo-6-fluoro-4-methyl-N-(1-(2-methyl-3-(trifluoromethyl)phenyl)ethyl)phthalazin-1-amine (80.0 mg, 0.18 mmol, 29.3% yield) as a yellow oil. LCMS [M+3]$^+$: 444.0.

Step E: To a solution of (R)-7-bromo-6-fluoro-4-methyl-N-(1-(2-methyl-3-(trifluoromethyl)phenyl)ethyl)phthalazin-1-amine (80.0 mg, 0.18 mmol, 1.00 eq.) and piperazine (32.0 mg, 0.36 mmol, 2.00 eq.) in dioxane (3.00 mL) were added Pd$_2$(dba)$_3$ (16.0 mg, 0.02 mmol, 0.10 eq.), RuPhos (16.0 mg, 0.04 mmol, 0.20 eq.) and cesium carbonate (300 mg, 0.90 mmol, 5.00 eq.) under a nitrogen atmosphere. The reaction mixture was stirred at 100° C. for 12 hours under a nitrogen atmosphere, then cooled to 25° C., quenched by addition water (10.0 mL), and extracted with ethyl acetate (20.0 mL×3). The combined organic layers were washed with brine (20.0 mL×3), dried over sodium sulfate, filtered, and concentrated under reduced pressure. The residue was purified by prep-TLC (dichloromethane/methanol=10/1) and then purified by prep-HPLC [column: Phenomenex luna C18 150×25 mm×10 um; mobile phase: phase A: water (0.225% formic acid), phase B: acetonitrile; B %: 3%-33%] to give (R)-6-fluoro-4-methyl-N-(1-(2-methyl-3-(trifluoromethyl)phenyl)ethyl)-7-(piperazin-1-yl)phthalazin-1-amine (8.97 mg, 0.02 mmol, 9.15% yield, 91.1% purity, formate salt) as a yellow solid. LCMS [M+1]$^+$: 448.2.

$^1$H NMR (400 MHz, DMSO-d$_6$) δ=8.30 (s, 1H), 7.86 (d, J=8.4 Hz, 1H), 7.76 (d, J=7.6 Hz, 1H), 7.68 (d, J=14.0 Hz, 1H), 7.61 (d, J=6.8 Hz, 1H), 7.52 (d, J=7.6 Hz, 1H), 7.30 (t, J=7.6 Hz, 1H), 5.70-5.65 (m, 1H), 3.21 (s, 4H), 3.00 (s, 4H), 2.57 (s, 3H), 2.52 (s, 3H), 1.55 (d, J=12 Hz, 3H).

SFC conditions: Column: Chiralcel OD-3 50×4.6 mm I.D., 3 um Mobile phase: Phase A: CO$_2$, Phase B: MeOH (0.05% diethylamine); Gradient elution: MeOH (0.05% diethylamine) in CO$_2$ from 5% to 40% Flow rate: 3 mL/min; Detector: PDA; Column Temp: 35 C; Back Pressure: 100 Bar.

Example 18-2

(R)-6-fluoro-4-methyl-N-(1-(2-methyl-3-(trifluoromethyl)phenyl)ethyl)-7-morpholinophthalazin-1-amine

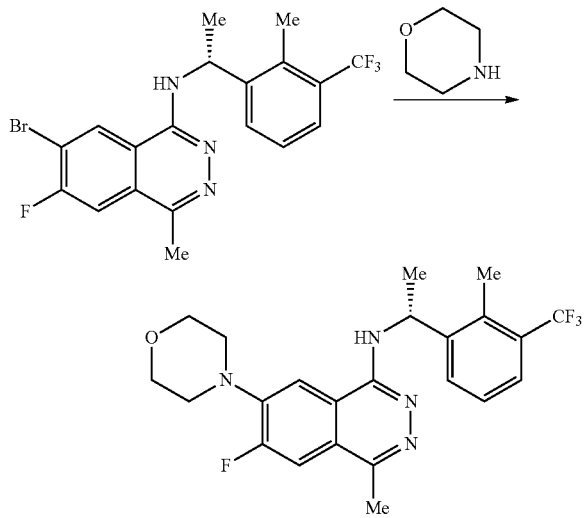

To a solution of (R)-7-bromo-6-fluoro-4-methyl-N-(1-(2-methyl-3-(trifluoromethyl)phenyl)ethyl)phthalazin-1-amine (60.0 mg, 136 μmol, 1.00 eq.) in dioxane (3.00 mL) were added morpholine (23.6 mg, 271 μmol, 23.9 μL, 2.00 eq.), RuPhos (12.7 mg, 27.1 μmol, 0.20 eq.), Pd$_2$(dba)$_3$ (12.4 mg, 13.6 μmol, 0.10 eq.) and cesium carbonate (88.4 mg, 271 μmol, 2.00 eq.) under a nitrogen atmosphere, and the mixture was at 110° C. for 2 hours. The reaction mixture was cooled to 25° C., poured into water (10.0 mL), and extracted with ethyl acetate (10.0 mL×3). The combined organic layers were washed with brine (10.0 mL), dried over sodium sulfate, filtered, and concentrated under reduced pressure. The residue was purified by prep-TLC (Silica gel plate, petroleum ether/ethyl acetate=2/1) and further purified by prep-HPLC [column: Phenomenex luna C18 150×25 mm×10 um; mobile phase: phase A: water(0.225% formic acid), phase B: acetonitrile, B %: 20%-50%] to give (R)-6-fluoro-4-methyl-N-(1-(2-methyl-3-(trifluoromethyl)phenyl)ethyl)-7-morpholinophthalazin-1-amine (4.92 mg, 10.7 μmol, 7.89% yield, 97.6% purity, formate salt) as an off-white solid. LCMS [M+1]$^+$: 449.0.

$^1$H NMR (400 MHz, DMSO-d$_6$) δ=8.27 (s, 1H), 7.87 (d, J=8.4 Hz, 1H), 7.76 (d, J=7.6 Hz, 1H), 7.71 (d, J=14.0 Hz, 1H), 7.59 (d, J=7.2 Hz, 1H), 7.52 (d, J=7.6 Hz, 1H), 7.32 (t, J=8.0 Hz, 1H), 5.76-5.61 (m, 1H), 3.86-3.81 (m, 4H), 3.27-3.23 (m, 4H), 2.58 (s, 3H), 2.54 (s, 3H), 1.56 (d, J=6.8 Hz, 3H).

SFC conditions: Chiralcel OD-3 50×4.6 mm I.D., 3 um Mobile phase: Phase A: CO$_2$, and Phase B: MeOH (0.05% diethylamine); Gradient elution: MeOH (0.05% diethylamine) in CO$_2$ from 5% to 40% Flow rate: 3 mL/min; Detector: PDA; Column Temp: 35 C; Back Pressure: 100 Bar.

Following the teachings of the General Reaction Scheme III, and the procedure described for the preparation of Examples 18-1-18-2, the following compounds of Formula (I), Examples 18-3-18-5 shown in Table 18 were prepared.

TABLE 18

| Ex. # | Structure | Spectral Data |
|---|---|---|
| 18-3 | (R)-3-(1-((6-fluoro-4-methyl-7-(4-methylpiperazin-1-yl)phthalazin-1-yl)amino)ethyl)-2-methylbenzonitrile | $^1$H NMR (400 MHz, DMSO-d$_6$) δ 7.82 (d, J = 8.5 Hz, 1H), 7.75 (d, J = 7.9 Hz, 1H), 7.67 (d, J = 13.8 Hz, 1H), 7.60 (dd, J = 7.7, 1.3 Hz, 1H), 7.56 (d, J = 6.7 Hz, 1H), 7.31 (t, J = 7.8 Hz, 1H), 5.57 (q, J = 6.9 Hz, 1H), 3.27-3.23 (m, 4H), 2.66 (s, 3H), 2.57-2.53 (m, 4H), 2.52 (s, 3H), 2.27 (s, 3H), 1.54 (d, J = 7.0 Hz, 3H). LCMS [M + 1]$^+$: 419.3. |
| 18-4 | (R)-3-(1-((6-fluoro-4-methyl-7-(piperazin-1-yl)phthalazin-1-yl)amino)ethyl)-2-methylbenzonitrile | $^1$H NMR (400 MHz, DMSO-d$_6$) δ 7.81 (d, J = 8.5 Hz, 1H), 7.75 (d, J = 7.9 Hz, 1H), 7.66 (d, J = 13.7 Hz, 1H), 7.62-7.54 (m, 2H), 7.31 (t, J = 7.8 Hz, 1H), 5.62-5.53 (m, 1H), 3.29 (s, 3H), 3.19-3.11 (m, 4H), 2.94-2.88 (m, 4H), 2.67 (s, 3H), 1.54 (d, J = 7.0 Hz, 3H). LCMS [M + 1]$^+$: 405.1. |

| Ex. # | Structure | Spectral Data |
|---|---|---|
| 18-5 | (R)-6-fluoro-4-methyl-N-(1-(2-methyl-3-(trifluoromethyl)phenyl)ethyl)-7-(4-methylpiperazin-1-yl)phthalazin-1-amine | $^1$H NMR (400 MHz, CD$_3$OD) δ 7.84 (d, J = 8.3 Hz, 1H), 7.72 (d, J = 7.8 Hz, 1H), 7.66 (d, J = 13.5 Hz, 1H), 7.49 (d, J = 7.8 Hz, 1H), 7.24 (t, J = 7.8 Hz, 1H), 5.74 (q, J = 6.9 Hz, 1H), 3.33-3.31 (m, 4H), 2.74-2.69 (m, 4H), 2.62 (s, 3H), 2.60 (s, 3H), 2.42 (s, 3H), 1.64 (d, J = 6.9 Hz, 3H). LCMS [M + 1]$^+$: 462.2. |

Example 19-1

(R)-3-(1-((7-(3-(dimethyl amino)-3-methyl azetidin-1-yl)-4-methyl-6-(trifluoromethyl)phthalazin-1-yl)amino)ethyl)-2-methylbenzonitrile

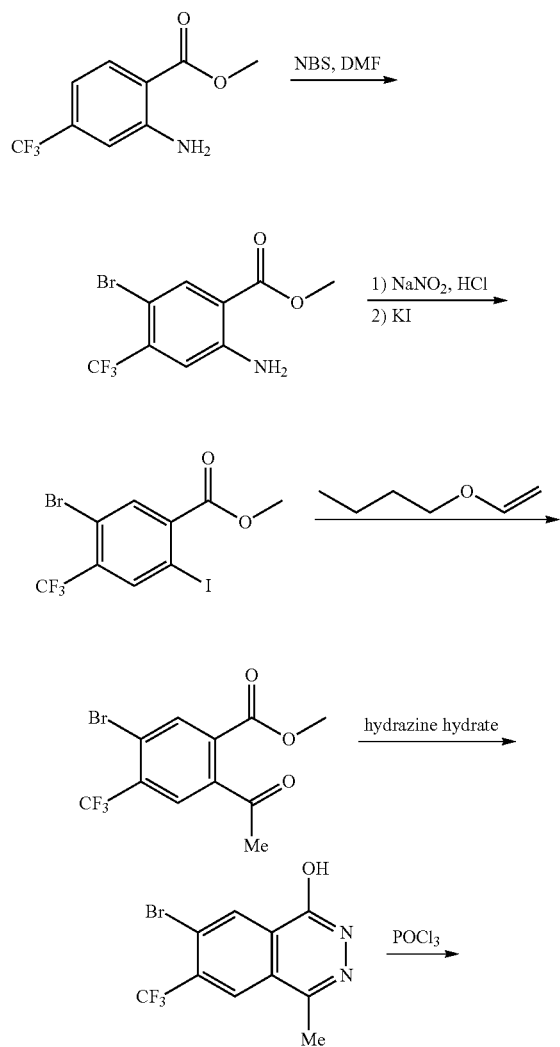

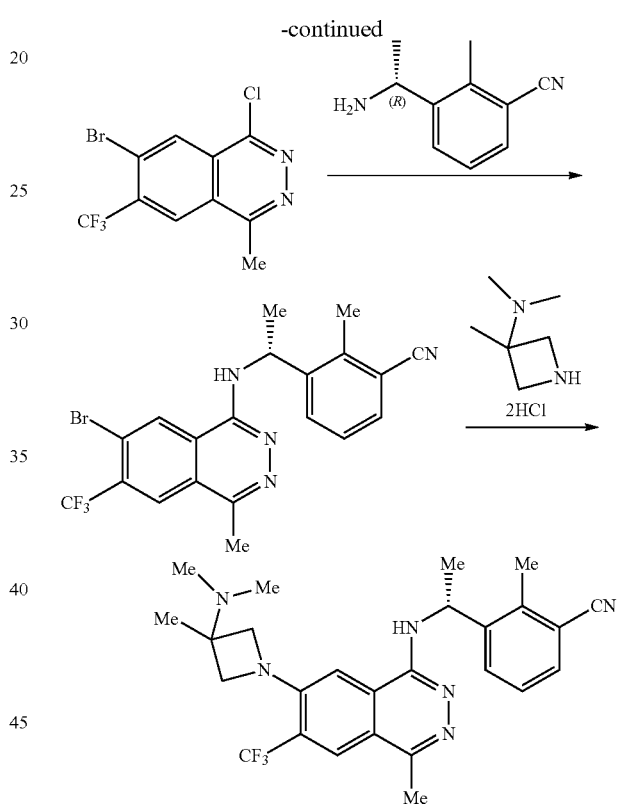

Step A: To a solution of methyl 2-amino-4-(trifluoromethyl)benzoate (3.00 g, 13.7 mmol, 1.00 eq.) in AA-dimethylformamide (50.0 mL) was added A-bromosuccinimide (2.68 g, 15.1 mmol, 1.10 eq.) and the mixture was stirred at 20° C. for 12 hours under a nitrogen atmosphere. The reaction mixture was poured into water (50.0 mL), and then extracted with ethyl acetate (50.0 mL×3), and the combined organic layers were washed with brine (40.0 mL), dried over sodium sulfate, filtered, and concentrated under reduced pressure. The residue was purified by column chromatography (silica gel, petroleum ether/ethyl acetate=50/1 to 10/1) to give methyl 2-amino-5-bromo-4-(trifluoromethyl)benzoate (3.30 g, 11.1 mmol, 80.9% yield) as yellow solid.

$^1$H NMR (400 MHz, DMSO-d$_6$): δ=8.06 (s, 1H), 6.93 (s, 1H), 5.86 (s, 2H), 3.84 (s, 3H).

Step B: To a solution of 2-amino-5-bromo-4-(trifluoromethyl)benzoate (3.30 g, 11.1 mmol, 1.00 eq.) in hydrochloric acid (4.00 M, 100 mL, 36.1 eq.) was added sodium nitrite (917 mg, 13.3 mmol, 1.20 eq.) at 0° C., and the mixture was stirred at 0° C. for 1 hour under a nitrogen atmosphere. Potassium iodide (3.68 g, 22.1 mmol, 2.00 eq.) was then added in portionwise to the reaction mixture at 0° C., and the mixture was slowly heated to 90° C. and stirred for 11 hours under a nitrogen atmosphere. The mixture was cooled 25° C., extracted with ethyl acetate (100 mL×3), and the combined organic layers were washed with brine (50.0 mL), dried over sodium sulfate, filtered, and concentrated under reduced pressure. The residue was purified by column chromatography (silica gel, petroleum ether/ethyl acetate=100/1 to 20/1) to give methyl 5-bromo-2-iodo-4-(trifluoromethyl)benzoate (4.10 g, 10.0 mmol, 90.5% yield) as a yellow solid.

$^1$H NMR (400 MHz, CDCl$_3$) δ=8.16 (s, 1H), 8.01 (s, 1H), 3.90 (s, 3H).

Step C: To a solution of methyl 5-bromo-2-iodo-4-(trifluoromethyl)benzoate (3.60 g, 8.80 mmol, 1.00 eq.) and 1-(vinyloxy)butane (1.06 g, 10.6 mmol, 1.36 mL, 1.20 eq.), N,N-dimethylformamide (10.0 mL) were added DPPF (244 mg, 440 μmol, 0.05 eq.), NN-diethylethanamine (2.67 g, 26.4 mmol, 3.68 mL, 3.00 eq.) and palladium (II) acetate (59.3 mg, 264 μmol, 0.03 eq.), and the mixture was stirred at 70° C. for 12 hours under a nitrogen atmosphere. The mixture was then cooled to 25° C., diluted with tetrahydrofuran (17.8 g, 247 mmol, 20.0 mL, 14.9 eq.) followed by hydrochloric acid (4.00 M, 20.0 mL, 4.82 eq.), and the mixture was stirred at 20° C. for 1 hour. The mixture was poured into water (30.0 mL), extracted with ethyl acetate (30.0 mL×3), and the combined organic layers were washed with brine (30.0 mL), dried over sodium sulfate, filtered, and concentrated under reduced pressure. The residue was purified by column chromatography (silica gel, petroleum ether/ethyl acetate=50/1 to 10/1) to give methyl 2-acetyl-5-bromo-4-(trifluoromethyl)benzoate (250 mg, 769 μmol, 8.74% yield) as a yellow solid.

$^1$H NMR (400 MHz, CDCl$_3$) δ=8.08 (s, 1H), 7.68 (s, 1H), 3.87 (s, 3H), 2.49 (s, 3H).

Step D: To a solution of methyl 2-acetyl-5-bromo-4-(trifluoromethyl)benzoate (250 mg, 769 μmol, 1.00 eq.) in ethanol (5.00 mL) was added hydrazine hydrate (46.2 mg, 923 μmol, 44.8 μL, 98%, 1.20 eq.) and the mixture was stirred at 95° C. for 030 minutes under a nitrogen atmosphere. The mixture was cooled to 25° C. and concentrated under reduced pressure to give 7-bromo-4-methyl-6-(trifluoromethyl)phthalazin-1-ol (170 mg, crude) as a yellow solid which was used without further purification. LCMS [M+3]$^+$: 309.1.

Step E: A solution of 7-bromo-4-methyl-6-(trifluoromethyl)phthalazin-1-ol (50.0 mg, 162.8 μmol, 1.00 eq.) in POCl$_3$ (4.95 g, 32.3 mmol, 3.00 mL, 198 eq.) was stirred at 110° C. for 1 hour under a nitrogen atmosphere. The mixture was cooled to 25° C., diluted with ethyl acetate (50.0 mL), and then quenched by addition saturated sodium bicarbonate (aqueous solution, 50.0 mL). The solution was extracted with ethyl acetate (50.0 mL×3), and the combined organic layers were washed with brine (40.0 mL), dried over sodium sulfate, filtered, and concentrated under reduced pressure to give a residue. The residue was purified by prep-TLC (silica gel plate, petroleum ether/ethyl acetate=1/1) to give 6-bromo-4-chloro-1-methyl-7-(trifluoromethyl)phthalazine (20.0 mg, 61.4 μmol, 37.7% yield) as a brown oil. LCMS [M+3]$^+$: 326.7.

Step F: To a solution of 7-bromo-4-chloro-1-methyl-7-(trifluoromethyl)phthalazine (120 mg, 369 μmol, 1.00 eq.) and (R)-3-(1-aminoethyl)-2-methylbenzonitrile (59.0 mg, 369 μmol, 1.00 eq.) in dimethyl sulfoxide (3.00 mL) was added potassium fluoride (107 mg, 1.84 mmol, 43.2 μL, 5.00 eq.), and the reaction was stirred at 130° C. for 12 hours under a nitrogen atmosphere. The reaction mixture was cooled to 25° C., poured into water (10.0 mL), and extracted with ethyl acetate (10.0 mL×3). The combined organic layers were washed with brine (10.0 mL), dried over sodium sulfate, filtered, and concentrated under reduced pressure. The residue was purified by prep-TLC (silica gel plate, dichloromethane/methyl alcohol=10/1) to give (R)-3-(1-((7-bromo-4-methyl-6-(trifluoromethyl)phthalazin-1-yl)amino)ethyl)-2-methylbenzonitrile (110 mg, 244 μmol, 66.4% yield) as a light yellow solid. LCMS [M+3]$^+$: 451.2.

Step G: To a solution of R)-3-(1-((7-bromo-4-methyl-6-(trifluoromethyl)phthalazin-1-yl)amino)ethyl)-2-methylbenzonitrile (30.0 mg, 0.07 mmol, 1.00 eq.) and N,N,3-trimethylazetidin-3-amine (20.0 mg, 0.13 mmol, 2.00 eq., HCl salt) in dioxane (2.00 mL) was added Pd$_2$(dba)$_3$ (6.00 mg, 0.10 eq.), RuPhos (6.00 mg, 0.20 eq.) and cesium carbonate (108 mg, 0.33 mmol, 5.00 eq.) was stirred at 100° C. for 12 hours under a nitrogen atmosphere. The reaction mixture was cooled to 25° C., quenched by addition of water (20.0 mL), and extracted with ethyl acetate (20.0 mL×3). The combined organic layers were washed with brine (20.0 mL×3), dried over sodium sulfate, filtered, and concentrated under reduced pressure. The residue was purified by prep-HPLC [column: Waters xbridge 150×25 mm×10 um; mobile phase: phase A: water(10 mM NH$_4$HCO$_3$), phase B: acetonitrile; B %: 38%-68%] to give (R)-3-(1-((7-(3-(dimethylamino)-3-methylazetidin-1-yl)-4-methyl-6-(trifluoromethyl)phthalazin-1-yl)amino)ethyl)-2-methylbenzonitrile (3.28 mg, 9.91% yield, 97.4% purity) as a yellow solid. LCMS [M+1]$^+$: 483.4.

$^1$H NMR (400 MHz, DMSO-d$_6$) δ=8.06 (s, 1H), 7.74 (d, J=8.0 Hz, 1H), 7.60 (d, J=7.2 Hz, 1H), 7.51 (d, J=6.8 Hz, 1H), 7.30 (t, J=7.6 Hz, 1H), 7.24 (s, 1H), 5.58-5.53 (m, 1H), 4.00-3.95 (m, 2H), 3.90-3.86 (m, 2H), 2.66 (s, 3H), 2.55 (s, 3H), 2.16 (s, 6H), 1.56 (d, J=7.2 Hz, 3H), 1.33 (s, 3H).

SFC conditions: Column: Chiralpak AS-3 50×4.6 mm I.D, 3 um Mobile phase: Phase A: CO$_2$, and Phase B: MeOH (0.05% diethylamine); Gradient elution: MeOH (0.05% diethylamine) in CO$_2$ from 5% to 40% Flow rate: 3 mL/min; Detector: PDA; Column Temp: 35C; Back Pressure: 100 Bar.

Example 19-2

(R)-2-methyl-3-(1-((4-methyl-7-morpholino-6-(trifluoromethyl)phthalazin-1-yl)amino)ethyl)benzonitrile

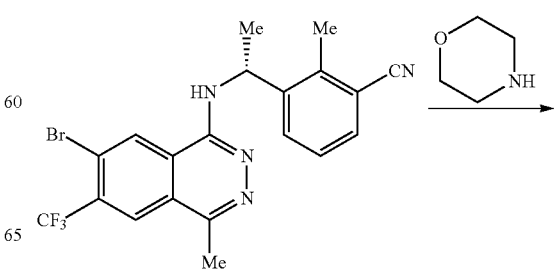

359
-continued

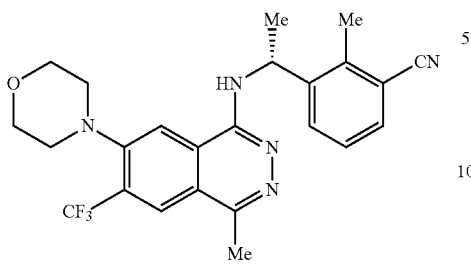

To a solution of (R)-3-(1-((7-bromo-4-methyl-6-(trifluoromethyl)phthalazin-1-yl)amino)ethyl)-2-methylbenzonitrile (40.0 mg, 89.0 μmol, 1.00 eq.) and morpholine (22.0 mg, 178 μmol, 22.2 μL, 2.00 eq.) in dioxane (3.00 mL) were added cesium carbonate (58.0 mg, 178 μmol, 2.00 eq.), Pd$_2$(dba)$_3$ (8.15 mg, 8.90 μmol, 0.10 eq.) and RuPhos (8.31 mg, 17.8 μmol, 0.20 eq.) under a nitrogen atmosphere, and the reaction mixture was stirred at 105° C. for 12 hours. The mixture was then cooled to 25° C., poured into water (30.0 mL), and extracted with ethyl acetate (30.0 mL×3). The combined organic layers were washed with water (20.0 mL), dried over sodium sulfate, filtered, and concentrated under reduced pressure. The residue was purified by prep-HPLC [column: Waters xbridge 150×25 mm 10 um; mobile phase: phase A: water 10 mM NH$_4$HCO$_3$), phase B: acetonitrile; B %: 37%-67%] to give (R)-2-methyl-3-(1-((4-methyl-7-morpholino-6-(trifluoromethyl)phthalazin-1-yl)amino)ethyl) benzonitrile (2.57 mg, 5.33 μmol, 5.99% yield, 94.5% purity) as a white solid. LCMS [M+1]$^+$: 456.3.
$^1$H NMR (400 MHz, DMSO-d$_6$) δ=8.58 (s, 1H), 8.22 (s, 1H), 7.83 (d, J=6.4 Hz, 1H), 7.75 (d, J=7.6 Hz, 1H), 7.62 (d, J=7.2 Hz, 1H), 7.33 (t, J=7.2 Hz, 1H), 5.63-5.54 (m, 1H), 3.83-3.78 (m, 4H), 3.10-3.05 (m, 4H), 2.68 (s, 3H), 2.66 (s, 3H), 1.58 (d, J=7.2 Hz, 3H).

SFC conditions: Column: Chiralpak AS-3 50×4.6 mm I.D., 3 um Mobile phase: Phase A: CO$_2$, and Phase B: MeOH (0.05% diethylamine); Gradient elution: MeOH (0.05% diethylamine) in CO$_2$ from 5% to 40% Flow rate: 3 mL/min; Detector: PDA; Column Temp: 35 C; Back Pressure: 100 Bar.

Following the teachings of the General Reaction Scheme IV, and the procedure described for the preparation of Examples 19-1-19-2, the following compound of Formula (I), Example 19-3 shown in Table 19 was prepared.

360
Example 20-1

1-(3-((R)-1-((7-((1R,4R)-2-oxa-5-azabicyclo[2.2.1]heptan-5-yl)-4-methylpyrido[3,4-<7]pyridazin-1-yl)amino)ethyl)-2-fluorophenyl)-1,1-difluoro-2-methylpropan-2-ol

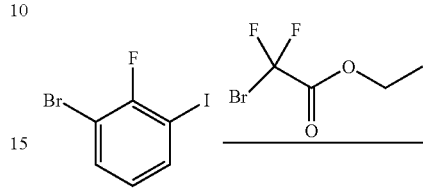

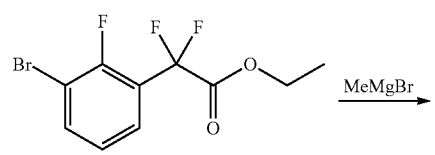

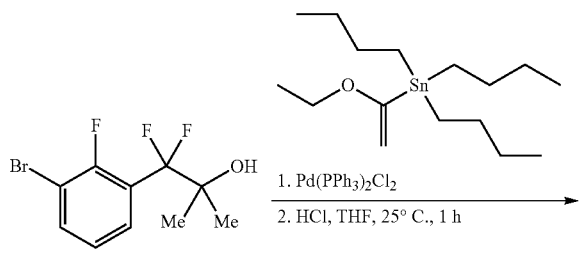

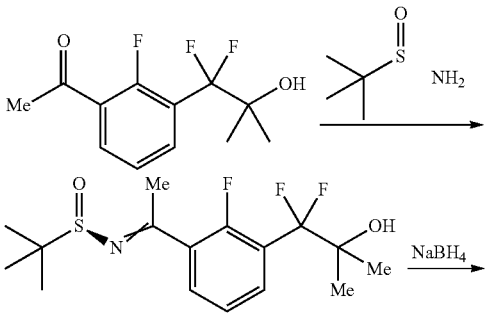

TABLE 19

| Ex. # | Structure | Spectral Data |
|---|---|---|
| 19-3 | ![structure](Me, OH, Me, Me, CN, HN, N, N, CF$_3$, Me) (R)-3-(1-((7-(3-hydroxy-3-methylazetidin-1-yl)-4-methyl-6-(trifluoromethyl)phthalazin-1-yl)amino)ethyl)-2-methylbenzonitrile | $^1$H NMR (400 MHz, DMSO-d$_6$) δ 8.06 (s, 1H), 7.74 (d, J = 7.8 Hz, 1H), 7.60 (d, J = 7.6 Hz, 1H), 7.54 (d, J = 6.8 Hz, 1H), 7.31 (t, J = 7.8 Hz, 1H), 7.23 (s, 1H), 5.69 (s, 1H), 5.60-5.52 (m, 1H), 4.11-4.00 (m, 4H), 3.30 (s, 5H), 2.66 (s, 3H), 2.55 (s, 3H), 2.33 (d, J = 1.9 Hz, 1H), 1.55 (d, J = 7.0 Hz, 3H), 1.51 (s, 3H). LCMS [M + 1]$^+$: 456.4. |

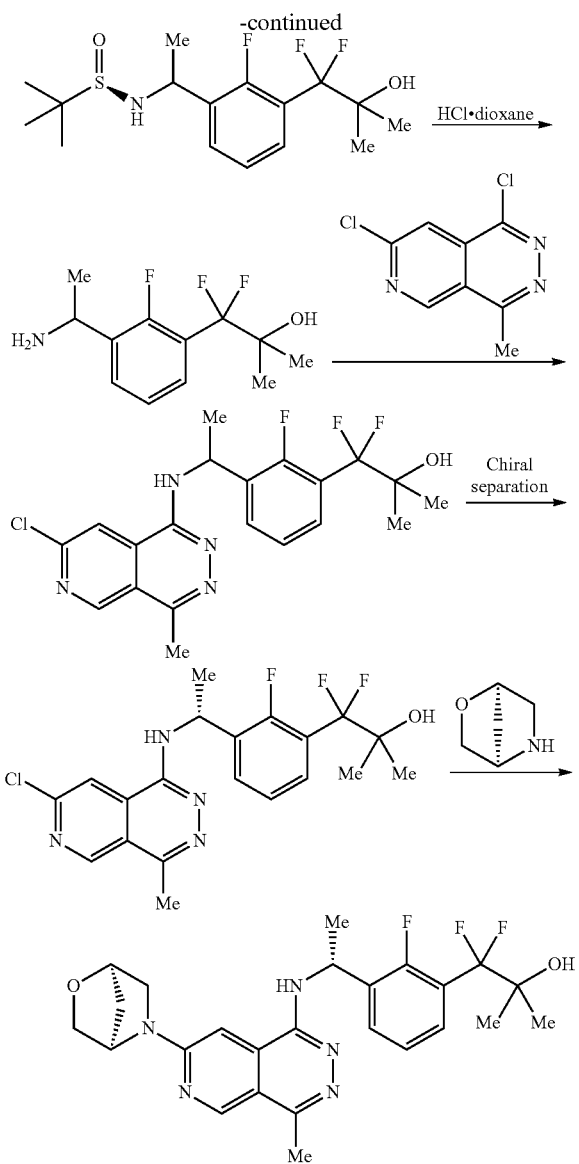

Step A: To a solution of 1-bromo-2-fluoro-3-iodobenzene (4.00 g, 13.3 mmol, 1.00 eq.) and ethyl 2-bromo-2,2-difluoroacetate (3.80 g, 18.6 mmol, 2.40 mL, 1.40 eq.) in dimethyl sulfoxide (50.0 mL) was added copper (2.53 g, 39.9 mmol, 3.00 eq.), and the mixture was stirred at 70° C. for 12 hours. The reaction mixture was cooled to 25° C., quenched by addition water (100 mL) and extracted with ethyl acetate (200 mL×3). The combined organic layers were washed with brine (100 mL×3), dried over sodium sulfate, filtered, and concentrated under reduced pressure. The residue was purified by column chromatography (silica gel, petroleum ether/ethyl acetate=10/1 to 5/1) to give ethyl 2-(3-bromo-2-fluorophenyl)-2,2-difluoroacetate (2.00 g, 6.73 mmol, 50.6% yield) as a yellow oil.

$^1$H NMR (400 MHz, CDCl$_3$) δ=7.72-7.69 (m, 1H), 7.61-7.57 (m, 1H), 7.15 (t, J=8.0 Hz, 1H), 4.39-4.34 (m, 2H), 1.35-1.32 (m, 3H).

Step B: To a solution of ethyl 2-(3-bromo-2-fluorophenyl)-2,2-difluoroacetate (2.00 g, 6.73 mmol, 1.00 eq.) in tetrahydrofuran (30.0 mL) was added methylmagnesium bromide solution (3.00 M, 6.75 mL, 3.00 eq.) at 0° C., and the mixture was stirred at 0° C. for 2 hours. The mixture was then warmed to 25° C., diluted with water (10.0 mL) and extracted with ethyl acetate (20.0 mL×3). The combined organic layers were washed with brine (20.0 mL×3), dried over sodium sulfate, filtered, and concentrated under reduced pressure. The residue was purified by column chromatography (silica gel, petroleum ether/ethyl acetate=10/1 to 3/1) to give 1-(3-bromo-2-fluorophenyl)-1,1-difluoro-2-methylpropan-2-ol (1.70 g, 6.01 mmol, 89.2% yield) as a yellow oil.

$^1$H NMR (400 MHz, CDCl$_3$) δ=7.67-7.65 (m, 1H), 7.43-7.39 (m, 1H), 7.12-7.09 (m, 1H), 1.35 (d, J=0.8 Hz, 6H).

Step C: To a solution of 1-(3-bromo-2-fluorophenyl)-1,1-difluoro-2-methylpropan-2-ol (1.50 g, 5.30 mmol, 1.00 eq.) and tributyl(1-ethoxyvinyl)tin (3.83 g, 10.6 mmol, 3.58 mL, 2.00 eq.) in 1,4-dioxane (15.0 mL) was added PdCl$_3$(PPh$_3$)$_2$ (380 mg, 0.53 mmol, 0.10 eq.), and the mixture was stirred at 80° C. for 12 hours under a nitrogen atmosphere. The reaction mixture was then cooled to 25° C., diluted with saturated potassium fluoride solution (100 mL) and extracted with ethyl acetate (200 mL×3). The combined organic layers were washed with brine (200 mL×3), dried over sodium sulfate, filtered, and concentrated under reduced pressure to give 1-(3-(1-ethoxyvinyl)-2-fluorophenyl)-1,1-difluoro-2-methylpropan-2-ol (2.00 g, crude) as a black oil. A solution of 1-(3-(1-ethoxyvinyl)-2-fluorophenyl)-1,1-difluoro-2-methylpropan-2-ol (2.00 g, 7.29 mmol, 1.00 eq.) in tetrahydrofuran (20.0 mL) was added hydrochloride (4.00 M, 10.0 mL), and the mixture was stirred at 25° C. for 1 hour. The reaction mixture was quenched by addition water (100 mL) and extracted with ethyl acetate (200 mL×3). The combined organic layers were washed with brine (200 mL×3), dried over sodium sulfate, filtered, and concentrated under reduced pressure. The residue was purified by column chromatography (silica gel, petroleum ether/ethyl acetate=10/1 to 1/1) to give 1-(3-(1,1-difluoro-2-hydroxy-2-methylpropyl)-2-fluorophenyl)ethan-1-one (1.50 g, 6.09 mmol, 83.5% yield) as a yellow oil.

$^1$H NMR (400 MHz, CDCl$_3$) δ=7.97-7.91 (m, 1H), 7.66-7.61 (m, 1H), 7.31-7.27 (m, 1H), 2.66 (d, J=4.0 Hz, 3H), 1.37 (d, J=1.2 Hz, 6H).

Step D: To a solution of 1-(3-(1,1-difluoro-2-hydroxy-2-methylpropyl)-2-fluorophenyl)ethan-1-one (1.50 g, 6.09 mmol, 1.00 eq.) and (R)-2-methylpropane-2-sulfinamide (2.22 g, 18.3 mmol, 3.00 eq.) in tetrahydrofuran (10.0 mL) was added titanium (IV) isopropoxide (3.46 g, 12.2 mmol, 3.60 mL, 2.00 eq.) and 1-methoxy-2-(2-methoxyethoxy)ethane (1.63 g, 12.2 mmol, 1.74 mL, 2.00 eq.), and the mixture was stirred at 70° C. for 6 hours under a nitrogen atmosphere. The mixture was then cooled to 25° C., diluted with water (50.0 mL) and extracted with ethyl acetate (50.0 mL×3). The combined organic layers were washed with brine (50.0 mL×3), dried over sodium sulfate, filtered, and concentrated under reduced pressure. The residue was purified by column chromatography (silica gel, petroleum ether/ethyl acetate=10/1 to 1/1) to give (R)—N-(1-(3-(1,1-difluoro-2-hydroxy-2-methylpropyl)-2-fluorophenyl)ethylidene)-2-methylpropane-2-sulfinamide (1.50 g, 4.29 mmol, 70.1% yield) as a yellow oil.

$^1$H NMR (400 MHz, CDCl$_3$) δ=7.73-7.68 (m, 1H), 7.60-7.52 (m, 1H), 7.26-7.22 (m, 1H), 1.37-1.35 (m, 3H), 1.32 (s, 6H), 1.24 (s, 9H)

Step E: To a solution of (R)—N-(1-(3-(1,1-difluoro-2-hydroxy-2-methyl propyl)-2-fluorophenyl)ethylidene)-2-methylpropane-2-sulfinamide (1.50 g, 4.29 mmol, 1.00 eq.) in tetrahydrofuran (10.0 mL) was added sodium boron hydrocarbon (488 mg, 12.9 mmol, 3.00 eq.) at 0° C. slowly, and the mixture was stirred at 0° C. for 12 hours. The mixture was then diluted with water (50.0 mL) and extracted with ethyl acetate (100 mL×3). The combined organic layers were washed with brine (50.0 mL×3), dried over sodium sulfate, filtered, and concentrated under reduced pressure. The residue was purified by column chromatography (silica gel, petroleum ether/ethyl acetate=10/1 to 1/1) to give (R)—N-(1-(3-(1,1-difluoro-2-hydroxy-2-methylpropyl)-2-fluorophenyl)ethyl)-2-methylpropane-2-sulfinamide (1.30 g, 3.70 mmol, 86.2% yield) as a yellow oil.

$^1$H NMR (400 MHz, CDCl$_3$)<δ=7.45-7.27 (m, 2H), 7.16-7.10 (m, 1H), 4.60-4.55 (m, 1H), 3.66-3.58 (m, 1H), 1.30-1.26 (m, 3H), 1.16 (s, 6H), 1.14-1.10 (m, 9H).

Step F: To a solution of (R)—N-(1-(3-(1,1-difluoro-2-hydroxy-2-methylpropyl)-2-fluorophenyl)ethyl)-2-methylpropane-2-sulfinamide (600 mg, 1.71 mmol, 1.00 eq.) in dichloromethane (5.00 mL) was added hydrochloride (4.00 M, 5.00 mL), and the mixture was stirred at 25° C. for 30 minutes. The mixture was then concentrated under reduced pressure to give 1-(3-(1-aminoethyl)-2-fluorophenyl)-1,1-difluoro-2-methylpropan-2-ol (400 mg, 1.41 mmol, 82.3% yield, hydrochloride salt) as a yellow oil.

Step G: To a solution of 1-(3-(1-aminoethyl)-2-fluorophenyl)-1,1-difluoro-2-methylpropan-2-ol (200 mg, 0.81 mmol, 1.00 eq.) and 1,7-dichloro-4-methylpyrido[3,4-d]pyridazine (175 mg, 0.81 mmol, 1.00 eq.) in dimethyl sulfoxide (2.00 mL) was added potassium fluoride (235 mg, 4.04 mmol, 5.00 eq.), and the mixture was stirred at 130° C. for 12 hours. The mixture was then cooled to 25° C., diluted with water (10.0 mL), and extracted with ethyl acetate (10.0 mL×3). The combined organic layers were washed with brine (10.0 mL), dried over sodium sulfate, filtered, and concentrated under reduced pressure. The residue was purified by prep-HPLC [column: Welch Xtimate C18 150×25 mm×5 um; mobile phase: phase A: water (0.05% HCl), phase B: acetonitrile; B %: 14%-44%] to give 1-(3-(1-((7-chloro-4-methylpyrido[3,4-d]pyridazin-1-yl)amino)ethyl)-2-fluorophenyl)-1,1-difluoro-2-methylpropan-2-ol (140 mg, 321 μmol, 39.7% yield, 97.5% purity) as a yellow solid. LCMS [M+1]$^+$: 425.0.

Step H: The solid 1-[3-[1-[(7-chloro-4-methyl-pyrido[3,4-d]pyridazin-1-yl)amino]ethyl]-2-fluoro-phenyl]-1,1-difluoro-2-methyl-propan-2-ol (140 mg, 330 μmol, 1.00 eq.) was separated into two enantiomers via SFC purification [column: REGIS(S,S)WHELK-O1 (250 mm×25 mm, 10 um); mobile phase A: 0.1% NH$_4$OH in IPA, phase B: CO$_2$; B %: 55%-55%] to give (R)-1-(3-(1-((7-chloro-4-methylpyrido[3,4-d]pyridazin-1-yl)amino)ethyl)-2-fluorophenyl)-1,1-difluoro-2-methylpropan-2-ol (first eluting isomer, 70.0 mg, 0.16 mmol, 50.0% yield) as a yellow solid.

SFC characterization: Column: (S,S)Whelk-O1 50×4.6 mm I.D., 1.8 um Mobile phase: Phase A: for CO$_2$, and Phase B: IPA (0.05% diethylamine); Gradient elution: 40% IPA (0.05% diethylamine) in CO$_2$Flow rate: 3 mL/min; Detector: PDA; Column Temp: 35° C.; Back Pressure: 100 Bar.

Step I: To a solution of (R)-1-(3-(1-((7-chloro-4-methylpyrido[3,4-d]pyridazin-1-yl)amino)ethyl)-2-fluorophenyl)-1,1-difluoro-2-methylpropan-2-ol (20.0 mg, 0.05 mmol, 1.00 eq.) and (1R,4R)-2-oxa-5-azabicyclo[2.2.1]heptane (12.8 mg, 0.09 mmol, 2.00 eq., hydrochloride salt) in 1,4-dioxane (1.50 mL) was added Pd$_2$(dba)$_3$ (4.31 mg, 4.71 μmol, 0.10 eq.), RuPhos (4.39 mg, 9.42 μmol, 0.20 eq.) and cesium carbonate (76.8 mg, 0.24 mmol, 5.00 eq.), and the mixture was stirred at 100° C. for 12 hours under a nitrogen atmosphere. The mixture was cooled to 25° C., diluted with water (10.0 mL) and extracted with ethyl acetate (20.0 mL×3). The combined organic layers were washed with brine (20.0 mL), dried over sodium sulfate, filtered, and concentrated under reduced pressure. The residue was purified by prep-HPLC [column: Waters xbridge 150×25 mm 10 um; mobile phase: phase A: water (10 mM NH$_4$HCO$_3$), phase B: acetonitrile; B %: 20%-50%] to give 1-(3-((R)-1-((7-((1R,4R)-2-oxa-5-azabicyclo[2.2.1]heptan-5-yl)-4-methylpyrido[3,4-d]pyridazin-1-yl)amino)ethyl)-2-fluorophenyl)-1,1-difluoro-2-methylpropan-2-ol (11.4 mg, 0.02 mmol, 48.6% yield, 97.6% purity) as a yellow solid. LCMS [M+1]$^+$: 488.3.

$^1$H NMR (400 MHz, DMSO-d) δ=8.97 (s, 1H), 7.51-7.46 (m, 1H), 7.36 (d, J=8.0 Hz, 1H), 7.30-7.26 (m, 1H), 7.20-7.14 (m, 2H), 5.72-5.63 (m, 1H), 5.34 (s, 1H), 5.08 (s, 1H), 4.78 (s, 1H), 3.88 (d, J=8.0 Hz, 1H), 3.72 (d, J=8.0 Hz, 1H), 3.62 (d, J=12.0 Hz, 1H), 3.40 (d, J=8.0 Hz, 1H), 2.55 (s, 3H), 2.02-1.93 (m, 2H), 1.58 (d, J=4.0 Hz, 3H), 1.22 (d, J=4.0 Hz, 6H).

SFC conditions: Column: Chiralpak AS-3 50×4.6 mm I.D., 3 um Mobile phase: Phase A: CO$_2$, and Phase B: MeOH (0.05% diethylamine); Gradient elution: MeOH (0.05% diethylamine) in CO$_2$ from 5% to 40% Flow rate: 3 mL/min; Detector: PDA; Column Temp: 35° C.; Back Pressure: 100 Bar.

Following the teachings of the General Reaction Scheme III, and the procedure described for the preparation of Example 20-1, the following compounds of Formula (I), Examples 20-2-20-3 shown in Table 20 were prepared.

TABLE 20

| Ex. # | Structure | Spectral Data |
|---|---|---|
| 20-2 | 1,1-difluoro-1-(2-fluoro-3-((R)-1-((7-((S)-hexahydropyrazino[2,1-c][1,4]oxazin-8(1H)-yl)-4-methylpyrido[3,4-d]pyridazin-1-yl)amino)ethyl)phenyl)-2-methylpropan-2-ol | $^1$H NMR (400 MHz, DMSO-d$_6$) δ 9.00 (s, 1H), 7.49 (t, J = 7.1 Hz, 1H), 7.46-7.41 (m, 2H), 7.29 (t, J = 7.2 Hz, 1H), 7.16 (t, J = 7.7 Hz, 1H), 5.71-5.63 (m, 1H), 5.35 (s, 1H), 4.46 (d, J = 12.6 Hz, 1H), 4.39 (d, J = 12.3 Hz, 1H), 3.87-3.77 (m, 2H), 3.64-3.54 (m, 1H), 3.28-3.21 (m, 1H), 3.14-3.04 (m, 1H), 2.93 (d, J = 11.4 Hz, 1H), 2.78-2.70 (m, 1H), 2.65-2.58 (m, 1H), 2.57 (s, 3H), 2.32-2.17 (m, 2H), 1.59 (d, J = 7.0 Hz, 3H), 1.24 (s, 4H), 1.23 (s, 3H). LCMS [M + 1]$^+$: 531.3. |

TABLE 20-continued

| Ex. # | Structure | Spectral Data |
|---|---|---|
| 20-3 | ![structure] 1-(3-((1R)-1-((7-(6-oxa-3-azabicyclo[3.1.1]heptan-3-yl)-4-methylpyrido[3,4-d]pyridazin-1-yl)amino)ethyl)-2-fluorophenyl)-1,1-difluoro-2-methylpropan-2-ol | $^1$H NMR (400 MHz, DMSO-$d_6$) δ 9.06 (s, 1H), 7.56-7.47 (m, 2H), 7.32-7.25 (m, 2H), 7.16 (t, J = 7.7 Hz, 1H), 5.75-5.67 (m, 1H), 5.35 (s, 1H), 4.82 (d, J = 6.4 Hz, 2H), 3.96-3.87 (m, 2H), 3.78-3.68 (m, 2H), 3.24-3.16 (m, 1H), 2.59 (s, 3H), 1.96 (d, J = 8.8 Hz, 1H), 1.59 (d, J = 7.0 Hz, 3H), 1.24 (s, 3H), 1.23 (s, 3H). LCMS [M + 1]$^+$: 488.4. |

Example 21-1

(R)-3-(1-((4-methyl-7-morpholinopyrido[3,4-d]pyridazin-1-yl)amino)ethyl)-5-(trifluoromethyl)phenol

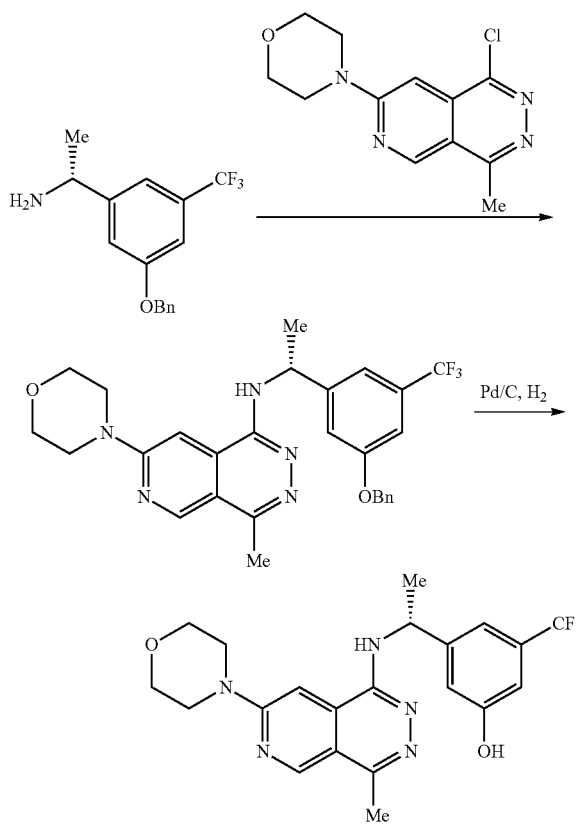

Step A: To a solution of (R)-1-(3-(benzyloxy)-5-(trifluoromethyl)phenyl)ethan-1-amine (120 mg, 359 μmol, 0.95 eq., HCl) and 4-(1-chloro-4-methylpyrido[3,4-d]pyridazin-7-yl)morpholine (100 mg, 378 μmol, 1.00 eq.) in dimethyl sulfoxide (3.00 mL) was added potassium fluoride (87.8 mg, 1.51 mmol, 35.4 μL, 4.00 eq.) under a nitrogen atmosphere, and the solution was stirred at 130° C. for 12 hours. The reaction mixture was diluted with water (15.0 mL), extracted with ethyl acetate (10.0 mL×3), washed with brine (5.00 mL×3), dried over anhydrous sodium sulfate, filtered, and concentrated under reduced pressure to give a residue. The residue was purified by prep-TLC (dichloromethane/methanol=10/1) to give (R)—N-(1-(3-(benzyloxy)-5-(trifluoromethyl)phenyl)ethyl)-4-methyl-7-morpholinopyrido[3,4-d]pyridazin-1-amine (65.0 mg, 121 μmol, 32.1% yield, 97.8% purity) as a yellow solid. LCMS [M+1]$^+$: 524.3.

A solution of (R)—N-(1-(3-(benzyloxy)-5-(trifluoromethyl)phenyl)ethyl)-4-methyl-7-morpholinopyrido[3,4-d]pyridazin-1-amine (65.0 mg, 124 μmol, 1.00 eq.), Pd/C (20.0 mg, 10% purity) and palladium hydroxide (20.0 mg) in methanol (5.00 mL) at 25° C. under a hydrogen atmosphere (15 Psi) at 20° C. for 30 minutes. The solution was filtered and concentrated under reduced pressure to give a residue. The residue was purified by prep-HPLC [(Phenomenex luna C18 150×25 mm×10 um; mobile phase: phase A: water (0.225% formic acid), phase B: MeCN; B %: 12%-42%)] to give (R)-3-(1-((4-methyl-7-morpholinopyrido[3,4-d]pyridazin-1-yl)amino)ethyl)-5-(trifluoromethyl)phenol (12.2 mg, 25.2 μmol, 20.3% yield, 99.4% purity, formate salt) as a yellow solid. LCMS [M+1]$^+$: 434.2.

$^1$H NMR (400 MHz, DMSO-$d_6$) δ=10.06-9.94 (m, 1H), 9.02 (s, 1H), 8.13 (s, 1H), 7.46 (d, J=0.8 Hz, 1H), 7.40 (s, 1H), 7.16 (s, 1H), 7.06 (s, 1H), 6.85 (s, 1H), 5.39 (m, 1H), 3.78-3.77 (m, 4H), 3.70-3.69 (m, 4H), 2.58 (s, 3H), 1.56 (d, J=6.8 Hz, 3H).

SFC conditions: "Column: Chiralcel OD-3 50×4.6 mm I.D., 3 um Mobile phase: Phase A for CO$_2$, and Phase B for methnol (0.05% DEA); gradient elution:methnol (0.05% DEA) in CO$_2$ from 5% to 40% flow rate: 3 mL/min; Detector: PDA; Column Temp: 35° C.; Back Pressure: 100 Bar".

Example 21-2

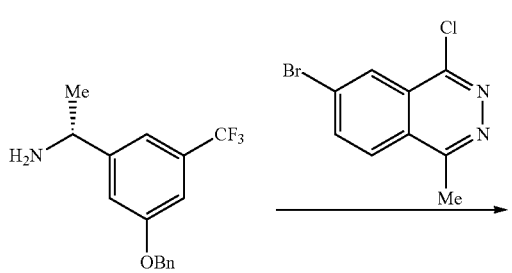

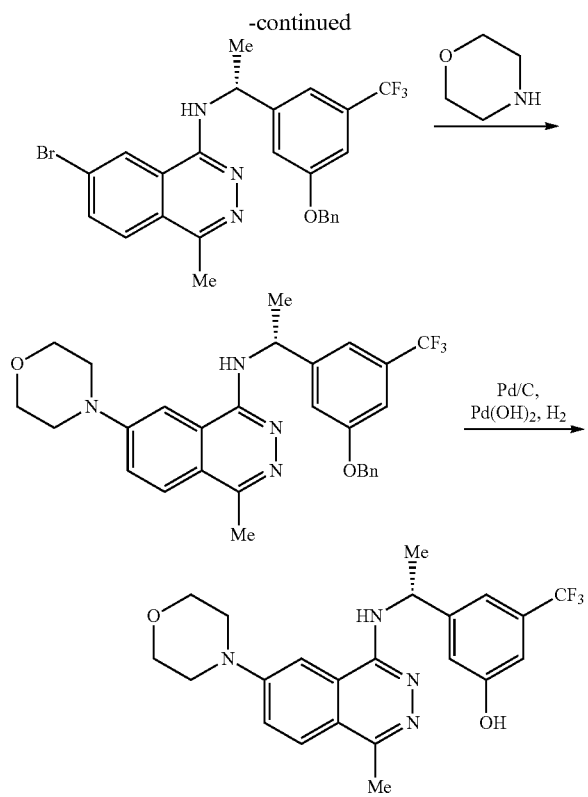

¹H NMR (400 MHz, DMSO-d₆) δ=7.98 (d, J=9.2 Hz, 1H), 7.83 (d, J=8.8 Hz, 1H), 7.70 (dd, J=2.8, 9.2 Hz, 1H), 7.61-7.57 (m, 2H), 7.35-7.29 (m, 5H), 7.17-7.13 (m, 2H), 5.50 (t, J=6.8 Hz, 1H), 5.14 (s, 2H), 3.85 (m, 4H), 3.44-3.39 (m, 4H), 2.55 (s, 3H), 1.59 (d, J=6.8 Hz, 3H).

Step C: To a solution of (R)—N-(1-(3-(benzyl oxy)-5-(trifluoromethyl)phenyl)ethyl)-4-methyl-7-morpholinophthalazin-1-amine (120 mg, 0.03 mmol, 1.00 eq.) in methanol (10.0 mL) were added Pd/C (80.0 mg, 0.03 mmol, 10% purity, 1.00 eq.) and palladium hydroxide (80.0 mg, 0.03 mmol, 1.00 eq.), then the reaction was stirred at 40° C. for 1 hour under a hydrogen atmosphere (15 psi). The reaction was filtered and concentrated under reduced pressure to give a residue. The residue was purified by prep-HPLC [(column: Waters Xbridge 150×25 mm 10 um; mobile phase: phase A: water (10 mM NH₄HCO₃), phase B: MeCN; B %: 28%-58%)] to give (R)-3-(1-((4-methyl-7-morpholinophthalazin-1-yl)amino)ethyl)-5-(trifluoromethyl)phenol (34.0 mg, 78.6 µmol, 34.2% yield) as a yellow solid. LCMS [M+1]⁺: 433.3.

¹H NMR (400 MHz, DMSO-d₆): δ=9.95 (s, 1H), 7.78-7.76 (m, 1H), 7.60-7.58 (m, 2H), 7.29 (d, J=7.2 Hz, 1H), 7.18 (s, 1H), 7.09 (s, 1H), 6.84 (s, 1H), 5.48-5.41 (m, 1H), 3.84-3.82 (m, 4H), 3.43-3.40 (m, 4H), 2.55 (s, 3H), 1.57 (d, J=7.2 Hz, 3H).

SFC conditions: Chiralcel OD-3 50×4.6 mm I.D., 3 um Mobile phase: Phase A for CO₂, and Phase B for MeOH (0.05% DEA); Gradient elution: MeOH (0.05% DEA) in CO₂ from 5% to 40% Flow rate: 3 mL/min; Detector: PDA; Column Temp: 35° C.; Back Pressure: 100 Bar.

Step A: To a solution of 6-bromo-4-chloro-1-methylphthalazine (279 mg, 1.09 mmol, 1.20 eq.) and (R)-1-(3-(benzyloxy)-5-(trifluoromethyl)phenyl)ethan-1-amine (300 mg, 0.90 mmol, 1.00 eq., HCl) in dimethyl sulfoxide (5.00 mL) was added potassium fluoride (263 mg, 4.52 mmol, 106 µL, 5.00 eq.), and the mixture was stirred at 130° C. for 12 hours. The mixture was diluted with water (20.0 mL) and extracted with ethyl acetate (20.0 mL×3). The combined organic layers were washed with brine (20.0 mL×2), dried over sodium sulfate, filtered, and concentrated under reduced pressure to give a residue. The residue was purified by prep-TLC (silica gel plate, petroleum ether:ethyl acetate=1:1, Rf=0.2) to give (R)—N-(1-(3-(benzyloxy)-5-(trifluoromethyl)phenyl)ethyl)-7-bromo-4-methylphthalazin-1-amine (300 mg, 581 µmol, 64.3% yield) as a yellow solid. LCMS [M+1]⁺: 516.0.

Step B: To a solution of (R)—N-(1-(3-(benzyloxy)-5-(trifluoromethyl)phenyl)ethyl)-7-bromo-4-methylphthalazin-1-amine (150 mg, 0.29 mmol, 1.00 eq.), morpholine (50.6 mg, 0.58 mmol, 51.1 µL, 2.00 eq.), RuPhos (13.6 mg, 0.03 mmol, 0.10 eq.) and cesium carbonate (284 mg, 872 µmol, 3.00 eq.) in dioxane (10.0 mL) was added Pd₂(dba)₃ (26.6 mg, 0.03 mmol, 0.10 eq.), then the reaction was stirred at 100° C. for 12 hours under a nitrogen atmosphere. The reaction was quenched with water (15.0 mL) and the mixture was extracted with ethyl acetate (15.0 mL×3). The combined organic layers were washed with brine (15.0 mL×2), dried over sodium sulfate, filtered, and concentrated under reduced pressure to give a residue. The residue was purified by prep-TLC (silica gel plate, dichloromethane:methyl alcohol=10:1, Rf=0.3) to give (R)—N-(1-(3-(benzyloxy)-5-(trifluoromethyl)phenyl)ethyl)-4-methyl-7-morpholinophthalazin-1-amine (120 mg, 230 µmol, 79.1% yield) as a yellow oil. LCMS [M+1]⁺: 523.3.

Example 21-3

(R)-3-methyl-5-(1-((4-methyl-7-morpholinopyrido[3,4-b]pyridazin-1-yl)amino)ethyl)benzonitrile

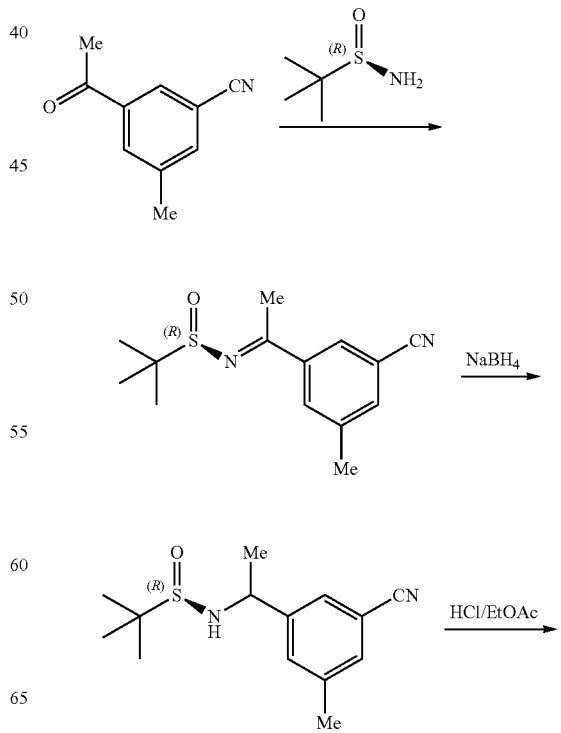

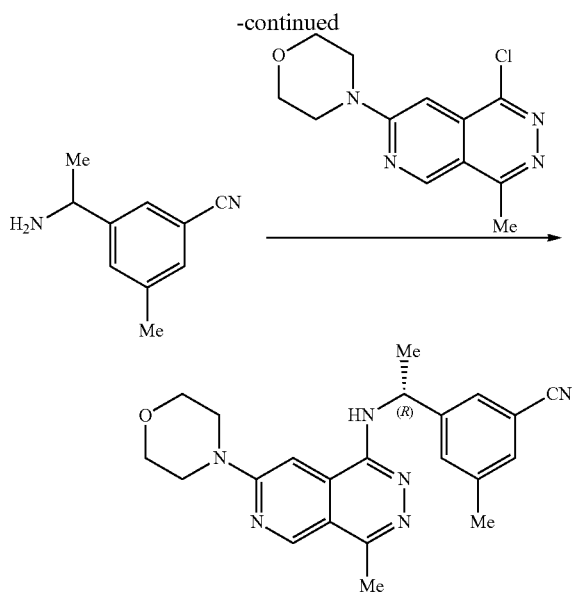

Step A: A mixture of 3-acetyl-5-methylbenzonitrile (0.50 g, 3.14 mmol, 1.00 eg.), (R)-2-methylpropane-2-sulfinamide (495 mg, 4.08 mmol, 1.30 eq.) and titanium ethoxide (1.43 g, 6.28 mmol, 1.30 mL, 2.00 eg.) in tetrahydrofuran (5.00 mL) was degassed and purged with nitrogen for 3 times, and then the mixture was stirred at 70° C. for 12 hours under a nitrogen atmosphere. The reaction mixture was then quenched by addition water (10.0 mL) at 25° C., and extracted with ethyl acetate (20.0 mL×3), dried over anhydrous sodium sulfate, filtered, and concentrated under reduced pressure to give a residue. The residue was purified by column chromatography (SiO$_2$, petroleum ether/ethyl acetate=10/1 to 1/1) to give (R,E)-N-(1-(3-cyano-5-methylphenyl)ethylidene)-2-methylpropane-2-sulfinamide (730 mg, 2.78 mmol, 88.6% yield) as a yellow oil. LCMS [M+1]$^+$: 263.0.

$^1$H NMR (400 MHz, DMSO-d$_6$) δ=8.10 (s, 1H), 8.01 (s, 1H), 7.86 (d, J=0.4 Hz, 1H), 2.73 (s, 3H), 2.42 (s, 3H), 1.23 (s, 9H).

Step B: To a solution of (R,E)-N-(1-(3-cyano-5-methylphenyl)ethylidene)-2-methylpropane-2-sulfinamide (0.30 g, 1.14 mmol, 1.00 eq.) in tetrahydrofuran (3.00 mL) was added sodium borohydride (130 mg, 3.43 mmol, 3.00 eq.) at 0° C. The mixture was stirred at 20° C. for 2 hours. The mixture was quenched with ammonium chloride solution (10.0 mL) and concentrated under reduced pressure to give a residue. The residue was diluted with ethyl acetate (60.0 ml) and the organic layer was washed with brine (20.0 mL), dried over anhydrous sodium sulfate, filtered and concentrated under reduced pressure to give a residue. The residue was purified by prep-TLC (SiO$_2$, petroleum ether/ethyl acetate=1/1) to give (R)—N-(1-(3-cyano-5-methylphenyl)ethyl)-2-methylpropane-2-sulfinamide (280 mg, 1.06 mmol, 92.6% yield) as a yellow oil. LCMS [M+1]$^+$: 265.1.

$^1$H NMR (400 MHz, DMSO-t/6) 5=7.67 (s, 1H), 7.56-7.52 (m, 2H), 5.76 (d, J=7.6 Hz, 1H), 4.45-4.35 (m, 1H), 2.35 (s, 3H), 1.38 (d, J=7.2 Hz, 3H), 1.12 (s, 9H).

Step C: A mixture of (R)—N-(1-(3-cyano-5-methyl phenyl)ethyl)-2-methyl propane-2-sulfinamide (250 mg, 946 μmol, 1.00 eq.) in hydrochloric acid/ethyl acetate (4.0 M, 2.60 mL, 11.0 eq.) was stirred at 25° C. for 1 hour. The reaction mixture was quenched with saturated sodium bicarbonate solution (5.00 mL), and extracted with ethyl acetate (10.0 mL×3), dried over anhydrous sodium sulfate, filtered, and concentrated under reduced pressure to give 3-(1-aminoethyl)-5-methylbenzonitrile (130 mg, 811 μmol, 85.8% yield) as a yellow oil.

$^1$H NMR (400 MHz, DMSO-d$_6$) δ=7.62 (s, 1H), 7.53 (s, 1H), 7.48 (d, J=0.4 Hz, 1H), 4.01 (q, J=6.8 Hz, 1H), 2.34 (s, 3H), 1.24 (d, J=6.8 Hz, 3H).

Step D: A mixture of 3-(1-aminoethyl)-5-methylbenzonitrile (100 mg, 624 μmol, 1.00 eq.), 4-(1-chloro-4-methylpyrido[3,4-d]pyridazin-7-yl)morpholine (165 mg, 624 μmol, 1.00 eq.) and potassium fluoride (109 mg, 1.87 mmol, 3.00 eq.) in dimethyl sulfoxide (0.20 mL) was degassed and purged with nitrogen for 3 times, and then the mixture was stirred at 130° C. for 12 hours under a nitrogen atmosphere. The reaction mixture was quenched by water (10.0 mL) at 25° C., and extracted with ethyl acetate (10.0 mL×3), dried over anhydrous sodium sulfate, filtered, and concentrated under reduced pressure to give a residue. The residue was purified by prep-HPLC [column: Waters Xbridge 150×25 mm 10 um; mobile phase: phase A: water (10 mM NH$_4$HCO$_3$), phase B: MeCN; B %: 24%-54%] to give 3-methyl-5-(1-((4-methyl-7-morpholinopyrido[3,4-d]pyridazin-1-yl)amino)ethyl)benzonitrile (80.0 mg, 206 μmol, 32.9% yield, 99.9% purity) as a yellow solid. The enantiomers were separated with SFC [column: DAICEL CHIRALPAK AD (250 mm×30 mm, 10 urn); mobile phase: phase A: 0.1% NH$_4$OH in MeOH, phase B: CO$_2$; B %: 25%].

Example 21-3, (R)-3-methyl-5-(1-((4-methyl-7-morpholinopyrido[3,4-d]pyridazin-1-yl)amino)ethyl)benzonitrile (first eluting isomer)

$^1$H NMR (400 MHz, CD$_3$OD) δ=8.97 (s, 1H), 7.56 (s, 2H), 7.34 (s, 1H), 7.27 (s, 1H), 5.37 (q, J=6.8 Hz, 1H), 3.85-3.80 (m, 4H), 3.76-3.72 (m, 4H), 2.62 (s, 3H), 2.33 (s, 3H), 1.63 (d, 6.8 Hz, 3H)

LCMS [M+1]$^+$: 389.2.

SFC conditions: "Column: Chiralpak AD-3 50×4.6 mm I.D., 3 um Mobile phase: Phase A for CO$_2$, and Phase B for MeOH (0.05% DEA); Gradient elution: MeOH (0.05% DEA) in CO$_2$ from 5% to 40% Flow rate: 3 mL/min; Detector: PDA; Column Temp: 35° C.; Back Pressure: 100 Bar"

Example 21-4

(R)-3-methyl-5-(1-((4-methyl-7-morpholinophthalazin-1-yl)amino)ethyl)benzonitrile

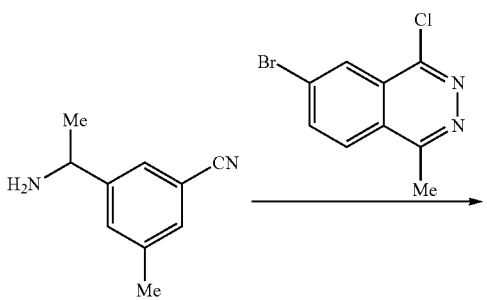

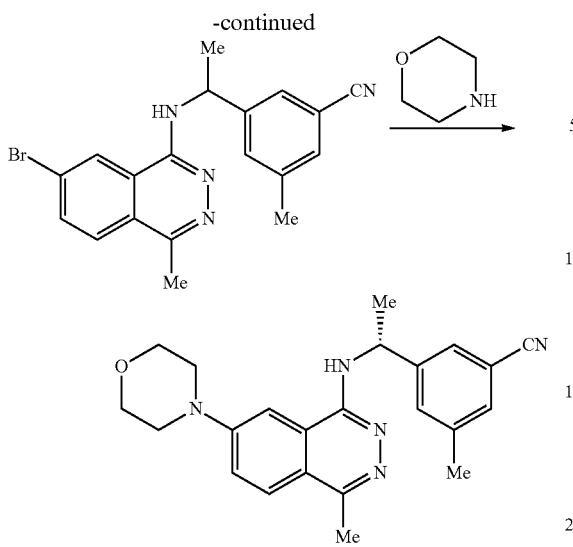

Step A: A mixture of 3-(1-aminoethyl)-5-methylbenzonitrile (100 mg, 624 μmol, 1.00 eq.), 6-bromo-4-chloro-1-methylphthalazine (161 mg, 624 μmol, 1.00 eq.) and cesium fluoride (284 mg, 1.87 mmol, 69.0 μL, 3.00 eq.) in dimethylsulfoxide (0.20 mL) was degassed and purged with nitrogen for 3 times, and then the mixture was stirred at 130° C. for 1 hour under a nitrogen atmosphere. The reaction mixture was quenched by addition water (10.0 mL) at 25° C., extracted with ethyl acetate (10.0 mL×3), dried over anhydrous sodium sulfate, filtered, and concentrated under reduced pressure to give a residue. The residue was purified by prep-TLC (SiO₂, petroleum ether/ethyl acetate=1:1) to give 3-(1-((7-bromo-4-methylphthalazin-1-yl)amino)ethyl)-5-methylbenzonitrile (50.0 mg, 131 μmol, 21.0% yield) as a yellow oil. LCMS [M+1]⁺: 382.9.

A mixture of 3-(1-((7-bromo-4-methylphthalazin-1-yl)amino)ethyl)-5-methylbenzonitrile (40.0 mg, 105 μmol, 1.00 eq.), morpholine (36.6 mg, 420 μmol, 36.9 μL, 4.00 eq.), cesium carbonate (103 mg, 315 μmol, 3.00 eq.) and RuPhos Pd G₃ (87.8 mg, 105 μmol, 1.00 eq.) in dioxane (1.00 mL) was degassed and purged with nitrogen for 3 times, and then the mixture was stirred at 80° C. for 2 hours under a nitrogen atmosphere. The reaction mixture was quenched by addition water (10.0 mL) at 25° C., extracted with ethyl acetate (10.0 mL×3), dried over anhydrous sodium sulfate, filtered, and concentrated under reduced pressure to give a residue. The residue was purified by preparative HPLC J column: Waters Xbridge 150×25 mm 10 um; mobile phase: phase A: water (10 mM NH₄HCO₃, phase B: MeCN; B %: 25%-55%] to give 3-methyl-5-(1-((4-methyl-7-morpholinophthalazin-1-yl)amino)ethyl)benzonitrile (20.0 mg, 51.5 μmol, 49.0% yield, 99.7% purity) as a white solid. The pure (R)-enantiomer was obtained using SFC (column: DAICEL CHIRALPAK AD (250 mm×30 mm, 10 um); mobile phase: phase A: NH₄OH in MeOH, phase B: CO₂; B %: 30%] give (R)-3-methyl-5-(1-((4-methyl-7-morpholinophthalazin-1-yl)amino)ethyl)benzonitrile (4.51 mg) as yellow solid. LCMS [M+1]⁺: 388.2.

¹H NMR (400 MHz, CD₃OD) δ=7.88 (d, J=9.2 Hz, 1H), 7.59-7.52 (m, 4H), 7.32 (s, 1H), 5.41 (q, J=6.8 Hz, 1H), 3.91-3.84 (m, 4H), 3.46-3.40 (m, 4H), 2.61 (s, 3H), 2.32 (s, 3H), 1.64 (d, J=7.2 Hz, 3H).

SFC conditions: Column: Chiralpak AD-3 50×4.6 mm I.D., 3 um Mobile phase: Phase A for CO₂, and Phase B for MeOH (0.05% DEA); Gradient elution: MeOH (0.05% DEA) in CO₂ from 5% to 40% Flow rate: 3 mL/min; Detector: PDA; Column Temp: 35° C.; Back Pressure: 100 Bar.

Example 21-5 and Example 21-6

7-((R)-4-(dimethylamino)-3,3-difluoropiperidin-1-yl)-4-methyl-N—((R)-1-(2-methyl-3-(trifluoromethyl)phenyl)ethyl)phthalazin-1-amine 7-((S)-4-(dimethylamino)-3,3-difluoropiperidin-1-yl)-4-methyl-N—((R)-1-(2-methyl-3-(trifluoromethyl)phenyl)ethyl)phthalazin-1-amine

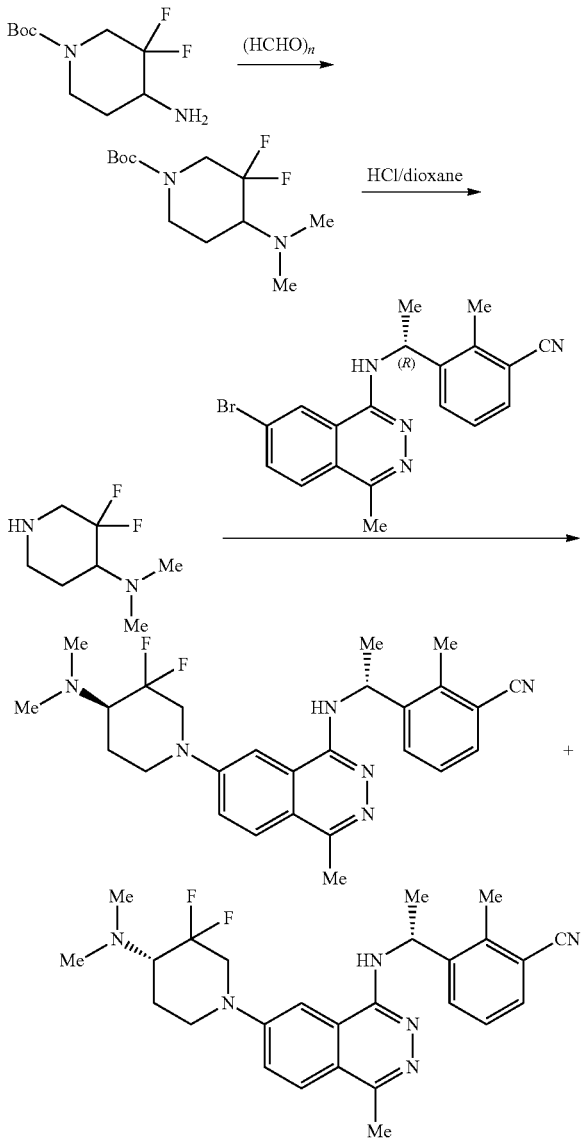

Step A: To a solution of tert-butyl 4-amino-3,3-difluoropiperidine-1-carboxylate (300 mg, 1.27 mmol, 1.00 eq.) in methanol (10.0 mL) was added paraformaldehyde (1.00 g, 1.27 mmol, 1.00 eq.) and acetic acid (7.63 mg, 127 μmol, 7.26 μL, 0.10 eq.), the reaction was stirred at 50° C. for 30 minutes, then sodium cyanoborohydride (479 mg, 7.62 mmol, 6.00 eq.) was added to the reaction in one portion. The reaction mixture was stirred at 50° C. for 16 hours, then concentrated under reduced pressure to give a residue. The residue was diluted with water (50.0 mL) and extracted with ethyl acetate (30.0 mL×3). The combined organic layers were washed with brine (50.0 mL×3), dried over sulfate sodium, filtered, and concentrated under reduced pressure to give a residue. The residue was purified by column chromatography (SiO$_2$, petroleum ether/ethyl acetate=5/1 to 3/1) to give compound tert-butyl 4-(dimethylamino)-3,3-difluoropiperidine-1-carboxylate (320 mg, 1.21 mmol, 95.4% yield) as a white solid. LCMS [M+1]$^+$: 265.1.

Step B: To a solution of tert-butyl 4-(dimethylamino)-3,3-difluoropiperidine-1-carboxylate (320 mg, 1.21 mmol, 1.00 eq.) in acetonitrile (1.00 mL) was added HCl in dioxane (4.00 M, 5.33 mL, 17.6 eq.). The reaction mixture was stirred at 0° C. for 30 minutes, then concentrated under reduced pressure give compound 3,3-difluoro-N,N-dimethylpiperidin-4-amine (190 mg, 1.16 mmol, 95.6% yield) as a white solid which was used in next step directly.

Step C: A mixture of (R)-7-bromo-4-methyl-N-(1-(2-methyl-3-(trifluoromethyl)phenyl)ethyl)phthalazin-1-amine (220 mg, 519 μmol, 1.00 eq.), 3,3-3,3-difluoro-N,N-dimethylpiperidin-4-amine (128 mg, 778 μmol, 1.50 eq.), sodium tert-butoxide (199 mg, 2.07 mmol, 4.00 eq.) and RuPhos Pd G$_3$ (43.4 mg, 51.9 μmol, 0.10 eq.) in dioxane (5.00 mL) was degassed and purged with nitrogen for 3 times, and then the reaction mixture was stirred at 110° C. for 16 hours under a nitrogen atmosphere. The reaction mixture was cooled to 25° C., diluted with water (30.0 mL) and extracted with ethyl acetate (30.0 mL×3). The combined organic layers were washed with brine (40.0 mL×3), dried over sulfate sodium, filtered, and concentrated under reduced pressure to give a residue. The residue was first purified by prep-TLC (dichloromethane:methanol=10:1) to give a white solid. LCMS [M+1]+: 508.3.

The compound was further purified and the diastereomers were separated using SFC (column: DAICEL CHIRALCEL OD-H (250 mm×30 mm, 5 μm); mobile phase: phase A: 0.1% NEB in H2O, phase B: MeOH; B %: 20%) to give the separated isomers 7-((R)-4-(dimethylamino)-3,3-difluoropiperidin-1-yl)-4-methyl-N—((R)-1-(2-methyl-3-(trifluoromethyl)phenyl)ethyl)phthalazin-1-amine and 7-((S)-4-(dimethylamino)-3,3-difluoropiperidin-1-yl)-4-methyl-N—((R)-1-(2-methyl-3-(trifluoromethyl)phenyl)ethyl)phthalazin-1-amine.

Spectral Data for Example 21-5 (first eluting isomer): LCMS [M+1]$^+$:508.2

$^1$H NMR (400 MHz, CD$_3$OD) δ=8.24 (d, J=9.2 Hz, 1H), 8.00 (d, J=2.0 Hz, 1H), 7.88 (dd, J=2.4, 9.2 Hz, 1H), 7.78-7.72 (m, 1H), 7.55 (br d, J=7.6 Hz, 1H), 7.34-7.25 (m, 1H), 5.62-5.51 (m, 1H), 5.01-4.95 (m, 1H), 4.77-4.64 (m, 1H), 4.38-4.20 (m, 1H), 3.78-3.63 (m, 1H), 3.44 (br t, J=12.0 Hz, 1H), 3.10 (s, 6H), 2.80 (s, 3H), 2.65 (s, 3H), 2.62-2.53 (m, 1H), 2.27-2.13 (m, 1H), 1.71 (d, J=6.8 Hz, 3H).

Spectral Data for Example 21-6 (second eluting isomer): LCMS [M+1]$^+$:508.2

$^1$H NMR (400 MHz, CD$_3$OD) δ=8.24 (d, J=9.2 Hz, 1H), 8.01 (d, J=2.0 Hz, 1H), 7.87 (dd, J=2.4, 9.2 Hz, 1H), 7.77 (d, J=7.6 Hz, 1H), 7.55 (d, J=8.0 Hz, 1H), 7.35-7.24 (m, 1H), 5.62-5.52 (m, 1H), 5.01-4.95 (m, 1H), 4.76-4.66 (m, 1H), 4.38-4.20 (m, 1H), 3.81-3.62 (m, 1H), 3.44 (br t, J=12.4 Hz, 1H), 3.15 (s, 6H), 2.80 (s, 3H), 2.65 (s, 3H), 2.61-2.52 (m, 1H), 2.28-2.13 (m, 1H), 1.72 (d, J=6.8 Hz, 3H).

Example 21-7

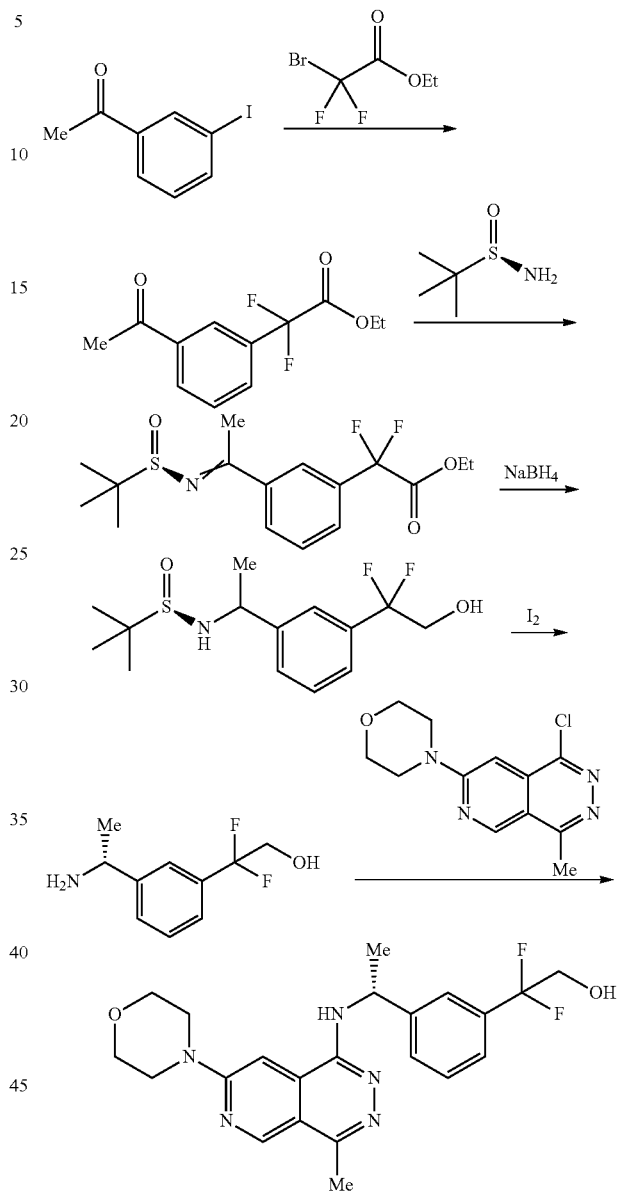

Step A: A mixture of 1-(3-iodophenyl)ethan-1-one (4.60 g, 18.7 mmol, 1.00 eq.), ethyl 2-bromo-2,2-difluoroacetate (4.17 g, 20.6 mmol, 2.64 mL, 1.10 eq.) and copper powder (3.56 g, 56.1 mmol, 398 μL, 3.00 eq.) in DMSO (50.0 mL) was degassed and purged with nitrogen 3 times, and the mixture was stirred at 60° C. for 12 hours under a nitrogen atmosphere. The mixture was diluted with ethyl acetate (100 mL). filtered, and the filtrate was washed with brine (50.0 mL×3), dried, and concentrated under reduced pressure. The residue was purified by column chromatography (SiO$_2$, petroleum ether/ethyl acetate=80/1 to 30/1) to give ethyl 2-(3-acetylphenyl)-2,2-difluoroacetate (3.80 g, 15.7 mmol, 83.9% yield) as colorless oil.

$^1$H NMR (400 MHz, CDCl$_3$) δ=8.20 (s, 1H), 8.10 (d, J=7.6 Hz, 1H), 7.84-7.80 (m, 1H), 7.59 (t, J=7.2 Hz, 1H), 4.37-4.29 (m, 2H), 2.65 (s, 3H), 1.32 (t, J=7.2 Hz, 3H).

Step B: To a solution of ethyl 2-(3-acetylphenyl)-2,2-difluoroacetate (2.00 g, 8.26 mmol, 1.00 eq.) and (R)-2-methylpropane-2-sulfinamide (1.30 g, 10.8 mmol, 1.30 eq.) in THF (40.0 mL) was added titanium (IV) butoxide (3.77 g, 16.5 mmol, 3.42 mL, 2.00 eq.) and 1,2-dimethoxyethane (744 mg, 8.26 mmol, 858 μL, 1.00 eq.), and the mixture was stirred at 70° C. for 12 hours. The reaction mixture was diluted with ethyl acetate (100 mL) and water (5.00 mL), filtered, and the filtrate was concentrated under reduced pressure. The residue was purified by column chromatography (SiO$_2$, petroleum ether/ethyl acetate=10/1 to 5/1) to give ethyl (R)-2-(3-(1-(((tert-butylsulfinyl)imino)ethyl)phenyl)-2,2-difluoroacetate (2.40 g, 6.95 mmol, 84.2% yield) as yellow oil.

Step C: To a solution of ethyl (R)-2-(3-(1-(((tert-butylsulfinyl)imino)ethyl)phenyl)-2,2-difluoroacetate (2.20 g, 6.37 mmol, 1.00 eq.) in methanol (20.0 mL) was added sodium borohydride (964 mg, 25.5 mmol, 4.00 eq.) at 0° C., and the mixture was stirred at 28° C. for 1 hour. The mixture was diluted with water (20.0 mL) and extracted with ethyl acetate (50.0 mL×3), and the combined organic phases were dried and concentrated under reduced pressure. The residue was purified by column chromatography (SiO$_2$, petroleum ether/ethyl acetate=2/1 to 1/1) to give (R)—N—((R)-1-(3-(1,1-difluoro-2-hydroxyethyl)phenyl)ethyl)-2-methylpropane-2-sulfinamide (0.90 g, 2.95 mmol, 46.3% yield) as yellow oil and (R)—N—((R)-1-(3-(1,1-difluoro-2-hydroxyethyl)phenyl)ethyl)-2-methylpropane-2-sulfinamide (0.90 g, 2.95 mmol, 46.3% yield) as yellow oil. LCMS [M+1]$^+$: 306.1.

Step D: To a solution of (R)—N—((R)-1-(3-(1,1-difluoro-2-hydroxyethyl)phenyl)ethyl)-2-methylpropane-2-sulfinamide (0.90 g, 2.95 mmol, 1.00 eq.) in THF (8.00 mL) and water (2.00 mL) was added iodine (224 mg, 884 μmol, 178 μL, 0.30 eq.), and the mixture was stirred at 50° C. for 1 hour. The reaction mixture was then diluted with saturated sodium sulfite aqueous solution (10.0 ml) and sodium bicarbonate aqueous solution (10.0 mL), and the resulting mixture was extracted with dichloromethane/methanol (10:1, 10.0 mL×3). The combined organic phases were dried and concentrated under reduced pressure to give (R)-2-(3-(1-aminoethyl)phenyl)-2,2-difluoroethane-1-ol (450 mg, crude) as yellow oil.

Step E: A mixture of 4-(1-chloro-4-methylpyrido[3,4-d]pyridazin-7-yl)morpholine (200 mg, 756 μmol, 1.00 eq.), (R)-2-(3-(1-aminoethyl)phenyl)-2,2-difluoroethane-1-ol (152 mg, 756 μmol, 1.00 eq.), BrettPhos Pd G$_3$ (68.5 mg, 75.6 μmol, 0.10 eq.) and sodium tert-butoxide (218 mg, 2.27 mmol, 3.00 eq.) in dioxane (3.00 mL) was degassed and purged with nitrogen 3 times, and then the mixture was stirred at 100° C. for 1 hour under a nitrogen atmosphere. The reaction mixture was filtered and concentrated under reduced pressure. The residue was purified by prep-HPLC [column: Phenomenex Luna C18 150×25 mm×10 um; mobile phase: phase A: water (0.225% formic acid, phase B: acetonitrile; B %: 9%-39%) to give (R)-2,2-difluoro-2-(3-(1-((4-methyl-7-morpholinopyrido[3,4-d]pyridazin-1-yl)amino)ethyl)phenyl)ethan-1-ol (73.0 mg, 170 μmol, 22.5% yield, 99.9% purity) as a yellow solid. LCMS [M+1]$^+$: 430.1.

$^1$H NMR (400 MHz, CD$_3$OD) δ=9.11 (s, 1H), 8.48 (s, 1H), 7.62 (s, 1H), 7.56 (br d, J=6.4 Hz, 1H), 7.46-7.35 (m, 3H), 5.44-5.34 (m, 1H), 3.95-3.81 (m, 10H), 2.71 (s, 3H), 1.69 (d, 6.8 Hz, 3H).

Example 21-8

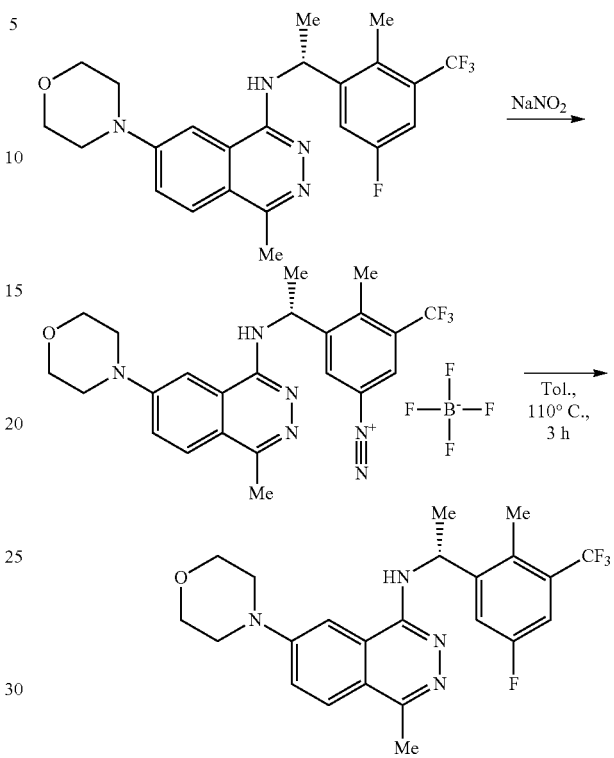

Step A: The sodium nitrite (20.1 mg, 292 μmol, 1.30 eq.) in water (0.60 mL) was added dropwise to a mixture of (R)—N-(1-(5-amino-2-methyl-3-(trifluoromethyl)phenyl)ethyl)-4-methyl-7-morpholinophthalazin-1-amine (100 mg, 224 μmol, 1.00 eq.) and tetrafluoroboric acid (253 mg, 1.15 mmol, 179 μL, 40.0% purity, 5.13 eq.) in water (3.00 mL) at 0° C., the mixture was stirred at 0° C. for 30 minutes. The reaction mixture was filtered and the after cake was concentrated under reduced pressure to give (R)-4-methyl-3-(1-((4-methyl-7-morpholinophthalazin-1-yl)amino)ethyl)-5-(trifluoromethyl)benzenediazonium tetrafluoroborate (100 mg, crude) as a yellow solid. LCMS [M−28]$^+$: 429.0.

Step B: A solution of (R)-4-methyl-3-(1-((4-methyl-7-morpholinophthalazin-1-yl)amino)ethyl)-5-(trifluoromethyl)benzenediazonium tetrafluoroborate (100 mg, 184 μmol, 1.00 eq.) in toluene (1.00 mL) was heated to 110° C., the mixture was stirred at 110° C. for 3 hours. The reaction mixture was concentrated under reduced pressure to give a residue. The residue was purified by prep-HPLC [column: Phenomenex luna C18 80×40 mm×3 um; mobile phase: phase A: water(0.04% HCl), phase B: acetonitrile; B %: 28%-52%] to give (R)—N-(1-(5-fluoro-2-methyl-3-(trifluoromethyl)phenyl)ethyl)-4-methyl-7-morpholinophthalazin-1-amine (13.1 mg, 28.9 μmol, 15.8% yield, 99.3% purity, hydrochloride salt) as a yellow solid. LCMS [M+1]$^+$: 449.1.

$^1$H NMR (400 MHz, DMSO-d$_6$) δ=14.75 (br s, 1H), 8.58-8.41 (m, 1H), 8.22-8.15 (m, 1H), 7.81 (s, 1H), 7.79-7.74 (m, 1H), 7.62-7.56 (m, 1H), 7.48-7.43 (m, 1H), 5.50-5.37 (m, 1H), 3.85-3.80 (m, 4H), 3.72-3.65 (m, 4H), 2.73 (s, 3H), 2.54 (s, 3H), 1.64-1.58 (m, 3H).

SFC conditions: Chiralcel OD-3 3 μm, 0.46 cm id×5 cm L; Mobile phase: A for SFC CO$_2$ and B for MeOH (0.05% isopropylamine); Gradient elution: B in A from 10% to 40% in 3 minutes; Flowrate: 4.0 mL/min; Column Temp: 35° C.; Back Pressure: 100 Bar.

Example 21-9

3-((R)-1-((5-fluoro-7-((R)-hexahydro-2H,6H-pyrasine[1,2-c][1,3]oxazin-2-yl)-4-methylphthalazin-1-yl)amino)ethyl)-2-methylbenzonitrile

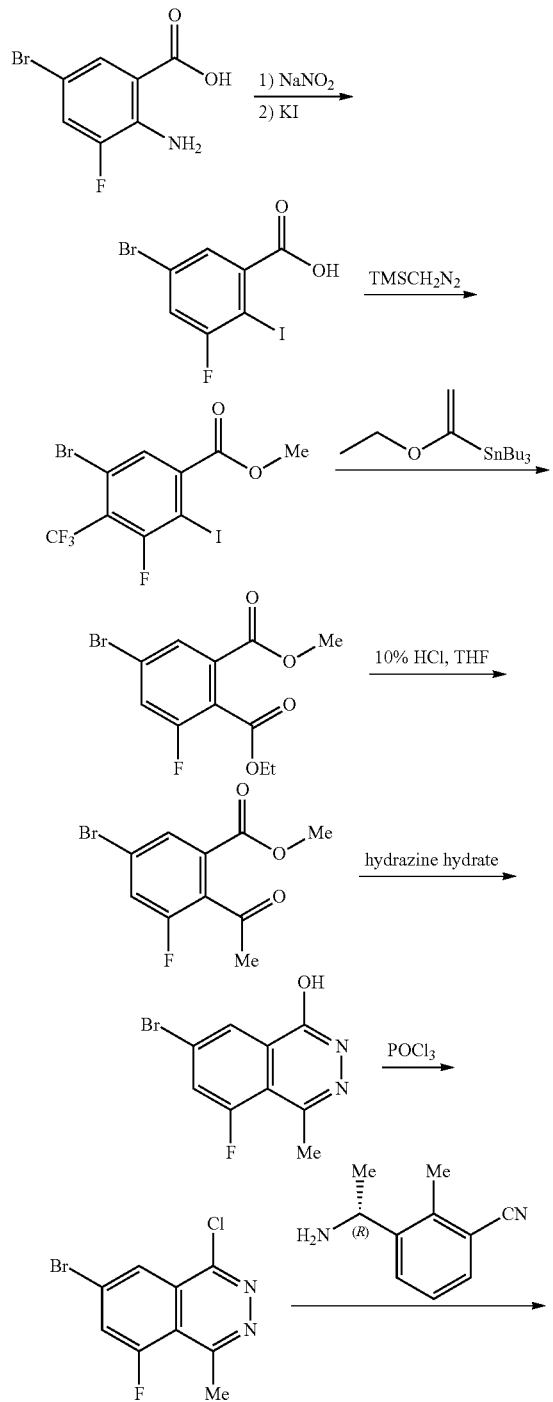

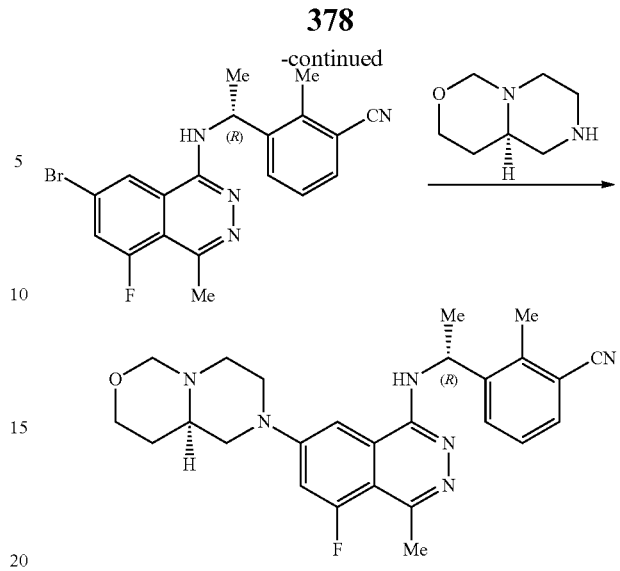

Step A: To a solution of 2-amino-5-bromo-3-fluorobenzoic acid (2.00 g, 8.55 mmol, 1.00 eq.) in hydrochloric acid (4.0 M, 21.4 mL, 10.0 eq.) and water (10.0 mL) was added sodium nitrite (708 mg, 10.3 mmol, 1.20 eq.) at 0° C., then the mixture was stirred at the same temperature for 30 minutes. After this time a solution of potassium iodide (2.13 g, 12.8 mmol, 1.50 eq.) was added dropwise, and then the mixture was heated to 90° C. and stirred for 30 minutes. The mixture was the cooled, and the pH adjusted to pH=9 with potassium carbonate and then filtered. The filtrate was adjusted to pH=4 with HCl (4.0 M in water), filtered, and the precipitate was dried under vacuum to give 5-bromo-3-fluoro-2-iodobenzoic acid (2.40 g, 6.96 mmol, 81.4% yield) as a yellow solid.

$^1$H NMR (400 MHz, DMSO-$d_6$) δ=14.06-13.55 (m, 1H), 7.79-7.72 (m, 1H), 7.69-7.64 (m, 1H).

Step B: To a solution of 5-bromo-3-fluoro-2-iodobenzoic acid (2.40 g, 6.96 mmol, 1.00 eq.) in toluene (24.0 mL) and methanol (8.00 mL) was added trimethylsilyldiazomethane (2.0 M, 6.96 mL, 2.00 eq.) dropwise at 0° C., and the mixture was stirred at 20° C. for 30 minutes. The reaction mixture was then concentrated under reduced pressure, and the residue was purified by column chromatography (SiO$_2$, petroleum ether/ethyl acetate=1/0 to 10/1) to give methyl 5-bromo-3-fluoro-2-iodobenzoate (2.47 g, 6.88 mmol, 98.9% yield) as a yellow solid.

$^1$H NMR (400 MHz, CDCl$_3$) δ=7.76-7.69 (m, 1H), 7.40-7.33 (m, 1H), 3.96 (s, 3H).

Step C: A mixture of methyl 5-bromo-3-fluoro-2-iodobenzoate (2.47 g, 6.88 mmol, 1.00 eq.), tributyl(1-ethoxyvinyl)tin (2.73 g, 7.57 mmol, 2.55 mL, 1.10 eq.) and Pd(PPh$_3$)$_2$Cl$_2$ (483 mg, 688 μmol, 0.10 eq.) in dioxane (30.0 mL) was degassed and purged with nitrogen (3 times), and then the mixture was stirred at 80° C. for 12 hours under a nitrogen atmosphere. The mixture was then poured into a saturated solution of potassium fluoride (in water, 50.0 mL) and stirred for 30 minutes. The aqueous phase was extracted with ethyl acetate (100 mL×3), and the combined organic phases were washed with brine (50.0 mL×3), dried over anhydrous sodium sulfate, filtered, and concentrated under reduced pressure. The residue was purified by column chromatography (SiO$_2$, petroleum ether/ethyl acetate=100/1 to 20/1) to give methyl 5-bromo-2-(1-ethoxyvinyl)-3-fluorobenzoate (1.80 g, 5.94 mmol, 86.3% yield) as yellow oil.

¹H NMR (400 MHz, CDCl₃) δ=7.69-7.65 (m, 1H), 7.44-7.37 (m, 1H), 4.50 (d, J=2.4 Hz, 1H), 4.38-4.34 (m, 1H), 3.90-3.85 (m, 5H), 1.32 (t, J=6.8 Hz, 3H).

Step D: To a solution of methyl 5-bromo-2-(1-ethoxyvinyl)-3-fluorobenzoate (1.80 g, 5.94 mmol, 1.00 eq.) in THF (20.0 mL) was added hydrochloric acid (2.0 M, 8.91 mL, 3.00 eq.), and the mixture was stirred at 20° C. for 1 hour. The pH of the mixture was then adjusted to pH=7 with saturated sodium bicarbonate aqueous solution, and the solution was extracted with ethyl acetate (30.0 mL×2). The combined organic phases were dried over anhydrous sodium sulfate and concentrated under reduced pressure. The residue was purified by column chromatography (SiO₂, petroleum ether/ethyl acetate=50/1 to 30/1) to give methyl 2-acetyl-5-bromo-3-fluorobenzoate (1.40 g, 5.09 mmol, 85.7% yield) as yellow oil.

¹H NMR (400 MHz, CDCl₃) δ=7.91 (s, 1H), 7.54-7.41 (m, 1H), 3.91 (s, 3H), 2.59 (s, 3H).

Step E: To a solution of methyl 2-acetyl-5-bromo-3-fluorobenzoate (1.20 g, 4.36 mmol, 1.00 eq.) in ethanol (10.0 mL) was added hydrazine hydrate (334 mg, 6.54 mmol, 325 µL, 98% purity, 1.50 eq.), and the mixture was stirred at 60° C. for 1 hour. The mixture was then cooled to 20° C., filtered, and the precipitate was dried under vacuum to give 7-bromo-5-fluoro-4-methylphthalazin-1-ol (580 mg, 2.26 mmol, 51.7% yield) as a white solid.

¹H NMR (400 MHz, DMSO-d₆) δ=12.7 (br s, 1H), 8.17 (d, J=1.6 Hz, 1H), 8.15-8.08 (m, 1H), 2.56 (d, J=6.8 Hz, 3H).

Step F: To a solution of 7-bromo-5-fluoro-4-methylphthalazin-1-ol (300 mg, 1.17 mmol, 1.00 eq.) in phosphorus oxychloride (6.00 mL) was added N,N-diisopropylethylamine (453 mg, 3.50 mmol, 10.0 µL, 3.00 eq.), and the mixture was stirred at 110 C for 2 hours. The mixture was then quenched by sodium bicarbonate aqueous solution and extracted with ethyl acetate (10.0 mL×3). The combined organic phases were dried over anhydrous sodium sulfate, concentrated under reduced pressure, and the residue was purified by column chromatography (SiO₂, petroleum ether/ethyl acetate=5/1) to give 7-bromo-1-chloro-5-fluoro-4-methylphthalazine (150 mg, 544 µmol, 46.7% yield) as an orange solid. LCMS [M+1]⁺: 276.8.

Step G: To a solution of 7-bromo-1-chloro-5-fluoro-4-methylphthalazine (150 mg, 544 µmol, 1.00 eq.) in DMSO (1.00 mL) was added cesium fluoride (124 mg, 817 µmol, 30.1 µL, 1.50 eq.) and (R)-3-(1-aminoethyl)-2-methylbenzonitrile (87.2 mg, 544 µmol, 1.00 eq.), and the mixture was stirred at 130° C. for 30 minutes. The mixture was then cooled to 25° C., diluted with ethyl acetate (20.0 mL), washed with brine (10.0 mL×3), and the separated organic phases were dried and concentrated under reduced pressure. The residue was purified by column chromatography (SiO₂, petroleum ether/ethyl acetate=5/1 to 2/1) to give (R)-3-(1-((7-bromo-5-fluoro-4-methylphthalazin-1-yl)amino)ethyl)-2-methylbenzonitrile (160 mg, 401 µmol, 73.6% yield) as a yellow solid. LCMS [M+1]⁺: 399.1.

Step H: A mixture of (R)-3-(1-((7-bromo-5-fluoro-4-methylphthalazin-1-yl)amino)ethyl)-2-methylbenzonitrile (15.0 mg, 37.6 µmol, 1.00 eq.), (R)-hexahydro-2H,6H-pyrazino[1,2-c][1,3]oxazine (10.5 mg, 48.8 µmol, 1.30 eq., 2 HCl), cesium carbonate (61.2 mg, 188 µmol, 5.00 eq.), RuPhos (3.51 mg, 7.51 µmol, 0.20 eq.) and Pd₂(dba)₃ (3.44 mg, 3.76 µmol, 0.10 eq.) in dioxane (1.00 mL) was degassed and purged with nitrogen (3 times), and then the mixture was stirred at 105° C. for 2 hours under a nitrogen atmosphere. The mixture was cooled to 25° C., filtered, and concentrated under reduced pressure. The residue was then purified by prep-HPLC [column: Phenomenex luna C18 150×25 mm×10 um; mobile phase: phase A: water (0.225% formic acid), phase B: acetonitrile; B %: 2%-32%] to give 3-((R)-1-((5-fluoro-7-((R)-hexahydro-2H,6H-pyrazino[1,2-c][1,3]oxazin-2-yl)-4-methylphthalazin-1-yl)amino)ethyl)-2-methylbenzonitrile (7.70 mg, 15.2 µmol, 40.5% yield, 99.9% purity, formate salt) as an off-white solid. LCMS [M+1]⁺: 461.2.

¹H NMR (400 MHz, CD₃OD) δ=8.52 (br s, 1H), 7.70 (d, J=7.6 Hz, 1H), 7.50 (d, J=7.2 Hz, 1H), 7.41 (d, J=2.0 Hz, 1H), 7.39-7.33 (m, 1H), 7.25 (t, J=8.0 Hz, 1H), 5.59-5.51 (m, 1H), 4.11 (br d, J=13.2 Hz, 1H), 3.96 (br d, J=12.4 Hz, 1H), 3.92-3.84 (m, 2H), 3.77-3.68 (m, 1H), 3.39-3.33 (m, 1H), 3.21-3.11 (m, 1H), 2.97 (br d, J=11.6 Hz, 1H), 2.80 (br d, J=11.6 Hz, 1H), 2.75-2.63 (m, 7H), 2.51-2.35 (m, 3H), 1.62 (d, J=7.2 Hz, 3H).

Example 21-10

(R)-3-(1-((5-fluoro-7-(3-hydroxy-3-methylazetidin-1-yl)-4-methylphthalazin-1-yl)amino)ethyl)-2-methylbenzonitrile

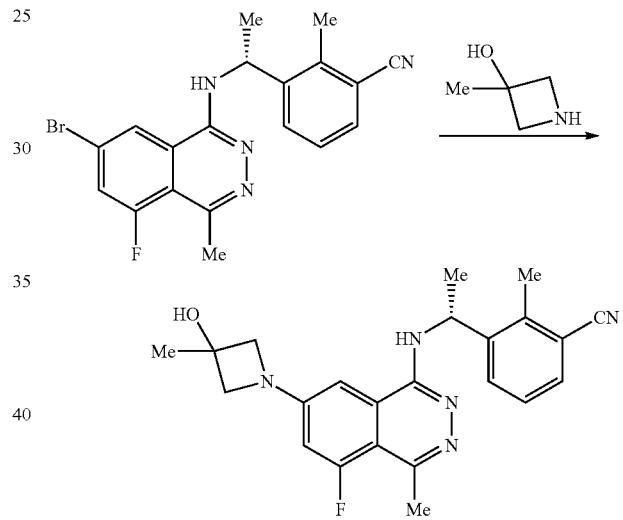

A mixture of (R)-3-(1-((7-bromo-5-fluoro-4-methylphthalazin-1-yl)amino)ethyl)-2-methylbenzonitrile (60.0 mg, 150 µmol, 1.00 eq.), 3-methylazetidin-3-ol (27.9 mg, 225 µmol, 1.50 eq., HCl), cesium carbonate (245 mg, 751 µmol, 5.00 eq.), RuPhos (14.0 mg, 30.1 µmol, 0.20 eq.) and Pd₂(dba)₃ (13.8 mg, 15.0 µmol, 0.10 eq.) in dioxane (1.00 mL) was degassed and purged with nitrogen (3 times), and the mixture was stirred at 100° C. for 2 hours under a nitrogen atmosphere. The n mixture was filtered and concentrated under reduced pressure, and the residue was purified by prep-HPLC [column: Phenomenex luna C18 150×25 mm×10 um; mobile phase: phase A: water(0.225% formic acid, phase B: acetonitrile; B %: 10%-40%] to give (R)-3-(1-((5-fluoro-7-(3-hydroxy-3-methylazetidin-1-yl)-4-methylphthalazin-1-yl)amino)ethyl)-2-methylbenzonitrile (39.0 mg, 86.0 µmol, 57.3% yield, 99.6% purity, formate salt) as a yellow solid. LCMS [M+1]⁺: 406.1.

¹H NMR (400 MHz, CD₃OD) δ=8.51 (s, 1H), 7.70 (d, J=7.6 Hz, 1H), 7.55-7.47 (m, 1H), 7.27 (t, J=8.0 Hz, 1H), 7.07 (d, J=2.0 Hz, 1H), 6.87-6.77 (m, 1H), 5.54-5.37 (m, 1H), 4.14-4.07 (m, 2H), 4.07-4.00 (m, 2H), 2.79-2.65 (m, 6H), 1.68-1.55 (m, 6H).

Example 21-11

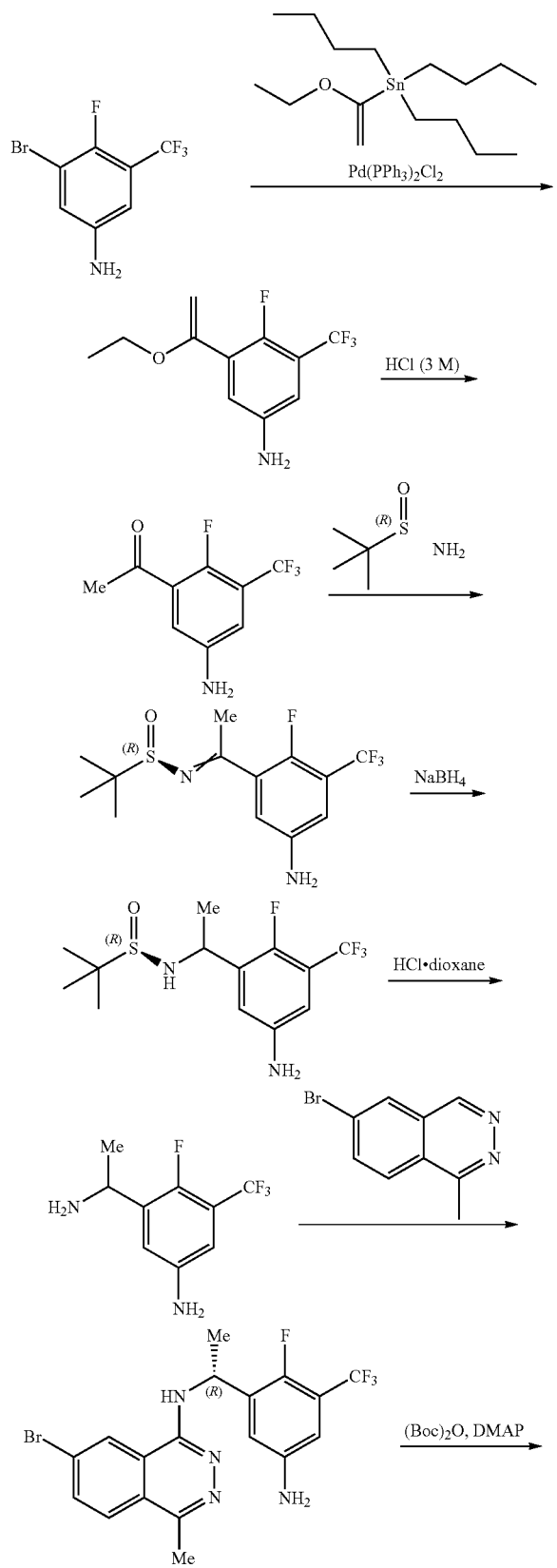

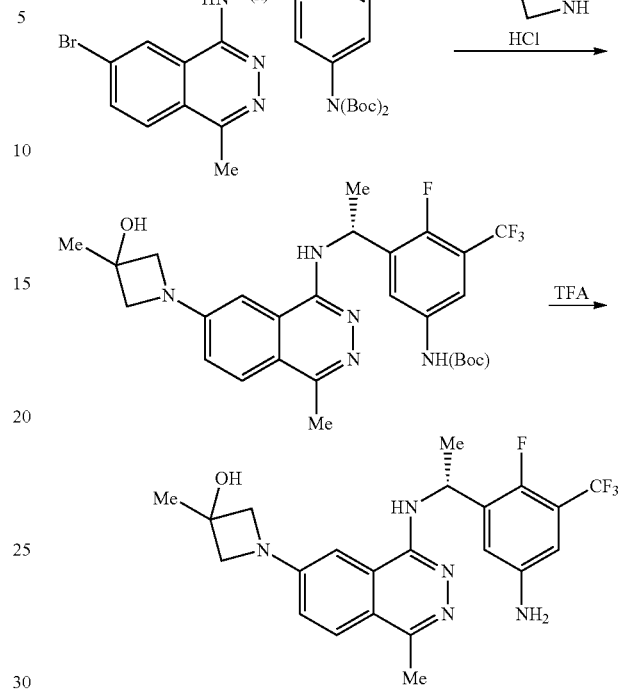

Step A: To a solution of 3-bromo-4-fluoro-5-(trifluoromethyl)aniline (4.00 g, 15.5 mmol, 1.00 eq.), tributyl(1-ethoxyvinyl)tin (5.60 g, 15.5 mmol, 5.23 mL, 1.00 eq.), and $PdCl_2(PPh)_3$ (326 mg, 0.47 mmol, 0.03 eq.) in 1,4-dioxane (10.0 mL) was stirred at 80° C. for 10 hours under a nitrogen atmosphere. The r mixture was cooled to 25° C., poured into saturated potassium fluoride aqueous solution (200 mL) and stirred for 30 minutes to give a suspension, and the suspension was filtered, then the filtrate was solution was extracted with ethyl acetate (200 mL×3). The combined organic layers were washed with brine (200 mL), dried over sodium sulfate, filtered, and concentrated under reduced pressure to give a crude product 3-(1-ethoxyvinyl)-4-fluoro-5-(trifluoromethyl)aniline (6.00 g, 24.1 mmol, 1.00 eq., crude) which was used into the next step without further purification.

Step B: To a solution of 3-(1-ethoxyvinyl)-4-fluoro-5-(trifluoromethyl)aniline (6.00 g, 24.1 mmol, 1.00 eq., crude) in tetrahydrofuran (20.0 mL) was added hydrochloric acid (3.00 M, 8.03 mL, 1.00 eq.) under a nitrogen atmosphere, and the mixture was stirred at 20° C. for 1 hour. The mixture was poured into water (40.0 mL), and then extracted with ethyl acetate (40.0 mL×3). The combined organic layers were washed with brine (40.0 mL), dried over sodium sulfate, filtered, and concentrated under reduced pressure. The residue was purified by column chromatography (silica gel, petroleum ether/ethyl acetate=50/1 to 3/1) to give 1-(5-amino-2-fluoro-3-(trifluoromethyl)phenyl)ethan-1-one (2.00 g, 9.04 mmol) as a yellow solid.

$^1$H NMR (400 MHz, DMSO-$d_6$) δ=7.18 (dd, J=3.0, 5.6 Hz, 1H), 7.08 (dd, J=3.2, 5.6 Hz, 1H), 5.67 (s, 2H), 2.54 (d, J=4.4 Hz, 3H).

Step C: To a solution of 1-(5-amino-2-fluoro-3-(trifluoromethyl)phenyl)ethan-1-one (2.00 g, 9.04 mmol, 1.00 eq.) and (R)-2-methylpropane-2-sulfinamide (1.42 g, 11.8 mmol, 1.30 eq.) in tetrahydrofuran (20.0 mL) was added titanium (IV) isopropoxide (5.14 g, 18.1 mmol, 5.34 mL, 2.00 eq.) and 1-methoxy-2-(2-methoxyethoxy)ethane (4.69 g, 34.9 mmol, 5.00 mL, 3.86 eq.), and the mixture was stirred at 70° C. for 12 hours a under nitrogen atmosphere. The mixture was then concentrated under reduced pressure and the residue was purified by column chromatography (silica gel, petroleum ether/ethyl acetate=30/1 to 1/1) to give (R)—N-(1-(5-amino-2-fluoro-3-(trifluoromethyl)phenyl)ethylidene)-2-methylpropane-2-sulfinamide (500 mg, 1.54 mmol, 17.1% yield) as a yellow oil.

$^1$H NMR (400 MHz, CDCl$_3$) δ=7.07 (br s, 1H), 6.95 (br s, 1H), 3.83 (br s, 2H), 2.74 (br d, J=2.4 Hz, 3H), 1.31 (s, 9H).

Step D: To a solution of (R)—N-(1-(5-amino-2-fluoro-3-(trifluoromethyl)phenyl)ethylidene)-2-methylpropane-2-sulfinamide (1.10 g, 3.39 mmol, 1.00 eq.) in tetrahydrofuran (15.0 mL) was added sodium borohydride (385 mg, 10.2 mmol, 3.00 eq) portionwise at 0° C., under a nitrogen atmosphere. The mixture was stirred at 0° C. for 1 hour, then slowly diluted with saturated ammonium chloride aqueous solution (40.0 mL), and the resulting mixed solution extracted with ethyl acetate (30.0 mL×3). The combined organic layers were washed with brine (30.0 mL), dried over sodium sulfate, filtered, and concentrated under reduced pressure. The residue was purified by column chromatography (silica gel, petroleum ether/ethyl acetate=30/1 to 1/1) to give (R)—N-(1-(5-amino-2-fluoro-3-(trifluoromethyl)phenyl)ethyl)-2-methylpropane-2-sulfinamide (600 mg, 1.84 mmol, 54.2% yield) as a yellow oil. LCMS [M+1]$^+$: 327.0.

$^1$H NMR (400 MHz, CDCl$_3$) δ=6.97-6.83 (m, 1H), 6.82-6.76 (m, 1H), 4.83-4.69 (m, 1H), 3.71-3.44 (m, 2H), 1.59-1.50 (m, 3H), 1.25-1.19 (m, 9H). (the ratio of diastereoisomers was 2:1).

Step E: To a solution of (R)—N-(1-(5-amino-2-fluoro-3-(trifluoromethyl)phenyl)ethyl)-2-methylpropane-2-sulfinamide (600 mg, 1.84 mmol, 1.00 eq.) in dichloromethane (5.00 mL) was added HCl (4.00 M in dioxane, 5.00 mL, 10.9 eq.) dropwise, then the reaction mixture was stirred at 20° C. for 1 hour. The reaction mixture was concentrated under reduced pressure, and the pH of the residue was adjusted to pH=8 by slow addition saturated sodium bicarbonate aqueous solution. The aqueous solution was extracted with DCM:methanol (10:1, 20.0 mL×5), and the combined organic phases were washed with brine (10.0 mL), dried over sodium sulfate, filtered and concentrated under reduced pressure to give 3-(1-aminoethyl)-4-fluoro-5-(trifluoromethyl)aniline (350 mg, 1.58 mmol, 85.7% yield) as a yellow solid which was used directly without further purification.

Step F: To a solution of 3-(1-aminoethyl)-4-fluoro-5-(trifluoromethyl)aniline (140 mg, 630 μmol, 1.00 eq.), 6-bromo-4-chloro-1-methylphthalazine (162 mg, 0.63 mmol, 1.00 eq.) and potassium fluoride (183 mg, 3.15 mmol, 73.8 μL, 5.00 eq.) in DMSO (3.00 mL) was stirred at 130° C. for 1 hour under a nitrogen atmosphere. The mixture was poured into water (20.0 mL), and the resulting aqueous solution was extracted with ethyl acetate (20.0 mL×3). The combined organic layers were washed with brine (20.0 mL), dried over sodium sulfate, filtered, and concentrated under reduced pressure. The residue was purified by prep-HPLC [column: Welch Xtimate C18 150×25 mm×5 um; mobile phase: phase A: water (0.05% HCl), phase B: acetonitrile; B %: 14%-44%] to give N-(1-(5-amino-2-fluoro-3-(trifluoromethyl)phenyl)ethyl)-7-bromo-4-methylphthalazin-1-amine (10.0 mg, 18.1 μmol, 2.86% yield, 80.0% purity) as a white solid. LCMS [M+1]$^+$: 443.1.

The racemic A-(1-(5-amino-2-fluoro-3-(trifluoromethyl) phenyl)ethyl)-7-bromo-4-methylphthalazin-1-amine (100 mg, 226 μmol, 1.00 eq.) was then purified by SFC [column: DAICEL CHIRALPAK AS (250 mm×30 mm, 10 um); mobile phase: phase A: (0.1% NH$_4$OH) in MeOH, phase B: CO$_2$; B %: 25%-25%] to give (R)—N-(1-(5-amino-2-fluoro-3-(trifluoromethyl)phenyl)ethyl)-7-bromo-4-methylphthalazin-1-amine as the first eluting isomer (20.0 mg, 45.1 μmol, 20.0% yield) as a white solid.

Step G: To a solution of (R)—N-(1-(5-amino-2-fluoro-3-(trifluoromethyl)phenyl)ethyl)-7-bromo-4-methylphthalazin-1-amine (20.0 mg, 45.1 μmol, 1.00 eq.), di-Zc N-butyl dicarbonate (11.8 mg, 54.2 μmol, 12.4 μL, 1.20 eq.) and N,N-dimethylpyridin-4-amine (5.51 mg, 45.1 μmol, 1.00 eq.) in dichloromethane (1.00 mL) was stirred at 20° C. for 1 hour. The mixture was poured into water (20.0 mL), and then extracted with ethyl acetate (20.0 mL G), and the combined organic layers were washed with brine (20.0 mL), dried over sodium sulfate, filtered, and concentrated under reduced pressure. The residue was purified by prep-TLC (silica gel, dichloromethane/methyl alcohol=20/1) to give tert-butyl (R)-(3-(1-((7-bromo-4-methylphthalazin-1-yl)amino)ethyl)-4-fluoro-5-(trifluoromethyl)phenyl)(tert-butoxycarbonyl)carbamate (15.0 mg, 23.3 μmol, 51.7% yield) as a gray solid. LCMS [M+3]$^+$: 644.9.

Step H: To a solution of tert-butyl (R)-(3-(1-((7-bromo-4-methylphthalazin-1-yl)amino)ethyl)-4-fluoro-5-(trifluoromethyl)phenyl)(tert-butoxycarbonyl)carbamate (15.0 mg, 23.3 μmol, 1.00 eq.), 3-methylazetidin-3-ol (7.46 mg, 46.6 μmol, 2.00 eq., HCl salt), RuPhos (2.18 mg, 4.66 μmol, 0.20 eq.), Pd$_2$(dba)$_3$ (2.13 mg, 2.33 μmol, 0.10 eq.) and cesium carbonate (38.0 mg, 0.12 mmol, 5.00 eq.) in 1,4-dioxane (2.00 mL) was stirred at 100° C. for 12 hours under a nitrogen atmosphere. The mixture was cooled to 25° C., poured into water (10.0 mL), and the resulting aqueous solution was extracted with ethyl acetate (10.0 mL×3). The combined organic layers were washed with brine (10.0 mL), dried over sodium sulfate, filtered, and concentrated under reduced pressure. The residue was purified by prep-TLC (silicon dioxide, dichloromethane:methyl alcohol=10:1) to give tert-butyl (R)-(4-fluoro-3-(1-((7-(3-hydroxy-3-methylazetidin-1-yl)-4-methylphthalazin-1-yl)amino)ethyl)-5-(trifluoromethyl)phenyl)carbamate (10.0 mg, 15.3 μmol, 66.0% yield) as a white solid. LCMS [M+1]$^+$: 550.1.

To a solution of tert-butyl (R)-(4-fluoro-3-(1-((7-(3-hydroxy-3-methyl azetidin-1-yl)-4-methylphthalazin-1-yl) amino)ethyl)-5-(trifluoromethyl)phenyl)carbamate (10.0 mg, 15.4 μmol, 1.00 eq.) in dichloromethane (1.00 mL) was added TFA (308 mg, 2.70 mmol, 0.20 mL, 175 eq.) dropwise at 20° C., and the reaction mixture was stirred at 20° C. for 1 hour. The mixture was then concentrated under reduced pressure, and the residue was purified by prep-HPLC [column: 3_Phenomenex Luna C18 75×30 mm×3 um; mobile phase: phase A: water(10 mM NH$_4$HCO$_3$), phase B: acetonitrile; B %: 20%-50%] to give (R)-1-(4-((1-(5-amino-2-fluoro-3-(trifluoromethyl)phenyl)ethyl)amino)-1-methylphthalazin-6-yl)-3-methylazetidin-3-ol (1.12 mg, 2.41 μmol, 15.6% yield, 96.6% purity) as an off-white solid. LCMS [M+1]$^+$: 450.4.

$^1$H NMR (400 MHz, CD$_3$OD) δ=7.80 (d, J=8.8 Hz, 1H), 7.10 (d, J=2.0 Hz, 1H), 6.97 (dd, J=8.8, 2.0 Hz, 1H), 6.83-6.80 (m, 1H), 6.67-6.64 (m, 1H), 5.51-5.45 (m, 1H), 3.99-3.95 (m, 2H), 3.89-3.84 (m, 2H), 2.51 (s, 3H), 1.55 (d, J=7.2 Hz, 3H), 1.51 (s, 3H).

SFC: Column: Chiralcel OD-3 50×4.6 mm I.D., 3 um Mobile phase: Phase A for CO$_2$, and Phase B for MeOH (0.05% diethylamine); Gradient elution: MeOH (0.05% diethylamine) in $CO_2$ from 5% to 40%; Flow rate: 3 mL/min; Detector: PDA; Column Temp: 35° C.; Back Pressure: 100 Bar.

Example A

This Example illustrates that exemplary compounds of the present invention bind to SOS1 and prevent a labeled tracer ligand from occupying the SOS1 binding site.

The ability of a compound of Formula (I) to bind to SOS1 was measured using a HTRF displacement assay. A recombinant human SOS1 polypeptide (corresponding to amino acids 564-1049, expressed in E. Coli with N-terminal StrepII-TEV, C-terminal His-tag. MW=60.59 kDa) was incubated with an exemplary compound of Formula (I) (in a DMSO stock solution) in buffer (25 mM HEPES pH 7.5, 25 mM NaCl, 1 mM DTT, 0.01% Brij 35, 0.02% BSA, 0.1% DMSO). After a 15-minute incubation at room temperature, a solution comprised of a custom-made Cy5 labelled tracer and MAb Anti-6HIS Tb cryptate Gold (Cisbio 61HI2TLA) in buffer was added to the solution containing the SOS1 polypeptide and exemplary compound of Formula (I). After a 1-hour incubation at room temperature, the HTRF signal was measured using Envision plate reader (Perkin Elmer) according to the manufacturer's instructions. Excitation was from over a range of 245-395 nm, and emission 1 was detected at (657.5-672.5) nm and emission 2 detected at (606.5-623.5) nm. The HTRF ratio was calculated using the formula: [emission 1/emission 2]*10000.

Background signals were calculated from well without protein added. The background subtracted signals were converted to % binding relative to DMSO controls. Data were analyzed using GraphPad Prism 4 software with the settings: "sigmoidal dose-response (variable slope)"; 4 parameters with Hill Slope (Constraints: Bottom=Constant equal to 0; Top=Must be less than 120).

The results are shown in Table 21. Key: N.D.=not determined.

TABLE 21

Inhibition of Labeled Tracer Binding to SOS1 by Exemplary Compounds of Formula (I)

| Example No. | $IC_{50}$ (nM) |
|---|---|
| 1-1 | 61 |
| 1-2 | 35 |
| 1-3 | 2.3 |
| 1-4 | 2.1 |
| 1-5 | 2.5 |
| 1-6 | 6.8 |
| 1-7 | 2.1 |
| 1-8 | 1.6 |
| 1-9 | 2.3 |
| 1-10 | 2.3 |
| 1-11 | >10000 |
| 1-12 | 664 |
| 1-13 | 31 |
| 1-14 | 25 |
| 1-15 | 2.7 |
| 1-16 | 1.6 |
| 1-17 | 6.2 |
| 1-18 | 0.73 |
| 1-19 | 2.6 |
| 1-20 | 145 |
| 1-21 | 1.8 |
| 1-22 | 1.7 |
| 1-23 | 2.4 |
| 2-1 | N.D. |
| 2-2 | 13 |
| 2-3 | 10 |

TABLE 21-continued

Inhibition of Labeled Tracer Binding to SOS1 by Exemplary Compounds of Formula (I)

| Example No. | $IC_{50}$ (nM) |
|---|---|
| 2-4 | 47.6 |
| 3-1 | 5.2 |
| 3-2 | 3.6 |
| 3-3 | 2.3 |
| 3-4 | 129 |
| 3-5 | 4 |
| 3-6 | 133 |
| 4-1 | 6.5 |
| 4-2 | 6.3 |
| 4-3 | 4.5 |
| 4-4 | 2.5 |
| 5-1 | 7.2 |
| 5-2 | 5.9 |

Example B

This Example illustrates that exemplary compounds of the present invention bind to SOS1 and prevent a labeled tracer ligand from occupying the S0S1 binding site.

The ability of a compound of Formula (I) to bind to SOS1 was measured using a HTRF displacement assay. A recombinant human SOS1 polypeptide (corresponding to amino acids 560-1049, expressed in E. Coli with N-terminal His-TEV-AviTag-SOS1 (MW=59.4 kDa) and lanthanide labeled streptavidin (CisBio) was incubated with an exemplary compound of Formula (I) (in a DMSO stock solution) in buffer (25 mM HEPES pH 7.5, 25 mM NaCl, 1 mM DTT, 0.01% Brij 35, 0.02% BSA, 0.1% DMSO). After a 10-15 minute incubation at room temperature, a solution comprised of a custom-made Cy5 labelled tracer and MAb Anti-6HIS Tb cryptate Gold (Cisbio 61HI2TLA) in buffer was added to the solution containing the SOS1 polypeptide and exemplary compound of Formula (I). After a 1-hour incubation at room temperature, the HTRF signal was measured using Clairostar plate reader (BMG Labtech) according to the manufacturer's instructions. Excitation filter EX-TR was used, and emission 1 was detected at 650-610 nm and emission 2 detected at 620-610 nm. The HTRF ratio was calculated using the formula: [emission 1/emission 2]*10000.

Background signals were calculated from well with a 10 µM inhibitor, known to inhibit 100% at that concentration. The background subtracted signals were converted to % binding relative to DMSO controls. Data were analyzed using XLFIT software (IDBS) using a Morrison equation for competitive binding and Ki's were generated compound of Formula (I).

The results are shown in Table 22.

TABLE 22

Inhibition of Labeled Tracer Binding to SOS1 by Exemplary Compounds of Formula (I)

| Example No. | $K_i$ (nM) |
|---|---|
| 1-24 | |
| 1-25 | 0.95 |
| 1-26 | 1.16 |
| 1-27 | |
| 1-28 | 0.17 |
| 1-29 | 0.51 |
| 1-30 | |
| 1-31 | |

TABLE 22-continued

Inhibition of Labeled Tracer Binding to SOS1 by Exemplary Compounds of Formula (I)

| Example No. | $K_i$ (nM) |
|---|---|
| 1-32 | 0.42 |
| 1-33 | 0.70 |
| 1-34 | 0.45 |
| 1-35 | 0.47 |
| 1-36 | |
| 1-37 | 0.25 |
| 1-38 | 0.50 |
| 1-39 | |
| 1-40 | 0.27 |
| 1-41 | |
| 1-42 | |
| 1-43 | 1.36 |
| 1-44 | 0.42 |
| 1-45 | 0.42 |
| 1-46 | |
| 1-47 | 2.08 |
| 1-48 | 0.56 |
| 1-49 | |
| 1-50 | |
| 2-5 | 1.78 |
| 2-6 | 2.10 |
| 2-7 | |
| 2-8 | 2.99 |
| 2-9 | |
| 2-10 | 1.72 |
| 2-11 | 2.83 |
| 2-12 | 5.75 |
| 5-3 | 390.50 |
| 5-4 | 47.90 |
| 6-1 | 0.11 |
| 6-2 | 1.35 |
| 6-3 | 0.02 |
| 6-4 | 0.11 |
| 6-5 | 0.12 |
| 6-6 | 0.11 |
| 6-7 | 0.29 |
| 6-8 | 39.20 |
| 6-9 | 0.24 |
| 6-10 | <0.01 |
| 6-11 | 9.10 |
| 6-12 | 0.88 |
| 6-13 | 0.29 |
| 6-14 | 5.51 |
| 6-15 | 12.55 |
| 6-16 | 10.07 |
| 6-17 | 56.45 |
| 6-18 | 316.70 |
| 6-19 | 2.32 |
| 7-1 | 0.40 |
| 7-2 | 0.33 |
| 7-3 | 0.32 |
| 7-4 | 0.47 |
| 7-5 | 0.82 |
| 7-6 | 1.41 |
| 7-7 | 0.92 |
| 8-1 | 1.38 |
| 8-2 | 3.74 |
| 9-1 | 109.00 |
| 9-2 | 0.93 |
| 10-1 | 3.07 |
| 10-2 | 14.90 |
| 10-3 | 0.71 |
| 10-4 | 0.08 |
| 10-5 | <0.01 |
| 10-6 | 0.64 |
| 10-7 | 0.07 |
| 10-8 | 0.09 |
| 10-9 | 0.05 |
| 10-10 | 0.01 |
| 10-11 | 0.01 |
| 10-12 | 0.40 |
| 10-13 | 0.49 |
| 10-14 | |
| 10-15 | |
| 10-16 | 7.75 |
| 10-17 | |
| 10-18 | 1.41 |
| 10-19 | 0.28 |
| 10-20 | |
| 10-21 | |
| 10-22 | 0.45 |
| 10-23 | 0.42 |
| 10-24 | 1.34 |
| 10-25 | 1.47 |
| 10-26 | 0.47 |
| 10-27 | 0.46 |
| 10-28 | 0.45 |
| 10-29 | 0.39 |
| 10-30 | 0.41 |
| 10-31 | 0.35 |
| 10-32 | 0.20 |
| 10-33 | 0.69 |
| 10-34 | 0.56 |
| 10-35 | 0.31 |
| 10-36 | 0.23 |
| 10-37 | 0.24 |
| 10-38 | 0.71 |
| 10-39 | 1.49 |
| 10-40 | 0.43 |
| 10-41 | 0.52 |
| 10-42 | 0.31 |
| 10-43 | 1.13 |
| 10-44 | 0.51 |
| 10-45 | 2.16 |
| 10-46 | 1.13 |
| 10-47 | 1.19 |
| 10-48 | 1.35 |
| 10-49 | 0.56 |
| 10-50 | 3.74 |
| 10-51 | 1.40 |
| 10-52 | 44.45 |
| 10-53 | |
| 10-54 | 1.34 |
| 10-55 | 0.76 |
| 10-56 | 1.59 |
| 10-57 | 0.75 |
| 10-58 | 5.78 |
| 10-59 | 30.91 |
| 10-60 | 2.00 |
| 10-61 | 1.61 |
| 10-62 | 0.90 |
| 10-63 | 0.54 |
| 10-64 | 1.70 |
| 10-65 | 0.95 |
| 10-66 | 0.78 |
| 10-67 | 2.57 |
| 10-68 | 0.75 |
| 10-69 | 3.07 |
| 10-70 | 0.89 |
| 10-71 | 0.39 |
| 10-72 | 46.10 |
| 10-73 | 0.63 |
| 10-74 | 4.26 |
| 10-75 | 6.51 |
| 10-76 | 3.44 |
| 10-77 | 0.75 |
| 10-78 | 1.16 |
| 10-79 | 4.15 |
| 10-80 | 5.75 |
| 10-81 | 0.90 |
| 10-82 | 0.86 |
| 10-83 | 4.54 |
| 10-84 | 2.01 |
| 10-85 | 0.78 |
| 10-86 | 1.51 |
| 10-87 | |
| 11-1 | 0.01 |
| 11-2 | <0.01 |
| 11-3 | <0.01 |
| 11-4 | 0.01 |

TABLE 22-continued

Inhibition of Labeled Tracer Binding to SOS1 by Exemplary Compounds of Formula (I)

| Example No. | $K_i$ (nM) |
|---|---|
| 11-5 | 0.01 |
| 11-6 | 0.42 |
| 12-1 | 0.20 |
| 12-2 | 0.60 |
| 12-3 | 0.74 |
| 12-4 | |
| 12-5 | |
| 12-6 | 0.87 |
| 12-7 | 0.40 |
| 12-8 | 1.14 |
| 12-9 | 0.47 |
| 12-10 | 1.78 |
| 12-11 | 8.76 |
| 12-12 | 21.64 |
| 12-13 | 1.57 |
| 12-14 | 0.55 |
| 12-15 | 0.25 |
| 12-16 | 0.87 |
| 12-17 | 0.46 |
| 12-18 | 0.62 |
| 12-19 | 1.00 |
| 12-20 | 1.60 |
| 12-21 | 1.32 |
| 12-22 | 1.24 |
| 12-23 | 1.05 |
| 12-24 | 1.24 |
| 12-25 | 2.41 |
| 12-26 | 0.45 |
| 12-27 | 2.81 |
| 12-28 | 1.53 |
| 12-29 | 1.67 |
| 12-30 | 2.63 |
| 12-31 | 1.02 |
| 12-32 | 0.97 |
| 12-33 | 0.30 |
| 12-34 | 4.24 |
| 12-35 | 3.78 |
| 12-36 | 0.99 |
| 12-37 | 0.85 |
| 12-38 | 1.29 |
| 12-39 | 0.91 |
| 12-40 | 0.64 |
| 12-41 | 40.24 |
| 12-42 | 0.79 |
| 12-43 | 3.38 |
| 12-44 | 1.16 |
| 12-45 | 3.78 |
| 12-46 | 0.92 |
| 12-47 | 38.69 |
| 12-48 | 16.96 |
| 12-49 | 39.66 |
| 12-50 | 3.02 |
| 12-51 | 0.79 |
| 12-52 | 1.06 |
| 12-53 | 0.83 |
| 12-54 | 5.37 |
| 12-55 | 3.10 |
| 12-56 | 31.09 |
| 12-57 | 92.17 |
| 12-58 | 14.62 |
| 12-59 | 0.47 |
| 12-60 | 0.25 |
| 12-61 | 1.68 |
| 12-62 | |
| 12-63 | 0.83 |
| 12-64 | 0.51 |
| 12-65 | 0.72 |
| 12-66 | 2.10 |
| 12-67 | 0.36 |
| 12-68 | 0.37 |
| 12-69 | 0.93 |
| 12-70 | 0.68 |
| 12-71 | 4.48 |
| 12-72 | 4.39 |
| 12-73 | 1.67 |
| 12-74 | 10.48 |
| 12-75 | 13.99 |
| 12-76 | 1.06 |
| 12-77 | 28.51 |
| 12-78 | 2.66 |
| 12-79 | 36.27 |
| 12-80 | 37.38 |
| 12-81 | 28.98 |
| 12-82 | 20.95 |
| 12-83 | 50.64 |
| 12-84 | 43.44 |
| 12-85 | 27.62 |
| 12-86 | 0.98 |
| 12-87 | 3.17 |
| 12-88 | 2.03 |
| 12-89 | 0.25 |
| 12-90 | |
| 12-91 | |
| 12-92 | |
| 12-93 | |
| 12-94 | |
| 12-95 | |
| 12-96 | |
| 12-97 | |
| 12-98 | 19.04 |
| 12-99 | 0.93 |
| 12-100 | 1.07 |
| 12-101 | 1.45 |
| 12-102 | 0.25 |
| 12-103 | 10.93 |
| 12-104 | 6.10 |
| 12-105 | 10.89 |
| 12-106 | 11.05 |
| 12-107 | 35.65 |
| 12-108 | 22.11 |
| 12-109 | 2.61 |
| 12-110 | 3.54 |
| 12-111 | 8.09 |
| 12-112 | 2.20 |
| 12-113 | 2.62 |
| 12-114 | 69.26 |
| 12-115 | 1.66 |
| 12-116 | |
| 12-117 | |
| 12-118 | |
| 12-119 | |
| 12-120 | 49.78 |
| 12-121 | 39.24 |
| 12-122 | 170.30 |
| 12-123 | 50.43 |
| 12-124 | 64.46 |
| 12-125 | 10.29 |
| 12-126 | 14.04 |
| 12-127 | 6.08 |
| 12-128 | |
| 12-129 | |
| 12-130 | |
| 12-131 | 3.6 |
| 12-132 | 11 |
| 12-133 | 11.5 |
| 12-134 | 7.1 |
| 13-1 | 2.77 |
| 13-2 | 191.10 |
| 13-3 | 12.23 |
| 14-1 | 8.97 |
| 14-2 | |
| 14-3 | 14.46 |
| 14-4 | 8.55 |
| 14-5 | 2.54 |
| 14-6 | 2.56 |
| 15-1 | 3.37 |
| 15-2 | 0.42 |
| 15-3 | 0.94 |
| 16-1 | 14.42 |
| 16-2 | 19.40 |

TABLE 22-continued

Inhibition of Labeled Tracer Binding to SOS1 by Exemplary Compounds of Formula (I)

| Example No. | $K_i$ (nM) |
|---|---|
| 16-3 | 13.41 |
| 16-4 | 10.41 |
| 16-5 | 5.50 |
| 16-6 | 6.50 |
| 16-7 | 78.79 |
| 16-8 | 21.24 |
| 16-9 | 35.62 |
| 16-10 | 81.01 |
| 16-11 | 107.50 |
| 16-12 | 9.58 |
| 16-13 | 25.82 |
| 16-14 | 1.71 |
| 17-1 | 4.33 |
| 17-2 | 12.47 |
| 17-3 | 12.80 |
| 17-4 | 14.39 |
| 18-1 | 0.98 |
| 18-2 | 5.27 |
| 18-3 | 1.37 |
| 18-4 | 1.64 |
| 19-1 | 6.16 |
| 19-2 | 95.00 |
| 19-3 | 19.28 |
| 20-1 | 0.92 |
| 20-2 | 0.75 |
| 20-3 | 0.92 |
| 20-5 | 0.40 |
| 21-1 | 2.93 |
| 21-2 | 1.67 |
| 21-3 | 14.41 |
| 21-4 | 13.69 |
| 21-5 | 1.34 |
| 21-6 | 0.93 |
| 21-7 | 0.71 |
| 21-8 | 3.17 |
| 21-9 | 2.10 |
| 21-10 | 5.73 |
| 21-11 | |

As shown in Table 22, exemplary compounds of the present invention potently inhibited the binding of a SOS1 labeled tracer to SOS1 protein.

Example C

This Example illustrates that exemplary compounds of the present invention bind to SOS1 and inhibit the SOS1-mediated nucleotide exchange of mantGDP (preloaded into human KRAS) with GTP within a recombinant human KRAS.

The ability of an exemplary compound of Formula (I) to bind to SOS1 and inhibit the nucleotide exchange of mantGDP with GTP within recombinant human KRAS was measured using a fluorescence assay. Recombinant human SOS1 polypeptide (corresponding to amino acids 564-1049, expressed in E. coli with a C-terminal StrepII tag. MW=60.59 kDa) in buffer (40 mM HEPES 7.4, 10 mM MgCl2, 1 mM DTT, 0.002% Triton X100, 0.1% DMSO) was incubated with an exemplary compound of Formula (I) (in a DMSO stock solution) at room temperature for 15 minutes. A mixture of preloaded mantGDP recombinant human KRAS polypeptide (corresponding to amino acids 2-169, expressed in E. coli with an N-terminal TEV cleavable his-tag. MW 21.4 kDa) and GTP was incubated for 5 minutes in buffer (40 mM HEPES 7.4, 10 mM MgCl2, 1 mM DTT 0.002%, Triton X100, 0.1% DMSO) at room temperature, then added to the SOS1/compound mixture. Reaction progress was monitored at room temperature for 60 minutes using a Clariostar plate reader (excitation 370±15 nm, emission 450±20 nm) according to the manufacturer's instructions. The slope of the linear portion of the progress curve was calculated using a Clariostar software. Typical analysis interval was 8-30 minutes. Background signals were calculated from well without protein added. The background subtracted signals were converted to % activity relative to DMSO controls. Data were analyzed using GraphPad Prism 4 software with the settings: "sigmoidal dose-response (variable slope)"; 4 parameters with Hill Slope (Constraints: Bottom=Constant equal to 0; Top=Must be less than 120).

The fluorescence readout $IC_{50}$ for exemplary compounds of Formula (I) is shown in Table 23.

TABLE 23

| Example No. | $IC_{50}$(nM) |
|---|---|
| 1-1 | 35 |
| 1-2 | 20 |
| 1-4 | 7 |
| 1-5 | 9 |
| 1-6 | 12 |
| 1-7 | 8 |
| 1-8 | 8 |
| 1-9 | 7 |
| 1-10 | 9 |

As shown in Table 23, exemplary compounds of the present invention were capable of potently inhibiting SOS1-mediated GTP nucleotide exchange by blocking mant-GDP exchange.

Example D

This Example illustrates that exemplary compounds of the present invention prevent KRas-mediated GTP nucleotide exchange mediated by SOS1 to inhibit KRas activity thereby inhibiting the generation of the downstream effector pERK.

MKN1 cells (15,000/w) or H358 (30,000/w) were seeded in a black clear flat bottom 96-well cell culture plate (Corning, #3904) and incubated at 37° C. overnight. Assay day 1, cells were dosed with compounds of Formula (I) with a 10 µm starting concentration and serially diluted 3× for a total of 9 concentrations. The cells were incubated for approximately 0.5-1 hour with the compounds solubilized in DMSO at 37° C. Cells were immediately fixed by adding 50 µL of 4% formaldehyde to all wells in a fume hood and the plates were incubated for 20 minutes at room temperature. The formaldehyde was discarded from the plates and 150 µL of ice-cold methanol was added to permeabilize the cells for 10 minutes at −20° C. The methanol was discarded from each of the plates and any liquid remaining in the plate by tapping the plate against paper towels. Cells were then blocked with 150 µL of Odyssey blocking buffer (LI-COR Biosciences #927-50010) using 0.05% Tween for 1 hour at room temperature on a shaker. The blocking buffer was discarded and 50 µL of primary antibodies pERK (cell signaling Technology #9101L; Rabbit, 1:500) and GapDH (Millipore #MAB34; Mouse, 1:5000) diluted in Odyssey blocking buffer was added. The plates were incubated overnight at 4° C. on a shaker.

On Assay day 2, the primary antibody solution was removed. Each plate was washed 3× times with 150 µL of 1×PBST (PBS+0.1% Tween 20) and incubated with 50 µL of secondary antibodies: Anti-Rabbit (LI-COR Biosciences #926-32211) and Anti-Mouse (LI-COR Biosciences #68070) at 1:800 dilution in Odyssey blocking buffer with Tween at room temperature on a shaker for 2 hours (protected from light). The secondary antibody solution as removed and each plate was washed with PBST 3× times. Any liquid remaining was discarded and the plate was imaged using the Licor Odyssey machine according to the manufacturer's instruction, using a set focus length at 3 mm and both 800 nm and 700 nm filters. The GAPDH normalized scan values for each well were divided by the average of vehicle wells to get the % of pERK inhibition. The IC50 values were then calculated with the Graph pad Prism software.

The results are shown in Table 24. Key: N.D.=not determined.

TABLE 24

| Example No. | $IC_{50}$ (nM) |
|---|---|
| 1-2 | 1050 |
| 1-3 | 52 |
| 1-4 | 134 |
| 1-5 | 60 |
| 1-6 | 54 |
| 1-7 | 31 |
| 1-8 | 66 |
| 1-9 | 90 |
| 1-10 | 132 |
| 1-11 | >10,000 |
| 1-12 | 3965 |
| 1-13 | 378 |
| 1-14 | 165 |
| 1-15 | 24 |
| 1-16 | 348 |
| 1-17 | 414 |
| 1-18 | 58 |
| 1-19 | 116 |
| 1-20 | 3739 |
| 1-21 | 187 |
| 1-22 | 70 |
| 1-23 | 58 |
| 1-24 | 25 |
| 1-25 | 47 |
| 1-26 | 57 |
| 1-27 | 61 |
| 1-28 | 61 |
| 1-29 | 71 |
| 1-30 | 79 |
| 1-31 | 83 |
| 1-32 | 101 |
| 1-33 | 109 |
| 1-34 | 119 |
| 1-35 | 123 |
| 1-36 | 125 |
| 1-37 | 131 |
| 1-38 | 136 |
| 1-39 | 170 |
| 1-40 | 171 |
| 1-41 | 195 |
| 1-42 | 201 |
| 1-43 | 216 |
| 1-44 | 235 |
| 1-45 | 335 |
| 1-46 | 341 |
| 1-47 | 349 |
| 1-48 | 364 |
| 1-49 | 426 |
| 1-50 | 453 |
| 2-1 | 308 |
| 2-2 | 118 |
| 2-3 | 45 |
| 2-4 | 1929 |
| 2-5 | 82 |
| 2-6 | 83 |
| 2-7 | 142 |
| 2-8 | 148 |
| 2-9 | 172 |
| 2-10 | 223 |
| 2-11 | 243 |

TABLE 24-continued

| Example No. | $IC_{50}$ (nM) |
|---|---|
| 2-12 | 304 |
| 3-1 | 128 |
| 3-2 | 69 |
| 3-3 | 20 |
| 3-4 | 1059 |
| 3-5 | 4218 |
| 3-6 | 4259 |
| 4-1 | 327 |
| 4-2 | 131 |
| 4-3 | 71 |
| 4-4 | 130 |
| 5-1 | 669 |
| 5-2 | 120 |
| 5-3 | N.D. |
| 5-4 | 1623 |
| 6-1 | 79 |
| 6-2 | 100 |
| 6-3 | 12 |
| 6-4 | 47 |
| 6-5 | 10 |
| 6-6 | 40 |
| 6-7 | 74 |
| 6-8 | N.D. |
| 6-9 | 48 |
| 6-10 | 271 |
| 6-11 | 31 |
| 6-12 | 30 |
| 6-13 | 20 |
| 6-14 | 320 |
| 6-15 | 172 |
| 6-16 | 333 |
| 6-17 | 412 |
| 6-18 | 3696 |
| 6-19 | 242 |
| 7-1 | 79 |
| 7-2 | 73 |
| 7-3 | 28 |
| 7-4 | 14 |
| 7-5 | 110 |
| 7-6 | 110 |
| 7-7 | 115 |
| 8-1 | 164 |
| 8-2 | 605 |
| 9-1 | >10,000 |
| 9-2 | 176 |
| 10-1 | 183 |
| 10-2 | 1366 |
| 10-3 | 85 |
| 10-4 | 14 |
| 10-5 | 108 |
| 10-6 | 21 |
| 10-7 | 22 |
| 10-8 | 34 |
| 10-9 | 54 |
| 10-10 | 17 |
| 10-11 | 22 |
| 10-12 | 29 |
| 10-13 | 39 |
| 10-14 | 1150 |
| 10-15 | 844 |
| 10-16 | 325 |
| 10-17 | 2629 |
| 10-18 | 291 |
| 10-19 | 69 |
| 10-20 | 1646 |
| 10-21 | 444 |
| 10-22 | 38 |
| 10-23 | 19 |
| 10-24 | 69 |
| 10-25 | 103 |
| 10-26 | 164 |
| 10-27 | 154 |
| 10-28 | 161 |
| 10-29 | 70 |
| 10-30 | 48 |
| 10-31 | 3585 |
| 10-32 | 28 |
| 10-33 | 275 |

TABLE 24-continued

| Example No. | IC$_{50}$ (nM) |
|---|---|
| 10-34 | 136 |
| 10-35 | 1000 |
| 10-36 | 79 |
| 10-37 | 55 |
| 10-38 | 29 |
| 10-39 | 110 |
| 10-40 | 11 |
| 10-41 | 30 |
| 10-42 | 43 |
| 10-43 | 138 |
| 10-44 | 53 |
| 10-45 | 57 |
| 10-46 | 157 |
| 10-47 | 55 |
| 10-48 | 75 |
| 10-49 | 107 |
| 10-50 | 205 |
| 10-51 | 39 |
| 10-52 | 286 |
| 10-53 | |
| 10-54 | 48 |
| 10-55 | 76 |
| 10-56 | 26 |
| 10-57 | 46 |
| 10-58 | 52 |
| 10-59 | 570 |
| 10-60 | 961 |
| 10-61 | 57 |
| 10-62 | 76 |
| 10-63 | 50 |
| 10-64 | 513 |
| 10-65 | 23 |
| 10-66 | 108 |
| 10-67 | 44 |
| 10-68 | 36 |
| 10-69 | 39 |
| 10-70 | 15 |
| 10-71 | 19 |
| 10-72 | 466 |
| 10-73 | 49 |
| 10-74 | 65 |
| 10-75 | 56 |
| 10-76 | 85 |
| 10-77 | 102 |
| 10-78 | 114 |
| 10-79 | 16 |
| 10-80 | |
| 10-81 | |
| 10-82 | 52 |
| 10-83 | |
| 10-84 | |
| 10-85 | 18 |
| 10-86 | 21 |
| 10-87 | |
| 11-1 | 10 |
| 11-2 | 27 |
| 11-3 | 48 |
| 11-4 | 25 |
| 11-5 | 12 |
| 11-6 | 55 |
| 12-1 | 5 |
| 12-2 | 9 |
| 12-3 | 30 |
| 12-4 | 370 |
| 12-5 | 850 |
| 12-6 | 522 |
| 12-7 | 66 |
| 12-8 | 38 |
| 12-9 | 10 |
| 12-10 | 46 |
| 12-11 | 142 |
| 12-12 | 249 |
| 12-13 | 39 |
| 12-14 | 17 |
| 12-15 | 17 |
| 12-16 | 11 |
| 12-17 | 17 |
| 12-18 | 37 |
| 12-19 | 59 |
| 12-20 | 62 |
| 12-21 | 57 |
| 12-22 | 89 |
| 12-23 | 46 |
| 12-24 | 38 |
| 12-25 | 35 |
| 12-26 | 27 |
| 12-27 | 14 |
| 12-28 | 17 |
| 12-29 | 16 |
| 12-30 | 54 |
| 12-31 | 70 |
| 12-32 | 18 |
| 12-33 | 55 |
| 12-34 | 51 |
| 12-35 | 35 |
| 12-36 | 12 |
| 12-37 | 32 |
| 12-38 | 97 |
| 12-39 | 75 |
| 12-40 | 24 |
| 12-41 | 1274 |
| 12-42 | 27 |
| 12-43 | 44 |
| 12-44 | 38 |
| 12-45 | 250 |
| 12-46 | 37 |
| 12-47 | 307 |
| 12-48 | 114 |
| 12-49 | 161 |
| 12-50 | 25 |
| 12-51 | 48 |
| 12-52 | 60 |
| 12-53 | 47 |
| 12-54 | 45 |
| 12-55 | 59 |
| 12-56 | 301 |
| 12-57 | 1857 |
| 12-58 | 38 |
| 12-59 | 19 |
| 12-60 | 24 |
| 12-61 | 21 |
| 12-62 | |
| 12-63 | |
| 12-64 | 29 |
| 12-65 | 16 |
| 12-66 | 77 |
| 12-67 | |
| 12-68 | |
| 12-69 | |
| 12-70 | 13 |
| 12-71 | |
| 12-72 | 19 |
| 12-73 | |
| 12-74 | |
| 12-75 | 87 |
| 12-76 | 56 |
| 12-77 | |
| 12-78 | 94 |
| 12-79 | 173 |
| 12-80 | 295 |
| 12-81 | |
| 12-82 | 330 |
| 12-83 | 749 |
| 12-84 | 280 |
| 12-85 | 602 |
| 12-86 | |
| 12-87 | |
| 12-88 | |
| 12-89 | |
| 12-90 | |
| 12-91 | |
| 12-92 | |
| 12-93 | |
| 12-94 | |
| 12-95 | |
| 12-96 | |

TABLE 24-continued

| Example No. | IC$_{50}$ (nM) |
|---|---|
| 12-97 | |
| 12-98 | |
| 12-99 | |
| 12-100 | |
| 12-101 | 22 |
| 12-102 | |
| 12-103 | 107 |
| 12-104 | 92 |
| 12-105 | 97 |
| 12-106 | 114 |
| 12-107 | |
| 12-108 | |
| 12-109 | |
| 12-110 | |
| 12-111 | |
| 12-112 | |
| 12-113 | |
| 12-114 | |
| 12-115 | 19 |
| 12-116 | |
| 12-117 | |
| 12-118 | |
| 12-119 | |
| 12-120 | |
| 12-121 | |
| 12-122 | |
| 12-123 | |
| 12-124 | 856 |
| 12-125 | 114 |
| 12-126 | |
| 12-127 | |
| 12-128 | |
| 12-129 | |
| 12-130 | |
| 12-131 | 28 |
| 12-132 | 76 |
| 12-133 | 97 |
| 12-134 | |
| 13-1 | 149 |
| 13-2 | 2068 |
| 13-3 | 195 |
| 14-1 | 68 |
| 14-2 | 139 |
| 14-3 | |
| 14-4 | 89 |
| 14-5 | 70 |
| 14-6 | 142 |
| 15-1 | 28 |
| 15-2 | 8 |
| 15-3 | 34 |
| 16-1 | 245 |
| 16-2 | 284 |
| 16-3 | 208 |
| 16-4 | 371 |
| 16-5 | 71 |
| 16-6 | 239 |
| 16-7 | 2904 |
| 16-8 | 93 |
| 16-9 | 643 |
| 16-10 | 919 |
| 16-11 | |
| 16-12 | |
| 16-13 | >10000 |
| 16-14 | 37 |
| 17-1 | 30 |
| 17-2 | 50 |
| 17-3 | 188 |
| 17-4 | 116 |
| 18-1 | 128 |
| 18-2 | 380 |
| 18-3 | |
| 18-4 | 41 |
| 19-1 | 156 |
| 19-2 | 779 |
| 19-3 | 114 |
| 20-1 | 11 |
| 20-2 | 8 |
| 20-3 | 16 |
| 20-5 | |
| 21-1 | 77 |
| 21-2 | 137 |
| 21-3 | 221 |
| 21-4 | 118 |
| 21-5 | 1114 |
| 21-6 | 176 |
| 21-7 | 26 |
| 21-8 | 90 |
| 21-9 | 54 |
| 21-10 | 58 |
| 21-11 | |

The results in Table 24 illustrate that the compounds of the present invention are capable of potently inhibiting KRas-mediated activation and formation of pERK thereby blocking intracellular KRas-mediated signaling.

Example E

This Example illustrates that exemplary compounds of the present invention prevent KRas-mediated GTP nucleotide exchange mediated by SOS1, in a SOS1 N233Y mutant cell line, to inhibit KRas activity thereby inhibiting the generation of the downstream effector Perk.

Three cell lines harboring SOS1 N233Y activation mutations, LXF289 (DSMZ, Leibniz Institute, Germany) RL95-2 (ATCC CRL-1671); and OCI AML-5 (DSMZ, Leibniz Institute, Germany) were used in the studies. SOS1 N233Y mutant cells (15,000/w) were seeded in a black clear flat bottom 96-well cell culture plate (Corning, #3904) and incubated at 37° C. overnight. Assay day 1, cells were dosed with compounds of Formula (I) with a 10 µm starting concentration and serially diluted 3× for a total of 9 concentrations. The cells were incubated for 1 hour with the compounds solubilized in DMSO at 37° C. Cells were immediately fixed by adding 50 µL of 4% formaldehyde to all wells in a fume hood and the plates were incubated for 20 minutes at room temperature. The formaldehyde was discarded from the plates and 150 µL of ice-cold methanol was added to permeabilize the cells for 10 minutes at −20° C. The methanol was discarded from each of the plates and any liquid remaining in the plate by tapping the plate against paper towels. Cells were then blocked with 150 µL of Odyssey blocking buffer (LI-COR Biosciences #927-50010) using 0.05% Tween for 1 hour at room temperature on a shaker. The blocking buffer was discarded and 50 µL of primary antibodies pERK (cell signaling Technology #9101L; Rabbit, 1:500) and GapDH (Millipore #MAB34; Mouse, 1:5000) diluted in Odyssey blocking buffer was added. The plates were incubated overnight at 4° C. on a shaker.

On Assay day 2, the primary antibody solution was removed. Each plate was washed 3× times with 150 µL of 1×PBST (PBS+0.1% Tween 20) and incubated with 50 µL of secondary antibodies: Anti-Rabbit (LI-COR Biosciences #926-32211) and Anti-Mouse (LI-COR Biosciences #68070) at 1:800 dilution in Odyssey blocking buffer with Tween at room temperature on a shaker for 2 hours (protected from light). The secondary antibody solution as removed and each plate was washed with PBST 3× times. Any liquid remaining was discarded and the plate was imaged using the Licor Odyssey machine according to the manufacturer's instruction, using a set focus length at 3 mm and both 800 nm and 700 nm filters. The GAPDH normalized scan values for each well were divided by the average of vehicle wells to get the % of pERK inhibition. The IC50 values were then calculated with the Graph pad Prism software.

The results are shown in Table 25.

TABLE 25

| Cell Line | Example No. | IC$_{50}$ (nM) |
|---|---|---|
| LXF289 | 6-10 | 294 |
|  | 6-11 | 41 |
| RL95-2 | 6-10 | 214 |
|  | 6-11 | 20 |
| OCI AML-5 | 6-10 | 333 |
|  | 6-11 | 32 |

The results in Table 25 illustrate that the compounds of the present invention are capable of potently inhibiting KRas-mediated activation and formation of pERK in cells harboring a SOS1 activating mutation thereby blocking intracellular KRas-mediated signaling driven by increased SOS1 activity.

Example F

This Example illustrates that exemplary compounds of the present invention prevent increased KRas-mediated GTP nucleotide exchange mediated by SOS1 in NF-1 mutant cell lines to inhibit KRas activity thereby inhibiting the generation of the downstream effector pERK.

Two cell lines harboring activating mutations in NF-1 gene, Kasuma-1 (ATCC CRL-2724; and NCI-H1435 (ATCC CRL-5870), were employed in these studies. NF-1 mutant cells (15,000/w) were seeded in a black clear flat bottom 96-well cell culture plate (Corning, #3904) and incubated at 37° C. overnight. Assay day 1, cells were dosed with compounds of Formula (I) with a 10 µm starting concentration and serially diluted 3× for a total of 9 concentrations. The cells were incubated for 1 hour with the compounds solubilized in DMSO at 37° C. Cells were immediately fixed by adding 50 µL of 4% formaldehyde to all wells in a fume hood and the plates were incubated for 20 minutes at room temperature. The formaldehyde was discarded from the plates and 150 µL of ice-cold methanol was added to permeabilize the cells for 10 minutes at −20° C. The methanol was discarded from each of the plates and any liquid remaining in the plate by tapping the plate against paper towels. Cells were then blocked with 150 µL of Odyssey blocking buffer (LI-COR Biosciences #927-50010) using 0.05% Tween for 1 hour at room temperature on a shaker. The blocking buffer was discarded and 50 µL of primary antibodies pERK (cell signaling Technology #9101L; Rabbit, 1:500) and GapDH (Millipore #MAB34; Mouse, 1:5000) diluted in Odyssey blocking buffer was added. The plates were incubated overnight at 4° C. on a shaker.

On Assay day 2, the primary antibody solution was removed. Each plate was washed 3× times with 150 µL of 1×PBST (PBS+0.1% Tween 20) and incubated with 50 µL of secondary antibodies: Anti-Rabbit (LI-COR Biosciences #926-32211) and Anti-Mouse (LI-COR Biosciences #68070) at 1:800 dilution in Odyssey blocking buffer with Tween at room temperature on a shaker for 2 hours (protected from light). The secondary antibody solution as removed and each plate was washed with PBST 3× times. Any liquid remaining was discarded and the plate was imaged using the Licor Odyssey machine according to the manufacturer's instruction, using a set focus length at 3 mm and both 800 nm and 700 nm filters. The GAPDH normalized scan values for each well were divided by the average of vehicle wells to get the % of pERK inhibition. The IC$_{50}$ values were then calculated with the Graph pad Prism software.

The results are shown in Table 26.

TABLE 26

| Cell Line | Example No. | IC$_{50}$ (nM) |
|---|---|---|
| Kasumi | 6-10 | 902 |
|  | 6-11 | 97 |
| H1435 | 6-3 | 25 |
|  | 6-4 | 51 |
|  | 6-5 | 9 |
|  | 6-6 | 29 |
|  | 6-9 | 52 |
|  | 6-10 | 542 |
|  | 6-11 | 65 |
|  | 6-12 | 63 |
|  | 7-3 | 55 |
|  | 7-4 | 83 |
|  | 10-4 | 33 |
|  | 10-6 | 75 |
|  | 10-7 | 87 |
|  | 10-8 | 94 |
|  | 10-9 | 152 |
|  | 10-10 | 15 |
|  | 10-11 | 63 |
|  | 11-1 | 6 |
|  | 11-2 | 17 |
|  | 11-3 | 62 |
|  | 11-4 | 19 |

The results in Table 26 illustrate that the compounds of the present invention are capable of potently inhibiting KRas-mediated activation and formation of pERK in cells harboring NF-1 activating mutations thereby blocking intracellular KRas-mediated signaling driven by NF-1 driven increased SOS1 activity.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound of Formula (I):

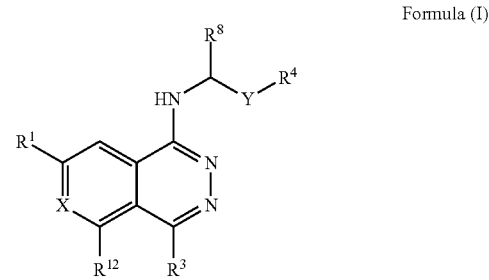

Formula (I)

or a pharmaceutically acceptable salt thereof, wherein:

$R^1$ is hydrogen, hydroxyl, C1-C6 alkyl, alkoxy, —N($R^6$)$_2$, —N$R^6$C(O)$R^6$, —C(O)N($R^6$)$_2$, —SO$_2$alkyl, —SO$_2$N$R^6$alkyl, cycloalkyl, -Q-heterocyclyl, aryl, or heteroaryl, wherein the cycloalkyl, the heterocyclyl, the aryl, and the heteroaryl are each optionally substituted with one or more $R^2$ or L-$R^2$;

each Q is independently a bond, O, or N$R^6$;

X is N;

each $R^2$ is independently C1-C3 alkyl, oxo, hydroxy, halogen, cyano, hydroxyalkyl, haloalkyl, alkoxy, —C(O)N($R^6$)$_2$, —N($R^6$)$_2$, —SO$_2$alkyl, —N$R^6$C(O) C1-C3 alkyl, —C(O)cycloalkyl, —C(O)C1-C3 alkyl, —C(O)heterocyclyl, aryl, heteroaryl or heterocyclyl, wherein the cycloalkyl, the heterocyclyl, the aryl, the heteroaryl or the heterocyclyl are each optionally substituted with one or more $R^{11}$;

$R^3$ is hydrogen, C1-C6 alkyl, alkoxy, —N($R^{10}$)$_2$, -L-N($R^{10}$)$_2$, cycloalkyl, haloalkyl or heterocyclyl, wherein the C1-C6 alkyl, the cycloalkyl and the heterocyclyl, are each optionally substituted with one or more $R^9$;

Y is a bond or heteroarylene;

$R^4$ is aryl or heteroaryl, each optionally substituted with one or more $R^5$;

each $R^5$ is independently hydroxy, halogen, cyano, hydroxyalkyl, alkoxy, C1-C3 alkyl, haloalkyl, haloalkyl-OH, —N($R^6$)$_2$, -L-N($R^6$)$_2$ or —SO$_2$alkyl;

L is C1-C3 alkylene;

each $R^6$ is independently hydrogen, C1-C3 alkyl, haloalkyl, or cycloalkyl;

$R^7$ is hydrogen, cyano, CF$_3$, F, or alkoxy;

$R^8$ is C1-C2 alkyl or halo-C1-C2 alkyl;

each $R^9$ is independently hydroxy, halogen, amino, cyano, alkoxy, or C1-C3 alkyl;

each $R^{10}$ is independently hydrogen, C1-C3 alkyl or cycloalkyl;

each $R^{11}$ is independently C1-C3 alkyl, halogen or haloalkyl; and $R^{12}$ is hydrogen, halogen or C1-C3 alkyl.

2. The compound according to claim 1, wherein $R^1$ is alkoxy or -Q-heterocyclyl, wherein the heterocyclyl is optionally substituted with one or more $R^2$ or L-$R^2$.

3. The compound according to claim 2, wherein $R^1$ is -Q-heterocyclyl, and wherein Q is a bond or —O— and the heterocyclyl is morpholinyl, piperazinyl, or piperazinone.

4. The compound according to claim 3, wherein $R^1$ is -Q-heterocyclyl, and wherein the heterocyclyl is bridged morpholinyl, bridged piperazinyl, or bridged piperazinone.

5. The compound according to claim 2, wherein $R^1$ is -Q-heterocyclyl, and wherein the heterocyclyl is spirocyclic ring system containing two or more rings.

6. The compound according to claim 5, wherein the spirocyclic ring system comprises two rings each containing a heteroatom.

7. The compound according to claim 5, wherein the spirocyclic ring system contains a ring with no heteroatom.

8. The compound according to claim 1, wherein $R^1$ is heteroaryl, wherein the heteroaryl is optionally substituted with one or more $R^2$ or L-$R^2$.

9. The compound according to claim 8, wherein the heteroaryl is a bicyclic or tricyclic ring system comprising a non-aromatic ring.

10. The compound according to claim 9, wherein the bicyclic or tricyclic ring system is 5,6,7,8-tetrahydro-[1,2,4]triazolopyrazinyl, 5,6,7,8-tetrahydroimidazopyrazinyl, 2,4,5,6-tetrahydropyrrolopyrazolyl, 1,2,3,4-tetrahydrobenzo[4,5]imidazopyrazinyl or 4,5,6,7-tetrahydropyrazolopyrazinyl.

11. The compound according to claim 1, wherein $R^1$ is hydrogen.

12. The compound according to claim 1, wherein $R^1$ is hydroxyl.

13. The compound according to claim 1, wherein $R^1$ is —N($R^6$)$_2$.

14. The compound according to claim 1, wherein $R^1$ is —N$R^6$C(O)$R^6$.

15. The compound according to claim 1, wherein $R^1$ is —C(O)N($R^6$)$_2$.

16. The compound according to claim 1, wherein $R^1$ is cycloalkyl optionally substituted with one or more $R^2$.

17. The compound according to claim 16, wherein the cycloalkyl is cyclobutyl, cyclopentyl or cyclohexyl, each optionally substituted with one or more $R^2$.

18. The compound according to claim 17, wherein the cyclobutyl, cyclopentyl or the cyclohexyl are substituted with one $R^2$, wherein $R^2$ is C1-C3 alkyl, alkoxy, halogen, hydroxyl or —N($R^6$)$_2$.

19. The compound according to claim 1, wherein $R^1$ is -Q-heterocyclyl optionally substituted with one or more $R^2$.

20. The compound according to claim 19, wherein Q is a bond and the heterocyclyl is morpholinyl, piperdinyl, piperazinyl, N-methylpiperazinyl, piperazin-2-one, 1-methylpiperazin-2-one, diazepanyl, 6,6-difluoro-1,4-diazepan-1-yl, or 4-methylthiomorpholine 1,1-dioxide.

21. The compound according to claim 19, wherein Q is a bond and the heterocyclyl is pyrrolidinyl or tetrahydropyranyl, each optionally substituted with one or more $R^2$.

22. The compound according to claim 21, wherein the pyrrolidinyl or the tetrahydropyranyl are substituted with one $R^2$, wherein $R^2$ is C1-C3 alkyl, alkoxy, hydroxyl or —N($R^6$)$_2$.

23. The compound according to claim 20, wherein Q is a bond and the heterocyclyl is piperazinyl optionally substituted with one or more $R^2$.

24. The compound according to claim 23, wherein the piperazinyl is substituted with one $R^2$, wherein $R^2$ is heteroaryl, —C(O)cycloalkyl or —C(O)heterocyclyl, wherein the heteroaryl, or the cycloalkyl or heterocyclyl portion of the —C(O)cycloalkyl or —C(O)heterocyclyl are each optionally substituted with one or more $R^{11}$.

25. The compound according to claim 24, wherein $R^2$ is —C(O)cycloalkyl, wherein the cycloalkyl is cyclopropyl substituted with one $R^{11}$, wherein $R^{11}$ is C1-C3 alkyl.

26. The compound according to claim 24, wherein $R^2$ is —C(O)cycloalkyl, wherein the cycloalkyl is cyclopropyl substituted with one $R^{11}$, wherein $R^{11}$ is haloalkyl.

27. The compound according to claim 24, wherein $R^2$ is —C(O)heterocyclyl, wherein the heterocyclyl is oxetanyl, tertrahydrofuranyl, or tetrahydropyranyl.

28. The compound according to claim 19, wherein Q is a bond and the heterocyclyl is a bicyclic heterocyclyl.

29. The compound according to claim 28, wherein the bicyclic heterocyclyl is diazabicyclo[3.2.0]heptan-2-yl, (1R,5R)-2,6-diazabicyclo[3.2.0]heptan-2-yl, diazabicyclo[3.2.0]heptan-6-yl, (1R,5R)-2,6-diazabicyclo[3.2.0]heptan-6-yl, 6,7-dihydropyrazolo[1,5-a]pyrazin-5(4H)-yl, 5,6-dihydroimidazo[1,5-a]pyrazin-7(8H)-yl, 1,3-dimethyl-5,6-dihydroimidazo[1,5-a]pyrazin-7(8H)-yl or (R)-2-methylhexahydropyrrolo[1,2-a]pyrazin-6(2H)-one.

30. The compound according to claim 19, wherein Q is O and the heterocyclyl is azetidinyl, tetrahydrofuranyl, pyrrolidinyl, or piperdinyl.

31. The compound according to claim 1, wherein $R^1$ is aryl optionally substituted with one or more $R^2$.

32. The compound according to claim 31, wherein the aryl is phenyl optionally substituted with one or more $R^2$.

33. The compound according to claim 32, wherein the phenyl is substituted with one $R^2$, wherein $R^2$ is C1-C3 alkyl, alkoxy, hydroxyl or —N($R^6$)$_2$.

34. The compound according to claim 1, wherein $R^1$ is heteroaryl optionally substituted with one or more $R^2$.

35. The compound according to claim 34, wherein the heteroaryl is pyrazolyl optionally substituted with one or more $R^2$.

36. The compound according to claim 35, wherein the pyrazolyl is substituted with one $R^2$, wherein $R^2$ is C1-C3 alkyl, alkoxy, hydroxyl or —N($R^6$)$_2$.

37. The compound according to claim 1, wherein $R^7$ is cyano or alkoxy.

38. The compound according to claim 37, wherein $R^7$ is alkoxy, and the alkoxy is methoxy.

39. The compound according to claim 38, wherein $R^1$ is alkoxy.

40. The compound according to claim 39, wherein the alkoxy is methoxy.

41. The compound according to claim 1, wherein Y is heteroarylene.

42. The compound according to claim 41, wherein the heteroarylene is thiophenylene.

43. The compound according to claim 1, wherein Y is a bond.

44. The compound according to claim 1, wherein $R^4$ is heteroaryl, optionally substituted with one or more $R^5$.

45. The compound according to claim 44, wherein $R^4$ is aryl optionally substituted with one or more $R^5$.

46. The compound according to claim 45, wherein the aryl is phenyl optionally substituted with one or more $R^5$.

47. The compound according to claim 46, wherein the phenyl is substituted with one $R^5$, wherein $R^5$ is C1-C4 alkyl, haloalkyl or -L-N($R^6$)$_2$.

48. The compound according to claim 47, wherein $R^5$ is -L-N($R^6$)$_2$, wherein L is methylene and one $R^6$ is hydrogen and the second $R^6$ is C1-C3 alkyl.

49. The compound according to claim 48, wherein the second $R^6$ is methyl.

50. The compound according to claim 49, wherein $R^5$ is -L-N($R^6$)$_2$, wherein L is methylene and each $R^6$ is C1-C3 alkyl.

51. The compound according to claim 50, wherein each C1-C3 alkyl is methyl.

52. The compound according to claim 46, wherein the phenyl is substituted with two $R^5$, wherein one $R^5$ is C1-C3 alkyl and the second $R^5$ is haloalkyl.

53. The compound according to claim 52, wherein C1-C3 alkyl is methyl and the haloalkyl is trifluoromethyl.

54. The compound according to claim 46, wherein the phenyl is substituted with two $R^5$, wherein one $R^5$ is C1-C3 alkyl and the second $R^5$ is -L-N($R_6$)$_2$.

55. The compound according to claim 48, wherein C1-C3 alkyl is methyl, L is methylene and each $R^6$ is C1-C3 alkyl.

56. The compound according to claim 1, wherein $R^3$ is C1-C6 alkyl.

57. The compound according to claim 56, wherein C1-C6 alkyl is methyl, ethyl or isopropyl.

58. The compound according to claim 1, wherein $R^3$ is haloalkyl.

59. The compound according to claim 1, wherein $R^3$ is cycloalkyl optionally substituted with halogen amino, hydroxy or alkoxy.

60. The compound according to claim 59, wherein the cycloalkyl is cyclopropyl.

61. The compound according to claim 1, wherein $R^3$ is alkoxy.

62. The compound according to claim 1, wherein $R^3$ is —N($R^{10}$)$_2$.

63. The compound according to claim 1, wherein $R^3$ is hydrogen.

64. The compound according to claim 1, wherein $R^8$ is C1-C2 alkyl.

65. The compound according to claim 64, wherein the C1-C2 alkyl is methyl.

66. The compound according to claim 1, wherein $R^8$ is haloC1-C2 alkyl.

67. The compound according to claim 66, wherein the haloC1-C2 alkyl is fluoromethyl, difluoromethyl or trifluoromethyl.

68. The compound of claim 1, wherein the compound is selected from the group consisting of:

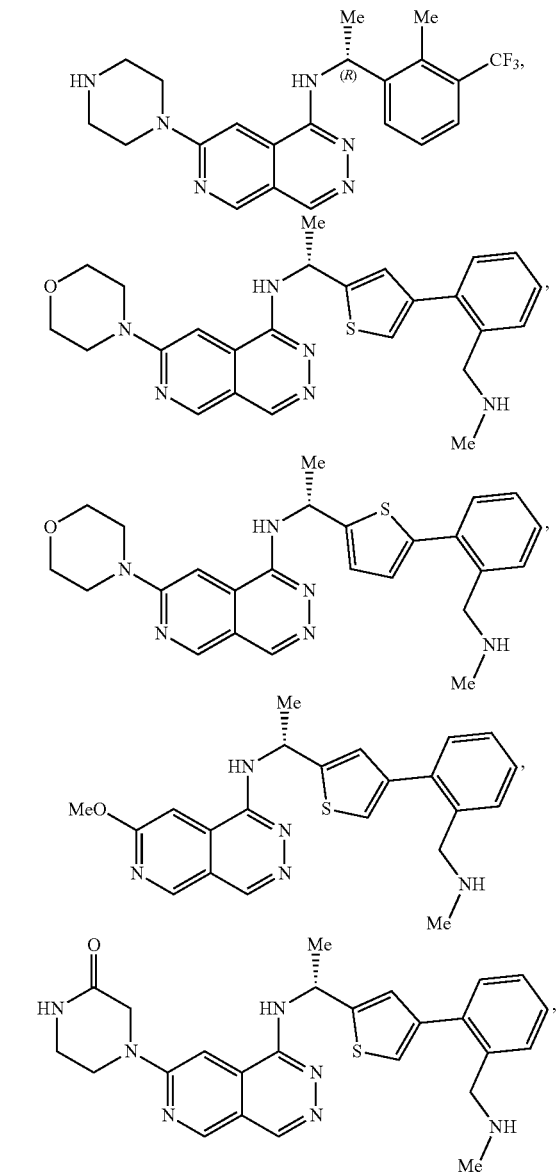

405
-continued
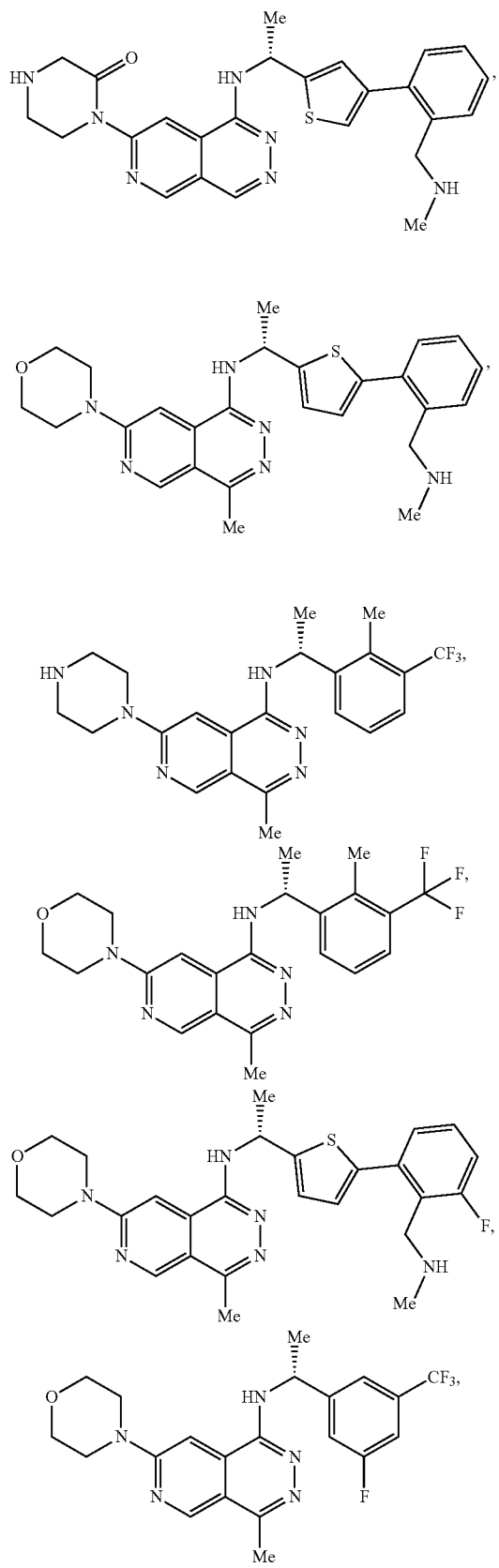
406
-continued
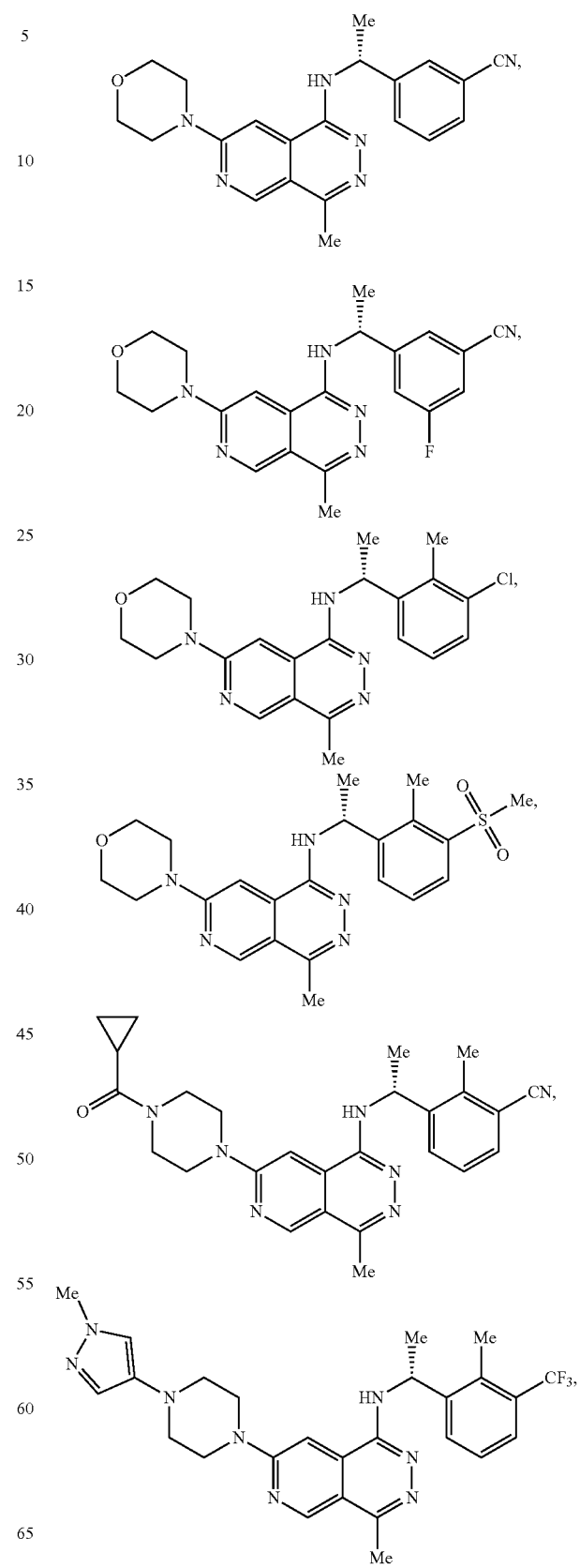

407
-continued
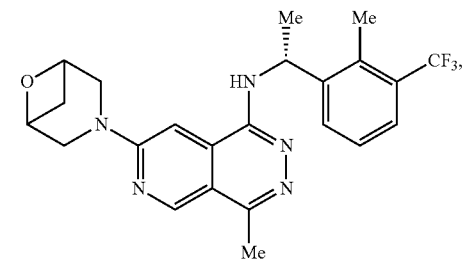
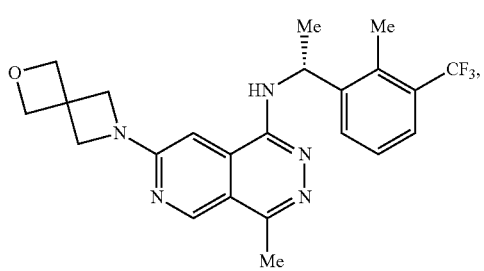
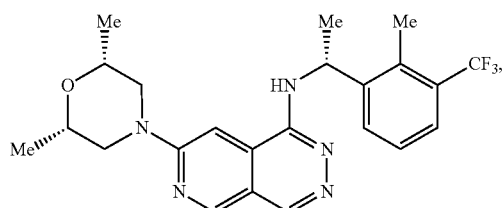
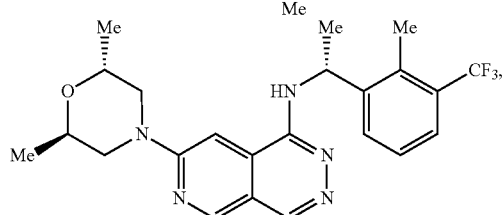
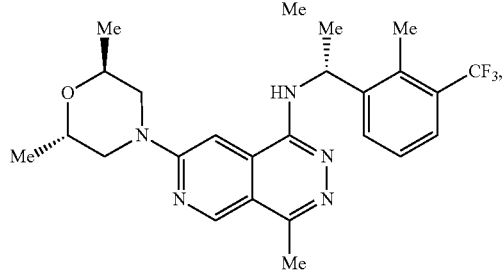
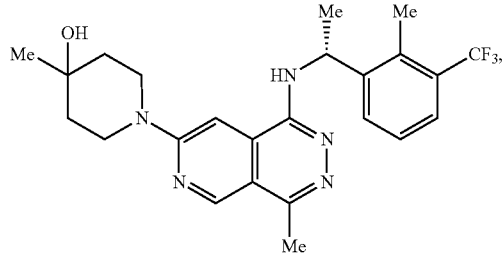
408
-continued
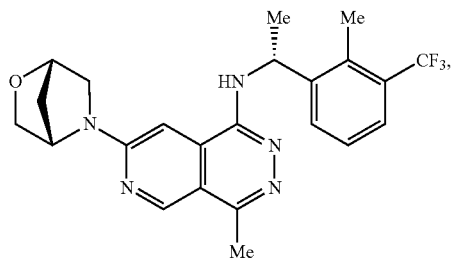
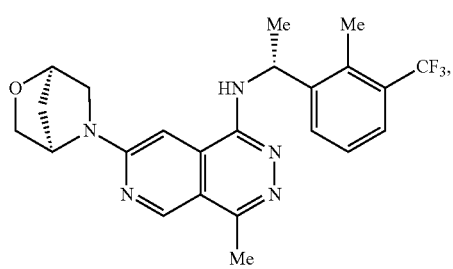
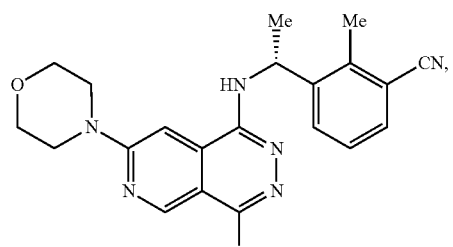
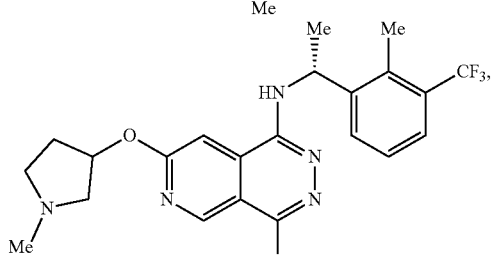
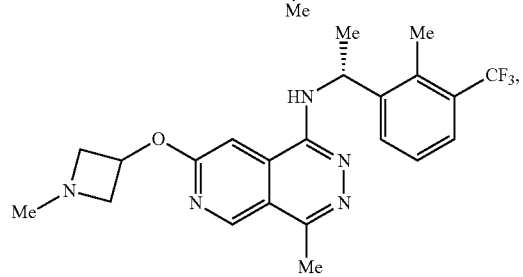
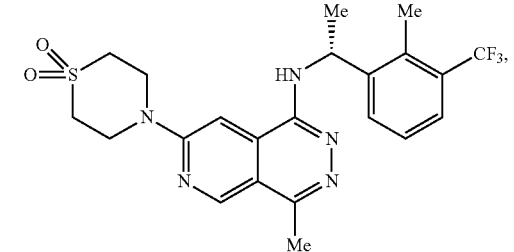

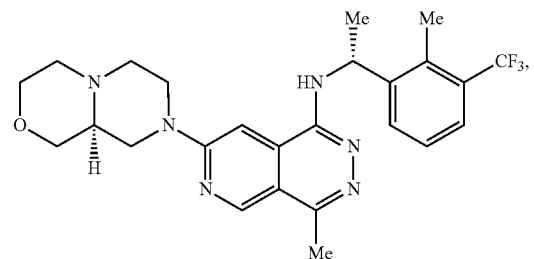
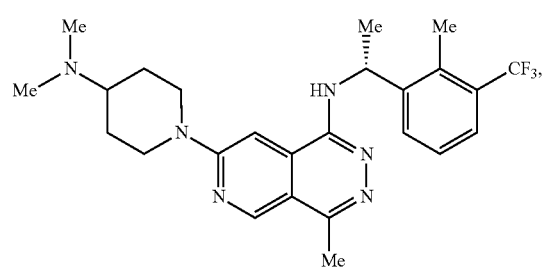
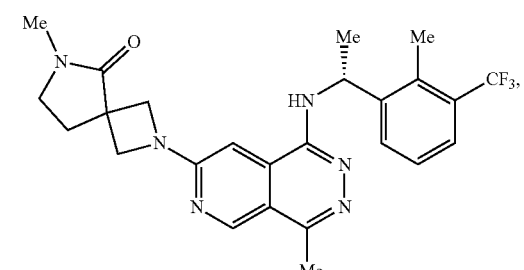
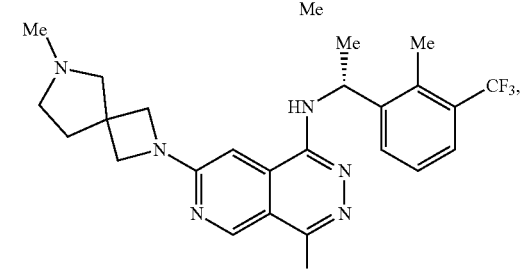
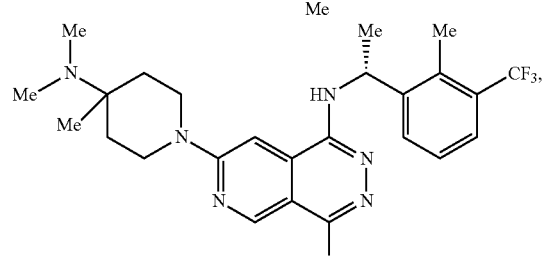
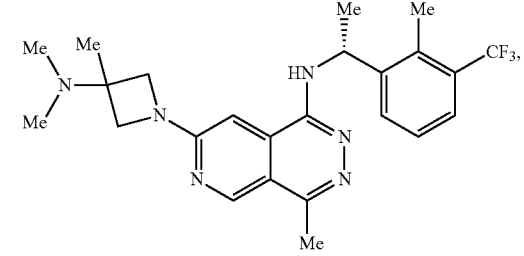
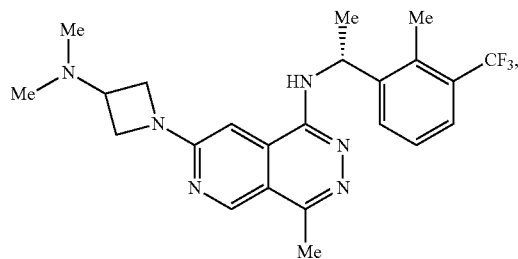
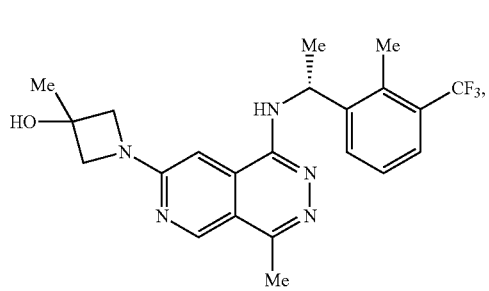
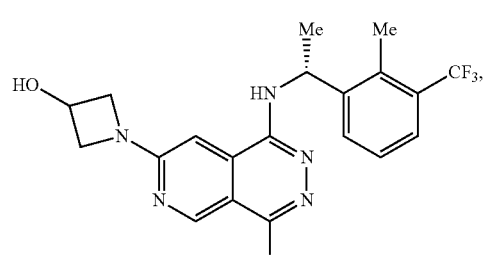
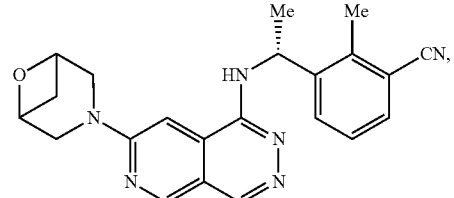
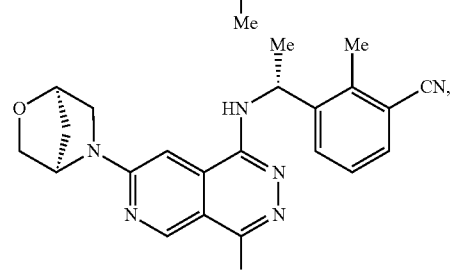
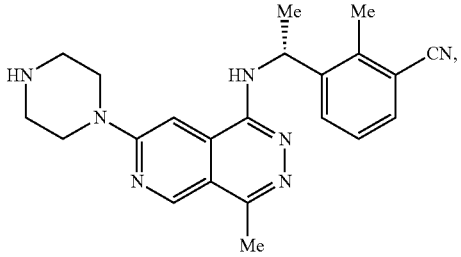

-continued
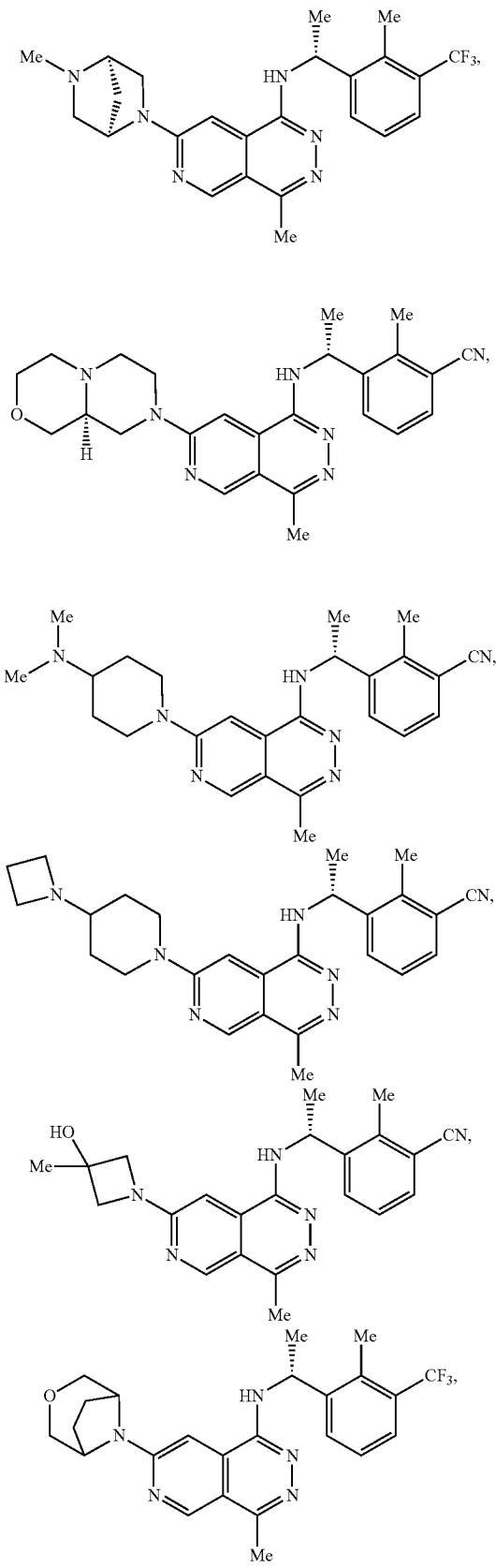
-continued
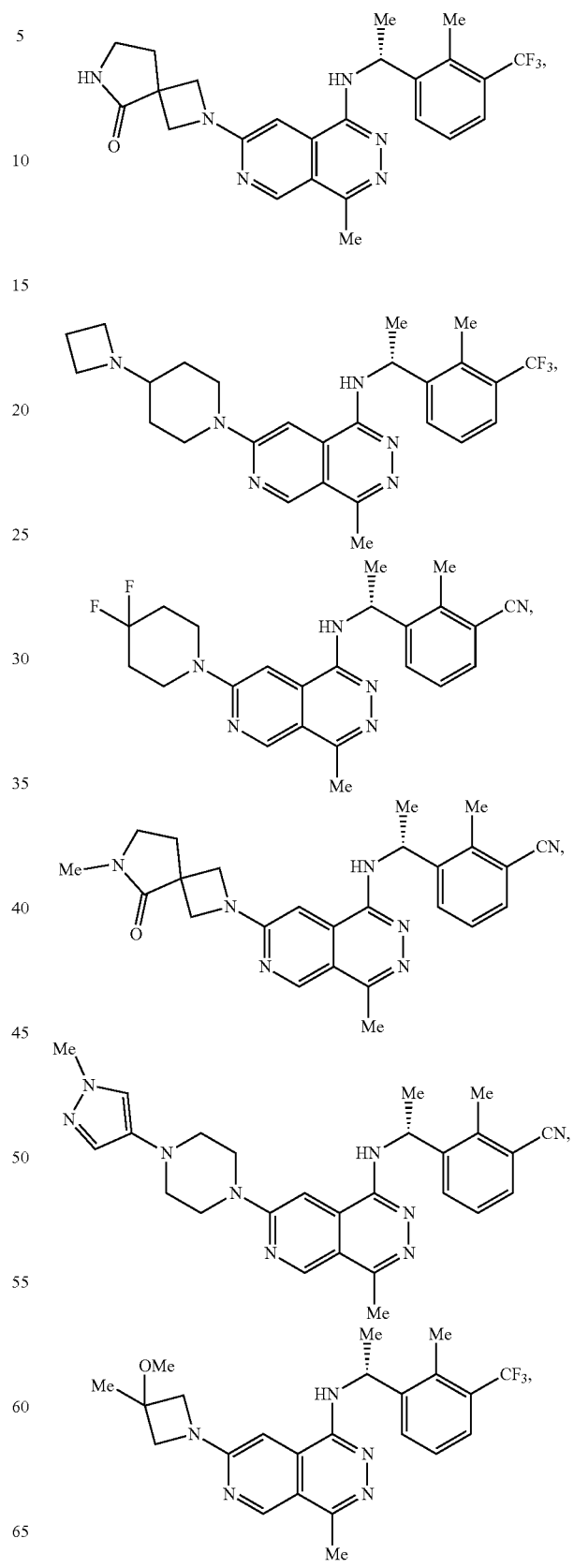

413
-continued
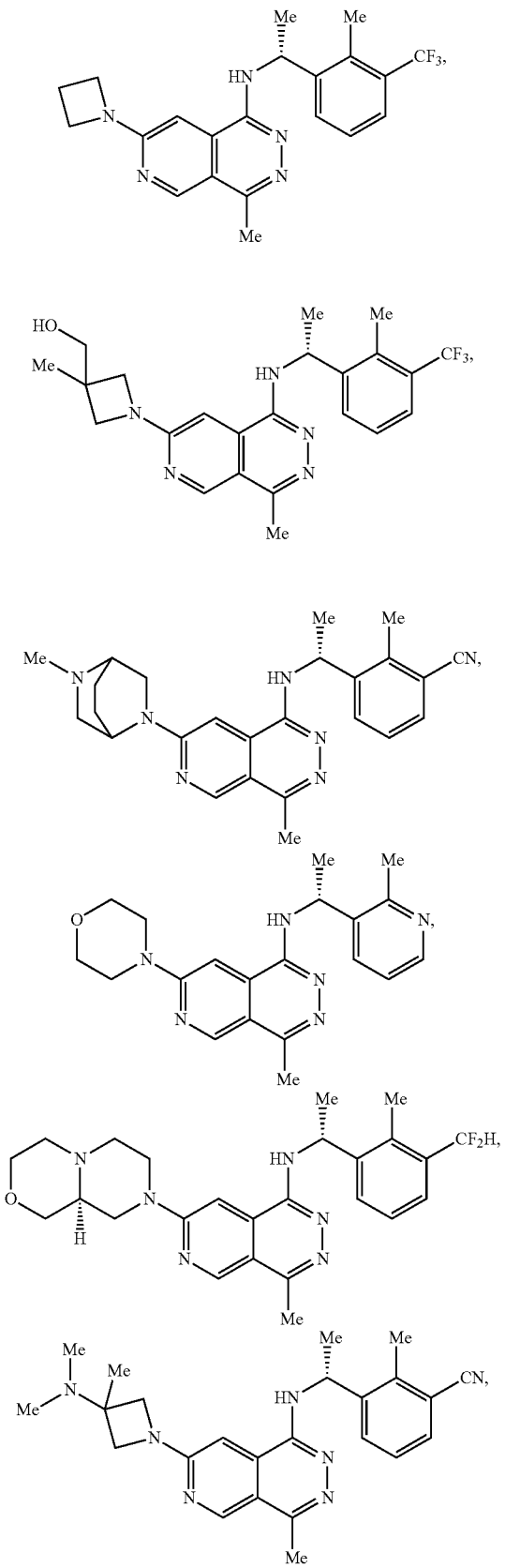
414
-continued
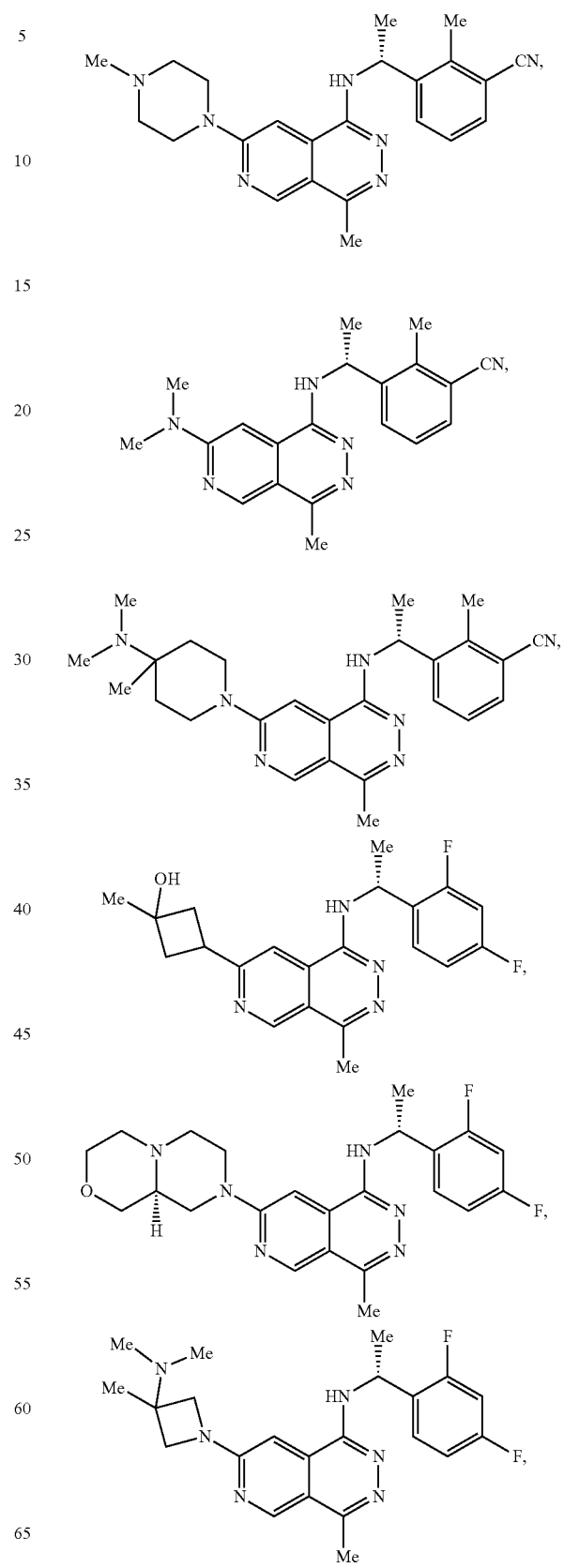

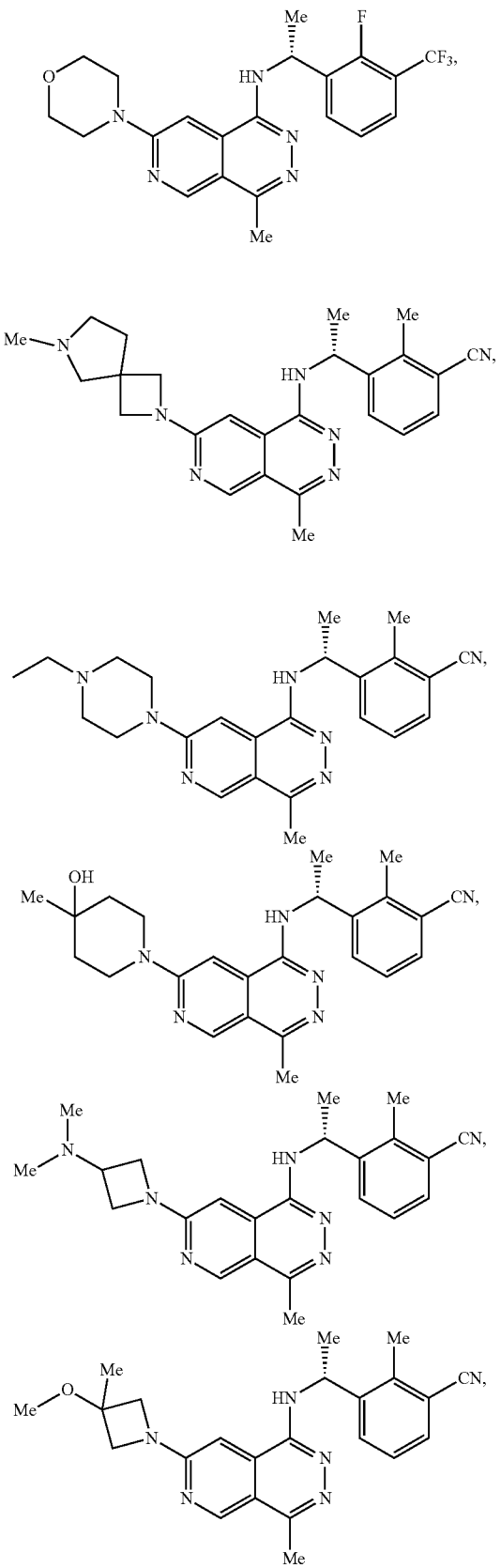
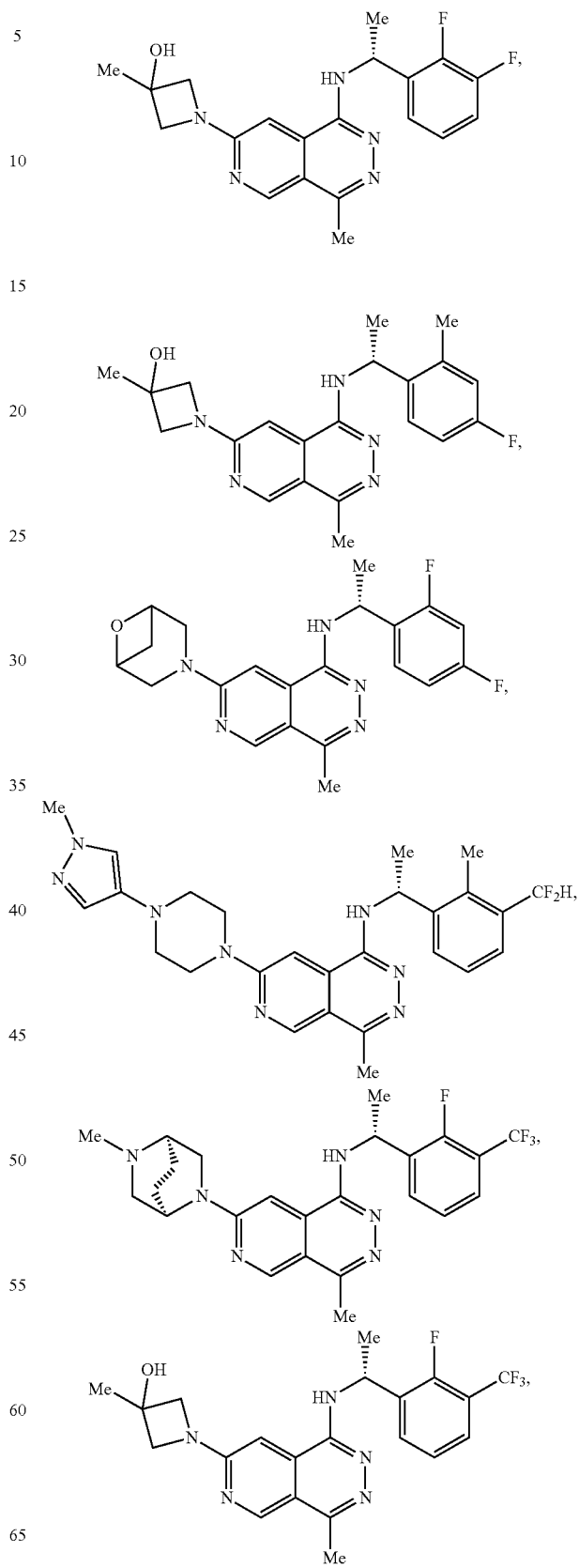

417
-continued
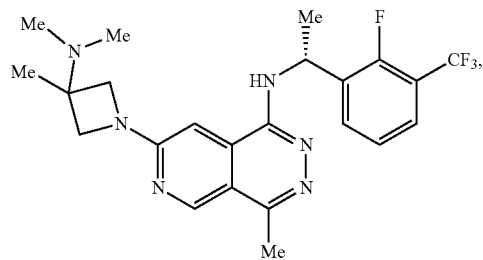
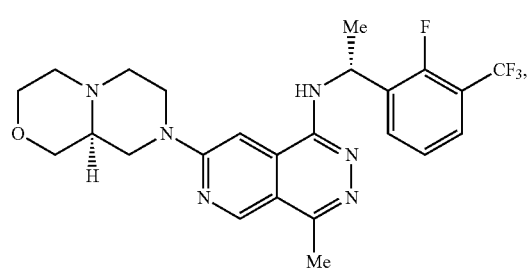
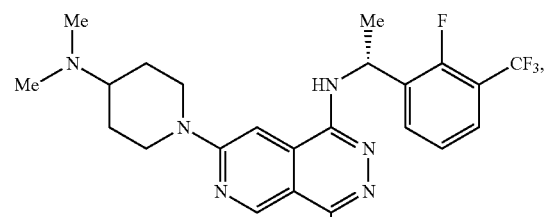
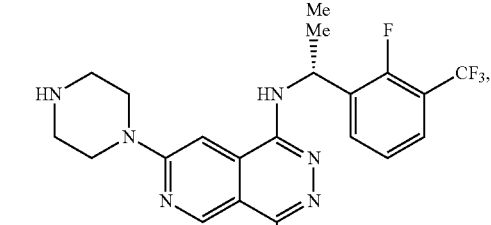
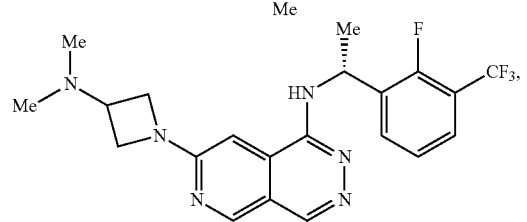
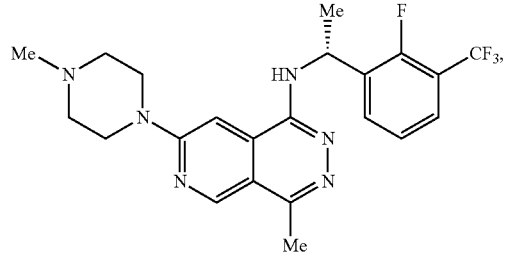
418
-continued
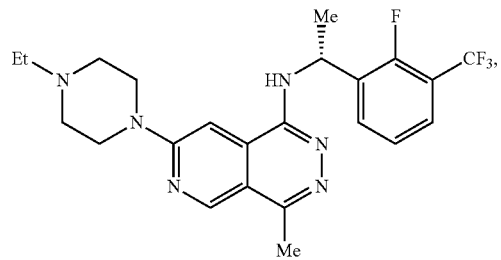
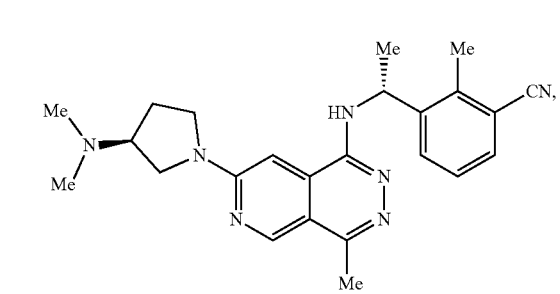
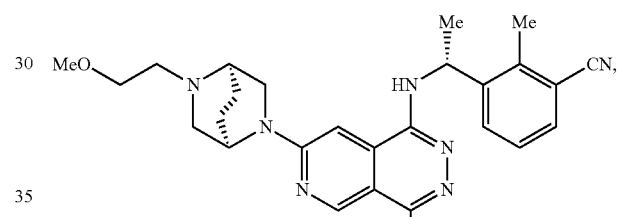
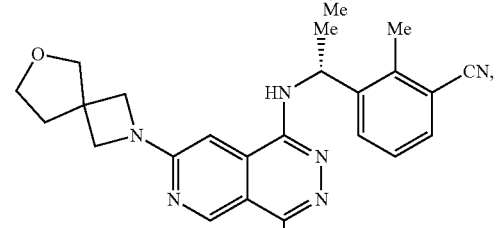
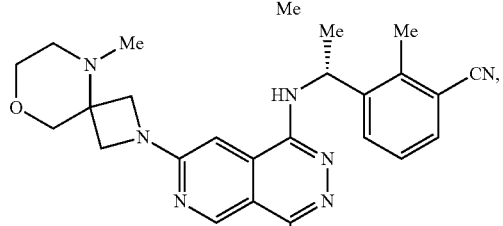
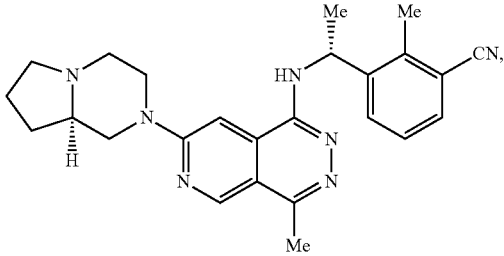

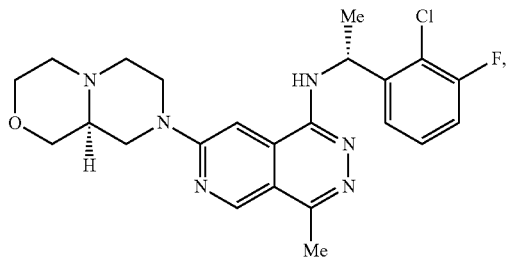
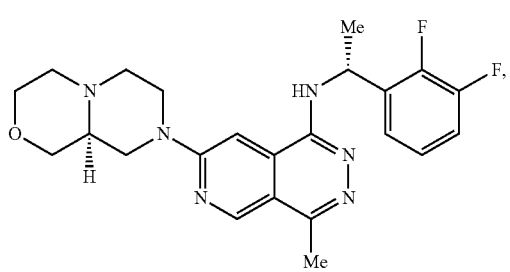
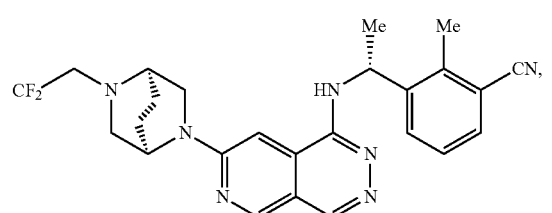
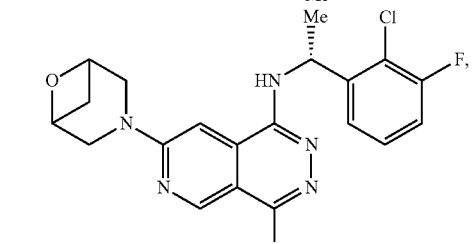
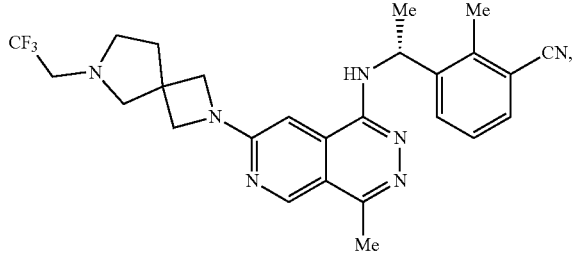
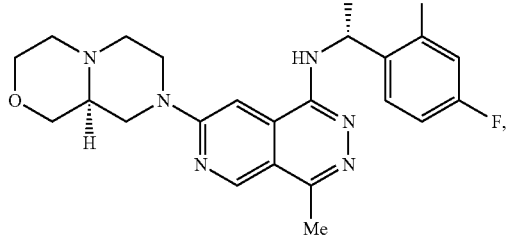
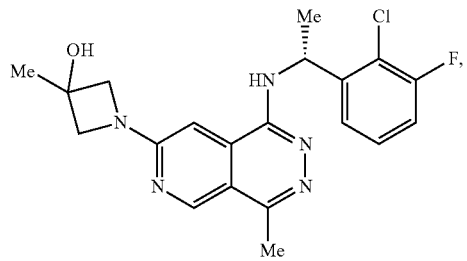
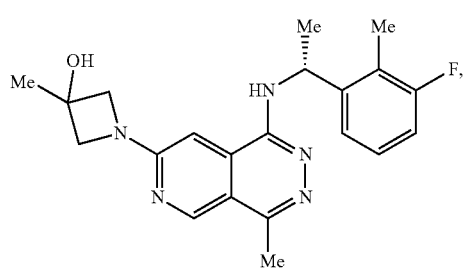
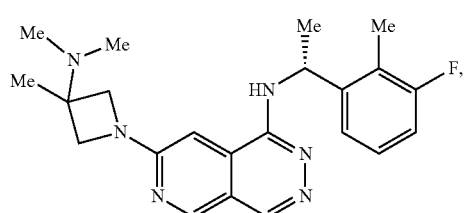
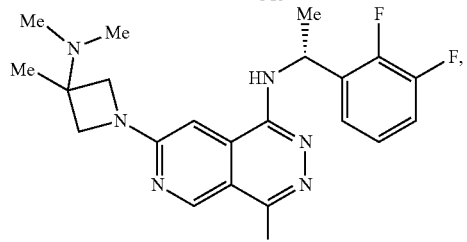
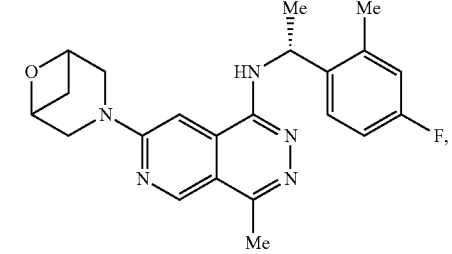
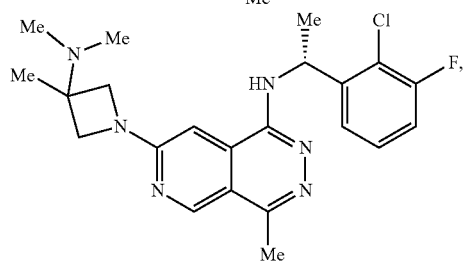

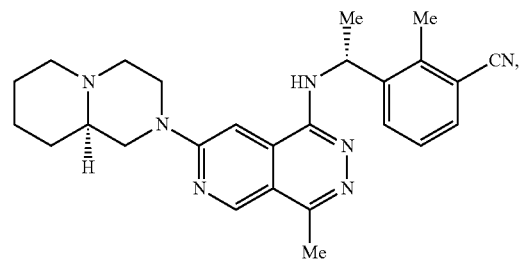
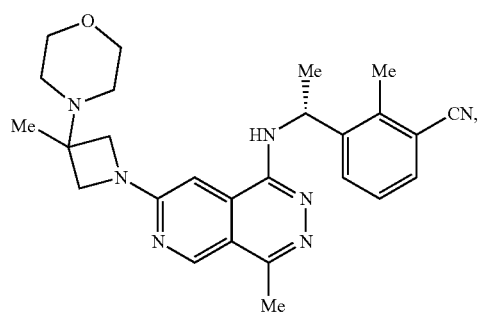
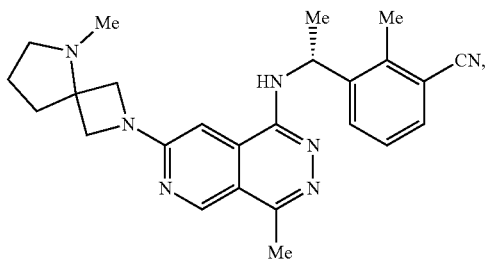
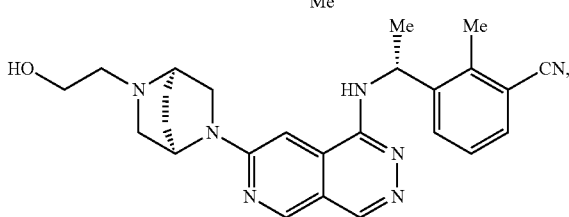
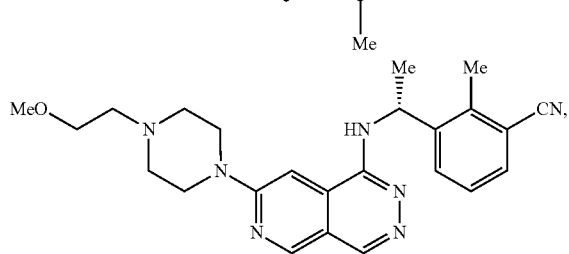
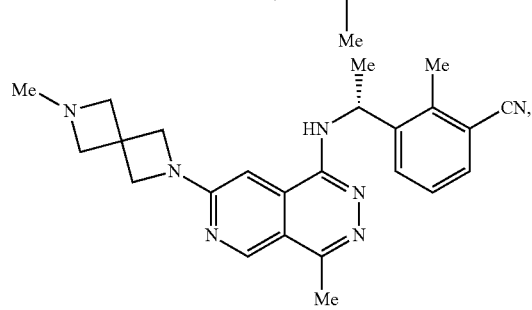
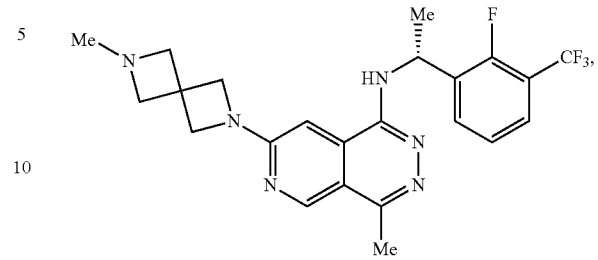
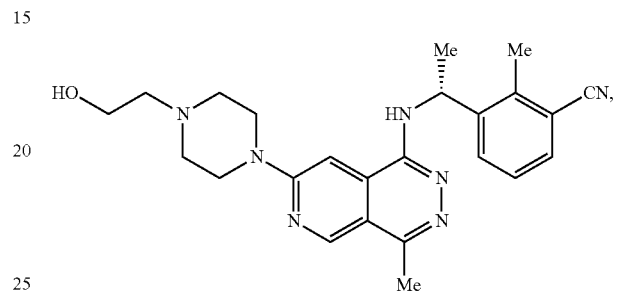
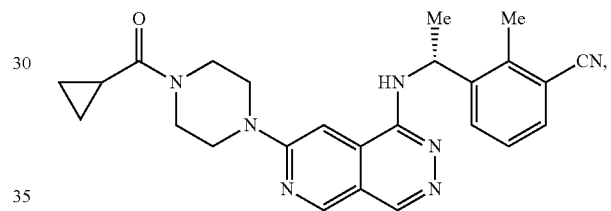
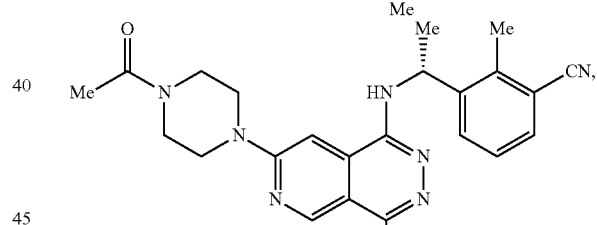
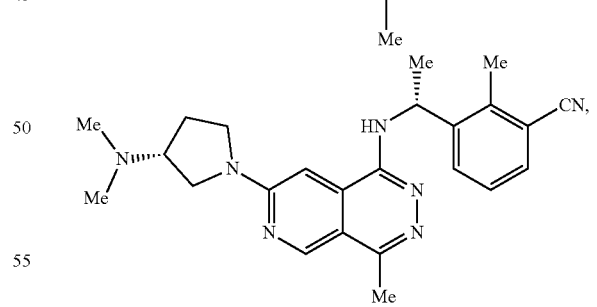
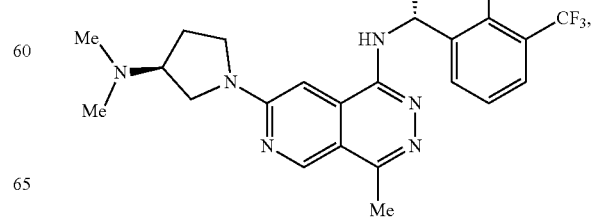

423
-continued
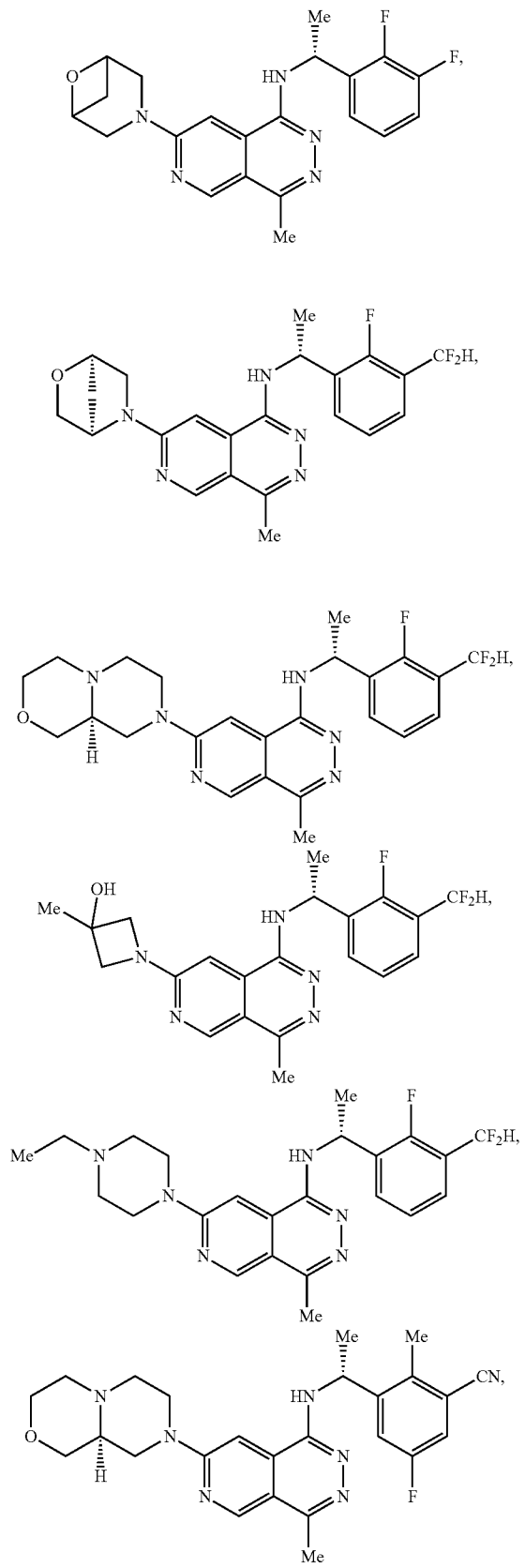
424
-continued
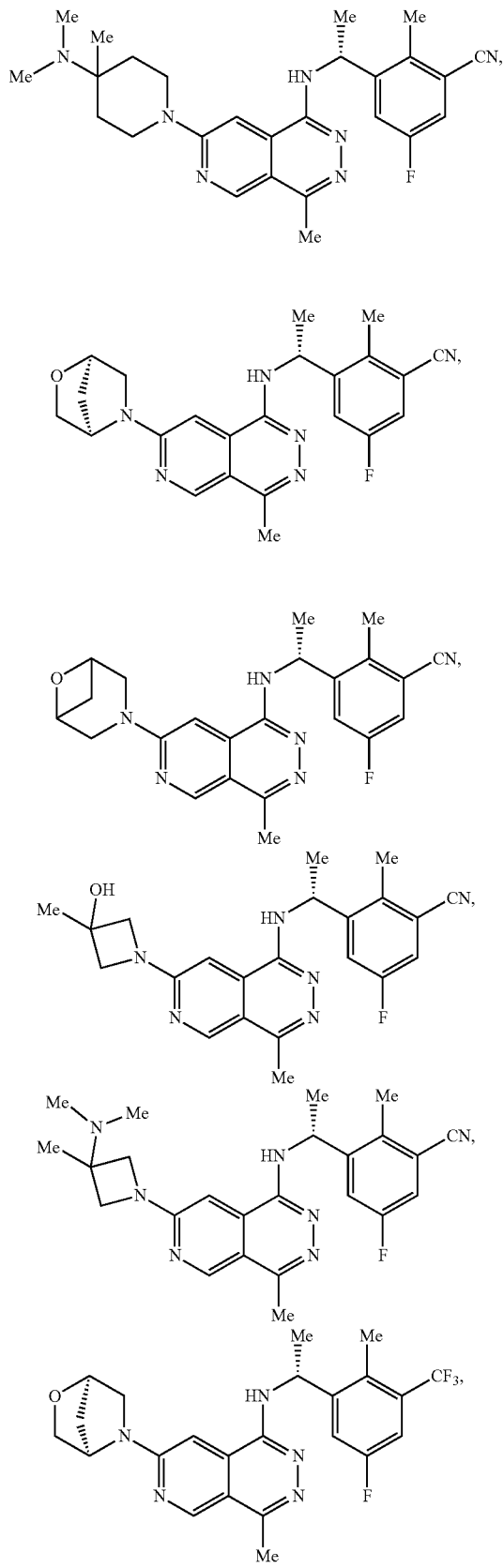

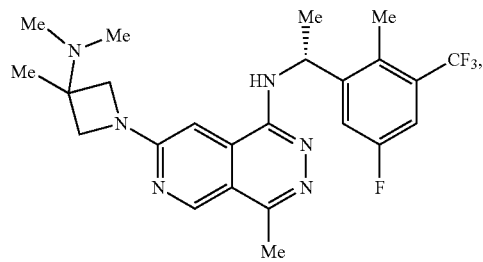
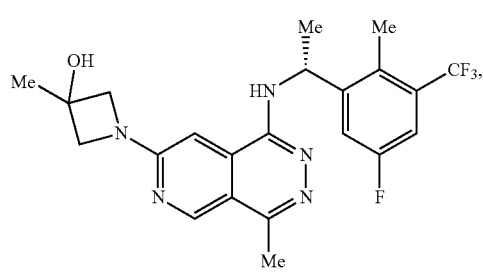
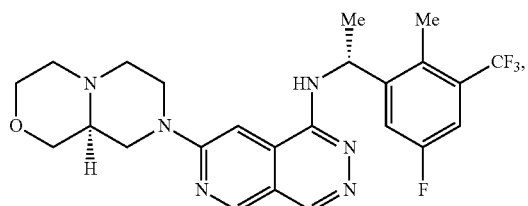
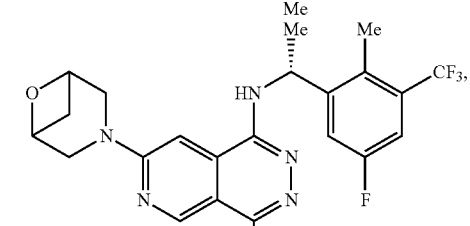
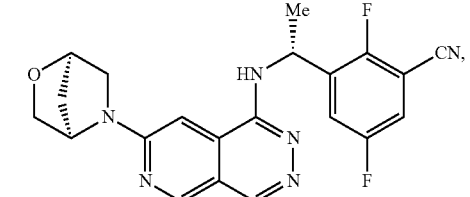
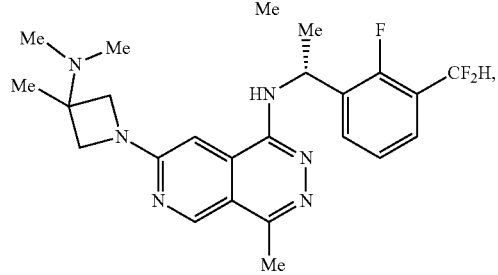
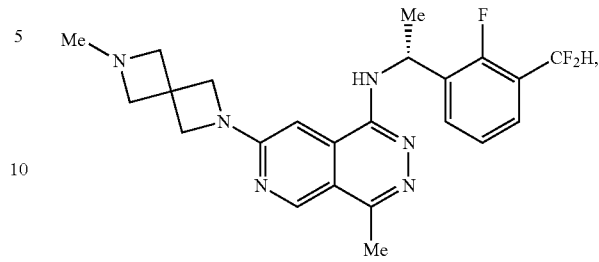
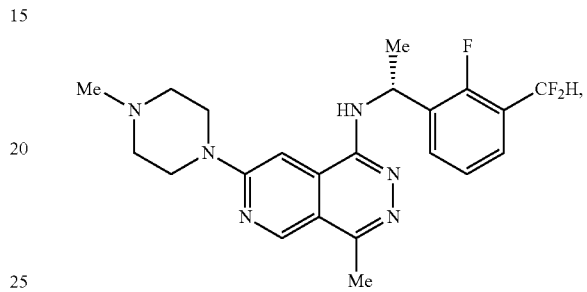
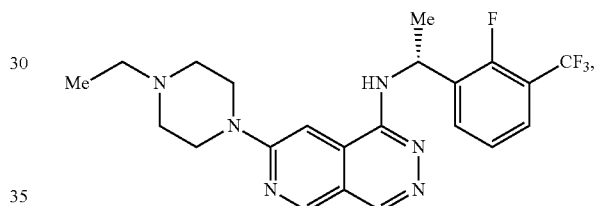
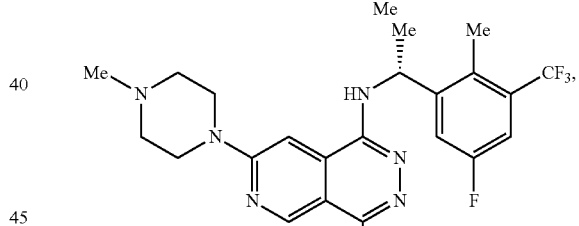
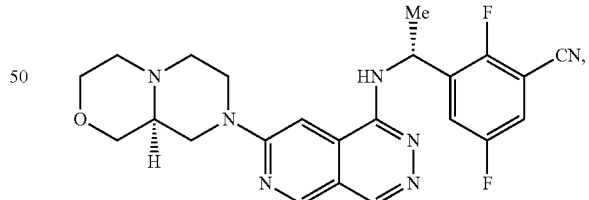
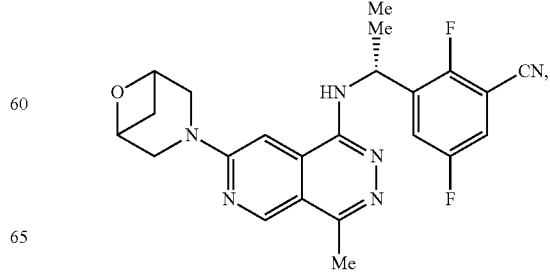

-continued
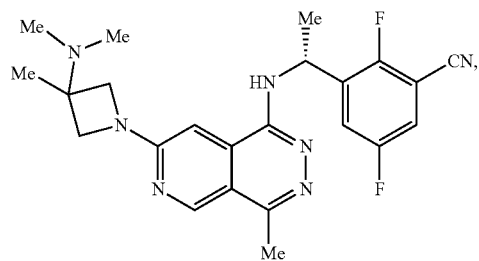
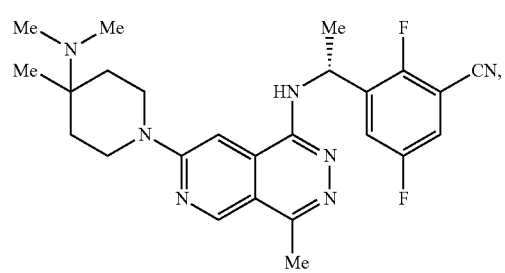
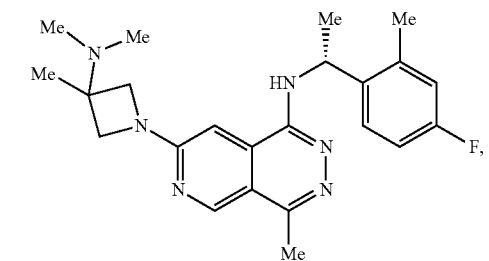
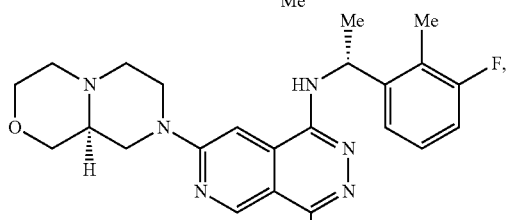
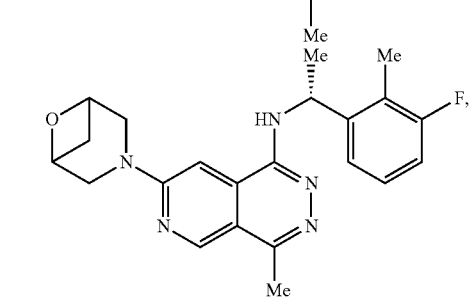
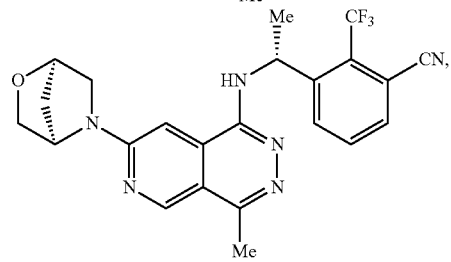
-continued
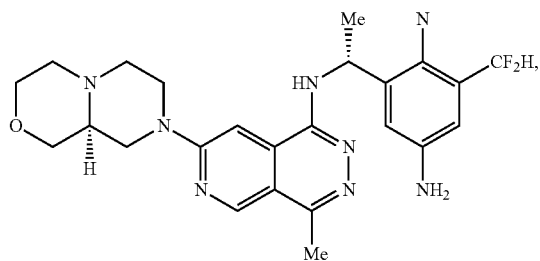
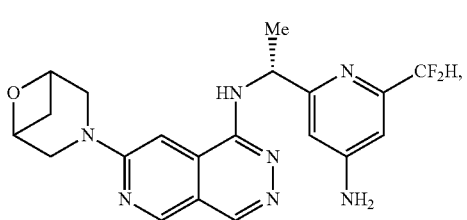
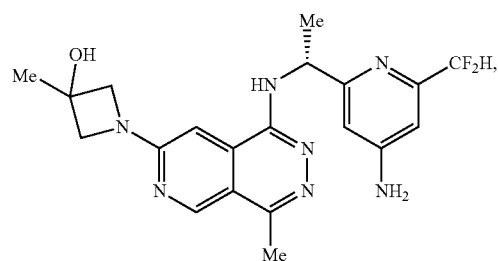
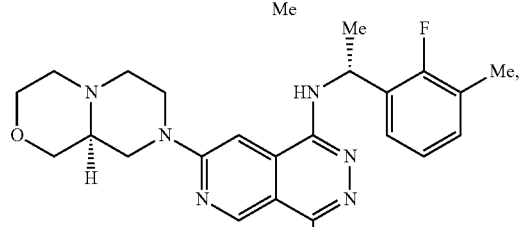
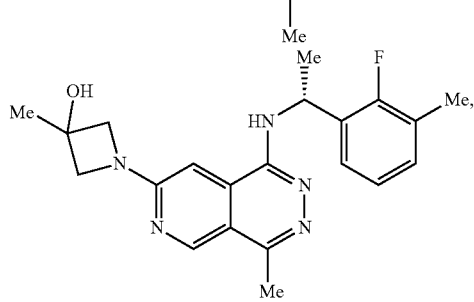
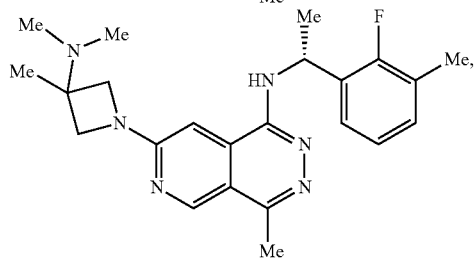

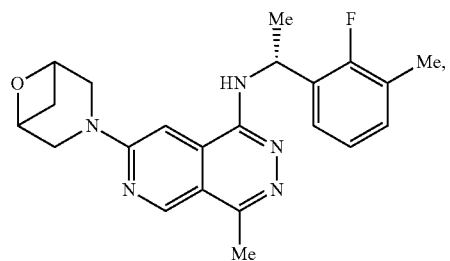
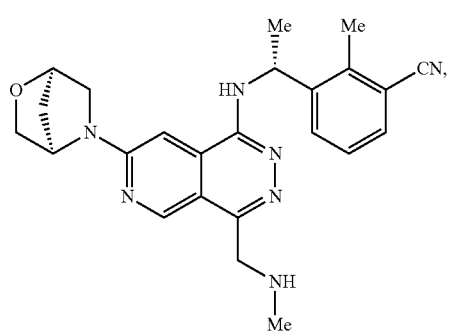
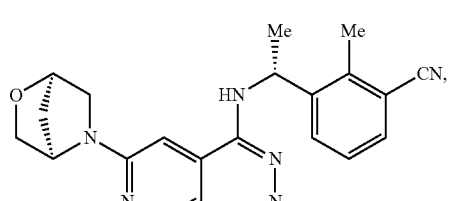
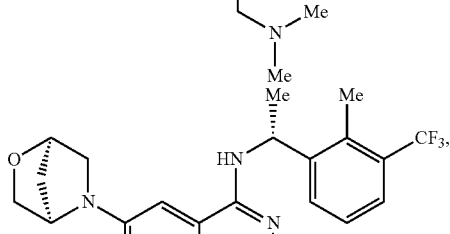
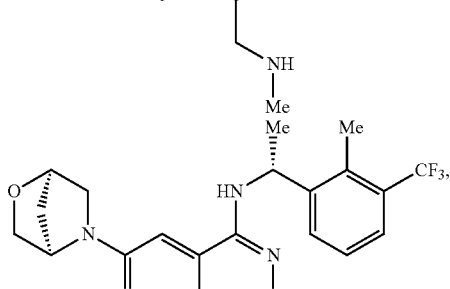
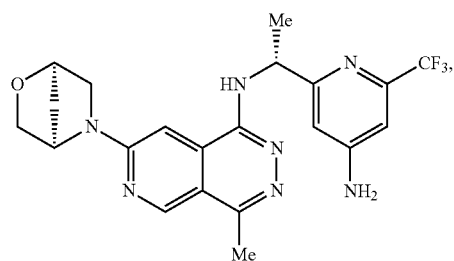
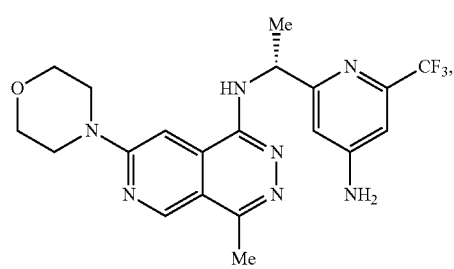
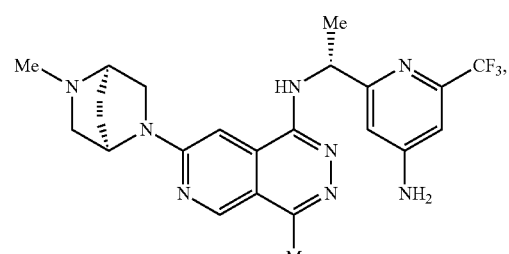
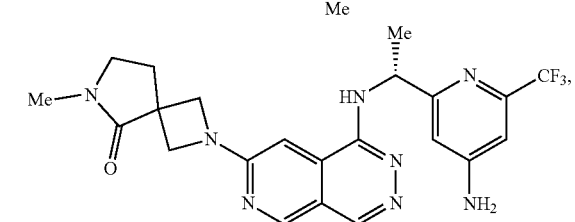
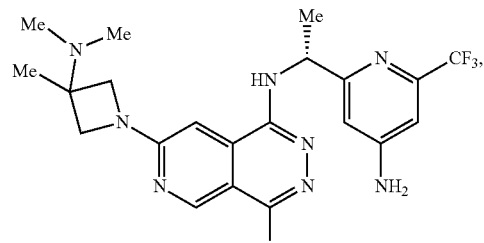
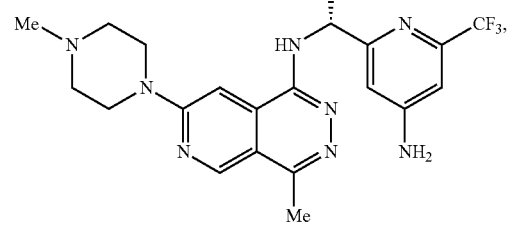

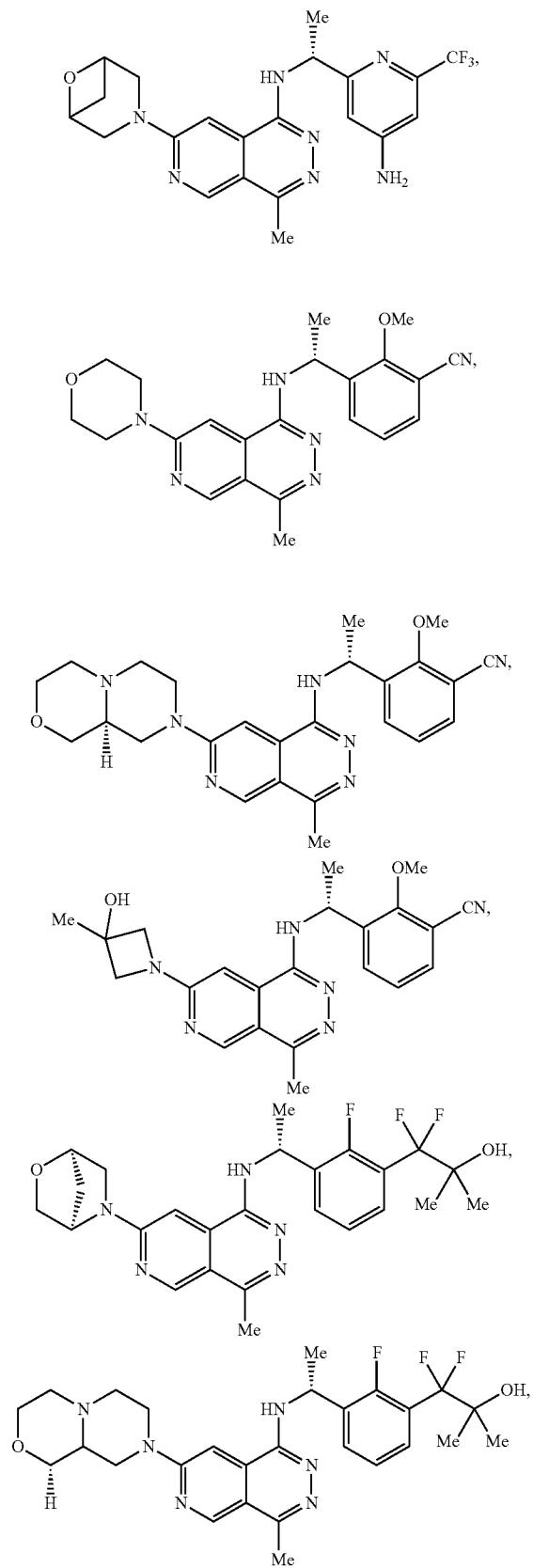

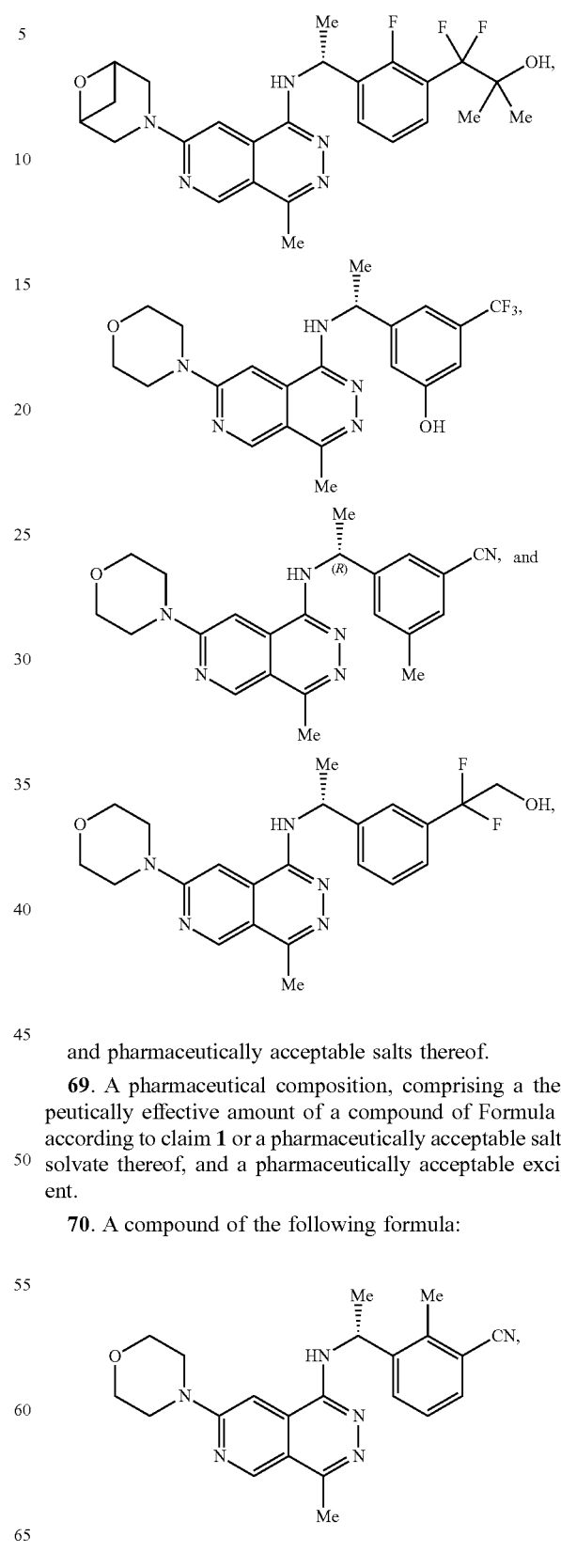

and pharmaceutically acceptable salts thereof.

69. A pharmaceutical composition, comprising a therapeutically effective amount of a compound of Formula (I) according to claim 1 or a pharmaceutically acceptable salt or solvate thereof, and a pharmaceutically acceptable excipient.

70. A compound of the following formula:

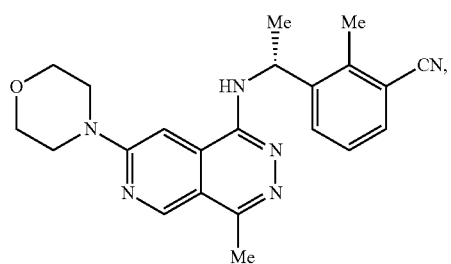 [SMILES: Cc1c(C#N)cccc1[C@@H](C)Nc1nnc(C)c2cnc(N3CCOCC3)cc12]

or a pharmaceutically acceptable salt thereof.

71. A compound of the following formula:
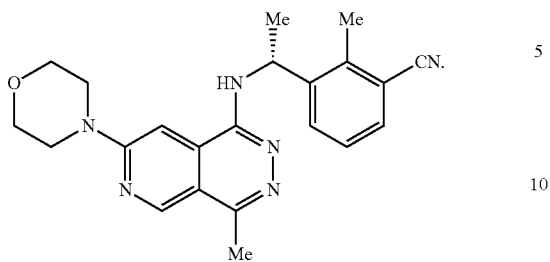
72. A pharmaceutically acceptable salt of a compound of the following formula:
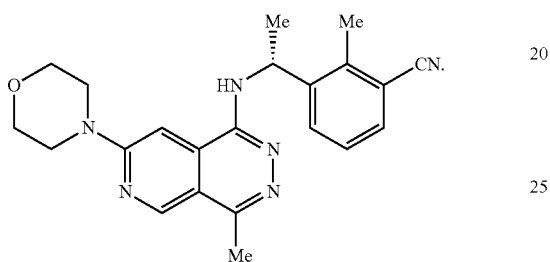
* * * * *